US010533051B2

(12) United States Patent
Saunders et al.

(10) Patent No.: US 10,533,051 B2
(45) Date of Patent: *Jan. 14, 2020

(54) ANTI SEZ6 ANTIBODIES AND METHODS OF USE

(71) Applicant: ABBVIE STEMCENTRX LLC, North Chicago, IL (US)

(72) Inventors: Laura Saunders, San Francisco, CA (US); Scott J. Dylla, Emerald Hills, CA (US); Orit Foord, Foster City, CA (US); Robert A. Stull, Alameda, CA (US); Michael Torgov, Los Angeles, CA (US); Hui Shao, Foster City, CA (US); David Liu, San Francisco, CA (US)

(73) Assignee: ABBVIE STEMCENTRX LLC, North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,548

(22) Filed: Jun. 5, 2017

(65) Prior Publication Data

US 2017/0369571 A1   Dec. 28, 2017

Related U.S. Application Data

(63) Continuation of application No. 14/380,665, filed as application No. PCT/US2013/027476 on Feb. 22, 2013, now Pat. No. 9,676,850.

(60) Provisional application No. 61/603,203, filed on Feb. 24, 2012.

(51) Int. Cl.
*C07K 16/18* (2006.01)
*C07K 16/28* (2006.01)
*A61K 47/68* (2017.01)
*A61K 39/00* (2006.01)

(52) U.S. Cl.
CPC .......... *C07K 16/28* (2013.01); *A61K 47/6849* (2017.08); *A61K 2039/505* (2013.01); *C07K 2317/24* (2013.01); *C07K 2317/33* (2013.01); *C07K 2317/565* (2013.01); *C07K 2317/76* (2013.01); *C07K 2317/77* (2013.01)

(58) Field of Classification Search
CPC ................ C07K 16/28; C07K 2317/24; C07K 2317/565
USPC .......................... 530/388.2; 424/133.1, 178.1
See application file for complete search history.

(56) References Cited

U.S. PATENT DOCUMENTS

| | | |
|---|---|---|
| 5,112,946 A | 5/1992 | Maione |
| 5,336,603 A | 8/1994 | Capon et al. |
| 5,349,053 A | 9/1994 | Landolfi |
| 5,359,046 A | 10/1994 | Capon et al. |
| 5,447,851 A | 9/1995 | Beutler et al. |
| 5,530,101 A | 6/1996 | Queen |
| 5,622,929 A | 4/1997 | Willner et al. |
| 5,693,762 A | 12/1997 | Queen et al. |
| 6,180,370 B1 | 1/2001 | Queen et al. |
| 6,214,345 B1 | 4/2001 | Firestone et al. |
| 6,362,331 B1 | 3/2002 | Kamal et al. |
| 7,049,311 B1 | 5/2006 | Thurston et al. |
| 7,087,409 B2 | 8/2006 | Barbas, III et al. |
| 7,189,710 B2 | 3/2007 | Kamal et al. |
| 7,407,951 B2 | 8/2008 | Thurston et al. |
| 7,422,739 B2 | 9/2008 | Anderson et al. |
| 7,429,658 B2 | 9/2008 | Howard et al. |
| 7,521,541 B2 | 4/2009 | Eigenbrot et al. |
| 7,557,099 B2 | 7/2009 | Howard et al. |
| 7,619,068 B2 | 11/2009 | Pilkington et al. |
| 7,632,678 B2 | 12/2009 | Hansford et al. |
| 7,741,319 B2 | 6/2010 | Howard et al. |
| 8,034,808 B2 | 10/2011 | Delavault et al. |
| 8,163,736 B2 | 4/2012 | Gauzy et al. |
| 8,788,213 B2 | 7/2014 | Bright |
| 8,889,833 B2 | 11/2014 | Yue et al. |
| 9,676,850 B2 * | 6/2017 | Saunders ............... C07K 16/28 |
| 9,993,566 B2 * | 6/2018 | Liu ......................... C07K 16/28 |
| 10,035,853 B2 * | 7/2018 | Arathoon ............... C07K 16/28 |
| 2003/0211991 A1 | 11/2003 | Su |
| 2004/0067490 A1 | 4/2004 | Zhong et al. |
| 2004/0101920 A1 | 5/2004 | Radziejewski et al. |
| 2005/0008625 A1 | 1/2005 | Balint et al. |
| 2005/0238649 A1 | 10/2005 | Doronina et al. |
| 2007/0292414 A1 | 12/2007 | Duntsch et al. |
| 2008/0138313 A1 | 6/2008 | Frankel |
| 2008/0171043 A1 | 7/2008 | Lin et al. |
| 2008/0175870 A1 | 7/2008 | Mather et al. |
| 2009/0155255 A1 | 6/2009 | Glaser et al. |
| 2010/0076178 A1 | 3/2010 | Ghayur et al. |
| 2010/0162416 A1 | 6/2010 | Krtolica et al. |

(Continued)

FOREIGN PATENT DOCUMENTS

| | | |
|---|---|---|
| CN | 1343774(A) | 4/2002 |
| EP | 0 307 434 | 3/1989 |

(Continued)

OTHER PUBLICATIONS

Official action dated Jun. 1, 2017, issued in European patent application (No. 13707529.7).
Official action dated Jun. 28, 2017, issued in Australian patent application (No. 2016225828).
Official action dated Jun. 28, 2017, issued in Thai patent application (No. 1401004861).

(Continued)

*Primary Examiner* — Lynn A Bristol
(74) *Attorney, Agent, or Firm* — Womble Bond Dickinson (US) LLP

(57) ABSTRACT

Provided are novel seizure related 6 (SEZ6) modulators, including antibodies and derivatives thereof, and methods of using such modulators to treat proliferative disorders.

17 Claims, 60 Drawing Sheets

Specification includes a Sequence Listing.

(56) References Cited

U.S. PATENT DOCUMENTS

| | | | |
|---|---|---|---|
| 2010/0273160 A1 | 10/2010 | Donahoe et al. | |
| 2010/0275280 A1 | 10/2010 | Clevers et al. | |
| 2011/0020221 A1 | 1/2011 | Berman et al. | |
| 2011/0033378 A1 | 2/2011 | Dimasie et al. | |
| 2011/0091372 A1 | 4/2011 | Ghayur et al. | |
| 2011/0256157 A1 | 10/2011 | Howard et al. | |
| 2012/0078028 A1 | 3/2012 | Satpayev et al. | |
| 2013/0061340 A1 | 3/2013 | Dylla et al. | |
| 2013/0061342 A1 | 3/2013 | Dylla et al. | |
| 2013/0260385 A1 | 10/2013 | Dylla et al. | |
| 2015/0030636 A1 | 1/2015 | Dylla et al. | |
| 2018/0112004 A1* | 4/2018 | Liu | C07K 16/2896 |
| 2018/0346565 A1* | 12/2018 | Arathoon | C07K 16/28 |
| 2019/0022241 A1* | 1/2019 | Liu | C07K 16/28 |

FOREIGN PATENT DOCUMENTS

| | | |
|---|---|---|
| EP | 0 367 166 | 5/1990 |
| WO | WO 91/06570 | 5/1991 |
| WO | WO 96/04388 | 2/1996 |
| WO | WO 98/52976 | 11/1998 |
| WO | WO 00/34317 | 6/2000 |
| WO | WO 01/083552 | 11/2001 |
| WO | WO 03/075957 | 9/2003 |
| WO | WO 2011/112978 | 9/2011 |
| WO | WO 2011/128650 | 10/2011 |
| WO | WO 2011/130613 | 10/2011 |
| WO | WO 2011/130616 | 10/2011 |
| WO | WO 2012/012801 | 1/2012 |
| WO | WO 2012/031280 | 3/2012 |
| WO | WO 2013/119964 | 8/2013 |
| WO | WO 2015/031541 | 3/2015 |
| WO | WO 2015/031698 | 3/2015 |
| WO | WO 2016/064749 | 4/2016 |
| WO | WO 2018/119351 | 6/2018 |

OTHER PUBLICATIONS

Office Action dated Aug. 11, 2017, issued in Chilean Patent application (No. 2014-02237).
Official action received Aug. 23, 2017, issued in Colombian patent application (No. NC2017/0000403).
Official action dated Aug. 24, 2017, issued in Israeli patent application (No. 234208).
Summons to attend oral proceedings dated May 3, 2018, issued in European patent application (No. 13707529.7).
Office Action dated Dec. 14, 2018, issued in Canadian application (No. 2,865,415).
Official action/opposition demand dated Sep. 12, 2018, in Chilean application (No. 02823-2017).
Official action dated Oct. 2, 2018, issued in Israeli patent application (No. 234208).
Final official action dated Nov. 17, 2017, issued in Japanese patent application (No. 2014-558901).
Official action dated Apr. 18, 2018, issued in Mexican patent application (No. MX/a/2014/010094).
Official action dated Jun. 29, 2018, issued in Phillippine patent application (No. 1-2014-501914).
Official action dated Jan. 26, 2018, issued in Russian patent application (No. 2014138420).
Official action dated May 31, 2018, issued in Thai patent application (No. 1-2015-03483).
NP_001092105 seizure protein 6 homolog isoform 2 precursor [Homo sapiens].
NP_001099224 seizure protein 6 homolog precursor [Rattus norvegicus].
NP_001139913 synaptojanin-1 [Salmo salar].
NP_066938 seizure 6-like protein isoform 1 precursor [Homo sapiens].
NP_067261 seizure protein 6 isoform 1 precursor [Mus musculus].
NP_849191.3 seizure protein 6 homolog isoform 1 precursor [Homo sapiens].
XP_511368 Predicted: seizure protein 6 homolog isoform X2 [Pan troglodytes].
Ashkenazi et al.,"Protection against endotoxic shock by a tumor necrosis factor receptor immunoadhesin," *Proc Natl Acad Sci U S A*. (Dec. 1, 1991) 88(23):10535-10539.
Bjellqvist et al., 1993, Electrophoresis 14:1023.
Boder et al., "Yeast surface display for screening combinatorial polypeptide libraries," *Nature Biot*, (Jun 1997) 15:553-557.
Bork et al. "The CUB domain. A widespread module in developmentally regulated proteins," *J Mol Biol*. (1993) 231(2):539-45.
Capel et al., "Heterogeneity of human IgG Fc receptors," *Immunomethods* (Feb. 1994) 4(1):25-34.
Carrodus, N.L., et al., "Seizure-Related Gene 6: A Modulator of Excitatory Synapse Development," Australian Neuroscience Society Annual Meeting, Auckland (Jan. 31-Feb. 3, 2011) p. 87.
Chao et al., "Isolating and engineering human antibodies using yeast surface display," *Nature* (2006) 1(2):755-768 (with erratum).
Chothia et al.,"Canonical Structures for Hypervariable Regions of Immunoglobulins," *J. Mol. Biol.* (1987) 196:901-917.
Chothia et al., "Conformations o fimmunoglobulin," *Nature* (1989) 342, pp. 877-883.
Cochran et al., "Domain-level antibody epitope mapping through yeast surface display of epidermal growth factor receptor fragments," *J Immunol Methods* (2004) 287(1-2):147-58.
Denardo et al., "Comparison of 1,4,7,10-tetraazacyclododecane-N,N',N",N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts," *Clin Cancer Res* (1998) 4:2483-2490.
Dubowchik et al.,"Cathepsin B-labile dipeptide linkers for lysosomal release of doxorubicin from internalizing immunoconjugates: model studies of enzymatic drug release and antigen-specific in vitro anticancer activity," *Bioconjug Chem.* (Jul-Aug 2002) 13(4):855-69.
Dylla et al., "Colorectal Cancer Stem Cells Are Enriched in Xenogeneic Tumors Following Chemotherapy," PLoS One (2008) 3(6):e2428.
Fuhrmann et al., "Poster Presentations—Immunomodulatory Agents and Interventions Abstract 5625: In vitro and in vivo pharmacology of MEDI-565 (MT111), a novel CEA/CD3—bispecific singlechain BiTE antibody in development for the treatment of gastrointestinal adenocarcinomas," *Annual Meeting of AACR Abstract Cancer Research* (Apr. 15, 2010) vol. 70, Issue 8, Supplement 1 No. 5625.
Galluzzo et al., "Notch signaling in lung cancer,"*Expert Rev Anticancer Ther.* (Apr. 2011) 11(4):533-40 PMID: 21504320.
Garnett "Targeted drug conjugates: principles and progress,"*Advanced Drug Delivery Reviews* (2001) 53:171-216.
Gene Cards ("SEZ6 Gene" definition; pp. 1-14(Jan. 15, 2016)).
Gorlov et al., "Seizure 6-Like (SEZ6L) Gene and Risk for Lung Cancer," Cancer Res (Sep. 1, 2007) 67(17):8406-11.
Gunnersen et al., "Sez-6 proteins affect dendritic arborization patterns and excitability of cortical pyramidal neurons," *Neuron*. (Nov. 21, 2007) 56(4):621-39.PMID: 18031681.
Gunnersen, Jenny M, et al., "Seizure-related gene 6 (Sez-6) in amacrine cells of the rodent retina and the consequence of gene deletion," PLOS ONE (2009) 4(8):e6546.
Harris et al., "Targeting embryonic signaling pathways in cancer therapy," *Expert Opin Ther Targets*. (Jan. 2012) 16(1):131-45.
Herbst et al., "SEZ-6: promoter selectivity, genomic structure and localized expression in the brain," *Brain Res Mol Brain Res*. (Mar. 1997) 44(2):309-22. PMID: 9073173.
Hochleitner et al., "Characterization of a discontinuous epitope of the human immunodeficiency virus (HIV) core protein p24 by epitope excision and differential chemical modification followed by mass spectrometric peptide mapping analysis," *Protein Sci*. (Mar. 2000) 9(3):487-96. PMID: 10752610.
Hoey et al., "DLL4 blockade inhibits tumor growth and reduces tumor-initiating cell frequency," *Cell Stem Cell*. (Aug. 7, 2009) 5(2):168-77. PMID: 19664991.
Ishikawa et al., "Characterization of SEZ6L2 cell-surface protein as a novel prognostic marker for lung cancer," *Cancer Sci*. (2006) 97(8):737-45.

(56) References Cited

OTHER PUBLICATIONS

Jones et al., "Replacing the complementarity-determining regions in a human antibody with those from a mouse," *Nature* (1986) 321:522-525—Abstract.

Klimstra et al., "The pathologic classification of neuroendocrine tumors: a review of nomenclature, grading, and staging systems," *Pancreas*. (Aug. 2010) 39(6):707-12 PMID: 20664470.

Klöppel "Classification and pathology of gastroenteropancreatic neuroendocrine neoplasms," *Endocr Relat Cancer* (Oct. 17, 2011) 18 Suppl 1:S1-16. PMID: 22005112.

Maccallum et al., "Antibody-antigen interactions: contact analysis and binding site topography," *J. Mot. Biol.* (1996) 262:732-745.

Mulley et al., "The Role of Seizure-Related SEZ6 as a Susceptibility Gene in Febrile Seizures," *Neurol Res Int*. (2011) 2011:917565. PMID: 21785725.

NCBI protein database search (("human seizure related 6 homologue" or "SEZ6") and (homo sapiens)) (pp. 1-2, Jun. 3, 2016).

Osaki, George, et al., "The distribution of the seizure-related gene 6 (Sez-6) protein during postnatal development of the mouse forebrain suggests multiple functions for this protein: An analysis using a new antibody," *Brain Research*, (Feb. 10, 2011) 1386:58-69 XP028186555.

Peterson et al., "Enzymatic Cleavage of Peptide-Linked Radiolabels from Immunoconjugates," *Bioconjugate Chem*. (1999) (10)4:553-557.

Ravetch et al., "Fc receptors," *Annu Rev Immunol*. (1991) 9:457-92.

Reineke "Antibody Epitope Mapping Using Arrays of Synthetic Peptides," *Methods Mol Biol*. (2004) 2 48:443-63.

Schulenburg et al., "Neoplastic stem cells: current concepts and clinical perspectives," *Crit Rev Oncol Hematol*. (Nov. 2010) 76(2):79-98 PMID: 20185329.

Shao et al., "Expression of SEZ6 gene in human tumor cell," *Journal of Tongji University (Medical Science)* (2009) 30(1):36-39 (English translation).

Shimizu-Nishikawa K et al., "Cloning and expression of SEZ-6, a brain-specific and seizure-related cDNA," *Brain Res Mol Brain Res*. (Feb. 1995) 28(2):201-10. PMID 7723619.

Shimizu-Nishikawa K et al., "Cloning and Characterization of Seizure-Related Gene, SEZ-6," *Biochem Biophys Res Comm* (Nov. 2, 1995) 216(1):382-389.

Tang et al., "Picoplatin overcomes resistance to cell toxicity in small-cell lung cancer cells previously treated with cisplatin and carboplatin," *Cancer Chemo Pharm* (Aug. 31, 2010) 67:1389-1400.

Vermeer et al., "The thermal stability of immunoglobulin: unfolding and aggregation of a multi-domain protein," *Biophys J*. (Jan. 2000) 78(1):394-404.

Vermeer et al., "The unfolding/denaturation of immunogammaglobulin of isotype 2b and its F(ab) and F(c) fragments," *Biophys. J*. (2000) 79(4): 2150-2154 PMID: 11023918.

Viéet al., Human fusion proteins between interleukin 2 and IgM heavy chain are cytotoxic for cells expressing the interleukin 2 receptor, *Proc Natl Acad Sci U S A* (Dec. 1, 1992) 89(23): 11337-11341.

Visvader et al., "Cancer stem cells in solid tumours: accumulating evidence and unresolved questions," *Nat Rev Cancer*. (Oct. 2008) 8(10):755-68. PMID: 18784658.

Waldmann et al., "Microarray analysis reveals differential expression of benign and malignant pheochromocytoma," *Endocr. Relat. Cancer* (2010) 17(3):743-56.

Yao, JC, et al., "One hundred years after "carcinoid": epidemiology of and prognostic factors for neuroendocrine tumors in 35,825 cases in the United States," *J Clin Oncol*. (2008) 26:3063-72. PMID: 18565894.

Yu, ZL, et al., "Febrile seizures are associated with mutation of seizure-related (SEZ) 6, a brain-specific gene," *J Neurosci Res*. (2007) 85:166-72. PMID: 17086543.

Zheng et al., "Administration of noncytolytic IL-10/Fc in murine models of lipopolysaccharide-induced septic shock and allogeneic islet transplantation," *J Immunol*. (May 15, 1995) 154(10):5590-600. PMID: 7730658.

Zimmerman et al., "A triglycine linker improves tumor uptake and biodistributions of 67-Cu-labeled anti-neuroblastoma MAb chCE7 F(ab')2 fragments," *Nucl Med Biol*. (1999) 26(8):943-50. PMID: 10708309.

International Search Report dated Apr. 16, 2013, issued in PCT counterpart application (PCT/US2013/027476).

IPRP issued in PCT counterpart application (PCT/US2013/027476).

Official Action dated Oct. 10, 2014, issued in Australian patent application (No. 2013203506).

Official Action dated Jan. 6, 2016, issued in Australian patent application (No. 2013203506).

Official Action dated Apr. 6, 2016, issued in Chinese patent application (No. 201380010534.6).

Official action dated Mar. 10, 2017, issued in Chinese patent application (No. 201380010534.6).

Official Action dated Jun. 20, 2016, issued in Colombian patent application (No. 14-210.871).

Official Action dated Mar. 30, 2017, issued in Colombian patent application (No. NC2016/0002654).

Official Action dated Jun. 10, 2016, issued in European patent application (No. 13707529.7).

Official Action dated Dec. 6, 2016, issued in Japanese patent application (No. 2014-558901).

Office Action dated May 15, 2015, issued in New Zealand patent application (No. 631197).

Official Action dated Jan. 10, 2017, issued in New Zealand patent application (No. 631197).

Written Opinion issued in PCT counterpart application (PCT/US2013/027476).

IPRP dated Mar. 1, 2016, in PCT application (PCT/US2014/053014).

International Search Report and Written Opinion dated Dec. 12, 2014, in PCT application (PCT/US2014/053014).

Rybalsky et al., "Monoclonal antibodies and hybridomas," Ukrainian Scientific Research Veterinary Institute, Moscow, 1989, pp. 27-45.

Extended European Search Report dated Jul. 16, 2019, issued in European application (No. 19154773.6).

Official action dated Jun. 27, 2019, issued in Australian patent application (No. 2018223053).

Official action dated Feb. 11, 2019, issued in Indian patent application (No. 2029/KOLNP/2014).

Official action dated May 21, 2019, issued in Japanese application (No. 2018-52506).

Official action dated May 17, 2019, issued in South Korean application (No. 10-2014-7026846).

Official action dated Apr. 9, 2019, issued in Mayalsian patent application (No. PI 2014002467).

Official action dated Nov. 8, 2018, issued in Mexican patent application (No. MX/a/2014/010094).

Official action dated May 24, 2019, issued in Mexican patent application (No. MX/a/2014/010094).

Official action dated Nov. 20, 2018, issued in Peruvian patent application (No. 001301-2014/DIN).

Decision to Grant issued Mar. 27, 2019, in Russian application (No. 2014138420).

* cited by examiner

Homo sapiens seizure related 6 homolog (SEZ6), transcript variant 1, mRNA
>gi|148839279|ref|NM_178860.4|

(SEQ ID NO: 1)

```
GATCCCGGCGCCGTCGCCAGGCGCTGGCCGTGGTGCTGATTCTGTCAGGCGCTGGCGGCGGCAGCGGCGGTGACGGCTGCGG
CCCCGCTCCCTCTACCCGGCCGGACCCGGCTCTGCCCCGCGCCCAAGCCCCACCAAGCCCCCCGCCCTCCCGCCGCGGTCCC
AGCCCAGGGCGCGGCCGCAACCAGCACCATGGCGCCCGGTAGCCCTGCTGCTCCTGCCCTCGCTGCTGGCGCTCCTGGCTCACG
GACTCTCTTTAGAGGCCCCAACCGTGGGAAAGGACAAGCCCCAGGCATCGAGGAGACAGATGGCGAGCTGACAGCAGCCCCC
ACACCTGAGCAGCCAGAACGAGGCGTCCACTTTGTCACAACAGCCCCCACCTTGAAGCTGCTCAACCACCACCCGCTGCTTGA
GGAATTCCTACAAGAGGGGCTGGAAAAGGGAGATGAGGAGCTGAGGCCAGCACTGCCCTTCCAGCCTGACCCACCTGCACCCT
TCACCCCAAGTCCCCTTCCCCGCCTGGCCAACCAGGACAGCCGCCCTGTCTTTACCAGCCCACTCCAGCCATGGCTGCGGTA
CCCACTCAGCCCCAGTCCAAGGAGGGACCCTGGAGTCCGGAGTCAGAGTCCCCTATGCTTCGAATCACAGCTCCCCTACCTCC
AGGGCCCAGCATGGCCAGTGCCCACCCTAGGCCCAGGGGAGATGGCCAGCACTACACCCCCAGCAGAGCCTGGACACCAACCC
AAGCAGGGTCCTGGAGACATGGGAAGGCCGTGGGTTGCAGAGGTTGTGTCCCAGGGCGCAGGGATCGGGATCCAGGGGACCATC
ACCTCCTCCACAGCTTCAGGAGATGATGAGGAGACCACCACTACCACCACCATCATCACCACCACCATCACCACAGTCCAGAC
ACCAGGCCCTTGTAGCTGGAATTTCTCAGGCCCAGAGGGCTCTCTGGACTCCCCTACAGACCTCAGCTCCCCCACTGATGTTG
GCCTGGACTGCTTCTTCTACATCTCTGTCTACCCTGGCTATGGCGTGGAAATCAAGGTCCAGAATATCAGCCTCCGGGAAGGG
GAGACAGTGACTGTGGAAGGCCTGGGGGGCCTGACCCACTGCCCCTGGCCAACCAGTCTTTCCTGCTGCGGGGCCAAGTCAT
CCGCAGCCCCACCCACCAAGCGGCCCTGAGGTTCCAGAGCCTCCGCCACCGGCTGGCCCTGGCACCTTCCATTTCCATTACC
AAGCCTATCTCCTGAGCTGCCACTTTCCCCGTCGTCCAGCTTATGGAGATGTGACTGTCACCAGCCTCCACCCAGGGGGTAGT
GCCCGCTTCCATTGTGCCACTGGCTACCAGCTGAAGGGCGCCAGGCATCTCACCTGTCTCAATGCCACCCAGCCCTTCTGGGA
TTCAAAGGAGCCCGTCTGCATCGCTGCTTGCGGCGGAGTGATCCGCAATGCCACCACCGGCCGCATCGTCTCTCCAGGCTTCC
CGGGCAACTACAGCAACAACCTCACCTGTCACTGGCTGCTTGAGGCTCCTGAGGGCCAGCGGCTACACCTGCACTTTGAGAAG
GTTTCCCTGGCAGAGGATGATGACAGGCTCATCATTCGCAATGGGGACAACGTGGAGGCCCCACCAGTGTATGATTCCTATGA
GGTGGAATACCTGCCCATTGAGGGCCTGCTCAGCTCTGGCAAACACTTCTTTGTTGAGCTCAGTACTGACAGCAGCGGGGCAG
CTGCAGGCATGGCCCTGCGCTATGAGGCCTTCCAGCAGGGCCATTGCTATGAGCCCTTTGTCAAATACGGTAACTTCAGCAGC
AGCACACCCACCTACCCTGTGGGTACCACTGTGGAGTTCAGCTGCGACCCTGGCTACACACCCTGGAGTAGGCTCCATCATCAT
CGAGTGTGTTGACCCCCACGACCCCCAGTGGAATGAGACAGAGCCAGCCTGCCGAGCCGTGTGCAGCGGGGAGATCACAGACT
CGGCTGGCGTGGTACTCTCTCCCAACTGGCCAGAGCCCTACGGTCGTGGGCAGGATTGTATCTGGGGTGTGCATGTGGAAGAG
GACAAGCGCATCATGCTGGACATCCGAGTGCTGCGCATAGGCCCTGGTGATGTGCTTACCTTCTATGATGGGGATGACCTGAC
GGCCCGGGTTCTGGGCCAGTACTCAGGGCCCCGTAGCCACTTCAAGCTCTTTACCTCCATGGCTGATGTCACCATTCAGTTCC
AGTCGGACCCCGGGACCTCAGTGCTGGGCTACCAGCAGGGCTTCGTCATCCACTTCTTTGAGGTGCCCCGCAATGACACATGT
CCGGAGCTGCCTACCAGGGTAGTGGGATCCAGTGTCCTCATGTGCCAGTGGGACCTAACTTGGAGTGAGTGCCCCTCATGCC
CTACCCTGGCTACCAGGTAGTGGGATCCAGTGTCCTCATGTGCCAGTGGGACCTAACTTGGAGTGAGTGCCCCTCATGCC
AGAGGGTGACTTCCTGCCACGATCCTGGAGATGTGGAGCACAGCCGACGCCTCATATCCAGCCCAAGTTTCCCGTGGGGCC
ACCGTGCAATATATCTGTGACCAGGGTTTTGTGCTGATGGGCAGCTCCATCCTCACCTGCCATGATCGCCAGGCTGGCAGCCC
CAAGTGGAGTGACCGGGCCCCTAAATGTCTCCTGGAACAGCTCAAGCCATGCCATGGTCTCAGTGCCCCTGAGAATGGTGCCC
GAAGTCCTGAGAAGCAGCTACACCCAGCAGGGGCCACCATCCACTTCTCGTGTGCCCCTGGCTATGTGCTGAAGGGCCAGGCC
AGCATCAAGTGTGTGCCTGGGCACCCCTCGCATTGGAGTGACCCCCCACCCATCTGTAGGGCTGCCTCTCTGGATGGGTTCTA
CAACAGTCGCAGCCTGGATGTTGCCAGGCACCTGCTGCCTCCAGCAGCCCTGGATGCTGCCCACATTGCAGCTGCCCATCTTCT
TGCCACTGGTGGCCGATGGTGTTGTTGGTAGGAGGTGTATACTTCTACTTCTCCAGGCTCCAGGGAAAAAGCTCCCTGCAGCTG
CCCCGCCCCCGCCCCGCCCCTACAACCGCATTACCATAGAGTCAGCGTTTGACAATCCAACTTACGAGACTGGATCTCTTTC
CTTTGCAGGAGACGAGAGAATATGAAGTCTCCATCTAGGTGGGGGCAGTCTAGGGAAGTCAACTCAGACTTGCACCACAGTCC
AGCAGCAAGGCTCCTTGCTTCCTGCTGTCCCTCCACCTCCTGTATATACCACCTAGGAGGAGATGCCACCAAGCCCTCAAGAA
GTTGTGCCCTTCCCCGCCTGCGATGCCCACCATGGCCTATTTTCTTGGTGTCATTGCCCACTTGGGGCCCTTCATTGGGCCCA
TGTCAGGGGGCATCTACCTGTGGGAAGAACATAGCTGGAGCACAAGCATCAACAGCCAGCATCCTGAGCCTCCTCATGCCCTG
GACCAGCCTGGAACACCTAGCAGAGCAGGAGTACCTTTCTCCACATGACCACCATCCCGCCCTGGCATGGCAACCTGCAGCA
GGATTAACTTGACCATGGTGGAACTGCACCAGGGTACTCCTCACAGCCATCACCAATGGCCAAAACTCCTCTCAACGGTGA
CCTCTGGGTAGTCCTGGCATGCCAACATCAGCCTCTTGGGAGGTCTCTAGTTCTCTAAAGTTCTGGACAGTTCTGCCTCCTGC
CCTGTCCCAGTGGAGGCAGTAATTCTAGGAGATCCTAAGGGGTTCAGGGGGACCCTACCCCCACCTCAGGTTGGGCTTCCCTG
GGCACTCATGCTCCACACCAAAGCAGGACACGCCATTTTCCACTGACCACCCTATACCCTGAGGAAAGGGAGACTTTCCTCCG
ATGTTTATTTAGCTGTTGCAAACATCTTCACCCTAATAGTCCCTCCTCCAATTCCAGCCACTTGTCAGGCTCTCCTCTTGACC
ACTGTGTTATGGGATAAGGGGGTGGGCATATTCTGGAGGAGCAGAGGTCCAAGGACCCAGGAATTTGGCATGGAAC
AGGTGTAGGAGGCCCCAGGGAGACGCCCAGGAGCTGCTGAAAGCCACTTTGTACATGTAATGTATTATATGGGGTCTGGG
CTCCAGCCAGAGAACAATCTTTTATTTCTGTTGTTTCCTTATTAAAATGGTGTTTTTGAAAAAAAAAAAAAAAAAAAAAA
AAAAAAAAAAAAAAAA
```

FIG. 1A

Homo sapiens seizure related 6 homolog (SEZ6), transcript variant 2,
mRNA>gi|148839345|ref|NM_001098635.1|

(SEQ ID NO: 2)

```
GATCCCCGGCGCCGTCGCCAGGCGCTGGCCGTGGTGCTGATTCTGTCAGGCGCTGGCGGCGGCAGCGGCGGTGACGGCTGCGG
CCCCGCTCCCTCTACCCGGCCGGACCCGGCTCTGCCCCCGCGCCCAAGCCCCACCAAGCCCCCCGCCCTCCCGCCGCGGTCCC
AGCCCAGGGCGCGGCCGCAACCAGCACCATGCGCCCGGTAGCCCTGCTGCTCCTGCCCTCGCTGCTGGCGCTCCTGGCTCACG
GACTCTCTTTAGAGGCCCCAACCCTGGGAAAGGACAAGCCCCAGGCATCGAGGAGACAGATGGCGAGCTGACAGCAGCCCCC
ACACCTGAGCAGCCAGAACGAGGCGTCCACTTTGTCACAACAGCCCCCACCTTGAAGCTGCTCAACCACCACCCGCTGCTTGA
GGAATTCCTACAAGAGGGCTGGAAAAGGGAGATGAGGAGCTGAGGCCAGCACTGCCCTTCCAGCCTGACCCACCTGCACCCT
TCACCCCAAGTCCCCTTCCCCGCCTGGCCAACCAGGACAGCCGCCCTGTCTTTACCAGCCCCACTCCAGCCATGGCTGCGGTA
CCCACTCAGCCCCAGTCCAAGGAGGGACCCTGGAGTCCGAGTCAGAGTCCCCTATGCTTCGACAGCTCCCCTACCTCC
AGGGCCCAGCATGGCAGTGCCCACCCTAGGCCCAGGGGAGATAGCCAGCACTACACCCCCCAGCAGAGCCTGGACACCAACCC
AAGAGGGTCCTGGAGACATGGGAAGGCCGTGGGTTGCAGAGGTTGTGTCCCAGGGCGCAGGGATCGGGATCCAGGGGACCATC
ACCTCCTCCACAGCTTCAGGAGATGATGAGGAGACCACCACTACCACCACCATCATCACCACCACCATCACCACAGTCCAGAC
ACCAGGCCCTTGTAGCTGGAATTTCTCAGGCCCAGAGGGCTCTCTGGACTCCCCTACAGACCTCAGCTCCCCCACTGATGTTG
CCCTGGACTGCTTCTTCTACATCTCTGTCTACCCTGGCTATGGCGTGGAAATCAAGGTCCAGAATATCAGCCTCCGGGAAGGG
GAGACAGTGACTGTGGAAGGCCTGGGGGGCCTGACCCACTGCCCCTGGCCAACCAGTCTTTCCTGCTGCGGGGCCAAGTCAT
CCGCAGCCCCACCCACCAAGCGGCCCTGAGGTTCCAGAGCCTCCCGCCACCGGCTGGCCCTGGCACCTTCCCATTTCCATTACC
AAGCCTATCTCTCTGAGCTGCCCACTTTCCCCGTCGTCCAGCTTATGGAGATGTGACTGTCACCGCTCCACCCAGGGGGTAGT
GCCCGCTTCCATTGTGCCACTGGCTACCAGCTGAAGGGCGCCAGGCATCTCACCTGTCTCAATGCCACCCAGCCCTTCTGGGA
TTCAAAGGAGCCCGTCTGCATCGCTGCTTGCGGCGGAGTGATCCGCAATGCCACCACCGGCCGCATCGTCTCTCCAGGCTTCC
CGGGCAACTACAGCAACAACCTCACCTGTCACTGGCTGCTTGAGGCTCCTGAGGGCCAGCGGCTACACCTGCACTTTGAGAAG
GTTTCCCTGGCAGAGGATGATGACAGGCTCATCATTCGCAATGGGGACAACGTGGAGGCCCCACCAGTGTATGATTCCTATGA
GGTGGAATACCTGCCCATTGAGGGCCTGCTGAGCTCTGGCAAACACTTCTTGTTGAGCTCAGTACTGACAGCAGCGGGGCAG
CTGCAGGCATGGCCCTGCGCTATGAGGCCTTCCAGCAGGGCCATTGCTATGAGCCCTTTGTCAAATACGGTAACTTCAGCAGC
AGCACACCCACCTACCCTGTGGGTACCACTGTGGAGTTCAGCTGCGACCCTGGCTACACCCCTGGAGCAGGGCTCCATCATCAT
CGAGTGTGTTGACCCCCACGACCCCCAGTGGAATGAGACAGAGCCAGCCTGCCGAGCCGTGTGCAGCGGGGAGATCACAGACT
CGGCTGGCGTGGTACTCTCTCCCAACTGGCCAGAGCCCTACGGTCGTGGGCACGATTGTATCTGGGGTGTGCATGTGGAAGAG
GACAAGCGCATCATGCTGGACATCCGAGTGCTGCGCATAGGCCCTGGTGATGTGCTTACCTTCTATGATGGGGATGACCTGAC
GGCCCGGGTTCTGGGCCAGTACTCAGGGCCCCGTAGCCACTTCAAGCTCTTTACCTCCATGGCTGATGTCACCATTCAGTTCC
AGTCGGACCCCGGGACCCTCAGTGCTGGGCTACCAGCAGGGCTTCGTCATCCACTTCTTTGAGGTGCCCCGCAATGACACATGT
CCGGAGCTGCCTGAGATCCCCAATGGCTGGAAGAGCCCCATCGCAGCCTGAGCCTAGTGCACGGCACCGTGGTCACTTACCAGTG
CTACCCTGGGCTACCAGGTAGTGGGATCCAGTGTCCTCATGTGCCAGTGGGACCTAACTTGGAGTGAGGACCTGCCCTCATGCC
AGAGGGTGACTTCCTGCCACGATCCTGGAGATGTGGAGCACAGCCGACGCCTCATATCCAGCCCCAAGTTTCCCGTGGGGGCC
ACCGTGCAATATATCTGTGACCAGGGTTTTGTGCTGATGGGCAGCTCCATCCTCACCTGCCATGATCGCCAGGCTGGCAGCCC
CAAGTGGAGTGACCGGGCCCCTAAATGTCTCCTGGAACAGCTCAAGCCATGCCATGGTCTCAGTGCCCCTGAGAATGGTGCCC
GAAGTCCTGAGAAGCAGCTACACCCAGCAGGGGCCACCATCCACTTCTCGTGTGCCCCTGGCTATGTGCTGAAGGGCCAGGCC
AGCATCAAGTGTGTGCCTGGGCACCCCTCGCATTGGAGTGACCCCCCACCCATCTGTAGGGCTGCCTCTCTGGATGGGTTCTA
CAACAGTCGCAGCCTGGATGTTGCCAAGGCACCTGCTGCCTCCAGCACCCTGGATGCTGCCCACATTGCAGCTGCCATCTTCT
TGCCCACTGGTGGCGATGGTGTTGTTGGTAGGAGGTCATTACCATAGAGTTCTACTTCTTCCAGGCTCCAGGGAAAAAGCTCCCTGCAGCTG
CCCCGCCCCCGCCCCTACAACCGCCATTACCATAGAGTAGTCGGCGTTTGACAATCCAACTTACGAGACTGGACAGACGAG
AGAATATGAAGTCTCCATCTAGGTGGGGCAGTCTAGGGAAGTCAACTCAGACTTGCACCACAGTCCAGCAGCAAGGCTCCTT
GCTTCCTGCTGTCCCTCCACCTCCTGTATATACCACCTAGGAGGAGATGCCACCAAGCCCTCAAGAAGTTGTGCCCTTCCCCG
CCTGCGATGCCCACCATGGCCTATTTTCTTGGTGTCATTGCCCACTTGGGGCCCTTCATTGGGCCCATGTCAGGGGCATCTA
CCTGTGGGAAGAACATAGCTGGAGCACAAGCATCAACAGCCAGCATCCTGAGCCTCCTCATGCCCTGGACCAGCCTGGAACAC
ACTAGCAGAGCAGGAGTACCTTTCTCCACATGACCACCATCCCGCCCTGGCATGGCAACCTGCAGCAGGATTAACTTGACCAT
GGTGGGAACTGCACCAGGGTACTCCTCACAGCCCATCACCAGGGCCAAAACTCCTCTCAACGGTGACCTCTGGGTAGTCCT
GGCATGCCAACATCAGCCTCTTGGGAGGTCTCTAGTTCTCTAAAGTTCTGACAGTTCTGCCTCCTGCCCTGTCCCAGTGGAG
GCAGTAATTCTAGGAGATCCTAAGGGGTTCAGGGGGACCCTACCCCCACCTCAGGTTGGGCTTCCCTGGGCACTCATGCTCCA
CACCAAAGCAGGACACGCCATTTTCCACTGACCACCCTATACCCTGAGGAAAGGGACACTTTCCTCCGATGTTTATTTAGCTG
TTGCAAACATCTTCACCCTAATAGTCCCTCCTCCAATTCCAGCCACTTGTCAGGCTCTCCTCTTGACCACTGTGTTATGGGAT
AAGGGGAGGGGGTGGGCATATTCTGGAGAGGAGCAGAGGTCCAAGGACCCAGGAATTTGGCATGGAACAGGTGGTAGGAGAGC
CCCAGGGAGACGCCCAGGAGCTGGCTGAAAGCCACTTTGTACATGTAATGTATTATATGGGTCTGGGCTCCAGCCAGAGAAC
AATCTTTTATTTCTGTTGTTTCCTTATTAAAATGGTGTTTTTGGAAAAAAAAAAAAAAAAAAAAAAAAAAAAAAAAAAAAAA
A
```

FIG. 1B

Homo sapiens seizure protein 6 homolog isoform 1 precursor
>gi|148839280|ref|NP_849191.3|

(SEQ ID NO: 3)

MRPVALLLPSLLALLAHGLSLEAPTVGKGQAPGIEETDGELTAAPTPEQPERGVHFVTTAPTLKLLNHH
PLEEFLQEGLEKGDEELRPALPFQPDPPAPFTPSPLPRLANQDSRPVFTSPTPAMAAVPTQPQSKEGP
WSPESESPMLRITAPLPPGPSMAVPTLGPGEIASTTPPSRAWTPTQEGPGDMGRPWVAEVSQGAGI
GIQGTITSSTASGDEETTTTTTTTTTVQTPGPCSWNFSGPEGSLDSPTDLSSPTDVGLDCFFYISVYP
GYGVEIKVQNISLREGETVTVEGLGGPDPLPLANQSFLLRGQVIRSPTHQAALRFQSLPPAGPGTFHFH
YQAYLLSCHFPRRPAYGDVTVTSLHPGGSARFHCATGYQLKGARHLTCLNATQPFWDSKEPVCIAAGG
VIRNATTGRIVSPGFPGNYSNNLTCHWLLEAPEGQRLHLHFEKVSLAEDDDRLIIRNGDNVEAPPVYDSY
EVEYLPIEGLLSSGKHFFVELSTDSSGAAAGMALRYEAFQQGHCYEPFVKYGNFSSSTPTYPVGTTVEFS
CDPGYTLEQGSIIECVDPHDPQWNETEPACRAVCSGEITDSAGVVLSPNWPEPYGRGQDCIWGVHVE
EDKRIMLDIRVLRIGPGDVLTFYDGDDLTARVLGQYSGPRSHFKLFTSMADVTIQFQSDPGTSVLGYQQ
GFVIHFFEVPRNDTCPELPEIPNGWKSPSQPELVHGTVVTVQCYPGYQVVGSSVLMCQWDLTWSEDL
PSCQRVTSCHDPGDVEHSRRLLSSPKFPVGATVQYICDQGFVLMGSSILTCHDRQAGSPKWSDRAPKCL
LEQLKPCHGLSAPENGARSPEKQLHPAGATIHFSCAPGYVLKQASIKCVPGHPSHWSDPPICRAASL
DGFYNSRSLDVAKAPAASSTLDAAHIAAAIFLPLVAMLLVGGVYFYESRLQGKSSLQLPRPRPYNRITI
ESAFDNPTYETGSLSFAGDERI

FIG. 1C

Homo sapiens seizure protein 6 homolog isoform 2 precursor
>gi|148839346|ref|NP_001092105.1|

(SEQ ID NO: 4)

MRPVALILPSLLALLAHGLSLEAPTVGKGQAPGIEETDGELTAAPTPEQPERGVHFVTTAPT
LKLLNHHPLEEFLQEGLEKGDEELRPALPFQPDPPAPFTPSPLPRLANQDSRPVFTSPTPAM
AAVPTQPQSKEGPWSPESESPMLRITAPLPPGPSMAVPTLGPEIASTTPPSRAWTPTQEG
PGDMGRPWVAEVVSQGAGIGIQGTITSSTASGDOEETTTTTTTTTTVQTPGPCSWNFS
GPEGSLDSPTDLSSPTDVGLDCFFYISVYPGYGVEIKVQNISLREGETVTVEGLGGPDPLPLA
NQSFLLRGQVIRSPTHQAALRFQSLPPPAGPGTFHFHYQAYLLSCHFPRRPAYGDVTVTSLH
PGGSARFHCATGYQLKGARHLTCLNATQPFWDSKEPVCIAACGGVIRNATTGRIVSPGFPG
NYSNNLTCHWLLEAPEGQRLHLHFEKVSLAEDDDRLIIRNGDNVEAPPVYDSYEVEYLPIEG
LLSSGKHFFVELSTDSSGAAAGMALRYEAFQQGHCYEPFVKYGNFSSSTPTYPVGTTVEFSC
DPGYTLEQGSIIIECVDPHDPQWNETEPACRAVCSGEITDSAGVVLSPNWPEPYGRGQDCI
WGVHVEEDKRIMLDIRVLRIGPGDVLTFYDGDDLTARVLGQYSGPRSHFKLFTSMADVTIQ
FQSDPGTSVLGYQQGFVIHFFEVPRNDTCPELPEIPNGWKSPSQPELVHGTVTVYQCYPGY
QVVGSSVLMCQWDLTWSEDLPSCQRVTSCHDPGDVEHSRRLISSPKFPVGATVQYICDQG
FVLMGSSILTCHDROAGSPKWSDRAPKCLLEQLKPCHGLSAPENGARSPEKQLHPAGATIH
FSCAPGYVLKGQASIKCVPGHPSHWSDPPPICRAASLDGFYNSRSLDVAKAPAASSTLDAAH
IAAAIFLPILVAMVLLVGGVYFYFSRLQGKSSLQLPRPRPYNRITIESAFDNPTYETGETREYE
VSI

Alignment of SEZ6 isoforms

```
                          1                                                                        60
hSEZ6v1 (NP_849191)   (1) MRPVALLLLPSLHLLALLAHGLSLRAPTVGKGQAPGILETDGELTAAPTPEQPERGVRFVTTAPTLKLLNHHPLLEEFLQEG
hSEZ6v2 (NP_001092105)(1) MRPVALLLLPSLLALLARGLSLRAPTVGKGQAPGILEHDGELTAAPTPEQPERGVHFVTTAPTLNLLNHHPLLEEFLQEG
                          81                                                                       160
hSEZ6v1 (NP_849191)  (81) LEKGDEELRPALPFQPDPPAPTVPSFLPRLANQDSRPVFTSPTPAMAAVPTQPQSKEGPWSPESESPMLRITAPLPEGPS
hSEZ6v2 (NP_001092105)(81)LEKGDEELRPALPFQPDPPAPTFPSPLPRLANQDSRPVFTSPTPAMAAVPTQPQSKEGPWSPESESPMLRITAPLPEGPS
                          161                                                                      240
hSEZ6v1 (NP_849191)  (161)MAVPTLGPGELASTTPPSRAWTFTQSGPGDMGRPWWAEVVSQGAGIGIGQGTTRSSTASQDDEETTTTTITTTITTVQT
hSEZ6v2 (NP_001092105)(161)MAVPTLGPGELASTTFPSRAWTFTQEGPGDMGRFWWAEVVSQGAGIGIGIQGTTTTSSTASQDDEETTTTTTTITTTVQT
                          241                                                                      320
hSEZ6v1 (NP_849191)  (241)PGPCSWNPSGPEGSSLDSPTDLSSPTDVGLRCFPVISVYPGVGVEIKVQNISLREGETVVEGLGPDPLPLANQSFLLRG
hSEZ6v2 (NP_001092105)(241)PGPCSWNPSGPEGSLDEPTDLSSPTDVGLDCFFTISVYPGVGVEIKVQNISLREGETVVEGLGPDPLPLANQSFLLRG
                          321                                                                      400
hSEZ6v1 (NP_849191)  (321)QVIRSPTHQAALRPQSLPFPAGPGTFHFPYQAYLLSCHFPRRPAYGDVTVTSLHPGGSARFHCATGYQLKGARHLTCLNA
hSEZ6v2 (NP_001092105)(321)QVIRSPTHQAALRPQSLPPPAGPGTFHFPYQAYLLSCHFPRRPAYGDVTVTSLHPGGSARFHCANGYQLKGARHJTCLNA
                          401                                                                      480
hSEZ6v1 (NP_849191)  (401)TQPFWDSKEPVCIAACGGVIRNATTGRIVSPGFPGNYSNMLTCHWLLEAPEGORLHFEKVSLAEDDDRLIIRNGDNVE
hSEZ6v2 (NP_001092105)(401)TQPFWDSKEPVCIAACGGVIRMATTGRIVSPGFPCNYSNMLTCHWLLEAPEGORLHFEKVSLAEDDDRLIIRNGDNVE
                          481                                                                      560
hSEZ6v1 (NP_849191)  (481)AFPVYDYSTEVVLPIEGHLSSGKHFFVELSTIDSSGRAARGSALRYEAFQQGHCTEPFVKYGMFSSSTPTYPVGTTVESCD
hSEZ6v2 (NP_001092105)(481)APPVYDSVYUVNLPIEGLLSSGKHFFVELSTDSSGRAAGMALRYEAFQQGHCYEPFVKYGMFSSSTPTYPVGTTVESCD
                          561                                                                      640
hSEZ6v1 (NP_849191)  (561)PGYTLEQGSIIIECVDPEHDPQWNETHEACRAVCSGEHTDSAGVVLSPNWPEPTGRGQDCIWGVEEDKRIMLDIRVLRI
hSEZ6v2 (NP_001092105)(561)PGYTLEQGSIIIECVDPEHDPQWNETEPACRAVCSGEHTHSAGVVLSPNWPEPGRGQDCIWGVVEDKRIMLDIRVLRI
                          641                                                                      720
hSEZ6v1 (NP_849191)  (641)GPGDVLTFVTDGDRLTARVLGQYSGERLTSMADVTTQFQSDPGTSVLGYQQGFVTHFFEVERNDTCPELPEIPNGW
hSEZ6v2 (NP_001092105)(641)GRGDVLTFYDSRHTARVLGQYSGPRSHFKLFTSMADVTTIQFQSDPGTSVLGYQQGFVTHFFEYPKNDTCPELPEIPNGW
                          721                                                                      800
hSEZ6v1 (NP_849191)  (721)KSPSQPELVHGFVVTYQCYPGIQVVGSSVLMCCWHLFTWSEDLPSCQRVTSCHFPGDVEHSRRLISSPKFPVGATVCYICD
hSEZ6v2 (NP_001092105)(721)KSPSQPELWHGTVVTYQCIPGIQVVGSSVLMCQWDLTWSEBLESCQRVTSCHFPGDVEHSRRLISSPKFPVGATVCYICD
                          801                                                                      880
hSEZ6v1 (NP_849191)  (801)QGFVLMGSSILTCHDRQAGSPKWSDRAPKCLLEQIKPCKGLSAPENGARSPEKQLHPAGAFIHFSCAPGVLKGQASIKC
hSEZ6v2 (NP_001092105)(801)QGFVLMGSSILTCHDRQAGSPKWSDRAPKCLLRQLKPCHGLSAPENKARSFKQLHPAGATIHFSCAPGVVLKGQASIKC
                          881                                                                      960
hSEZ6v1 (NP_849191)  (881)VPGHPSEWSDEPPICRAASLGPYNSRSLDVAKAPAASSTLDAAHIAAAITPLVAMVLLVGGVYFYFSRLQGKSSLQLP
hSEZ6v2 (NP_001092105)(881)VPGHFSHWSDPPICRAASLKGFYNSRSLDVAKAPAASSTLDAAHIAAAIFLPLVAMVLLNGGVYFYFSRLQGKSSLQLP
                          961                                     934
hSEZ6v1 (NP_849191)  (961)RPRPRFYNRITIESAFDNPFYTGSLSFAGDERI             (SEQ ID NO: 3)
hSEZ6v2 (NP_001092105)(961)RPRPRPYNRITIESAFDNPFYTGEETRETEVSI-            (SEQ ID NO: 4)
```

FIG. 1E

Percent Identity Between Full Length Mature SEZ6 Proteins from Various Species

| SEZ6 | rhesus (XP_001110503) | cynomolgus (herein) | mouse (NP_067261) | rat (NP_001099224) |
|---|---|---|---|---|
| Human1 (NP_849191) | 91.7% | 97.5% | 90.5% | 90.4% |
| Human2 (NP_001092105) | | 93.0% | | |
| rhesus (XP_001110503) | | | | |
| mouse (NP_067261) | | | | 96.7% |

FIG. 2A

Homo Sapiens SEZ6, SEZ6L, and SEZ6L2 Sequence Accession Numbers - NCBI

| | | mRNA | protein |
|---|---|---|---|
| SEZ6 | 1 | NM_178860 | NP_849191 |
| | 2 | NM_001098635 | NP_001092105 |
| SEZ6L | 1 | NM_021115 | NP_066938 |
| | 2 | NM_001184773 | NP_001171702 |
| | 3 | NM_001184774 | NP_001171703 |
| | 4 | NM_001184775 | NP_001701704 |
| | 5 | NM_001184776 | NP_001171705 |
| | 6 | NM_001184777 | NP_001171706 |
| SEZ6L2 | 1 | NM_012410 | NP_036542 |
| | 2 | NM_201575 | NP_963869 |
| | 3 | NM_001114099 | NP_001107571 |
| | 4 | NM_001114100 | NP_001107572 |
| | 5 | NM_001243332 | NP_001230261 |
| | 6 | NM_001243333 | NP_001230262 |

FIG. 2B

Percent Identity between Various Human SEZ6, SEZ6L and SEZ6L2 Proteins

| Homo sapiens | Complete protein | |
|---|---|---|
| | SEZ6L1 (NP_065938) | SEZ6L2 (NP_001230261) |
| SEZ6v1 (NP_849191) | 42.5% | 42.9% |
| SEZ6L1 (NP_065938) | | 41.1% |

| Homo sapiens | ECD | |
|---|---|---|
| | SEZ6L1 (NP_065938) | SEZ6L2 (NP_001230261) |
| SEZ6v1 (NP_849191) | 42.4% | 43.2% |
| SEZ6L1 (NP_065938) | | 40.5% |

FIG. 2C

>cDNA Sequence of hSCRx17 Clone ORF (SEQ ID NO: 5)

CTGAGCCTGGAGGCCCAACCGTGGGAAGGACAAGCCCAGGCATGAGGAGACAGATGGCGAGCTGACACTGAGCAGCAGAAC
GAGGCGTCCACTTGTCACACAGCCCACCTTGAAGCTGCTCAACACCGTGCTTCCCCGCTGACAGTCCTTACAAGAGGACAGAGGATGAGG
AGTTGAGGCAGCACTGCCTTCCAGCTGACCACCTGACCCAAGTCCTGGGTACCCAGCAGACCAGCGCCTGTCTTACCAGC
CCACTCCAGCGCCATGGCTGCGATGGCAGTGCCCACCTGGGGTACCCAGGGAGGACCAGCAGGTCGGAGTCAGAGTCGGAGAGCCTGGAATCACAGCTCCCTAC
CTCCAGGGCCAGCATGGCAGTGCCCTAGGCGCCCACCCAGGGAGGAGTAGCCAGCACTACACCAGAGAGCCTGGACACCAACCCAAGAGGGTCCTGGA
GACATGGGAAGGCCGTGGGTTGCAGAGGTTGTCCAGGGCGGGAGGTTGTCCAGGGCGCGGAGACATCGGGATCGGGGGACATCACCTCCTCACAGCTTCAGGAGATGATGAGG
AGACCACCACTACCTCAGTCTCCCCACTGATTGGCCTGACTGTCTTCTTCTACATCTGTGCCCTGGCCGACTCTTCTTCTACATCTGTGCCCTGGACACTGTGCTCCTGGAATTCTCAGCCCTTGTAGCTGAGCTTCTGGACTCT
CCTACAGACCTCAGTCTCCCCACTGATTGGCCTGACTGTCTTCTTCTACATCTGTGCCCTGGACACTGTGCTCCTGGAATTCTCAGCCCTTGTAGCTGAGCTTCTGGACTCT
CGGGAAGGGAGACAGTGACCTGGAAGGCCTCCGAGCCTGCCCGGCAGCCTCTGAGCTGCCAAGTCATCCGCAGCC
CACCCCACCAAGCGGCTCCGAGTTCAGAGCTCCACCAGCCTGCCCTGGCCCTGCCACCGCTGCTCCAGAAGCCTATCTCCTGAGCTGCCACTTTCCCC
GTCGTCAGCTTATGGAGATGTGACTGTCACCAGCCCTTCGTGGGATTCAAAGGAGCCCTTGTCGCATGCTCGTCTGCTTGCGGGGAGTGATCCGACGCCAGCCGCATCGT
CTCTCAGGCTTCCCGGGCAACTACACAGCTCATCATTCGCAATGGTAACTTCAGCACAGTGACAACGTGGACAGCGGAGTGATCCTTGAGGCCCGCCGCTGCGCCCATCGAGGTGAAGGTTCC
CCTGGCAGGATGATGACAGGCTCATCATTCGTTGAGCTCAGCAGTGGGACAGCAGCACCACCTGGAATGAGACAGAGCCAGCGTGCGACGGTGCTCAGAGGGACAGTCAGCAGGCCA
TTGCTATGAGCCTTTGTCAATACGGTAACTTCAGCGACAGCACAGACCCCGCCCTGGAAGTTCAGTCAGCCGTGCGACCTGGCTACACCTG
GAGCAGGGCTCCGGTGGTGGTCCAACTGCTCTCCCAACTGCCCAGAGCCTGTATCTCTGGGGTTCATGTCGAAGAGGACAAGGCATCATGCT
CTGGCTCGGCTGTGCTGCGATAGGCCCTGGTGATGGCTACTTCTAGTGTGATGGGATGACCTGACGGCCGGGTTCTGGGCCAGTACTCAGGCCCGTAG
GGACATCCGAGTGTCGCCAGTAGGCCCTGGTGATGGCTACTTCTAGTGTGATGGGATGACCTGACGGCCGGGTTCTGGGCCAGTACTCAGGCCCGTAG
CCACTTCAAGCTCTTTACCTCCTGATGTCACATTCAGTTCGGAGATCTCGGAGATCCCCATGTGCCAGTGCTGACTTGGAGTGAGGACCTAACTTGGAGTGGGCCACCGTGCCCTCAT
TTGAGGTGCCCCGACAATGACACATGTCCGGAGTAGTGGATTGGGATCTCCCTGAAGATCCCCAAGTTGCCACTTTGGAGTGGGCCACCGTGCCCTCATGCGGACCTAGTGCACGGCACCGTGGTCACTT
ACCAGTGCTACCTGGCTACCCAGATGTGGAGCACAGTGGAGCACAGCCCAAGTTTCCCGTGGGGGCCACCGTCAATATATCTGTGACCAGGTTTGT
CCTGCCACGATCCTGGAGATGTGGAGCACAGTGGAGCACACAGCCCAAGTTTCCCGTGGGGGCCACCGTCAATATATCTGTGACCAGGTTTGT
GCTGATGGGCAGCTCCATCCTCCACCTGCCATGATCGCCGATAGGCTGGCAGCCCTGCCAGCCCCAAGTGGAGTGACCGGGCCTAAATGTCTCGGAACAGTCAAGCATG
CCATGGGTCCAGTGCCCTGAGAATGTGCCCAGGCCAGATCAAGTGTGTGCCTGGGCACCCTGAGCTGGGCATTGAGGTGCCCACCCTGAGGTGCTGCCTCTCTGGATGGGTTCTACAACAGT
AAGGGCCAGGCCAGCCATCAAGGTGCCCTGGCCCTGTGCCTGCTCTGCTCCAGCTGCCACACCCTGAGCTGCACCCCTCACCTGCGCTGCCATCTTCTTGCCACTGTAGGGCTGCTAGTGGGCAATGAGGTGCCCACCGTGCCCTCATCTTCTTGCCACTGTAGGGCTGCTTCTTGCCACTGTGGCGATGGTGGTTGTTGG
CGCAGCCTGATGTTGCCAAGGCACCTGCTGCTCCAGCTCGGCATTGAGGTGCTGCTGCACATGCAGCAGCTCGGCATTGCAGCCCCGCCCCGCCCCGCCCCTACACACCCCTACACAACCGCATTACCACATAGAGTCAGC
TAGGAGGTGTATACTTCTCCAGGGATCTCTTTCCTTTGCAGGAGACGAGAGAATA
GTTTGACAATCCAACTTACGAGACTGGATCTCTTTCCTTTGCAGGAGACGAGAGAATA

FIG. 3A

> Translation of hSCRx17 clone ORF (SEQ ID NO: 6)

LSLEAPTVGKGQAPGIEETDGELTAAPTPEQPERGVHFVTTAPTLKLLNHHPLLEEFLQEGLEKGDE
ELRPALPFQPDPPAPFTPSPLPRLANQDSRPVFTSPTPAMAAVPTQPQSKEGPWSPESESPMLRIT
APLPPGPSMAVPTLGPGEIASTTPPSRAWTPTQEGPGDMGRPWVAEVVSQGAGIGIQGTITSST
ASGDDEETTTTTTTITTTVQTPGPCSWNFSGPEGSLDSPTDLSSPTDVGLDCFFYISVYPGYGVE
IKVQNISLREGETVTVEGLGGPDPLPLANQSFLLRGQVIRSPTHQAALRFQSLPPAGPGTFHFHY
QAYLLSCHFPRRPAYGDVTVTSLHPGGSARFHCATGYQLKGARHLTCLNATQPFWDSKEPVCIAA
CGGVIRNATTGRIVSPGFPGNYSNNLTCHWLLEAPEGQRLHLHFEKVSLAEDDDRLIIRNGDNVE
APPVYDSYEVEYLPIEGLLSSGKHFFVELSTDSSGAAAGMALRYEAFQQGHCYEPFVKYGNFSSST
PTYPVGTTVEFSCDPGYTLEQGSIIIECVDPHDPQWNETEPACRAVCSGEITDSAGWLSPNWPEP
YGRGQDCIWGVHVEEDKRIMLDIRVLRIGPGDVLTFYDGDDLTARVLGQYSGPRSHFKLFTSMAD
VTIQFQSDPGTSVLGYQQGFVIHFFEVPRNDTCPELPEIPNGWKSPSQPELVHGTVTVTYQCYPGY
QVVGSSVLMCQWDLTWSEDLPSCQRVTSCHDPGDVEHSRRLLISSPKFPVGATVQYICDQGFVL
MGSSILTCHDRQAGSPKWSDRAPKCLLEQLKPCHGLSAPENGARSPEKQLHPAGATIHFSCAPGY
VLKGQASIKCVPGHPSHWSDPPPICRAASLDGFYNSRSLDVAKAPAASSTLDAAHIAAAIFLPLVA
MVLLVGGVFYFSRLQGKSSLQLPRPRPYNRITIESAFDNPTYETGSLSFAGDERI

FIG. 3B

Alignment of SEZ6 Variants

```
                      1                                                                               80
hSEZ6 BC146292    (1) MRPVALLLLPSLLALLAHGLLEAPTVGKGQAPGIETGELTAAPTPEQPERGVHFVTTAPLKLLANHHPLLEEFLQEG
hSEZ6 NP_849191   (1) MRPVALLLLPSLLALLAHGLLEAPTVGKGQAPGIETGELTAAPTPEQPERGVHFVTTAPLKLLNHHPLLEEFLQEG
                     81                                                                              160
hSEZ6 BC146292   (81) LEKGDEHLRPALFQPDPPAPTPSPLPRLANQDSRPVFTSPTPAMAAVTPQPQSKEGFWSPEKSEPMLRITAPLPPGPS
hSEZ6 NP_849191  (81) LEKGDEELRPALFQPDFPAPTPSPLPRLANQDSRPVFTSPTPAMAAVTPQPQSKEGPWSPEKSEPMLRITAPLPPGPS
                    161                                                                              240
hSEZ6 BC146292  (161) MAVPTLGPGEIASTTPPSRAWTPTQEGPGMGRPWVAEVVSQGAGIGIQGTITSSPASGDDEKTTTTTITTTITTVQT
hSEZ6 NP_849191 (161) MAVPTLGPGEIASTTPPSRAWTPTQEGPGMGRPWVAEVVSQGAGIGIQGTITSSASGDDEKTTTTITTTITTVQT
                    241                                                                              320
hSEZ6 BC146292  (241) PGPCSWNPSGPEGSLDSPTDLSSPTDVLLDCFFYISVYPGYGVEIKVQNISLREGEVTVEGLQGPDPLPLANQSFLLRG
hSEZ6 NP_849191 (241) PGPCSWNPSGPEGSLDSPTDLSSPTDVLLDCFFYISVYPGYGVEIKVQNISLREGEVTVEGLQGPDPLPLANQSFLLRG
                    321                                                                              400
hSEZ6 BC146292  (321) QVIRSPTHGAALRFQSLPPPAGPGTFHFPYQAYLLSCHFPRRPAYGDVTVTVSLHPGGSARFHCATGYQLKGARHLTCLNA
hSEZ6 NP_849191 (321) QVIRSPTHQAALRFQSLPPPAGPGTFHFPYQAYLLSCHFPRRPAYGDVTVTVSLHPGGSARFHCATGYQLKGARHLTCLNA
                    401                                                                              480
hSEZ6 BC146292  (401) TQPFWDSKEPVCIGECPGVIRNATTGRIVSPGFFGGNYSMNLTCHWLLEAPEGQRLHLHPEKVSLAEDDRLIIRNGDNVE
hSEZ6 NP_849191 (401) TQPFWDSKEPVCIAACGGVIRNATTGRTVSPGFPGMVSMNLTCHWLLEAPEGQRLHLHPEKVSLAEDDRLIIRNGDNVE
                    481                                                                              560
hSEZ6 BC146292  (481) APFVDSYEVEYLPIEGLLSSGKHFPVELSTDSSGAAAGMALRYEAFQQGHCYEPFVKVGNFSSSTPTYPVGTTVEFSCD
hSEZ6 NP_849191 (481) APFVDSYEVEYLPIEGLLSSGKHFPVELSTDSSGAAAGMALRYEAFQQGHCYEPFVKVGNFSSSTPTYPVGTTVEFSCD
                    561                                                                              640
hSEZ6 BC146292  (561) PGYTLEQGSIIEEVDPHDPQWNETEPACRAVCSGEITTDSAGVVLSFNWPRFYGRGQDCIWGVEVEEDKRLMLDIKVLRI
hSEZ6 NP_849191 (561) PGYTLEQGSIIEEVDPHDPQWNETEPACRAVCSGEITTDSAGVVLSPNWFEPYGRGQDCIWGVEVEEDRELMLDIRVLRI
                    641                                                                              720
hSEZ6 BC146292  (641) GPGDVLTFYDGDDIHARVLGQYSGPRSHKLFTSMADVVTIQFQSDPGTSVLGNQQGFVIHFFEVPRNDTCPELPEIPNGW
hSEZ6 NP_849191 (641) GPGDVLTFYDGHDATARVLGQYSGPRSHKLFTSMADVVTIQFQSDPGTSVLGYQQGFVIHFFEVPRNDTCPELPEIPNGW
                    721                                                                              800
hSEZ6 BC146292  (721) KSPSQPELVHGTVVTYQCYPGYQVVGSSVLMCQWMLTWSEDLPSCQRVTSCHDPGDVEHSRKLISSPKFPVGATVQYICD
hSEZ6 NP_849191 (721) KSPSQPELVHGTVVTYQCYPGYQVVGSSVLMCQWMLTWSEDLRSCQRVTSCHDPGDVERSERLISSEKFPVGATVQYICD
                    801                                                                              880
hSEZ6 BC146292  (801) QGFVLMGSSILFCHHRQAGSPKWSDRAPKCLLELKPCHGLSAPENGARSPEKQLHPAGATIHFSCAPGYVLKGQASLKC
hSEZ6 NP_849191 (801) QGFVLMGSSILFCHHRQAGSPKWSDRAPKCLLEQKPCHGLSAPENGARSPEKQLHPAGATIHFSCAPGYVLKGQASLKC
                    881                                                                              960
hSEZ6 BC146292  (881) VPGHPSHWSDPPPICRAASLLDGFYNSRSLDVAKAPAASSTLDAAHIAAAIFLPLVAMVLLVGGVYFYFSRLQCKSSLQLP
hSEZ6 NP_849191 (881) VPGHPSHWSDPPPICRAASLLGFYNSRSLDVAKAPAASSTLDAAHIAAAIFLPLVAMVLLVGGVYFYFSRLQGKSSLQLP
                    961           994
hSEZ6 BC146292  (961) RPRPRPYMRITHRSAFDNPTYETGSLSPAGDERI    (SEQ ID NO: 7)
hSEZ6 NP_849191 (961) RPRPRPYMRITHRSAFDNPTYETGSLSFAGDERI    (SEQ ID NO: 3)
```

FIG. 3C

>hSCRx17-Fc ORF (SEQ ID NO: 8)

ATGGAGACAGACACACTCCTGCTATGGGTACTGCTGCTCTGGGTTCCAGGTTCCACTGGTGACGGCGCCTGGATCCCTGAGCCTGGAGGCCCAACCGTGGGGAAGG
ACAAGCCCCAGGCATGCGAGCTGACAGCAGAATTGCCGAGCTGAGCTGAGAAGGAGCAGCAGAACGAGGCGTCCACTTTGTCACAACAGCCTGAGGCCTGAGCTGCT
CAACCACCACCGCTGTTGCCCTGCTGCCCAACCAGGACAGCAGCCGCCGCCTGTCTTACCAGCCCACTGCCCTTCCAGCCCTTGACCCGCTGCCCCTGCACCTTCACCCC
AAGTCCCCTTCCCGCCTGGCCAACGACAGCAGCCGCCGCCTGTCTTACCAGCCCATGCAGTGCCCCATGCAGTGCCCGCTGCCATGCAGTGCCAAGGAGGACCTGGAGT
CCGGAGTCAGAGTCCCTATGCTTCAAGAGACATACAGCTCCTGCGAGAATCACAGGACCCCTGCAGAGGTCTCAGGAAGGCCGTGGGTTGTGTGCAGAGGTTGTGTCAGCCGTCGCCGCATGGGGATCGGGGATTCAGGGGATCATCAGGCCTCCTC
GAGCTGGACACCAAGAGTGAGGAGGATGATGAGGAAGACCTGCTCAGAGGATCCAGAGGATCAGACACCAGACCAGGCCCTTGTAGCTGGAATTTCTCAGGCCCAGAGG
ACAGTTCAGGAGATCCCCTACAGACCTGCAGTGGCCTGACCTCAGTGCTGAGGCCCTTGGCTATGGCGTGGAAATCAAGGTCCAGAATATCA
GCCTCCGGGAGGACTCCGCTCAGTTGCTTCCTCCGCCCACTGACGTGTGAGGCCTGCGGGCCAACAGGACCTTCCGCAGGATCCTCTCCAGGCTTCCCGGGCAACTACAGCAACAA
CACCAAGCGGGCCCTCGAGGTCCAGAGCTCCACCACAGTGTCCAGAGCCTCCAGCGGGTAGTGCTTGCCGGGACACCGACGCGGCCATCATCGGCCTTGGCAGCTACAGGGCTCATCATTGCAATGGGGAC
GGAGATGTGACTGTCAAAGGAGCCCTCGCGTGCTGCTCTGAGGCTCTACACCTCGGTCGTGGGGATCACAGACATCGGGTGGGCAGGATTGTATCGGGGGTGTGCATGTGGA
CCTCACCGTGCTGAGGCTCTGAGGCTGAGCCAGATCACATGTGAACCTTGGATGGTTCCTGGCAGAGGATGATGACGGGCCGGGTTCTGGGCAGTACTC
AACAGGACAAGCGCATCATGGTCAAGTCTATTCAAGTCCACCACTTCAAGCTTCAGTCGAAAGAGCCATCGAGCCAGCTGCCCTGATCTGCTGGTGATTCACTACTACCACT
AGGCCCCCGTAGCGTGGCCTACCCTGGCTACCAGAGCAGTCAGTGATCTGGGATCCTCAGAGTCCTCATGGTGGAGCCCATGCGCCAGAGAGGTGACTTCTGCAAGTCCTGG
TCTTTGAGGTGCCGCCACTCAGCACCCCACTCTGCCCTCACCAGGCTCTGCCCTTGTGCCCCTCAAATGAGGTGGCGGCTGAGGCATCCTCTGCCTGTGATCTGTGAACAGCAGGGACACGGCGGATGTGGAAGGGTGTGCACCCCTG
GCTACCTGCTACCAGGGAGTGCCGTACCAGGGTGACCAAGACCAGGCACCCTCATGTGCTCCTCATGGTGGAGCCCATGCGCCAGAGAGGTGACTTCTGCAAGTCCTGG
AGATGATGCAGCAGACAGCCGCTGGCCCAAGTTCCCGGTGGGGCCACCGTGAATATCTGTGAACAGTCTCTGAACAGTCTCTGGAACAGTCTCTGAAAGTGTCCCTATGTCTCAGTGCCATCAAGTGTGCTGAAGGGCCAGGGCAGGGCCAGCATCAAGTGCTCCTATGTGCTGAAGGGGCCAGCCAGCCAGCCAGCCAGCCAGCCTGCTCCCAGCACCTGCTCCAGCCTGCTCCCAGCCTGCTCCCAGCCGGATGGTG
TGCATGATCGCAAGCAGTACACCACCATCGTAGGGGCTGCTGCTGCGCAGCCTAAGCAGGGCCGATCCTCAGCCACGCCAGCCACGGCCAAGGCCAGGCCAGGCCAGGCCAGGCCAGGCCAGGCCAGGCCAGGCCAGGCCAGGCCAGGCCAGGCCAGGCCAGG
AGTCCTGAGAAGCAGTCAGTACCCACCATCGTAGGGGCTGGCTGCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAGCCTCCAG
CATTGGAGGTGACCCCCACCATCGTAGGGGCTGCCGCCTGCCCTGGAATGGGTTCTACAAGTGTTGGCCAGCCGATGTTGCCAGCACCTGCTCCAGCACCTGCTCCAGCACCTGCTCCTGATGTGTG
CCCACCTGCGGCCACCAGATCTGCGTGGTGTGGTGGACGTGAGCCACGAAGACCCCGAGGTCCAGTTCAACTGGTACGTGGACGGCGTGGAGGTGCATAATGCCAAGACAAAGCC
ACGGGAGGAGCAGTTCAACAGCACGTTCCGTGTGGTCAGCGTCCTCACCGTCCTGCACCAGGACTGGCTGAATGGCAAGGAGTACAAGTGCAAGGTCTCCAACAAAGGCCT
CCCAGCCCCCATCGAGAAACCATCTCCAAAAACCAAAGGGCAGCCCCGAGAACCACAGGTGTACACCCTGCCCCCATCCCGGGAGGAGATGACCAAGAACCAGGTCAGCCT
GACCTGCCTGGTCAAAGGCTTCTACCCCAGCGACATCGCCGTGGAGTGGGAGAGCAATGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAA
GAGCCTCTCCCTGTCTCCGGGTGA

FIG. 4A

>hSCRx17-Fc protein                                                         (SEQ ID NO: 9)

METDTLLLWLLLWVPGSIGDGAPGSLSLEAPTVGKGQAPGIEETDGELTAAPTPEQPERGVHFVTTAPTLKLLN
HHPLLEEFLQEGLEKGDEELRPALPFQPDPPAPFTPSPLPRLANQDSRPVFTSPTPAMAAVPTQPQSKEGPWSPES
ESPMLRITAPLPPGPSMAVPTLGPGEIASTPPSRAWTPTQEGPGDMGRPWVAEVVSQGAGIGIQGTITSSTASG
DDEETTTTTTTTTTTVQTGPGCSWNFSGPEGSLDSPTDLSSPTDVGLDCFFYISVYPGYGVEIKVQNISLREGETV
TVEGLGGPDPLPLANQSFLLRGQVIRSPTHQAALRFQSLPPPAGPGTFHFHYQAYLLSCHFPRRPAYGDVTVTSLH
PGGSARFHCATGYQLKGARHLTCLNATQPFWDSKEPVCIAACGGVIRNATTGRIVSPGFGNYSNNLTCHWLLEA
PEGQRLHLHFEKVSLAEDDDRLIIRNGDNVEAPPVYDSYEVEYLPIEGLLSSGKHFFVELSTDSSGAAAGMALRYEA
FQQGHCYEPFVKYGNFSSSPTYPVGTTVEFSCDPGYTLEQGSIIIECVDPHDPQWNETEPACRAVCSGEITDSAG
VVLSPNWPEPYGRGQDCIWGVHHVEEDKRIMLDIRVLRIGPGDVLTFYDGDDLTARVLGQVSGPRSHFKLFTSMA
DVTIQFQSDPGTSVLGYQQGFVIHFFEVPRNDTCPELPEIPNGWKSPSQPELVHGTVVTYQCYPGYQVVGSSVLM
CQWDLITWSEDLPSCQRVTSCHDPGDVEHSRRLISSPKFPVGATVQYICDQGFVLMGSSILTCHDRQAGSPKWSD
RAPKCLLEQLKPCHGLSAPENGARSPEKQLHPAGATIHFSCAPGYVLKGQASIKCVPGHPSHWSDPPPICRAASLD
GFYNSRSLDVAKAPAASSTLDAAHLAGHRSVECPPCPAPPVAGPSVFLFPPKPKDTLMISRTPEVTCVVVDVSHED
PEVQFNWYVDGVEVHNAKTKPREEQFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTTPPMLDSDGSFFLYSKLTVDKSRWQQ
GNVFSCSVMHEALHNHYTQKSLSLSPG

FIG. 4B

>cDNA sequence encoding mature murine SEZ6

(SEQ ID NO: 10)

FIG. 5A

>Translation of mSCRx17 clone ORF (SEQ ID NO: 11)

LSSEAPITGEGHATGIRETDGELTAAPTPEQSDRGVHFVTTAPTLKLLNHHPLLEEFLQEGLEREEAPQPALPFQPDSPTHFT
PSPLPRLTNQDNRPVFTSPTPAVAAAPTQPHSREKPWNLESKPPELSITSSLPPGPSMAVPTLLPEDRPSTTPPSQAWTPT
QEGPGDMDRPWVPEVMSKTTGLGVEGTIATSTASGDEETTTIIITFVTVQPPGPCSWNFSGPEGSLDSPTAPSSPSD
VGLDCFYYISVYPGYGVEIKVENISLQEGETIIVEGLGGPDPLPLANQSFLLRGQVIRSPTHQAALRFQSILPAGPGTFHFR
YQAYLLSCHFPRRPAYGDVTVTSLHPGGSAHFHCATGYQLKGARFLTCLNATQPFWDSQEPVCIAACGGVIRNATTGRIVS
PGFPGNYSNNLITCHWLLEAPESQRLHFEEKVSLAEDDRLIIRNGNNVEAPPVVDSYEVEYLPIEGLLSSGRHFFVEFSTD
SSGAAGMALRYEAFQQGHCYEPFVKYGNFSSSAPSYPVGTTVEFSCDPGYTLEQGSIIECVDLHDPQWNETEPACRAV
CSGEITDSAGVVLSPNWPEPYGRGQDCIWGVHFFEVPRNDTCPELPEIPNGWKNPSQPELVHGTVVTYQCYPGYQVVGSSILMC
TSMADVTIQFQSDPGTSALGYQQGFVIHFFEVPRNDTCPELPEIPNGWKNPSQPELVHGTVVTYQCYPGYQVVGSSILMC
QWDLSWSEDIPSCQRVTSCHDPGDVEHSRRLISSPKFPVGATVQYVCDQGFVLTGSAILTCHDRQAGSPKWSDRAPKCLL
EQFKPCHGLSAPENGARSPEKRLHPAGATIHFSCAPGYVLKGQASIKCVPGHPSHWSDPPPICRAASLDGFYNGRSLDVAK
APAASSALDAAHLAAAIFLPLVAMVLLVGGVYLYFSRFQGKSPLQLPRTHPRPYNRITVESAFDNPTYE TGSLSFAGDERI

FIG. 5B

>cDNA sequence of rSCRx17 clone ORF (SEQ ID NO: 12)

FIG. 5C

>Translation of rSCRx17 clone ORF (SEQ ID NO: 13)

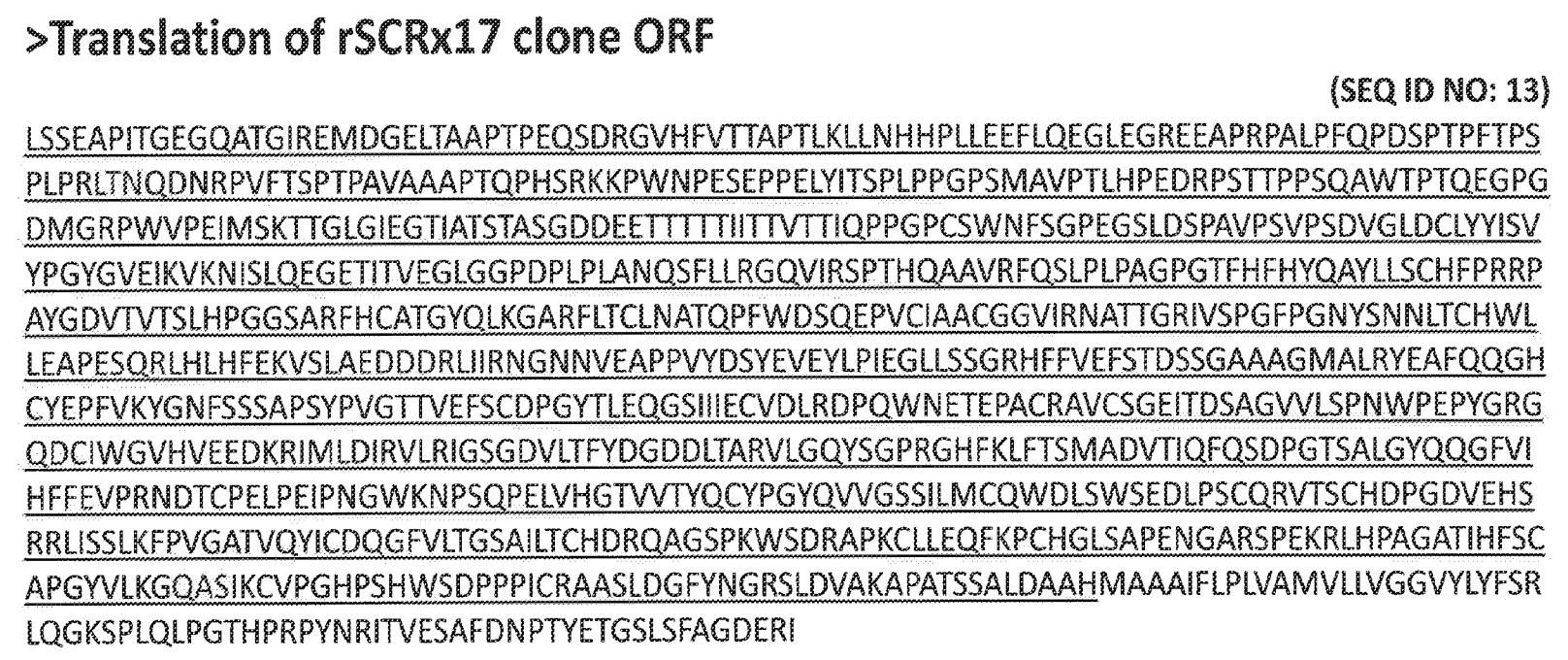

LSSEAPITGEGQATGIREMDGELTAAPTPEQSDRGVHFVTTAPTLKLLNHHPLLEEFLQEGLEGREEAPRPALPFQPDSPTPFTPS
PLPRLTNQDNRPVFTSPTPAVAAAPTQPHSRKKPWNPESEPPELYITSPLPPGPSMAVPTLHPEDRPSTTPPSQAWTPTQEGPG
DMGRPWVPEIMSKTTGLGIEGTIATSTASGDDEETTTTTIITTVTTIQPPGPCSWNFSGPEGSLDSPAVPSVPSDVGLDCLYYISV
YPGYGVEIKVKNISLQEGETITVEGLGGPDPLPLANQSFLLRGQVIRSPTHQAAVRFQSLPLPAGPGTFHFHYQAYLLSCHFPRRP
AYGDVTVTSLHPGGSARFHCATGYQLKGARFLTCLNATQPFWDSQEPVCIAACGGVIRNATTGRIVSPGFPGNYSNNLTCHWL
LEAPESQRLHLHFEKVSLAEDDDRLIIRNGNNVEAPPVYDSYEVEYLPIEGLLSSGRHFFVEFSTDSSGAAAGMALRYEAFQQGH
CYEPFVKYGNFSSSAPSYPVGTTVEFSCDPGYTLEQGSIIIECVDLRDPQWNETEPACRAVCSGEITDSAGVVLSPNWPEPYGRG
QDCIWGVHVEEDKRIMLDIRVLRIGSGDVLTFYDGDDLTARVLGQYSGPRGHFKLFTSMADVTIQFQSDPGTSALGYQQGFVI
HFFEVPRNDTCPELPEIPNGWKNPSQPELVHGTVVTYQCYPGYQVVGSSILMCQWDLSWSEDLPSCQRVTSCHDPGDVEHS
RRLISSLKFPVGATVQYICDQGFVLTGSAILTCHDRQAGSPKWSDRAPKCLLEQFKPCHGLSAPENGARSPEKRLHPAGATIHFSC
APGYVLKGQASIKCVPGHPSHWSDPPPICRAASLDGFYNGRSLDVAKAPATSSALDAAHMAAAIFLPLVAMVLLVGGVYLYFSR
LQGKSPLQLPGTHPRPYNRITVESAFDNPTYETGSLSFAGDERI

FIG. 5D

>cDNA sequence of cSCRx17 clone ORF (SEQ ID NO: 14)

FIG. 5E

>Translation of cSCRx17 clone ORF (SEQ ID NO: 15)

METDTLLLWVLLLWVPGSTGDGAPLSSEAPTMGKGQAPGIEETDGELTAAPTPEQPER
GVHFVTTAPTLKLLNHHPLLEEFLOEGLEKGDEELRPALPFQPDPPTPFTPSPLPRLANQ
DSRPVFTSPTPATAAVPTQPQSKEGPWSLESEPPVLRITAPLPPGPSMAVPTLGPERPS
TPPSRAWTPTQEGPGDMGRPWVPEVVSQGAGIGQTIASSTASGDDEETTTTTTTTTT
TITTVQTPGPCSWNFSGPEGSLDSPTDLSPPDVGLDCFFYISVYPGYGVEIKVQNISLR
EGETVTVEGLGGPAPLPLANQSFLLRGQVIRSPTHQAALRFQSLPPPAGPGTFHFHYQAY
LLSCHFPHRPAYGDVTVTSLHPGGSARFHCATGYQLKGARHLTCLNATQPFWDSKEPVCI
AACGGVIRNATTGRIVSPGFGPGNYSNNITCHWLLEAPEGQRLHLHFEKVSLAEDDDRLII
RNGDNVEAPPVVDSYEVEYLPIEGLLSSGKHFFVELSTDSSGAAAGMALRYEAFQQGHCY
EPFVKYGNFSSSAPTYPVGTTVEFSCDPGYTLEQGSIIIECVDPHDPQWNETEPACRAVC
SGEITDSAGVVLSPNWPEPYGRGQDCIWGVHVEEDKRIMLDVRVLRIGPDVLTFYDGDD
LTARVLGQYSGPHSHFKLFTSMADVTIQFQSDPGTSVLGYOQGFVIHFFEVPRNDTCPEL
PEIPNGWKSPSQPDLVHGTVVTYQCYPGYQVVGSSVLMCQWDLTWSEDLPSCQRVTSCHD
PGDVEHSRRLISSPKFPVGATVQYICDQGFVLTGTSILITCHDRQAGSPKWSDRAPKCLLE
QLKPCHGLSAPENGARSPEKRLHPAGATIHFSCAPGYVLKQOASIKCVPGHPSHWSDPPP
ICKAASLDGFYNSRSLDVAKAPAASSTLDAAHIAAAIFLPLVAMVLLVGGVYFYFSRLQG
KSSLQLPRTRPYNRITVESAFDNPTYETGSLSFAGDERI

FIG. 5F

>cDNA sequence of human SEZ6L ECD (SEQ ID NO: 16)

FIG. 5G

>human SEZ6L ECD protein (SEQ ID NO: 17)

METDTLLLWVLLLWVPGSTGDHGAPLERDALPEGDASPLGPYLLPSGAPERGSPGKEHPEERVVT
APPSSSQSAEVLGEIVLDGTAPSAHHDIPALSPLLPEEARPKHALPPKKKLPSLKQVNSARKQLRPK
ATSAATVQRAGSQPASQGLDLLSSTEKPGPPGDPDPIVASEEASEVPLWLDRKESAVPTTPAPLQI
SPFTSQPYVAHTLPQRPEPGEPGPDMAQEAPQEDTSPMALMDKGENELTGSASEESQETTISTII
TTTVITTEQAPALCSVSFSNPEGYIDSSDYPLLPLNNFLECTYNVTVTGYGVELQVKSVNLSDGELL
SIRGVDGPTLTVLANQTLLVEGQVIRSPTNTISVYFRTFQDDGLGTFQLHYQAFMLSCNFPRRPDS
GDVTVMDLHSGGVAHFHCHLGYELQGAKMLTCINASKPHWSSQEPICSAPCGGAVHNATIGRV
LSPSYPENTNGSQFCIWTIEAPEGQKLHLHFERLLLHDKDRMTVHSGQTNKSALLYDSLQTESVPF
EGLLSEGNTIRIEFTSDQARAASTFNIRFEAFEKGHCYEPYIQNGNFTTSDPTYNIGTIVEFTCDPGH
SLEQGPAIIECINVRDPYWNDTEPLCRAMCGGELSAVAGVVLSPNWPEPYVEGEDCIWKIHVGEE
KRIFLDIQFLNLSNSDILTIYDGDEVMPHILGQYLGNSGPQKLYSSTPDLTIQFHSDPAGLIFGKGQG
FIMNYIEVSRNDSCSDLPEIQNGWKTTSHTELVRGARITYQCDPGYDIVGSDTLTCQWDLSWSSD
PPFCEKIMYCTDPGEVDHSTRLISDPVLLVGTTIQYTCNPGFVLEGSSLLTCYSRETGTPIWTSRLPH
CVSEESLACDNPGLPENGYQILYKRLYLPGESLTFMCYEGFELMGEVTIRCILGQPSHWNGPLPVC
KVNQDSFEHALEVAEAAETSLEGGLAGHHHHHHHHHH

FIG. 5H

>cDNA sequence of human SEZ6L2 ECD (SEQ ID NO: 18)

FIG. 51

>human SEZ6L2 ECD protein (SEQ ID NO: 19)

METDTLLLWVLLLMWVPGSTGDGAPLPLKEEILPEPGSETPTVASEALAELLHGALLRRGPEMGYL
PGSDRDPTLATPPAGQTLAVPSLPRATEPGTGPLTTAVTPNGVRGAGPTAPELLTPPPGTAPPPS
PASPGPPLGPEGGEEETTTTTTTTTTVTTVTTVTSPVLCNNNISEGEGYVESPDLGSPVSRTLGLLDCTY
SIHVYPGYGIEIQVQTLNLSQEEELLVLAGGGSPGLAPRLLANSSMLGEGQVLRSPTNRLLHFQSP
RVPRGGGFRIHYQAYLLSCGFPPRPAHGDVSVTDLHPGGTATFHCDSGYQLQGEETLICLNGTRPS
WNGETPSCMASCGGTIHNATLGRIVSPEPGGAVGPNLTCRWVIEAAEGRRLHLHFERVSLDEDN
DRLMVRSGGSPLSPVIYDSDMDDVPERGLISDAQSLYVELLSETPANPLLSLRFEAFEEDRCFAPF
LAHGNVTTTDPEYRPGALATFSCLPGYALEPPGPPNAIECVDPTEPHWNDTEPACKAMCGGELSE
PAGVVLSPDWPQSYSPGQDCVWGVHVQEEKRILLQVEILNVREGDMLTLFDGDGPSARVLAQL
RGPQPRRRLLSSGPDLTLQFQAPPGPPNPGLGQGFVLHFKEVPRNDTCPELPPPEWGWRTASH
GDLIRGTVLTYQCEPGYELLGSDILTCQWDLSWSAAPPACQKIMTCADPGEIANGHRTASDAGFP
VGSHVQYRCLPGYSLEGAAMLTCYSRDTGTPKWSDRVPKCALKYEPCLNPGVPENGYQTLYKHH
YQAGESLRFFCYEGFELIGEVTITCVPGHPSQWTSQPPLCKVAYEELLDNRKLEVTQTTDPSRQLEG
GLAGHHHHHHHHHH

FIG. 5J

Relative Expression Values for mRNA Transcripts Associated With
Neuroendocrine Tumors in NTX Lines using Whole Transcriptome Sequencing

| | DDL1 | DDL3 | DDL4 | NOTCH1 | NOTCH2 | NOTCH3 | NOTCH4 | ASCL1 | NCAM1 | CHGA | HES1 | HES6 | HEY1 |
|---|---|---|---|---|---|---|---|---|---|---|---|---|---|
| LU37p3 - LCNEC | 86.2 | 93.7 | 4.5 | 0.1 | 14.4 | 7.8 | 0.7 | 2690.8 | 72.0 | 94.0 | 2.7 | 55.1 | 5.6 |
| LU64p2 - SCLC | 10.9 | 34.3 | 10.8 | 8.2 | 0.7 | 0.7 | 5.7 | 418.4 | 57.8 | 729.5 | 6.3 | 2605.8 | 2.0 |
| LU73p1 - SCLC | 176.1 | 227.6 | 16.6 | 4.2 | 0.2 | 33.0 | 79.7 | 3429.1 | 77.5 | 515.0 | 34.5 | 3270.6 | 33.9 |
| LU86p3 - SCLC | 4.7 | 11.9 | 12.2 | 18.7 | 176.8 | 14.5 | 0.5 | 0.4 | 294.9 | 17.7 | 13.9 | 285.2 | 9.9 |
| LU95p2 - SCLC | 2.4 | 16.0 | 1.6 | 2.1 | 0.4 | 8.5 | 12.2 | 273.2 | 171.5 | 18.2 | 2.8 | 72.6 | 9.3 |
| LU137p0 - LU_Ad | 1.8 | 0.0 | 4.3 | 10.6 | 247.7 | 27.5 | 0.4 | 0.0 | 0.0 | 0.0 | 54.6 | 1.5 | 1.7 |
| LU146p0 - LU_Ad | 0.0 | 0.0 | 0.3 | 5.6 | 56.8 | 37.9 | 3.9 | 0.0 | 0.8 | 0.0 | 42.8 | 0.8 | 0.3 |
| LU153p0 - LU_Ad | 0.8 | 0.0 | 5.7 | 8.1 | 195.1 | 8.0 | 6.5 | 0.2 | 4.4 | 0.0 | 4.8 | 0.2 | 1.4 |
| LU49p4 - LU_SCC | 2.6 | 0.7 | 0.0 | 7.6 | 104.2 | 0.0 | 1.3 | 0.0 | 0.0 | 0.3 | 62.1 | 4.3 | 0.0 |
| LU70p4 - LU_SCC | 4.7 | 0.0 | 0.8 | 12.6 | 123.2 | 1.8 | 0.1 | 0.0 | 0.0 | 0.3 | 42.3 | 2.1 | 0.0 |
| LU76p5 - LU_SCC | 0.8 | 0.0 | 4.8 | 20.0 | 32.5 | 0.1 | 0.0 | 3.4 | 0.3 | 0.3 | 23.0 | 0.8 | 0.0 |
| OV26p3 - OV | 34.2 | 65.4 | 15.7 | 0.0 | 101.0 | 17.4 | 0.6 | 2253.7 | 128.8 | 23.1 | 4.3 | 35.1 | 7.1 |
| OV100p0 - OV | 0.0 | 0.5 | 0.4 | 3.6 | 154.2 | 16.3 | 0.5 | 0.0 | 2.0 | 0.0 | 84.1 | 0.0 | 17.3 |
| OV45p3 - OV | 1.7 | 1.9 | 0.1 | 14.9 | 53.2 | 84.5 | 2.7 | 0.0 | 60.4 | 0.1 | 14.6 | 2.4 | 64.4 |
| OV55p5 - OV | 0.3 | 0.2 | 0.0 | 31.0 | 139.8 | 71.7 | 1.4 | 0.0 | 11.4 | 0.0 | 19.4 | 1.9 | 6.7 |
| OV72METp0 - OV | 0.0 | 0.1 | 0.2 | 1.6 | 303.1 | 46.8 | 0.2 | 0.3 | 34.5 | 0.1 | 17.1 | 1.9 | 2.0 |
| OV91METp0 - OV | 0.3 | 1.6 | 0.1 | 10.5 | 340.1 | 345.3 | 2.3 | 0.0 | 3.9 | 0.0 | 31.7 | 1.2 | 1.0 |
| Normal Lung 1 | 1.7 | 1.0 | 5.7 | 8.2 | 85.9 | 33.1 | 11.4 | 0.4 | 3.4 | 0.0 | 13.8 | 0.1 | 11.4 |
| Normal Lung 2 | 17.0 | 0.1 | 8.8 | 24.0 | 81.5 | 54.0 | 62.8 | 5.3 | 4.6 | 0.4 | 23.2 | 2.4 | 43.0 |
| Normal Lung 3 | 26.9 | 0.2 | 41.6 | 146.0 | 25.6 | 239.3 | 91.7 | 0.8 | 1.8 | 1.3 | 11.9 | 8.1 | 40.2 |
| Normal Lung 4 | 0.2 | 0.0 | 6.0 | 11.8 | 81.5 | 40.4 | 15.8 | 0.0 | 1.2 | 0.0 | 11.4 | 0.3 | 14.1 |
| Normal Ovary | 0.3 | 0.0 | 5.1 | 7.8 | 250.9 | 44.1 | 5.1 | 0.6 | 125.5 | 0.2 | 8.5 | 0.7 | 0.4 |

FIG. 6A

Microarray Data Showing Clusters of Tumors with Neuroendocrine Features

Average Normalized Intensity Values
for Common Markers of Neuroendocrine Phenotype

| | Gene Symbol | Median (48 samples) | Cluster C | | | | | Cluster D | | | Cluster E | | Cluster G | |
|---|---|---|---|---|---|---|---|---|---|---|---|---|---|---|
| | | | KD66 | LU50(LCNEC) | OV26 | LU102(SCLC) | LU37-qc(LCNEC) | LU86(SCLC) | LU64-qc(SCLC) | LU95(SCLC) | EM6 | LU100(SCLC) | LU49(SCC) | LU85(SCC) |
| Achaete-scute complex homolog 1 | ASCL1 | 9 | 6589 | 8238 | 9382 | 12169 | 9664 | 11 | 3390 | 10298 | 14 | 261 | 8 | 5 |
| Calcitonin | CALCA | 73 | 16183 | 8352 | 10035 | 14633 | 14547 | 70 | 24 | 2477 | 53 | 45 | 52 | 39 |
| CGRP | CALCB | 143 | 2534 | 1147 | 1547 | 2584 | 2757 | 13189 | 433 | 1264 | 309 | 135 | 65 | 81 |
| CD117, Kit receptor | KIT | 343 | 5978 | 4907 | 3561 | 6416 | 6254 | 12760 | 11215 | 15187 | 712 | 948 | 34 | 301 |
| Chromogranin A | CHGA | 53 | 6167 | 8902 | 12848 | 8206 | 7408 | 7950 | 19869 | 35715 | 9726 | 4378 | 1249 | 2364 |
| Chromogranin B | CHGB | 22 | 1615 | 2152 | 1516 | 1456 | 1242 | 2365 | 1362 | 4151 | 4656 | 1833 | 32 | 24 |
| Dopa decarboxylase | DDC | 2441 | 21606 | 24512 | 23595 | 31824 | 25707 | 1498 | 4234 | 9297 | 85 | 334 | 134 | 286 |
| Gamma (Neural) Enolase | ENO2 | 1910 | 2054 | 1881 | 1911 | 1573 | 1262 | 4043 | 4737 | 11120 | 6394 | 1824 | 2472 | 2241 |
| GDNF family receptor alpha 1 | GFRA1 | 9 | 263 | 29 | 37 | 146 | 133 | 90 | 4 | 6 | 77 | 47 | 9 | 4 |
| CD56 | NCAM1 | 82 | 551 | 875 | 801 | 999 | 727 | 2618 | 2519 | 3296 | 361 | 2899 | 425 | 106 |
| PGP9.5 | UCHL1 | 415 | 16415 | 13168 | 12862 | 24212 | 19977 | 13414 | 9749 | 25738 | 7789 | 4249 | 122 | 8251 |
| Proopiomelanocortin | POMC | 94 | 751 | 427 | 590 | 750 | 657 | 66 | 560 | 5204 | 68 | 84 | 213 | 160 |
| Somatostatin | SST | 67 | 27000 | 1316 | 19913 | 5869 | 12189 | 35 | 9 | 62 | 1992 | 3613 | 90 | 28 |
| Somatostatin Receptor 5 | SSTR5 | 613 | 733 | 906 | 875 | 636 | 633 | 907 | 344 | 622 | 916 | 662 | 918 | 401 |
| Synaptophysin | SYP | 19 | 15 | 15 | 9 | 17 | 15 | 27 | 53 | 91 | 49 | 19 | 11 | 19 |
| TTF1 | NKX2-1 | 18 | 3137 | 3508 | 2734 | 5180 | 3315 | 1258 | 3585 | 2229 | 27 | 311 | 85 | 8 |

FIG. 7B

Average Normalized Intensity Values for Selected Genes in the Notch Pathway and ASCL1

| | Median (48 samples) | Cluster C | | | | | Cluster D | | | Cluster G | |
|---|---|---|---|---|---|---|---|---|---|---|---|
| | | KD66 | LU50(LCNEC) | OV26 | LU102(SCLC) | LU37(LCNEC) | LU86(SCLC) | LU64(SCLC) | LU95(SCLC) | LU49(SCC) | LU85(SCC) |
| ASCL1 | 9 | 6589 | 8238 | 9382 | 12169 | 9664 | 11 | 3390 | 10298 | 8 | 5 |
| DLL1 | 51 | 348 | 565 | 406 | 497 | 179 | 2181 | 98 | 514 | 29 | 120 |
| DLL3 | 350 | 4584 | 3985 | 6232 | 5884 | 5233 | 1686 | 3137 | 5814 | 601 | 492 |
| DLL4 | 614 | 601 | 445 | 592 | 301 | 280 | 763 | 198 | 673 | 357 | 469 |
| HES1 | 670 | 128 | 129 | 160 | 92 | 82 | 551 | 137 | 335 | 2665 | 2024 |
| HES6 | 117 | 196 | 361 | 481 | 416 | 279 | 5456 | 2716 | 3535 | 28 | 33 |
| HEY1 | 89 | 86 | 101 | 116 | 103 | 77 | 1660 | 680 | 2502 | 3776 | 231 |
| HEYL | 87 | 157 | 132 | 128 | 148 | 132 | 2645 | 102 | 267 | 333 | 80 |
| JAG1 | 630 | 159 | 114 | 110 | 95 | 111 | 743 | 521 | 311 | 9131 | 678 |
| JAG2 | 125 | 335 | 529 | 398 | 420 | 247 | 324 | 513 | 611 | 159 | 153 |
| NOTCH1 | 666 | 34 | 23 | 41 | 17 | 14 | 1039 | 381 | 202 | 4720 | 438 |
| NOTCH2 | 26 | 6 | 11 | 12 | 16 | 12 | 105 | 11 | 1 | 37 | 5 |
| NOTCH3 | 101 | 13 | 27 | 91 | 81 | 72 | 302 | 37 | 136 | 1474 | 322 |
| NOTCH4 | 14 | 6 | 7 | 13 | 9 | 5 | 14 | 15 | 69 | 14 | 7 |
| RBPJ | 1289 | 1891 | 2255 | 1933 | 2717 | 2278 | 4502 | 2678 | 5167 | 1226 | 1029 |

FIG. 7C

Levels of Selected Genes Linked to Neural Phenotypes

| Gene | Gene Symbol | Median (48 samples) | Cluster C ||||| Cluster D |||| Cluster E || Cluster G ||
|---|---|---|---|---|---|---|---|---|---|---|---|---|---|---|
| | | | KO86 | LU50 (LCNEC) | OV26 | LU102 (SCLC) | LU37 (LNEC) | LU86 (SCLC) | LU84 (SCLC) | LU95 (SCLC) | EM6 | LU100 (SCLC) | LU49 (SCC) | LU85 (SCC) |
| Achaete-scute complex homolog 1 | ASCL1 | 9 | 6589 | 8238 | 9382 | 12169 | 9664 | 11 | 3390 | 10298 | 14 | 261 | 8 | 5 |
| Brain-expressed X-linked protein 1 | BEX1 | 62 | 2393 | 4403 | 5349 | 5987 | 3653 | 10549 | 15134 | 21994 | 14246 | 81 | 764 | 50 |
| Brain-expressed X-linked protein 3 | NGFRAP1 | 8484 | 3367 | 4346 | 5975 | 10692 | 5222 | 21096 | 28966 | 45936 | 23887 | 21665 | 25401 | 17685 |
| Brain-expressed X-linked protein 4 | BEX4 | 36 | 8 | 8 | 36 | 14 | 6 | 2108 | 3743 | 6528 | 2113 | 197 | 511 | 406 |
| CD56 | NCAM1 | 82 | 551 | 875 | 801 | 999 | 727 | 2618 | 2519 | 3296 | 361 | 2899 | 425 | 106 |
| Claudin 11 | CLDN11 | 7 | 670 | 739 | 2374 | 5820 | 3373 | 548 | 126 | 213 | 14 | 108 | 18 | 3 |
| Cytokeratin 10 | KRT10 | 2624 | 3096 | 2503 | 2855 | 5373 | 5057 | 2731 | 1642 | 4621 | 3756 | 1026 | 12186 | 2310 |
| Cytokeratin 17 | KRT17 | 5858 | 5436 | 7664 | 9874 | 11215 | 8933 | 2600 | 3701 | 5971 | 63 | 304 | 5283 | 5662 |
| Cytokeratin 19 | KRT19 | 19604 | 2081 | 2432 | 3214 | 2435 | 2532 | 445 | 317 | 7074 | 877 | 816 | 2060 | 26391 |
| Cytokeratin 7 | KRT7 | 123 | 249 | 348 | 396 | 515 | 312 | 23 | 9 | 333 | 12 | 54 | 18 | 600 |
| Delta-like 1 | DLL1 | 51 | 348 | 565 | 406 | 497 | 179 | 218 | 98 | 514 | 146 | 162 | 29 | 120 |
| Delta-like 3 | DLL3 | 350 | 4584 | 3985 | 6232 | 5884 | 5233 | 1686 | 3137 | 5814 | 758 | 676 | 601 | 492 |
| Hairy and enhancer of split 1 | HES1 | 670 | 128 | 129 | 160 | 92 | 82 | 551 | 137 | 335 | 118 | 528 | 2665 | 2024 |
| Hairy and enhancer of split 6 | HES6 | 117 | 196 | 361 | 481 | 416 | 279 | 5456 | 2716 | 3535 | 1634 | 694 | 28 | 33 |
| Islet 1 | ISL1 | 48 | 18 | 23 | 22 | 33 | 16 | 1807 | 40056 | 37811 | 121 | 672 | 34 | 26 |
| Lim homeobox 1 | LHX2 | 21 | 9 | 12 | 29 | 8 | 1 | 6849 | 6671 | 10091 | 6243 | 1663 | 161 | 29 |
| Neurogenic differentiation 1 | NEUROD1 | 8 | 44 | 11 | 35 | 62 | 91 | 331 | 135 | 799 | 4917 | 1475 | 6 | 2 |
| Neurogenic differentiation 2 | NEUROD2 | 59 | 49 | 40 | 52 | 32 | 25 | 808 | 231 | 416 | 3019 | 450 | 61 | 65 |
| Neuronal cell adhesion molecule | NRCAM | 66 | 721 | 797 | 870 | 1156 | 1409 | 3981 | 4359 | 4579 | 1311 | 1619 | 5191 | 659 |
| NK2 homeobox 2 | NKX2-2 | 7 | 4 | 7 | 7 | 10 | 4 | 9725 | 206 | 1168 | 63 | 201 | 0 | 247 |
| Rhombotin-3 | LMO3 | 145 | 6875 | 13564 | 7101 | 6912 | 6886 | 45 | 2252 | 27415 | 182 | 9992 | 72 | 271 |
| Secretagogin | SCGN | 77 | 1950 | 2620 | 2468 | 1701 | 3052 | 1164 | 9356 | 32767 | 147 | 935 | 42 | 20 |
| Secretagogin II | SCG2 | 23 | 445 | 299 | 423 | 1122 | 1265 | 37 | 693 | 4085 | 1002 | 3050 | 108 | 51 |
| Secretagogin III | SCG3 | 26 | 1552 | 1961 | 1723 | 1870 | 1892 | 2331 | 3164 | 10139 | 5925 | 3721 | 54 | 19 |
| Semaphorin 4C | SEMA4C | 1647 | 941 | 651 | 781 | 1123 | 742 | 9648 | 5452 | 6341 | 2769 | 3426 | 5124 | 957 |
| Semaphorin 6C | SEMA6C | 118 | 323 | 318 | 279 | 241 | 220 | 1313 | 1859 | 619 | 512 | 432 | 1106 | 107 |
| Seizure related 6 homolog | SEZ6 | 60 | 153 | 143 | 135 | 75 | 86 | 1087 | 435 | 2324 | 135 | 690 | 51 | 61 |
| Seizure related 6 homolog like | SEZ6L | 113 | 43 | 25 | 53 | 42 | 26 | 48 | 64 | 116 | 108 | 114 | 18 | 119 |
| Seizure related 6 homolog like2 | SEZ6L2 | 1464 | 1136 | 1667 | 1852 | 1336 | 1089 | 2317 | 3026 | 5631 | 3793 | 4933 | 1491 | 3247 |
| SRY (sex determining region Y)-box 11 | SOX11 | 13 | 426 | 360 | 361 | 597 | 768 | 3754 | 6124 | 981 | 10 | 1880 | 11 | 17 |
| SRY (sex determining region Y)-box 2 | SOX2 | 8 | 171 | 175 | 270 | 396 | 312 | 2816 | 74 | 3267 | 0 | 2937 | 1376 | 348 |
| SRY (sex determining region Y)-box 4 | SOX4 | 5404 | 5693 | 5641 | 4070 | 3872 | 5240 | 12537 | 30389 | 36920 | 19178 | 13442 | 6451 | 1367 |
| Synaptosomal-associated protein, 25kDa | SNAP25 | 10 | 1037 | 1040 | 1027 | 1108 | 1040 | 1112 | 921 | 565 | 618 | 1612 | 37 | 27 |
| Synaptotagmin IV | SYT4 | 26 | 1418 | 1237 | 2115 | 3958 | 3076 | 1150 | 1061 | 11120 | 2775 | 2488 | 11 | 10 |
| TTF-1 | NKX2-1 | 18 | 3137 | 3508 | 2734 | 5180 | 3315 | 1258 | 3585 | 2229 | 27 | 311 | 85 | 8 |
| Zic family member 2 | ZIC2 | 163 | 25 | 18 | 29 | 10 | 5 | 7683 | 5555 | 2940 | 697 | 279 | 93 | 227 |

FIG. 7E

Protein Sequences of Exemplary Murine SEZ6 Modulator Light Chain Variable Regions

| mAb | FW1 | CDRL1 | FW2 | CDRL2 | FW3 | CDRL3 | SEQ ID NO. |
|---|---|---|---|---|---|---|---|
| SC17.1 | QIVLTQSPALMSASPGEKVSITC | SANSTVSF | MYWYQQKPRSSPTPWIY | LTSNLAS | GVPARFSGSGSGTSYSLTISSMEAEDAATYYC | QQWSSNSPITFGAGTKLELK | 20 |
| SC17.2 | DIVMSQSPSSLAVSVGEKVTMSC | KSSQSLLYSSNQKSY | LAWYQQKPGQSPKLLIY | WASTRES | GVPDRFTGSGSGTDFTLTISSVQAEDLAVYYC | KQSYNLRTFGGGTKLEIK | 22 |
| SC17.9 | DIVMSQSPSSLAVSVGEKVTMSC | KSSQSLLYSSNQKNY | LAWYQQKPGQSPKLLIY | WASTRES | GVPDRFTGSGSGTDFTLTISSVKAEDLAVYFC | QQYNYPYTFGGGTKLK | 24 |
| SC17.16 | DIKMTQSPASLSVSVGETVTITC | RASANINSN | LVWFQQKPGQSPQLLVY | AATNLAD | GVPSRFSGSGSGTQYSLKINSLQSEDFGNYYC | QHFWGTPRTFGSSGTKLEIK | 26 |
| SC17.38 | DIVVTQSPASLAVSLGQRATISC | RASESVEYYGTSL | MQWFQQKPGQPPKLLIY | AASNVES | GVPARFSGSGSGTDFSLNIHPVEEDDAMYFC | QQDRKVPWTFGGGTKLEIK | 28 |
| SC17.3 | DIVMSQSPSSLAVSVGERVTMSC | KSSQSLLYSSNQKNY | LAWYQQKPGQSPKLLIY | WASTRES | GVPDRFTGSGSGTDFTLTISSVKAEDLAVYYC | QQYSYPYTFGGGTKLEIK | 30 |
| SC17.4 | DIKMTQSPSSMYAELGERVTITC | KASQDINSY | LTWFQQRPGKSPKTLIY | RANRLID | GVPSRFSGSGSGQDYSLTISSLDYEDMGIYYC | LQYDFPWTFGGGTKLEIK | 32 |
| SC17.8 | DVVMTQTPLSLPVSLGDQASISC | RSSQSLVHSNGDTY | LHWYLQKPGQSPKLLIY | KVSNRFS | GVPDRFSGSGSGTDFTLKISRVEAEDLGLYFC | SQSTLIPYTFGGGTKLDIKR | 34 |
| SC17.10 | DIVMSQSPSSLAVSVGEKVTMSC | KSSQSLLYSSNQKNY | LAWYQQKPGQSPKLLIY | WASTRES | GVPDRFTGSGSGTDFTLTISSVKTEDLALYFC | QQYYWFPYTFGGGTKLEIK | 36 |
| SC17.11 | ENVLTQSPAIMSASPGERVTMTC | RASSSVSSSY | LHWYYQQRSGASPKLWIY | STSNLAS | GVPARFSGSGSGTSYSLTISSVEAEDLGVYYC | QQYSDYPFTFGSGTKLVIK | 38 |
| SC17.14 | DVLMTQTPLSLPVSLGDQASISC | RSSQSIVHSNGNTY | LEWFLQKPGQSPKLLIY | KVSNRFS | GVPDRFSGSGSGTDFTLKISRVEAEDLGVYYC | FQGSHVPYTFGGGTKLEIKR | 40 |
| SC17.15 | QIVLTQSPALMSASPGERVTMTC | SASSSVNY | MYWYQQKPRSSPKPWIY | LTSNLAS | GVPVRFSGSGSGTSYSLTISSMEAEDAATYYC | QQWSNNPPTFGSGTKLEIK | 42 |
| SC17.17 | QIVLTQSPAIMSASPGEKVTMTC | SASSSVSY | MHWYQQKSGTSPKRWIY | DTSKLPS | GVPARFSGSGSGKDYTLSITSLQTEDVATYYC | QQWSSTPPTFGAGTKLEIK | 44 |
| SC17.18 | DIQMTQSSSYLSVSLGGRVTITC | KASDHIMRW | LAWYQQKPGNAPRLLIS | GATSLET | GVPSRFSGSGSGKGKDYTLSITSLQTEDFLNIHPVEEDAATYYC | QQWYSIPLTFGAGTKLEIK | 46 |
| SC17.19 | DIVLTQSPASLAVSLGQRAAISC | KPSGSVDYDGDSY | MNWYQQKPGQPPKLLIY | AASNLES | GIPARFSGSGSGTDFTLNIHPVEEDAATYYC | HQNDDPWTFGGGTKLK | 48 |
| SC17.22 | DVVLTQTPLSVPVSLGDQASISC | RSSQSIVHHNRHTY | LGWYLQKPGQSLKLLIY | GVSNRFS | GVPDRFTGSGSGTDFTLTISSVQAEDLAVYYC | FQGTHVPFTFGSGTKLEIK | 50 |
| SC17.24 | DIVMSQSPSSLAVSVGEKVTMSC | KSSQSLLYSSNQKSY | LAWYQQKPGQSPKLLIY | WASTRES | GVPDRFTGSGSGTDFTLTISSVQAEDLAVYYC | KQSYNLRTFGGGTKLEIK | 52 |
| SC17.27 | DVVMTQTPETLSVTIGQPASISCK | KSSQSLLESDGKTY | INWLLQRPGQSPKRIY | LVSKLDS | GVPDRFTGSGSGTDFTLKISRVEAEDLGVYYC | WQGIQHPRTFGGGTKLEIK | 54 |
| SC17.28 | DILLTQSPAILSVSPGEGVSFSC | RASQSIGTS | IHWYQQRTNGSPRLLIK | YASESIS | GIPSRFSGSGSGTDFTLRINSLESEDIADYYC | QQSNSWPLTFGAGTKLEIK | 56 |
| SC17.29 | DIVMTQSHKFMSTSVGERVSITC | KASQDQDVGTD | VAWYQQKPGQSPKLLIY | WASTRHT | GVPDRFTGSGSGTDFTLTISNVQSEDLADYFC | QQYSSYPYFGGGTKLEIKR | 58 |
| SC17.30 | ENVLTQSPAIMSASPGEKVTMTC | CRASSSVESY | LHWYYQQKSGASPKLWIY | STSNLAS | GVPARFSGSASGTSYSLTISSVEAEDAATYYC | QQYSGYPLTFGAGTKLEIK | 60 |

FIG. 10A

Protein Sequences of Exemplary Murine SEZ6 Modulator Light Chain Variable Regions

| mAb | FW1 | CDRH1 | FW2 | CDRH2 | FW3 | CDRH3 | SEQ ID NO. |
|---|---|---|---|---|---|---|---|
| SC17.32 | DIQMTQSPASLSASVGETVTMTC | RASGNIHNY | LVWYQQKQGKPQLLVY | NAKTLAD | GVPSRFSGSGSGTQYSLKINSLQPEDFGSYY | QHFWSTPPTFGGGTKLEIK | 62 |
| SC17.34 | DIKMTQSPSSMYASLGERVTFC | KASQDINSY | LSWFQQKPGKSKTLIY | RANRLVD | GVPSRFSGSGSGQDYSLTISSLEYEDMGHYYC | LQYDEFPPTFGGGTKLEIK | 64 |
| SC17.35 | ENVLTQSPAIMSASPGEKVTLTC | RASSSMSSSY | LHWYQQKSGASPKLWIY | STSNLAS | GVPARFSGSGSGTSYSLTISSVEAEDAATYYC | QQYSAYPPTFGSGTKLEIK | 66 |
| SC17.36 | QIVLTQSPAIMSASPGEKVTMTC | SASSSVSY | MYWYQQKPRSSPKPWIY | LTSNLAS | GVPARFSGSGSGTSYSLTISSMEAEDAATYYC | CQWSSNPPTFGGGTKLEIKR | 68 |
| SC17.39 | DVLMTQTPLSLPVSLGDQASISC | RSSQSLVHRNGNTY | FHWYLQKPGQSPKLLIY | KVSNRFS | GVPDRFSGSGSGTDFTLKISRVEAEDLGVYFC | SQSTYVPWTFGGGTKLEIK | 70 |
| SC17.40 | DVVMTQTPLSRPVTLGDQASISC | RSSQSLVHSNGNTY | LHWYLQKPGQSPKLLIY | KVSNRFS | GVPDRFSGSGSGTDFTLKISRVEAEDLGVYFC | SQNTHVPFTFGSGTKLEIK | 72 |
| SC17.41 | QIVLTQSPAIMSASPGEKVTMTC | SASSSVSY | MYWYQQKPRSSPKPWIY | LTSNLAS | GVPTRFSGSGSGTSYSLTISSMGAEDAATYYC | CQWMTNPPTFGAGTKLEIK | 74 |
| SC17.42 | ENVLTQSPAIMSASPGEKVTMTC | SASSSVNY | MYWYQQKSSTSPKLWIY | DTSKLTS | GVPGRFSGSGSGNSYSLTISNMEAEDVATYYC | FQGSGYPLTFGSGTKLEIK | 76 |
| SC17.45 | ENVLTQSPAIMSASPGEKVTMTC | SASSSVNY | MYWYQQKSSTSPKLWIY | DTSKLT | GVPGRFSGSGSGNSYSLTISNMEAEDVATYYC | FQGSGYPLTFGSGTKLEIK | 78 |
| SC17.46 | SFVMTQTPKFLLVSAGDRVTFTC | KASCSVNND | VAWYQQKPGQSPKLLIY | YASNRYT | GVPDRFTGSGYGTDFTFTISTVQAEDLAVYFC | QQDYSSPRTFGGGTKLEIK | 80 |
| SC17.47 | QIVLTQSPAIMSASPGEKVSMTC | SASSSVSY | MHWYQQKSGTSPKRWIY | DTSKLAS | GVPARFSGSGSGTSYSLTISSMEAEDAATYYC | CQWSSTPPTFGGGTKLEIKR | 82 |
| SC17.49 | DVVMTQTPLTLSVTIGQPASISC | KSSQSLLESDGKTY | LNWLLQRPGQSPKRLIY | LVSKLDS | GVPDRFTGSGSGTDFTLKISRVEAEDLGVYYC | WQGIQHPRTFGGGTKLEIKR | 84 |
| SC17.50 | DIVLTQSPASLAASLGQRATISC | RASQSVSTSSYSY | MHWYQQKPGQPPKLLIK | YASNLES | GVPARFSGSGSGTDFTLNIHPVEEEDTATYYC | QHSWEIPWTFGGGTKLEIK | 86 |
| SC17.53 | DIVLTQSPASLAASLGQRATISC | RACQSVSTSSYSY | MHWYQQKPGHPPKLLIR | YASNLES | GVPARFSGSGSGTDFTLMHPVEEEDTATYYC | QHSWEIPVTFGGGTKLEIKR | 88 |
| SC17.54 | DVVLTQTPLTLSVTIGQPASISC | KSSQSLLYSDGKTY | LNWLLQRPGQSPKRLIY | LVSKLDS | GVPDRFTGSGSGTDFTLKISRVEAEDLGLYYC | WQGTHFPWTFGGGTKLEIK | 90 |
| SC17.56 | DIVMSQSPSSLAVSVGERVTMSC | KSSQSLLYSSNQKNY | LAWYQQKPGQSPKLLIY | WASTRES | GVPDRFTGSGSGTDFLTISSVKAEDLAVYFC | QQYYNYPYTFGGGTKLEIKR | 92 |
| SC17.57 | QIVLTQSPAIMSASLGERVTMTC | TASSSVSSSY | LHWYQQKPGSSPKLWIY | STSNLAS | GVPSRFSGSGSGTQYSLKINSLQPEDFGTYFC | HQYHRSPPTFGGGTKLEIK | 94 |
| SC17.59 | DIKMTQSPASLSASVGETVTITC | RASGNIHNY | LAWYQQKQGKSPQLLVY | NAKTLAD | GVPSRFSGSGSGTQYSLKINSLQPEDFGTYFC | QHFWSIPPTFGGGTKLEIK | 96 |
| SC17.61 | QIVLTQSPAIMSASPGEKVTISC | SASSSVSY | IYWYQQKPGSSPKPWIY | RTSNLAS | GVPARFSGSGSGTSYSLTISSMEAEDAATYYC | QQYHSYPWTFGGGTKLEIK | 98 |
| SC17.63 | SIVMTQTPKFLLVSAGDRVAITC | KASCSVSMD | VAWYQQKPGQSPTLLISY | ASNRYT | GVPDRFTGSGVGTDFTFTISTVQAEDLAVYFC | QQGYSSPFTFGGGTKLEIKR | 100 |

FIG. 10A (Cont.)

Protein Sequences of Exemplary Murine SEZ6 Modulator Light Chain Variable Regions

| mAb | FW1 | CDRH1 | FW2 | CDRH2 | FW3 | CDRH3 | SEQ ID NO. |
|---|---|---|---|---|---|---|---|
| SC17.71 | DIQMTQSPASLSASVGETVTIAC | RASGNIHNY | LTWYQQRQGKSPQLLVY | NAKTLAV | GVPSRFSGSGSGTQYSLKINSLQPEDFGSYYC | QHFWNIPPTFGSGTKLEIK | 102 |
| SC17.72 | DIQMTQITSSLSASLGDRVTISC | SASQGISNY | LNWYQQKPDGTVKLLIY | YTSSLHS | GVPSKFSGSGSGGTDYSLTISNLEPEDIATYYC | QQYSKLPYTFGGGTKLEIK | 104 |
| SC17.74 | DIQMTQSSSYLVSLGGRVTITC | KASDHINNW | LAWYQQKPGNAPRLLIS | GATSLET | GVPSRFSGSGSGKDYTLSITSLQTEDVATYYC | QQYWSTPPTFGAGTKLEIK | 106 |
| SC17.76 | DIVITQDELSNPVTSGESVSISC | RSSKSLLYKDGKTY | LNWFLQRPGQSPQLLIY | LMSTPAS | GVSDRFSGSGSGTDFTLEISRVKAEDVGVYYC | QQLVEYPRTFGGGTKLEIK | 108 |
| SC17.77 | DIQMTQSPASLSASVGETVTITC | RASGNIHNY | LAWYQQKQGKSPQLLVY | NAKALAD | GVPSRFSGSGSGTQYSLKINSLQPEDFGSYYC | QHFWSIPPTFGGGTKLEIK | 110 |
| SC17.79 | DIQMTQSPASLSASVGETVTITC | RASGNIHNY | LAWYQQKQGKSPQLLVY | NAKTLAD | GVPSRFSGSGSGTQYSLRINSLQPEDFGSYYC | QHFWSTPPTFGGGTKVEIK | 112 |
| SC17.81 | DIVMSQSPSSLTVSVGEKVTLSC | KSSQSLLYSTNQKIY | LAWYQQKPGQSPKLLIY | WASTRES | GVPDRFTGSGSGTDFTLAISNVKAEDLAVYYC | QQYSVPYTFGSGTKLEIK | 114 |
| SC17.82 | QIVLTQSPAIMSASLGEENLTC | SASSSVSY | MHWYQQKSGTSPKLLIY | STSNLAS | GVPARFSGSGSGSGTFYSLTISSVEAEDAADYYC | HQWSSFTFGSGTKLEIK | 116 |
| SC17.84 | QIVLTQSPAIMSASPGEKVTMTC | SASSSISY | MHWYQQKSGTSPKRWIY | DTSKLAS | GVPARFSGSGSGTSYSLTISNMEAEDAATYYC | QQWSSTPPTFGGGTKLEIKR | 118 |
| SC17.85 | DIVMTQAAFSNPVTLGTSASISC | RSSKSLLHSNGITY | LYWYLQKPGQSPQLLIY | QMSNLAS | GVPERFSSSGSGSGSDFTLRISRVEAEDVGVYYC | AQNLEHPTFGGGTKLEIKR | 120 |
| SC17.87 | DVLMTQTPLSLPVSLGDQASISC | RSSQSLVHSNGNTY | LHWYLQKPGQSPKLLIS | KVSNRFS | GVPDRFSGSGSGTDFTLKISRVEAEDLGVYYC | SQSTHVPPMFGGGTKLEIK | 122 |
| SC17.89 | DVLMTQTPLSLPVSLGDQASISC | RSSQSLVHSNGNTY | LEWYLQKPGQSPKLLIY | KVSNRFS | GVPDRFSGSGSGTDFTLKSRVEAEDLGVYYC | FQGSHVPFTFGSGTKLEIK | 124 |
| SC17.90 | DVLMTQTPLSLPVSLGDQASISC | KSSQSLVHSSNQKNY | LAWYQQKPGQSPKLLIY | WASTRKS | GVPDRFTGSGSGTDFTLTISSVKAEDLAVYYC | HQYYSYPLTFAAGTKLEIK | 126 |
| SC17.91 | DVVMTQTPLSLPVSLGDQASISC | RSSQSLVHSNGNTY | LLWYLQKPGQSPKLLIY | KVSNRFS | GVPDRFSGSGSGTDFALKISRVEAEDLGVYYC | SQSTHVPWTFGGGTKLEIK | 128 |
| SC17.93 | DIVMSQSPSSLAVSVGEKVTMTC | KSSQSLLYSSNQKNY | LAWYQQKPGQSPKLLIY | WASTRES | GVPDRFIGSGSGTDFTLTISSVKAEDLAVYC | QQYYRYPLTFGAGTKLEIK | 130 |
| SC17.95 | DIQMTQITSSLSASLGDRVTISC | SASQGINNY | LNWYQQKPDGTVTLLIY | YTSSLHS | GVPSRFSGSGSGTDYSLTISMLEPEDIATYYC | QQYSKLPWTFGGGTKLEIK | 132 |
| SC17.97 | DVVMTQTPLSLPVSLGDQASISC | RSSQSLVHNNGNTY | LHWYLQKPGQSPNLLIY | KVSNRFS | GVPDRFSGSGSGTDFTLKISNVKAEDLGLYYC | SQSTHVPRTFGGGTKLEIK | 134 |
| SC17.99 | DIVMSQSPSSLAVSVGEKVTMNC | ESSQSLLYSSNQKNY | LAWYQQKPGQSPKLLIY | WASTRDS | GVPDRFTGSGSGTDFTLTISSVRAEDPAVYYC | QQYYSYPLTFGAGTKLEIK | 136 |
| SC17.102 | QIVLTQSPAIMSASPGEKVTMTC | SASSSVSY | MHWYQQKSGTSPKRWIY | DTSKLAS | GVPPRFSGSRGSGTSYSLTISSMEAEDAATYYC | QHWSSNPPTFGAGTKLEMK | 138 |

FIG. 10A (Cont.)

Protein Sequences of Exemplary Murine SEZ6 Modulator Light Chain Variable Regions

| mAb | FW1 | CDRH1 | FW2 | CDRH2 | FW3 | CDRH3 | SEQ ID NO. |
|---|---|---|---|---|---|---|---|
| SC17.114 | DVVMTQSPLSLPVSLGDQASISC | RSSQSLVHSNGNTY | LHWYLQKPGQSPKLLIY | KVSSRFS | GVPDRFSGSGSGTDFTLKISRVEAEDLGVYFC | SQSTHVPFTFGSGTKLEIK | 140 |
| SC17.115 | DVVMTQSPLSLPVSLGDQASISC | RSSQSLVHSNGNTY | LHWYLQKPGQSPKLLIY | RVSNRFS | GVPDRFSGSGSGTDFTLTSRVEAEDLGVYFC | SQSTHLPRTFGGGTKLEIK | 142 |
| SC17.120 | DIVLTQSPASLAVSLGQRATISC | RASESVDSYGNSF | MHWYQQKPGQPPKVLIY | RASNLES | GIPARFSGSGSRTDFTLTINPVEDEDVATYYC | QQSNEDPYTFGGGTKLEIK | 144 |
| SC17.121 | QIVLTQSPAIMSASPGEKVTMTC | SASSSVSY | MHWYQQKSGTSPKRWIY | DTSKLAS | GVPARFSGSGSGTSYSLTISSMETEDAATYYC | QQWSNTPPTFGSVTKLEIK | 146 |
| SC17.122 | DIVITQDDLSNPVTSGESVSISC | RSSKSLLYKDGKTY | LNWFLQRPGQSPQLLIY | LMSTRAS | GVSDRFSGSGSGTDFFLEISRVKAEDVGVYYC | QQLVEYPRTFGGGTKLEIK | 148 |
| SC17.140 | QIVLTQSPAIMSASPGEKVTMTC | SASSSVSY | MHWYQQKSGTSPKRWIY | DTSKLAS | GVPARFSGSGSGTSYSLTISSMEAEDAATYYC | QQWSSTPPTFGSGTKLEIK | 150 |
| SC17.151 | DIVLTQFPASLAVSLGQRATIPC | RASESVDSYGNSF | MHWFQQKPGQPPKLLIY | RASNLES | EIPARFSGSGSGTDFTLKISRVEAEDLGVYYC | QQSHEDPYTFGGGTKMEIKR | 152 |
| SC17.156 | DVVMTQSPLSLPVSLGDQASISC | RSSQSNVHSNGNTY | LEWYLQKPGGSPRLLIY | KVSNRFS | GVPDRFSGSGSGTDFTLTSSVRADDPAVYYC | FQGSHVPPTFGGGTKLEIK | 154 |
| SC17.161 | DIVMSQSPSSLAVSVGEKVTMNC | ESSQSLLYNSMCKNY | LAWYQQKPGQSPKRWIY | WASTRDS | GVPDRFTGSGSGTDFTLTSSVRADDPAVYYC | QQYFNVPLTFGAGTKLEIK | 156 |
| SC17.166 | QIVLTQSPAIMSASPGEKVTMTC | SASSSISY | MHWYQQKSGTSPKRWIY | DTSKLAS | GVPARFSGSGSGTSYSLTISNMEAEDAATYYC | QQWSSTPPTFGGGTKLEIKR | 158 |
| SC17.187 | DIKMTQSPSSMYASLGERVTLTC | KASQDINSY | LSWFQQKPGKSPETLIY | RANKLID | GVPSRFSGSGSGQDYSLTISLEYEDMGIYYC | LQYDEFPPTFGGGTKLEIK | 160 |
| SC17.191 | QIVLTQSPAIMSASPGEKVTMTC | SASSSVSY | MHWYQQKSGTSPKRWIY | DTSKLAS | GVPARFTGSGSGTSYSLTISSMEAEDAATYYC | QQWSSSPPTFGAGTKLEIK | 162 |
| SC17.193 | DIVLTQSPASLAVSLGQRATISC | RASESVSTSGVSY | MHWYQQKPGQPPKLLIY | LASNLES | GVPARFSGSGSGTDFTLNIHPVEEEDATTYYC | QHSRELPYTFGGGTKLEIKR | 164 |
| SC17.199 | DIVLTQSPASLAVSLGQRATISC | RASESVDSYGNSF | MHWYQQKPGQPPKPLIY | RASNLES | GIPARFSGSGSRTDFTLTINPVEEEDAATYYC | QQSNEDPYTFGGGTKLEIKR | 166 |
| SC17.200 | DIVLTQSPASLAVSLGQRATIFC | RASQSVDYNGISY | MHWFQQKPGQPPKLLIY | AASNVQS | GIPARFSGSGSGTDFTLNIHPVEEEDAATYYC | QQSIEDPPTFGGGTKLEIK | 168 |

FIG. 10A (Cont.)

Protein Sequences of Exemplary Humanized SEZ6 Modulator Light Chain Variable Regions

| mAb | FW1 | CDRL1 | FW2 | CDRL2 | FW3 | CDRL3 | SEQ ID NO. |
|---|---|---|---|---|---|---|---|
| hSC17.16 | DIQMTQSPSSLSASVGDRVTITCR | RASANINSN | LVWYQQKPGKAPKLLIY | AATNLAD | GVPSRFSGSGSGTDFTLTISSLQPEDFATYYC | QHFWGTPRTFGGGTKLEIK | 170 |
| hSC17.17 | EIVLTQSPATLSLSPGERATLSC | SASSSVSY | MHWYQQKPGQAPRLLIY | DTSKLPS | GIPARFSGSGSGTDFTLTISSLEPEDFAVYYC | QQWSSTPPTFGQGTKLEIK | 172 |
| hSC17.24 | DIVMTQSPDSLAVSLGERATINC | KSSQSLLYSSNQKSY | LAWYQQKPGQPPKLLIY | WASTRES | GVPDRFSGSGSGTDFTLTISSLQAEDVAVYYC | KQGYNLRTFGGGTKVEIK | 174 |
| hSC17.28 | EIVLTQSPDFQSVTPKEKVTITC | RASQSIGTS | IHWYQQKPDQSPKLLIK | YASESIS | GVPSRFSGSGSGTDYTLTISSLQPEDFATYYC | QQNSWPLTFGGGTKLEIK | 176 |
| hSC17.34 | DIQMTQSPSSLSASVGDRVTITC | KASQDINSY | LSWFQQKPGKAPKSLIY | RANRLVD | GVPSRFSGSGSGTDYTLTINSLEAEDAATYYC | LQYDEFPPTFGQGTKLEIK | 178 |
| hSC17.46 | AIQMTQSPSSLSASVGDRVTITC | KASQSVRND | VAWYQQKPGKAPKLLIY | YASNRYT | GVPSRFSGSGSGTDFTLTISSLQPEDFATYFC | QQDYSSPRTFGQGTKLEIK | 180 |
| hSC17.151 | EIVLTQSPATLSLSPGERATLSC | RASESVDSYGMSF | MHWYQQKPGQAPRLLIY | RASNLES | GIPARFSGSGSGTDFTLTISSLEPEDFAVYYC | QQSHEDPVTFGQGTKLEIK | 182 |
| hSC17.155 | DIVMTQSPDSLAVSLGERATINC | KSSQSLLYSSNQKNY | LAWYQQKPGQPPKLLIYW | WASTRKS | GVPDRFSGSGSGTDFTLTISSLQAEDVAVYYC | HQYYSYPLTFGQGTKLEIK | 184 |
| hSC17.156 | DIVMTQTPLSLPVTPGEPASISC | RSSQSIVHSNGNTY | LEWYLQKPGQSPQLLIY | KVSNRFS | GVPDRFSGSGSGTDFTLKISRVEAEDVGVYY | CFQGSHVPPTFGGGTKLEIK | 186 |
| hSC17.161 | DIVMTQSPDSLAVSLGERATINC | ESSQSLLYNSNQKNY | LAWYQQKPGQPPKLLIY | WASTRES | GVPDRFSGSGSGTDFTLTISSLQAEDVAVYYC | QQYFNVPLTFGQGTKLEKR | 188 |
| hSC17.200 | EIVLTQSPATLSLSPGERATLSC | RASQSVDYNGISY | MHWYQQKPGQAPRLLIY | AASNVQS | GIPARFSGSGSGTDFTLTISSLEPEDFAVYYC | QQSHEDPPTFGGGTKVEIK | 190 |
| hSC17.200v1 | EIVLTQSPATLSLSPGERATLSC | RASQSVDYDGISY | MHWYQQKPGQAPRLLIY | AASNVQS | GIPARFSGSGSGTDFTLTISSLEPEDFAVYYC | QQSHEDPPTFGGGTKVEIK | 192 |

FIG. 10A (Cont.)

Protein Sequences of Exemplary Murine SEZ6 Modulator Heavy Chain Variable Regions

| mAb | FW1 | CDRH1 | FW2 | CDRH2 | FW3 | CDRH3 | SEQ ID NO. |
|---|---|---|---|---|---|---|---|
| SC17.1 | SDVKLQLQSGPGLVKPSQSLSVTCTVT | GVSITWGY | YMNWIRQPPGNKLEWMAGM | IHNSGGTN | YNPSLKSRISITRDTSKNQFFLQLNSVTTEDTATYYC | ATTRWDYFDYWGQGTTLTVSS | 21 |
| SC17.2 | QVQLQQSDAELVKPGASVKISCKVS | GYTFTDHT | IHWMKQRPEQGLEWIGY | IYPRDGST | KYNEEFKGKATLTADKSSSTAYMQLNSLTSEDSAVYFC | ARSYSNYFDYWGQGTTLTVSS | 23 |
| SC17.9 | QVQLQQPGAEIVRPGASVKLSCKAS | SGYTFTDYW | MNWVKQRPGQGLEWIGA | IDPSDSYT | SYNPKFKGKATLTVDTSSSAYMQLSSLTSEDSAVYFC | ARRGTPGKPLVYWGQGTLVTVSA | 25 |
| SC17.16 | EVQLQQSGPELMKPGASVKMSCKAS | GYTFTDYN | MYMWVKQNQGKSLEWIGE | INPNNGGT | AYNQKFRGKATLTVDKSSSTAYMELRSLTSEDSAVYYC | ARYDKGFDYWGQGTLLTVSS | 27 |
| SC17.38 | QVTLKESGPGHLQPSQTLSLTCSFS | GFSLNTSGMS | VGWVRQPSGRGLEWLAH | IWWNGDK | YYNPALKSRLTISKDTSNNQVFLKIASVVTADTATYFC | ARRCYYYAMDYWGQGTSVTVSS | 29 |
| SC17.3 | QVQLQQPGAELVKPGASVKLSCKAS | SGYTFPSYW | IHCVKQRPGQGLEWIGY | INPSNGRT | YNYNEKFKNKATLTVDKSSSTAYMQLSSLTSEDSAVYYC | VRGGTGYTMDYWGQGTSVTVSS | 31 |
| SC17.4 | QIQLVQSGPELKKPGETVKISCKAS | GYTFTDYS | MHWVKQAPGKGLEWMLGW | INTETGEP | TYSEDFKGRFAFSLETSASTAYLQINNLKNEDTATYFC | VKNKGWFAYWGQGTLVTVSA | 33 |
| SC17.8 | QVHLQQSGTEVMKPGASVKLSCKAT | GYTFSSYW | IEWIKQRPGHGLEWIGE | ILPGSGNT | NNNEKFKGKATTADTSSNIAYIQLSSLTSEDSAVYYC | AGGPAAYWGQGTLVTVSA | 35 |
| SC17.10 | EVQLQQSGAELVKPGASVKLSCTAS | GFNIKDTY | MHWVKQRPEQGLEWIGR | IEPARVNT | KYDPKFQGKATITADTSSNTAYLQLSSLTSEDTAVYYC | VRGNVYWGQGTLVTVSA | 37 |
| SC17.11 | EVQLQQSGPELVKPGALVVMMSCKAS | GYTFTDYY | MHWVKQSHGQSLEWIGEV | IPYNDET | FYNEKFKDKATLTVDKSSSTAYMELRSLTSEDSAVYYC | APRHRYDGFRYAIDYWGQGTSVTVSS | 39 |
| SC17.14 | EVQLQQSGPVLVKPGASVKMSCKAS | GYTFTDYN | MNWVKQSHGKSLEWIGV | INPYNGNT | RYNQMFKGKATLTVHKSSSTAYMELMSLTSEDSAVYYC | TRWGTTVVGANWGQGTTLTVSS | 41 |
| SC17.15 | DVKLVESGGGLVRLGGSLKLSCAAS | GFTFSSYA | MSWVRQTPEKRLEWVAT | ITSGGGNT | YYPDSVKGRFTISRDNAKMTLYLQMSSLKSEDTANYYC | ARRDYYGSSYVMFAYWGQGTLVTVSA | 43 |
| SC17.17 | EVQLQQSGPEVMKPGASVKMSCKAS | GYTFFDYN | MHWVKQNQGKSLEWIGE | INPNNGGT | GYNQKFKGKATLTVHKSSSTAYMELRSLTSEDSAVYYC | ARTYSYYSYEFAYWGQGTTLTVSA | 45 |
| SC17.18 | QVTLKESGPGILQPSQTLSLTCSFGFS | GFSLSTSTMG | VGWVRQPSGKGKLEWLAD | IWWDDSK | YYNPSLKSRLTISKDTSSNQVFLKITSVDTADTATYYC | ARKGRTARATRGFAYWGHGTLVTVSA | 47 |
| SC17.19 | SDVQLQESGPGLVKPSQSLSVTCTVT | GYSITSSYT | WNWIRQFPGNKLEWMAGY | IHYSGST | NYNPSLRSRISRHTRDTSKNQFFLQLNSVTTEDTATYYC | ARSRYYYDAYGFAYWGCGTLVTVSA | 49 |
| SC17.22 | QIQMMQSGPELKKPGETVKISCKAS | GYSFTNVG | MNWVKQAPGKGLKWMGW | INTYTGEP | TYADDFKGRFAFSLETSASTAYLQINNLKNEDMATYFC | TRGYYGSSYDALDYWGQGTSVTVSS | 51 |
| SC17.24 | QVQLQQSDAELVKPGASVKISCKVS | GYTFTDHT | IHWMKRPEQGLEWIGY | IYPADGST | KYNEEFKGKATLTADKSSSTAYMELRSLTSEDSAVYFC | CARSYSNYFDYWGQGTTLTVSS | 53 |
| SC17.27 | QVQLQQSGAELVRPGASVTLSCKAS | GYTFTDYE | MHWVKQTPVHGLEWIGG | IDPETGGTA | YNQKFKGKATLTADKSSSTAYMELRSLTSEDSAVYFC | TRWFSYWGPGTLVTVSA | 55 |
| SC17.28 | QVHLPQSRPELVKPGASVKISCKAS | GYGFTRSY | IHWVKRPGQGLEWIGE | ISSGSGGT | TYNQKFKGKASITADNPSSTAYMHLSSLTSEDSAIYFC | ARGGVRYFDYWGAGTVTVSS | 57 |
| SC17.29 | EVQLQQSGPELMKPGASVKMSCKAS | GYTFTDYN | MHWVKQNQGKSLEWIGE | IMPHNGGT | GYNQKFKGKATLTVDKSSSTSYMELRSLTSEDSAVYYC | AGGYPAFDYWGQGTTLTVSS | 59 |
| SC17.30 | EVKLVESEGGLVQPGSSMKISCTAS | GFTFSDYY | MAWVRQVPEKGLEWVAN | INVDGSST | YVLDSLKSRFIISRDNAKNILYLQMASSLKSEDTATYYC | AREDYYGSSPSYWYFDVWGAGTTVTVSS | 61 |

FIG. 10B

Protein Sequences of Exemplary Murine SEZ6 Modulator Heavy Chain Variable Regions

| mAb | FW1 | CDRH1 | FW2 | CDRH2 | FW3 | CDRH3 | SEQ ID NO |
|---|---|---|---|---|---|---|---|
| SC17.32 | EVKLEESGGGLVQPGGSMKLSCVAS | GFTFSNYW | MSWVRQSPEKGLEWVAE | IRLKSNNYAT | HYAESVKGRFTISRDDSKSSVFLQMNNLRTEDTGIYYC | TRHYYYAMDYWGQGTSVTVSS | 63 |
| SC17.34 | EVQLQLQQSGPELVKPGSSVKISCKAS | GYTFTDYN | MDWVKQSHGKRLEWIGY | IYPDNGGA | GYNQKFKGKATLTVDKSSSTAYMELRSLTSEDSAVYYC | SRSITTAWFAYWGQGTLVTVSA | 65 |
| SC17.35 | EVQLQQSGPELVKPGALVKMSCKAS | GYTFTDYY | IHWVKQSHGKSLEWIGE | INPYNGET | FYNQKFKGKATLTVDKSSSTAYMELRSLTSEDSAVYYC | ARRGWYLTGYAMDYWGQGTLVTVSS | 67 |
| SC17.36 | EVQLQESGPSLVKPSQSQSLTCSVT | GDSITSDY | WNWIRKFPGKKYEYMGY | INYSGST | YYNPSLKSRISFRDTSKNCYFLQINSVTSEDTATYYC | ARTSYNKFLPFAYWGQGTLVTVSA | 69 |
| SC17.39 | EVQLVESGGGLVKPGGSRKLSCAAS | GFTFSSYG | MHWVRQAPEKGLEWVAY | ISSNDGTI | YYADTVRGFTISRDNAKNTLFLQMTSLRSEDTAMYYC | ARPSNWVFDYWGQGTLVTVSS | 71 |
| SC17.40 | QVQLQQPGAEIVRPGASVKLSCKAS | GYTFTDYW | MNWVKQRPGDGLEWIGT | IDPSDSYT | RYNQKFKGKATLTVDTSFSSAYMQLSSLTSEDSAVYFC | ASGGKGFGYWGQGTPVTVSV | 73 |
| SC17.41 | DVKLVESGGGLVKLGGSLKLSCAAS | GFTFSSYA | MSWVRQTPEKRLEWVAT | ISSGGGNT | YYPDSVKGRFTISRDNAKNTLYLQMSSLKSEDTAMYYC | ARRDYYGTSYVMFAYWGQGTLVTVSA | 75 |
| SC17.42 | DVKLVESGGGLVRPGGSLKLSCAAS | GFTFSRYT | MSWVRQTPEKRLEWAAT | INSSGSNT | YYPDSVKGRFTISRDNAKNTLFLQMESLKSEDTAMYYC | TWGNHWGQGTTLTVSS | 77 |
| SC17.45 | QVQLQQPGSSVLVRPGDSEKLSCKAS | GYTFTSYW | MHWVKQSPGQGLEWIGE | IHPHSGST | NVNEKFKGKATLTVDTSSSTAYVDLSSLTSEDSAVYYC | VGGHYDYWGQGTTLTVSS | 79 |
| SC17.46 | QVQLQQPGAELVKPGASMKLSCKAS | GYTFTSYW | INWVKQRPSQGLEWIGN | IFPDTTTT | NVNEKFKSKATLTVDTSSSTAYMQLSSLTSEDSAVYYC | AREYYDGTYDAMDYWGQGTSVTVS | 81 |
| SC17.47 | EVQLQQSGPELVKPGASVTLSCKAS | GYSFTDYY | MRWVKQRPGKSLEWIGE | INPSTGGTT | TYNQNFKAKATLTVDKSSSTAYMQLKSLTSEDSAVYFC | ARGGYFLYYFDYWGQGTLVTVSS | 83 |
| SC17.49 | QVQLQQSGAELVRPGASVTISCKAS | GYTFTDYE | MHWVKQTPVHGLEWIGG | IDPETGGT | AYNQKFKGKATLTADKSSSTAYMELRSLTSEDSAVYFC | TRWFSYWGPGTLVTVSA | 85 |
| SC17.50 | EVQLVESGGGLVKPGGSLKLSCAAS | GFTFSDYG | MHWVRQAPEKGLEWVAY | ISSGSRTI | YYADTVKGRFTISRDNAKNTLFLQMTSLRSEDTAMYYC | ARVYYGSTYGYFDYWGTGTTVTYSS | 87 |
| SC17.53 | EVQLQQSGPELVKPGASVKISCKAS | GYTFTDYN | MHWVKSHGKRLEWIGY | IHPYNGGS | GYNQKFKRKATLTVDNSSNTTYMELRSLTSEDSAVYYC | ARSYDYDTWFGYWGQGTLVTVRA | 89 |
| SC17.54 | EVKLEESGGGLVQPGGSMKLSCVAS | GFTFSNYW | INWVRQSPEKGLEWVAE | IRMKSNNYAT | HYAESVKGRFTISRDDSKSSVFLQMNNLRPEDTGIYYC | TRGGYWGQGTTLTVSS | 91 |
| SC17.56 | QIQLVQSGPELKKPGETVKISCKAS | GYTFTNYG | MNWVKQAPGKGLKWMAW | INTYTGEP | TYADDFKGRFAFSLETSASTASLQHNLKNEDTATYFC | ARKGDSSPSDYWGQGTTLTVS | 93 |
| SC17.57 | QIQLVQSGPELKKPGETVKISCKAS | GYTFTMYG | IHWVRQSPGKGLRVWMGW | INTETGEPT | VAEDFKGRFAFSLETSASTAFLQIYNLKNEDSATYFC | ARGRYYGHDYAMDYWGQGTSVTVSS | 95 |
| SC17.59 | EVKLEESGGGLVQPGGSMKLSCVAS | GFTFSNYW | MRWVRQSPEKGLEWVAE | IRLKSNNYAT | HYAESVKGRFTISRDDSKSSVLQMNNLRAEDTGIYYC | TRLWDFAMDYWGQGTSVTVSS | 97 |
| SC17.61 | QVTLKESGPGILQPSQTLSLTCSFS | GFSLSTFGMG | VGWIRQPSGKGLEWLAQ | IWWDDYK | YYNPALKSRLTISKDTSKNCYFLKJAAVDTADTATYYC | ARIGYYSGSSRCWNFDVWGTGSTVTVSS | 99 |
| SC17.63 | QVQLQQSGDAELVKPGASVKISCKAA | GYTFTDLT | IHWVKQRFEQGLEWIGY | IYPGDSNT | KYNEKFKGKATLTADKSSSTAYMQLNSLTSEDSVVYFC | ARMITPYYFDYWGQGTTLTVS | 101 |

FIG. 10B (Cont.)

Protein Sequences of Exemplary Murine SEZ6 Modulator Heavy Chain Variable Regions

| mAb | FW1 | CDRH1 | FW2 | CDRH2 | FW3 | CDRH3 | SEQ ID NO. |
|---|---|---|---|---|---|---|---|
| SC17.71 | EVKLEESGGGLVQPGGSMKLSCVAS | GFHFSNYW | MNWVRQSPEKGLEWVAE | IRLKSNNYST | HYAESVKGRFTISRSREDSKSSVVLQMNNLRAEDTGIYYC | TRHYYYAMDYWGQGTSVTVSS | 103 |
| SC17.72 | EVQLVESGGGLVKPGGSLKLSCAAS | GFTFSSYG | MSWVRQTPEKRLEWVAA | INSNGGST | YYPDTVKGRLTISRDNGKNTLYLQMSSLRSEDTALYYC | VRDDGYYVFFAYWGQGTLVTVSA | 105 |
| SC17.74 | QVQLKQSGPGLVAPSQSLSITCTVS | GFSLTSYG | VDWVRQSPGKGLEWLGV | IWGGGST | MYNSALKSRLSITKDNSKSQVFLKMNSLQTDDTAMYYC | ASGDYDGSLWFAYWGQGTLVTVSA | 107 |
| SC17.76 | EVQLVESGGDLVKPGGSLKLSCVAS | GFTFSSYG | MSWVRQTPDKRLEWVAT | ISSGGTFT | YYPDSVKGRFTVSRDMAKNTLYLQMSSLKSEDTAMYYC | SRHGWGWGQGTLVTVSA | 109 |
| SC17.77 | EVKLEESGGGLVQPGGSMKLSCVAS | GFTFSNYW | MNWVRQSPEKGLEWVAE | IRLKSNNYAT | HYAESVKGRFTISRSREDSKSSVVLQMNNLRVEDTAIYYC | TRHYDYAMDYWGQGTSVTVSS | 111 |
| SC17.79 | EVKLEESGGGLVQPGGSMKLSCVAS | GFTFSDYW | MNWVRQSPEKGLEVAE | IRLISNNYAT | HYAESVKGRFTISRSREDSKSSVVLQMNNLRAEDTGIYYC | TRHYYALDYWGQGTSVTVSS | 113 |
| SC17.81 | EVQLQQSGAELVKPGASVKLSCTAS | GFNINDTY | YHWLKQRPEQGLEWIGR | IDPANVNT | KYDPKFQGKATLTADTSSNTAYLQLSSLTSEDTAVYYC | GRSNAYWGQGTLVTSS | 115 |
| SC17.82 | EVQLQQSGPELVKPGASVKMSCKAS | GYTFTDSY | MNWVKQSHGKGLEWIGR | VNPNNGGA | SYNHKFKGKATLTVDKSLSTAYMRLNSLTSEDSAVYYC | SRSGDLYYAMDYWGQGTSVTVSS | 117 |
| SC17.84 | EVQLQQSGPELMKPGASVKMSCKAS | GYIFTDYN | NMHWVKQMQGKSLEWIGE | VNPNIGGI | GYNQKFKGKATLTVDKSSSTAYMDLRSLTSEDSAVYYC | ARDGNYCFDYWGQGTLTVSS | 119 |
| SC17.85 | EVQLVESGGDLVKPGGSLKLSCAAS | GFTFSNYG | MSWVRQTPDKRLEWVAT | ISTGGTYT | YYPDSVKGRFTISRDNAKNTLYLQMSSLKSEDTAMYYC | VGQSYDYVSFAYWGQGTQVTVSA | 121 |
| SC17.87 | EVQLQQPSGAELLKPGASVKLSCTAS | GLNIKDYY | IHWVYQRPEQGLEWGR | IDPESDNT | LYDPKFQGKASHTADTSSNTAYLQLSSLTSEDTAVYYC | TTNTPFAYWSQGTLVTVST | 123 |
| SC17.89 | QVQLQQSGAELVRPGTSVKVSCKTS | GYAFFNYL | IEWVKQRPGQGLEWMGY | IMPGSGGT | NYMEKFKVKATLTADKSSSTAYMQLTSLTSDDSAVYFC | TRRDGYFPWFAYWGQGTLVTVSA | 125 |
| SC17.90 | QVQLQQPGSVLVRPGASVKLSCKAS | GYTFTSYW | MHWVKQRPGQGLEWIGE | IHPNNGST | NYNEKFKGKATLTVDTSSSTAYVDLSSLTSEDSAVYYC | ARWTLFYWGQGTLVTVSA | 127 |
| SC17.91 | EVQLVESGGGLVKPGGSRKLSCAAS | GFTFSDYG | MHHWVRQAPEKGLEWVAY | ISRGSSTI | HYADTVKGRFTISRDNAKNTLFLQMTSLRSEDTAMYYC | ARPINWYFDVWGAGTTVTVSS | 129 |
| SC17.93 | QVQLQQPGAELVKPGASVMLSCKAS | GYTFTSYW | VHWVKQRPGQGLEWIGV | INPRNGRN | NYMEKFKTKATLTVDKSSSTAYMQLSSPFTSEDSAVYYC | AREDYDGSDYAMDYWGQGTSVTVSS | 131 |
| SC17.95 | EVELQQSGPELVKPGASVKISCKTS | GMTYTEYT | MQWVKLSHGKSLEWIGG | INPNNIGHT | SYNQKFKGKATLTVDKSSSTAYMELRSLKSEDSAVYYC | ARAGLGNYVWAMDYWGQGASVTVSS | 133 |
| SC17.97 | QVQLPQSGAELAKPGASVKISCKAS | GFTFSYW | MHWVKQRPGQGLEWGY | INPSTDYT | EYNQKFKDKATLTADKSSSTAYMQLGSLTSEDSAVYYC | ARSSVGSSPFDYWGQGSTLTVSS | 135 |
| SC17.99 | EVKLEESGGGLVQPGGSMKLSCAAS | GFTFSDAW | MDWVRQSPEKGLEWVAE | IRSKAMMHAT | YYAESVKGRFTISRDSKSSAVLQMNSLRAEDTGHYYC | VSTGTSYWGQGTLVTVSA | 137 |
| SC17.102 | EVQLQQSGPELMKPGASVKMSCKAS | GDTFFDYN | IHWVKQNQGSKLEWIGE | VNPNIGGI | GYNQKFKGKATLTVDKSSSTAYMELRSLTSEDSAVYYC | AMGRWYFDVWGAGTTVTVSS | 139 |

FIG. 10B (Cont.)

Protein Sequences of Exemplary Murine SEZ6 Modulator Heavy Chain Variable Regions

| mAb | FW1 | CDRH1 | FW2 | CDRH2 | FW3 | CDRH3 | SEQ ID NO. |
|---|---|---|---|---|---|---|---|
| SC17.114 | EVQLQQSGPEMVKPGASVKISCKA | GYTFTDYY | MHWVKQSHGKSLEWIGR | VNTMNGGT | SYDQKFEGKATLTVDKSSSTAYMELNSLTSEDSAVYYC | VIPAWFAYWGQGTLVTVSA | 141 |
| SC17.115 | QVQLQQSGSGVLVRPGASVLSCKAS | GYTFTSY | MHWVKQRPGQGLEWIGE | IHPNSGNT | NYNEKFKGKATLTVDTSSSTAYVDLSLLTSEDSAVYYC | AGGNYDYWGQGTLVTVSS | 143 |
| SC17.120 | EVQLEQSGTVLARPGASVKMSCKAS | GYTFTSYW | MHWVKQRPGQGLEWIGA | FYPGNSGT | YYNQKFKDKAKLTAVTSASTAYMELSSLTNEDSAVYYC | SRSGSGRFAYWGQGTLVTVSS | 145 |
| SC17.121 | EVQLQQSGPELMKPGASVKMSCKAS | GYTFTDHN | IHWVKQHQGKSLEWIGE | INPNTGGT | GYNQKFQGKATMTVDKSSSTAYMELRSLTSEDSAVYYC | VRGLYFFDYWGQGTLVTVSS | 147 |
| SC17.122 | EVHLVESGGDLVKPGGSLKLSCAAS | GFTFSSYG | MSWVRQTPDKRLEWVAT | ISSGGTYY | YYPDSVKGRFTISRDNAKNTLYLQMSSLKSEDTAMYYC | SRHGWGWGQGTLVTVSS | 149 |
| SC17.140 | EVQLQQSGPELMKPGASVKMSCKA | GYTFTDYN | MHWVKQNCGKSLEWIGE | INPNTGGT | GYNQKFKGKATLTVDKFSSTAFIELRSLTSEDSAIYYC | TRGGYDHYWYFDVWGAGTTVTVSS | 151 |
| SC17.151 | EVQLQQSGPELMKPGASVKMSCKA | GYTFTSYW | MHWVKQRPGQGLEWIGA | IYPGKNDT | TYMQKFKGKAKLTAVTSASTLYMELSSLTNEDSAVYYC | TRSGKGYFAYWGQGTLVTVSS | 153 |
| SC17.156 | QVTLKESGPGILQPSQTLSLTCSFS | GFSLSTSGMGV | VSWIRKTSGKGLEWLAH | IFWDDDK | WYMPSLKSRLTISKATSSNQVFLILTSVDTADTATYYC | ATFYGLYFAYWGQGTLVTVSA | 155 |
| SC17.161 | EVKLEESGGGLVQPGGSMKLSCAAS | GFTFSDAW | MDWVRQSPEKGLEWVAE | IRSKPNNHAT | YYAESVKGRFTISRDDSKSSAYLQMNSLRAEDTGIYYC | VSTGTSYWGQGTLVTVSA | 157 |
| SC17.166 | EVQLQQSGPELMKPGASVKMSCKAS | GYTFTDYN | MHWVKQNQKGKSLEWIGE | VNPNTGGI | GYNQKFKGKATLTVDKSSTAYMDLRSLTSEDSAVYYC | ARDGNYCFDYWGQGTLVTVSS | 159 |
| SC17.187 | EVHLQQSGPELVNPGSSVKISCRAA | GYTFTDYN | MDWVKQSHGKRLEWIGN | IYPMNGGA | GYNQNFKDKATLTVDKSSTAYMELRSLTSEDSAVYYC | ARSHTAAWFAYWGQGTLVTVSA | 161 |
| SC17.191 | EVQLQQSGPELMMPGASVKMSCKAS | GYTFTDYN | MHWVKQNCGKSLEWIGE | INPNTGGT | GYNQKFKDKATLTVDKSSSTAYMELRSLTSEDSAVYYC | ARIPSLRAYYFDYWGQGTLVTVSS | 163 |
| SC17.193 | QVTLKESGPGILQPSQTLSLTCSFS | GFSLITYIG | VGWIRQPSGKGLEWLAH | IWWNDNK | YYNTALKSRLTISKDTSMNQVFLKIARVDTADTATYYC | ARMVVYDYDGGFAYWGQGTLVTVSA | 165 |
| SC17.199 | EVQLQQSGTVLARPGASVRMSLKAS | GYTFTSYW | MHWVKQRPGQGLEWIGA | IYPGNSDT | SYNHKFKGKAKLTAVTSASTAYMELSSLTNEDSAVYYC | TRSGTGWFAYWGQGTLVTVSS | 167 |
| SC17.200 | QVQLQQSGPELVKPGASVKISCKAS | GYAFSSSW | INWVKQRPGQGLEWIGR | IYPGEGDT | NYSGNFEGKATLTACKSTTAYMQLSSLTSVDSAVYFC | TRGLVMDYWGQGTALTVSS | 169 |

FIG. 10B (Cont.)

Protein Sequences of Exemplary Humanized SEZ6 Modulator Heavy Chain Variable Regions

| mAb | FW1 | CDRH1 | FW2 | CDRH2 | FW3 | CDRH3 | SEQ ID NO. |
|---|---|---|---|---|---|---|---|
| hSC17.16 | QVQLVQSGAEVKKPGASVKVSCKAS | GYTFTDYN | MYWVRQAPGQGLEWMGE | INPNNGGT | AYNQKFRGKVTMTRDTSISTAYMELSRLRSDDTAVYYC | ARYDKGFDYWGQGTTVTVSS | 171 |
| hSC17.17 | QVQLVQSGAEVKKPGASVKVSCKAS | GYTFTDYN | MHWVRQAPGQGLEWMGE | INPNIGGT | GYNQKFKGRVTMTRDTSISTAYMELSRLRSDDTAVYYC | ARTYSYYSEFAYWGQGTLVTVSS | 173 |
| hSC17.24 | EVQLVQSGAEVKKPGATVKISCKVS | GYTFTDHT | IHWVRQAPGKGLEWIGY | IYPRDGST | KYNEEFKGRVTITADTSTDTAYMELSSLRSEDTAVYYC | ARSYSNYFDYWGQGTTVTVSS | 175 |
| hSC17.28 | QVQLVQSGAEVKKPGASVRVSCKAS | GYTFTRSY | IHWVRQAPGQGLEWMGY | ISSGSGGT | TYNQKFKGRVTSTRDTSISTAYMELSRLRSDDTAVYYC | ARGGVRYFDVWGQGTTVTVSS | 177 |
| hSC17.34 | QVQLVQSGAEVKKPGASVKVSCKAS | GYTFTDYN | MDWVRQAPGQRLEWIGY | IYPDNGGA | GYNQKFKGRVTITVDTSASTAYMELSSLRSEDTAVYYC | SRSITTAWFAYWGQGTLVTVSS | 179 |
| hSC17.46 | QVQLVQSGAEVKKPGASVKVSCKAS | GYTFTSYW | INWVRQAPGQGLEWIGN | IFPDTTTT | NYNEKFKGRVTLTRDTSISTAYMELSRLRSDDTAVYYC | AREYYDGTYDAMDYWGQGTLVTVSS | 181 |
| hSC17.151 | QVQLVQSGAEVKKPGASVRVSCKAS | GYTFTSYW | MHWVRQAPGQGLEWMGA | IYPGKSDT | TYNQKFKGRVTMTRDTSTSTVYMELSSLRSEDTAVYYC | ARSGKGYFAYWGQGTLVTVSS | 183 |
| hSC17.155 | QVQLVQSGAEVKKPGASVKVSCKAS | GYTFNSYW | MHWVRQAPGQGLEWMGE | IHPNNGGT | NYNEKFKGRVTMTRDTSTSTVYMELSSLRSEDTAVYYC | ARWTLFTYWGQGTLVTVSS | 185 |
| hSC17.156 | QVTLKESGPVLVKPTETLTLTCTVS | GFSLSTSGMG | VSWIRQPPGKALEWLAH | IFWDDDK | WYNPSLKSRLTISKDTSKQVVLTMTNMDPVDTATYYC | ATFYGLYFAYWGQGTLVTVS | 187 |
| hSC17.161 | QVQLVQSGAEVKKPGASVKVSCKAS | GFTFSDAW | MDWVRQAPGQRLEWMGE | IRSKPNNHAT | YYAESVKGRVTITRDTSASTAYMELSSLRSEDTAVYYC | ARTGTSYWGQGTLVTVSS | 189 |
| hSC17.200 | EVQLVQSGAEVKKPGESLKISCKGS | GYSFTSSW | INWVRQMPGKGLEWMGR | IYPGEGDT | NYSGNFEGQVTISADKSISTAYLQWSSLKASDTAMYYC | TRGLVMDYWGQGTLVFVS | 191 |
| hSC17.155vH1 | QVQLVQSGAEVKKPGASVKVSCKAS | GYTFDSYW | MHWVRQAPGQGLEWMGE | IHPNNGST | NYNEKFKGRVTMTRDTSTSTVYMELSSLRSEDTAVYYC | ARWTLFTYWGQGTLVTVSS | 193 |
| hSC17.155vH2 | QVQLVQSGAEVKKPGASVKVSCKAS | GYTFTSYW | MHWVRQAPGQGLEWMGE | IHPNNGST | NYMEKFKGRVTMTRDTSTSTVYMELSSLRSEDTAVYYC | ARWTLFTYWGQGTLVTVSS | 194 |
| hSC17.155vH3 | QVQLVQSGAEVKKPGASVKVSCKAS | GYTFNYYW | MHWVRQAPGQGLEWMGE | IHPNNGST | NYNEKFKGRVTMTRDTSTSTVYMELSSLRSEDTAVYYC | ARWTLFTYWGQGTLVTVSS | 195 |
| hSC17.155vH4 | QVQLVQSGAEVKKPGASVKVSCKAS | GYTFNSYW | MHWVRQAPGQGLEWMGE | IHPNDGST | NYNEKFKGRVTMTRDTSTSTVYMELSSLRSEDTAVYYC | ARWTLFTYWGQGTLVTVSS | 196 |
| hSC17.155vH5 | QVQLVQSGAEVKKPGASVKVSCKAS | GYTFNSYW | MHWVRQAPGQGLEWMGE | IHPNGGST | NYNEKFKGRVTMTRDTSTSTVYMELSSLRSEDTAVYYC | ARWTLFTYWGQGTLVTVSS | 197 |
| hSC17.155vH6 | QVQLVQSGAEVKKPGASVKVSCKAS | GYTFNSYW | MHWVRQAPGQGLEWMGE | IHPNSGST | NYNEKFKGRVTMTRDTSTSTVYMELSSLRSEDTAVYYC | ARWTLFTYWGQGTLVTVSS | 198 |
| hSC17.161vH1 | EVQLVESGGGLVQPGGSLRLSCAAS | GFTFSDAW | MDWVRQAPGKGLEWVGE | IRSKPNNHAT | YYAESVKGRFTISRDDSKNSLYLQMNSLKTEDTAVYYC | ARTGTSYWGQGTLVTVSS | 199 |

FIG. 10B (Cont.)

SEZ6 Modulator Characteristics

| Clone | Bin | Hu Affinity (Kd, nM) | Mouse XR | Rat XR (Kd, nM) | Cyno XR | SEZ6L XR | SEZ6L2 XR |
|---|---|---|---|---|---|---|---|
| SC17.3 | D | N.D. | No | No | N.D. | No | No |
| SC17.4 | A | N.D. | No | No | N.D. | No | No |
| SC17.6 | B | <1 | Yes | Yes (<1) | N.D. | No | Yes |
| SC17.7 | A | N.D. | Yes | No | No | Yes | Yes |
| SC17.17 | U | 1.8 | Yes | Yes (5.0) | Yes | No | No |
| SC17.19 | E | 5.3 | Yes | Yes | N.D. | No | Yes |
| SC17.24 | C | 5.1 | Yes | No | Yes | No | No |
| SC17.26 | F | 62.0 | No | Yes (17.4) | Yes | No | Yes |
| SC17.28 | U | 22.1 | No | Yes (31) | N.D. | No | Yes |
| SC17.34 | A | 15.1 | No | Yes (79.5) | Yes | No | No |
| SC17.36 | A | 6.3 | No | No | Yes | No | No |
| SC17.42 | A | 2.7 | Yes | Yes (3.0) | No | No | No |
| SC17.45 | A | 17.4 | No | No | Yes | No | No |
| SC17.46 | E | N.D. | No | No | No | No | No |
| SC17.49 | U | 23.1 | No | No | N.D. | No | No |

FIG. 11A

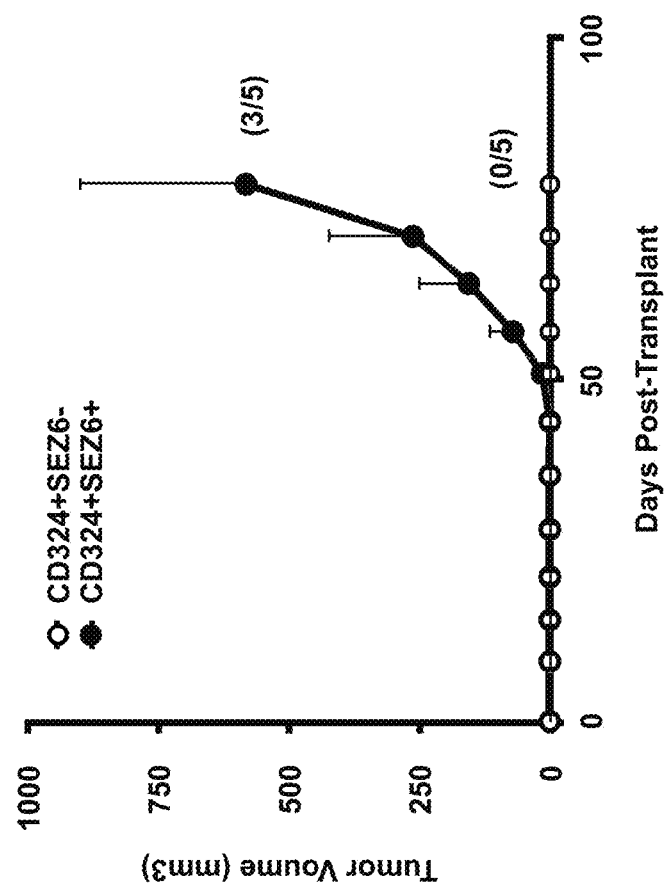
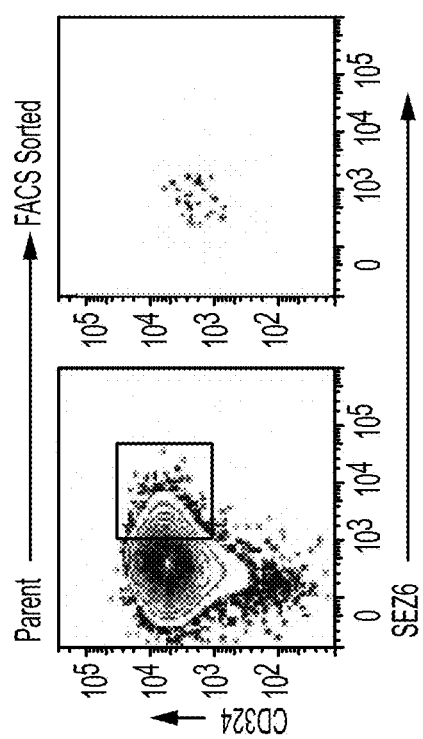
FIG. 14A
FIG. 14B

SEZ6 Modulators Facilitate Delivery of Cytotoxic Agents to SEZ6-Expressing HEK-293T Cells

| Clone | 100pM | 50pM | 10pM |
|---|---|---|---|
| IgG1 | 103.1 | ND | 94.3 |
| IgG2a | 97.3 | 100.4 | 94.7 |
| IgG2b | 102.3 | ND | 96.9 |
| SC17.1 | 26.3 | ND | 70.1 |
| SC17.3 | 16.9 | ND | 38.5 |
| SC17.4 | 18.7 | ND | 34.7 |
| SC17.6 | 8.8 | ND | 14.3 |
| SC17.7 | 23.9 | ND | 49.4 |
| SC17.8 | 15.2 | ND | 22.8 |
| SC17.9 | 13.8 | ND | 24.4 |
| SC17.10 | 56.6 | ND | 92.2 |
| SC17.11 | 23.8 | ND | 64.5 |
| SC17.12 | 112.4 | ND | 111.7 |
| SC17.13 | 107.0 | ND | 103.4 |
| SC17.14 | 34.9 | ND | 71.8 |
| SC17.15 | 95.1 | ND | 110.6 |
| SC17.17 | 11.3 | 12.8 | 21.4 |
| SC17.18 | 59.3 | ND | 89.6 |
| SC17.19 | 9.2 | ND | 14.4 |
| SC17.21 | 36.4 | ND | 62.7 |
| SC17.22 | 46.9 | ND | 68.9 |
| SC17.23 | 13.3 | ND | 38.0 |
| SC17.24 | 49.5 | ND | 77.5 |
| SC17.25 | 58.7 | ND | 88.8 |
| SC17.26 | 13.4 | ND | 15.6 |
| SC17.27 | 21.7 | ND | 33.6 |
| SC17.28 | 12.8 | ND | 17.9 |

| Clone | 100pM | 50pM | 10pM |
|---|---|---|---|
| SC17.29 | 112.4 | ND | 103.3 |
| SC17.30 | 22.6 | ND | 50.0 |
| SC17.31 | 47.0 | ND | 87.4 |
| SC17.32 | 104.7 | ND | 122.9 |
| SC17.33 | 10.4 | ND | 17.6 |
| SC17.34 | 8.8 | ND | 16.7 |
| SC17.35 | 15.9 | ND | 41.8 |
| SC17.36 | 9.8 | ND | 12.9 |
| SC17.37 | 78.4 | ND | 92.2 |
| SC17.38 | 104.9 | ND | 104.8 |
| SC17.39 | 121.7 | ND | 121.8 |
| SC17.40 | 9.6 | ND | 11.3 |
| SC17.41 | 60.3 | ND | 98.1 |
| SC17.42 | 58.5 | ND | 91.7 |
| SC17.43 | 21.5 | ND | 36.8 |
| SC17.44 | 47.3 | ND | 86.3 |
| SC17.45 | 11.1 | ND | 12.6 |
| SC17.46 | 12.7 | 16.3 | 23.6 |
| SC17.47 | 15.0 | ND | 39.2 |
| SC17.49 | 21.3 | ND | 39.3 |
| SC17.50 | 102.7 | ND | 109.9 |
| SC17.51 | 105.4 | ND | 102.1 |
| SC17.52 | 8.2 | ND | 8.6 |
| SC17.53 | 111.6 | ND | 99.9 |
| SC17.54 | 77.0 | ND | 99.6 |
| SC17.55 | 11.0 | ND | 28.9 |
| SC17.56 | 12.4 | ND | 16.5 |

| Clone | 100pM | 50pM | 10pM |
|---|---|---|---|
| SC17.57 | 111.7 | ND | 103.0 |
| SC17.58 | 102.3 | ND | 95.1 |
| SC17.59 | 111.4 | ND | 114.5 |
| SC17.60 | 110.8 | ND | 101.2 |
| SC17.61 | 114.0 | ND | 113.7 |
| SC17.72 | ND | 101.3 | ND |
| SC17.73 | ND | 96.4 | ND |
| SC17.74 | ND | 105.1 | ND |
| SC17.75 | ND | 108.3 | ND |
| SC17.76 | ND | 99.6 | ND |
| SC17.81 | ND | 62.8 | ND |
| SC17.82 | ND | 97.7 | ND |
| SC17.83 | ND | 95.4 | ND |
| SC17.84 | ND | 107.8 | ND |
| SC17.86 | ND | 111.7 | ND |
| SC17.87 | ND | 100.9 | ND |
| SC17.88 | ND | 97.8 | ND |
| SC17.89 | ND | 17.0 | ND |
| SC17.90 | ND | 105.4 | ND |
| SC17.91 | ND | 104.0 | ND |
| SC17.92 | ND | 107.4 | ND |
| SC17.93 | ND | 106.3 | ND |
| SC17.95 | ND | 113.0 | ND |
| SC17.96 | ND | 53.5 | ND |
| SC17.97 | ND | 111.9 | ND |
| SC17.99 | ND | 18.8 | ND |
| SC17.100 | ND | 97.0 | ND |

FIG. 15A

SEZ6 Modulators Facilitate Delivery of Cytotoxic Agents to SEZ6-Expressing HEK-293T Cells

| Clone | 100pM | 50pM | 10pM |
|---|---|---|---|
| SC17.101 | ND | 50.7 | ND |
| SC17.102 | ND | 13.6 | ND |
| SC17.103 | ND | 111.4 | ND |
| SC17.104 | ND | 39.4 | ND |
| SC17.105 | ND | 115.2 | ND |
| SC17.106 | ND | 116.6 | ND |
| SC17.107 | ND | 36.0 | ND |
| SC17.108 | ND | 104.7 | ND |
| SC17.109 | ND | 108.3 | ND |
| SC17.112 | ND | 102.7 | ND |
| SC17.114 | ND | 11.4 | ND |
| SC17.115 | ND | 10.7 | ND |
| SC17.116 | ND | 95.4 | ND |
| SC17.117 | ND | 107.4 | ND |
| SC17.119 | ND | 111.0 | ND |
| SC17.120 | ND | 9.1 | ND |
| SC17.121 | ND | 16.2 | ND |
| SC17.122 | ND | 107.1 | ND |
| SC17.124 | ND | 109.9 | ND |
| SC17.125 | ND | 98.7 | ND |
| SC17.129 | ND | 102.9 | ND |
| SC17.130 | ND | 80.4 | ND |
| SC17.133 | ND | 108.2 | ND |
| SC17.134 | ND | 37.3 | ND |
| SC17.135 | ND | 99.0 | ND |

| Clone | 100pM | 50pM | 10pM |
|---|---|---|---|
| SC17.136 | ND | 92.9 | ND |
| SC17.137 | ND | 15.3 | ND |
| SC17.138 | ND | 107.7 | ND |
| SC17.140 | ND | 22.5 | ND |
| SC17.142 | ND | 101.4 | ND |
| SC17.143 | ND | 97.0 | ND |
| SC17.145 | ND | 100.8 | ND |
| SC17.146 | ND | 96.7 | ND |
| SC17.147 | ND | 108.9 | ND |
| SC17.149 | ND | 45.9 | ND |
| SC17.151 | ND | 8.1 | ND |
| SC17.154 | ND | 102.0 | ND |
| SC17.155 | ND | 15.3 | ND |
| SC17.156 | ND | 19.5 | ND |
| SC17.161 | ND | 18.3 | ND |
| SC17.162 | ND | 30.1 | ND |
| SC17.163 | ND | 106.5 | ND |
| SC17.166 | ND | 19.2 | ND |
| SC17.167 | ND | 103.4 | ND |
| SC17.168 | ND | 46.0 | ND |
| SC17.169 | ND | 109.7 | ND |
| SC17.170 | ND | 108.9 | ND |
| SC17.173 | ND | 68.9 | ND |
| SC17.175 | ND | 15.9 | ND |
| SC17.176 | ND | 82.8 | ND |

| Clone | 100pM | 50pM | 10pM |
|---|---|---|---|
| SC17.177 | ND | 102.5 | ND |
| SC17.178 | ND | 102.1 | ND |
| SC17.179 | ND | 70.2 | ND |
| SC17.180 | ND | 21.7 | ND |
| SC17.181 | ND | 101.2 | ND |
| SC17.182 | ND | 10.9 | ND |
| SC17.184 | ND | 63.2 | ND |
| SC17.186 | ND | 105.1 | ND |
| SC17.187 | ND | 13.5 | ND |
| SC17.188 | ND | 21.2 | ND |
| SC17.189 | ND | 98.8 | ND |
| SC17.190 | ND | 91.3 | ND |
| SC17.191 | ND | 17.3 | ND |
| SC17.192 | ND | 103.6 | ND |
| SC17.193 | ND | 21.1 | ND |
| SC17.195 | ND | 38.0 | ND |
| SC17.196 | ND | 106.8 | ND |
| SC17.197 | ND | 7.0 | ND |
| SC17.198 | ND | 108.0 | ND |
| SC17.199 | ND | 21.0 | ND |
| SC17.200 | ND | 9.9 | ND |
| SC17.201 | ND | 40.1 | ND |
| SC17.203 | ND | 96.2 | ND |
| SC17.204 | ND | 114.1 | ND |

IHC Measurements of SEZ6 Expression in Various Tumors

| position | sex | age | organ | pathology | stage | Clone 140 |
|---|---|---|---|---|---|---|
| A1 | M | 50 | Lung | Small cell carcinoma | I | 0 |
| A2 | F | 51 | Lung | Small cell carcinoma | I | 1 |
| A3 | M | 75 | Lung | Small cell carcinoma | I | 0 |
| A4 | F | 65 | Lung | Small cell carcinoma | I | 0 |
| A5 | M | 56 | Lung | Small cell carcinoma | I | 1 |
| A6 | M | 53 | Lung | Small cell carcinoma | II | 1 |
| A7 | M | 61 | Lung | Small cell carcinoma | I | 0 |
| A8 | M | 43 | Lung | Small cell carcinoma | I | 1 |
| A9 | M | 56 | Lung | Small cell carcinoma | I | 1 |
| B1 | F | 62 | Lung | Small cell carcinoma | I | 0 |
| B2 | M | 55 | Lung | Small cell carcinoma | I | 0 |
| B3 | M | 61 | Lung | Small cell carcinoma | I | 0 |
| B4 | M | 54 | Lung | Small cell carcinoma | II | 1 |
| B5 | F | 66 | Lung | Small cell carcinoma | I | 1 |
| B6 | M | 52 | Lung | Small cell carcinoma | I | 2 |
| B7 | M | 54 | Lung | Small cell carcinoma | II | 1 |
| B8 | M | 62 | Lung | Small cell carcinoma | II | 1 |
| B9 | F | 40 | Lung | Small cell carcinoma | II | 1 |
| C1 | M | 62 | Lung | Small cell carcinoma | II | 0 |
| C2 | M | 58 | Lung | Small cell carcinoma | II | 1 |
| C3 | F | 60 | Lung | Small cell carcinoma | II | 1 |
| C4 | M | 58 | Lung | Small cell carcinoma | II | 1 |
| C5 | F | 67 | Lung | Small cell carcinoma | II | 0 |
| C6 | M | 35 | Lung | Small cell carcinoma | II | 1 |
| C7 | M | 39 | Lung | Small cell carcinoma | II | 1 |
| C8 | F | 55 | Lung | Small cell carcinoma | II | 0 |
| C9 | F | 52 | Lung | Small cell carcinoma | II | 1 |
| D1 | M | 59 | Lung | Small cell carcinoma | II | 0 |
| D2 | M | 59 | Lung | Small cell carcinoma | II | 3 |
| D3 | F | 53 | Lung | Small cell carcinoma | II | 1 |
| D4 | M | 61 | Lung | Small cell carcinoma | IIIa | 1 |
| D5 | M | 70 | Lung | Small cell carcinoma | IIIa | 0 |
| D6 | M | 60 | Lung | Small cell carcinoma | II | 1 |
| D7 | M | 28 | Lung | Small cell carcinoma | II | 0 |
| D8 | M | 34 | Lung | Small cell carcinoma | II | 2 |
| D9 | M | 44 | Lung | Small cell carcinoma | IIIa | 0 |
| E1 | F | 49 | Lung | Small cell carcinoma | IIIa | 3 |
| E2 | F | 52 | Lung | Small cell carcinoma | IIIa | 0 |
| E3 | M | 44 | Lung | Small cell carcinoma | IIIb | 3 |
| E4 | F | 55 | Lung | Small cell carcinoma | IIIa | 1 |
| E5 | - | - | Blank | Empty core | - | XXXX |
| E6 | M | 41 | Lung | Small cell carcinoma | IIIb | 1 |
| E7 | M | 73 | Lung | Small cell carcinoma | IIIa | 1 |
| E8 | M | 51 | Lung | Small cell carcinoma | IIIb | 0 |
| E9 | M | 16 | Lung | Small cell carcinoma | IIIb | 1 |

| Tissue Type | 0 | 1 | 2 | 3 | Number of Cases |
|---|---|---|---|---|---|
| Primary SCLC | 36% | 52% | 5% | 7% | N=44 |

SEQUENCE LISTING

<160> NUMBER OF SEQ ID NOS: 403

<210> SEQ ID NO 1
<211> LENGTH: 4249
<212> TYPE: DNA
<213> ORGANISM: Homo sapiens

<400> SEQUENCE: 1

```
gatcccggc  gccgtcgcca  ggcgctggcc  gtggtgctga  ttctgtcagg  cgctggcggc      60
ggcagcggcg  gtgacggctg  cggccccgct  ccctctaccc  ggccggaccc  ggctctgccc    120
```

```
ccgcgcccaa gccccaccaa gcccccgcc ctcccgccgc ggtcccagcc cagggcgcgg    180
ccgcaaccag caccatgcgc ccggtagccc tgctgctcct gccctcgctg ctggcgctcc    240
tggctcacgg actctcttta gaggccccaa ccgtggggaa aggacaagcc ccaggcatcg    300
aggagacaga tggcgagctg acagcagccc ccacacctga gcagccagaa cgaggcgtcc    360
actttgtcac aacagccccc accttgaagc tgctcaacca ccacccgctg cttgaggaat    420
tcctacaaga ggggctggaa aagggagatg aggagctgag gccagcactg cccttccagc    480
ctgacccacc tgcacccttc accccaagtc cccttccccg cctggccaac caggacagcc    540
gccctgtctt taccagcccc actccagcca tggctgcggt acccactcag ccccagtcca    600
aggagggacc ctggagtccg gagtcagagt ccctatgct tcgaatcaca gctcccctac    660
ctccagggcc cagcatggca gtgcccaccc taggcccagg ggagatagcc agcactacac    720
cccccagcag agcctggaca ccaacccaag agggtcctgg agacatggga aggccgtggg    780
ttgcagaggt tgtgtcccag ggcgcaggga tcgggatcca ggggaccatc acctcctcca    840
cagcttcagg agatgatgag gagaccacca ctaccaccac catcatcacc accaccatca    900
ccacagtcca gacaccaggc ccttgtagct ggaatttctc aggcccagag ggctctctgg    960
actcccctac agacctcagc tcccccactg atgttggcct ggactgcttc ttctacatct   1020
ctgtctaccc tggctatggc gtggaaatca aggtccagaa tatcagcctc cgggaagggg   1080
agacagtgac tgtggaaggc ctgggggggc ctgacccact gccccctggcc aaccagtctt   1140 tcctgctgcg gggccaagtc atccgcagcc ccacccacca agcggccctg aggttccaga   1200
gcctcccgcc accggctggc cctggcacct tccatttcca ttaccaagcc tatctcctga   1260
gctgccactt tcccgtcgt ccagcttatg agatgtgac tgtcaccagc ctccacccag   1320
ggggtagtgc ccgcttccat tgtgccactg gctaccagct gaagggcgcc aggcatctca   1380
cctgtctcaa tgccacccag cccttctggg attcaaagga gcccgtctgc atcgctgctt   1440
gcggcggagt gatccgcaat gccaccaccg gccgcatcgt ctctccaggc ttcccgggca   1500
actacagcaa caacctcacc tgtcactggc tgcttgaggc tcctgagggc cagcggctac   1560
acctgcactt tgagaaggtt ccctggcag aggatgatga caggctcatc attcgcaatg   1620
gggacaacgt ggaggcccca ccagtgtatg attcctatga ggtggaatac ctgcccattg   1680
agggcctgct cagctctggc aaacacttct ttgttgagct cagtactgac agcagcgggg   1740
cagctgcagg catggccctg cgctatgagg ccttccagca gggccattgc tatgagccct   1800
ttgtcaaata cggtaacttc agcagcagca cacccaccta ccctgtgggt accactgtgg   1860
agttcagctg cgaccctggc tacaccctgg agcagggctc catcatcatc gagtgtgttg   1920 accccacga cccccagtgg aatgagacag agccagcctg ccgagccgtg tgcagcgggg   1980
agatcacaga ctcggctggc gtggtactct ctcccaactg ccagagccc tacggtcgtg   2040 gcaggattg tatctggggt gtgcatgtgg aagaggacaa gcgcatcatg ctggacatcc   2100
gagtgctgcg cataggccct ggtgatgtgc ttaccttcta tgatgggat gacctgacgg   2160 cccgggttct gggccagtac tcagggcccc gtagccactt caagctcttt acctccatgg   2220
ctgatgtcac cattcagttc agtcggacc ccgggacctc agtgctgggc taccagcagg   2280
gcttcgtcat ccacttcttt gaggtgcccc gcaatgacac atgtccggag ctgcctgaga   2340
tccccaatgg ctggaagagc ccatcgcagc ctgagctagt gcacggcacc gtggtcactt   2400
accagtgcta ccctgctac caggtagtgg atccagtgt cctcatgtgc cagtgggacc   2460
taacttggag tgaggacctg ccctcatgcc agagggtgac ttcctgccac gatcctggag   2520
```

| | |
|---|---|
| atgtggagca cagccgacgc ctcatatcca gccccaagtt tcccgtgggg gccaccgtgc | 2580 |
| aatatatctg tgaccagggt tttgtgctga tgggcagctc catcctcacc tgccatgatc | 2640 |
| gccaggctgg cagccccaag tggagtgacc gggcccctaa atgtctcctg aacagctca | 2700 |
| agccatgcca tggtctcagt gcccctgaga atggtgcccg aagtcctgag aagcagctac | 2760 |
| acccagcagg ggccaccatc cacttctcgt gtgcccctgg ctatgtgctg aagggccagg | 2820 |
| ccagcatcaa gtgtgtgcct gggcacccct cgcattggag tgaccccca cccatctgta | 2880 |
| gggctgcctc tctggatggg ttctacaaca gtcgcagcct ggatgttgcc aaggcacctg | 2940 |
| ctgcctccag caccctggat gctgcccaca ttgcagctgc catcttcttg ccactggtgg | 3000 |
| cgatggtgtt gttggtagga ggtgtatact tctacttctc caggctccag ggaaaaagct | 3060 |
| ccctgcagct gccccgcccc cgccccgccc ctacaaccg cattaccata gagtcagcgt | 3120 |
| ttgacaatcc aacttacgag actggatctc tttcctttgc aggagacgag agaatatgaa | 3180 |
| gtctccatct aggtggggc agtctaggga agtcaactca gacttgcacc acagtccagc | 3240 |
| agcaaggctc cttgcttcct gctgtccctc cacctcctgt ataccacc taggaggaga | 3300 |
| tgccaccaag ccctcaagaa gttgtgccct tccccgcctg cgatgcccac catggcctat | 3360 |
| tttcttggtg tcattgccca cttggggccc ttcattgggc ccatgtcagg gggcatctac | 3420 |
| ctgtgggaag aacatagctg gagcacaagc atcaacagcc agcatcctga gcctcctcat | 3480 |
| gccctggacc agcctggaac acactagcag agcaggagta cctttctcca catgaccacc | 3540 |
| atcccgccct ggcatggcaa cctgcagcag gattaacttg accatggtgg gaactgcacc | 3600 |
| agggtactcc tcacagcgca tcaccaatgg ccaaaactcc tctcaacggt gacctctggg | 3660 |
| tagtcctggc atgccaacat cagcctcttg ggaggtctct agttctctaa agttctggac | 3720 |
| agttctgcct cctgccctgt cccagtggag gcagtaattc taggagatcc taagggttc | 3780 |
| agggggaccc tacccccacc tcaggttggg cttccctggg cactcatgct ccacaccaaa | 3840 |
| gcaggacacg ccattttcca ctgaccaccc tatacccctga ggaaagggag actttcctcc | 3900 |
| gatgtttatt tagctgttgc aaacatcttc accctaatag tccctcctcc aattccagcc | 3960 |
| acttgtcagg ctctcctctt gaccactgtg ttatgggata aggggagggg gtgggcatat | 4020 |
| tctggagagg agcagaggtc caaggaccca ggaatttggc atggaacagg tggtaggaga | 4080 |
| gccccaggga gacgcccagg agctggctga agccacttt gtacatgtaa tgtattatat | 4140 |
| ggggtctggg ctccagccag agaacaatct tttatttctg ttgtttcctt attaaaatgg | 4200 |
| tgtttttgga aaaaaaaaa aaaaaaaaa aaaaaaaaa aaaaaaaa | 4249 |

<210> SEQ ID NO 2
<211> LENGTH: 4234
<212> TYPE: DNA
<213> ORGANISM: Homo sapiens

<400> SEQUENCE: 2

| | |
|---|---|
| gatccccggc gccgtcgcca ggcgctggcc gtggtgctga ttctgtcagg cgctggcggc | 60 |
| ggcagcggcg gtgacggctg cggccccgct ccctctaccc ggccggaccc ggctctgccc | 120 |
| ccgcgcccaa gccccaccaa gccccccgcc ctcccgccgc ggtcccagcc cagggcgcgg | 180 |
| ccgcaaccag caccatgcgc ccggtagccc tgctgctcct gcccctcgctg ctggcgctcc | 240 |
| tggctcacgc actctctttta gaggcccaa ccgtggggaa aggacaagcc ccaggcatcg | 300 |
| aggagacaga tggcgagctg acagcagccc ccacacctga gcagccagaa cgaggcgtcc | 360 |

```
actttgtcac aacagccccc accttgaagc tgctcaacca ccacccgctg cttgaggaat    420
tcctacaaga ggggctggaa aagggagatg aggagctgag gccagcactg cccttccagc    480
ctgacccacc tgcacccttc accccaagtc cccttccccg cctggccaac caggacagcc    540
gccctgtctt taccagcccc actccagcca tggctgcggt acccactcag ccccagtcca    600
aggagggacc ctggagtccg gagtcagagt cccctatgct tcgaatcaca gctcccctac    660
ctccagggcc cagcatggca gtgcccaccc taggcccagg ggagatagcc agcactacac    720
cccccagcag agcctggaca ccaacccaag agggtcctgg agacatggga aggccgtggg    780
ttgcagaggt tgtgtcccag ggcgcaggga tcgggatcca ggggaccatc acctcctcca    840
cagcttcagg agatgatgag gagaccacca ctaccaccac catcatcacc accaccatca    900
ccacagtcca gaccaggc ccttgtagct ggaatttctc aggcccagag ggctctctgg    960
actcccctac agacctcagc tcccccactg atgttggcct ggactgcttc ttctacatct   1020
ctgtctaccc tggctatggc gtggaaatca aggtccagaa tatcagcctc cgggaagggg   1080
agacagtgac tgtggaaggc ctggggggggc ctgacccact gccccctggcc aaccagtctt   1140
tcctgctgcg gggccaagtc atccgcagcc ccacccacca agcggccctg aggttccaga   1200
gcctcccgcc accggctggc cctggcacct tccatttcca ttaccaagcc tatctcctga   1260
gctgccactt tccccgtcgt ccagcttatg gagatgtgac tgtcaccagc ctccacccag   1320
ggggtagtgc ccgcttccat tgtgccactg gctaccagct gaaggcgcc aggcatctca   1380
cctgtctcaa tgccacccag cccttctggg attcaaagga gcccgtctgc atcgctgctt   1440
gcggcggagt gatccgcaat gccaccaccg gccgcatcgt ctctccaggc ttcccgggca   1500
actacagcaa caacctcacc tgtcactggc tgcttgaggc tcctgagggc cagcggctac   1560
acctgcactt tgagaaggtt tccctggcag aggatgatga caggctcatc attcgcaatg   1620
gggacaacgt ggaggcccca ccagtgtatg attcctatga ggtggaatac ctgcccattg   1680
agggcctgct cagctctggc aaacacttct ttgttgagct cagtactgac agcagcgggg   1740
cagctgcagg catggccctg cgctatgagg ccttccagca gggccattgc tatgagccct   1800
ttgtcaaata cggtaacttc agcagcagca cacccaccta ccctgtgggt accactgtgg   1860
agttcagctg cgaccctggc tacaccctgg agcagggctc catcatcatc gagtgtgttg   1920
accccacga ccccccagtgg aatgagacag agccagcctg ccgagccgtg tgcagcgggg   1980
agatcacaga ctcggctggc gtggtactct ctcccaactg gccagagccc tacggtcgtg   2040
ggcaggattg tatctggggt gtgcatgtgg aagaggacaa gcgcatcatg ctggacatcc   2100
gagtgctgcg cataggccct ggtgatgtgc ttaccttcta tgatgggggat gacctgacgg   2160
cccgggttct gggccagtac tcagggcccc gtagccactt caagctcttt acctccatgg   2220
ctgatgtcac cattcagttc cagtcggacc ccggacctc agtgctgggc taccagcagg   2280
gcttcgtcat ccacttcttt gaggtgcccc gcaatgacac atgtccggag ctgcctgaga   2340
tccccaatgg ctggaagagc ccatcgcagc ctgagctagt gcacggcacc gtggtcactt   2400
accagtgcta ccctggctac caggtagtgg atccagtgt cctcatgtgc cagtgggacc   2460
taacttggag tgaggacctg ccctcatgcc agagggtgac ttcctgccac gatcctggag   2520
atgtggagca cagccgacgc ctcatatcca gccccaagtt tccgtgggg gccaccgtgc   2580
aatatatctg tgaccagggt tttgtgctga tgggcagctc catcctcacc tgccatgatc   2640
gccaggctgg cagcccaag tggagtgacc gggcccctaa atgtctcctg gaacagctca   2700
agccatgcca tggtctcagt gcccctgaga atggtgcccg aagtcctgag aagcagctac   2760
```

```
acccagcagg ggccaccatc cacttctcgt gtgcccctgg ctatgtgctg aagggccagg    2820
ccagcatcaa gtgtgtgcct gggcacccct cgcattggag tgacccccca cccatctgta    2880
gggctgcctc tctggatggg ttctacaaca gtcgcagcct ggatgttgcc aaggcacctg    2940
ctgcctccag caccctggat gctgcccaca ttgcagctgc catcttcttg ccactggtgg    3000
cgatggtgtt gttggtagga ggtgtatact tctacttctc caggctccag ggaaaaagct    3060
ccctgcagct gccccgcccc cgccccgccc cctacaaccg cattaccata gagtcagcgt    3120
ttgacaatcc aacttacgag actggagaga cgagagaata tgaagtctcc atctaggtgg    3180
gggcagtcta gggaagtcaa ctcagacttg caccacagtc cagcagcaag gctccttgct    3240
tcctgctgtc cctccacctc ctgtatatac cacctaggag gagatgccac caagccctca    3300
agaagttgtg cccttccccg cctgcgatgc ccaccatggc ctattttctt ggtgtcattg    3360
cccacttggg gcccttcatt gggcccatgt caggggcat ctacctgtgg aagaacata     3420 gctggagcac aagcatcaac agccagcatc ctgagcctcc tcatgccctg gaccagcctg    3480
gaacacacta gcagagcagg agtacctttc tccacatgac caccatcccg ccctggcatg    3540
gcaacctgca gcaggattaa cttgaccatg gtgggaactg caccagggta ctcctcacag    3600
cgccatcacc aatggccaaa actcctctca acggtgacct ctgggtagtc ctggcatgcc    3660
aacatcagcc tcttgggagg tctctagttc tctaaagttc tggacagttc tgcctcctgc    3720
cctgtcccag tggaggcagt aattctagga gatcctaagg ggttcagggg gaccctaccc    3780
ccacctcagg ttgggcttcc ctgggcactc atgctccaca ccaaagcagg acacgccatt    3840
ttccactgac caccctatac cctgaggaaa gggagacttt cctccgatgt ttatttagct    3900
gttgcaaaca tcttcaccct aatagtccct cctccaattc cagccacttg tcaggctctc    3960
ctcttgacca ctgtgttatg ggataagggg aggggtggg catattctgg agaggagcag    4020
aggtccaagg acccaggaat ttggcatgga acaggtggta ggagagcccc agggagacgc    4080
ccaggagctg gctgaaagcc actttgtaca tgtaatgtat tatatggggt ctgggctcca    4140
gccagagaac aatcttttat ttctgttgtt tccttattaa aatggtgttt ttggaaaaaa    4200
aaaaaaaaaa aaaaaaaaa aaaaaaaaaa aaaa                                4234

<210> SEQ ID NO 3
<211> LENGTH: 994
<212> TYPE: PRT
<213> ORGANISM: Homo sapiens

<400> SEQUENCE: 3

Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
                20                  25                  30

Pro Gly Ile Glu Glu Thr Asp Gly Glu Leu Thr Ala Ala Pro Thr Pro
            35                  40                  45

Glu Gln Pro Glu Arg Gly Val His Phe Val Thr Thr Ala Pro Thr Leu
        50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110
```

```
Gln Asp Ser Arg Pro Val Phe Thr Ser Pro Thr Pro Ala Met Ala Ala
            115                 120                 125
Val Pro Thr Gln Pro Gln Ser Lys Glu Gly Pro Trp Ser Pro Glu Ser
130                 135                 140
Glu Ser Pro Met Leu Arg Ile Thr Ala Pro Leu Pro Pro Gly Pro Ser
145                 150                 155                 160
Met Ala Val Pro Thr Leu Gly Pro Gly Glu Ile Ala Ser Thr Thr Pro
                165                 170                 175
Pro Ser Arg Ala Trp Thr Pro Thr Gln Glu Gly Pro Gly Asp Met Gly
                180                 185                 190
Arg Pro Trp Val Ala Glu Val Val Ser Gln Gly Ala Gly Ile Gly Ile
            195                 200                 205
Gln Gly Thr Ile Thr Ser Ser Thr Ala Ser Gly Asp Asp Glu Glu Thr
        210                 215                 220
Thr Thr Thr Thr Thr Ile Ile Thr Thr Thr Ile Thr Thr Val Gln Thr
225                 230                 235                 240
Pro Gly Pro Cys Ser Trp Asn Phe Ser Gly Pro Glu Gly Ser Leu Asp
                245                 250                 255
Ser Pro Thr Asp Leu Ser Ser Pro Thr Asp Val Gly Leu Asp Cys Phe
            260                 265                 270
Phe Tyr Ile Ser Val Tyr Pro Gly Tyr Gly Val Glu Ile Lys Val Gln
        275                 280                 285
Asn Ile Ser Leu Arg Glu Gly Glu Thr Val Thr Val Glu Gly Leu Gly
    290                 295                 300
Gly Pro Asp Pro Leu Pro Leu Ala Asn Gln Ser Phe Leu Leu Arg Gly
305                 310                 315                 320
Gln Val Ile Arg Ser Pro Thr His Gln Ala Ala Leu Arg Phe Gln Ser
                325                 330                 335
Leu Pro Pro Pro Ala Gly Pro Gly Thr Phe His Phe His Tyr Gln Ala
                340                 345                 350
Tyr Leu Leu Ser Cys His Phe Pro Arg Arg Pro Ala Tyr Gly Asp Val
            355                 360                 365
Thr Val Thr Ser Leu His Pro Gly Gly Ser Ala Arg Phe His Cys Ala
        370                 375                 380
Thr Gly Tyr Gln Leu Lys Gly Ala Arg His Leu Thr Cys Leu Asn Ala
385                 390                 395                 400
Thr Gln Pro Phe Trp Asp Ser Lys Glu Pro Val Cys Ile Ala Ala Cys
                405                 410                 415
Gly Gly Val Ile Arg Asn Ala Thr Thr Gly Arg Ile Val Ser Pro Gly
            420                 425                 430
Phe Pro Gly Asn Tyr Ser Asn Asn Leu Thr Cys His Trp Leu Leu Glu
        435                 440                 445
Ala Pro Glu Gly Gln Arg Leu His Leu His Phe Glu Lys Val Ser Leu
    450                 455                 460
Ala Glu Asp Asp Asp Arg Leu Ile Ile Arg Asn Gly Asp Asn Val Glu
465                 470                 475                 480
Ala Pro Pro Val Tyr Asp Ser Tyr Glu Val Glu Tyr Leu Pro Ile Glu
                485                 490                 495
Gly Leu Leu Ser Ser Gly Lys His Phe Phe Val Glu Leu Ser Thr Asp
            500                 505                 510
Ser Ser Gly Ala Ala Ala Gly Met Ala Leu Arg Tyr Glu Ala Phe Gln
        515                 520                 525
```

-continued

```
Gln Gly His Cys Tyr Glu Pro Phe Val Lys Tyr Gly Asn Phe Ser Ser
        530                 535                 540

Ser Thr Pro Thr Tyr Pro Val Gly Thr Val Glu Phe Ser Cys Asp
545                 550                 555                 560

Pro Gly Tyr Thr Leu Glu Gln Gly Ser Ile Ile Ile Glu Cys Val Asp
                565                 570                 575

Pro His Asp Pro Gln Trp Asn Glu Thr Glu Pro Ala Cys Arg Ala Val
            580                 585                 590

Cys Ser Gly Glu Ile Thr Asp Ser Ala Gly Val Val Leu Ser Pro Asn
        595                 600                 605

Trp Pro Glu Pro Tyr Gly Arg Gly Gln Asp Cys Ile Trp Gly Val His
    610                 615                 620

Val Glu Glu Asp Lys Arg Ile Met Leu Asp Ile Arg Val Leu Arg Ile
625                 630                 635                 640

Gly Pro Gly Asp Val Leu Thr Phe Tyr Asp Gly Asp Leu Thr Ala
                645                 650                 655

Arg Val Leu Gly Gln Tyr Ser Gly Pro Arg Ser His Phe Lys Leu Phe
                660                 665                 670

Thr Ser Met Ala Asp Val Thr Ile Gln Phe Gln Ser Asp Pro Gly Thr
            675                 680                 685

Ser Val Leu Gly Tyr Gln Gln Gly Phe Val Ile His Phe Glu Val
        690                 695                 700

Pro Arg Asn Asp Thr Cys Pro Glu Leu Pro Glu Ile Pro Asn Gly Trp
705                 710                 715                 720

Lys Ser Pro Ser Gln Pro Glu Leu Val His Gly Thr Val Val Thr Tyr
                725                 730                 735

Gln Cys Tyr Pro Gly Tyr Gln Val Val Gly Ser Ser Val Leu Met Cys
            740                 745                 750

Gln Trp Asp Leu Thr Trp Ser Glu Asp Leu Pro Ser Cys Gln Arg Val
        755                 760                 765

Thr Ser Cys His Asp Pro Gly Asp Val Glu His Ser Arg Arg Leu Ile
    770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
                805                 810                 815

Gln Ala Gly Ser Pro Lys Trp Ser Asp Arg Ala Pro Lys Cys Leu Leu
            820                 825                 830

Glu Gln Leu Lys Pro Cys His Gly Leu Ser Ala Pro Glu Asn Gly Ala
        835                 840                 845

Arg Ser Pro Glu Lys Gln Leu His Pro Ala Gly Ala Thr Ile His Phe
    850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
                885                 890                 895

Ala Ala Ser Leu Asp Gly Phe Tyr Asn Ser Arg Ser Leu Asp Val Ala
            900                 905                 910

Lys Ala Pro Ala Ala Ser Ser Thr Leu Asp Ala Ala His Ile Ala Ala
        915                 920                 925

Ala Ile Phe Leu Pro Leu Val Ala Met Val Leu Leu Val Gly Gly Val
    930                 935                 940

Tyr Phe Tyr Phe Ser Arg Leu Gln Gly Lys Ser Ser Leu Gln Leu Pro
```

```
                    945                 950                 955                 960
Arg Pro Arg Pro Arg Pro Tyr Asn Arg Ile Thr Ile Glu Ser Ala Phe
                965                 970                 975
Asp Asn Pro Thr Tyr Glu Thr Gly Ser Leu Ser Phe Ala Gly Asp Glu
                980                 985                 990
Arg Ile

<210> SEQ ID NO 4
<211> LENGTH: 993
<212> TYPE: PRT
<213> ORGANISM: Homo sapiens

<400> SEQUENCE: 4

Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
                20                  25                  30

Pro Gly Ile Glu Glu Thr Asp Gly Glu Leu Thr Ala Ala Pro Thr Pro
            35                  40                  45

Glu Gln Pro Glu Arg Gly Val His Phe Val Thr Thr Ala Pro Thr Leu
50                  55                  60

Lys Leu Leu Asn His His Pro Leu Leu Glu Glu Phe Leu Gln Glu Gly
65                  70                  75                  80

Leu Glu Lys Gly Asp Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
            115                 120                 125

Val Pro Thr Gln Pro Gln Ser Lys Glu Gly Pro Trp Ser Pro Glu Ser
130                 135                 140

Glu Ser Pro Met Leu Arg Ile Thr Ala Pro Leu Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
            180                 185                 190

Arg Pro Trp Val Ala Glu Val Val Ser Gln Gly Ala Gly Ile Gly Ile
            195                 200                 205

Gln Gly Thr Ile Thr Ser Ser Thr Ala Ser Gly Asp Asp Glu Glu Thr
    210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Glu Gly Ser Leu Asp
                245                 250                 255

Ser Pro Thr Asp Leu Ser Ser Pro Thr Asp Val Gly Leu Asp Cys Phe
            260                 265                 270

Phe Tyr Ile Ser Val Tyr Pro Gly Tyr Gly Val Glu Ile Lys Val Gln
            275                 280                 285

Asn Ile Ser Leu Arg Glu Gly Glu Thr Val Thr Val Glu Gly Leu Gly
            290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
```

```
              325                 330                 335
Leu Pro Pro Pro Ala Gly Pro Gly Thr Phe His Phe His Tyr Gln Ala
            340                 345                 350
Tyr Leu Leu Ser Cys His Phe Pro Arg Arg Pro Ala Tyr Gly Asp Val
            355                 360                 365
Thr Val Thr Ser Leu His Pro Gly Gly Ser Ala Arg Phe His Cys Ala
            370                 375                 380
Thr Gly Tyr Gln Leu Lys Gly Ala Arg His Leu Thr Cys Leu Asn Ala
385                 390                 395                 400
Thr Gln Pro Phe Trp Asp Ser Lys Glu Pro Val Cys Ile Ala Ala Cys
                405                 410                 415
Gly Gly Val Ile Arg Asn Ala Thr Thr Gly Arg Ile Val Ser Pro Gly
                420                 425                 430
Phe Pro Gly Asn Tyr Ser Asn Asn Leu Thr Cys His Trp Leu Leu Glu
                435                 440                 445
Ala Pro Glu Gly Gln Arg Leu His Leu His Phe Glu Lys Val Ser Leu
                450                 455                 460
Ala Glu Asp Asp Arg Leu Ile Ile Arg Asn Gly Asp Asn Val Glu
465                 470                 475                 480
Ala Pro Pro Val Tyr Asp Ser Tyr Glu Val Glu Tyr Leu Pro Ile Glu
                485                 490                 495
Gly Leu Leu Ser Ser Gly Lys His Phe Phe Val Glu Leu Ser Thr Asp
                500                 505                 510
Ser Ser Gly Ala Ala Ala Gly Met Ala Leu Arg Tyr Glu Ala Phe Gln
                515                 520                 525
Gln Gly His Cys Tyr Glu Pro Phe Val Lys Tyr Gly Asn Phe Ser Ser
                530                 535                 540
Ser Thr Pro Thr Tyr Pro Val Gly Thr Val Glu Phe Ser Cys Asp
545                 550                 555                 560
Pro Gly Tyr Thr Leu Glu Gln Gly Ser Ile Ile Ile Glu Cys Val Asp
                565                 570                 575
Pro His Asp Pro Gln Trp Asn Glu Thr Glu Pro Ala Cys Arg Ala Val
                580                 585                 590
Cys Ser Gly Glu Ile Thr Asp Ser Ala Gly Val Val Leu Ser Pro Asn
                595                 600                 605
Trp Pro Glu Pro Tyr Gly Arg Gly Gln Asp Cys Ile Trp Gly Val His
            610                 615                 620
Val Glu Glu Asp Lys Arg Ile Met Leu Asp Ile Arg Val Leu Arg Ile
625                 630                 635                 640
Gly Pro Gly Asp Val Leu Thr Phe Tyr Asp Gly Asp Asp Leu Thr Ala
                645                 650                 655
Arg Val Leu Gly Gln Tyr Ser Gly Pro Arg Ser His Phe Lys Leu Phe
                660                 665                 670
Thr Ser Met Ala Asp Val Thr Ile Gln Phe Gln Ser Asp Pro Gly Thr
            675                 680                 685
Ser Val Leu Gly Tyr Gln Gln Gly Phe Val Ile His Phe Glu Val
            690                 695                 700
Pro Arg Asn Asp Thr Cys Pro Glu Leu Pro Glu Ile Pro Asn Gly Trp
705                 710                 715                 720
Lys Ser Pro Ser Gln Pro Glu Leu Val His Gly Thr Val Val Thr Tyr
                725                 730                 735
Gln Cys Tyr Pro Gly Tyr Gln Val Val Gly Ser Ser Val Leu Met Cys
            740                 745                 750
```

Gln Trp Asp Leu Thr Trp Ser Glu Asp Leu Pro Ser Cys Gln Arg Val
                755                 760                 765

Thr Ser Cys His Asp Pro Gly Asp Val Glu His Ser Arg Arg Leu Ile
    770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
                805                 810                 815

Gln Ala Gly Ser Pro Lys Trp Ser Asp Arg Ala Pro Lys Cys Leu Leu
                820                 825                 830

Glu Gln Leu Lys Pro Cys His Gly Leu Ser Ala Pro Glu Asn Gly Ala
                835                 840                 845

Arg Ser Pro Glu Lys Gln Leu His Pro Ala Gly Ala Thr Ile His Phe
    850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
                885                 890                 895

Ala Ala Ser Leu Asp Gly Phe Tyr Asn Ser Arg Ser Leu Asp Val Ala
                900                 905                 910

Lys Ala Pro Ala Ala Ser Ser Thr Leu Asp Ala His Ile Ala Ala
                915                 920                 925

Ala Ile Phe Leu Pro Leu Val Ala Met Val Leu Leu Val Gly Gly Val
    930                 935                 940

Tyr Phe Tyr Phe Ser Arg Leu Gln Gly Lys Ser Ser Leu Gln Leu Pro
945                 950                 955                 960

Arg Pro Arg Pro Arg Pro Tyr Asn Arg Ile Thr Ile Glu Ser Ala Phe
                965                 970                 975

Asp Asn Pro Thr Tyr Glu Thr Gly Glu Thr Arg Glu Tyr Glu Val Ser
                980                 985                 990

Ile

<210> SEQ ID NO 5
<211> LENGTH: 2925
<212> TYPE: DNA
<213> ORGANISM: Homo sapiens

<400> SEQUENCE: 5

| ctgagcctgg aggccccaac cgtggggaaa ggacaagccc caggcatcga ggagacagat | 60 |
| ggcgagctga cagcagcccc cacacctgag cagccagaac gaggcgtcca ctttgtcaca | 120 |
| acagccccca ccttgaagct gctcaaccac cacccgctgc ttgaggaatt cctacaagag | 180 |
| gggctggaaa agggagatga ggagttgagg ccagcactgc ccttccagcc tgacccacct | 240 |
| gcacccttca ccccaagtcc ccttccccgc ctggccaacc aggacagccg ccctgtcttt | 300 |
| accagcccca ctccagccat ggctgcggta cccactcagc cccagtccaa ggagggaccc | 360 |
| tggagtccgg agtcagagtc ccctatgctt cgaatcacag ctcccctacc tcagggccc | 420 |
| agcatggcag tgcccaccct aggcccaggg gagatagcca gcactacacc cccagcaga | 480 |
| gcctggacac caacccaaga gggtcctgga gacatgggaa ggccgtgggt tgcagaggtt | 540 |
| gtgtcccagg gcgcggggat cgggatccag ggaccatca cctcctccac agcttcagga | 600 |
| gatgatgagg agaccaccac taccaccacc atcatcacca ccaccatcac cacagtccag | 660 |
| acaccaggcc cttgtagctg gaatttctca ggcccagagg gctctctgga ctcccctaca | 720 |

```
gacctcagct cccccactga tgttggcctg gactgcttct tctacatctc tgtctaccct    780
ggctatggcg tggaaatcaa ggtccagaat atcagcctcc gggaagggga gacagtgact    840
gtggaaggcc tggggggggcc cgacccactg cccctggcca accagtctt cctgctgcgg    900
ggccaagtca tccgcagccc cacccaccaa gcggccctga ggttccagag cctcccgcca    960
ccggctggcc ctggcacctt ccatttccat taccaagcct atctcctgag ctgccacttt   1020
ccccgtcgtc cagcttatgg agatgtgact gtcaccagcc tccacccagg gggtagtgcc   1080
cgcttccatt gtgccactgg ctaccagctg aagggcgcca ggcatctcac ctgtctcaat   1140
gccacccagc ccttctggga ttcaaaggag cccgtctgca tcgctgcttg cggcggagtg   1200
atccgcaatg ccaccaccgg ccgcatcgtc tctccaggct tcccgggcaa ctacagcaac   1260
aacctcacct gtcactggct gcttgaggct cctgagggcc agcggctaca cctgcacttt   1320
gagaaggttt ccctggcaga ggatgatgac aggctcatca ttcgcaatgg ggacaacgtg   1380
gaggccccac cagtgtatga ttcctatgag gtggaatacc tgcccattga gggcctgctc   1440
agctctggca aacacttctt tgttgagctc agtactgaca gcagcggggc agctgcaggc   1500
atggccctgc gctatgaggc cttccagcag ggccattgct atgagccctt tgtcaaatac   1560
ggtaacttca gcagcagcac acccacctac cctgtgggta ccactgtgga gttcagctgc   1620
gaccctggct acacccctgga gcagggctcc atcatcatcg agtgtgttga ccccacgac   1680
ccccagtgga atgagacaga gccagcctgc cgagccgtgt gcagcgggga gatcacagac   1740
tcggctggcg tggtactctc tcccaactgg ccagagccct acggtcgtgg gcaggattgt   1800
atctggggtg tgcatgtgga agaggacaag cgcatcatgc tggacatccg agtgctgcgc   1860
ataggccctg gtgatgtgct taccttctat gatggggatg acctgacggc ccgggttctg   1920
ggccagtact cagggccccg tagccacttc aagctcttta cctccatggc tgatgtcacc   1980
attcagttcc agtcggaccc cgggacctca gtgctgggct accagcaggg cttcgtcatc   2040
cacttcttg aggtgccccg caatgacaca tgtccggagc tgcctgagat ccccaatggc   2100
tggaagagcc catcgcagcc tgagctagtg cacggcaccg tggtcactta ccagtgctac   2160
cctggctacc aggtagtggg atccagtgtc ctcatgtgcc agtgggacct aacttggagt   2220
gaggacctgc cctcatgcca gagggtgact tcctgccacg atcctggaga tgtggagcac   2280
agccgacgcc tcatatccag cccccaagttt cccgtgggg ccaccgtgca atatatctgt   2340
gaccagggtt ttgtgctgat gggcagctcc atcctcacct gccatgatcg ccaggctggc   2400
agccccaagt ggagtgaccg ggcccctaaa tgtctcctgg aacagctcaa gccatgccat   2460
ggtctcagtg ccctgagaa tggtgcccga gtcctgaga gcagctaca cccagcaggg   2520
gccaccatcc acttctcgtg tgcccctggc tatgtgctga agggccaggc cagcatcaag   2580
tgtgtgcctg gcacccctc gcattggagt gacccccac ccatctgtag ggctgcctct   2640
ctggatgggt tctacaacag tcgcagcctg gatgttgcca aggcacctgc tgcctccagc   2700
accctggatg ctgcccacat tgcagctgcc atcttcttgc cactggtggc gatggtgttg   2760
ttggtaggag gtgtatactt ctacttctcc aggctccagg gaaaaagctc cctgcagctg   2820
ccccgccccc gccccgccc ctacaaccgc attaccatag agtcagcgtt tgacaatcca   2880
acttacgaga ctggatctct ttcctttgca ggagacgaga gaata                   2925
```

<210> SEQ ID NO 6
<211> LENGTH: 975
<212> TYPE: PRT

<213> ORGANISM: Homo sapiens

<400> SEQUENCE: 6

```
Leu Ser Leu Glu Ala Pro Thr Val Gly Lys Gly Gln Ala Pro Gly Ile
1               5                   10                  15

Glu Glu Thr Asp Gly Glu Leu Thr Ala Ala Pro Thr Pro Glu Gln Pro
            20                  25                  30

Glu Arg Gly Val His Phe Val Thr Thr Ala Pro Thr Leu Lys Leu Leu
        35                  40                  45

Asn His His Pro Leu Leu Glu Glu Phe Leu Gln Gly Leu Glu Lys
    50                  55                  60

Gly Asp Glu Glu Leu Arg Pro Ala Leu Pro Phe Gln Pro Asp Pro Pro
65                  70                  75                  80

Ala Pro Phe Thr Pro Ser Pro Leu Pro Arg Leu Ala Asn Gln Asp Ser
                85                  90                  95

Arg Pro Val Phe Thr Ser Pro Thr Pro Ala Met Ala Ala Val Pro Thr
            100                 105                 110

Gln Pro Gln Ser Lys Glu Gly Pro Trp Ser Pro Glu Ser Glu Ser Pro
        115                 120                 125

Met Leu Arg Ile Thr Ala Pro Leu Pro Gly Pro Ser Met Ala Val
    130                 135                 140

Pro Thr Leu Gly Pro Gly Glu Ile Ala Ser Thr Thr Pro Ser Arg
145                 150                 155                 160

Ala Trp Thr Pro Thr Gln Glu Gly Pro Gly Asp Met Gly Arg Pro Trp
                165                 170                 175

Val Ala Glu Val Val Ser Gln Gly Ala Gly Ile Gly Ile Gln Gly Thr
            180                 185                 190

Ile Thr Ser Ser Thr Ala Ser Gly Asp Asp Glu Glu Thr Thr Thr Thr
        195                 200                 205

Thr Thr Ile Ile Thr Thr Thr Ile Thr Thr Val Gln Thr Pro Gly Pro
    210                 215                 220

Cys Ser Trp Asn Phe Ser Gly Pro Glu Gly Ser Leu Asp Ser Pro Thr
225                 230                 235                 240

Asp Leu Ser Ser Pro Thr Asp Val Gly Leu Asp Cys Phe Phe Tyr Ile
                245                 250                 255

Ser Val Tyr Pro Gly Tyr Gly Val Glu Ile Lys Val Gln Asn Ile Ser
            260                 265                 270

Leu Arg Glu Gly Glu Thr Val Thr Val Glu Gly Leu Gly Gly Pro Asp
        275                 280                 285

Pro Leu Pro Leu Ala Asn Gln Ser Phe Leu Leu Arg Gly Gln Val Ile
    290                 295                 300

Arg Ser Pro Thr His Gln Ala Ala Leu Arg Phe Gln Ser Leu Pro Pro
305                 310                 315                 320

Pro Ala Gly Pro Gly Thr Phe His Phe His Tyr Gln Ala Tyr Leu Leu
                325                 330                 335

Ser Cys His Phe Pro Arg Arg Pro Ala Tyr Gly Asp Val Thr Val Thr
            340                 345                 350

Ser Leu His Pro Gly Gly Ser Ala Arg Phe His Cys Ala Thr Gly Tyr
        355                 360                 365

Gln Leu Lys Gly Ala Arg His Leu Thr Cys Leu Asn Ala Thr Gln Pro
    370                 375                 380

Phe Trp Asp Ser Lys Glu Pro Val Cys Ile Ala Ala Cys Gly Gly Val
385                 390                 395                 400
```

```
Ile Arg Asn Ala Thr Thr Gly Arg Ile Val Ser Pro Gly Phe Pro Gly
            405                 410                 415

Asn Tyr Ser Asn Asn Leu Thr Cys His Trp Leu Leu Glu Ala Pro Glu
        420                 425                 430

Gly Gln Arg Leu His Leu His Phe Glu Lys Val Ser Leu Ala Glu Asp
    435                 440                 445

Asp Asp Arg Leu Ile Ile Arg Asn Gly Asp Asn Val Glu Ala Pro Pro
450                 455                 460

Val Tyr Asp Ser Tyr Glu Val Glu Tyr Leu Pro Ile Glu Gly Leu Leu
465                 470                 475                 480

Ser Ser Gly Lys His Phe Phe Val Glu Leu Ser Thr Asp Ser Ser Gly
                485                 490                 495

Ala Ala Ala Gly Met Ala Leu Arg Tyr Glu Ala Phe Gln Gln Gly His
            500                 505                 510

Cys Tyr Glu Pro Phe Val Lys Tyr Gly Asn Phe Ser Ser Ser Thr Pro
        515                 520                 525

Thr Tyr Pro Val Gly Thr Thr Val Glu Phe Ser Cys Asp Pro Gly Tyr
    530                 535                 540

Thr Leu Glu Gln Gly Ser Ile Ile Ile Glu Cys Val Asp Pro His Asp
545                 550                 555                 560

Pro Gln Trp Asn Glu Thr Glu Pro Ala Cys Arg Ala Val Cys Ser Gly
                565                 570                 575

Glu Ile Thr Asp Ser Ala Gly Val Val Leu Ser Pro Asn Trp Pro Glu
            580                 585                 590

Pro Tyr Gly Arg Gly Gln Asp Cys Ile Trp Gly Val His Val Glu Glu
        595                 600                 605

Asp Lys Arg Ile Met Leu Asp Ile Arg Val Leu Arg Ile Gly Pro Gly
    610                 615                 620

Asp Val Leu Thr Phe Tyr Asp Gly Asp Asp Leu Thr Ala Arg Val Leu
625                 630                 635                 640

Gly Gln Tyr Ser Gly Pro Arg Ser His Phe Lys Leu Phe Thr Ser Met
                645                 650                 655

Ala Asp Val Thr Ile Gln Phe Gln Ser Asp Pro Gly Thr Ser Val Leu
            660                 665                 670

Gly Tyr Gln Gln Gly Phe Val Ile His Phe Phe Glu Val Pro Arg Asn
        675                 680                 685

Asp Thr Cys Pro Glu Leu Pro Glu Ile Pro Asn Gly Trp Lys Ser Pro
    690                 695                 700

Ser Gln Pro Glu Leu Val His Gly Thr Val Val Thr Tyr Gln Cys Tyr
705                 710                 715                 720

Pro Gly Tyr Gln Val Val Gly Ser Ser Val Leu Met Cys Gln Trp Asp
                725                 730                 735

Leu Thr Trp Ser Glu Asp Leu Pro Ser Cys Gln Arg Val Thr Ser Cys
            740                 745                 750

His Asp Pro Gly Asp Val Glu His Ser Arg Leu Ile Ser Ser Pro
        755                 760                 765

Lys Phe Pro Val Gly Ala Thr Val Gln Tyr Ile Cys Asp Gln Gly Phe
    770                 775                 780

Val Leu Met Gly Ser Ser Ile Leu Thr Cys His Asp Arg Gln Ala Gly
785                 790                 795                 800

Ser Pro Lys Trp Ser Asp Arg Ala Pro Lys Cys Leu Leu Glu Gln Leu
                805                 810                 815

Lys Pro Cys His Gly Leu Ser Ala Pro Glu Asn Gly Ala Arg Ser Pro
```

```
                        820                 825                 830
Glu Lys Gln Leu His Pro Ala Gly Ala Thr Ile His Phe Ser Cys Ala
            835                 840                 845

Pro Gly Tyr Val Leu Lys Gly Gln Ala Ser Ile Lys Cys Val Pro Gly
        850                 855                 860

His Pro Ser His Trp Ser Asp Pro Pro Ile Cys Arg Ala Ala Ser
865                 870                 875                 880

Leu Asp Gly Phe Tyr Asn Ser Arg Ser Leu Asp Val Ala Lys Ala Pro
                885                 890                 895

Ala Ala Ser Ser Thr Leu Asp Ala Ala His Ile Ala Ala Ile Phe
            900                 905                 910

Leu Pro Leu Val Ala Met Val Leu Leu Val Gly Gly Val Tyr Phe Tyr
            915                 920                 925

Phe Ser Arg Leu Gln Gly Lys Ser Ser Leu Gln Leu Pro Arg Pro Arg
        930                 935                 940

Pro Arg Pro Tyr Asn Arg Ile Thr Ile Glu Ser Ala Phe Asp Asn Pro
945                 950                 955                 960

Thr Tyr Glu Thr Gly Ser Leu Ser Phe Ala Gly Asp Glu Arg Ile
                965                 970                 975

<210> SEQ ID NO 7
<211> LENGTH: 994
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Arg Pro Val Ala Leu Leu Leu Pro Ser Leu Leu Ala Leu Leu
1               5                   10                  15

Ala His Gly Leu Ser Leu Glu Ala Pro Thr Val Gly Lys Gly Gln Ala
            20                  25                  30

Pro Gly Ile Glu Glu Thr Asp Gly Glu Leu Thr Ala Ala Pro Thr Pro
        35                  40                  45

Glu Gln Pro Glu Arg Gly Val His Phe Val Thr Thr Ala Pro Thr Leu
    50                  55                  60

Lys Leu Leu Asn His His Pro Leu Leu Glu Glu Phe Leu Gln Glu Gly
65                  70                  75                  80

Leu Glu Lys Gly Asp Glu Glu Leu Arg Pro Ala Leu Pro Phe Gln Pro
                85                  90                  95

Asp Pro Pro Ala Pro Phe Thr Pro Ser Pro Leu Pro Arg Leu Ala Asn
            100                 105                 110

Gln Asp Ser Arg Pro Val Phe Thr Ser Pro Thr Pro Ala Met Ala Ala
        115                 120                 125

Val Pro Thr Gln Pro Gln Ser Lys Glu Gly Pro Trp Ser Pro Glu Ser
    130                 135                 140

Glu Ser Pro Met Leu Arg Ile Thr Ala Pro Leu Pro Pro Gly Pro Ser
145                 150                 155                 160

Met Ala Val Pro Thr Leu Gly Pro Gly Glu Ile Ala Ser Thr Thr Pro
                165                 170                 175

Pro Ser Arg Ala Trp Thr Pro Thr Gln Glu Gly Pro Gly Asp Met Gly
            180                 185                 190

Arg Pro Trp Val Ala Glu Val Val Ser Gln Gly Ala Gly Ile Gly Ile
        195                 200                 205
```

```
Gln Gly Thr Ile Thr Ser Ser Thr Ala Ser Gly Asp Asp Glu Glu Thr
    210                 215                 220

Thr Thr Thr Thr Thr Ile Ile Thr Thr Thr Ile Thr Thr Val Gln Thr
225                 230                 235                 240

Pro Gly Pro Cys Ser Trp Asn Phe Ser Gly Pro Glu Gly Ser Leu Asp
                245                 250                 255

Ser Pro Thr Asp Leu Ser Ser Pro Thr Asp Val Gly Leu Asp Cys Phe
            260                 265                 270

Phe Tyr Ile Ser Val Tyr Pro Gly Tyr Gly Val Glu Ile Lys Val Gln
        275                 280                 285

Asn Ile Ser Leu Arg Glu Gly Glu Thr Val Thr Val Glu Gly Leu Gly
    290                 295                 300

Gly Pro Asp Pro Leu Pro Leu Ala Asn Gln Ser Phe Leu Leu Arg Gly
305                 310                 315                 320

Gln Val Ile Arg Ser Pro Thr His Gln Ala Ala Leu Arg Phe Gln Ser
                325                 330                 335

Leu Pro Pro Pro Ala Gly Pro Gly Thr Phe His Phe His Tyr Gln Ala
            340                 345                 350

Tyr Leu Leu Ser Cys His Phe Pro Arg Arg Pro Ala Tyr Gly Asp Val
        355                 360                 365

Thr Val Thr Ser Leu His Pro Gly Gly Ser Ala Arg Phe His Cys Ala
    370                 375                 380

Thr Gly Tyr Gln Leu Lys Gly Ala Arg His Leu Thr Cys Leu Asn Ala
385                 390                 395                 400

Thr Gln Pro Phe Trp Asp Ser Lys Glu Pro Val Cys Ile Gly Glu Cys
                405                 410                 415

Pro Gly Val Ile Arg Asn Ala Thr Thr Gly Arg Ile Val Ser Pro Gly
            420                 425                 430

Phe Pro Gly Asn Tyr Ser Asn Asn Leu Thr Cys His Trp Leu Leu Glu
        435                 440                 445

Ala Pro Glu Gly Gln Arg Leu His Leu His Phe Glu Lys Val Ser Leu
    450                 455                 460

Ala Glu Asp Asp Arg Leu Ile Ile Arg Asn Gly Asp Asn Val Glu
465                 470                 475                 480

Ala Pro Pro Val Tyr Asp Ser Tyr Glu Val Glu Tyr Leu Pro Ile Glu
                485                 490                 495

Gly Leu Leu Ser Ser Gly Lys His Phe Phe Val Glu Leu Ser Thr Asp
            500                 505                 510

Ser Ser Gly Ala Ala Ala Gly Met Ala Leu Arg Tyr Glu Ala Phe Gln
        515                 520                 525

Gln Gly His Cys Tyr Glu Pro Phe Val Lys Tyr Gly Asn Phe Ser Ser
    530                 535                 540

Ser Thr Pro Thr Tyr Pro Val Gly Thr Thr Val Glu Phe Ser Cys Asp
545                 550                 555                 560

Pro Gly Tyr Thr Leu Glu Gln Gly Ser Ile Ile Glu Cys Val Asp
                565                 570                 575

Pro His Asp Pro Gln Trp Asn Glu Thr Glu Pro Ala Cys Arg Ala Val
            580                 585                 590

Cys Ser Gly Glu Ile Thr Asp Ser Ala Gly Val Val Leu Ser Pro Asn
        595                 600                 605

Trp Pro Glu Pro Tyr Gly Arg Gly Gln Asp Cys Ile Trp Gly Val His
    610                 615                 620
```

-continued

Val Glu Glu Asp Lys Arg Ile Met Leu Asp Ile Arg Val Leu Arg Ile
625                 630                 635                 640

Gly Pro Gly Asp Val Leu Thr Phe Tyr Asp Gly Asp Leu Thr Ala
            645                 650                 655

Arg Val Leu Gly Gln Tyr Ser Gly Pro Arg Ser His Phe Lys Leu Phe
        660                 665                 670

Thr Ser Met Ala Asp Val Thr Ile Gln Phe Gln Ser Asp Pro Gly Thr
            675                 680                 685

Ser Val Leu Gly Tyr Gln Gln Gly Phe Val Ile His Phe Phe Glu Val
        690                 695                 700

Pro Arg Asn Asp Thr Cys Pro Glu Leu Pro Glu Ile Pro Asn Gly Trp
705                 710                 715                 720

Lys Ser Pro Ser Gln Pro Glu Leu Val His Gly Thr Val Thr Tyr
            725                 730                 735

Gln Cys Tyr Pro Gly Tyr Gln Val Val Gly Ser Ser Val Leu Met Cys
            740                 745                 750

Gln Trp Asp Leu Thr Trp Ser Glu Asp Leu Pro Ser Cys Gln Arg Val
        755                 760                 765

Thr Ser Cys His Asp Pro Gly Asp Val Glu His Ser Arg Arg Leu Ile
770                 775                 780

Ser Ser Pro Lys Phe Pro Val Gly Ala Thr Val Gln Tyr Ile Cys Asp
785                 790                 795                 800

Gln Gly Phe Val Leu Met Gly Ser Ser Ile Leu Thr Cys His Asp Arg
            805                 810                 815

Gln Ala Gly Ser Pro Lys Trp Ser Asp Arg Ala Pro Lys Cys Leu Leu
        820                 825                 830

Glu Gln Leu Lys Pro Cys His Gly Leu Ser Ala Pro Glu Asn Gly Ala
        835                 840                 845

Arg Ser Pro Glu Lys Gln Leu His Pro Ala Gly Ala Thr Ile His Phe
        850                 855                 860

Ser Cys Ala Pro Gly Tyr Val Leu Lys Gly Gln Ala Ser Ile Lys Cys
865                 870                 875                 880

Val Pro Gly His Pro Ser His Trp Ser Asp Pro Pro Ile Cys Arg
            885                 890                 895

Ala Ala Ser Leu Asp Gly Phe Tyr Asn Ser Arg Ser Leu Asp Val Ala
            900                 905                 910

Lys Ala Pro Ala Ala Ser Ser Thr Leu Asp Ala Ala His Ile Ala Ala
        915                 920                 925

Ala Ile Phe Leu Pro Leu Val Ala Met Val Leu Leu Val Gly Gly Val
        930                 935                 940

Tyr Phe Tyr Phe Ser Arg Leu Gln Gly Lys Ser Ser Leu Gln Leu Pro
945                 950                 955                 960

Arg Pro Arg Pro Arg Pro Tyr Asn Arg Ile Thr Ile Glu Ser Ala Phe
            965                 970                 975

Asp Asn Pro Thr Tyr Glu Thr Gly Ser Leu Ser Phe Ala Gly Asp Glu
            980                 985                 990

Arg Ile

<210> SEQ ID NO 8
<211> LENGTH: 3483
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 8

```
atggagacag acacactcct gctatgggta ctgctgctct gggttccgg  gtccactggt    60
gacggcgcgc ctggatccct gagcctggag gccccaaccg tggggaaagg acaagcccca   120
ggcatcgagg agacagatgg cgagctgaca gcagccccca cacctgagca gccagaacga   180
ggcgtccact ttgtcacaac agccccacc  ttgaagctgc tcaaccacca cccgctgctt   240
gaggaattcc tacaagaggg gctggaaaag ggagatgagg agttgaggcc agcactgccc   300
ttccagcctg acccacctgc acccttcacc ccaagtcccc ttccccgcct ggccaaccag   360
gacagccgcc ctgtctttac cagccccact ccagccatgg ctgcggtacc cactcagccc   420
cagtccaagg agggaccctg gagtccggag tcagagtccc ctatgcttcg aatcacagct   480
cccctacctc cagggcccag catggcagtg cccaccctag cccagggga  gatagccagc   540
actacacccc ccagcagagc ctggacacca acccaagagg gtcctggaga catgggaagg   600
ccgtgggttg cagaggttgt gtcccagggc gcggggatcg gatccaggg  gaccatcacc   660
tcctccacag cttcaggaga tgatgaggag accaccacta ccaccaccat catcaccacc   720
accatcacca gcagtccagac accaggccct tgtagctgga atttctcagg cccagagggc   780
tctctggact cccctacaga cctcagctcc cccactgatg ttggcctgga ctgcttcttc   840
tacatctctg tctaccctgg ctatggcgtg gaaatcaagg tccagaatat cagcctccgg   900
gaagggagag cagtgactgt ggaaggcctg gggggccgg  acccactgcc cctggccaac   960
cagtctttcc tgctgcgggg ccaagtcatc cgcagcccca cccaccaagc ggccctgagg  1020
ttccagagcc tcgccaccgg cctggcct   gcaccttcc atttccatta ccaagcctat  1080
ctcctgagct gccactttcc ccgtcgtcca gcttatggag atgtgactgt caccagcctc  1140
cacccagggg gtagtgcccg cttccattgt gccactggct accagctgaa gggcgccagg  1200
catctcacct gtctcaatgc cacccagccc ttctgggatt caaaggagcc cgtctgcatc  1260
gctgcttgcg gcggagtgat ccgcaatgcc accaccggcc gcatcgtctc tccaggcttc  1320
ccgggcaact acagcaacaa cctcacctgt cactggctgc ttgaggctcc tgagggcag   1380
cggctacacc tgcactttga aaggtttcc ctggcagagg atgatgacag gctcatcatt  1440
cgcaatgggg acaacgtgga ggccccacca gtgtatgatt cctatgaggt ggaataccctg  1500
cccattgagg gcctgctcag ctctggcaaa cacttctttg ttgagctcag tactgacagc  1560
agcggggcag ctgcaggcat ggccctgcgc tatgaggcct tccagcaggg ccattgctat  1620
gagcccttg  tcaaatacgg taacttcagc agcagcacac ccacctaccc tgtgggtacc  1680
actgtggagt tcagctgcga ccctggctac accctggagc agggctccat catcatcgag  1740
tgtgttgacc cccacgaccc ccagtggaat gagacagagc cagcctgccg agccgtgtgc  1800
agcggggaga tcacagactc ggctggcgtg gtactctctc ccaactggcc agagccctac  1860
ggtcgtgggc aggattgtat ctggggtgtg catgtggaag aggacaagcg catcatgctg  1920
gacatccgag tgctgcgcat aggccctggt gatgtgctta ccttctatga tgggatgac   1980
ctgacggccc gggttctggg ccagtactca gggcccgta  gccacttcaa gctctttacc  2040
tccatggctg atgtcaccat tcagttccag tcggacccccg gacctcagt  gctgggctac  2100
cagcagggct tcgtcatcca cttctttgag gtgccccgca atgacacatg tccggagctg  2160
cctgagatcc ccaatggctg gaagagccca tcgcagcctg agctagtgca cggcaccgtg  2220
gtcacttacc agtgctaccc tggctaccag gtagtgggat ccagtgtcct catgtgccag  2280
```

```
tgggacctaa cttggagtga ggacctgccc tcatgccaga gggtgacttc ctgccacgat   2340
cctggagatg tggagcacag ccgacgcctc atatccagcc ccaagtttcc cgtgggggcc   2400
accgtgcaat atatctgtga ccagggtttt gtgctgatgg gcagctccat cctcacctgc   2460
catgatcgcc aggctggcag ccccaagtgg agtgaccggg cccctaaatg tctcctggaa   2520
cagctcaagc catgccatgg tctcagtgcc cctgagaatg gtgcccgaag tcctgagaag   2580
cagctacacc cagcagggc caccatccac ttctcgtgtg ccctggcta tgtgctgaag   2640 ggccaggcca gcatcaagtg tgtgcctggg caccctcgc attggagtga ccccccaccc   2700
atctgtaggg ctgcctctct ggatgggttc tacaacagtc gcagcctgga tgttgccaag   2760
gcacctgctg cctccagcac cctggatgct gcccacctgg ccggccacag atctgtcgag   2820
tgcccaccgt gccagcacc acctgtggca ggaccgtcag tcttcctctt ccccccaaaa   2880
cccaaggaca ccctcatgat ctcccggacc cctgaggtca cgtgcgtggt ggtggacgtg   2940
agccacgaag accccgaggt ccagttcaac tggtacgtgg acggcgtgga ggtgcataat   3000
gccaagacaa agccacggga ggagcagttc aacagcacgt tccgtgtggt cagcgtcctc   3060
accgttgtgc accaggactg gctgaacggc aaggagtaca agtgcaaggt ctccaacaaa   3120
ggcctcccag ccccatcga gaaaaccatc tccaaaacca agggcagcc ccgagaacca   3180 caggtgtaca ccctgccccc atccagggag gagatgacca gaaccaggt cagcctgacc   3240 tgcctggtca aaggcttcta ccccagcgac atcgccgtgg agtgggagag caatgggcag   3300
ccggagaaca actacaagac cacgcctccc atgctggact ccgacggctc cttcttcctc   3360
tacagcaagc tcaccgtgga caagagcagg tggcagcagg ggaacgtctt ctcatgctcc   3420
gtgatgcatg aggctctgca caaccactac acgcagaaga gcctctccct gtctccgggt   3480
tga                                                                3483
```

<210> SEQ ID NO 9
<211> LENGTH: 1160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Met Glu Thr Asp Thr Leu Leu Leu Trp Val Leu Leu Leu Trp Val Pro
1               5                   10                  15

Gly Ser Thr Gly Asp Gly Ala Pro Gly Ser Leu Ser Leu Glu Ala Pro
            20                  25                  30

Thr Val Gly Lys Gly Gln Ala Pro Gly Ile Glu Glu Thr Asp Gly Glu
        35                  40                  45

Leu Thr Ala Ala Pro Thr Pro Glu Gln Pro Glu Arg Gly Val His Phe
    50                  55                  60

Val Thr Thr Ala Pro Thr Leu Lys Leu Leu Asn His His Pro Leu Leu
65                  70                  75                  80

Glu Glu Phe Leu Gln Glu Gly Leu Glu Lys Gly Asp Glu Glu Leu Arg
                85                  90                  95

Pro Ala Leu Pro Phe Gln Pro Asp Pro Ala Pro Phe Thr Pro Ser
            100                 105                 110

Pro Leu Pro Arg Leu Ala Asn Gln Asp Ser Arg Pro Val Phe Thr Ser
        115                 120                 125
```

```
Pro Thr Pro Ala Met Ala Ala Val Pro Thr Gln Pro Gln Ser Lys Glu
    130                 135                 140

Gly Pro Trp Ser Pro Glu Ser Glu Ser Pro Met Leu Arg Ile Thr Ala
145                 150                 155                 160

Pro Leu Pro Pro Gly Pro Ser Met Ala Val Pro Thr Leu Gly Pro Gly
                165                 170                 175

Glu Ile Ala Ser Thr Thr Pro Pro Ser Arg Ala Trp Thr Pro Thr Gln
                180                 185                 190

Glu Gly Pro Gly Asp Met Gly Arg Pro Trp Val Ala Glu Val Val Ser
            195                 200                 205

Gln Gly Ala Gly Ile Gly Ile Gln Gly Thr Ile Thr Ser Ser Thr Ala
    210                 215                 220

Ser Gly Asp Asp Glu Glu Thr Thr Thr Thr Thr Ile Ile Thr Thr
225                 230                 235                 240

Thr Ile Thr Thr Val Gln Thr Pro Gly Pro Cys Ser Trp Asn Phe Ser
                245                 250                 255

Gly Pro Glu Gly Ser Leu Asp Ser Pro Thr Asp Leu Ser Ser Pro Thr
                260                 265                 270

Asp Val Gly Leu Asp Cys Phe Phe Tyr Ile Ser Val Tyr Pro Gly Tyr
            275                 280                 285

Gly Val Glu Ile Lys Val Gln Asn Ile Ser Leu Arg Glu Gly Glu Thr
    290                 295                 300

Val Thr Val Glu Gly Leu Gly Gly Pro Asp Pro Leu Pro Leu Ala Asn
305                 310                 315                 320

Gln Ser Phe Leu Leu Arg Gly Gln Val Ile Arg Ser Pro Thr His Gln
                325                 330                 335

Ala Ala Leu Arg Phe Gln Ser Leu Pro Pro Ala Gly Pro Gly Thr
                340                 345                 350

Phe His Phe His Tyr Gln Ala Tyr Leu Leu Ser Cys His Phe Pro Arg
            355                 360                 365

Arg Pro Ala Tyr Gly Asp Val Thr Val Thr Ser Leu His Pro Gly Gly
    370                 375                 380

Ser Ala Arg Phe His Cys Ala Thr Gly Tyr Gln Leu Lys Gly Ala Arg
385                 390                 395                 400

His Leu Thr Cys Leu Asn Ala Thr Gln Pro Phe Trp Asp Ser Lys Glu
                405                 410                 415

Pro Val Cys Ile Ala Ala Cys Gly Gly Val Ile Arg Asn Ala Thr Thr
            420                 425                 430

Gly Arg Ile Val Ser Pro Gly Phe Pro Gly Asn Tyr Ser Asn Asn Leu
    435                 440                 445

Thr Cys His Trp Leu Leu Glu Ala Pro Glu Gly Gln Arg Leu His Leu
450                 455                 460

His Phe Glu Lys Val Ser Leu Ala Glu Asp Asp Arg Leu Ile Ile
465                 470                 475                 480

Arg Asn Gly Asp Asn Val Glu Ala Pro Val Tyr Asp Ser Tyr Glu
                485                 490                 495

Val Glu Tyr Leu Pro Ile Glu Gly Leu Leu Ser Ser Gly Lys His Phe
            500                 505                 510

Phe Val Glu Leu Ser Thr Asp Ser Ser Gly Ala Ala Gly Met Ala
                515                 520                 525

Leu Arg Tyr Glu Ala Phe Gln Gln Gly His Cys Tyr Glu Pro Phe Val
    530                 535                 540

Lys Tyr Gly Asn Phe Ser Ser Ser Thr Pro Thr Tyr Pro Val Gly Thr
```

```
            545                 550                 555                 560
        Thr Val Glu Phe Ser Cys Asp Pro Gly Tyr Thr Leu Glu Gln Gly Ser
                            565                 570                 575

Ile Ile Ile Glu Cys Val Asp Pro His Asp Pro Gln Trp Asn Glu Thr
                            580                 585                 590

Glu Pro Ala Cys Arg Ala Val Cys Ser Gly Glu Ile Thr Asp Ser Ala
                            595                 600                 605

Gly Val Val Leu Ser Pro Asn Trp Pro Glu Pro Tyr Gly Arg Gly Gln
                            610                 615                 620

Asp Cys Ile Trp Gly Val His Val Glu Glu Asp Lys Arg Ile Met Leu
        625                 630                 635                 640

Asp Ile Arg Val Leu Arg Ile Gly Pro Gly Asp Val Leu Thr Phe Tyr
                            645                 650                 655

Asp Gly Asp Asp Leu Thr Ala Arg Val Leu Gly Gln Tyr Ser Gly Pro
                            660                 665                 670

Arg Ser His Phe Lys Leu Phe Thr Ser Met Ala Asp Val Thr Ile Gln
                            675                 680                 685

Phe Gln Ser Asp Pro Gly Thr Ser Val Leu Gly Tyr Gln Gln Gly Phe
                            690                 695                 700

Val Ile His Phe Phe Glu Val Pro Arg Asn Asp Thr Cys Pro Glu Leu
        705                 710                 715                 720

Pro Glu Ile Pro Asn Gly Trp Lys Ser Pro Ser Gln Pro Glu Leu Val
                            725                 730                 735

His Gly Thr Val Val Thr Tyr Gln Cys Tyr Pro Gly Tyr Gln Val Val
                            740                 745                 750

Gly Ser Ser Val Leu Met Cys Gln Trp Asp Leu Thr Trp Ser Glu Asp
                            755                 760                 765

Leu Pro Ser Cys Gln Arg Val Thr Ser Cys His Asp Pro Gly Asp Val
                            770                 775                 780

Glu His Ser Arg Arg Leu Ile Ser Ser Pro Lys Phe Pro Val Gly Ala
        785                 790                 795                 800

Thr Val Gln Tyr Ile Cys Asp Gln Gly Phe Val Leu Met Gly Ser Ser
                            805                 810                 815

Ile Leu Thr Cys His Asp Arg Gln Ala Gly Ser Pro Lys Trp Ser Asp
                            820                 825                 830

Arg Ala Pro Lys Cys Leu Leu Glu Gln Leu Lys Pro Cys His Gly Leu
                            835                 840                 845

Ser Ala Pro Glu Asn Gly Ala Arg Ser Pro Glu Lys Gln Leu His Pro
                            850                 855                 860

Ala Gly Ala Thr Ile His Phe Ser Cys Ala Pro Gly Tyr Val Leu Lys
        865                 870                 875                 880

Gly Gln Ala Ser Ile Lys Cys Val Pro Gly His Pro Ser His Trp Ser
                            885                 890                 895

Asp Pro Pro Ile Cys Arg Ala Ala Ser Leu Asp Gly Phe Tyr Asn
                            900                 905                 910

Ser Arg Ser Leu Asp Val Ala Lys Ala Pro Ala Ser Ser Thr Leu
                            915                 920                 925

Asp Ala Ala His Leu Ala Gly His Arg Ser Val Glu Cys Pro Pro Cys
        930                 935                 940

Pro Ala Pro Pro Val Ala Gly Pro Ser Val Phe Leu Phe Pro Pro Lys
        945                 950                 955                 960

Pro Lys Asp Thr Leu Met Ile Ser Arg Thr Pro Glu Val Thr Cys Val
                            965                 970                 975
```

```
Val Val Asp Val Ser His Glu Asp Pro Glu Val Gln Phe Asn Trp Tyr
            980                 985                 990

Val Asp Gly Val Glu Val His Asn Ala Lys Thr Lys Pro Arg Glu Glu
        995                 1000                1005

Gln Phe Asn Ser Thr Phe Arg Val Val Ser Val Leu Thr Val Val
    1010                1015                1020

His Gln Asp Trp Leu Asn Gly Lys Glu Tyr Lys Cys Lys Val Ser
    1025                1030                1035

Asn Lys Gly Leu Pro Ala Pro Ile Glu Lys Thr Ile Ser Lys Thr
    1040                1045                1050

Lys Gly Gln Pro Arg Glu Pro Gln Val Tyr Thr Leu Pro Pro Ser
    1055                1060                1065

Arg Glu Glu Met Thr Lys Asn Gln Val Ser Leu Thr Cys Leu Val
    1070                1075                1080

Lys Gly Phe Tyr Pro Ser Asp Ile Ala Val Glu Trp Glu Ser Asn
    1085                1090                1095

Gly Gln Pro Glu Asn Asn Tyr Lys Thr Thr Pro Pro Met Leu Asp
    1100                1105                1110

Ser Asp Gly Ser Phe Phe Leu Tyr Ser Lys Leu Thr Val Asp Lys
    1115                1120                1125

Ser Arg Trp Gln Gln Gly Asn Val Phe Ser Cys Ser Val Met His
    1130                1135                1140

Glu Ala Leu His Asn His Tyr Thr Gln Lys Ser Leu Ser Leu Ser
    1145                1150                1155

Pro Gly
    1160

<210> SEQ ID NO 10
<211> LENGTH: 2919
<212> TYPE: DNA
<213> ORGANISM: Mus sp.

<400> SEQUENCE: 10
ctctcctcag aggctccgat cacgggggaa ggtcatgcca cgggcatcag ggagacggat      60
ggggagctga ccgcagcccc tacacctgag cagtcagacc gaggcgtcca cttcgtcacc     120
acagccccta ccctcaagct gctcaaccac cacccacttc tggaagaatt tcttcaagag     180
gggctagaaa gagaggaagc gccgcagcct gcactgccct ccagccggga ctcacctaca     240
cactttactc caagccccct cccccgcctc accaaccagg acaaccgccc cgtctttacc     300
agtccgactc cagccgtggc tgcagcaccc acccagcccc actccaggga gaaaccttgg     360
aacctagaat ccaaaccccc tgagctttct atcacatcgt cccttcctcc agggccgagt     420
atggcagtgc ccacactgct cccagaggac agacccagta ctacaccccc tagccaagca     480
tggactccaa ctcaggaggg tcctggagac atggacagac cttgggttcc agaggtcatg     540
tctaagacca cagggcttgg tgtcgaggga accattgcca cctccacagc ttcagggat      600 gacgaagaga ccactaccac catcattacc actactgtca ccacagttca gccaccaggc     660
ccctgtagct ggaatttctc aggcccagag ggctctctgg attcccccac ggcccccagc     720
tcaccctctg atgttggcct ggactgtttc tactatatct ctgtctaccc tggatatgga     780
gtagagatca aggtggagaa catcagcctt caggaagggg agaccatcac cgtggagggc     840
ctggggggcc ccgatccact gcccttggct aaccagtcgt tcctgctgag ggccaggtc     900 atccgcagcc ccaccaccaa gcagccctga ggttccaga gcctcccgct accgctgggc     960
```

-continued

```
cctggcactt tccatttccg ctaccaagcc tatctcctga gctgccactt tccccgacgt    1020
ccagcgtatg gagatgtgac tgtcaccagt ctccacccag gaggcagcgc ccacttccat    1080
tgtgccactg ctaccagct caagggtgcc aggttcctca cctgtctcaa tgccacccag     1140
cccttttggg attcccaaga gcctgttttgc attgctgctt gtggtggagt gattcggaat   1200
gccaccactg gccgcattgt ctctcctggc ttcccgggga actacagcaa caacctcacc    1260
tgccactggt tgctagaggc tccagagagc cagcggctgc acctgcactt tgaaaaggtc    1320
tccctggcag aagacgacga caggctcatc atccgcaatg aaataacgt ggaggccccg     1380 ccggtgtacg actcctatga ggtggaatac ctgcccattg agggcctgct cagctctggc    1440
agacacttct tcgtggagtt cagtactgac agcagtgggg cagctgcagg catggccctg    1500
cgctatgagg cctccagca aggacattgc tatgagccct ttgtcaaata cggcaacttc     1560
agcagcagtg caccgtccta ccctgtgggt acaactgtgg agttcagctg tgaccctggc    1620
tacaccctgg agcagggctc catcatcatc gaatgcgtcg acctccacga cccccagtgg   1680
aatgagacag agccagcctg ccgagccgtg tgcagcgggg agatcacaga ctctgcaggc    1740
gtggtgctct ctccaaactg gccggagcct tatggccgag gcaggactg catctggggt     1800 gtgcatgtgg aggaggacaa gcgcatcatg ctggacatcc gagtgctgcg cataggctct    1860
ggggatgtac tgaccttcta cgatgggat gacctcacag cccgggtcct gggccaatac     1920
tcagggcccc gtggccactt caagctcttt acctccatgg ccgatgtcac catccagttc    1980
cagtcagacc ctgggacctc ggcgctgggt taccagcaag gatttgtcat ccacttcttt    2040
gaggttcccc gcaacgacac atgtccagag ctacccgaga tccccaacgg ctggaagaac    2100
ccatcacagc ctgagctggt gcacggcacg gtggtcacct atcagtgcta ccctggttac    2160
caggtggtgg gatccagtat tctcatgtgc cagtgggacc taagctggag tgaggacctg    2220
ccttcatgcc agagagtgac atcttgccat gacccagggg atgtggagca cagccgacgc    2280
ctcatatcca gccccaagtt tcccgtggga gcaactgtgc aatatgtctg tgaccagggt    2340
tttgtgctga cggggagtgc cattctcacc tgccatgatc ggcaagcagg cagtcccaag    2400
tggagtgaca gggcccccaa gtgtctcttg gaacaattca gccgtgcca tggcctcagc    2460 gccccggaga atggtgcccg cagccctgag aagcggcttc acccagcagg gccaccatc    2520 cacttctcct gtcccctgg ttatgtgctg aagggccagg ccagcatcaa atgcgtgcct    2580
ggacacccct cgcattggag tgacccacca cccatctgta gggctgcctc tctggatggg    2640
ttctacaacg gccgtagcct ggatgttgcc aaggcacctg ccgcctccag tgccctggac    2700
gctgctcacc tggctgctgc catcttccta ccattggtgg ccatggtgtt gctggtggga    2760
ggagtgtacc tctattttc cagattccag gggaaaagtc ccctgcaact tccccgaact    2820
catcctcgcc cctataaccg catcacggta gagtcagcat tgacaatcc aacttatgag     2880 actggatctc tttcctttgc aggagacgag agaatatga                           2919
```

<210> SEQ ID NO 11
<211> LENGTH: 972
<212> TYPE: PRT
<213> ORGANISM: Mus sp.

<400> SEQUENCE: 11

Leu Ser Ser Glu Ala Pro Ile Thr Gly Glu Gly His Ala Thr Gly Ile
1               5                   10                  15

Arg Glu Thr Asp Gly Glu Leu Thr Ala Ala Pro Thr Pro Glu Gln Ser

-continued

```
                20                  25                  30
Asp Arg Gly Val His Phe Val Thr Thr Ala Pro Thr Leu Lys Leu Leu
        35                  40                  45
Asn His His Pro Leu Leu Glu Glu Phe Leu Gln Gly Leu Glu Arg
    50                  55                  60
Glu Glu Ala Pro Gln Pro Ala Leu Pro Phe Gln Pro Asp Ser Pro Thr
65                  70                  75                  80
His Phe Thr Pro Ser Pro Leu Pro Arg Leu Thr Asn Gln Asp Asn Arg
                85                  90                  95
Pro Val Phe Thr Ser Pro Thr Pro Ala Val Ala Ala Pro Thr Gln
            100                 105                 110
Pro His Ser Arg Glu Lys Pro Trp Asn Leu Glu Ser Lys Pro Pro Glu
        115                 120                 125
Leu Ser Ile Thr Ser Ser Leu Pro Pro Gly Pro Ser Met Ala Val Pro
    130                 135                 140
Thr Leu Leu Pro Glu Asp Arg Pro Ser Thr Thr Pro Pro Ser Gln Ala
145                 150                 155                 160
Trp Thr Pro Thr Gln Glu Gly Pro Gly Asp Met Asp Arg Pro Trp Val
                165                 170                 175
Pro Glu Val Met Ser Lys Thr Thr Gly Leu Gly Val Glu Gly Thr Ile
            180                 185                 190
Ala Thr Ser Thr Ala Ser Gly Asp Asp Glu Thr Thr Thr Thr Ile
        195                 200                 205
Ile Thr Thr Thr Val Thr Thr Val Gln Pro Pro Gly Pro Cys Ser Trp
    210                 215                 220
Asn Phe Ser Gly Pro Glu Gly Ser Leu Asp Ser Pro Thr Ala Pro Ser
225                 230                 235                 240
Ser Pro Ser Asp Val Gly Leu Asp Cys Phe Tyr Tyr Ile Ser Val Tyr
                245                 250                 255
Pro Gly Tyr Gly Val Glu Ile Lys Val Glu Asn Ile Ser Leu Gln Glu
            260                 265                 270
Gly Glu Thr Ile Thr Val Glu Gly Leu Gly Gly Pro Asp Pro Leu Pro
        275                 280                 285
Leu Ala Asn Gln Ser Phe Leu Leu Arg Gly Gln Val Ile Arg Ser Pro
    290                 295                 300
Thr His Gln Ala Ala Leu Arg Phe Gln Ser Leu Pro Leu Pro Ala Gly
305                 310                 315                 320
Pro Gly Thr Phe His Phe Arg Tyr Gln Ala Tyr Leu Leu Ser Cys His
                325                 330                 335
Phe Pro Arg Arg Pro Ala Tyr Gly Asp Val Thr Val Thr Ser Leu His
            340                 345                 350
Pro Gly Gly Ser Ala His Phe His Cys Ala Thr Gly Tyr Gln Leu Lys
        355                 360                 365
Gly Ala Arg Phe Leu Thr Cys Leu Asn Ala Thr Gln Pro Phe Trp Asp
    370                 375                 380
Ser Gln Glu Pro Val Cys Ile Ala Ala Cys Gly Gly Val Ile Arg Asn
385                 390                 395                 400
Ala Thr Thr Gly Arg Ile Val Ser Pro Gly Phe Pro Gly Asn Tyr Ser
                405                 410                 415
Asn Asn Leu Thr Cys His Trp Leu Leu Glu Ala Pro Glu Ser Gln Arg
            420                 425                 430
Leu His Leu His Phe Glu Lys Val Ser Leu Ala Glu Asp Asp Arg
        435                 440                 445
```

```
Leu Ile Ile Arg Asn Gly Asn Asn Val Glu Ala Pro Pro Val Tyr Asp
    450                 455                 460

Ser Tyr Glu Val Glu Tyr Leu Pro Ile Glu Gly Leu Leu Ser Ser Gly
465                 470                 475                 480

Arg His Phe Phe Val Glu Phe Ser Thr Asp Ser Ser Gly Ala Ala Ala
                485                 490                 495

Gly Met Ala Leu Arg Tyr Glu Ala Phe Gln Gln Gly His Cys Tyr Glu
            500                 505                 510

Pro Phe Val Lys Tyr Gly Asn Phe Ser Ser Ser Ala Pro Ser Tyr Pro
            515                 520                 525

Val Gly Thr Thr Val Glu Phe Ser Cys Asp Pro Gly Tyr Thr Leu Glu
    530                 535                 540

Gln Gly Ser Ile Ile Glu Cys Val Asp Leu His Asp Pro Gln Trp
545                 550                 555                 560

Asn Glu Thr Glu Pro Ala Cys Arg Ala Val Cys Ser Gly Glu Ile Thr
                565                 570                 575

Asp Ser Ala Gly Val Val Leu Ser Pro Asn Trp Pro Glu Pro Tyr Gly
            580                 585                 590

Arg Gly Gln Asp Cys Ile Trp Gly Val His Val Glu Glu Asp Lys Arg
            595                 600                 605

Ile Met Leu Asp Ile Arg Val Leu Arg Ile Gly Ser Gly Asp Val Leu
            610                 615                 620

Thr Phe Tyr Asp Gly Asp Asp Leu Thr Ala Arg Val Leu Gly Gln Tyr
625                 630                 635                 640

Ser Gly Pro Arg Gly His Phe Lys Leu Phe Thr Ser Met Ala Asp Val
                645                 650                 655

Thr Ile Gln Phe Gln Ser Asp Pro Gly Thr Ser Ala Leu Gly Tyr Gln
                660                 665                 670

Gln Gly Phe Val Ile His Phe Phe Glu Val Pro Arg Asn Asp Thr Cys
            675                 680                 685

Pro Glu Leu Pro Glu Ile Pro Asn Gly Trp Lys Asn Pro Ser Gln Pro
690                 695                 700

Glu Leu Val His Gly Thr Val Val Thr Tyr Gln Cys Tyr Pro Gly Tyr
705                 710                 715                 720

Gln Val Val Gly Ser Ser Ile Leu Met Cys Gln Trp Asp Leu Ser Trp
                725                 730                 735

Ser Glu Asp Leu Pro Ser Cys Gln Arg Val Thr Ser Cys His Asp Pro
            740                 745                 750

Gly Asp Val Glu His Ser Arg Arg Leu Ile Ser Ser Pro Lys Phe Pro
            755                 760                 765

Val Gly Ala Thr Val Gln Tyr Val Cys Asp Gln Gly Phe Val Leu Thr
    770                 775                 780

Gly Ser Ala Ile Leu Thr Cys His Asp Arg Gln Ala Gly Ser Pro Lys
785                 790                 795                 800

Trp Ser Asp Arg Ala Pro Lys Cys Leu Leu Glu Gln Phe Lys Pro Cys
                805                 810                 815

His Gly Leu Ser Ala Pro Glu Asn Gly Ala Arg Ser Pro Glu Lys Arg
            820                 825                 830

Leu His Pro Ala Gly Ala Thr Ile His Phe Ser Cys Ala Pro Gly Tyr
        835                 840                 845

Val Leu Lys Gly Gln Ala Ser Ile Lys Cys Val Pro Gly His Pro Ser
    850                 855                 860
```

His Trp Ser Asp Pro Pro Ile Cys Arg Ala Ala Ser Leu Asp Gly
865                 870                 875                 880

Phe Tyr Asn Gly Arg Ser Leu Asp Val Ala Lys Ala Pro Ala Ala Ser
            885                 890                 895

Ser Ala Leu Asp Ala Ala His Leu Ala Ala Ala Ile Phe Leu Pro Leu
            900                 905                 910

Val Ala Met Val Leu Leu Val Gly Gly Val Tyr Leu Tyr Phe Ser Arg
            915                 920                 925

Phe Gln Gly Lys Ser Pro Leu Gln Leu Pro Arg Thr His Pro Arg Pro
            930                 935                 940

Tyr Asn Arg Ile Thr Val Glu Ser Ala Phe Asp Asn Pro Thr Tyr Glu
945                 950                 955                 960

Thr Gly Ser Leu Ser Phe Ala Gly Asp Glu Arg Ile
            965                 970

<210> SEQ ID NO 12
<211> LENGTH: 2919
<212> TYPE: DNA
<213> ORGANISM: Rattus sp.

<400> SEQUENCE: 12

| | | | | | |
|---|---|---|---|---|---|
| ctctcctcag | aggctccaat | cacgggggaa | ggtcaagcca | cgggcatcag | ggagatggat | 60 |
| ggggagctga | ccgcagcccc | tacacctgag | cagtcgagacc | gaggcgtcca | cttcgtcacc | 120 |
| acagcccta | ccctcaagct | actcaaccac | cacccacttc | tggaggaatt | tcttcaagag | 180 |
| gggctagaag | ggagagagga | agctccgagg | ccggcactgc | ccttccagcc | agactcacct | 240 |
| acacccttta | ctccaagccc | ccttccccgc | ctcaccaacc | aggacaaccg | ccctgtcttt | 300 |
| accagtccga | cgccagctgt | agctgcggca | cccacgcagc | cccactccag | aaagaaaccc | 360 |
| tggaacccag | agtcagagcc | cccggagctt | acatcacat | ctcccctccc | tccagggccg | 420 |
| agtatggcag | tgcccacact | gcacccgag | gacagaccca | gcactacacc | cccagccaa | 480 |
| gcatggactc | caacccagga | gggtcctgga | gacatgggca | gaccttgggt | tccagagatc | 540 |
| atgtctaaga | ccacagggct | tggtatcgag | gggaccattg | ccacctccac | agcttcaggg | 600 |
| gatgacgaag | agaccaccac | caccaccatc | attaccaccg | tcaccacaat | tcagccacca | 660 |
| ggccctgta | gctggaattt | ctcaggccg | gagggctctc | tggattcccc | tgcggtcccc | 720 |
| agcgtccccct | ctgatgttgg | cctggactgt | ctctactaca | tctctgtcta | ccctggatat | 780 |
| ggagtcgaga | tcaaggtgaa | gaacatcagc | cttcaggaag | gagagaccat | aaccgtggag | 840 |
| ggcctggggg | ggcctgaccc | actgcccttg | gctaaccagt | cttttcctgct | gaggggccag | 900 |
| gtcatccgca | gccccaccca | ccaggcagcc | gtgaggttcc | aaagccttcc | acttcccgct | 960 |
| ggacctggta | ctttccattt | ccactaccaa | gcctatctcc | tgagctgcca | ctttcctcgg | 1020 |
| cgtccagctt | atggagatgt | gactgtcacc | agcctccacc | caggaggcag | cgcccgcttc | 1080 |
| cactgtgcca | ctggctacca | gctaaagggt | gccaggttcc | tcacctgtct | caatgccacc | 1140 |
| cagcccttt | gggattccca | agagcctgtc | tgcattgctg | cttgtggagg | agtgattcgg | 1200 |
| aatgccacca | ctggccgcat | tgtctctcct | ggctttcccg | gaactacag | caacaacctc | 1260 |
| acctgccact | ggctgctaga | agcccccgag | agccagcggc | tgcacctgca | ctttgaaaag | 1320 |
| gtctccctgg | cagaagatga | cgacaggctc | atcatccgta | acgggaataa | cgtggaggcc | 1380 |
| ccgccagtgt | atgactccta | tgaggtggag | tacctgccca | ttgagggcct | gctcagttct | 1440 |
| ggcagacact | tcttcgtgga | gttcagtact | gacagcagcg | gggcagccgc | aggcatggca | 1500 |

```
ctgcgctatg aggccttcca gcaaggacat tgctatgagc cctttgtcaa atacggtaac    1560
ttcagcagca gcgcaccgtc ctaccctgtg ggtacgactg tggagttcag ctgtgaccct    1620
ggctacaccc tggagcaggg ttccatcatc atcgaatgcg tcgacctccg tgaccccag    1680 tggaatgaga cagaaccagc ctgccgagcc gtgtgcagcg gggagatcac agactctgca    1740
ggcgtggtgc tctctccaaa ctggccggag ccttatggcc gagggcagga ctgcatctgg    1800
ggtgtgcatg tggaggagga caagcgcatc atgctggaca tccgagtgct gcgcataggc    1860
tctggggatg tactgacctt ctacgatggg gatgacctga cagcccgggt cctgggccaa    1920
tactcagggc cccgtggcca cttcaagctc tttacctcca tggctgatgt caccattcag    1980
ttccagtcag accctgggac gtcggcgctg ggttaccagc aaggatttgt catccacttc    2040
tttgaggtgc cccgcaatga cacatgtcca gagcttcccg agatcccaa cggctggaag    2100 aacccatcac agcctgagct ggtgcatggc acggtggtca cctatcagtg ctaccccggt    2160
taccaggtgg tgggatccag tattctcatg tgccagtggg acctgagctg gagtgaggac    2220
ctgccctcat gccagagagt gacatcctgc catgacccag gggatgtgga gcacagccga    2280
cgcctcatat ccagcctcaa gtttcctgtg ggagcaactg tgcagtatat ctgtgaccag    2340
ggttttgtgc tcacgggtag cgccatcctt acttgccatg atcgtcaagc gggcagtccc    2400
aagtggagtg acagggcccc caagtgtctc ttggaacagt tcaaaccatg tcatggcctc    2460 agtgccctg agaatggtgc ccgcagccct gagaagaggc tccacccagc aggggccacc    2520
attcacttct cctgtgcccc tggttatgtg ctgaagggcc aggccagcat caaatgcgtg    2580
cctggacacc cctcacattg gagtgatcct ccacccatct gtagggctgc ttctctggat    2640
gggttctaca acggccgtag cctggatgtt gccaaggcac ctgccacctc cagtgccctg    2700
gatgctgccc acatggcagc tgccatcttt ctaccattgg tggccatggt gttgctggtg    2760
ggaggagtgt acctctattt ctccagactc cagggaaaaa gtcctctgca gcttcccgga    2820
actcatcctc gccccctataa ccgtatcacg gtagagtcag catttgacaa tccaacttat    2880
gagaccggat ctctttcctt tgcaggagac gagagaata                            2919
```

<210> SEQ ID NO 13
<211> LENGTH: 973
<212> TYPE: PRT
<213> ORGANISM: Rattus sp.

<400> SEQUENCE: 13

Leu Ser Ser Glu Ala Pro Ile Thr Gly Glu Gly Gln Ala Thr Gly Ile
1               5                   10                  15

Arg Glu Met Asp Gly Glu Leu Thr Ala Ala Pro Thr Pro Glu Gln Ser
                20                  25                  30

Asp Arg Gly Val His Phe Val Thr Thr Ala Pro Thr Leu Lys Leu Leu
            35                  40                  45

Asn His His Pro Leu Leu Glu Glu Phe Leu Gln Glu Gly Leu Glu Gly
        50                  55                  60

Arg Glu Glu Ala Pro Arg Pro Ala Leu Pro Phe Gln Pro Asp Ser Pro
65                  70                  75                  80

Thr Pro Phe Thr Pro Ser Pro Leu Pro Arg Leu Thr Asn Gln Asp Asn
                85                  90                  95

Arg Pro Val Phe Thr Ser Pro Thr Pro Ala Val Ala Ala Pro Thr
            100                 105                 110

Gln Pro His Ser Arg Lys Lys Pro Trp Asn Pro Glu Ser Glu Pro Pro
        115                 120                 125

```
Glu Leu Tyr Ile Thr Ser Pro Leu Pro Pro Gly Pro Ser Met Ala Val
        130                 135                 140

Pro Thr Leu His Pro Glu Asp Arg Pro Ser Thr Thr Pro Pro Ser Gln
145                 150                 155                 160

Ala Trp Thr Pro Thr Gln Glu Gly Pro Gly Asp Met Gly Arg Pro Trp
                165                 170                 175

Val Pro Glu Ile Met Ser Lys Thr Thr Gly Leu Gly Ile Glu Gly Thr
            180                 185                 190

Ile Ala Thr Ser Thr Ala Ser Gly Asp Asp Glu Glu Thr Thr Thr Thr
        195                 200                 205

Thr Ile Ile Thr Thr Val Thr Thr Ile Gln Pro Pro Gly Pro Cys Ser
    210                 215                 220

Trp Asn Phe Ser Gly Pro Glu Gly Ser Leu Asp Ser Pro Ala Val Pro
225                 230                 235                 240

Ser Val Pro Ser Asp Val Gly Leu Asp Cys Leu Tyr Tyr Ile Ser Val
                245                 250                 255

Tyr Pro Gly Tyr Gly Val Glu Ile Lys Val Lys Asn Ile Ser Leu Gln
            260                 265                 270

Glu Gly Glu Thr Ile Thr Val Glu Gly Leu Gly Gly Pro Asp Pro Leu
        275                 280                 285

Pro Leu Ala Asn Gln Ser Phe Leu Leu Arg Gly Gln Val Ile Arg Ser
290                 295                 300

Pro Thr His Gln Ala Ala Val Arg Phe Gln Ser Leu Pro Leu Pro Ala
305                 310                 315                 320

Gly Pro Gly Thr Phe His Phe His Tyr Gln Ala Tyr Leu Leu Ser Cys
                325                 330                 335

His Phe Pro Arg Arg Pro Ala Tyr Gly Asp Val Thr Val Thr Ser Leu
                340                 345                 350

His Pro Gly Gly Ser Ala Arg Phe His Cys Ala Thr Gly Tyr Gln Leu
            355                 360                 365

Lys Gly Ala Arg Phe Leu Thr Cys Leu Asn Ala Thr Gln Pro Phe Trp
        370                 375                 380

Asp Ser Gln Glu Pro Val Cys Ile Ala Ala Cys Gly Gly Val Ile Arg
385                 390                 395                 400

Asn Ala Thr Thr Gly Arg Ile Val Ser Pro Gly Phe Pro Gly Asn Tyr
                405                 410                 415

Ser Asn Asn Leu Thr Cys His Trp Leu Leu Glu Ala Pro Glu Ser Gln
            420                 425                 430

Arg Leu His Leu His Phe Glu Lys Val Ser Leu Ala Glu Asp Asp Asp
        435                 440                 445

Arg Leu Ile Ile Arg Asn Gly Asn Asn Val Glu Ala Pro Pro Val Tyr
    450                 455                 460

Asp Ser Tyr Glu Val Glu Tyr Leu Pro Ile Glu Gly Leu Leu Ser Ser
465                 470                 475                 480

Gly Arg His Phe Phe Val Glu Phe Ser Thr Asp Ser Ser Gly Ala Ala
                485                 490                 495

Ala Gly Met Ala Leu Arg Tyr Glu Ala Phe Gln Gln Gly His Cys Tyr
            500                 505                 510

Glu Pro Phe Val Lys Tyr Gly Asn Phe Ser Ser Ser Ala Pro Ser Tyr
        515                 520                 525

Pro Val Gly Thr Thr Val Glu Phe Ser Cys Asp Pro Gly Tyr Thr Leu
530                 535                 540
```

-continued

```
Glu Gln Gly Ser Ile Ile Glu Cys Val Asp Leu Arg Asp Pro Gln
545                 550                 555                 560

Trp Asn Glu Thr Glu Pro Ala Cys Arg Ala Val Cys Ser Gly Glu Ile
                565                 570                 575

Thr Asp Ser Ala Gly Val Val Leu Ser Pro Asn Trp Pro Glu Pro Tyr
                580                 585                 590

Gly Arg Gly Gln Asp Cys Ile Trp Gly Val His Val Glu Glu Asp Lys
            595                 600                 605

Arg Ile Met Leu Asp Ile Arg Val Leu Arg Ile Gly Ser Gly Asp Val
        610                 615                 620

Leu Thr Phe Tyr Asp Gly Asp Leu Thr Ala Arg Val Leu Gly Gln
625                 630                 635                 640

Tyr Ser Gly Pro Arg Gly His Phe Lys Leu Phe Thr Ser Met Ala Asp
                645                 650                 655

Val Thr Ile Gln Phe Gln Ser Asp Pro Gly Thr Ser Ala Leu Gly Tyr
                660                 665                 670

Gln Gln Gly Phe Val Ile His Phe Phe Glu Val Pro Arg Asn Asp Thr
            675                 680                 685

Cys Pro Glu Leu Pro Glu Ile Pro Asn Gly Trp Lys Asn Pro Ser Gln
690                 695                 700

Pro Glu Leu Val His Gly Thr Val Val Thr Tyr Gln Cys Tyr Pro Gly
705                 710                 715                 720

Tyr Gln Val Val Gly Ser Ser Ile Leu Met Cys Gln Trp Asp Leu Ser
                725                 730                 735

Trp Ser Glu Asp Leu Pro Ser Cys Gln Arg Val Thr Ser Cys His Asp
                740                 745                 750

Pro Gly Asp Val Glu His Ser Arg Arg Leu Ile Ser Ser Leu Lys Phe
            755                 760                 765

Pro Val Gly Ala Thr Val Gln Tyr Ile Cys Asp Gln Gly Phe Val Leu
        770                 775                 780

Thr Gly Ser Ala Ile Leu Thr Cys His Asp Arg Gln Ala Gly Ser Pro
785                 790                 795                 800

Lys Trp Ser Asp Arg Ala Pro Lys Cys Leu Leu Glu Gln Phe Lys Pro
                805                 810                 815

Cys His Gly Leu Ser Ala Pro Glu Asn Gly Ala Arg Ser Pro Glu Lys
                820                 825                 830

Arg Leu His Pro Ala Gly Ala Thr Ile His Phe Ser Cys Ala Pro Gly
            835                 840                 845

Tyr Val Leu Lys Gly Gln Ala Ser Ile Lys Cys Val Pro Gly His Pro
850                 855                 860

Ser His Trp Ser Asp Pro Pro Ile Cys Arg Ala Ala Ser Leu Asp
865                 870                 875                 880

Gly Phe Tyr Asn Gly Arg Ser Leu Asp Val Ala Lys Ala Pro Ala Thr
                885                 890                 895

Ser Ser Ala Leu Asp Ala Ala His Met Ala Ala Ile Phe Leu Pro
            900                 905                 910

Leu Val Ala Met Val Leu Leu Val Gly Gly Val Tyr Leu Tyr Phe Ser
        915                 920                 925

Arg Leu Gln Gly Lys Ser Pro Leu Gln Leu Pro Gly Thr His Pro Arg
        930                 935                 940

Pro Tyr Asn Arg Ile Thr Val Glu Ser Ala Phe Asp Asn Pro Thr Tyr
945                 950                 955                 960

Glu Thr Gly Ser Leu Ser Phe Ala Gly Asp Glu Arg Ile
```

<210> SEQ ID NO 14
<211> LENGTH: 2997
<212> TYPE: DNA
<213> ORGANISM: Macaca fascicularis

<400> SEQUENCE: 14

| | | | | | |
|---|---|---|---|---|---|
| atggagacag | acacactcct | gctatgggta | ctgctgctct | gggttccagg | ttccactggt | 60 |
| gacggcgcgc | cactcagcag | cgaagctccc | acaatgggca | agggacaggc | ccccggaatt | 120 |
| gaagaaaccg | atggcgaact | caccgctgcc | cctacccctg | agcaacccga | aagggagtg | 180 |
| cactttgtga | ccaccgctcc | caccctgaag | ctgctcaatc | accaccccct | cctggaggag | 240 |
| tttctgcagg | aaggcctgga | aaaggcgac | gaggaactca | gacctgccct | gcccttccaa | 300 |
| cccgaccctc | ctaccccctt | tacacctagc | cctctcccta | gactggccaa | ccaagactcc | 360 |
| agacctgtgt | tcaccagccc | tacacctgct | acagctgccg | tccctaccca | acctcaatcc | 420 |
| aaggagggac | cttggagcct | cgagagcgag | cctcccgtgc | tgagaatcac | agctcctctc | 480 |
| cctcctggcc | cttccatggc | tgtccccaca | ctcggacctg | gcgaaaggcc | cagcacaaca | 540 |
| cccccctcca | gagcctggac | ccctacacaa | gaaggccctg | gcgacatggg | aaggccttgg | 600 |
| gtccctgaag | tcgtgagcca | aggcgccggc | atcggaatcc | agggaaccat | cgccagctcc | 660 |
| acagccagcg | gagacgatga | ggaaacaacc | accacaacca | ccatcatcac | caccacaatc | 720 |
| acaacagtcc | agacccccgg | cccttgcagc | tggaattttt | ccggccctga | gggatccctg | 780 |
| gattccccca | cagatctgtc | ctcccctcct | gacgtgggcc | tcgactgttt | cttctatatc | 840 |
| tccgtgtatc | ctggctacgg | cgtcgaaatc | aaagtccaga | acatctccct | gagggagggc | 900 |
| gaaacagtca | ccgtggaagg | actgggcgga | cccgctcctc | tgcctctcgc | caaccaatcc | 960 |
| ttcctcctca | ggggccaagt | gattagatcc | cccacacatc | aagctgctct | caggttccaa | 1020 |
| agcctccctc | cccccgctgg | acccggaacc | tttcacttcc | actaccaagc | ctatctcctc | 1080 |
| agctgccatt | tcccccacag | gcccgcttat | ggagatgtca | cagtcacctc | cctgcatcct | 1140 |
| ggcggctccg | ctagattcca | ctgcgctacc | ggataccaac | tcaagggcgc | caggcatctg | 1200 |
| acatgtctca | atgctaccca | gcccttctgg | gacagcaagg | agcccgtctg | cattgccgct | 1260 |
| tgcgaggcg | tcatcagaaa | tgccaccacc | ggcagaatcg | tgagccccgg | cttccctggc | 1320 |
| aactactcca | caacctgac | atgccactgg | ctgctggaag | ctcctgaggg | ccagagactg | 1380 |
| catctgcact | tcgagaaggt | cagcctggcc | gaagatgacg | cagagtcat | catcaggaac | 1440 |
| ggcgacaacg | tggaggctcc | ccccgtctat | gattcctacg | aggtcgagta | cctccccatc | 1500 |
| gagggactgc | tgtcctccgg | caagcattt | ttcgtggagc | tgtccacaga | ttccagcgga | 1560 |
| gctgccgccg | gaatggctct | caggtacgag | gctttccaac | agggccactg | ttacgagccc | 1620 |
| tttgtgaagt | acggcaactt | ctccagctcc | gctcctacct | accccgtcgg | cacaaccgtc | 1680 |
| gaatttagct | gcgaccctgg | atacacactc | gagcaaggct | ccatcatcat | cgagtgtgtc | 1740 |
| gacccccacg | accccaatg | aacgagaca | gagcccgcct | gtagggccgt | gtgtagcgga | 1800 |
| gagattaccg | actccgccgg | agtggtgctc | tcccctaatt | ggcctgaacc | ctacggcaga | 1860 |
| ggacaagatt | gtatttgggg | cgtccatgtc | gaggaggaca | agaggattat | gctcgacgtg | 1920 |
| agggtgctga | ggattggacc | tggcgacgtg | ctcacattct | atgacggcga | cgatctcacc | 1980 |
| gccagagtcc | tggacaata | ctccggccct | cacagccact | tcaagctgtt | caccagcatg | 2040 |
| gctgacgtga | ccatccagtt | ccagtccgat | cctggaacat | ccgtgctggg | ataccagcag | 2100 |

```
ggcttcgtca tccacttctt cgaggtcccc aggaacgaca cctgccccga actgcccgag    2160
attcccaacg gctggaaatc cccctcccaa cctgatctcg tgcacggcac cgtcgtcacc    2220
taccaatgct accctggata ccaagtcgtc ggcagcagcg tgctgatgtg ccaatgggac    2280
ctcacctgga gcgaggatct gccctcctgc cagagagtca cctcctgcca cgatcccggc    2340
gatgtggaac actccaggag gctgattagc tcccccaagt ccctgtcgg agccaccgtg     2400 caatacatct gcgaccaggg ctttgtgctg accggaacca gcatcctcac atgccacgac    2460
aggcaagctg atcccccaa gtggtccgat agggccccca aatgcctcct ggaacagctg     2520
aagccttgtc atggcctcag cgctcctgaa acggcgcta ggagcccga aaagaggctc      2580 caccctgccg agccaccat ccactttcc tgtgccccg gatacgtgct gaagggccag       2640
gcctccatta agtgcgtgcc cggacatcct tcccactggt ccgacccccc tcccatctgt    2700
aaagccgcct ccctggacgg attctataac agcagaagcc tggacgtcgc taaggcccct    2760
gctgcttcct ccaccctgga tgctgctcac atcgctgctg ccatctttct gccctcgtc    2820 gccatggtgc tgctggtggg aggcgtctac ttctacttct ccaggctgca gggaaagagc    2880
tccctgcaac tgcctaggac aagacccagg ccctacaata ggatcacagt cgagagcgcc    2940
ttcgacaacc ccacatacga gacaggatcc ctgagctttg ccggagacga gagaatt       2997
```

<210> SEQ ID NO 15
<211> LENGTH: 999
<212> TYPE: PRT
<213> ORGANISM: Macaca fascicularis

<400> SEQUENCE: 15

```
Met Glu Thr Asp Thr Leu Leu Leu Trp Val Leu Leu Leu Trp Val Pro
1               5                   10                  15

Gly Ser Thr Gly Asp Gly Ala Pro Leu Ser Ser Glu Ala Pro Thr Met
                20                  25                  30

Gly Lys Gly Gln Ala Pro Gly Ile Glu Glu Thr Asp Gly Glu Leu Thr
            35                  40                  45

Ala Ala Pro Thr Pro Glu Gln Pro Glu Arg Gly Val His Phe Val Thr
50                  55                  60

Thr Ala Pro Thr Leu Lys Leu Leu Asn His His Pro Leu Leu Glu Glu
65                  70                  75                  80

Phe Leu Gln Glu Gly Leu Glu Lys Gly Asp Glu Leu Arg Pro Ala
                85                  90                  95

Leu Pro Phe Gln Pro Asp Pro Thr Pro Phe Thr Pro Ser Pro Leu
            100                 105                 110

Pro Arg Leu Ala Asn Gln Asp Ser Arg Pro Val Phe Thr Ser Pro Thr
        115                 120                 125

Pro Ala Thr Ala Ala Val Pro Thr Gln Pro Gln Ser Lys Glu Gly Pro
    130                 135                 140

Trp Ser Leu Glu Ser Glu Pro Val Leu Arg Ile Thr Ala Pro Leu
145                 150                 155                 160

Pro Pro Gly Pro Ser Met Ala Val Pro Thr Leu Gly Pro Gly Glu Arg
                165                 170                 175

Pro Ser Thr Thr Pro Pro Ser Arg Ala Trp Thr Pro Thr Gln Glu Gly
            180                 185                 190

Pro Gly Asp Met Gly Arg Pro Trp Val Pro Glu Val Val Ser Gln Gly
        195                 200                 205

Ala Gly Ile Gly Ile Gln Gly Thr Ile Ala Ser Ser Thr Ala Ser Gly
```

```
            210                 215                 220
Asp Asp Glu Glu Thr Thr Thr Thr Thr Ile Ile Thr Thr Thr Ile
225                 230                 235                 240

Thr Thr Val Gln Thr Pro Gly Pro Cys Ser Trp Asn Phe Ser Gly Pro
                245                 250                 255

Glu Gly Ser Leu Asp Ser Pro Thr Asp Leu Ser Ser Pro Pro Asp Val
                260                 265                 270

Gly Leu Asp Cys Phe Phe Tyr Ile Ser Val Tyr Pro Gly Tyr Gly Val
            275                 280                 285

Glu Ile Lys Val Gln Asn Ile Ser Leu Arg Glu Gly Glu Thr Val Thr
        290                 295                 300

Val Glu Gly Leu Gly Gly Pro Ala Pro Leu Pro Leu Ala Asn Gln Ser
305                 310                 315                 320

Phe Leu Leu Arg Gly Gln Val Ile Arg Ser Pro Thr His Gln Ala Ala
                325                 330                 335

Leu Arg Phe Gln Ser Leu Pro Pro Ala Gly Pro Gly Thr Phe His
                340                 345                 350

Phe His Tyr Gln Ala Tyr Leu Leu Ser Cys His Phe Pro His Arg Pro
            355                 360                 365

Ala Tyr Gly Asp Val Thr Val Thr Ser Leu His Pro Gly Gly Ser Ala
370                 375                 380

Arg Phe His Cys Ala Thr Gly Tyr Gln Leu Lys Gly Ala Arg His Leu
385                 390                 395                 400

Thr Cys Leu Asn Ala Thr Gln Pro Phe Trp Asp Ser Lys Glu Pro Val
                405                 410                 415

Cys Ile Ala Ala Cys Gly Gly Val Ile Arg Asn Ala Thr Thr Gly Arg
                420                 425                 430

Ile Val Ser Pro Gly Phe Pro Gly Asn Tyr Ser Asn Asn Leu Thr Cys
                435                 440                 445

His Trp Leu Leu Glu Ala Pro Glu Gly Gln Arg Leu His Leu His Phe
450                 455                 460

Glu Lys Val Ser Leu Ala Glu Asp Asp Arg Leu Ile Ile Arg Asn
465                 470                 475                 480

Gly Asp Asn Val Glu Ala Pro Pro Val Tyr Asp Ser Tyr Glu Val Glu
                485                 490                 495

Tyr Leu Pro Ile Glu Gly Leu Leu Ser Ser Gly Lys His Phe Phe Val
                500                 505                 510

Glu Leu Ser Thr Asp Ser Ser Gly Ala Ala Ala Gly Met Ala Leu Arg
                515                 520                 525

Tyr Glu Ala Phe Gln Gln Gly His Cys Tyr Glu Pro Phe Val Lys Tyr
            530                 535                 540

Gly Asn Phe Ser Ser Ser Ala Pro Thr Tyr Pro Val Gly Thr Thr Val
545                 550                 555                 560

Glu Phe Ser Cys Asp Pro Gly Tyr Thr Leu Glu Gln Gly Ser Ile Ile
                565                 570                 575

Ile Glu Cys Val Asp Pro His Asp Pro Gln Trp Asn Glu Thr Glu Pro
                580                 585                 590

Ala Cys Arg Ala Val Cys Ser Gly Glu Ile Thr Asp Ser Ala Gly Val
                595                 600                 605

Val Leu Ser Pro Asn Trp Pro Glu Pro Tyr Gly Arg Gly Gln Asp Cys
                610                 615                 620

Ile Trp Gly Val His Val Glu Glu Asp Lys Arg Ile Met Leu Asp Val
625                 630                 635                 640
```

Arg Val Leu Arg Ile Gly Pro Gly Asp Val Leu Thr Phe Tyr Asp Gly
                645                 650                 655

Asp Asp Leu Thr Ala Arg Val Leu Gly Gln Tyr Ser Gly Pro His Ser
            660                 665                 670

His Phe Lys Leu Phe Thr Ser Met Ala Asp Val Thr Ile Gln Phe Gln
        675                 680                 685

Ser Asp Pro Gly Thr Ser Val Leu Gly Tyr Gln Gln Gly Phe Val Ile
690                 695                 700

His Phe Phe Glu Val Pro Arg Asn Asp Thr Cys Pro Glu Leu Pro Glu
705                 710                 715                 720

Ile Pro Asn Gly Trp Lys Ser Pro Ser Gln Pro Asp Leu Val His Gly
                725                 730                 735

Thr Val Val Thr Tyr Gln Cys Tyr Pro Gly Tyr Gln Val Val Gly Ser
            740                 745                 750

Ser Val Leu Met Cys Gln Trp Asp Leu Thr Trp Ser Glu Asp Leu Pro
        755                 760                 765

Ser Cys Gln Arg Val Thr Ser Cys His Asp Pro Gly Asp Val Glu His
770                 775                 780

Ser Arg Arg Leu Ile Ser Ser Pro Lys Phe Pro Val Gly Ala Thr Val
785                 790                 795                 800

Gln Tyr Ile Cys Asp Gln Gly Phe Val Leu Thr Gly Thr Ser Ile Leu
                805                 810                 815

Thr Cys His Asp Arg Gln Ala Gly Ser Pro Lys Trp Ser Asp Arg Ala
            820                 825                 830

Pro Lys Cys Leu Leu Glu Gln Leu Lys Pro Cys His Gly Leu Ser Ala
        835                 840                 845

Pro Glu Asn Gly Ala Arg Ser Pro Glu Lys Arg Leu His Pro Ala Gly
850                 855                 860

Ala Thr Ile His Phe Ser Cys Ala Pro Gly Tyr Val Leu Lys Gly Gln
865                 870                 875                 880

Ala Ser Ile Lys Cys Val Pro Gly His Pro Ser His Trp Ser Asp Pro
                885                 890                 895

Pro Pro Ile Cys Lys Ala Ala Ser Leu Asp Gly Phe Tyr Asn Ser Arg
            900                 905                 910

Ser Leu Asp Val Ala Lys Ala Pro Ala Ser Ser Thr Leu Asp Ala
        915                 920                 925

Ala His Ile Ala Ala Ile Phe Leu Pro Leu Val Ala Met Val Leu
930                 935                 940

Leu Val Gly Gly Val Tyr Phe Tyr Phe Ser Arg Leu Gln Gly Lys Ser
945                 950                 955                 960

Ser Leu Gln Leu Pro Arg Thr Arg Pro Arg Pro Tyr Asn Arg Ile Thr
                965                 970                 975

Val Glu Ser Ala Phe Asp Asn Pro Thr Tyr Glu Thr Gly Ser Leu Ser
            980                 985                 990

Phe Ala Gly Asp Glu Arg Ile
        995

<210> SEQ ID NO 16
<211> LENGTH: 2781
<212> TYPE: DNA
<213> ORGANISM: Homo sapiens

<400> SEQUENCE: 16
ctcgagaggg atgctctgcc tgagggagat gcttcccctc tcggacctta tctgctgccc    60

```
agcggagctc ctgagagggg atcccccgga aaggagcatc ccgaagaaag agtggtcaca    120 gctccccta gctccagcca gagcgctgag gtgctgggag aactggtcct cgacggaaca    180
gccccttccg cccatcacga tattcctgcc ctcagccctc tcctccccga ggaagctagg    240
cctaaacacg ccctcccccc taaaaagaag ctgccttccc tcaagcaggt caattccgcc    300
aggaagcagc tcagacccaa ggccacctcc gctgctacag tccaaagagc tggatcccag    360
cctgccagcc agggactcga tctgctcagc agctccacag aaaaacctgg acctcctggc    420
gatcctgacc ctattgtggc cagcgaagaa gctagcgaag tccctctgtg gctggacagg    480
aaggagtccg ctgtccccac cacacccgct cctctccaga tcagcccctt cacctcccag    540
ccttatgtcg ctcatacact gcctcagagg cctgagcctg gcgaacctgg acctgacatg    600
gctcaggagg ctcctcagga ggacaccagc cctatggccc tgatggataa gggcgagaat    660
gaactgaccg gaagcgccag cgaggaaagc caggagacca ccaccagcac aatcatcacc    720
accaccgtca tcaccaccga acaggccccc gctctgtgtt ccgtgtcctt ttccaacccc    780
gagggctaca ttgacagcag cgattacccc ctgctccctc tcaacaactt cctcgagtgc    840
acctacaatg tgaccgtgta caccggctac ggagtcgaac tccaggtgaa gtccgtgaac    900
ctctccgatg gcgaactgct ctccattagg ggcgtcgatg ccctacact caccgtcctg    960 gctaaccaaa ccctgctcgt cgaaggccag gtgattaggt ccccaccaa caccatctcc    1020 gtctacttca ggacctttca agacgacgga ctgggaacct tccaactgca ttaccaggcc    1080
ttcatgctgt cctgtaattt ccccaggaga cccgactccg gagacgtcac cgtcatggat    1140
ctgcactccg gaggcgtggc ccactttcat tgtcacctcg gctacgagct ccagggcgcc    1200
aagatgctga catgcatcaa cgccagcaaa cctcactggt ccagccagga gcctatctgt    1260
agcgctcctt gcggcggagc cgtgcacaat gctacaattg gcagagtgct cagcccttcc    1320
taccctgaaa acaccaacgg ctcccagttc tgcatctgga caatcgaggc ccccgaaggc    1380
caaaagctgc acctgcactt tgagaggctc ctgctccacg acaaagacag gatgaccgtg    1440
cactccggcc agaccaataa gtccgccctc ctgtatgaca gcctgcagac agagtccgtc    1500
ccttttgaag gcctgctgtc cgagggcaat accatcagga ttgagttcac atccgaccaa    1560
gccagggctg ctagcacctt caacattagg tttgaggctt tcgaaaaggg acactgctac    1620
gagccctata ttcagaatgg caatttcaca acctccgacc ccacctacaa tatcggcaca    1680
attgtggagt ttacctgcga ccctggacac agcctggagc agggacctgc catcatcgaa    1740
tgcatcaacg tcagggaccc ctactggaac gacacagaac ctctgtgtag ggctatgtgc    1800
ggaggcgaac tgagcgctgt ggctggagtc gtgctctccc ctaactggcc cgaaccctat    1860
gtggagggcg aagattgcat ctggaagatc cacgtcggcg aggaaaaaag gatctttctg    1920
gacatccagt tcctgaatct ctccaacagc gacatcctga ccatctacga cggagatgag    1980
gtcatgcccc acattctggg ccagtatctc ggaaactccg gccccaaaaa gctctactcc    2040 tccaccccg acctcacaat ccaattccac agcgatcctg ctggcctcat ctttggaaag    2100
ggacaaggct ttatcatgaa ttacatcgag gtcagcagaa acgacagctg ctccgacctg    2160
cctgagatcc agaacggatg gaagaccacc tcccacaccg agctcgtcag gggagctagg    2220
atcacatacc agtgcgaccc cggatacgac atcgtcggct ccgataccct gacatgccag    2280
tgggatctga gctggagctc cgaccccccc ttttgtgaga agatcatgta ctgcaccgac    2340
cccggcgaag tcgatcatag caccaggctc atcagcgatc ctgtgctgct cgtcggcaca    2400
```

```
accatccaat acacctgtaa ccccggattc gtgctcgaag gatcctccct gctcacctgt    2460
tacagcaggg aaaccggcac ccccatttgg acatccaggc tgcctcactg cgtgtccgaa    2520
gagagcctgg cttgcgataa tcccggcctg cctgagaacg gataccagat tctgtacaaa    2580
aggctgtacc tccccggcga gtccctgacc ttcatgtgct acgaaggatt cgagctcatg    2640
ggcgaagtca ccatcaggtg catcctcggc cagccctccc actggaacgg acctctcccc    2700
gtctgtaagg tcaatcagga ttccttcgag cacgctctgg aagtcgctga ggctgccgcc    2760
gagacaagcc tggaaggcgg c                                              2781
```

<210> SEQ ID NO 17
<211> LENGTH: 964
<212> TYPE: PRT
<213> ORGANISM: Homo sapiens

<400> SEQUENCE: 17

```
Met Glu Thr Asp Thr Leu Leu Leu Trp Val Leu Leu Leu Trp Val Pro
1               5                   10                  15

Gly Ser Thr Gly Asp His Gly Ala Pro Leu Glu Arg Asp Ala Leu Pro
            20                  25                  30

Glu Gly Asp Ala Ser Pro Leu Gly Pro Tyr Leu Leu Pro Ser Gly Ala
        35                  40                  45

Pro Glu Arg Gly Ser Pro Gly Lys Glu His Pro Glu Glu Arg Val Val
    50                  55                  60

Thr Ala Pro Pro Ser Ser Gln Ser Ala Glu Val Leu Gly Glu Leu
65                  70                  75                  80

Val Leu Asp Gly Thr Ala Pro Ser Ala His His Asp Ile Pro Ala Leu
                85                  90                  95

Ser Pro Leu Leu Pro Glu Glu Ala Arg Pro Lys His Ala Leu Pro Pro
            100                 105                 110

Lys Lys Lys Leu Pro Ser Leu Lys Gln Val Asn Ser Ala Arg Lys Gln
        115                 120                 125

Leu Arg Pro Lys Ala Thr Ser Ala Ala Thr Val Gln Arg Ala Gly Ser
    130                 135                 140

Gln Pro Ala Ser Gln Gly Leu Asp Leu Leu Ser Ser Ser Thr Glu Lys
145                 150                 155                 160

Pro Gly Pro Pro Gly Asp Pro Asp Pro Ile Val Ala Ser Glu Ala
                165                 170                 175

Ser Glu Val Pro Leu Trp Leu Asp Arg Lys Glu Ser Ala Val Pro Thr
            180                 185                 190

Thr Pro Ala Pro Leu Gln Ile Ser Pro Phe Thr Ser Gln Pro Tyr Val
        195                 200                 205

Ala His Thr Leu Pro Gln Arg Pro Glu Pro Gly Glu Pro Gly Pro Asp
    210                 215                 220

Met Ala Gln Glu Ala Pro Gln Glu Asp Thr Ser Pro Met Ala Leu Met
225                 230                 235                 240

Asp Lys Gly Glu Asn Glu Leu Thr Gly Ser Ala Ser Glu Glu Ser Gln
                245                 250                 255

Glu Thr Thr Thr Ser Thr Ile Ile Thr Thr Val Ile Thr Thr Glu
            260                 265                 270

Gln Ala Pro Ala Leu Cys Ser Val Ser Phe Ser Asn Pro Glu Gly Tyr
        275                 280                 285

Ile Asp Ser Ser Asp Tyr Pro Leu Leu Pro Leu Asn Asn Phe Leu Glu
    290                 295                 300
```

-continued

Cys Thr Tyr Asn Val Thr Val Tyr Thr Gly Tyr Gly Val Glu Leu Gln
305                 310                 315                 320

Val Lys Ser Val Asn Leu Ser Asp Gly Glu Leu Leu Ser Ile Arg Gly
            325                 330                 335

Val Asp Gly Pro Thr Leu Thr Val Leu Ala Asn Gln Thr Leu Leu Val
            340                 345                 350

Glu Gly Gln Val Ile Arg Ser Pro Thr Asn Thr Ile Ser Val Tyr Phe
            355                 360                 365

Arg Thr Phe Gln Asp Asp Gly Leu Gly Thr Phe Gln Leu His Tyr Gln
        370                 375                 380

Ala Phe Met Leu Ser Cys Asn Phe Pro Arg Arg Pro Asp Ser Gly Asp
385                 390                 395                 400

Val Thr Val Met Asp Leu His Ser Gly Gly Val Ala His Phe His Cys
                405                 410                 415

His Leu Gly Tyr Glu Leu Gln Gly Ala Lys Met Leu Thr Cys Ile Asn
                420                 425                 430

Ala Ser Lys Pro His Trp Ser Ser Gln Glu Pro Ile Cys Ser Ala Pro
            435                 440                 445

Cys Gly Gly Ala Val His Asn Ala Thr Ile Gly Arg Val Leu Ser Pro
450                 455                 460

Ser Tyr Pro Glu Asn Thr Asn Gly Ser Gln Phe Cys Ile Trp Thr Ile
465                 470                 475                 480

Glu Ala Pro Glu Gly Gln Lys Leu His Leu His Phe Glu Arg Leu Leu
                485                 490                 495

Leu His Asp Lys Asp Arg Met Thr Val His Ser Gly Thr Asn Lys
            500                 505                 510

Ser Ala Leu Leu Tyr Asp Ser Leu Gln Thr Glu Ser Val Pro Phe Glu
            515                 520                 525

Gly Leu Leu Ser Glu Gly Asn Thr Ile Arg Ile Glu Phe Thr Ser Asp
        530                 535                 540

Gln Ala Arg Ala Ala Ser Thr Phe Asn Ile Arg Phe Glu Ala Phe Glu
545                 550                 555                 560

Lys Gly His Cys Tyr Glu Pro Tyr Ile Gln Asn Gly Asn Phe Thr Thr
                565                 570                 575

Ser Asp Pro Thr Tyr Asn Ile Gly Thr Ile Val Glu Phe Thr Cys Asp
            580                 585                 590

Pro Gly His Ser Leu Glu Gln Gly Pro Ala Ile Ile Glu Cys Ile Asn
            595                 600                 605

Val Arg Asp Pro Tyr Trp Asn Asp Thr Glu Pro Leu Cys Arg Ala Met
            610                 615                 620

Cys Gly Gly Glu Leu Ser Ala Val Ala Gly Val Val Leu Ser Pro Asn
625                 630                 635                 640

Trp Pro Glu Pro Tyr Val Glu Gly Glu Asp Cys Ile Trp Lys Ile His
                645                 650                 655

Val Gly Glu Glu Lys Arg Ile Phe Leu Asp Ile Gln Phe Leu Asn Leu
            660                 665                 670

Ser Asn Ser Asp Ile Leu Thr Ile Tyr Asp Gly Asp Glu Val Met Pro
            675                 680                 685

His Ile Leu Gly Gln Tyr Leu Gly Asn Ser Gly Pro Gln Lys Leu Tyr
            690                 695                 700

Ser Ser Thr Pro Asp Leu Thr Ile Gln Phe His Ser Asp Pro Ala Gly
705                 710                 715                 720

Leu Ile Phe Gly Lys Gly Gln Gly Phe Ile Met Asn Tyr Ile Glu Val

```
                725                 730                 735
Ser Arg Asn Asp Ser Cys Ser Asp Leu Pro Glu Ile Gln Asn Gly Trp
            740                 745                 750

Lys Thr Thr Ser His Thr Glu Leu Val Arg Gly Ala Arg Ile Thr Tyr
            755                 760                 765

Gln Cys Asp Pro Gly Tyr Asp Ile Val Gly Ser Asp Thr Leu Thr Cys
            770                 775                 780

Gln Trp Asp Leu Ser Trp Ser Asp Pro Phe Cys Glu Lys Ile
785                 790                 795                 800

Met Tyr Cys Thr Asp Pro Gly Glu Val Asp His Ser Thr Arg Leu Ile
            805                 810                 815

Ser Asp Pro Val Leu Leu Val Gly Thr Thr Ile Gln Tyr Thr Cys Asn
            820                 825                 830

Pro Gly Phe Val Leu Glu Gly Ser Ser Leu Leu Thr Cys Tyr Ser Arg
            835                 840                 845

Glu Thr Gly Thr Pro Ile Trp Thr Ser Arg Leu Pro His Cys Val Ser
            850                 855                 860

Glu Glu Ser Leu Ala Cys Asp Asn Pro Gly Leu Pro Glu Asn Gly Tyr
865                 870                 875                 880

Gln Ile Leu Tyr Lys Arg Leu Tyr Leu Pro Gly Glu Ser Leu Thr Phe
            885                 890                 895

Met Cys Tyr Glu Gly Phe Glu Leu Met Gly Glu Val Thr Ile Arg Cys
            900                 905                 910

Ile Leu Gly Gln Pro Ser His Trp Asn Gly Pro Leu Pro Val Cys Lys
            915                 920                 925

Val Asn Gln Asp Ser Phe Glu His Ala Leu Glu Val Ala Glu Ala Ala
            930                 935                 940

Ala Glu Thr Ser Leu Glu Gly Gly Leu Ala Gly His His His His
945                 950                 955                 960

His His His His

<210> SEQ ID NO 18
<211> LENGTH: 2487
<212> TYPE: DNA
<213> ORGANISM: Homo sapiens

<400> SEQUENCE: 18
ctgcctctca aagaggaaga gattctcccc gagcccggat ccgagacacc cacagtggct     60
tccgaagccc tcgctgaact gctgcacgga gccctcctga aaggggacc tgaaatgggc    120 tatctccctg gctccgacag agatcccaca ctcgccacac ctcctgctgg acagaccctc    180
gctgtgcctt ccctgcccag agccacagaa cccggaacag ccctctcac aacagctgtg    240 accctaacg gcgtcagagg agctggacct acagccctg agctgctgac acctcctcct    300
ggcacaaccg ctcctcctcc tccttcccct gctagccctg acccccctct cggacctgaa    360
ggaggcgagg aggagacaac caccaccatt attaccacca ccaccgtgac aaccacagtg    420
accagccctg tcctgtgcaa caacaacatc agcgaaggcg aaggctatgt ggaatcccct    480
gacctgggct cccctgtgtc cagaacactc ggctcctgg attgcacata ctccattcac    540
gtgtaccccg gctacggaat cgagattcag gtgcagaccc tgaatctgtc ccaggaggag    600
gaactgctgg tgctggctgg cggaggaagc cctggcctcg ctcctagact cctcgctaac    660
tcctccatgc tcggcaagg ccaggtcctc agatccccta ccaacaggct gctcctgcac    720
ttccagagcc ccagagtgcc tagaggaggc ggcttcagga ttcactacca ggcctatctc    780
```

```
ctgagctgtg gattccctcc cagacccgct catggcgatg tctccgtcac cgacctccac    840
cccggaggaa cagccacctt ccactgtgat tccggatacc agctgcaagg cgaggagacc    900
ctgatttgcc tcaatggcac caggcccagc tggaacggag agacacctag ctgcatggct    960
agctgcggcg aaccatcca taatgccacc ctcggcagga tcgtcagccc tgaacctggc    1020
ggagctgtgg gacctaacct cacatgcaga tgggtgatcg aagctgctga aggcaggaga    1080
ctccacctcc acttcgagag ggtgtccctg gacgaggaca cgacaggct catggtcaga     1140 agcggcggaa gccctctcag ccctgtgatt tacgacagcg acatggacga tgtgcctgag    1200
aggggcctca tctccgatgc ccaaagcctg tacgtggaac tcctctccga daccccgct    1260 aaccccctcc tcctgagcct cagattcgag gccttcgagg aggacagatg tttcgctcct    1320
tttctggccc atggcaacgt gaccacaacc gaccccgagt acagaccgg agctctggct    1380 accttcagct gtctgcctgg ctacgccctc gaacctcccg acctcctaa tgccatcgaa    1440 tgtgtggatc ccaccgaacc ccattggaac gacaccgagc ccgcttgtaa ggctatgtgc    1500
ggcggagaac tcagcgaacc tgccggagtg gtcctctccc ctgattggcc ccagagctat    1560 tccccggac aagactgtgt ctggggcgtg cacgtccagg aggaaaagag gatcctcctc    1620
caggtggaga ttctgaacgt cagagaggga gacatgctga ccctgttcga cggagacgga    1680
ccttccgcca gagtcctcgc tcagctgaga ggccctcagc ccagaaggag actgctcagc    1740
tccggccccg atctgacact ccagtttcag gccccccctg gcccccctaa tcctggcctg    1800
ggacagggct tcgtgctcca cttcaaggag gtccccagga atgatacatg ccccgaactg    1860
cctcctcccg agtggggatg gaggacagct tcccatggcg acctgatcag gggaaccgtg    1920
ctgacatatc agtgtgaacc cggctacgag ctgctgggaa gcgatatcct gacctgtcag    1980
tgggatctct cctggagcgc tgctccccct gcctgtcaga aaatcatgac ctgcgctgac    2040
cctggagaga tcgctaacgg ccacaggacc gcttccgacg ctggatttcc cgtgggctcc    2100
cacgtgcaat acaggtgcct ccccggatac tcccctcgaag gcgctgccat gctgacatgc    2160
tacagcaggg acaccggcac acccaagtgg tccgacaggg tgcccaaatg tgctctgaag    2220
tacgagccct gtctcaatcc cggagtgccc gagaacggat accagaccct gtacaagcac    2280
cactatcagg ccggcgaatc cctgagattc ttctgctacg agggcttcga gctcatcggc    2340
gaggtgacaa ttacctgtgt gcccggccat ccttcccagt ggaccagcca gccccctctc    2400
tgtaaggtcg cctacgaaga gctgctcgac aataggaagc tggaggtcac ccagaccacc    2460
gacccttcca gacaactgga aggcggc                                         2487
```

<210> SEQ ID NO 19
<211> LENGTH: 865
<212> TYPE: PRT
<213> ORGANISM: Homo sapiens

<400> SEQUENCE: 19

Met Glu Thr Asp Thr Leu Leu Leu Trp Val Leu Leu Trp Val Pro
1               5                   10                  15

Gly Ser Thr Gly Asp Gly Ala Pro Leu Pro Leu Lys Glu Glu Glu Ile
            20                  25                  30

Leu Pro Glu Pro Gly Ser Glu Thr Pro Thr Val Ala Ser Glu Ala Leu
        35                  40                  45

Ala Glu Leu Leu His Gly Ala Leu Leu Arg Arg Gly Pro Glu Met Gly
    50                  55                  60

```
Tyr Leu Pro Gly Ser Asp Arg Asp Pro Thr Leu Ala Thr Pro Pro Ala
 65                  70                  75                  80

Gly Gln Thr Leu Ala Val Pro Ser Leu Pro Arg Ala Thr Glu Pro Gly
             85                   90                  95

Thr Gly Pro Leu Thr Thr Ala Val Thr Pro Asn Gly Val Arg Gly Ala
            100                 105                 110

Gly Pro Thr Ala Pro Glu Leu Leu Thr Pro Pro Gly Thr Thr Ala
            115                 120                 125

Pro Pro Pro Ser Pro Ala Ser Pro Gly Pro Pro Leu Gly Pro Glu
        130                 135                 140

Gly Gly Glu Glu Thr Thr Thr Thr Ile Ile Thr Thr Thr Thr Val
145                 150                 155                 160

Thr Thr Thr Val Thr Ser Pro Val Leu Cys Asn Asn Asn Ile Ser Glu
            165                 170                 175

Gly Glu Gly Tyr Val Glu Ser Pro Asp Leu Gly Ser Pro Val Ser Arg
            180                 185                 190

Thr Leu Gly Leu Leu Asp Cys Thr Tyr Ser Ile His Val Tyr Pro Gly
            195                 200                 205

Tyr Gly Ile Glu Ile Gln Val Gln Thr Leu Asn Leu Ser Gln Glu Glu
            210                 215                 220

Glu Leu Leu Val Leu Ala Gly Gly Ser Pro Gly Leu Ala Pro Arg
225                 230                 235                 240

Leu Leu Ala Asn Ser Ser Met Leu Gly Glu Gly Gln Val Leu Arg Ser
                245                 250                 255

Pro Thr Asn Arg Leu Leu Leu His Phe Gln Ser Pro Arg Val Pro Arg
            260                 265                 270

Gly Gly Gly Phe Arg Ile His Tyr Gln Ala Tyr Leu Leu Ser Cys Gly
            275                 280                 285

Phe Pro Pro Arg Pro Ala His Gly Asp Val Ser Val Thr Asp Leu His
        290                 295                 300

Pro Gly Gly Thr Ala Thr Phe His Cys Asp Ser Gly Tyr Gln Leu Gln
305                 310                 315                 320

Gly Glu Glu Thr Leu Ile Cys Leu Asn Gly Thr Arg Pro Ser Trp Asn
            325                 330                 335

Gly Glu Thr Pro Ser Cys Met Ala Ser Cys Gly Gly Thr Ile His Asn
            340                 345                 350

Ala Thr Leu Gly Arg Ile Val Ser Pro Glu Pro Gly Gly Ala Val Gly
            355                 360                 365

Pro Asn Leu Thr Cys Arg Trp Val Ile Glu Ala Ala Glu Gly Arg Arg
        370                 375                 380

Leu His Leu His Phe Glu Arg Val Ser Leu Asp Glu Asp Asn Asp Arg
385                 390                 395                 400

Leu Met Val Arg Ser Gly Gly Ser Pro Leu Ser Pro Val Ile Tyr Asp
            405                 410                 415

Ser Asp Met Asp Asp Val Pro Glu Arg Gly Leu Ile Ser Asp Ala Gln
            420                 425                 430

Ser Leu Tyr Val Glu Leu Leu Ser Glu Thr Pro Ala Asn Pro Leu Leu
            435                 440                 445

Leu Ser Leu Arg Phe Glu Ala Phe Glu Glu Asp Arg Cys Phe Ala Pro
        450                 455                 460

Phe Leu Ala His Gly Asn Val Thr Thr Thr Asp Pro Glu Tyr Arg Pro
465                 470                 475                 480

Gly Ala Leu Ala Thr Phe Ser Cys Leu Pro Gly Tyr Ala Leu Glu Pro
```

```
                    485                 490                 495
Pro Gly Pro Pro Asn Ala Ile Glu Cys Val Asp Pro Thr Glu Pro His
                500                 505                 510

Trp Asn Asp Thr Glu Pro Ala Cys Lys Ala Met Cys Gly Gly Glu Leu
            515                 520                 525

Ser Glu Pro Ala Gly Val Val Leu Ser Pro Asp Trp Pro Gln Ser Tyr
        530                 535                 540

Ser Pro Gly Gln Asp Cys Val Trp Gly Val His Val Gln Glu Glu Lys
545                 550                 555                 560

Arg Ile Leu Leu Gln Val Glu Ile Leu Asn Val Arg Glu Gly Asp Met
                565                 570                 575

Leu Thr Leu Phe Asp Gly Asp Gly Pro Ser Ala Arg Val Leu Ala Gln
                580                 585                 590

Leu Arg Gly Pro Gln Pro Arg Arg Leu Leu Ser Ser Gly Pro Asp
            595                 600                 605

Leu Thr Leu Gln Phe Gln Ala Pro Pro Gly Pro Pro Asn Pro Gly Leu
            610                 615                 620

Gly Gln Gly Phe Val Leu His Phe Lys Glu Val Pro Arg Asn Asp Thr
625                 630                 635                 640

Cys Pro Glu Leu Pro Pro Pro Glu Trp Gly Trp Arg Thr Ala Ser His
                    645                 650                 655

Gly Asp Leu Ile Arg Gly Thr Val Leu Thr Tyr Gln Cys Glu Pro Gly
                660                 665                 670

Tyr Glu Leu Leu Gly Ser Asp Ile Leu Thr Cys Gln Trp Asp Leu Ser
            675                 680                 685

Trp Ser Ala Ala Pro Pro Ala Cys Gln Lys Ile Met Thr Cys Ala Asp
        690                 695                 700

Pro Gly Glu Ile Ala Asn Gly His Arg Thr Ala Ser Asp Ala Gly Phe
705                 710                 715                 720

Pro Val Gly Ser His Val Gln Tyr Arg Cys Leu Pro Gly Tyr Ser Leu
                725                 730                 735

Glu Gly Ala Ala Met Leu Thr Cys Tyr Ser Arg Asp Thr Gly Thr Pro
            740                 745                 750

Lys Trp Ser Asp Arg Val Pro Lys Cys Ala Leu Lys Tyr Glu Pro Cys
        755                 760                 765

Leu Asn Pro Gly Val Pro Glu Asn Gly Tyr Gln Thr Leu Tyr Lys His
    770                 775                 780

His Tyr Gln Ala Gly Glu Ser Leu Arg Phe Phe Cys Tyr Glu Gly Phe
785                 790                 795                 800

Glu Leu Ile Gly Glu Val Thr Ile Thr Cys Val Pro Gly His Pro Ser
                805                 810                 815

Gln Trp Thr Ser Gln Pro Pro Leu Cys Lys Val Ala Tyr Glu Glu Leu
            820                 825                 830

Leu Asp Asn Arg Lys Leu Glu Val Thr Gln Thr Thr Asp Pro Ser Arg
        835                 840                 845

Gln Leu Glu Gly Gly Leu Ala Gly His His His His His His His
    850                 855                 860
His
865

<210> SEQ ID NO 20
<211> LENGTH: 107
<212> TYPE: PRT
<213> ORGANISM: Artificial Sequence
```

<220> FEATURE:
<221> NAME/KEY: source
<223> OTHER INFORMATION: /note="Description of Artificial Sequence:
    Synthetic polypeptide"

<400> SEQUENCE: 20

Gln Ile Val Leu Thr Gln Ser Pro Ala Leu Met Ser Ala Ser Pro Gly
1               5                   10                  15

Glu Lys Val Ser Leu Thr Cys Ser Ala Asn Ser Thr Val Ser Phe Met
            20                  25                  30

Tyr Trp Tyr Gln Gln Lys Pro Arg Ser Ser Pro Thr Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Ser Pro Ile
                85                  90                  95

Thr Phe Gly Ala Gly Thr Lys Leu Glu Leu Lys
            100                 105

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 21

Ser Asp Val Gln Leu Gln Asp Ser Gly Pro Gly Leu Val Lys Pro Ser
1               5                   10                  15

Gln Ser Leu Ser Val Thr Cys Thr Val Thr Gly Tyr Ser Ile Thr Trp
            20                  25                  30

Gly Tyr Tyr Trp Asn Trp Ile Arg Gln Phe Pro Gly Asn Lys Leu Glu
        35                  40                  45

Trp Met Gly Asn Ile His Asn Ser Gly Gly Thr Asn Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Thr Thr Asn Trp Asp Tyr Phe Asp Tyr Trp Gly Gln Gly Thr
            100                 105                 110

Thr Leu Thr Val Ser Ser
        115

<210> SEQ ID NO 22
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 22

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Ser Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 23
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Ile Tyr Pro Arg Asp Gly Ser Thr Lys Tyr Asn Glu Glu Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Ser Tyr Ser Asn Tyr Phe Asp Tyr Trp Gly Gln Gly Thr Thr
            100                 105                 110

Leu Thr Val Ser Ser
        115

<210> SEQ ID NO 24
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr

```
                65                  70                  75                  80
Ile Ser Ser Val Lys Ala Glu Asp Leu Ala Val Tyr Phe Cys Gln Gln
                85                  90                  95

Tyr Tyr Asn Tyr Pro Tyr Thr Phe Gly Gly Gly Thr Lys Leu Lys
                100                 105                 110

<210> SEQ ID NO 25
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Gln Gln Pro Gly Ala Glu Ile Val Arg Pro Gly Ala
1               5                   10                  15

Ser Val Lys Leu Ser Cys Lys Ala Ser Gly Tyr Thr Phe Thr Asp Tyr
                20                  25                  30

Trp Met Asn Trp Val Lys Gln Arg Pro Gly Gln Gly Leu Glu Trp Ile
            35                  40                  45

Gly Ala Ile Asp Pro Ser Asp Ser Tyr Thr Ser Tyr Asn Pro Lys Phe
        50                  55                  60

Lys Gly Lys Ala Thr Leu Thr Val Asp Thr Ser Ser Ser Ser Ala Tyr
65                  70                  75                  80

Met Gln Leu Ser Ser Leu Thr Ser Glu Asp Ser Ala Val Tyr Phe Cys
                85                  90                  95

Ala Arg Arg Gly Thr Pro Gly Lys Pro Leu Val Tyr Trp Gly Gln Gly
                100                 105                 110

Thr Leu Val Thr Val Ser Ala
            115

<210> SEQ ID NO 26
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Gln Met Thr Gln Ser Pro Ala Ser Leu Ser Val Ser Val Gly
1               5                   10                  15

Glu Thr Val Thr Ile Thr Cys Arg Ala Ser Ala Asn Ile Asn Ser Asn
                20                  25                  30

Leu Val Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Asn Tyr Tyr Cys Gln His Phe Trp Gly Thr Pro Arg
                85                  90                  95

Thr Phe Gly Gly Gly Thr Lys Leu Glu Ile Lys
                100                 105

<210> SEQ ID NO 27
```

<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met Tyr Trp Val Lys Gln Asn Gly Lys Ser Leu Glu Trp Ile
        35                  40                  45

Gly Glu Ile Asn Pro Asn Asn Gly Gly Thr Ala Tyr Asn Gln Lys Phe
    50                  55                  60

Arg Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Tyr Asp Lys Gly Phe Asp Tyr Trp Gly Gln Gly Thr Thr Leu
            100                 105                 110

Thr Val Ser Ser
        115

<210> SEQ ID NO 28
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

Asp Ile Val Val Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Phe Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Asp Arg
                85                  90                  95

Lys Val Pro Trp Thr Phe Gly Gly Gly Thr Lys Leu Glu Ile Lys
            100                 105                 110

<210> SEQ ID NO 29
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
            20                  25                  30

Gly Met Ser Val Gly Trp Val Arg Gln Pro Ser Gly Arg Gly Leu Glu
        35                  40                  45

Trp Leu Ala Pro Ile Trp Trp Asn Gly Asp Lys Tyr Tyr Asn Pro Ala
50                  55                  60

Leu Lys Ser Arg Leu Thr Ile Ser Lys Asp Thr Ser Asn Asn Gln Val
65                  70                  75                  80

Phe Leu Lys Ile Ala Ser Val Val Thr Ala Asp Thr Ala Thr Tyr Phe
                85                  90                  95

Cys Ala Arg Ile Arg Gln Tyr Tyr Tyr Ala Met Asp Tyr Trp Gly Gln
                100                 105                 110

Gly Thr Ser Val Thr Val Ser Ser
                115                 120
```

<210> SEQ ID NO 30
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
                100                 105                 110
```

<210> SEQ ID NO 31
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Pro Ser Tyr
            20                  25                  30

Trp Ile His Cys Val Lys Gln Arg Pro Gly Gln Gly Leu Glu Trp Ile
        35                  40                  45

Gly Val Ile Asn Pro Ser Asn Gly Arg Thr Asn Tyr Asn Glu Lys Phe
```

```
                   50                  55                  60
Lys Asn Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                     85                  90                  95

Val Arg Gly Gly Thr Gly Tyr Thr Met Asp Tyr Trp Gly Gln Gly Thr
                100                 105                 110

Ser Val Thr Val Ser Ser
            115

<210> SEQ ID NO 32
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Thr Trp Phe Gln Gln Lys Pro Gly Lys Ser Pro Lys Thr Leu Ile
             35                  40                  45

Tyr Arg Ala Asn Arg Leu Ile Asp Gly Val Pro Ser Arg Phe Ser Gly
 50                  55                  60

Ser Gly Ser Gly Gln Asp Tyr Ser Leu Thr Ile Ser Ser Leu Asp Tyr
 65                  70                  75                  80

Glu Asp Met Gly Ile Tyr Tyr Cys Leu Gln Tyr Asp Asp Phe Pro Trp
                 85                  90                  95

Thr Phe Gly Gly Gly Thr Lys Leu Glu Ile Lys
                100                 105

<210> SEQ ID NO 33
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asp Tyr
                 20                  25                  30

Ser Met His Trp Val Lys Gln Ala Pro Gly Lys Gly Leu Lys Trp Leu
             35                  40                  45

Gly Trp Ile Asn Thr Glu Thr Gly Glu Pro Thr Tyr Ser Glu Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Val Lys Asn Lys Gly Trp Phe Ala Tyr Trp Gly Gln Gly Thr Leu Val
                100                 105                 110
```

Thr Val Ser Ala
        115

<210> SEQ ID NO 34
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asp Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Thr Leu Ile Pro Tyr Thr Phe Gly Gly Gly Thr Lys Leu Asp Ile Lys
            100                 105                 110

Arg

<210> SEQ ID NO 35
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val His Leu Gln Gln Ser Gly Thr Glu Val Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Asn Thr Asn Asn Asn Glu Lys Phe
    50                  55                  60

Lys Gly Lys Ala Thr Ile Thr Ala Asp Thr Ser Ser Asn Ile Ala Tyr
65                  70                  75                  80

Ile Gln Leu Ser Ser Leu Thr Ser Glu Asp Ser Ala Val Tyr Tyr Cys
                85                  90                  95

Ala Gly Gly Pro Ala Ala Tyr Trp Gly Gln Gly Thr Leu Val Thr Val
            100                 105                 110

Ser Ala

<210> SEQ ID NO 36
<211> LENGTH: 113
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 36

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Thr Glu Asp Leu Ala Leu Tyr Tyr Cys Gln Gln
                85                  90                  95

Tyr Tyr Trp Phe Pro Tyr Thr Phe Gly Gly Gly Thr Lys Leu Glu Ile
            100                 105                 110

Lys

<210> SEQ ID NO 37
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Val Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Gly Asn Val Tyr Trp Gly Gln Gly Thr Leu Val Thr Val Ser
            100                 105                 110

Ala

<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Asn Val Leu Thr Gln Ser Pro Ala Ile Met Ser Ala Ser Pro Gly
1               5                   10                  15
```

```
Glu Lys Val Thr Met Thr Cys Arg Ala Ser Ser Val Ser Ser Ser
             20                  25                  30

Tyr Leu His Trp Tyr Gln Gln Lys Ser Gly Ala Ser Pro Lys Leu Trp
         35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Asp Tyr Pro
                 85                  90                  95

Phe Thr Phe Gly Ser Gly Thr Lys Leu Val Ile Lys
            100                 105
```

<210> SEQ ID NO 39
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Glu Val Gln Leu Gln Gln Ser Gly Pro Glu Leu Val Lys Pro Gly Ala
 1               5                  10                  15

Leu Val Met Met Ser Cys Lys Ala Ser Gly Tyr Thr Phe Thr Asp Tyr
                 20                  25                  30

Tyr Met His Trp Val Lys Gln Ser His Gly Gln Ser Leu Glu Trp Ile
             35                  40                  45

Gly Glu Val Ile Pro Tyr Asn Asp Glu Thr Phe Tyr Asn Arg Lys Phe
 50                  55                  60

Lys Asp Lys Ala Thr Leu Thr Val Asp Lys Ser Ser Thr Ala Tyr
 65                  70                  75                  80

Met Glu Leu Arg Ser Leu Thr Ser Glu Asp Ser Ala Ile Tyr Tyr Cys
                 85                  90                  95

Ala Arg Arg His Arg Tyr Asp Gly Phe Arg Tyr Ala Ile Asp Tyr Trp
                100                 105                 110

Gly Gln Gly Thr Ser Val Thr Val Ser Ser
            115                 120
```

<210> SEQ ID NO 40
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Phe Leu Gln Lys Pro Gly Gln Ser
             35                  40                  45

Pro Lys Leu Leu Ile Tyr Lys Val Ser Asn Arg Phe Ser Gly Val Pro
 50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110

Arg
```

<210> SEQ ID NO 41
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Glu Val Gln Leu Gln Gln Ser Gly Pro Val Leu Val Lys Pro Gly Ala
 1               5                  10                  15

Ser Val Lys Met Ser Cys Lys Ala Ser Gly Tyr Thr Ile Thr Asp Tyr
                20                  25                  30

Asn Met Asn Trp Val Lys Gln Ser His Gly Lys Ser Leu Glu Trp Ile
            35                  40                  45

Gly Val Ile Asn Pro Tyr Asn Gly Asn Thr Arg Tyr Asn Gln Met Phe
 50                  55                  60

Lys Gly Lys Ala Thr Leu Thr Val Asp Lys Ser Ser Ser Thr Ala Tyr
 65                  70                  75                  80

Met Glu Leu Asn Ser Leu Thr Ser Glu Asp Ser Ala Val Tyr Tyr Cys
                 85                  90                  95

Thr Arg Trp Gly Thr Thr Val Val Gly Ala Asn Trp Gly Gln Gly Thr
            100                 105                 110

Thr Leu Thr Val Ser Ser
            115
```

<210> SEQ ID NO 42
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Gln Ile Val Leu Thr Gln Ser Pro Ala Leu Met Ser Ala Ser Pro Gly
 1               5                  10                  15

Glu Lys Val Thr Met Thr Cys Ser Ala Ser Ser Ser Val Asn Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Val Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Asn Asn Pro Pro Thr
                 85                  90                  95

Phe Gly Ser Gly Thr Lys Leu Glu Leu Lys
            100                 105
```

<210> SEQ ID NO 43
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Asp Tyr Tyr Gly Ser Ser Tyr Val Met Phe Ala Tyr Trp
            100                 105                 110

Gly Gln Gly Thr Leu Val Thr Val Ser Ala
        115                 120

<210> SEQ ID NO 44
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Ala Gly Thr Lys Leu Glu Leu Lys
            100                 105

<210> SEQ ID NO 45
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

Glu Val Gln Leu Gln Gln Ser Gly Pro Glu Val Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Ser Leu Glu Trp Ile
        35                  40                  45

Gly Glu Ile Asn Pro Asn Ile Gly Gly Thr Gly Tyr Asn Gln Lys Phe
    50                  55                  60

Lys Gly Lys Ala Thr Leu Thr Val His Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Thr Tyr Ser Tyr Tyr Ser Tyr Glu Phe Ala Tyr Trp Gly Gln
            100                 105                 110

Gly Thr Leu Val Thr Val Ser Ala
        115                 120

<210> SEQ ID NO 46
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Leu
                85                  90                  95

Thr Phe Gly Ala Gly Thr Lys Leu Glu Leu Lys
            100                 105

<210> SEQ ID NO 47
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Thr Met Gly Val Gly Trp Ile Arg Gln Pro Ser Gly Lys Gly Leu Glu

```
            35                  40                  45

Trp Leu Ala Asp Ile Trp Trp Asp Asp Ser Lys Tyr Tyr Asn Pro Ser
     50                  55                  60

Leu Lys Ser Arg Leu Thr Ile Ser Lys Asp Thr Ser Ser Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Lys Gly Arg Thr Ala Arg Ala Thr Arg Gly Phe Ala Tyr
                100                 105                 110

Trp Gly His Gly Thr Leu Val Thr Val Ser Ala
            115                 120

<210> SEQ ID NO 48
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Asp Ile Val Leu Thr Gln Ser Pro Ala Ser Leu Ala Val Ser Leu Gly
 1               5                  10                  15

Gln Arg Ala Ala Ile Ser Cys Lys Pro Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys His Gln Ile Asn
                 85                  90                  95

Asp Asp Pro Trp Thr Phe Gly Gly Gly Thr Lys Leu Lys
                100                 105

<210> SEQ ID NO 49
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ser Asp Val Gln Leu Gln Glu Ser Gly Pro Gly Leu Val Lys Pro Ser
 1               5                  10                  15

Gln Ser Leu Ser Val Thr Cys Thr Val Thr Gly Tyr Ser Ile Thr Ser
                20                  25                  30

Ser Tyr Thr Trp Asn Trp Ile Arg Gln Phe Pro Gly Asn Lys Leu Glu
            35                  40                  45

Trp Met Gly Tyr Ile His Tyr Ser Gly Ser Thr Asn Tyr Asn Pro Ser
     50                  55                  60

Leu Arg Ser Arg Ile Ser Ile Thr Arg Asp Thr Ser Lys Asn Gln Phe
 65                  70                  75                  80

Phe Leu Gln Leu Asn Ser Val Thr Thr Glu Asp Thr Ala Thr Tyr Tyr
                 85                  90                  95
```

Cys Ala Arg Ser Arg Tyr Tyr Asp Ala Tyr Gly Phe Ala Tyr Trp
            100                 105                 110

Gly Gln Gly Thr Leu Val Thr Val Ser Ala
        115                 120

<210> SEQ ID NO 50
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Val Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ile
            20                  25                  30

Asn Arg His Thr Tyr Leu Gly Trp Tyr Leu Gln Lys Pro Gly Gln Ser
        35                  40                  45

Leu Lys Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Phe Gln Gly
                85                  90                  95

Thr His Val Pro Phe Thr Phe Gly Ser Gly Thr Lys Leu Glu Ile Lys
            100                 105                 110

<210> SEQ ID NO 51
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Ile Gln Met Met Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Thr Arg Gly Tyr Tyr Gly Ser Ser Tyr Asp Ala Leu Asp Tyr Trp Gly
            100                 105                 110

Gln Gly Thr Ser Val Thr Val Ser Ser
        115                 120

<210> SEQ ID NO 52
<211> LENGTH: 112

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52
```

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Ser Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

```
<210> SEQ ID NO 53
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53
```

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Glu Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Ser Tyr Ser Asn Tyr Phe Asp Tyr Trp Gly Gln Gly Thr Thr
            100                 105                 110

Leu Thr Val Ser Ser
        115

```
<210> SEQ ID NO 54
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54
```

Asp Val Val Met Thr Gln Thr Pro Leu Thr Leu Ser Val Thr Ile Gly

```
          1               5                  10                 15
       Gln Pro Ala Ser Ile Ser Cys Lys Ser Ser Gln Ser Leu Leu Glu Ser
                       20                  25                  30

Asp Gly Lys Thr Tyr Leu Asn Trp Leu Leu Gln Arg Pro Gly Gln Ser
                       35                  40                  45

Pro Lys Arg Leu Ile Tyr Leu Val Ser Lys Leu Asp Ser Gly Val Pro
                  50                  55                  60

Asp Arg Phe Thr Gly Ser Gly Ser Gly Thr Asp Phe Thr Leu Lys Ile
        65                  70                  75                  80

Ser Arg Val Glu Ala Glu Asp Leu Gly Val Tyr Tyr Cys Trp Gln Gly
                       85                  90                  95

Ile Gln His Pro Arg Thr Phe Gly Gly Gly Thr Lys Leu Glu Ile Lys
                      100                 105                 110
```

<210> SEQ ID NO 55
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

```
       Gln Val Gln Leu Gln Gln Ser Gly Ala Glu Leu Val Arg Pro Gly Ala
        1               5                  10                 15

Ser Val Thr Leu Ser Cys Lys Ala Ser Gly Tyr Thr Phe Thr Asp Tyr
                       20                  25                  30

Glu Met His Trp Val Lys Gln Thr Pro Val His Gly Leu Glu Trp Ile
                       35                  40                  45

Gly Gly Ile Asp Pro Glu Thr Gly Gly Thr Ala Tyr Asn Gln Lys Phe
                  50                  55                  60

Lys Gly Lys Ala Thr Leu Thr Ala Asp Lys Ser Ser Ser Thr Ala Tyr
        65                  70                  75                  80

Met Glu Leu Arg Ser Leu Thr Ser Glu Asp Ser Ala Val Tyr Phe Cys
                       85                  90                  95

Thr Arg Trp Phe Ser Tyr Trp Gly Pro Gly Thr Leu Val Thr Val Ser
                      100                 105                 110

Ala
```

<210> SEQ ID NO 56
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

```
       Asp Ile Leu Leu Thr Gln Ser Pro Ala Ile Leu Ser Val Ser Pro Gly
        1               5                  10                 15

Glu Gly Val Ser Phe Ser Cys Arg Ala Ser Gln Ser Ile Gly Thr Ser
                       20                  25                  30

Ile His Trp Tyr Gln Gln Arg Thr Asn Gly Ser Pro Arg Leu Leu Ile
                       35                  40                  45

Lys Tyr Ala Ser Glu Ser Ile Ser Gly Ile Pro Ser Arg Phe Ser Gly
                  50                  55                  60
```

```
Ser Gly Ser Gly Thr Asp Phe Thr Leu Arg Ile Asn Ser Leu Glu Ser
 65                  70                  75                  80

Glu Asp Ile Ala Asp Tyr Tyr Cys Gln Gln Ser Asn Ser Trp Pro Leu
                 85                  90                  95

Thr Phe Gly Ala Gly Thr Lys Leu Glu Leu Lys
            100                 105

<210> SEQ ID NO 57
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val His Leu Pro Gln Ser Arg Pro Glu Leu Val Lys Pro Gly Ala
 1               5                  10                  15

Ser Val Lys Ile Ser Cys Lys Ala Ser Gly Tyr Gly Phe Thr Arg Ser
             20                  25                  30

Tyr Ile His Trp Val Lys Gln Arg Pro Gly Gln Gly Leu Glu Trp Ile
         35                  40                  45

Gly Tyr Ile Ser Ser Gly Ser Gly Thr Thr Tyr Asn Gln Lys Phe
 50                  55                  60

Lys Gly Lys Ala Ser Leu Thr Ala Asp Asn Pro Ser Ser Thr Ala Tyr
 65                  70                  75                  80

Met His Leu Ser Ser Leu Thr Ser Glu Asp Ser Ala Ile Tyr Phe Cys
                 85                  90                  95

Ala Arg Gly Gly Val Arg Tyr Phe Asp Val Trp Gly Ala Gly Thr Thr
            100                 105                 110

Val Thr Val Ser Ser
            115

<210> SEQ ID NO 58
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Gly Thr Asp
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Tyr
                 85                  90                  95

Thr Phe Gly Gly Gly Thr Lys Leu Glu Ile Lys Arg
            100                 105
```

```
<210> SEQ ID NO 59
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Ser Leu Glu Trp Ile
        35                  40                  45

Gly Glu Ile Asn Pro His Asn Gly Gly Thr Gly Tyr Asn Gln Lys Phe
    50                  55                  60

Lys Gly Lys Ala Thr Leu Thr Val Asp Lys Ser Ser Ser Thr Ser Tyr
65                  70                  75                  80

Met Glu Leu Arg Ser Leu Thr Ser Glu Asp Ser Ala Val Tyr Tyr Cys
                85                  90                  95

Ala Gly Gly Tyr Pro Ala Phe Asp Tyr Trp Gly Gln Gly Thr Thr Leu
            100                 105                 110

Thr Val Ser Ser
            115

<210> SEQ ID NO 60
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Glu Asn Val Leu Thr Gln Ser Pro Ala Ile Val Ser Ala Ser Pro Gly
1               5                   10                  15

Glu Lys Val Thr Met Thr Cys Arg Ala Ser Ser Ser Val Ile Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Ala Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys
            100                 105

<210> SEQ ID NO 61
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61
```

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Asp Asp Tyr Tyr Gly Ser Ser Pro Ser Tyr Trp Tyr Phe Asp
                100                 105                 110

Val Trp Gly Ala Gly Thr Thr Val Thr Val Ser Ser
            115                 120

<210> SEQ ID NO 62
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Ile Gln Met Thr Gln Ser Pro Ala Ser Leu Ser Ala Ser Val Gly
1               5                   10                  15

Glu Thr Val Thr Met Thr Cys Arg Ala Ser Gly Asn Ile His Asn Tyr
            20                  25                  30

Leu Val Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Pro
                85                  90                  95

Thr Phe Gly Gly Gly Thr Lys Leu Glu Ile Lys
            100                 105

<210> SEQ ID NO 63
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

```
Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Phe Leu Gln Met Asn Asn Leu Arg Thr Glu Asp Thr Gly Ile Tyr
                85                  90                  95

Tyr Cys Thr Arg His Tyr Tyr Tyr Ala Met Asp Tyr Trp Gly Gln Gly
                100                 105                 110

Thr Ser Val Thr Val Ser Ser
            115
```

<210> SEQ ID NO 64
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105
```

<210> SEQ ID NO 65
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Glu Val Gln Leu Gln Gln Ser Gly Pro Glu Leu Val Lys Pro Gly Ser
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ser His Gly Lys Arg Leu Glu Trp Ile
            35                  40                  45

Gly Tyr Ile Tyr Pro Asp Asn Gly Ala Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Ser Ile Thr Thr Ala Trp Phe Ala Tyr Trp Gly Gln Gly Thr
```

```
                     100                 105                 110

Leu Val Thr Val Ser Ala
            115

<210> SEQ ID NO 66
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Glu Asn Val Leu Thr Gln Ser Pro Ala Ile Met Ser Ala Ser Pro Gly
1               5                   10                  15

Glu Lys Val Thr Leu Thr Cys Arg Ala Ser Ser Ser Met Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Ala Tyr Pro
                85                  90                  95

Phe Thr Phe Gly Ser Gly Thr Lys Leu Glu Ile Lys
            100                 105

<210> SEQ ID NO 67
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Val Gln Leu Gln Gln Ser Gly Pro Glu Leu Val Lys Pro Gly Ala
1               5                   10                  15

Leu Val Lys Met Ser Cys Lys Ala Ser Gly Tyr Thr Phe Thr Asp Tyr
            20                  25                  30

Tyr Ile His Trp Val Lys Gln Ser His Gly Lys Ser Leu Glu Trp Ile
        35                  40                  45

Gly Glu Ile Asn Pro Tyr Asn Gly Glu Thr Phe Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Trp Tyr Leu Thr Gly Tyr Ala Met Asp Tyr Trp Gly
            100                 105                 110

Gln Gly Thr Ser Val Thr Val Ser Ser
        115                 120

<210> SEQ ID NO 68
<211> LENGTH: 107
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 68
```

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys Arg
            100                 105

```
<210> SEQ ID NO 69
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69
```

Glu Val Gln Leu Gln Glu Ser Gly Pro Ser Leu Val Lys Pro Ser Gln
1               5                   10                  15

Ser Gln Ser Leu Thr Cys Ser Val Thr Gly Asp Ser Ile Thr Ser Asp
            20                  25                  30

Tyr Trp Asn Trp Ile Arg Lys Phe Pro Gly Lys Lys Val Glu Tyr Met
            35                  40                  45

Gly Tyr Ile Asn Tyr Ser Gly Ser Thr Tyr Tyr Asn Pro Ser Leu Lys
        50                  55                  60

Ser Arg Ile Ser Ile Thr Arg Asp Thr Ser Lys Asn Gln Tyr Tyr Leu
65                  70                  75                  80

Gln Leu Asn Ser Val Thr Ser Glu Asp Thr Ala Thr Tyr Tyr Cys Ala
                85                  90                  95

Arg Thr Ser Tyr Tyr Asn Lys Phe Leu Pro Phe Ala Tyr Trp Gly Gln
            100                 105                 110

Gly Thr Leu Val Thr Val Ser Ala
        115                 120

```
<210> SEQ ID NO 70
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70
```

Asp Val Leu Met Thr Gln Thr Pro Leu Ser Leu Pro Val Ser Leu Gly
1               5                   10                  15

```
Asp Gln Ala Ser Ile Ser Cys Arg Ser Ser Gln Ser Leu Val His Arg
                20                  25                  30

Asn Gly Asn Thr Tyr Phe His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Tyr Val Pro Trp Thr Phe Gly Gly Gly Thr Lys Leu Glu Ile Lys
                100                 105                 110

<210> SEQ ID NO 71
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Glu Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Tyr
                20                  25                  30

Gly Met His Trp Val Arg Gln Ala Pro Glu Lys Gly Leu Glu Trp Val
            35                  40                  45

Ala Tyr Ile Ser Ser Asn Asp Gly Thr Ile Tyr Tyr Ala Asp Thr Val
    50                  55                  60

Arg Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Ser Asn Trp Val Phe Asp Tyr Trp Gly Gln Gly Thr Thr
                100                 105                 110

Leu Thr Val Ser Ser
        115

<210> SEQ ID NO 72
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Val Val Met Thr Gln Thr Pro Leu Ser Arg Pro Thr Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Phe Cys Ser Gln Asn
                    85                  90                  95

Thr His Val Pro Phe Thr Phe Gly Ser Gly Thr Lys Leu Glu Ile Lys
                    100                 105                 110

<210> SEQ ID NO 73
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Val Gln Leu Gln Gln Pro Gly Ala Glu Ile Val Arg Pro Gly Ala
1               5                   10                  15

Ser Val Lys Leu Ser Cys Lys Ala Ser Gly Tyr Thr Phe Thr Asp Tyr
                20                  25                  30

Trp Met Asn Trp Val Lys Gln Arg Pro Gly Gln Gly Leu Glu Trp Ile
            35                  40                  45

Gly Thr Ile Asp Pro Ser Asp Ser Tyr Thr Arg Tyr Asn Gln Lys Phe
        50                  55                  60

Lys Gly Lys Ala Thr Leu Thr Val Asp Thr Ser Phe Ser Ser Ala Tyr
65                  70                  75                  80

Met Gln Leu Ser Ser Leu Thr Ser Glu Asp Ser Ala Val Tyr Phe Cys
                85                  90                  95

Ala Ser Gly Gly Arg Gly Phe Gly Tyr Trp Gly Gln Gly Thr Pro Val
                100                 105                 110

Thr Val Ser Val
            115

<210> SEQ ID NO 74
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Lys Pro Trp Ile Tyr
            35                  40                  45

Leu Thr Ser Asn Leu Ala Ser Gly Val Pro Thr Arg Phe Ser Gly Ser
        50                  55                  60

Gly Ser Gly Thr Ser Tyr Ser Leu Thr Ile Ser Ser Met Gly Ala Glu
65                  70                  75                  80

Asp Ala Ala Thr Tyr Tyr Cys Gln Gln Trp Asn Thr Asn Pro Pro Thr
                85                  90                  95

Phe Gly Ala Gly Thr Lys Leu Glu Leu Lys
                100                 105

<210> SEQ ID NO 75
```

<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Asp Tyr Tyr Gly Ser Tyr Val Met Phe Ala Tyr Trp
            100                 105                 110

Gly Gln Gly Thr Leu Val Thr Val Ser Ala
        115                 120

<210> SEQ ID NO 76
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Ser Ser Thr Ser Pro Lys Leu Trp Ile Tyr
        35                  40                  45

Asp Thr Ser Lys Leu Thr Ser Gly Val Pro Gly Arg Phe Ser Gly Ser
    50                  55                  60

Gly Ser Gly Asn Ser Tyr Ser Leu Thr Ile Ser Asn Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ser Gly Thr Lys Leu Glu Ile Lys
            100                 105

<210> SEQ ID NO 77
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Asp Val Lys Leu Val Glu Ser Gly Gly Gly Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Ala
        35                  40                  45

Ala Thr Ile Asn Ser Gly Gly Ser Asn Thr Tyr Tyr Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Ser Ser Leu Lys Ser Glu Asp Thr Ala Met Tyr Tyr Cys
                85                  90                  95

Thr Asn Gly Asn His Trp Gly Gln Gly Thr Leu Thr Val Ser Ser
            100                 105                 110

<210> SEQ ID NO 78
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Ser Ser Thr Ser Pro Lys Leu Trp Ile Tyr
        35                  40                  45

Asp Thr Ser Lys Leu Thr Gly Val Pro Gly Arg Phe Ser Gly Ser Gly
    50                  55                  60

Ser Gly Asn Ser Tyr Ser Leu Thr Ile Ser Asn Met Glu Ala Glu Asp
65                  70                  75                  80

Val Ala Thr Tyr Tyr Cys Phe Gln Gly Ser Gly Tyr Pro Leu Thr Phe
                85                  90                  95

Gly Ser Gly Thr Lys Leu Glu Ile Lys
            100                 105

<210> SEQ ID NO 79
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Val Gln Leu Gln Gln Pro Gly Ser Val Leu Val Arg Pro Gly Asp
1               5                   10                  15

Ser Val Lys Leu Ser Cys Lys Ala Ser Gly Tyr Thr Phe Thr Ser Tyr
            20                  25                  30

Trp Met His Trp Val Lys Gln Ser Pro Gly Gln Gly Leu Glu Trp Ile
        35                  40                  45

Gly Glu Ile His Pro His Ser Gly Ser Thr Asn Tyr Asn Glu Lys Phe
    50                  55                  60

Lys Gly Lys Ala Thr Leu Thr Val Asp Thr Ser Ser Ser Thr Ala Tyr

```
              65                  70                  75                  80
Val Asp Leu Ser Ser Leu Thr Ser Glu Asp Ser Ala Val Tyr Tyr Cys
                  85                  90                  95

Val Gly Gly His Tyr Asp Tyr Trp Gly Gln Gly Thr Thr Leu Thr Val
                 100                 105                 110

Ser Ser
```

<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

```
Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Arg
                85                  90                  95

Thr Phe Gly Gly Gly Thr Lys Leu Glu Ile Lys
            100                 105
```

<210> SEQ ID NO 81
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

```
Gln Val Gln Leu Gln Gln Pro Gly Ala Glu Leu Val Lys Pro Gly Ala
1               5                   10                  15

Ser Met Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Phe Pro Asp Thr Thr Thr Asn Tyr Asn Glu Lys Phe
50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Glu Tyr Tyr Asp Gly Thr Tyr Asp Ala Met Asp Tyr Trp Gly
                100                 105                 110

Gln Gly Thr Ser Val Thr Val Ser
            115                 120
```

```
<210> SEQ ID NO 82
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Ile Val Leu Thr Gln Ser Pro Ala Ile Met Ser Ala Ser Pro Gly
1               5                   10                  15

Glu Lys Val Ser Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Ser Ser Tyr Ser Leu Thr Ile Ser Ser Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Gly Gly Thr Lys Leu Glu Ile Lys Arg
            100                 105

<210> SEQ ID NO 83
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met Arg Trp Val Lys Gln Ser Pro Glu Lys Ser Leu Glu Trp Ile
        35                  40                  45

Gly Glu Ile Asn Pro Ser Thr Gly Gly Thr Thr Tyr Asn Gln Asn
    50                  55                  60

Phe Lys Ala Lys Ala Thr Leu Thr Val Asp Lys Ser Ser Ser Thr Ala
65                  70                  75                  80

Tyr Met Gln Leu Lys Ser Leu Thr Ser Glu Asp Ser Ala Val Tyr Tyr
                85                  90                  95

Cys Ala Arg Gly Gly Tyr Phe Leu Tyr Tyr Phe Asp Tyr Trp Gly Gln
            100                 105                 110

Gly Thr Thr Leu Thr Val Ser Ser
        115                 120

<210> SEQ ID NO 84
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 84

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ile Gln His Pro Arg Thr Phe Gly Gly Gly Thr Lys Leu Glu Ile Lys
            100                 105                 110

<210> SEQ ID NO 85
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Gly Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Thr Arg Trp Phe Ser Tyr Trp Gly Pro Gly Thr Leu Val Thr Val Ser
            100                 105                 110

Ala

<210> SEQ ID NO 86
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Asp Ile Val Leu Thr Gln Ser Pro Ala Ser Leu Ala Ala Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45
```

```
Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Thr Ala Thr Tyr Tyr Cys Gln His Ser Trp
                85                  90                  95

Glu Ile Pro Trp Thr Phe Gly Gly Gly Thr Lys Leu Glu Ile Lys
            100                 105                 110
```

<210> SEQ ID NO 87
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Arg Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Val Tyr Tyr Gly Ser Thr Tyr Gly Tyr Phe Asp Val Trp Gly
            100                 105                 110

Thr Gly Thr Thr Val Thr Val Ser Ser
        115                 120
```

<210> SEQ ID NO 88
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Asp Ile Val Leu Thr Gln Ser Pro Ala Ser Leu Ala Ala Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly His Pro Pro
        35                  40                  45

Lys Leu Leu Ile Arg Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
```

<210> SEQ ID NO 89
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Arg Leu Glu Trp Ile
        35                  40                  45

Gly Tyr Ile His Pro Tyr Asn Gly Gly Ser Gly Tyr Asn Gln Lys Phe
    50                  55                  60

Lys Arg Lys Ala Thr Leu Thr Val Asp Asn Ser Ser Asn Thr Thr Tyr
65                  70                  75                  80

Met Glu Leu Arg Ser Leu Thr Ser Glu Asp Ser Ala Val Tyr Tyr Cys
                85                  90                  95

Ala Arg Ser Tyr Asp Tyr Asp Thr Trp Phe Gly Tyr Trp Gly Gln Gly
            100                 105                 110

Thr Leu Val Thr Val Arg Ala
        115

<210> SEQ ID NO 90
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 91
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 91

Glu Val Lys Leu Glu Glu Ser Gly Gly Gly Leu Val Gln Pro Gly
1               5                   10                  15

Ser Met Lys Leu Ser Cys Val Ala Ser Gly Phe Thr Phe Ser Asn Tyr
            20                  25                  30

Trp Ile Asn Trp Val Arg Gln Ser Pro Glu Lys Gly Leu Glu Trp Val
        35                  40                  45

Ala Glu Ile Arg Met Lys Ser Asn Asn Tyr Ala Thr His Tyr Ala Glu
    50                  55                  60

Ser Val Lys Gly Arg Phe Thr Ile Ser Arg Asp Asp Ser Lys Ser Cys
65                  70                  75                  80

Val Tyr Leu Gln Met Asn Asn Leu Arg Pro Glu Asp Thr Gly Ile Tyr
                85                  90                  95

Tyr Cys Thr Arg Gly Gly Tyr Trp Gly Gln Gly Thr Thr Leu Thr Val
            100                 105                 110

Ser Ser

<210> SEQ ID NO 92
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Phe Cys Gln Gln
                85                  90                  95

Tyr Tyr Asn Tyr Pro Tyr Thr Phe Gly Gly Gly Thr Lys Leu Glu Ile
            100                 105                 110

Lys Arg

<210> SEQ ID NO 93
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

```
Gly Met Asn Trp Val Lys Gln Ala Pro Gly Lys Gly Leu Lys Trp Met
            35                  40                  45

Ala Trp Ile Asn Thr Tyr Thr Gly Glu Pro Thr Tyr Ala Asp Asp Phe
 50                  55                  60

Lys Gly Arg Phe Ala Phe Ser Leu Glu Thr Ser Ala Ser Thr Ala Ser
 65                  70                  75                  80

Leu Gln Ile Ile Asn Leu Lys Asn Glu Asp Thr Ala Thr Tyr Phe Cys
                85                  90                  95

Ala Arg Ile Gly Asp Ser Ser Pro Ser Asp Tyr Trp Gly Gln Gly Thr
            100                 105                 110

Thr Leu Thr Val Ser
            115

<210> SEQ ID NO 94
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Pro Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys
            100                 105

<210> SEQ ID NO 95
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Ile Gln Leu Val Gln Ser Gly Pro Glu Leu Lys Lys Pro Gly Glu
 1               5                  10                  15

Thr Val Lys Ile Ser Cys Lys Ala Ser Asp Tyr Thr Phe Thr Asp Phe
                20                  25                  30

Ser Ile His Trp Val Arg Gln Ser Pro Gly Lys Gly Leu Lys Trp Met
            35                  40                  45

Gly Trp Ile Asn Thr Glu Thr Gly Glu Pro Thr Val Ala Glu Asp Phe
 50                  55                  60

Lys Gly Arg Phe Ala Phe Ser Leu Glu Thr Ser Ala Ser Thr Ala Phe
 65                  70                  75                  80
```

```
Leu Gln Ile Tyr Asn Leu Lys Asn Glu Asp Ser Ala Thr Tyr Phe Cys
            85                  90                  95

Ala Arg Gly Arg Tyr Tyr Gly His Asp Tyr Ala Met Asp Tyr Trp Gly
            100                 105                 110

Gln Gly Thr Ser Val Thr Val Ser Ser
            115                 120
```

<210> SEQ ID NO 96
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Leu His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Phe Cys Gln His Phe Trp Ser Ile Pro Pro
                85                  90                  95

Thr Phe Gly Gly Gly Thr Lys Leu Glu Ile Lys Arg
            100                 105
```

<210> SEQ ID NO 97
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Leu Trp Asp Phe Ala Met Asp Tyr Trp Gly Gln Gly
            100                 105                 110

Thr Ser Val Thr Val Ser Ser
            115
```

-continued

<210> SEQ ID NO 98
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Ile
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Trp Thr
                85                  90                  95

Phe Gly Gly Gly Thr Lys Leu Glu Ile Lys
            100                 105

<210> SEQ ID NO 99
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala Gln Ile Trp Trp Asp Asp Tyr Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ile Gly Tyr Tyr Ser Gly Ser Ser Arg Cys Trp Tyr Phe
            100                 105                 110

Asp Val Trp Gly Thr Gly Ser Thr Val Thr Val Ser Ser
        115                 120                 125

<210> SEQ ID NO 100
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

```
Ser Ile Val Met Thr Gln Thr Pro Lys Phe Leu Leu Val Ser Ala Gly
1               5                   10                  15

Asp Arg Val Ala Ile Thr Cys Lys Ala Ser Gln Ser Val Ser Asn Asp
            20                  25                  30

Val Ala Trp Tyr Gln Lys Pro Gly Gln Ser Pro Thr Leu Leu Ile
        35                  40                  45

Ser Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Gly Tyr Ser Ser Pro Phe
                85                  90                  95

Thr Phe Gly Gly Gly Thr Lys Leu Glu Ile Lys Arg
            100                 105
```

<210> SEQ ID NO 101
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

```
Gln Val Gln Leu Gln Gln Ser Asp Ala Glu Leu Val Lys Pro Gly Ala
1               5                   10                  15

Ser Val Lys Ile Ser Cys Lys Ala Ala Gly Tyr Thr Phe Thr Asp Leu
            20                  25                  30

Thr Ile His Trp Val Lys Gln Arg Pro Glu Gln Gly Leu Glu Trp Ile
        35                  40                  45

Gly Tyr Ile Tyr Pro Gly Asp Ser Asn Thr Lys Tyr Asn Glu Lys Phe
50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Val Val Tyr Phe Cys
                85                  90                  95

Ala Arg Met Ile Thr Pro Tyr Tyr Phe Asp Tyr Trp Gly Gln Gly Thr
            100                 105                 110

Thr Leu Thr Val Ser
        115
```

<210> SEQ ID NO 102
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

```
Asp Ile Gln Met Thr Gln Ser Pro Ala Ser Leu Ser Ala Ser Val Gly
1               5                   10                  15

Glu Thr Val Thr Ile Ala Cys Arg Ala Ser Gly Asn Ile His Asn Tyr
            20                  25                  30

Leu Thr Trp Tyr Gln Gln Arg Gln Gly Lys Ser Pro Gln Leu Leu Val
        35                  40                  45
```

Tyr Asn Ala Lys Thr Leu Ala Val Gly Val Pro Ser Arg Phe Ser Gly
 50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Asn Thr Pro Pro
             85                  90                  95

Thr Phe Gly Gly Gly Thr Lys Leu Glu Ile Lys
            100                 105

<210> SEQ ID NO 103
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Glu Val Lys Leu Glu Glu Ser Gly Gly Gly Leu Val Gln Pro Gly Gly
1               5                   10                  15

Ser Met Lys Leu Ser Cys Val Ala Ser Gly Ile Ile Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ser Thr His Tyr Ala Glu
 50                 55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
             85                  90                  95

Tyr Cys Thr Arg His Tyr Tyr Ala Met Asp Tyr Trp Gly Gln Gly
            100                 105                 110

Thr Ser Val Thr Val Ser Ser
            115

<210> SEQ ID NO 104
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Lys Phe Ser Gly
 50                 55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
             85                  90                  95

Thr Phe Gly Gly Gly Thr Lys Leu Glu Ile Lys Arg

<210> SEQ ID NO 105
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Ala Ile Asn Ser Asn Gly Gly Ser Thr Tyr Tyr Pro Asp Thr Val
    50                  55                  60

Lys Gly Arg Leu Thr Ile Ser Arg Asp Asn Gly Lys Asn Thr Leu Tyr
65                  70                  75                  80

Leu Gln Met Ser Ser Leu Arg Ser Glu Asp Thr Ala Leu Tyr Tyr Cys
                85                  90                  95

Val Arg Asp Asp Gly Tyr Tyr Val Phe Phe Ala Tyr Trp Gly Gln Gly
            100                 105                 110

Thr Leu Val Thr Val Ser Ala
        115

<210> SEQ ID NO 106
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 106

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Pro
                85                  90                  95

Thr Phe Gly Ala Gly Thr Lys Leu Glu Leu Lys
            100                 105

<210> SEQ ID NO 107
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 107

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Val Arg Gln Ser Pro Gly Lys Gly Leu Glu Trp Leu
        35                  40                  45

Gly Val Ile Trp Gly Gly Ser Thr Asn Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Ser Gly Asp Tyr Asp Gly Ser Leu Trp Phe Ala Tyr Trp Gly Gln Gly
            100                 105                 110

Thr Leu Val Thr Val Ser Ala
        115

<210> SEQ ID NO 108
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Asp Ile Val Ile Thr Gln Asp Glu Leu Ser Asn Pro Val Thr Ser Gly
1               5                   10                  15

Glu Ser Val Ser Ile Ser Cys Arg Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Arg Thr Phe Gly Gly Gly Thr Lys Leu Glu Ile Lys
            100                 105                 110

<210> SEQ ID NO 109
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Val Gln Leu Val Glu Ser Gly Gly Asp Leu Val Lys Pro Gly Gly
1               5                   10                  15

Ser Leu Lys Leu Ser Cys Val Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Thr Phe Thr Tyr Tyr Pro Asp Ser Val
 50                  55                  60

Lys Gly Arg Phe Thr Val Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ser Arg His Gly Trp Gly Trp Gly Gln Gly Thr Leu Val Thr Val Ser
            100                 105                 110

Ala

<210> SEQ ID NO 110
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Asn Tyr
             20                  25                  30

Leu Ala Trp Tyr Gln Gln Lys Gln Gly Lys Ser Pro Gln Leu Leu Val
         35                  40                  45

Tyr Asn Ala Lys Ala Leu Ala Asp Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Ile Pro Pro
                 85                  90                  95

Thr Phe Gly Gly Gly Thr Lys Leu Glu Ile Lys
            100                 105

<210> SEQ ID NO 111
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
             20                  25                  30

Trp Met Asn Trp Val Arg Gln Ser Pro Glu Lys Gly Leu Glu Trp Val
         35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Thr Ala Ile Tyr
                 85                  90                  95

```
Tyr Cys Thr Arg His Tyr Asp Tyr Ala Met Asp Tyr Trp Gly Gln Gly
                100                 105                 110

Thr Ser Val Thr Val Ser Ser
        115
```

<210> SEQ ID NO 112
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Arg Ile Asn Ser Leu Gln Pro
65                  70                  75                  80

Glu Asp Phe Gly Ser Tyr Tyr Cys Gln His Phe Trp Ser Thr Pro Pro
                85                  90                  95

Thr Phe Gly Gly Gly Thr Lys Val Glu Ile Lys
            100                 105
```

<210> SEQ ID NO 113
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Leu Val
        35                  40                  45

Ala Glu Ile Arg Leu Ile Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg His Tyr Tyr Tyr Ala Leu Asp Tyr Trp Gly Gln Gly
                100                 105                 110

Thr Ser Val Thr Val Ser Ser
        115
```

<210> SEQ ID NO 114
<211> LENGTH: 114

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Asp Ile Val Met Ser Gln Ser Pro Ser Ser Leu Thr Val Ser Val Gly
1               5                   10                  15

Glu Lys Val Thr Leu Ser Cys Lys Ser Ser Gln Ser Leu Leu Tyr Ser
                20                  25                  30

Thr Asn Gln Lys Ile Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Ala
65                  70                  75                  80

Ile Ser Asn Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg

<210> SEQ ID NO 115
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Asn Asp Thr
                20                  25                  30

Tyr Tyr His Trp Leu Lys Gln Arg Pro Glu Gln Gly Leu Glu Trp Ile
            35                  40                  45

Gly Arg Ile Asp Pro Ala Asn Val Asn Thr Lys Tyr Asp Pro Lys Phe
        50                  55                  60

Gln Gly Lys Ala Thr Leu Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Gly Arg Gly Asn Ala Tyr Trp Gly Gln Gly Thr Leu Val Thr Val Ser
            100                 105                 110

Ala

<210> SEQ ID NO 116
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Val Ser Tyr Met
            20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
50                  55                  60

Gly Ser Gly Thr Phe Tyr Ser Leu Thr Ile Ser Val Glu Ala Glu
65                  70                  75                  80

Asp Ala Ala Asp Tyr Tyr Cys His Gln Trp Ser Ser Phe Thr Phe Gly
                85                  90                  95

Ser Gly Thr Lys Leu Glu Ile Lys
            100

<210> SEQ ID NO 117
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Ser
            20                  25                  30

Tyr Met Asn Trp Val Lys Gln Ser His Gly Lys Ser Leu Glu Trp Ile
            35                  40                  45

Gly Arg Val Asn Pro Asn Asn Gly Gly Ala Ser Tyr Asn His Lys Phe
50                  55                  60

Lys Gly Lys Ala Thr Leu Thr Val Asp Lys Ser Leu Ser Thr Ala Tyr
65                  70                  75                  80

Met Arg Leu Asn Ser Leu Thr Ser Glu Asp Ser Ala Val Tyr Tyr Cys
                85                  90                  95

Ser Arg Ser Gly Asp Leu Tyr Tyr Ala Met Asp Tyr Trp Gly Gln
            100                 105                 110

Gly Thr Ser Val Thr Val Ser Ser
            115                 120

<210> SEQ ID NO 118
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ile Ser Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser

```
                    50                  55                  60

Gly Ser Gly Thr Ser Tyr Ser Leu Thr Ile Ser Asn Met Glu Ala Glu
 65                  70                  75                  80

Asp Ala Ala Thr Tyr Tyr Cys Gln Gln Trp Ser Ser Thr Pro Pro Thr
                 85                  90                  95

Phe Gly Gly Gly Thr Lys Leu Glu Ile Lys Arg
                100                 105
```

<210> SEQ ID NO 119
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 119

```
Glu Val Gln Leu Gln Gln Ser Gly Pro Glu Leu Met Lys Pro Gly Ala
 1               5                  10                  15

Ser Val Lys Met Ser Cys Lys Ala Ser Gly Tyr Ile Phe Thr Asp Tyr
                20                  25                  30

Asn Met His Trp Val Lys Gln Asn Gly Lys Ser Leu Glu Trp Ile
            35                  40                  45

Gly Glu Val Asn Pro Asn Thr Gly Gly Ile Gly Tyr Asn Gln Lys Phe
         50                 55                  60

Lys Gly Lys Ala Thr Leu Thr Val Asp Lys Ser Ser Ser Thr Ala Tyr
 65                  70                  75                  80

Met Asp Leu Arg Ser Leu Thr Ser Glu Asp Ser Ala Val Tyr Tyr Cys
                 85                  90                  95

Ala Arg Asp Gly Asn Tyr Cys Phe Asp Tyr Trp Gly Gln Gly Thr Thr
                100                 105                 110

Leu Thr Val Ser Ser
            115
```

<210> SEQ ID NO 120
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 120

```
Asp Ile Val Met Thr Gln Ala Ala Phe Ser Asn Pro Val Thr Leu Gly
 1               5                  10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
         50                 55                  60

Glu Arg Phe Ser Ser Ser Gly Ser Gly Ser Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu His Pro Thr Phe Gly Gly Gly Thr Lys Leu Glu Ile Lys
                100                 105                 110
```

<210> SEQ ID NO 121
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Thr Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Gly Gln Ser Tyr Ser Asp Tyr Val Ser Phe Ala Tyr Trp Gly Gln
            100                 105                 110

Gly Thr Gln Val Thr Val Ser Ala
        115                 120

<210> SEQ ID NO 122
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 122

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Met Phe Gly Gly Gly Thr Arg Leu Glu Ile Lys
            100                 105                 110

<210> SEQ ID NO 123
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Glu Val Gln Leu Gln Gln Ser Gly Ala Glu Leu Leu Lys Pro Gly Ala
1               5                   10                  15

Ser Val Lys Leu Ser Cys Thr Ala Ser Gly Leu Asn Ile Lys Asp Tyr
            20                  25                  30

Tyr Ile His Trp Val Tyr Gln Arg Pro Glu Gln Gly Leu Glu Trp Ile
        35                  40                  45

Gly Arg Ile Asp Pro Glu Ser Asp Asn Thr Leu Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Asn Thr Pro Phe Ala Tyr Trp Gly Gln Gly Thr Leu Val Thr
            100                 105                 110

Val Ser Thr
        115

<210> SEQ ID NO 124
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 125
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Gln Val Gln Leu Gln Gln Ser Gly Ala Glu Leu Val Arg Pro Gly Thr
1               5                   10                  15

Ser Val Lys Val Ser Cys Lys Thr Ser Gly Tyr Ala Phe Thr Asn Tyr
            20                  25                  30

Leu Ile Glu Trp Val Lys Gln Arg Pro Gly Gln Gly Leu Glu Trp Ile

```
                35                  40                  45
Gly Val Ile Asn Pro Gly Ser Gly Gly Thr Asn Tyr Asn Glu Lys Phe
 50                  55                  60

Lys Val Lys Ala Thr Leu Thr Ala Asp Lys Ser Ser Thr Ala Tyr
 65                  70                  75                  80

Met Gln Leu Thr Ser Leu Thr Ser Asp Asp Ser Ala Val Tyr Phe Cys
                 85                  90                  95

Thr Arg Arg Asp Gly Tyr Phe Phe Pro Trp Phe Ala Tyr Trp Gly Gln
                100                 105                 110

Gly Thr Leu Val Thr Val Ser Ala
            115                 120

<210> SEQ ID NO 126
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Lys Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys His Gln
                 85                  90                  95

Tyr Tyr Ser Tyr Pro Leu Thr Phe Ala Ala Gly Thr Lys Leu Glu Leu
                100                 105                 110

Lys

<210> SEQ ID NO 127
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Gln Val Gln Leu Gln Gln Pro Gly Ser Val Leu Val Arg Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile His Pro Asn Asn Gly Ser Thr Asn Tyr Asn Glu Lys Phe
 50                  55                  60

Lys Gly Lys Ala Thr Leu Thr Val Asp Thr Ser Ser Ser Thr Ala Tyr
 65                  70                  75                  80
```

```
Val Asp Leu Ser Ser Leu Thr Ser Glu Asp Ser Ala Val Tyr Tyr Cys
            85                  90                  95

Ala Arg Trp Thr Leu Phe Thr Tyr Trp Gly Gln Gly Thr Leu Val Thr
            100                 105                 110

Val Ser Ala
        115

<210> SEQ ID NO 128
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Leu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Ala Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 129
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Arg Gly Ser Ser Thr Ile His Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Phe Asn Trp Tyr Phe Asp Val Trp Gly Ala Gly Thr Thr
            100                 105                 110

Val Thr Val Ser Ser
        115
```

<210> SEQ ID NO 130
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 130

```
Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Lys Ala Glu Asp Leu Ala Ile Tyr Tyr Cys Gln Gln
                85                  90                  95

Tyr Tyr Arg Tyr Pro Leu Thr Phe Gly Ala Gly Thr Lys Leu Glu Leu
            100                 105                 110

Lys
```

<210> SEQ ID NO 131
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 131

```
Gln Val Gln Leu Gln Gln Pro Gly Ala Glu Leu Val Lys Pro Gly Ala
1               5                   10                  15

Ser Val Met Leu Ser Cys Lys Ala Ser Gly Tyr Thr Phe Thr Ser Tyr
            20                  25                  30

Trp Val His Trp Val Lys Gln Arg Pro Gly Gln Gly Leu Glu Trp Ile
        35                  40                  45

Gly Val Ile Asn Pro Arg Asn Gly Arg Asn Asn Tyr Asn Glu Lys Phe
    50                  55                  60

Lys Thr Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Asp Tyr Asp Gly Gly Asp Tyr Ala Met Asp Tyr Trp Gly
            100                 105                 110

Gln Gly Thr Ser Val Thr Val Ser Ser
        115                 120
```

<210> SEQ ID NO 132
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 132

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Thr Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 133
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Glu Val Glu Leu Gln Gln Ser Gly Pro Glu Leu Val Lys Pro Gly Ala
1               5                   10                  15

Ser Val Lys Ile Ser Cys Lys Thr Ser Gly Asn Thr Tyr Thr Glu Tyr
            20                  25                  30

Thr Met Gln Trp Val Lys Leu Ser His Gly Lys Ser Leu Glu Trp Ile
        35                  40                  45

Gly Gly Ile Asn Pro Asn Gly Ile Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Lys Ser Glu Asp Ser Ala Val Tyr Tyr Cys
                85                  90                  95

Ala Arg Ala Gly Leu Gly Asn Tyr Val Trp Ala Met Asp Tyr Trp Gly
            100                 105                 110

Gln Gly Ala Ser Val Thr Val Ser Ser
        115                 120

<210> SEQ ID NO 134
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu His Trp Tyr Leu Gln Lys Pro Gly Gln Ser

```
                    35                  40                  45
Pro Asn Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Ile Val Glu Ala Glu Asp Leu Gly Leu Tyr Phe Cys Ser Gln Ser
                85                  90                  95

Thr His Val Pro Arg Thr Phe Gly Gly Gly Thr Lys Leu Glu Ile Lys
                100                 105                 110

<210> SEQ ID NO 135
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Gln Val Gln Leu Pro Gln Ser Gly Ala Glu Leu Ala Lys Pro Gly Ala
1               5                   10                  15

Ser Val Lys Ile Ser Cys Lys Ala Ser Gly Phe Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Thr Asp Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Gly Ser Leu Thr Ser Glu Asp Ser Ala Val Tyr Tyr Cys
                85                  90                  95

Ala Arg Ser Ser Tyr Gly Ser Ser Pro Phe Asp Tyr Trp Gly Gln Gly
                100                 105                 110

Ser Thr Leu Thr Val Ser Ser
        115

<210> SEQ ID NO 136
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Asp Ile Val Met Ser Gln Ser Pro Ser Ser Leu Ala Val Ser Val Gly
1               5                   10                  15

Glu Lys Val Thr Met Asn Cys Glu Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Pro Ala Val Tyr Tyr Cys Gln Gln
                85                  90                  95
```

Tyr Tyr Ser Tyr Pro Leu Thr Phe Gly Ala Gly Thr Lys Leu Glu Leu
            100                 105                 110

Lys

<210> SEQ ID NO 137
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Ala Tyr Leu Gln Met Asn Ser Leu Arg Ala Glu Asp Thr Gly Ile Tyr
                85                  90                  95

Tyr Cys Val Ser Thr Gly Thr Ser Tyr Trp Gly Gln Gly Thr Leu Val
            100                 105                 110

Thr Val Ser Ala
        115

<210> SEQ ID NO 138
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Pro Arg Phe Ser Gly Arg
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Trp Ser Ser Asn Pro Pro Thr
                85                  90                  95

Phe Gly Ala Gly Thr Lys Leu Glu Met Lys
            100                 105

<210> SEQ ID NO 139
<211> LENGTH: 116
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Glu Val Gln Leu Gln Gln Ser Gly Pro Glu Leu Met Lys Pro Gly Ala
1               5                   10                  15

Ser Val Lys Met Ser Cys Lys Ala Ser Gly Asp Thr Phe Thr Asp Tyr
            20                  25                  30

Asn Ile His Trp Val Lys Gln Asn Gly Lys Ser Leu Glu Trp Ile
        35                  40                  45

Gly Glu Val Asn Pro Asn Ile Gly Ile Gly Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Met Gly Arg Trp Tyr Phe Asp Val Trp Gly Ala Gly Thr Thr Val
            100                 105                 110

Thr Val Ser Ser
            115

<210> SEQ ID NO 140
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 141
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Gln Gln Ser Gly Pro Glu Met Val Lys Pro Gly Ala
1               5                   10                  15

```
Ser Val Lys Ile Ser Cys Lys Ala Gly Tyr Thr Phe Thr Asp Tyr Tyr
             20                  25                  30

Met His Trp Val Lys Gln Ser His Gly Lys Ser Leu Glu Trp Ile Gly
         35                  40                  45

Arg Val Asn Thr Asn Asn Gly Gly Thr Ser Tyr Asp Gln Lys Phe Glu
     50                  55                  60

Gly Lys Ala Thr Leu Thr Val Asp Lys Ser Ser Ser Thr Ala Tyr Met
 65                  70                  75                  80

Glu Leu Asn Ser Leu Thr Ser Glu Asp Ser Ala Val Tyr Tyr Cys Val
                 85                  90                  95

Ile Pro Ala Trp Phe Ala Tyr Trp Gly Gln Gly Thr Leu Val Thr Val
            100                 105                 110

Ser Ala
```

<210> SEQ ID NO 142
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

```
Asp Ile Val Met Thr Gln Ser Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Leu Gly Val Tyr Phe Cys Ser Gln Ser
                 85                  90                  95

Thr His Leu Pro Arg Thr Phe Gly Gly Gly Thr Lys Leu Glu Ile Lys
            100                 105                 110
```

<210> SEQ ID NO 143
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

```
Gln Val Gln Leu Gln Gln Ser Gly Ser Val Leu Val Arg Pro Gly Ala
 1               5                  10                  15

Ser Val Lys Leu Ser Cys Lys Ala Ser Gly Tyr Thr Phe Thr Ser Tyr
             20                  25                  30

Met His Trp Val Lys Gln Arg Pro Gly Gln Gly Leu Glu Trp Ile Gly
         35                  40                  45

Glu Ile His Pro Asn Ser Gly Asn Thr Asn Tyr Asn Glu Lys Phe Lys
     50                  55                  60

Gly Lys Ala Thr Leu Thr Val Asp Thr Ser Ser Ser Thr Ala Tyr Val
```

```
                65                  70                  75                  80
Asp Leu Ser Ser Leu Thr Ser Glu Asp Ser Ala Val Tyr Tyr Cys Ala
                    85                  90                  95

Gly Gly Asn Tyr Asp Tyr Trp Gly Gln Gly Thr Thr Leu Thr Val Ser
                100                 105                 110

Ser
```

<210> SEQ ID NO 144
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 144

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Val Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Asp Glu Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
                100                 105                 110
```

<210> SEQ ID NO 145
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

```
Glu Val Gln Leu Glu Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Ala Phe Tyr Pro Gly Asn Ser Gly Thr Tyr Tyr Asn Gln Lys Phe
        50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Ser Arg Ser Gly Ser Gly Arg Phe Ala Tyr Trp Gly Gln Gly Thr Leu
                100                 105                 110

Val Thr Val Ser Ala
            115
```

<210> SEQ ID NO 146
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Ala Ala Thr Tyr Tyr Cys Gln Gln Trp Ser Asn Thr Pro Pro Thr
                85                  90                  95

Phe Gly Ser Val Thr Lys Leu Glu Ile Lys
            100                 105

<210> SEQ ID NO 147
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp His
            20                  25                  30

Asn Ile His Trp Val Lys Gln His Gly Lys Ser Leu Glu Trp Ile
        35                  40                  45

Gly Glu Ile Asn Pro Asn Thr Gly Gly Thr Gly Tyr Asn Gln Lys Phe
    50                  55                  60

Gln Gly Lys Ala Thr Met Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Gly Leu Tyr Phe Phe Asp Tyr Trp Gly Gln Gly Thr Thr Leu
            100                 105                 110

Thr Val Ser Ser
        115

<210> SEQ ID NO 148
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Asp Ile Val Ile Thr Gln Asp Asp Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Arg Thr Phe Gly Gly Gly Thr Lys Leu Glu Ile Lys
            100                 105                 110

<210> SEQ ID NO 149
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Arg His Gly Trp Gly Trp Gly Gln Gly Thr Leu Val Thr Val Ser
            100                 105                 110

Ala

<210> SEQ ID NO 150
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

```
Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Ser Gly Thr Lys Leu Glu Ile Lys
                100                 105
```

<210> SEQ ID NO 151
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Asn Gln Gly Lys Ser Leu Glu Trp Ile
            35                  40                  45

Gly Glu Ile Asn Pro Asn Thr Gly Gly Thr Gly Tyr Asn Gln Lys Phe
        50                  55                  60

Lys Gly Lys Ala Thr Leu Thr Val Asp Lys Ser Ser Thr Ala Phe
65                  70                  75                  80

Ile Glu Leu Arg Ser Leu Thr Ser Glu Asp Ser Ala Ile Tyr Tyr Cys
                85                  90                  95

Thr Arg Gly Gly Tyr Asp His Tyr Trp Tyr Phe Asp Val Trp Gly Ala
                100                 105                 110

Gly Thr Thr Val Thr Val Ser Ser
            115                 120
```

<210> SEQ ID NO 152
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

```
Asp Ile Val Leu Thr Gln Phe Pro Ala Ser Leu Ala Val Ser Leu Gly
1               5                   10                  15

Gln Arg Ala Thr Ile Pro Cys Arg Ala Ser Glu Ser Val Asp Ser Tyr
                20                  25                  30

Gly Asn Ser Phe Met His Trp Phe Gln Gln Lys Pro Gly Gln Pro Pro
            35                  40                  45

Lys Leu Leu Ile Tyr Arg Ala Ser Asn Leu Glu Ser Glu Ile Pro Ala
        50                  55                  60

Arg Phe Ser Gly Ser Gly Ser Gly Thr Asp Phe Thr Leu Thr Ile Asn
65                  70                  75                  80

Pro Val Glu Ala Asp Asp Val Ala Thr Tyr Tyr Cys Gln Gln Ser His
                85                  90                  95

Glu Asp Pro Tyr Thr Phe Gly Gly Gly Thr Lys Met Glu Ile Lys Arg
```

-continued

```
                100                 105                 110
```

<210> SEQ ID NO 153
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

```
Glu Val Gln Leu Gln Gln Ser Gly Thr Val Leu Ala Arg Pro Gly Ala
1               5                   10                  15

Ser Val Lys Met Ser Cys Lys Ala Gly Tyr Thr Phe Thr Ser Tyr Trp
            20                  25                  30

Met His Trp Val Lys Gln Arg Pro Gly Gln Gly Leu Glu Trp Ile Gly
        35                  40                  45

Ala Ile Tyr Pro Gly Lys Asn Asp Thr Thr Tyr Asn Gln Lys Phe Lys
    50                  55                  60

Gly Lys Ala Lys Leu Thr Ala Val Thr Ser Ala Ser Thr Leu Tyr Met
65                  70                  75                  80

Glu Leu Ser Ser Leu Thr Asn Glu Asp Ser Ala Val Tyr Tyr Cys Thr
                85                  90                  95

Arg Ser Gly Lys Gly Tyr Phe Ala Tyr Trp Gly Gln Gly Thr Leu Val
            100                 105                 110

Thr Val Ser Ala
        115
```

<210> SEQ ID NO 154
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

```
Asp Val Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110
```

<210> SEQ ID NO 155
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 155

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Val Ser Trp Ile Arg Lys Thr Ser Gly Lys Gly Leu
        35                  40                  45

Glu Trp Leu Ala His Ile Phe Trp Asp Asp Asp Lys Trp Tyr Asn Pro
    50                  55                  60

Ser Leu Lys Ser Arg Leu Thr Ile Ser Lys Ala Thr Ser Ser Asn Gln
65                  70                  75                  80

Val Phe Leu Ile Leu Thr Ser Val Asp Thr Ala Asp Thr Ala Thr Tyr
                85                  90                  95

Tyr Cys Ala Thr Phe Tyr Gly Leu Tyr Phe Ala Tyr Trp Gly Gln Gly
            100                 105                 110

Thr Thr Leu Thr Val Ser Ser
        115

<210> SEQ ID NO 156
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Asp Ile Val Met Ser Gln Ser Pro Ser Ser Leu Ala Val Ser Val Gly
1               5                   10                  15

Glu Lys Val Thr Met Asn Cys Glu Ser Ser Gln Ser Leu Leu Tyr Asn
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Arg Ala Asp Asp Pro Ala Val Tyr Tyr Cys Gln Gln
                85                  90                  95

Tyr Phe Asn Tyr Pro Leu Thr Phe Gly Ala Gly Thr Lys Leu Glu Leu
            100                 105                 110

Lys

<210> SEQ ID NO 157
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala

```
            20                  25                  30
Trp Met Asp Trp Val Arg Gln Ser Pro Glu Lys Gly Leu Glu Trp Val
        35                  40                  45

Ala Glu Ile Arg Ser Lys Pro Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Ala Tyr Leu Gln Met Asn Ser Leu Arg Ala Glu Asp Thr Gly Ile Tyr
                85                  90                  95

Tyr Cys Val Ser Thr Gly Thr Ser Tyr Trp Gly Gln Gly Thr Leu Val
            100                 105                 110

Thr Val Ser Ala
        115

<210> SEQ ID NO 158
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Thr Pro Pro Thr
                85                  90                  95

Phe Gly Gly Gly Thr Lys Leu Glu Ile Lys Arg
            100                 105

<210> SEQ ID NO 159
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Ile Phe Thr Asp Tyr
            20                  25                  30

Asn Met His Trp Val Lys Gln Asn Gly Lys Ser Leu Glu Trp Ile
        35                  40                  45

Gly Glu Val Asn Pro Asn Thr Gly Gly Ile Gly Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Asp Leu Arg Ser Leu Thr Ser Glu Asp Ser Ala Val Tyr Tyr Cys
                85                  90                  95

Ala Arg Asp Gly Asn Tyr Cys Phe Asp Tyr Trp Gly Gln Gly Thr Thr
            100                 105                 110

Leu Thr Val Ser Ser
        115
```

<210> SEQ ID NO 160
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 160

```
Asp Ile Lys Met Thr Gln Ser Pro Ser Ser Met Tyr Ala Ser Leu Gly
1               5                   10                  15

Glu Arg Val Thr Leu Thr Cys Lys Ala Ser Gln Asp Ile Asn Ser Tyr
            20                  25                  30

Leu Ser Trp Phe Gln Gln Lys Pro Gly Lys Ser Pro Glu Thr Leu Ile
        35                  40                  45

Tyr Arg Ala Asn Arg Leu Ile Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105
```

<210> SEQ ID NO 161
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Glu Val His Leu Gln Gln Ser Gly Pro Glu Leu Val Asn Pro Gly Ser
1               5                   10                  15

Ser Val Lys Ile Ser Cys Lys Ala Ala Gly Tyr Thr Phe Thr Asp Tyr
            20                  25                  30

Asn Met Asp Trp Val Lys Gln Ser His Gly Lys Arg Leu Glu Trp Ile
        35                  40                  45

Gly Asn Ile Tyr Pro Asn Asn Gly Ala Gly Tyr Asn Gln Asn Phe
    50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Ile Thr Ala Ala Trp Phe Ala Tyr Trp Gly Gln Gly Thr
            100                 105                 110

Leu Val Thr Val Ser Ala
        115
```

<210> SEQ ID NO 162
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 162

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Thr Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Ser Pro Pro Thr
                85                  90                  95

Phe Gly Ala Gly Thr Lys Leu Glu Leu Lys
            100                 105

<210> SEQ ID NO 163
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 163

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Ser Leu Glu Trp Ile
        35                  40                  45

Gly Glu Ile Asn Pro Asn Thr Gly Gly Thr Gly Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ile Pro Ser Leu Arg Arg Tyr Tyr Phe Asp Tyr Trp Gly Gln
            100                 105                 110

Gly Thr Thr Leu Thr Val Ser Ser
        115                 120

<210> SEQ ID NO 164
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

Asp Leu Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Thr Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

<210> SEQ ID NO 165
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ile Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Asn Val Asp Thr Ala Asp Thr Ala Thr Tyr Tyr
                85                  90                  95

Cys Ala Arg Met Val Tyr Tyr Asp Tyr Asp Gly Gly Phe Ala Tyr Trp
            100                 105                 110

Gly Gln Gly Thr Leu Val Thr Val Ser Ala
        115                 120

<210> SEQ ID NO 166
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Pro Leu Ile Tyr Arg Ala Ser Asn Leu Glu Ser Gly Ile Pro Ala
            50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Tyr Thr Phe Gly Gly Gly Thr Lys Leu Glu Ile Lys Arg
            100                 105                 110

<210> SEQ ID NO 167
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Val Gln Leu Gln Gln Ser Gly Thr Val Leu Ala Arg Pro Gly Ala
1               5                   10                  15

Ser Val Arg Met Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Ala Ile Tyr Pro Gly Asn Ser Asp Thr Ser Tyr Asn His Lys Phe
50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Ser Gly Thr Gly Trp Phe Ala Tyr Trp Gly Gln Gly Thr Leu
            100                 105                 110

Val Thr Val Ser Ala
            115

<210> SEQ ID NO 168
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Asp Ile Val Leu Thr Gln Ser Pro Ala Ser Leu Ala Val Ser Leu Gly
1               5                   10                  15

Gln Arg Ala Thr Ile Phe Cys Arg Ala Ser Gln Ser Val Asp Tyr Asn
                20                  25                  30

Gly Ile Ser Tyr Met His Trp Phe Gln Gln Lys Pro Gly Gln Pro Pro
            35                  40                  45

Lys Leu Leu Ile Tyr Ala Ala Ser Asn Val Gln Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Phe Tyr Cys Gln Gln Ser Ile
                85                  90                  95

```
Glu Asp Pro Pro Thr Phe Gly Gly Gly Thr Lys Leu Glu Ile Lys
            100                 105                 110
```

<210> SEQ ID NO 169
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Ile Asn Trp Val Lys Gln Arg Pro Gly Gln Gly Leu Glu Trp Ile
            35                  40                  45

Gly Arg Ile Tyr Pro Gly Glu Gly Asp Thr Asn Tyr Ser Gly Asn Phe
50                  55                  60

Glu Gly Lys Ala Thr Leu Thr Ala Asp Lys Ser Ser Thr Thr Ala Tyr
65                  70                  75                  80

Met Gln Leu Ser Ser Leu Thr Ser Val Asp Ser Ala Val Tyr Phe Cys
                85                  90                  95

Thr Arg Gly Leu Val Met Asp Tyr Trp Gly Gln Gly Thr Ala Leu Thr
            100                 105                 110

Val Ser Ser
        115
```

<210> SEQ ID NO 170
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Asn Ile Asn Ser Asn
                20                  25                  30

Leu Val Trp Tyr Gln Gln Lys Pro Gly Lys Ala Pro Lys Leu Leu Ile
            35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Arg
                85                  90                  95

Thr Phe Gly Gly Gly Thr Lys Leu Glu Ile Lys
            100                 105
```

<210> SEQ ID NO 171
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Tyr Trp Val Arg Gln Ala Pro Gly Gln Gly Leu Glu Trp Met
        35                  40                  45

Gly Glu Ile Asn Pro Asn Asn Gly Gly Thr Ala Tyr Asn Gln Lys Phe
    50                  55                  60

Arg Gly Lys Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Asp Lys Gly Phe Asp Tyr Trp Gly Gln Gly Thr Thr Val
            100                 105                 110

Thr Val Ser Ser
        115

<210> SEQ ID NO 172
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 172

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Pro Thr
                85                  90                  95

Phe Gly Gln Gly Thr Lys Leu Glu Ile Lys
            100                 105

<210> SEQ ID NO 173
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

```
Asn Met His Trp Val Arg Gln Ala Pro Gly Gln Gly Leu Glu Trp Met
        35                  40                  45

Gly Glu Ile Asn Pro Asn Ile Gly Gly Thr Gly Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Thr Tyr Ser Tyr Tyr Ser Tyr Glu Phe Ala Tyr Trp Gly Gln
                100                 105                 110

Gly Thr Leu Val Thr Val Ser Ser
            115                 120

<210> SEQ ID NO 174
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Ser Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gly Gly Thr Lys Val Glu Ile Lys
                100                 105                 110

Arg

<210> SEQ ID NO 175
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp His
            20                  25                  30

Thr Ile His Trp Val Arg Gln Ala Pro Gly Lys Gly Leu Glu Trp Ile
        35                  40                  45

Gly Tyr Ile Tyr Pro Arg Asp Gly Ser Thr Lys Tyr Asn Glu Glu Phe
    50                  55                  60

Lys Gly Arg Val Thr Ile Thr Ala Asp Thr Ser Thr Asp Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Ser Tyr Ser Asn Tyr Phe Asp Tyr Trp Gly Gln Gly Thr Thr
                100                 105                 110

Val Thr Val Ser Ser
            115

<210> SEQ ID NO 176
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Leu
                85                  90                  95

Thr Phe Gly Gln Gly Thr Lys Leu Glu Ile Lys
                100                 105

<210> SEQ ID NO 177
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Ser
                20                  25                  30

Tyr Ile His Trp Val Arg Gln Ala Pro Gly Gln Gly Leu Glu Trp Met
            35                  40                  45

Gly Tyr Ile Ser Ser Gly Ser Gly Thr Thr Tyr Asn Gln Lys Phe
        50                  55                  60

Lys Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Val Arg Tyr Phe Asp Val Trp Gly Gln Gly Thr Thr
                100                 105                 110

Val Thr Val Ser Ser
            115
```

<210> SEQ ID NO 178
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Pro
                85                  90                  95

Thr Phe Gly Gln Gly Thr Lys Leu Glu Ile Lys
            100                 105
```

<210> SEQ ID NO 179
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Arg Leu Glu Trp Ile
        35                  40                  45

Gly Tyr Ile Tyr Pro Asp Asn Gly Gly Ala Gly Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Ile Thr Thr Ala Trp Phe Ala Tyr Trp Gly Gln Gly Thr
            100                 105                 110

Leu Val Thr Val Ser Ser
        115
```

<210> SEQ ID NO 180
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Ala Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asn Asn Asp
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Arg
                85                  90                  95

Thr Phe Gly Gln Gly Thr Lys Leu Glu Ile Lys
                100                 105

<210> SEQ ID NO 181
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asn Ile Phe Pro Asp Thr Thr Thr Asn Tyr Asn Glu Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Tyr Tyr Asp Gly Thr Tyr Asp Ala Met Asp Tyr Trp Gly
                100                 105                 110

Gln Gly Thr Leu Val Thr Val Ser Ser
        115                 120

<210> SEQ ID NO 182
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr
            20                  25                  30

Gly Asn Ser Phe Met His Trp Tyr Gln Gln Lys Pro Gly Gln Ala Pro 35                  40                  45

Arg Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser His
                85                  90                  95

Glu Asp Pro Tyr Thr Phe Gly Gln Gly Thr Lys Leu Glu Ile Lys
            100                 105                 110

<210> SEQ ID NO 183
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Ala Ile Tyr Pro Gly Lys Ser Asp Thr Thr Tyr Asn Gln Lys Phe
 50                 55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Lys Gly Tyr Phe Ala Tyr Trp Gly Gln Gly Thr Leu
            100                 105                 110

Val Thr Val Ser Ser
        115

<210> SEQ ID NO 184
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Lys Ser Gly Val
 50                 55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

```
Tyr Tyr Ser Tyr Pro Leu Thr Phe Gly Gln Gly Thr Lys Leu Glu Ile
            100                 105                 110

Lys
```

<210> SEQ ID NO 185
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Trp Met His Trp Val Arg Gln Ala Pro Gly Gln Gly Leu Glu Trp Met
            35                  40                  45

Gly Glu Ile His Pro Asn Asn Gly Ser Thr Asn Tyr Asn Glu Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115
```

<210> SEQ ID NO 186
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gly Gly Thr Lys Leu Glu Ile Lys
            100                 105                 110
```

<210> SEQ ID NO 187
<211> LENGTH: 118
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 187

```
Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser Thr Ser
            20                  25                  30
Gly Met Gly Val Ser Trp Ile Arg Gln Pro Pro Gly Lys Ala Leu Glu
        35                  40                  45
Trp Leu Ala His Ile Phe Trp Asp Asp Lys Trp Tyr Asn Pro Ser
    50                  55                  60
Leu Lys Ser Arg Leu Thr Ile Ser Lys Asp Thr Ser Lys Ser Gln Val
65                  70                  75                  80
Val Leu Thr Met Thr Asn Met Asp Pro Val Asp Thr Ala Thr Tyr Tyr
                85                  90                  95
Cys Ala Thr Phe Tyr Gly Leu Tyr Phe Ala Tyr Trp Gly Gln Gly Thr
            100                 105                 110
Leu Val Thr Val Ser Ser
        115
```

<210> SEQ ID NO 188
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 188

```
Asp Ile Val Met Thr Gln Ser Pro Asp Ser Leu Ala Val Ser Leu Gly
1               5                   10                  15
Glu Arg Ala Thr Ile Asn Cys Glu Ser Ser Gln Ser Leu Leu Tyr Asn
            20                  25                  30
Ser Asn Gln Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Phe Asn Tyr Pro Leu Thr Phe Gly Gln Gly Thr Lys Leu Glu Ile
            100                 105                 110
Lys Arg
```

<210> SEQ ID NO 189
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Ala
                20                  25                  30

Trp Met Asp Trp Val Arg Gln Ala Pro Gly Gln Arg Leu Glu Trp Met
            35                  40                  45

Gly Glu Ile Arg Ser Lys Pro Asn Asn His Ala Thr Tyr Tyr Ala Glu
    50                  55                  60

Ser Val Lys Gly Arg Val Thr Ile Thr Arg Asp Thr Ser Ala Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Thr Gly Thr Ser Tyr Trp Gly Gln Gly Thr Leu Val
            100                 105                 110

Thr Val Ser Ser
            115

<210> SEQ ID NO 190
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asn
                20                  25                  30

Gly Ile Ser Tyr Met His Trp Tyr Gln Gln Lys Pro Gly Gln Ala Pro
            35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys
            100                 105                 110

<210> SEQ ID NO 191
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
                20                  25                  30

Trp Ile Asn Trp Val Arg Gln Met Pro Gly Lys Gly Leu Glu Trp Met
            35                  40                  45

Gly Arg Ile Tyr Pro Gly Glu Gly Asp Thr Asn Tyr Ser Gly Asn Phe

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Thr Arg Gly Leu Val Met Asp Tyr Trp Gly Gln Gly Thr Leu Val Thr
            100                 105                 110

Val Ser

<210> SEQ ID NO 192
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asp
            20                  25                  30

Gly Ile Ser Tyr Met His Trp Tyr Gln Gln Lys Pro Gly Gln Ala Pro
        35                  40                  45

Arg Leu Leu Ile Tyr Ala Ala Ser Asn Val Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ile
                85                  90                  95

Glu Asp Pro Pro Thr Phe Gly Gly Gly Thr Lys Val Glu Ile Lys
            100                 105                 110

<210> SEQ ID NO 193
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Ser Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 194
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 195
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Tyr Tyr
            20                  25                  30

Trp Met His Trp Val Arg Gln Ala Pro Gly Gln Gly Leu Glu Trp Met
        35                  40                  45

Gly Glu Ile His Pro Asn Asn Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 196
<211> LENGTH: 115
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Trp Met His Trp Val Arg Gln Ala Pro Gly Gln Gly Leu Glu Trp Met
        35                  40                  45

Gly Glu Ile His Pro Asn Asp Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 197
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Trp Met His Trp Val Arg Gln Ala Pro Gly Gln Gly Leu Glu Trp Met
        35                  40                  45

Gly Glu Ile His Pro Asn Gly Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 198
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198
```

```
Gln Val Gln Leu Val Gln Ser Gly Ala Glu Val Lys Pro Gly Ala
1               5                  10                 15

Ser Val Lys Val Ser Cys Lys Ala Ser Gly Tyr Thr Phe Asn Ser Tyr
            20                  25                  30

Trp Met His Trp Val Arg Gln Ala Pro Gly Gln Gly Leu Glu Trp Met
        35                  40                  45

Gly Glu Ile His Pro Asn Ser Gly Ser Thr Asn Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Thr Leu Phe Thr Tyr Trp Gly Gln Gly Thr Leu Val Thr
            100                 105                 110

Val Ser Ser
        115

<210> SEQ ID NO 199
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Pro Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Thr Gly Thr Ser Tyr Trp Gly Gln Gly Thr Leu Val
            100                 105                 110

Thr Val Ser Ser
        115

<210> SEQ ID NO 200

<400> SEQUENCE: 200

000

<210> SEQ ID NO 201

<400> SEQUENCE: 201

000

<210> SEQ ID NO 202

<400> SEQUENCE: 202
```

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 220

```
caaattgttc tcacccagtc tccagcactc atgtctgcat ctccagggga aaaggtctcc      60
ctgacctgca gtgccaactc aactgtaagt ttcatgtact ggtaccagca gaagccaaga     120
tcctccccca caccctggat ttatctcaca tccaacctgg cttctggagt ccctgctcgc     180
ttcagtggca gtgggtctgg gacctcttac tctcttacaa tcagcagcat ggaggctgaa     240
gatgctgcca cttattactg ccagcagtgg agtagtaact cacccatcac gttcggtgct     300
gggaccaagc tggagctgaa ac                                              322
```

<210> SEQ ID NO 221
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 221

```
tctgatgtgc agcttcagga ctcaggacct ggcctggtga aaccttctca gtctctgtcc    60
gtcacctgca ctgtcactgg ctactccatc acctggggtt attactggaa ctggatccgg   120
cagtttccag gaaacaaact ggagtggatg ggtaacatac acaacagtgg tggcactaac   180
tacaacccat ctctcaagag tcgaatctct atcactcgag acacatccaa gaaccagttc   240
ttcctgcagt tgaattctgt gactactgag acacagcca catattactg tgcaaccaca   300
aactgggact actttgacta ctggggccaa ggcaccactc tcacagtctc ctca         354
```

<210> SEQ ID NO 222
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 222

```
gacattgtga tgtcacagtc tccatcctcc ctggctgtgt cagttggaga aaggtcact     60 atgagctgca agtccagtca gagcctttta tatagtagca atcaaaagag ctacttggcc   120
tggtaccagc agaaaccagg gcagtctcct aaactgttaa tctactgggc atccactagg   180
gaatctgggg tccctgaccg cttcacaggc agtggatcag ggacagattt cactctcacc   240
atcagcagtg tgcaggctga agacctggcc gtttattact gcaagcaatc ttataatctt   300
cggacgttcg gtggaggcac caagctggaa atcaaac                            337
```

<210> SEQ ID NO 223
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 223

```
caggttcagc tgcagcagtc tgacgctgag ttggtgaaac ctggagcttc agtgaagata    60
tcctgcaagg tttctggcta caccttcact gaccatacta ttcactggat gaagcagagg   120
cctgaacagg gcctggaatg gattggatat atttatccta gagatggtag tactaagtac   180
aatgaggagt tcaagggcaa ggccacattg actgcagaca aatcctccag cacagcctac   240
atgcagctca acagcctgac atctgaggac tctgcagtct atttctgtgc aagatcatat   300
agtaactact ttgactactg gggccaaggc accactctca cagtctcctc a            351
```

<210> SEQ ID NO 224
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 224

```
gacattgtga tgtcacagtc tccatcctcc ctagctgtgt cagttggaga aaggttact     60 atgagctgca agtccagtca gagcctttta tatagtagca atcaaaagaa ctacttggcc   120
tggtaccagc agaaaccagg gcagtctcct aaactgctga tttactgggc atccactagg   180
gaatctgggg tccctgatcg cttcacaggc agtggatctg ggacagattt cactctcacc   240
```
atcagcagtg tgaaggctga agacctggca gtttatttct gtcagcaata ttataactat    300
ccgtacacgt tcggagggg gaccaagctg aaa    333

<210> SEQ ID NO 225
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
caggtccaac tgcagcaacc tggggctgaa attgtgaggc ctggggcttc agtgaagctg     60
tcctgcaagg cttctggcta cacctttacc gactattgga tgaactgggt aaaacagagg    120
cctggacaag gccttgagtg gatcggagca attgatcctt ctgatagtta tactagctac    180
aatccaaaat tcaagggcaa ggccacattg actgtagaca cctcctccag ctcagcctac    240
atgcagctca gcagcctgac atctgaggac tctgcggtct atttctgtgc aagaagagga    300
acccctggta aacccctgt ttactggggc caagggactc tggtcactgt ctctgca       357

<210> SEQ ID NO 226
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226
gacatccaga tgactcagtc tccagcctcc ctatctgtat ctgtgggaga aactgtcacc     60
atcacatgtc gagcaagtgc gaatattaac agtaatttag tatggtatca gcagaaacag    120
ggaaaatctc ctcagctcct ggtctatgct gcaacaaact tagcggatgg tgtgccatca    180
cggttcagtg gcagtggatc aggcacacag tattccctca agatcaacag cctgcagtct    240
gaagattttg ggaattacta ctgtcaacat ttttggggta ctcctcggac gttcggtgga    300
ggcaccaagc tggaaatcaa ac    322

<210> SEQ ID NO 227
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227
gaggtccagc tgcaacagtc tggacctgag ctaatgaagc ctggggcttc agtgaagatg     60
tcctgcaagg cttctggata cacattcact gactacaaca tgtactgggt gaagcagaac    120
caaggaaaga gcctagagtg gataggagaa attaatccta acaatggtgg tactgcctac    180
aaccagaagt tcagaggcaa ggccacgttg actgtagaca gtcctccag cacagcctac     240 atggagctcc gcagcctgac atctgaggac tctgcagtct attactgtgc aagatatgat    300 aagggggtttg actactgggg ccaaggcacc actctcacag tctcctca              348

<210> SEQ ID NO 228

```
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228
gacattgtgg tcacccaatc tccagcttct ttggctgtgt ctctggggca gagagccacc      60
atctcctgca gagccagtga aagtgttgaa tattatggca caagtttaat gcagtggttc     120
caacagaaac caggacagcc acccaaactc ctcatctatg ctgcatccaa cgtagaatct     180
ggggtccctg ccaggtttag tggcagtggg tctgggacag acttcagcct caacatccat     240
cctgtggagg aggatgatat tgcaatgtat ttctgtcagc aagataggaa ggttccttgg     300
acgttcggtg gaggcaccaa gctggaaatc aaac                                 334

<210> SEQ ID NO 229
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229
caggttactc tgaaagagtc tggccctggg atattgcagc cctcccagac cctcagtcta      60
acttgttctt tctctgggtt ttcactgaac acatctggta tgagtgtagg ctgggttcgt     120
cagccttcag ggaggggtct ggaatggctg ccccccattt ggtggaatgg tgataagtac     180
tataacccag ccctgaaaag ccggctcaca atctccaagg atacctccaa caaccaggtt     240
ttcctcaaga tcgccagtgt ggtcactgca gatactgcca catacttctg tgctcgaata     300
cggcaatatt actatgctat ggactactgg ggtcaaggaa cctcagtcac cgtctcctca     360

<210> SEQ ID NO 230
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
gacattgtga tgtcacagtc tccatcctcc ctagctgtgt cagttggaga gaaggttact      60
atgagctgca agtccagtca gagccttttta tatagtagca atcaaaagaa ctacttggcc     120
tggtaccagc agaaaccagg gcagtctcct aaactgctga tttactgggc atccactagg     180
gaatctgggg tccctgatcg cttcacaggc agtggatctg gacagattt cactctcacc     240 atcagcagtg tgaaggctga agacctggca gtttattact gtcagcaata ttatagctat     300
ccgacgttcg gtggaggcac caagctggaa atcaaac                              337

<210> SEQ ID NO 231
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 231

| | | |
|---|---|---|
| caggtccaac tgcagcagcc tggggctgag cttgtgaagc ctggggcttc agtgaagctg | 60 |
| tcctgcaagg cttctggcta caccttcccc agctactgga tacactgtgt gaagcagagg | 120 |
| cctggacaag gccttgagtg gattggagtg attaatccta gcaacggtcg tactaactac | 180 |
| aatgagaagt tcaagaacaa ggccacactg actgtagaca atcctccag cacagcctac | 240 |
| atgcaactca gcagcctgac atctgaggac tctgcggtct attactgtgt caggggggggg | 300 |
| acgggctata ctatggacta ctggggtcaa ggaacctcag tcaccgtctc ctca | 354 |

<210> SEQ ID NO 232
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 232

| | | |
|---|---|---|
| gacatcaaga tgacccagtc tccatcttcc atgtatgcct ctctaggaga gagagtcact | 60 |
| atcacttgca aggcgagtca ggacattaat agctatttaa cctggttcca gcagaaacca | 120 |
| gggaaatctc ctaagaccct gatctatcgt gcaaacagat tgatagatgg ggtcccatca | 180 |
| aggttcagtg gcagtggatc tgggcaagat tattctctca ccatcagcag cctggattat | 240 |
| gaagatatgg gaatttatta ttgtctacag tatgatgact ttccgtggac gttcggtgga | 300 |
| ggcaccaagc tggaaatcaa ac | 322 |

<210> SEQ ID NO 233
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 233

| | | |
|---|---|---|
| cagatccagt tggtgcagtc tggacctgag ctgaagaagc ctggagagac agtcaagatc | 60 |
| tcctgcaagg cttctggtta taccttcaca gactattcaa tgcactgggt gaagcaggct | 120 |
| ccaggaaagg gtttaaagtg gctgggctgg ataaacactg agactggcga gccaacatat | 180 |
| tcagaagact tcaagggacg gtttgccttc tctttggaaa cctctgccag cactgcctat | 240 |
| ttgcagatca acaacctcaa aaatgaagac acggctactt atttctgtgt taaaaataag | 300 |
| ggctggtttg cttattgggg ccaagggact ctggtcactg tctctgca | 348 |

<210> SEQ ID NO 234
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 234

| | | |
|---|---|---|
| gatgttgtga tgacccaaac tccactctcc ctgcctgtca gtcttggaga tcaagcctcc | 60 |
| atctcttgca gatctagtca gagccttgta cacagtaatg gagacaccta tttacattgg | 120 |

```
tacctgcaga agccaggcca gtctccaaaa ctcctgatct acaaagtttc caaccgattt      180
tctggggtcc cagacaggtt cagtggcagt ggatcaggga cagatttcac actcaagatc      240
agcagagtgg aggctgagga tctgggactt tatttctgct ctcaaagtac acttattccg      300
tacacgttcg gagggggac caagctggac ataaaacg                               338

<210> SEQ ID NO 235
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 235
caggttcacc tgcagcagtc tggaactgaa gtgatgaagc ctggggcctc agtgaagata      60
tcctgcaagg ctactggcta cacattcagt agctactgga tagagtggat aaagcagagg      120
cctggacatg gccttgagtg gattggagag attttgcctg gaagtggtaa tactaacaac      180
aatgagaagt tcaagggcaa ggccacaatc actgcagata catcctccaa tatagcctac      240
atacaattaa gcagcctgac atctgaggac tctgccgtct attactgtgc gggaggcccg      300
gcggcttact ggggccaagg gactctggtc actgtctctg ca                         342

<210> SEQ ID NO 236
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236
gacattgtga tgtcacagtc tccatcctcc ctagctgtgt cagttggaga gaaggttact      60
atgagctgca agtccagtca gagccttta tatagtagca atcaaaagaa ctacttggcc       120
tggtaccagc agaaaccagg gcagtctcct aaactgctga tttactgggc atccactagg      180
gaatctgggg tccctgatcg cttcacaggc agtggatctg ggacagattt cactctcacc      240
atcagcagtg tgaagactga agacctggca ctttattact gtcagcaata ttattggttt      300
ccgtacacgt tcggaggggg gaccaagctg gaaataaaac g                          341

<210> SEQ ID NO 237
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 237
gaggttcagc tgcagcagtc tggggcagaa cttgtgaagc caggggcctc agtcaagttg      60
tcctgcacag cttctggctt caacattaaa gacacctata tgcactgggt gaagcagagg      120
cctgaacagg gcctggagtg gattggaagg attgatcctg cgaatgttaa tactaaatat      180
gacccgaagt tccagggcaa ggccactata acagcagaca catcctccaa cacagcctac      240
ctgcagctca gcagcctgac atctgaggac actgccgtct attactgtgt taggggaat       300 gtttactggg gccaagggac tctggtcact gtctctgca                             339
```

<210> SEQ ID NO 238
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 238
gaaaatgtgc tcacccagtc tccagcaatc atgtctgcat ctccagggga aaaggtcacc      60
atgacctgca gggccagctc aagtgtaagt tccagttact tgcactgcta ccagcagaag     120
tcaggtgcct cccccaaact ctggatttat agcacatcca acttggcttc tggagtccct     180
gctcgcttca gtggcagtgg gtctgggacc tcttactctc tcacaatcag cagtgtggag     240
gctgaagatg ctgccactta ttactgccag cagtacagtg attacccatt cacgttcggc     300
tcggggacaa agttggtaat aaaac                                          325

<210> SEQ ID NO 239
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 239
gaggtccagc tgcagcagtc tggacctgag ctggtgaaac ctggggcttt agtgatgatg      60
tcctgcaagg cttctggata cacattcact gactactaca tgcactgggt gaagcagagc     120
catggacaga gccttgagtg gattggagag gttattcctt acaatgatga aactttctac     180
aaccggaagt tcaaggacaa ggccacattg actgtagaca atcctctag tacagcctac      240 atggagctcc ggagcctgac atctgaggac tctgcaatct attattgtgc aagaagacat     300
aggtacgacg ggtttcgtta tgctatagac tactggggtc aaggaacctc agtcaccgtc     360
tcctca                                                              366

<210> SEQ ID NO 240
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 240
gatgttttga tgacccaaac tccactctcc ctgcctgtca gtcttggaga tcaagcctcc      60
atctcttgca gatctagtca gagcattgtc catagtaatg gaaacaccta tttagagtgg     120
ttcctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gaggggggac caagctggaa ataaaacg                             338

<210> SEQ ID NO 241
<211> LENGTH: 354
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 241

| | | | | | |
|---|---|---|---|---|---|
| gaggtccagc | tgcaacagtc | tggacctgtg | ctggtgaagc | ctggggcttc | agtgaagatg | 60 |
| tcctgtaagg | cttctggata | cacaatcact | gactacaata | tgaactgggt | gaagcagagc | 120 |
| catggaaaga | gccttgagtg | gattggagtt | attaatcctt | acaacggtaa | tactagatat | 180 |
| aaccagatgt | tcaagggcaa | ggccacattg | actgttgaca | gtcctccag | cacagcctac | 240 |
| atggagctca | acagcctgac | atctgaggac | tctgcagtct | attactgtac | aagatggggt | 300 |
| actacggtgg | taggtgcgaa | ctggggccaa | ggcaccactc | tcacagtctc | ctca | 354 |

<210> SEQ ID NO 242
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242

| | | | | | |
|---|---|---|---|---|---|
| caaattgttc | tcacccagtc | tccagcactc | atgtctgcat | ctccagggga | gaaggtcacc | 60 |
| atgacctgca | gtgccagctc | aagtgtaaat | tacatgtact | ggtaccagca | gaagccaaga | 120 |
| tcctccccca | aaccctggat | ttatctcaca | tccaacctgg | cttctggagt | ccctgttcgc | 180 |
| ttcagtggca | gtgggtctgg | gacctcttac | tctctcacaa | tcagcagcat | ggaggctgaa | 240 |
| gatgctgcca | cttactactg | ccagcagtgg | agtaataacc | cacccacgtt | cggttctggg | 300 |
| accaagctgg | agctgaaac | | | | | 319 |

<210> SEQ ID NO 243
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243

| | | | | | |
|---|---|---|---|---|---|
| gacgtgaagc | tcgtggagtc | tgggggaggc | ttagtgaagc | ttggagggtc | cctgaaactc | 60 |
| tcctgtgcag | cctctggatt | cactttcagt | agctatgcca | tgtcttgggt | tcgccagact | 120 |
| ccggagaaga | ggctggagtg | ggtcgcaacc | attactagtg | gtggtggtaa | cacctactat | 180 |
| ccagacagtg | tgaagggtcg | attcaccatc | tccagagaca | atgccaagaa | caccctgtac | 240 |
| ctgcaaatga | gcagtttgaa | gtctgaggac | acggccatgt | attactgtgc | aagaagggat | 300 |
| tactacggta | gtagttacgt | tatgtttgct | tattggggcc | aagggactct | ggtcactgtc | 360 |
| tctgca | | | | | | 366 |

<210> SEQ ID NO 244
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244

```
caaattgttc tcacccagtc tccagcaatc atgtctgcat ctccagggga gaaggtcacc    60
atgacctgca gtgccagctc aagtgtaagt tacatgcact ggtaccagca gaagtcaggc   120
acctccccca aaagatggat ttatgacaca tccaaactgc cttctggagt ccctgctcgc   180
ttcagtggca gtgggtctgg gacctcttac tctctcacaa tcagcagcat ggaggctgaa   240
gatgctgcca cttattactg ccagcagtgg agtagtaccc acccacgtt cggtgctggg    300 accaagctgg agctgaaac                                                 319
```

<210> SEQ ID NO 245
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 245

```
gaggtccagc tgcaacagtc tggacctgag gtaatgaagc ctggggcttc agtgaagatg    60
tcctgcaagg cttctggata cacattcact gactacaaca tgcactgggt gaagcagaac   120
caaggaaaga gcctagagtg gataggagaa attaatccta acattggtgg tactggctac   180
aaccagaagt tcaaaggcaa ggccacattg actgtacaca agtcctccag cacagcctac   240
atggagctcc gcagcctgac atctgaggac tctgcagtct attactgtgc aagaacctat   300
agttactata gttcgagtt tgcttactgg ggccaaggga ctctggtcac tgtctctgca   360
```

<210> SEQ ID NO 246
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 246

```
gacatccaga tgacacaatc ttcatcctac ttgtctgtat ctctaggagg cagagtcacc    60
attacttgca aggcaagtga ccacattaat aattggttag cctggtatca gcagaaacca   120
ggaaatgctc ctaggctctt aatatctggt gcaaccagtt tggaaactgg ggttccttca   180
agattcagtg gcagtggatc tggaaaggat tacactctca gcattaccag tcttcagact   240
gaagatgttg ctacttatta ctgtcaacag tattggagta ttccgctcac gttcggtgcg   300
gggaccaagc tggagctgaa ac                                             322
```

<210> SEQ ID NO 247
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 247

```
caggttactc tgaaagagtc tggccctggg atattgcagc cctcccagac cctcagtctg    60
acttgttctt tctctgggtt ttcactgagc acttctacta tgggtgtagg ctggattcgt   120
```

```
cagccttcag gaaagggtct agagtggctg gcagacattt ggtgggatga cagtaagtac    180
tataatccat ccctgaagag ccggctcaca atctccaagg atacctccag caaccaggta    240
ttcctcaaga tcaccagtgt ggacactgca gatactgcca cttactactg tgcgcgaaag    300
ggaaggacag ctcgggctac gagagggttt gcttactggg gccacgggac tctggtcact    360
gtctctgca                                                            369

<210> SEQ ID NO 248
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
gacattgtgc tgacccaatc tccagcttct ttggctgtgt ctctagggca gagggccgcc     60
atctcttgca agcccagcca aagtgttgat tatgatggtg atagttatat gaactggtac    120
caacagaaac caggccagcc acccaaactc tcatttatg ctgcatccaa tctagaatct    180
gggatcccag ccaggtttag tggcagtggg tctgggacag acttcaccct caacatccat    240
cctgtggagg aggaggatgc tgcaacctat tactgtcacc aaattaatga cgatccgtgg    300
acgttcggtg gaggcaccaa gctgaaa                                        327

<210> SEQ ID NO 249
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
tctgatgtgc agcttcagga gtcaggacct ggcctggtga accttctca gtctctgtct     60 gtcacctgca ctgtcactgg ctactccatc accagtagtt atacctggaa ctggatccgg    120
cagtttccag gaaacaaact ggagtggatg ggctacatac attacagtgg tagcactaac    180
tacaacccat ctctcagaag tcgaatctct attactcgag acacgtccaa gaaccagttc    240
ttcctgcagt tgaattctgt gactactgag gacacagcca catattactg tgcaagatcc    300
cgttattact acgatgctta cgggtttgct tactggggcc aagggactct ggtcactgtc    360
tctgca                                                               366

<210> SEQ ID NO 250
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
gatgttgtgt tgacccaaac tccactctcc ctgcctgtca gtcttggaga tcaagcctcc     60
atctcttgca gatctagtca gagcattgta cacattaata gacacaccta cttaggatgg    120
tacctgcaga aaccaggcca gtcgctaaag ctcctgatat atgggggttc caaccgattt    180
tctggggtcc cagacaggtt cagtggcagt ggatcaggga cagatttcac actcaagatc    240
```

```
agcagagtgg aggctgagga tatgggagtt tattactgct ttcaaggtac acatgttcca      300
ttcacgttcg gctcggggac aaagttggaa ataaaac                               337

<210> SEQ ID NO 251
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
cagatccaga tgatgcagtc tggacctgag ctgaagaagc ctggagagac agtcaagatc       60
tcctgcaagg cttctgggta ttccttcaca aactatggaa tgaactgggt gaagcaggct      120
ccaggaaagg gtttaaagtg gatgggctgg ataaacacct acactggaga gccaacatat      180
gctgatgact tcaagggacg gtttgccttc tctttggaaa cctctgccag cactgcctat      240
ttgcagatca acaacctcaa aaatgaggac atggctacat atttctgtac aagaggttac      300
tacggtagta gctacgatgc tttggactac tggggtcaag gaacctcagt caccgtctcc      360
tca                                                                    363

<210> SEQ ID NO 252
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
gacattgtga tgtcacagtc tccatcctcc ctggctgtgt cagttggaga gaaggtcact       60
atgagctgca gtccagtca gagccttta tatagtagca atcaaaagag ctacttggcc       120
tggtaccagc agaaaccagg gcagtctcct aaactgttaa tctactgggc atccactagg      180
gaatctgggg tccctgaccg cttcacaggc agtggatcag gacagattt cactctcacc       240 atcagcagtg tgcaggctga agacctggcc gtttattact gcaagcaatc ttataatctt      300
cggacgttcg gtggaggcac caagctggaa atcaaac                               337

<210> SEQ ID NO 253
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253
caggttcagc tgcagcagtc tgacgctgag ttggtgaaac ctggagcttc agtgaagata       60
tcctgcaagg tttctggcta caccttcact gaccatacta ttcactggat gaagcagagg      120
cctgaacagg gcctggaatg gattggatat atttatccta gagatggtag tactaagtac      180
aatgaggagt tcaagggcaa ggccacattg actgcagaca atcctccag cacagcctac       240 atgcagctca acagcctgac atctgaggac tctgcagtct atttctgtgc aagatcatat      300
agtaactact ttgactactg ggaccaaggc accactctca cagtctcctc a               351
```

<210> SEQ ID NO 254
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 254
gatgttgtga tgacccagac tccactcact ttgtcggtta ccattggaca accagcctcc     60
atctcttgca agtcaagtca gagcctctta gaaagtgatg gaaagacata tttgaattgg    120
ttgttacaga ggccaggcca gtctccaaag cgcctaatct atctggtgtc taaactggac    180
tctggagtcc ctgacaggtt cacgggcagt ggatcaggga cagatttcac actgaaaatc    240
agcagagtgg aggctgagga tttgggagtt tattattgct ggcaaggtat acaacatcct    300
cggacgttcg gtggaggcac caagctggaa atcaaa                              336

<210> SEQ ID NO 255
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
caggttcaac tgcagcagtc tggggctgag ctggtgaggc ctggggcttc agtgacgctg     60
tcctgcaagg cttcgggcta cacatttact gactatgaaa tgcactgggt gaagcagaca    120
cctgtgcatg gcctggaatg gattggaggt attgatcctg aaactggtgg tactgcctac    180
aatcagaagt tcaagggcaa ggccacactg actgcagaca atcctccag cacagcctac    240 atggagctcc gcagcctgac atctgaggac tctgccgtct acttctgtac aagatggttt    300
tcttactggg gcccagggac tctggtcact gtctctgca                            339

<210> SEQ ID NO 256
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 256
gacatcttgc tgactcagtc tccagccatc ctgtctgtga gtccaggaga aggagtcagt     60
ttctcctgca gggccagtca gagcattggc acaagcatac actggtatca gcaaagaaca    120
aatggttctc caagacttct cataaagtat gcttctgagt ctatctctgg gatcccttct    180
aggtttagtg gcagtgggtc aggacagat tttactcttc gcatcaacag tctggagtct    240
gaagatattg cagattatta ctgtcaacaa agtaatagct ggccactcac gttcggtgct    300
gggaccaagc tggagctgaa ac                                              322

<210> SEQ ID NO 257
<211> LENGTH: 351
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"

<400> SEQUENCE: 257
caggtccacc tgccgcagtc tagacctgaa ctggtgaagc ctggagcttc agtgaagata      60
tcctgcaagg cttctggcta cggcttcaca cgcagctata tacactgggt gaagcagagg     120
cctggacagg gcctagagtg gattggatat atttcttctg gaagtggtgg tactacctac     180
aatcagaagt ttaagggcaa ggcctcactg actgcagaca tccctccag cactgcctac      240 atgcatctca gtagcctgac atctgaggac tctgcgatct atttctgtgc aagagggggg     300
gtacggtact tcgatgtctg gggcgcaggg accacggtca ccgtctcctc a              351

<210> SEQ ID NO 258
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 258
gacattgtga tgacccagtc tcacaaattc atgtccacat cagtaggaga cagggtcagc      60
atcacctgca aggccagtca ggatgtgggt actgatgtag cctggtatca acagaaacca     120
gggcaatctc ctaaactact gatttactgg gcatccaccc ggcacactgg agtccctgat     180
cgcttcacag gcagtggatc tgggacagat ttcactctca ccattagcaa tgtgcagtct     240
gaagacttgg cagattattt ctgtcagcaa tatagcagct atccgtacac gttcggaggg     300
gggacaaagc tggaaataaa acgs                                            324

<210> SEQ ID NO 259
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259
gaggtccagc tgcaacagtc tggacctgag ctaatgaagc ctggggcttc agtgaagatg      60
tcctgcaagg cttctggata cacattcact gactacaaca tgcactgggt gaagcagaac     120
caaggaaaga gcctagagtg gattggagaa attaatcctc acaatggtgg tactggctac     180
aaccagaagt tcaaaggcaa ggccacattg actgtagaca gtcctccag cacatcctac      240 atggagctcc gcagcctgac atctgaggac tctgcagtct attactgtgc aggcggttac     300
ccggcctttg actactgggg ccaaggcacc actctcacag tctcctca                  348

<210> SEQ ID NO 260
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 260
gaaaatgtgc tcacccagtc tccagcaatc gtgtctgcat ctccagggga aaaggtcacc      60
```

```
atgacctgca gggccagctc aagtgtaatt ccagttact tgcactggta ccagcagaag    120
tcaggtgcct cccccaaact ctggatttat agcacatcca acttggcttc tggagtccct    180
gctcgcttca gtggcagtgc gtctgggacc tcttactctc tcacaatcag cagtgtggag    240
gctgaagatg ctgccactta ttactgccag cagtacagtg gttacccgct cacgttcggt    300
gctgggacca agctggagct gaaa                                           324

<210> SEQ ID NO 261
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261
gaagtgaagc tggtggagtc tgagggaggc ttagtgcagc ctggaagttc catgaaactc     60
tcctgcacag cctctggatt cactttcagt gactattaca tggcttgggt ccgccaggtt    120
ccagaaaagg gtctagaatg ggttgcaaac attaattatg atggtagtag cacttactat    180
ctggactcct tgaagagccg tttcatcatc tcgagagaca atgcaaagaa cattctatac    240
ctgcaaatga gcagtctgaa gtctgaggac acagccacgt attactgtgc aagagatgat    300
tattacggta gtagcccaag ctactggtac ttcgatgtct ggggcgcagg gaccacggtc    360
accgtctcct ca                                                        372

<210> SEQ ID NO 262
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
gacatccaga tgactcagtc tccagcctcc ctatctgcat ctgtgggaga aactgtcacc     60
atgacatgtc gagcaagtgg gaatattcac aattatttag tatggtatca gcagaaacag    120
ggaaaatctc ctcagctcct ggtctataat gcaaaaacct tagcagatgg tgtgccatca    180
aggttcagtg gcagtggatc aggaacacaa tattctctca gatcaacag cctgcagcct    240 gaagattttg ggagttatta ctgtcaacat ttttggagta ctcctccgac gttcggtgga    300
ggcaccaagc tggaaatcaa a                                              321

<210> SEQ ID NO 263
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gaagtgaaac ttgaggagtc tggaggaggc ttggtgcaac ctggaggatc catgaaactc     60
tcctgtgttg cctctggatt cactttcagt aactactgga tgagctgggt ccgccagtct    120
ccagagaagg ggcttgagtg ggttgctgaa attagattga aatctaataa ttatgcaaca    180
cattatgcgg agtctgtgaa agggaggttc accatctcaa gagacgattc caaaagtagt    240
```

```
gtcttcctgc aaatgaacaa cttaagaact gaagacactg gcatttatta ctgtaccagg    300
cactattact atgctatgga ctactggggt caaggaacct cagtcaccgt ctcctca       357

<210> SEQ ID NO 264
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 264
gacatcaaga tgacccagtc tccatcttcc atgtatgcat ctctaggaga gagagtcact    60
atcacctgca aggcgagtca ggacattaat agctatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagtag cctggagtat   240
gaagatatgg gaatttatta ttgtctacag tatgatgagt ttcctccgac gttcggtgga   300
ggcaccaagc tggaaatcaa ac                                            322

<210> SEQ ID NO 265
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 265
gaggtccagc tacaacagtc tggacctgag ctggtgaagc ctgggtcttc agtgaagata    60
tcctgcaagg cttctggata cacattcact gactacaaca tggactgggt gaagcagagc   120
catggaaaga gacttgagtg gattggatat atttatcctg acaatggtgg tgctggctac   180
aaccagaagt tcaagggcaa ggccacattg actgtagaca gtcctccag cacagcctac   240 atggagctcc gcagcctgac atctgaggac tctgcagtct attactgttc aagatccatt   300
actacggctt ggtttgctta ctggggccaa gggactctgg tcactgtctc tgca          354

<210> SEQ ID NO 266
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 266
gaaaatgtgc tcacccagtc tccagcaatc atgtctgcat ctccagggga aaaggtcacc    60
ctgacctgca gggccagctc aagtatgagt tccagttact gcactggta ccagcagaag    120 tcaggtgcct cccccaaact ctggatttat agcacatcca acttggcttc tggagtccct   180
gctcgcttca gtggcagtgg gtctgggacc tcttactctc tcacaatcag cagtgtggag   240
gctgaagatg ctgccactta ttactgccag cagtacagtg cttacccatt cacgttcggc   300
tcggggacaa agttggaaat aaaac                                         325

<210> SEQ ID NO 267
```

<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 267

| | |
|---|---|
| gaggtccagc tgcagcagtc tggacctgag ctagtgaaac ctggggcttt agtgaagatg | 60 |
| tcctgcaagg cttctggata cacattcact gactactaca tacactgggt gaagcagagc | 120 |
| catggaaaga gccttgagtg gattggagaa attaatcctt acaatggtga actttctac | 180 |
| aaccagaagt tcaagggcaa ggccacattg actgtagaca atcctctag tacagcctac | 240 |
| atggaactcc ggagcctgac atctgaggac tctgcagtct attattgtgc aagaagggga | 300 |
| tggtatctaa caggctatgc tatggactac tggggtcaag aacctcagt caccgtctcc | 360 |
| tca | 363 |

<210> SEQ ID NO 268
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 268

| | |
|---|---|
| caaattgttc tcacccagtc tccagcactc atgtctgcat ctccagggga gaaggtcacc | 60 |
| atgacctgca gtgccagctc aagtgtaagt tacatgtact ggtaccagca gaagccaaga | 120 |
| tcctccccca aaccctggat ttatctcaca tccaacctgg cttctggagt ccctgctcgc | 180 |
| ttcagtggca gtgggtctgg gacctcttac tctctcacaa tcagcagcat ggaggctgaa | 240 |
| gatgctgcca cttattactg ccagcagtgg agtagtaacc cacccacgtt cggaggggggg | 300 |
| accaagctgg aaataaaacg | 320 |

<210> SEQ ID NO 269
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 269

| | |
|---|---|
| gaggtgcagc ttcaggagtc aggacctagc ctcgtgaaac cttctcagtc tcagtccctc | 60 |
| acctgttctg tcactggcga ctccatcacc agtgattact ggaactggat ccggaaattc | 120 |
| ccagggaaga aagttgagta catggggtac ataaactaca gtggtagcac ttactacaat | 180 |
| ccatctctca aaagtcgaat ctccatcact cgagacacat ccaagaacca gtactacctg | 240 |
| cagttgaact ctgtgacttc tgaggacaca gccacatatt actgtgcacg tacctcgtac | 300 |
| tataataagt ttctaccatt tgcttactgg ggccaaggga ctctggtcac tgtctctgca | 360 |

<210> SEQ ID NO 270
<211> LENGTH: 337
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic polynucleotide"

<400> SEQUENCE: 270
gatgttttaa tgacccaaac tccactctcc ctgcctgtca gtcttggaga tcaagcctcc    60
atctcttgca gatctagtca gagtcttgta cacagaaatg gaaacaccta ttttcattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac atatgttccg   300
tggacgttcg gtggaggcac caagctggaa atcaaac                             337

<210> SEQ ID NO 271
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271
gaggtgcagc tggtggagtc tgggggaggc ttagtgcagc ctggagggtc ccggaaactc    60
tcctgtgcag cctctggatt cactttcagt agctatggaa tgcactgggt ccgtcaggct   120
ccagagaagg ggctggagtg ggtcgcatat attagtagta cgatggtac catctactat    180 gcagacacag tgaggggccg attcaccatc tccagagaca atgccaagaa cacctgttc    240 ttgcaaatga ccagtctaag gtctgaggac acggccatgt attactgtgc aagaccttct   300
aactgggtct tgactactg gggccaaggc accactctca cagtctcctc a             351

<210> SEQ ID NO 272
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 272
gatgttgtga tgacccaaac tccactctcc cggcctgtca ctcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc ctgacaggtt cagtggcagt ggatcaggga cagatttcac actcaagatc   240
agcagagtgg aggctgagga tctgggagtt tatttctgct ctcaaaatac acatgttcca   300
ttcacgttcg gctcggggac aaagttggaa ataaaac                             337

<210> SEQ ID NO 273
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 273
caggtccaac tgcagcagcc tggggctgaa attgtgaggc ctggggcttc agtgaagctg    60
```

```
tcctgcaagg cttctggcta cacctttacc gactattgga tgaactgggt gaagcagagg    120
cctggacaag gccttgagtg gatcggaaca attgatcctt ctgatagtta tactcgttac    180
aatcaaaagt tcaagggcaa ggccacattg actgtagaca catccttcag ctcagcctac    240
atgcagctca gcagcctgac atctgaggac tctgcggtct atttctgtgc aagtggggga    300 cggggggtttg gttactgggg ccaagggact ccggtcactg tctctgta                348
```

<210> SEQ ID NO 274
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 274

```
caaattgttc tcacccagtc tccagcactc atgtctgcat ctccagggga gaaggtcacc     60
atgacctgca gtgccagctc aagtgtaagt tacatgtact ggtaccagca gaagccaaga    120
tcctccccca aacctggat ttatctcaca tccaacctgg cttctggagt ccctactcgc     180
ttcagtggca gtgggtctgg gacctcttac tctctcacaa tcagcagcat gggggctgaa    240
gatgctgcca cttattactg ccagcagtgg aatactaacc cacccacgtt cggtgctggg    300
accaagctgg agctgaaac                                                 319
```

<210> SEQ ID NO 275
<211> LENGTH: 365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 275

```
gacgtgaagc tcgtggagtc tgggggaggc ttagtgaagc ttggagggtc cctgaaactc     60
tcctgtgcag cctctggatt cactttcagt agctatgcca tgtcttgggt tcgccagact    120
ccggagaaga ggctggagtg ggtcgcaacc attagtagtg gtggtggtaa cacctactat    180
ccagacagtg tgaagggtcg attcaccatc tccagagaca tgccaagaa caccctgtac    240 ctgcaaatga gcagtttgaa gtctgaggac acggccatgt attactgtgc aagaagggat    300
tactacggta ctagctacgt tatgtttgct tactggggcc aagggactct ggtcactgtc    360
tctgc                                                                365
```

<210> SEQ ID NO 276
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 276

```
gaaaatgttc tcacccagtc tccagcaatc atgtctgcat ctccagggga aaaggtcacc     60
atgacctgta gtgccagctc aagtgtaaat tacatgtact ggtaccagca gaagtcaagc    120 acctcccccca aactctggat ttatgacaca tccaaactga cttctggagt cccaggtcgc    180
ttcagtggca gtgggtctgg aaactcttac tctctcacga tcagcaacat ggaggctgaa    240
```

```
gatgttgcca cttattactg ttttcagggg agtgggtacc cactcacgtt cggctcgggg    300
acaaaattgg aaataaaac                                                 319
```

<210> SEQ ID NO 277
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 277

```
gacgtgaagc tggtggagtc ggggggaggc ttagtgaggc ctggagggtc cctgaaactc    60
tcctgtgcag cctctggatt cactttcagt agatatacca tgtcttgggt tcgccagaca    120
ccggagaaga ggctggagtg ggccgcaacc attaatagtg gtggtagtaa cacctactat    180
ccagacagtg tgaagggccg attcaccatc tccagagaca atgccaagaa caccctgttc    240
ctgcaaatga gcagtctgaa gtctgaggac acagccatgt attactgtac aaatggtaac    300
cactggggcc aaggcaccac tctcacagtc tcctca                              336
```

<210> SEQ ID NO 278
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 278

```
gaaaatgttc tcacccagtc tccagcaatc atgtctgcat ctccagggga aaaggtcacc    60
atgacctgta gtgccagctc aagtgtaaat tacatgtact ggtaccagca gaagtcaagc    120
acctccccca aactctggat ttatgacaca tccaaactga cttctggagt cccaggtcgc    180
ttcagtggca gtgggtctgg aaactcttac tctctcacga tcagcaacat ggaggctgaa    240
gatgttgcca cttattactg ttttcagggg agtgggtacc cactcacgtt cggctcgggg    300
acaaaattgg aaataaaac                                                 319
```

<210> SEQ ID NO 279
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 279

```
caggtgcaac tgcagcagcc tgggtctgtg ctggtgaggc ctggagattc agtgaagctg    60
tcgtgcaagg cttctggcta cacattcacc agctactgga tgcactgggt gaagcagagc    120
cctggacaag gccttgagtg gattggagag attcatcctc atagtggtag tactaactac    180
aatgagaagt tcaagggcaa ggccacactg actgtagaca tcctccag cacagcctac     240 gtggatctca gcagcctgac atctgaggac tctgcggtct attactgtgt aggtggtcac    300
tacgactact ggggccaagg caccactctc acagtctcct ca                      342
```

<210> SEQ ID NO 280

```
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 280
agttttgtga tgacccaaac tcccaaattc ctgcttgtat cagcaggaga cagggttacc      60
ataacctgca aggccagtca gagtgtgaat aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctcctcggac gttcggtgga     300
ggcaccaagc tggaaatcaa ac                                              322

<210> SEQ ID NO 281
<211> LENGTH: 359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 281
caggtccaac tgcagcagcc tggtgctgag cttgtgaagc ctggggcctc aatgaagctg      60
tcctgcaagg cttctggcta cactttcacc agctactgga taaactgggt gaagcagagg     120
cctggacaag gccttgagtg gattggaaat atttttcctg atactactac tactaactac     180
aatgagaagt tcaagagcaa ggccacactg actgtagaca catcctccag cacagcctat     240
atgcagctca gcagcctgac atctgacgac tctgcggtct attattgtgc aagggagtac     300
tacgatggta cctacgatgc tatggattac tggggtcaag aacctcagt caccgtctc      359

<210> SEQ ID NO 282
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 282
caaattgttc tcacccagtc tccagcaatc atgtctgcat ctccagggga aaggtctcc      60 atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcagtggca gtgggtctgg gtcctcttac tctctcacaa tcagcagcat ggaggctgaa     240
gatgctgcca cttattactg ccagcagtgg agtagcaccc cccccacgtt cggaggggggg     300 accaagctgg aaataaaacg                                                 320

<210> SEQ ID NO 283
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

-continued

<400> SEQUENCE: 283

| gaggtccagc tgcagcagtc tggacctgag ctggtgaagc ctggggcttc agtgaagata | 60 |
| tcctgcaagg cttctggtta ctcattcact gactactaca tgcgctgggt gaagcaaagt | 120 |
| cctgaaaaga gccttgagtg gattggagag attaatccta gcactggtgg tactacctac | 180 |
| aaccagaact tcaaggccaa ggccacattg actgtagaca atcctccag cacagcctac | 240 |
| atgcagctca gagcctgac atctgaggac tctgcagtct attactgtgc aagaggggt | 300 |
| tacttcttgt actactttga ctactggggc caaggcacca ctctcacagt ctcctca | 357 |

<210> SEQ ID NO 284
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 284

| gatgttgtga tgacccagac tccactcact ttgtcggtta ccattggaca accagcctcc | 60 |
| atctcttgca agtcaagtca gagcctctta aaagtgatg gaaagacata tttgaattgg | 120 |
| ttgttacaga ggccaggcca gtctccaaag cgcctaatct atctggtgtc taaactggac | 180 |
| tctggagtcc ctgacaggtt cacgggcagt ggatcaggga cagatttcac actgaaaatc | 240 |
| agcagagtgg aggctgagga tttgggagtt tattattgct ggcaaggtat acaacatcct | 300 |
| cggacgttcg gtggaggcac caagctggaa atcaaac | 337 |

<210> SEQ ID NO 285
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 285

| caggttcaac tgcagcagtc tggggctgag ctggtgaggc ctggggcttc agtgacgctg | 60 |
| tcctgcaagg cttcgggcta cacatttact gactatgaaa tgcactgggt gaagcagaca | 120 |
| cctgtgcatg gcctggaatg gattggaggt attgatcctg aaactggtgg tactgcctac | 180 |
| aatcagaagt tcaagggcaa ggccacactg actgcagaca atcctccag cacagcctac | 240 |
| atggagctcc gcagcctgac atctgaggac tctgccgtct acttctgtac aagatggttt | 300 |
| tcttactggg gccagggac tctggtcact gtctctgca | 339 |

<210> SEQ ID NO 286
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 286

| gacattgtgc tgacacagtc tcctgcttcc ttagctgcat ctctggggca gagggccacc | 60 |
| atctcatgca gggccagcca aagtgtcagt acatctagct atagttatat gcactggtac | 120 |

```
caacagaaac caggacagcc acccaaactc ctcatcaagt atgcatccaa cctagaatct    180
ggggtccctg ccaggttcag tggcagtggg tctgggacag acttcaccct caacatccat    240
cctgtggagg aggaggatac tgcaacatat tactgtcagc acagttggga gattccgtgg    300
acgttcggtg gaggcaccaa gctggaaatc aaac                                334
```

<210> SEQ ID NO 287
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 287

```
gaggtgcagc tggtggagtc tgggggaggc ttagtgaagc ctggagggtc cctgaaactc     60
tcctgtgcag cctctggatt cactttcagt gactatggaa tgcactgggt tcgtcaggct    120
ccagagaagg ggctggagtg ggttgcatac attagtagtg gcagtagaac catctactat    180
gcagacacag tgaagggccg attcaccatc tccagagaca atgccaagaa caccctgttc    240
ctgcaaatga ccagtctgag gtctgaggac acggccatgt attactgtgc aagggtttac    300
tacggaagta cctacgggta tttcgatgtc tggggcacag ggaccacggt caccgtctcc    360
tca                                                                  363
```

<210> SEQ ID NO 288
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 288

```
gacattgtgc tgacacagtc tcctgcttcc ttagctgcat ctctggggca gagggccacc     60
atctcatgca gggccagtca aagtgtcagt acatctagct atagttatat gcactggtac    120
caacagaagc caggacatcc acccaaactc ctcatcaggt atgcatccaa cctagagtct    180
ggggtccctg ccaggttcag tggcagtggg tctgggacag acttcaccct caacatccat    240
cctgtggagg aggaggatac tgcaacatat tactgtcagc acagttggga gattccgtac    300
acgttcggag ggggaccaa gctggaaata aaacg                                335
```

<210> SEQ ID NO 289
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 289

```
gaggtccagc ttcagcagtc aggacctgag ctggtgaaac ctggggcctc agtgaagata     60
tcctgcaagg cttctggata cacattcact gactacaaca tgcactgggt gaagcagagc    120
catggaaagc gccttgagtg gattggatat attcatcctt acaatggtgg tagtggctac    180
aaccagaagt tcaagaggaa ggccacattg actgtagaca attcctccaa cacaacctac    240
atggagctcc gcagcctgac atctgaggac tctgcagtct attactgtgc aagatcttat    300
```

```
gattacgaca cctggtttgg ttactggggc aagggactc tggtcactgt ccgtgca         357
```

<210> SEQ ID NO 290
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 290

```
gatgttgtgc tgacccagac tccactcact ttgtcggtta ccattggaca accagcctcc    60
atctcttgca agtcaagtca gagcctctta tatagtgatg aaagacata tttgaattgg    120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggactt tattattgct ggcaaggtac acattttccg   300
tggacgttcg gtggaggcac caagctggaa atcaaac                            337
```

<210> SEQ ID NO 291
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291

```
gaagtgaaac ttgaggagtc tggaggaggc ttggtgcaac ctggaggatc catgaaactc    60
tcctgtgttg cctctggatt cactttcagt aactactgga taaactgggt ccgccagtct   120
ccagagaagg ggcttgagtg ggttgctgaa atcagaatga aatctaataa ttatgcaaca   180
cattatgcgg agtctgtgaa agggaggttc accatctcaa gagatgattc caaaagttgt   240
gtctacctgc aaatgaacaa cttaagacct gaagacactg gcatttatta ctgtaccagg   300
gggggctact ggggccaagg caccactctc accgtctcct c                       341
```

<210> SEQ ID NO 292
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 292

```
gacattgtga tgtcacagtc tccatcctcc ctagctgtgt cagttggaga aaggttact     60
atgagctgca agtccagtca gagccttta tatagtagca atcaaaagaa ctacttggcc    120
tggtaccagc agaaaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttatttct gtcagcaata ttataactat   300
ccgtacacgt tcggaggggg gaccaagctg gaaataaaac g                       341
```

<210> SEQ ID NO 293
<211> LENGTH: 350
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 293

```
cagatccagt tggtgcagtc tggacctgaa ctgaagaagc tggagagac agtcaagatc      60
tcctgcaagg cttctgggta taccttcaca aactatggaa tgaactgggt gaagcaggct     120
ccaggaaagg gtttaaagtg gatggcctgg ataaacacct acactggaga gccaacatat    180
gctgatgact tcaagggacg gtttgccttc tctttggaaa cctctgccag cactgcctct    240
ttgcagatca tcaacctcaa aaatgaggac acggctacat atttctgtgc aaggatcggc   300
gatagtagtc cctctgacta ctggggccag ggcaccactc tcacagtctc                350
```

<210> SEQ ID NO 294
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 294

```
caaattgttc tcacccagtc tccagcaatc atgtctgcat ctctagggga acgggtcacc      60
atgacctgca ctgccagctc aagtgtaagt tccagttact tgcactggta ccagcagaag    120
ccaggatcct cccccaaact ctggatttat agcacatcca acctggcttc tggagtccca    180
cctcgcttca gtggcagtgg gtctgggacc tcttactctc tcacaatcag cagcatggag    240
gctgaagatg ctgccactta ttactgccac cagtatcatc gttccccacc gacgttcggt    300
ggaggcacca agctggaaat caaac                                          325
```

<210> SEQ ID NO 295
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 295

```
cagatccagt tggtgcagtc tggacctgaa ctgaagaagc tggagagac agtcaagatc      60
tcctgcaagg cttctgatta taccttcaca gacttttcaa tacactgggt gaggcagtct    120
ccaggaaagg gtttaaagtg gatgggctgg ataaacactg agactggtga gccaacagtt    180
gcagaagact tcaagggacg gtttgccttc tctttggaga cctctgccag cactgccttt    240
ttgcagatct acaacctcaa aaatgaggac tcggcaacat atttctgtgc taggggcgt     300
tactacggcc atgactatgc tatggactac tggggtcaag aacctcagt caccgtctcc    360
tca                                                                    363
```

<210> SEQ ID NO 296
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 296

| gacatccaga tgactcagtc tccagcctcc ctatctgcat ctgtgggaga aactgtcacc | 60 |
| atcacatgtc gagcaagtgg gaatcttcac aattatttag catggtatca gcagaaacag | 120 |
| ggaaaatctc ctcagctcct ggtctataat gcaaaaacct tagcagatgg tgtgccatca | 180 |
| aggttcagtg gcagtggatc aggaacacaa tattctctca agatcaacag cctgcagcct | 240 |
| gaagattttg ggacttattt ctgtcaacat ttttggagta ttcctcccac gttcggggggg | 300 |
| gggaccaagc tggaaataaa acg | 323 |

<210> SEQ ID NO 297
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 297

| gaagtgaagc ttgaggagtc tggaggaggc ttggtgcaac ctgggggatc catgaaactc | 60 |
| tcctgtgttg cctctggatt cactttcagt aactattgga tgaactgggt ccgccagtct | 120 |
| ccagagaagg ggcttgagtg ggttgctgaa attagattga aatctaataa ttatgcaaca | 180 |
| cattatgcgg agtctgtgaa agggaggttc accatctcaa gagatgattc caaaagtagt | 240 |
| gtctacctgc aaatgaacaa cttaagagct gaagacactg gcatttatta ctgtaccaga | 300 |
| ctctgggact ttgctatgga ctactgggt caaggaacct cagtcaccgt ctcctca | 357 |

<210> SEQ ID NO 298
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 298

| caaattgttc tcacccagtc tccagcaatc atgtctgcat ctccagggga gaaggtcacc | 60 |
| atatcctgca gtgccagctc aagtgtaagt tacatatact ggtaccagca gaagccagga | 120 |
| tcctcccca aaccctggat ttatcgcaca tccaacctgg cttctggagt ccctgctcgc | 180 |
| ttcagtggca gtgggtctgg gacctcttac tctctcacaa tcagcagcat ggaggctgaa | 240 |
| gatgctgcca cttattactg ccagcagtat catagttacc cgtggacgtt cggtggaggc | 300 |
| accaagctgg aaatcaaac | 319 |

<210> SEQ ID NO 299
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 299

| caggttactc tgaaagagtc tggccctggg atattgcagc cctcccagac cctcagtctg | 60 |
| acttgttctt tctctgggtt ttcactgagc acttttggta tgggtgtagg ctggattcgt | 120 |

```
cagccttcag ggaagggtct ggagtggctg gcacagattt ggtgggatga ttataagtac      180
tataacccag ccctgaagag tcggctcaca atctccaagg atacctccaa aaaccaggta      240
ttcctcaaga tcgccaatgt ggacactgca gatactgcca catactactg tgctcgaatc      300
ggatattact ccggtagtag ccgttgctgg tacttcgatg tctggggcac agggagcacg      360
gtcaccgtct cctca                                                      375
```

<210> SEQ ID NO 300
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 300

```
agtattgtga tgacccagac tcccaaattc ctgcttgtat cagcaggaga cagggttgcc       60
ataacctgca aggccagtca gagtgtgagt aatgatgtag cttggtacca acagaagcca      120
gggcagtctc ctacactgct gatatcctat gcatccaatc gctacactgg agtccctgat      180
cgcttcactg gcagtggata tgggacggat ttcactttca ccatcagcac tgtgcaggct      240
gaagacctgg cagtttattt ctgtcagcag ggttatagct ctccgttcac gttcggaggg      300
gggaccaagc tggaaataaa acg                                             323
```

<210> SEQ ID NO 301
<211> LENGTH: 350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 301

```
caggttcagc tgcaacagtc tgacgctgag ttggtgaaac ctggggcttc agtgaagata       60
tcctgcaagg ctgctggcta caccttcact gaccttacta ttcactgggt gaaacagagg      120
cctgaacagg gcctggagtg gattggatat atttatcctg agatagtaa tactaagtac       180 aatgagaagt tcaagggcaa ggccacattg actgcagata atcctccag cactgcctat       240 atgcagctca acagcctgac atctgaggat tctgtagtgt atttctgtgc aagaatgatt      300
actccttact actttgacta ctggggccaa ggcaccactc tcacagtctc                 350
```

<210> SEQ ID NO 302
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 302

```
gacatccaga tgactcagtc tccagcctcc ctatctgcct ctgtgggaga aactgtcacc       60
atcgcatgtc gagcaagtgg gaatattcac aattatttaa catggtatca gcagagacag      120
ggaaaatctc ctcagctcct ggtctataat gcaaaaacct tagcagttgg tgtgccatca      180
aggttcagtg gcagtggctc aggaacacaa tattctctca agatcaacag cctgcagcct      240
gaagattttg ggagttatta ctgtcaacat ttttggaata ctcctccgac gttcggtgga      300
```
ggcaccaagc tggaaatcaa ac    322

<210> SEQ ID NO 303
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
gaagtgaagc ttgaggagtc tggaggaggc ttggtgcaac ctggaggatc catgaaactc    60
tcctgtgttg cctctggaat cattttcagt aactactgga tgaattgggt ccgccagtct    120
ccagagaagg ggcttgagtg ggttgctgaa attagattga atctaataa ttattcaaca    180 cattatgcgg agtctgtgaa agggaggttc accatctcaa gagatgattc caaaagtagt    240
gtctacctgc aaatgaacaa cttaagagct gaagacactg gcatttatta ctgtaccagg    300
cactattact atgctatgga ctactgggt caaggaacct cagtcaccgt ctcctca    357

<210> SEQ ID NO 304
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
gatatccaga tgacacagac tacatcctcc ctgtctgcct ctctgggaga cagagtcacc    60
atcagttgca gtgcaagtca gggcattagc aattatttaa actggtatca gcagaaacca    120
gatggaactg ttaaactcct gatctattac acatcaagtt tacactcagg agtcccatca    180
aagttcagtg gcagtgggtc tgggacagat tattctctca ccatcagcaa cctggaacct    240
gaagatatcg ccacttacta ttgtcagcag tatagtaagc ttccgtacac gttcggaggg    300
gggaccaagc tggaaataaa acg    323

<210> SEQ ID NO 305
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
gaggtgcagc tggtggagtc tgggggaggc ttagtgaagc ctggagggtc cctgaaactc    60
tcctgtgcag cctctggatt cactttcagt agctatggca tgtcttgggt tcgccagact    120
ccggagaaga ggctggagtg ggtcgcagcc attaatagta atggtggtag cacctactat    180
ccagacactg tgaagggccg actcaccatc tccagacaca tggcaagaa cacccctgtac    240 ctgcaaatga gcagtctgag gtctgaggac acagccttgt attactgtgt aagggatgat    300
ggttactacg ttttctttgc ttactggggc caagggactc tggtcactgt ctctgca    357

<210> SEQ ID NO 306
<211> LENGTH: 322
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 306
gacatccaga tgacacaatc ttcatcctac ttgtctgtat ctctaggagg cagagtcacc    60
attacttgca aggcaagtga ccacattaat aattggttag cctggtatca gcagaaacca   120
ggaaatgctc ctaggctctt aatatctggt gcaaccagtt tggaaactgg ggttccttca   180
agattcagtg gcagtggatc tggaaaggat tacactctca gcattaccag tcttcagact   240
gaagatgttg ctacttatta ctgtcaacag tattggagta ctcctcccac gttcggtgct   300
gggaccaagc tggagctgaa ac                                            322

<210> SEQ ID NO 307
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307
caggtgcagc tgaagcagtc aggacctggc ctagtggcgc cctcacagag cctgtccatc    60
acatgcactg tctctgggtt ctcattaacc agctatggtg tagactgggt tcgccagtct   120
ccaggaaagg gtctggagtg gctgggagtg atatggggtg gtggaagcac aaattataat   180
tcagctctca aatccagact gagcatcacc aaggacaact ccaagagcca gttttctta   240 aaaatgaaca gtctgcaaac tgatgacaca gccatgtact actgtgccag tggagactac   300
gatggtagcc tctggtttgc ttactgggga agggactct gtcactgt ctctgca       357

<210> SEQ ID NO 308
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 308
gatattgtga taacccagga tgaactctcc aatcctgtca cttctggaga atcagtttcc    60
atctcctgca ggtctagtaa gagtctccta tataaggatg gaagacata cttgaattgg   120 tttctgcaga gaccaggaca atctcctcag ctcctgatct atttgatgtc cacccgtgca   180
tcaggagtct cagaccggtt tagtggcagt gggtcaggaa cagatttcac cctggaaatc   240
agtagagtga aggctgagga tgtgggtgtg tattactgtc aacaacttgt agagtatcct   300
cggacgttcg gtggaggcac caagctggaa atcaaac                            337

<210> SEQ ID NO 309
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309
```

```
gaggtgcagc tggtggagtc tgggggagac ttagtgaagc ctggagggtc cctgaaactc     60
tcctgtgtag cctctggatt cactttcagt agctatggca tgtcttgggt tcgccagact    120
ccagacaaga ggctggagtg ggtcgcaacc attagtagtg gtggtacttt cacctactat    180
ccagacagtg tgaaggggcg attcaccgtc tccagagaca atgccaagaa cacctgtac     240 ctgcaaatga gcagtctgaa gtctgaggac acagccatgt attactgttc aagacatggg    300
tggggctggg gccaagggac tctggtcact gtctctgca                           339
```

<210> SEQ ID NO 310
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 310

```
gacatccaga tgactcagtc tccagcctcc ctatctgcat ctgtgggaga aactgtcacc     60
atcacatgtc gagcaagtgg gaatattcac aattatttag catggtatca gcagaaacag    120
ggaaaatctc ctcagctcct ggtctataat gcaaaagcct tagcagatgg tgtgccatca    180
aggttcagtg gcagtggatc aggaacacaa tattctctca agatcaacag cctgcagcct    240
gaagattttg ggagttatta ctgtcaacat ttttggagta ttcctccgac gttcggtgga    300
ggcaccaagc tggaaatcaa ac                                            322
```

<210> SEQ ID NO 311
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 311

```
gaagtgaagc ttgaggagtc tggaggaggc ttggtgcaac ctggaggatc catgaaactc     60
tcctgtgttg cctctggatt cactttcagt aactactgga tgaactgggt ccgccagtct    120
ccagagaagg ggcttgagtg ggttgctgaa attagattga atctaataa ttatgcaaca    180 cattatgcgg agtctgtgaa agggaggttc accatctcaa gagatgattc caaaagtagt    240
gtctacctgc aaatgaacaa cttaagagtt gaagacactg ccatttatta ctgtaccagg    300
cactatgact atgctatgga ctactggggt caaggaacct cagtcaccgt ctcctca       357
```

<210> SEQ ID NO 312
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 312

```
gacatccaga tgactcagtc tccagcctcc ctatctgcat ctgtgggaga aactgtcacc     60
atcacatgtc gagcaagtgg gaatattcac aattatttag catggtatca gcagaaacag    120
ggaaaatctc ctcagctcct ggtctataat gcaaaaacct tagcagatgg tgtgccatca    180
```

```
aggttcagtg gcagtggatc aggaacacaa tattctctca ggatcaacag cctgcagcct      240
gaagattttg ggagttatta ctgtcaacat ttttggagta ctcctccgac gttcggtgga      300
ggcaccaagg tggaaatcaa ac                                               322

<210> SEQ ID NO 313
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 313
gaagtgaagc ttgaggagtc tggaggaggc ttggtacaac ctggaggatc catgaaactc       60
tcctgtgttg cctctggatt cacttttcagt gactactgga tgaactgggt ccgccagtct    120
ccagagaagg ggcttgagtt ggttgctgaa attagattga tatctaataa ttatgcaaca     180
cattatgcgg agtctgtgaa agggaggttc accatctcaa gagatgattc caaaagtagt    240
gtctacctgc aaatgaacaa cttaagagct gaagacactg gcatttatta ctgtaccagg    300
cactattact atgctttgga ctactggggt caaggaacct cagtcaccgt ctcctca        357

<210> SEQ ID NO 314
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 314
gacattgtga tgtcacagtc tccatcctcc ctaactgtgt cagttggaga aaggttact       60 ttgagctgca gtccagtca gagccttta tatagtacca atcaaaagat ctacttggcc      120
tggtaccagc agaaaccagg gcagtctcct aaactgctga tttactgggc atccactagg    180
gaatctgggg tccctgatcg cttcacaggc agtggatctg ggacagattt cactctcgcc    240
atcagcaatg tgaaggctga agacctggca gtttattact gtcagcaata ttatagctat    300
ccgtacacgt tcggaggggg gaccaagctg gaaataaaac g                         341

<210> SEQ ID NO 315
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 315
gaggttcagc tgcagcagtc tggggcagag cttgtgaagc caggggcctc agtcaagttg       60
tcctgcacag cttctggctt caacattaat gacacctatt accattggtt gaagcagagg    120
cctgaacagg gcctggagtg gattggaagg attgatcctg cgaatgttaa tactaaatat    180
gacccgaagt tccagggcaa ggccacttta acagcagaca catcctccaa cacagcctac    240
ctgcagctca gcagcctgac atctgaggac actgccgtct attactgtgg tagggggaat    300
gcttactggg gccaagggac tctggtcact gtctctgca                            339
```

```
<210> SEQ ID NO 316
<211> LENGTH: 313
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 316
caaattgttc tcacccagtc tccagcaatc atgtctgcat ctctagggga ggagatcacc      60
ctaacctgca gtgccagttc gagtgtaagt tacatgcact ggtaccagca gaagtcaggc     120
acttctccca aactcttgat ttatagcaca tccaacctgg cttctggagt cccttctcgc     180
ttcagtggca gtgggtctgg gacctttat tctctcacaa tcagcagtgt ggaggctgaa      240
gatgctgccg attattactg ccatcagtgg agtagtttca cgttcggctc ggggacaaag     300
ttggaaataa aac                                                       313

<210> SEQ ID NO 317
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 317
gaggtccagc tgcaacagtc tggacctgag ctggtgaagc ctggggcttc agtgaagatg      60
tcctgtaagg cttctggata cacattcact gactcctaca tgaactgggt gaagcagagt     120
catggaaaga gccttgagtg gattggacgt gttaatccta acaatggtgg tgctagctac     180
aaccacaagt tcaagggcaa ggccacattg acagtagaca atccctcag cacagcctac      240 atgcgcctca acagcctgac atctgaggac tctgcggtct attactgttc aagatctgga     300
gacctttatt actatgctat ggactactgg ggtcaaggaa cctcagtcac cgtctcctca     360

<210> SEQ ID NO 318
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 318
caaattgttc tcacccagtc tccagcaatc atgtctgcat ctccagggga gaaggtcacc      60
atgacctgca gtgccagctc aagtataagt tacatgcact ggtaccagca gaagtcaggc     120
acctccccca aaagatggat ttatgacaca tccaaactgg cttctggagt ccctgctcgc     180
ttcagtggca gtgggtctgg gacctcttac tctctcacaa tcagcaacat ggaggctgaa     240
gatgctgcca cttattactg ccagcagtgg agtagtaccc acccacgtt cggaggggg      300 accaagctgg aaataaaacg                                                320

<210> SEQ ID NO 319
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 319

```
gaggtccagt tgcaacagtc tggacctgag ctaatgaagc ctggggcttc agtgaagatg      60
tcctgcaagg cttctggata tatttact gactacaaca tgcactgggt gaagcagaac       120
caaggaaaga gcctagagtg gataggagaa gttaatccta acactggtgg tattggctac     180
aatcagaaat tcaaaggcaa ggccacattg actgtagaca gtcctccag cacagcctac      240 atggacctcc gcagcctgac atctgaggac tctgcagtct attactgtgc aagagatggc    300
aattattgct ttgactactg gggccaaggc accactctca cagtctcctc a             351
```

<210> SEQ ID NO 320
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 320

```
gatattgtga tgacgcaggc tgcattctcc aatccagtca ctcttggaac atcagcttcc      60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagagaggtt cagtagcagt gggtcaggat ctgatttcac actgagaatc    240
agcagagtgg aggctgagga tgtgggtgtt tattactgtg ctcaaaatct agaacatccg    300
acgttcggtg gaggcaccaa gctggaaatc aaac                                334
```

<210> SEQ ID NO 321
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 321

```
gaggtgcagc tggtggagtc tgggggagac ttagtgaagc ctggagggtc cctgaaactc      60
tcctgtgcag cctctggatt cactttcagt aactatggca tgtcttgggt tcgccagact    120
ccagacaaga ggctggagtg ggtcgcaacc attagtactg gtggtactta cacctactat    180
ccagacagtg tgaaggggcg attcaccatc tccagagaca atgccaagaa caccctgtac    240
ctgcaaatga gcagtctgaa gtctgaggac acagccatgt attactgtgt aggacagtcc    300
tatagtgact acgtctcgtt tgcttattgg ggccaaggga ctcaggtcac tgtctctgca    360
```

<210> SEQ ID NO 322
<211> LENGTH: 338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 322

```
gatgttgtga tgacccaaac tccactctcc ctgcctgtca gtcttggaga tcaagcctcc      60
atctcttgca gatctagtca gagccttgta cacagtaatg gaaacaccta tttacattgg    120
```

```
tacctgcaga agccaggcca gtctccaaag ctcctgatct ccaaagtttc aaccgattt      180 tctggggtcc cagacaggtt cagtggcagt ggatcaggga cagatttcac tctcaagatc     240
agcagagtgg aggctgaaga tctgggagtt tatttctgct ctcaaagtac acatgttcct    300
cccatgttcg aggggggggac caggctggaa ataaaacg                              338
```

```
<210> SEQ ID NO 323
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 323
gaggttcagc tgcagcagtc tggggctgag cttctgaagc caggggcctc agtcaagttg     60
tcctgcacag cttctggcct caacattaaa gactactata tacactgggt gtaccagagg    120
cctgaacagg gcctggagtg gattggaagg attgatcctg agagtgataa tactttatat    180
gacccgaagt tccagggcaa ggccagtata acagcagaca catcctccaa cacagcctac    240
ctgcagctca gcagcctgac atctgaggac actgccgtct attactgtac tactaatacc    300
ccttttgctt actggggcca agggactctg gtcactgtct ctaca                     345
```

```
<210> SEQ ID NO 324
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 324
gatgttttga tgacccaaac tccactctcc ctgcctgtca gtcttggaga tcaagcctcc     60
atctcttgca gatctagtca gagcattgta catagtaatg gaaacaccta tttagaatgg    120
tacctgcaga accaggcca gtctccaaag ctcctgatct acaaagtttc aaccgattt      180 tctggggtcc cagacaggtt cagtggcagt ggatcaggga cagatttcac actcaagatc    240
agtagagtgg aggctgagga tctgggagtt tattattgct ttcaaggttc acatgttcca    300
ttcacgttcg gctcggggac aaagttggaa ataaaac                             337
```

```
<210> SEQ ID NO 325
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 325
caggtccagt tgcaacagtc tggagctgaa ctggtaaggc ctgggacttc agtgaaggtg     60
tcctgcaaga cttctggata cgccttcact aattacttga tagagtgggt aaagcagagg    120
cctggacagg gccttgagtg gattggggtg attaatcctg gaagtggtgg tactaactac    180
aatgagaagt tcaaggtcaa ggcaacactg actgcagaca aatcctccag cactgcctac    240
atgcagctca ccagcctgac atctgatgac tctgcggtct atttctgtac aagaagggat    300
```
ggttacttct ttccctggtt tgcttactgg ggccaaggga ctctggtcac tgtctctgca    360

<210> SEQ ID NO 326
<211> LENGTH: 340
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 326
gacattgtga tgtcacagtc tccatcctcc ctagctgtgt cagttggaga gaaggttact    60
atgagctgca agtccagtca gagccttttta tatagtagca atcaaaagaa ctacttggcc    120
tggtaccagc agaaaccagg gcagtctcct aaactgctga tttactgggc atccactagg    180
aaatctgggg tccctgatcg cttcacaggc agtggatctg ggacagattt cactctcacc    240
atcagcagtg tgaaggctga agacctggca gtttattact gtcatcaata ttatagctat    300
ccgctcacgt tcgctgctgg gaccaagctg gagctgaaac                          340

<210> SEQ ID NO 327
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 327
caggtgcaac tgcagcagcc tgggtctgtg ctggtgaggc ctggagcttc agtgaagctg    60
tcctgcaagg cttctggcta cacattcacc agctactgga tgcactgggt gaagcagagg    120
cctggacaag gccttgagtg gattggagag attcatccta ataatggtag tactaactac    180
aatgagaagt tcaagggcaa ggccacactg actgtagaca catcctccag cacagcctac    240
gtggatctca gcagcctgac atctgaggac tctgcggtct attactgtgc aagatggact    300
ttgtttactt actggggcca agggactctg gtcactgtct ctgca                    345

<210> SEQ ID NO 328
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 328
gatgttgtga tgacccaaac tccactctcc ctgcctgtca gtcttggaga tcaagcctcc    60
atctcttgca gatctagtca gagccttgta cacagtaatg gaaacaccta tttactttgg    120
tacctgcaga agccaggcca gtctccaaag ctcctgatct acaaagtttc caaccgattt    180
tctggggtcc cagacaggtt cagtggcagt ggatcaggga cagatttcgc actcaagatc    240
agcagagtgg aggctgagga tctgggagtt tatttctgct ctcaaagtac acatgttccg    300
tggacgttcg gtggaggcac caagctggaa atcaaac                             337

<210> SEQ ID NO 329
<211> LENGTH: 351
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 329
gaggtgcagc tggtggagtc tgggggaggc ttagtgaagc ctggagggtc ccggaaactc      60
tcctgtgcag cctctggatt cactttcagt gactatggaa tgcactgggt ccgtcaggct     120
ccagagaagg ggctggagtg ggttgcatac attagtcgtg gcagtagtac catccactat     180
gcagacacag tgaagggccg attcaccatc tccagagaca atgccaagaa caccctgttc     240
ctgcaaatga ccagtctaag gtctgaggac acagccatgt attactgtgc aaggcctttc     300
aactggtact tcgatgtctg gggcgcaggg acaacggtca ccgtctcctc a              351

<210> SEQ ID NO 330
<211> LENGTH: 340
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 330
gacattgtga tgtcacagtc tccatcctcc ctagctgtgt cagttggaga gaaggttact      60
atgacctgca agtccagtca gagccttttta tatagtagca atcaaaagaa ctacttggcc    120
tggtaccagc agaaaccagg gcagtctcct aaactactaa tttactgggc atccactagg    180
gaatctgggg tccctgatcg cttcataggc agtggctctg gacagatttt cactctcacc    240
atcagcagtg tgaaggctga agacctggca atttattact gtcagcaata ttatcgctat    300
ccgctcacgt tcggtgctgg gaccaaactg gagctgaaac                            340

<210> SEQ ID NO 331
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 331
caggtccaac tgcagcagcc tggggctgag cttgtgaagc ctggggcttc agtgatgctg      60
tcctgcaagg cttctggcta caccttcacc agctactggg tacactgggt gaagcagagg    120
cctggacaag gccttgagtg gattggagtg attaatccta gaaacggtcg taacaattac    180
aatgagaagt tcaagaccaa ggccacactg actgtagaca aatcatccag cacagcctac    240
atgcaactca gcagcccgac atctgaggac tctgcggtct attactgtgc acgagaggat    300
tacgacgggg gggactatgc tatggactac tggggtcaag gaacctcagt caccgtctcc    360
tca                                                                    363

<210> SEQ ID NO 332
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<400> SEQUENCE: 332
gatatccaga tgacacagac tacatcctcc ctgtcggcct ctctgggaga cagggtcacc    60
atcagttgca gtgcaagtca gggcattaac aattatttaa actggtatca gcagaaacca   120
gatggaactg ttacactcct gatctattac acatcaagtt tacactcagg agtcccatcc   180
aggttcagtg gcagtgggtc tgggacagat tattctctca ccatcagcaa cctggaacct   240
gaagatattg ccacttacta ttgtcagcag tatagtaagc ttccgtggac gttcggtgga   300
ggcaccaagc tggaaatcaa ac                                            322

<210> SEQ ID NO 333
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 333
gaggtcgagc tgcaacagtc tggacctgag ctggtgaagc cggggcttc agtgaagata    60 tcctgcaaga cttccggaaa cacatacact gaatacacca tgcagtgggt gaagctgagc   120
catggaaaga gccttgagtg gattggaggt attaatccta acaatggtat tactagttac   180
aaccagaagt tcaagggcaa ggccacattg actgtagaca gtcctccag cacagcctac    240 atggagctcc gcagcctgaa atctgaggat tctgcagtct attactgtgc aagagcggga   300
cttggtaact acgtttgggc tatggactac tggggtcaag agcctcagt caccgtctcc    360 tca                                                                  363

<210> SEQ ID NO 334
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 334
gatgttgtga tgacccaaac tccactctcc ctgcctgtca gtcttggaga tcaagcctcc    60
atctcttgca gatctagtca gagccttgta cacaataatg gaaacaccta tttacattgg   120
tacctgcaga agccaggcca gtctccaaac ctcctgatct acaaagtttc caaccgattt   180
tctggggtcc cagacaggtt cagtggcagt ggatcaggga cagatttcac actcaagatc   240
agcatagtgg aggctgagga tctgggactt tatttctgct ctcaaagtac acatgttcct   300
cggacgttcg gtggaggcac caagctggaa atcaaac                             337

<210> SEQ ID NO 335
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 335
caggtccagc ttccgcagtc tggggctgaa ctggcaaaac ctggggcctc agtgaaaatc    60
tcctgcaagg cttctggctt caccttact tcctactgga tgcactgggt aaaacagagg   120
```

```
cctggacagg gtctggaatg gattggatac attaatccta gcactgatta tactgagtac    180
aatcagaagt tcaaggacaa ggccacattg actgcagaca atcctccag cacagcctac     240 atgcaactgg gcagcctgac atctgaggac tctgcagtct attactgtgc aagatcttcc    300
tacggtagta gccccttga ttattggggc caaggctcca ctctcacagt ctcctca        357
```

<210> SEQ ID NO 336
<211> LENGTH: 340
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 336

```
gacattgtga tgtcacagtc tccatcctcc ctagctgtgt ctgttggaga aaggttact     60 atgaactgcg agtccagtca gagccttta tatagtagca atcaaaagaa ctacttggcc     120
tggtaccagc agaaaccagg gcagtctcct aaactgctga tttactgggc atccactagg    180
gattctgggg tccctgatcg cttcacaggc agtggatctg ggacagattt cactctcacc    240
atcagcagtg tgagggctga agacccggca gtttattact gtcagcaata ttatagctat    300
ccgctcacgt tcggtgctgg gaccaagctg gagctgagac                          340
```

<210> SEQ ID NO 337
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 337

```
gaagtgaagc ttgaggagtc tggaggaggc ttggtgcaac ctggaggatc catgaaactc    60
tcttgcgctg cctctggatt cactttagt gacgcctgga tggactgggt ccgccagtct    120
ccagagaagg ggcttgagtg ggttgctgaa ataagaagca aagctaataa tcatgcaaca    180
tactatgctg agtctgtgaa agggaggttc accatctcaa gagatgattc caaaagtagt    240
gcctacctgc aaatgaacag cttaagagct gaagacactg gcatttatta ttgtgtttca    300
acagggactt cttactgggg ccaagggact ctggtcactg tctctgca                 348
```

<210> SEQ ID NO 338
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 338

```
caaattgttc tcacccagtc tccagcaatc atgtctgcat ctccagggga gaaggtcacc    60
atgacctgca gtgccagctc aagtgtaagt tacatgcact ggtaccagca gaagtcaggc    120
acctccccca aaagatggat ttatgacaca tccaaactgg cttctggagt cccctcctcgc   180 ttcagtggcc gtgggtctgg gacctcttac tctctcacaa tcagcagcat ggaggctgaa    240
gatgctgcca cttattactg ccagcattgg agtagtaacc cacccacgtt cggtgctggg    300
```
accaagctgg agatgaaac 319

<210> SEQ ID NO 339
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 339
gaggtccagc tgcaacagtc tggacctgag ctaatgaagc ctggggcttc agtgaagatg 60
tcctgcaagg cttctggaga cacattcact gactacaaca tacactgggt gaagcagaac 120
caaggaaaga gcctagagtg gataggagaa gttaatccta acattggtgg tattggctat 180
aaccagaagt tcaaaggcaa ggccacattg actgtagaca agtcctccag cacagcctac 240
atggagctcc gcagcctgac atctgaggac tctgcagtct attactgtgc aatggggagg 300
tggtacttcg atgtctgggg cgcagggacc acggtcaccg tctcctca 348

<210> SEQ ID NO 340
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 340
gatattgtga tgacccagtc tccactctcc ctgcctgtca gtcttggaga tcaagcctcc 60
atctcttgca gatctagtca gagccttgta cacagtaatg aaacaccta tttacattgg 120 tacctgcaga agccaggcca gtctccaaag ctcctgatct acagagtttc caaccgattt 180
tctggggtcc cagacaggtt cagtggcagt ggatcaggga cagatttcac actcacgatc 240
agcagagtgg aggctgagga tctgggagtt tatttctgct ctcaaagtac acatcttcct 300
cggacgttcg gtggaggcac caagctggag atcaaac 337

<210> SEQ ID NO 341
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 341
gaggtccagc tgcagcagtc tggacctgag atggtgaagc ctggggcttc agtgaagata 60
tcctgcaagg cttctggata cacattcact gactactaca tgcactgggt gaaacagagc 120
catggaaaga gccttgagtg gattggacgt gttaatacta caatggtgg aactagctac 180 gaccagaagt tcgagggcaa ggccacattg actgttgaca atcttccag cacagcctac 240 atggagctca cagcctgac atctgaggac tctgcggtct attactgtgt aatccctgcc 300
tggtttgctt actggggcca aggactctg gtcactgtct ctgca 345

<210> SEQ ID NO 342
<211> LENGTH: 337
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 342
gatattgtga tgacccagtc tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acagagtttc caaccgattt   180
tctggggtcc cagacaggtt cagtggcagt ggatcaggga cagatttcac actcacgatc   240
agcagagtgg aggctgagga tctgggagtt tatttctgct ctcaaagtac acatcttcct   300
cggacgttcg gtggaggcac caagctggag atcaaac                            337

<210> SEQ ID NO 343
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 343
caggtgcaac tgcagcagtc tgggtctgtg ctggtgaggc ctggagcttc agtgaagctg    60
tcctgcaagg cttctggcta cacattcacc agctactgga tgcactgggt gaagcagagg   120
cctggacaag gccttgagtg gattggagag attcatccta atagtgggaa tactaattac   180
aatgagaagt tcaagggcaa ggccacactg actgtagaca tcctccagac acagcctac    240 gtggatctca gcagcctgac atctgaggac tctgcggtct attattgtgc aggtggtaac   300
tacgactact ggggccaagg caccactctc acagtctcct ca                      342

<210> SEQ ID NO 344
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 344
gacattgtgc tgacccaatc tccagcttct ttggctgtat ctctagggca gagggccacc    60
atatcctgca gagccagtga aagtgttgat agttatggca atagttttat gcactggtac   120
cagcagaaac caggacagcc acccaaagtc ctcatctatc gtgcatccaa cctagaatct   180
gggatccctg ccaggttcag tggcagtggg tctaggacag acttcaccct caccattaat   240
cctgtggagg atgaagatgt tgcaacctat tactgtcagc aaagtaatga ggatccgtac   300
acgttcgggg gggggaccaa gctggaaata aaacg                              335

<210> SEQ ID NO 345
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 345
```

```
gaggttcagc tcgagcagtc tgggactgtg ctggcaaggc ctggggcttc agtgaagatg    60
tcctgcaagg cttctggcta cacctttacc agctactgga tgcactgggt gaaacagagg   120
cctggacagg gtctggaatg gattggcgct ttttatcctg gaaacagtgg tacttattac   180
aaccaaaaat tcaaggacaa ggccaaactg actgcagtca catctgccag cactgcctac   240
atggagctca gcagcctgac aaatgaggac tctgcggtct attactgttc aagatcaggg   300
tcaggaaggt ttgcttactg gggccaaggg actctggtca ctgtctctgc a            351
```

<210> SEQ ID NO 346
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 346

```
caaattgttc tcacccagtc tccagcaatc atgtctgcat ctccagggga aaggtcacc    60 atgacctgca gtgccagctc aagtgtgagt tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggagactgaa   240
gatgctgcca cttattactg ccagcagtgg agtaataccc cacccacgtt cggctcggtg   300
acaaagttgg aaataaaac                                                319
```

<210> SEQ ID NO 347
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 347

```
gaggtccagc tgcaacagtc tggacctgag ctaatgaagc ctggggcttc agtgaagatg    60
tcctgcaagg cttctggata cacattcact gaccacaaca tacactgggt gaaacagcac   120
caaggaaaga gcctagagtg gataggagaa attaatccta acactggtgg tactggctac   180
aaccagaagt tccaaggcaa ggccacaatg actgtagaca agtcctccag cacagcctac   240
atggaactcc gcagcctgac atctgaggac tctgcagtct attactgtgt tagaggactg   300
tacttctttg actactgggg ccaaggcacc actctcacag tctcctca               348
```

<210> SEQ ID NO 348
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 348

```
gatattgtga taacccagga tgatctctcc aatcctgtca cttctggaga atcagtttcc    60
atctcctgca ggtctagtaa gagtctccta tataaggatg ggaagacata cttgaattgg   120
tttctgcaga gaccaggaca atctcctcag ctcctgatct atttgatgtc cacccgtgca   180
tcaggagtct cagaccggtt tagtggcagt gggtcaggaa cagatttcac cctggaaatc   240
```

```
agtagagtga aggctgagga tgtgggtgtg tattactgtc aacaacttgt agagtatcct    300
cggacgttcg gtggaggcac caagctggaa atcaaac                            337
```

<210> SEQ ID NO 349
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 349

```
gaggtgcacc tggtggagtc tgggggagac ttagtgaagc ctggagggtc cctgaaactc    60
tcctgtgcag cctctggatt cactttcagt agctatggca tgtcttgggt tcgccagact   120
ccagacaaga ggctggagtg ggtcgcaacc attagtagtg gtggtactta cacctactat   180
ccagacagtg tgaaggggcg attcaccatc tccagagaca atgccaagaa cacccctgtat  240 ctgcaaatga gcagtctgaa gtctgaggac acagccatgt attactgttc aagacatggg   300
tggggctggg gccaagggac tctggtcact gtctctgca                         339
```

<210> SEQ ID NO 350
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 350

```
caaattgttc tcacccagtc tccagcaatc atgtctgcat ctccagggga gaaggtcacc    60
atgacctgca gtgccagctc aagtgttagt tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaccc cacccacgtt cggctcgggg   300
acaaagttgg aaataaaac                                               319
```

<210> SEQ ID NO 351
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 351

```
gaggtccagc tgcaacagtc tggacctgag ctaatgaagc ctggggcttc agtgaagatg    60
tcctgcaagg cttctggata cacattcact gactacaaca tgcactgggt gaagcagaac   120
caaggaaaga gcctagagtg gataggagaa attaatccca acactggtgg tactggctac   180
aaccagaagt tcaaggcaa ggccacattg actgtagaca gttttccag cacagccttc    240 attgagctcc gcagcctgac atctgaggac tctgcaatct attactgtac aagaggggt   300 tacgaccact attggtactt cgatgtctgg ggcgcaggga ccacggtcac cgtctcctca   360
```

<210> SEQ ID NO 352

```
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 352
gacattgtgc tgacccaatt tccagcttct ttggctgtgt ctctagggca gagggccacc      60 atacccctgca gagccagtga agtgttgat agttatggca atagttttat gcactggttc     120
cagcagaaac caggacagcc acccaaactc ctcatctatc gtgcatccaa cctagaatct     180
gagatccctg ccaggttcag tggcagtggg tctgggacag acttcaccct caccattaat     240
cctgtggagg ctgatgatgt tgcaacctat tactgtcagc aaagtcatga ggatccgtac     300
acgttcggag gggggaccaa gatggaaata aaacg                                 335

<210> SEQ ID NO 353
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 353
gaggttcagc tgcagcagtc tgggactgtg ctggcaaggc ctggggcttc agtgaagatg      60
tcctgcaagg cttctggcta tacctttacc agctactgga tgcactgggt aaaacagagg     120
cctggacagg gtctggaatg gattggcgct atttatcctg gaaagaatga tactacctac     180
aaccagaagt tcaagggcaa ggccaaactg actgcagtca catctgccag cacttttatac   240 atggagctca gcagcctgac aaatgaggac tctgcggtct attactgtac aagatctgga     300
aagggttact tgcttactg gggccaaggg actctggtca ctgtctctgc a                351

<210> SEQ ID NO 354
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 354
gatgttgtga tgacccagtc tccactctcc ctgcctgtca gtcttggaga tcaagcctcc      60
atctcttgca gatctagtca gagcattgta catagtaatg aaacaccta tttagaatgg      120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caaactggaa atcaaac                              337

<210> SEQ ID NO 355
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 355

```
caggttactc tgaaagagtc tggccctggg atattgcagc cctcccagac cctcagtctg      60
acttgttctt tctctgggtt ttcactgagc acttctggta tgggtgtgag ctggattcgt     120
aagacttcag gaaagggtct ggaatggctg gcacacattt tctgggatga tgacaagtgg     180
tataatccat ccctgaagag ccggctcaca atctccaagg ctacctccag caaccaggta     240
ttcctcatac tcaccagtgt ggatactgcc gatactgcca catactactg tgctaccttc     300
tatggtctct actttgccta ctggggccaa ggcaccactc tcacagtctc ctca           354
```

<210> SEQ ID NO 356
<211> LENGTH: 340
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 356

```
gacattgtga tgtcacagtc tccatcctcc ctagctgtgt ctgttggaga aaggttact      60
atgaactgcg agtccagtca gagcctttta tataatagca atcaaaagaa ctacttggcc    120
tggtaccagc agaaaccagg gcagtctcct aaactgctga tttactgggc atccactagg    180
gattctgggg tccctgatcg cttcacaggc agtggatctg ggacagattt cactctcacc    240
atcagcagtg tgagggctga tgacccggca gtttattact gtcagcaata ttttaactat    300
ccgctcacgt tcggtgctgg gaccaagctg gagctgaaac                          340
```

<210> SEQ ID NO 357
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 357

```
gaagtgaagc ttgaggagtc tggaggaggc ttggtgcaac ctggaggatc catgaaactc     60
tcttgcgctg cctctggatt cactttagt gacgcctgga tggactgggt ccgccagtct    120
ccagagaagg ggcttgagtg ggttgctgaa ataagaagca aacctaataa tcatgcaaca    180
tactatgctg agtctgtgaa agggaggttc accatctcaa gagatgattc caaaagtagt    240
gcctacctgc aaatgaacag cttaagagct gaagacactg gcatttatta ctgtgtttca    300
acagggactt cttactgggg ccaagggact ctggtcactg tctctgca                 348
```

<210> SEQ ID NO 358
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 358

```
caaattgttc tcacccagtc tccagcaatc atgtctgcat ctccagggga gaaggtcacc     60
atgacctgca gtgccagctc aagtataagt tacatgcact ggtaccagca gaagtcaggc    120
```

```
acctccccca aaagatggat ttatgacaca tccaaactgg cttctggagt ccctgctcgc      180
ttcagtggca gtgggtctgg gacctcttac tctctcacaa tcagcaacat ggaggctgaa      240
gatgctgcca cttattactg ccagcagtgg agtagtaccc cacccacgtt cggagggggg      300
accaagctgg aaataaaacg g                                                321
```

<210> SEQ ID NO 359
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 359

```
gaggtccagt tgcaacagtc tggacctgag ctaatgaagc ctggggcttc agtgaagatg       60
tcctgcaagg cttctggata tatttact gactacaaca tgcactgggt gaagcagaac      120
caaggaaaga gcctagagtg gataggagaa gttaatccta acactggtgg tattggctac      180
aatcagaaat tcaaaggcaa ggccacattg actgtagaca gtcctccag cacagcctac      240 atggacctcc gcagcctgac atctgaggac tctgcagtct attactgtgc aagagatggc      300
aattattgct ttgactactg gggccaaggc accactctca cagtctcctc a              351
```

<210> SEQ ID NO 360
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 360

```
gacatcaaga tgacccagtc tccatcttcc atgtatgcat ctctaggaga gagagtcact       60
ctcacttgca aggcgagtca ggacattaat agctatttaa gctggttcca gcagaaacca      120
gggaaatctc ctgagaccct gatctatcgt gcaaacagat tgatagatgg ggtcccatca      180
aggttcagtg gcagtggatc tgggcaagat tattctctca ccatcagcag cctggagtat      240
gaagatatgg ggatttatta ttgtctacag tatgatgagt ttcctccgac gttcggtgga      300
ggcaccaagc tggaaatcaa ac                                               322
```

<210> SEQ ID NO 361
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 361

```
gaggtccacc tacaacagtc tggacctgaa ctggtgaacc ctgggtcttc agtgaagata       60
tcctgcaagg ctgctggata cacattcact gactacaaca tggactgggt gaagcagagc      120
catggaaaga gacttgagtg gattggaaat atttatccta acaatggtgg tgctggatac      180
aaccagaact tcaaggacaa ggccacattg actgtagaca gtcctccag cacagcctac      240 atggagctcc gcagcctgac atctgaggac tctgcagtct attactgtgc aagatccatt      300
actgcggctt ggtttgctta ctggggccaa gggactctgg tcactgtctc tgca            354
```

<210> SEQ ID NO 362
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 362

```
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagatggat ttatgacaca tccaaactgg cttctggagt ccctgctcgc     180
ttcactggca gtgggtctgg gacctcttac tctctcacaa tcagcagcat ggaggctgaa     240
gatgctgcca cttattactg ccagcagtgg agtagtagcc acccacgtt cggtgctggg      300
accaagctgg aactgaaac                                                   319
```

<210> SEQ ID NO 363
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 363

```
gaggtccagc tgcaacagtc tggacctgag ctaatgaagc ctggggcttc agtgaagatg      60
tcctgcaagg cttctggata cacattcact gactacaaca tgcactgggt gaagcagaac     120
caaggaaaga gcctagagtg gataggagaa attaatccta acactggtgg tactggctac     180
aaccagaagt tcaaagacaa ggccacattg actgtagaca gtcctccag cacagcctac      240
atggagctcc gcagcctgac atctgaggac tctgcagtct attactgtgc aagaattccc     300
tccctgagac gatactactt tgactactgg ggccaaggca ccactctcac agtctcctca     360
```

<210> SEQ ID NO 364
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 364

```
gaccttgtgc tgacacagtc tcctgcttcc ttagctgtat ctctggggca gagggccacc      60
atctcatgca gggccagcga aagtgtcagt acatctggct atagttatat gcactggtac     120
caacagaaac caggacagcc acccaaactc ctcatctatc ttgcatccaa cctcgaatct     180
ggggtccctg ccaggttcag tggcagtggg tctgggacag acttcaccct caacatccat     240
cctgtggagg aggaggatgc tacaacctat tactgtcagc acagtaggga gcttccgtac     300
acgttcggag gggggaccaa gctggaaata aaacg                                 335
```

<210> SEQ ID NO 365
<211> LENGTH: 366
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 365
caggttactc tgaaagagtc tggccctggg atattgcagc cctcccagac cctcagtctg      60
acttgttctt tctctgggtt ttcactgatc acttatggta taggagtagg ctggattcgt     120
cagccttcag ggaagggtct ggagtggctg gcacacattt ggtggaatga taataagtac     180
tataacacag ccctgaagag ccggctcaca atctccaagg atacctccaa caaccaggta     240
ttcctcaaga tcgccaatgt ggacactgca gatactgcca catactactg tgctcgaatg     300
gtctactatg attacgacgg ggggtttgct tactggggcc aagggactct ggtcactgtc     360
tctgca                                                                366

<210> SEQ ID NO 366
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 366
gacattgtgc tgacccaatc tccagcttct ttggctgtgt ctctagggca gagggccacc      60
atatcctgca gagccagtga aagtgttgat agttatggca atagttttat gcactggtac     120
cagcagaaac caggacagcc acccaaaccc ctcatttatc gtgcatccaa cctagaatct     180
gggatccctg ccagattcag tggcagtggg tctaggacag acttcaccct caccattaat     240
cctgtggagg ctgatgatgt tgcaacctat tactgtcagc aaagtaatga ggatccgtac     300
acgttcggag gggggaccaa gctggaaata aaacg                                335

<210> SEQ ID NO 367
<211> LENGTH: 350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 367
gaggtgcagc tgcagcagtc tggggactgtg ctggcaaggc ctggggcttc agtaaggatg      60
tcctgcaagg cttctggcta cacctttacc agctactgga tgcactgggt aaaacaaagg     120
cctggacagg gtctggaatg gattggcgct atttatcctg gaaatagtga tactagctac     180
aaccataagt tcaagggcaa ggccaaactg actgcagtca catctgccag cactgcctac     240
atggagctca gcagcctgac aaatgaggac tctgcggtct attactgtac aagatctggg     300
acgggctggt ttgcttactg gggccaaggg actctggtca ctgtctctgc                 350

<210> SEQ ID NO 368
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 368
```

```
gacattgtgc tgacccaatc tccagcttct ttggctgtgt ctctaggaca gagagccact    60
atcttctgca gagccagcca gagtgtcgat tataatggaa ttagttatat gcactggttc   120
caacaaaaac caggacagcc acccaaactc tcatctatg ctgcatccaa cgttcaatct    180
gggatccctg ccaggttcag tggcagtggg tctgggacag acttcaccct caacatccat   240
cctgtggagg aggaagatgc tgcaaccttt tactgtcagc aaagtattga ggatcctccg   300
acgttcggtg gaggcaccaa gctggaaatc aaac                               334

<210> SEQ ID NO 369
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 369
caggtccagc tgcagcagtc tggacctgag ctggtgaaac ctggggcctc agtgaagatt    60
tcctgcaaag cttctggcta cgcattcagt agttcttgga ttaactgggt gaagcagagg   120
cctggacagg tcttgagtg gattggacgg atttatcctg agaaggtga tactaactac     180 agtgggaatt tcgagggcaa ggccacactg actgcagaca aatcctccac cacagcctac   240
atgcagctca gcagtctgac ctctgtggac tctgcggtct atttctgtac aagaggacta   300
gtcatggact actggggcca aggcaccgct ctcacagtct cctca                   345

<210> SEQ ID NO 370
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 370
gacatccaga tgacccagtc tccatcctcc ctgtctgcat ctgtaggaga cagagtcacc    60
atcacttgcc gggcaagtgc gaacattaac agcaatttag tttggtatca gcagaaacca   120
gggaaagccc ctaagctcct gatctatgct gcaaccaatt tggcagatgg ggtcccatca   180
aggttcagtg gcagtggatc tgggacagat ttcactctca ccatcagcag tctgcaacct   240
gaagattttg caacttacta ctgtcaacat ttttgggta ctcctcggac gttcggtgga    300
ggcaccaagc tggaaatcaa a                                             321

<210> SEQ ID NO 371
<211> LENGTH: 349
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 371
caggtgcagc tggtgcagtc tggggctgag gtgaagaagc ctggggcctc agtgaaggtc    60
tcctgcaagg cttctggata caccttcacc gactacaata tgtactgggt gcgacaggcc   120
cctggacaag gcttgagtg gatgggagag atcaacccta caatggtgg cacagcctat     180
```

```
aatcagaagt ttaggggcaa ggtcaccatg accagggaca cgtccatcag cacagcctac    240
atggagctga gcaggctgag atctgacgac acggccgtgt attactgtgc gagatatgat    300
aaggggtttg actactgggg ccaaggcacc actgtcacag tctcctcag               349
```

<210> SEQ ID NO 372
<211> LENGTH: 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 372

```
gaaattgtgt tgacacagtc tccagccacc ctgtctttgt ctccagggga aagagccacc     60
ctctcctgca gtgccagtag cagtgttagc tacatgcatt ggtaccaaca gaaacctggc    120
caggctccca ggctcctcat ctatgataca tccaaattgc ccagtggcat cccagccagg    180
ttcagtggca gtgggtctgg gacagacttc actctcacca tcagcagcct agagcctgaa    240
gattttgcag tttattactg tcagcagtgg agtagtaccc cacccacgtt cggtcagggg    300
accaagctgg agattaaac                                                 319
```

<210> SEQ ID NO 373
<211> LENGTH: 361
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 373

```
caggtgcagc tggtgcagtc tggggctgag gtgaagaagc ctggggcctc agtgaaggtc     60
tcctgcaagg cttctggata caccttcacc gactacaata tgcactgggt gcgacaggcc    120
cctggacaag gcttgagtg gatgggagag atcaaccctaa acattggtgg cacaggctat    180
aaccagaagt ttaagggcag ggtcaccatg accagggaca cgtccatcag cacagcctac    240
atggagctga gcaggctgag atctgacgac acggccgtgt attactgtgc gagaacctat    300
agttactata gttacgagtt tgcttactgg ggccaaggga ctctggtcac tgtctcttca    360
g                                                                    361
```

<210> SEQ ID NO 374
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (339)..(339)
<223> OTHER INFORMATION: n is a, c, g, or t

<400> SEQUENCE: 374

```
gacatcgtga tgacccagtc tccagactcc ctggctgtgt ctctgggcga gagggccacc     60
atcaactgca gtccagcca gagtcttctc tacagctcca accagaagag ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
```

| atcagcagcc tgcaggctga agatgtggca gtttattact gtaagcaatc ttataatctt | 300 |
| cggacgttcg gtggaggcac caaggtggaa atcaaamgn | 339 |

<210> SEQ ID NO 375
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 375

| gaagtgcagc tggtgcagtc tggggctgag gtgaagaagc ctggggccac cgtgaagata | 60 |
| tcctgcaagg tgtctggata caccttcaca gaccacacta tacactgggt gcgacaggcc | 120 |
| cctggaaagg ggcttgagtg gatgggatac atctaccctc gtgatggtag cacaaaatac | 180 |
| aacgaggagt tcaaaggcag agtcaccatc accgccgaca cgtccacgga cacagcctac | 240 |
| atggagctga gcagcctgag atctgaggac acggccgtgt attactgtgc gagatcatat | 300 |
| agtaactact ttgactactg gggccaaggc accactgtca cagtctcctc ag | 352 |

<210> SEQ ID NO 376
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 376

| gaaattgtgc tgactcagtc tccagacttt cagtctgtga ctccaaagga gaaagtcacc | 60 |
| atcacctgcc gggccagtca gagcattggt actagcatac actggtacca gcagaaacca | 120 |
| gatcagtctc caaagctcct catcaagtat gcttccgagt ccatctcagg ggtcccctcg | 180 |
| aggttcagtg gcagtggatc tgggacagat ttcacccctca ccatcaatag cctggaagct | 240 |
| gaagatgctg caacgtatta ctgtcagcaa agtaatagct ggccactcac gttcggtcaa | 300 |
| gggaccaagc tggagataaa ac | 322 |

<210> SEQ ID NO 377
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 377

| caggtgcagc tggtgcagtc tggggctgag gtgaagaagc ctggggcctc agtgaaggtc | 60 |
| tcctgcaagg cttctggata caccttcacc agaagctata tccactgggt gcgacaggcc | 120 |
| cctggacaag ggcttgagtg gatgggatac atcagcagtg gcagtggtgg cacaacctat | 180 |
| aaccagaagt ttaagggcag ggtcaccagt accagggaca cgtccatcag cacagcctac | 240 |
| atggagctga gcaggctgag atctgacgac acggccgtgt attactgtgc gagaggggg | 300 |
| gtacggtact cgatgtctg gggccaaggg accacggtca ccgtctcctc ag | 352 |

<210> SEQ ID NO 378

```
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 378
gacatccaga tgacccagtc tccatcctca ctgtctgcat ctgtaggaga cagagtcacc      60
atcacttgta aggcgagtca ggacattaat agttatttat cctggtttca gcagaaacca     120
gggaaagccc ctaagtccct gatctataga gcaaacagat tggtagatgg ggtcccatca     180
aggttcagcg gcagtggatc tgggacagat tacactctca ccatcagcag cctgcagcct     240
gaagattttg caacttatta ctgcctacag tatgatgagt ttcctccgac gttcggtcag     300
ggcaccaagc tggaaatcaa ac                                              322

<210> SEQ ID NO 379
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 379
caggtccagc ttgtgcagtc tggggctgag gtgaagaagc ctggggcctc agtgaaggtt      60
tcctgcaagg cttctggata caccttcact gactataata tggattgggt gcgccaggcc     120
cccggacaaa ggcttgagtg gattggatac atctaccctg acaatggtgg cgcaggatat     180
aatcagaagt tcaagggcag agtcaccatt accgtggaca catccgcgag cacagcctac     240
atggagctga gcagcctgag atctgaagac acggctgtgt attactgttc aagatccatt     300
actacggctt ggtttgctta ctggggccaa gggactctgg tcactgtctc ttcag         355

<210> SEQ ID NO 380
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 380
gccatccaga tgacccagtc tccatcctcc ctgtctgcat ctgtaggaga cagagtcacc      60
atcacttgca aggcaagtca gagcgttaat aatgatgtag cctggtatca gcagaaacca     120
gggaaagccc ctaagctcct gatctattat gcatccaatc gatatactgg ggtcccatca     180
aggttcagcg gcagtggatc tggcacagat ttcactctca ccatcagcag cctgcagcct     240
gaagattttg caacttattt ctgtcagcag gattatagct ctcctcggac gttcggtcag     300
gggaccaagc tggaaataaa gc                                              322

<210> SEQ ID NO 381
<211> LENGTH: 364
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 381

| | | | | | |
|---|---|---|---|---|---|
| caggtgcagc | tggtgcagtc | tggggctgag | gtgaagaagc | ctggggcctc | agtgaaggtc | 60 |
| tcctgcaagg | cttctggata | caccttcacc | agctactgga | tcaactgggt | gcgacaggcc | 120 |
| cctggacaag | ggcttgagtg | gattggaaac | atcttccctg | acactactac | acaaactat | 180 |
| aacgagaagt | ttaagggcag | ggtcaccctg | accagggaca | cgtccatcag | cacagcctac | 240 |
| atggagctga | gcaggctgag | atctgacgac | acggccgtgt | attactgtgc | gagagagtac | 300 |
| tacgatggta | cctacgatgc | tatggattac | tggggtcaag | gaaccctagt | caccgtctcc | 360 |
| tcag | | | | | | 364 |

<210> SEQ ID NO 382
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 382

| | | | | | |
|---|---|---|---|---|---|
| gagatcgtgc | tgacccagag | ccctgctaca | ctgtccctgt | ccctggaga | gagggccaca | 60 |
| ctctcctgca | gggcttccga | gtccgtggat | tcctacggca | actccttcat | gcactggtac | 120 |
| cagcagaaac | ccggccaggc | ccctaggctg | ctgatctaca | gggcctccaa | cctggagtcc | 180 |
| ggcatccctg | ctaggttctc | cggatccggc | tccggcaccg | actttaccct | gaccatctcc | 240 |
| tccctggagc | ccgaggactt | cgccgtgtac | tactgccagc | agtcccacga | ggaccctac | 300 |
| accttcggcc | agggcaccaa | gctggagatc | aagagg | | | 336 |

<210> SEQ ID NO 383
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 383

| | | | | | |
|---|---|---|---|---|---|
| caggtccagc | tggtgcagag | cggcgctgag | gtgaagaagc | ctggcgccag | cgtgaaggtg | 60 |
| tcctgcaaag | ccagcggcta | caccttcacc | tcctactgga | tgcattgggt | gaggcaggct | 120 |
| cctggccaag | gactggagtg | gatgggcgcc | atctaccccg | gcaagtccga | caccacctac | 180 |
| aaccagaagt | tcaagggcag | ggtgaccatg | acacgggaca | cctccacctc | caccgtgtac | 240 |
| atggagctgt | cctccctgag | gtccgaggac | accgccgtgt | actactgcgc | caggtccggc | 300 |
| aagggctatt | tcgcctactg | gggccagggc | acactggtga | ccgtgtcctc | c | 351 |

<210> SEQ ID NO 384
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 384

| | | | | | |
|---|---|---|---|---|---|
| gacatcgtga | tgacccagtc | tccagactcc | ctggctgtgt | ctctgggcga | gagggccacc | 60 |

```
atcaactgca agtccagcca gagtttatta tacagctcca accaaaagaa ctacttagct      120
tggtaccagc agaaaccagg acagcctcct aagctgctca tttactgggc atctacccgg      180
aaatccgggg tccctgaccg attcagtggc agcgggtctg ggacagattt cactctcacc      240
atcagcagcc tgcaggctga agatgtggca gtttattact gtcatcaata ttatagctat      300
ccgctcacgt tcggtcaagg caccaagctg gaaatcaaa                             339
```

<210> SEQ ID NO 385
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 385

```
caggtgcagc tggtgcagtc tggggctgag gtgaagaagc ctggggcctc agtgaaggtt      60
tcctgcaagg catctggata caccttcaac agctactgga tgcactgggt gcgacaggcc     120
cctggacaag ggcttgagtg gatgggagaa atccacccta ataatggtag cacaaactac     180
aacgagaagt tcaagggcag agtcaccatg accagggaca cgtccacgag cacagtctac     240
atggagctga gcagcctgag atctgaggac acggccgtgt attactgtgc gagatggact     300
ttgtttactt actggggcca agggactctg gtcactgtct c                         341
```

<210> SEQ ID NO 386
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 386

```
gacatcgtga tgacccagac ccctctgtcc ctgcctgtga cccctggaga accgccagc       60 atctcctgca ggtcctccca gtccatcgtg cactccaacg gcaacaccta cctggagtgg     120
tacctgcaga agcccggaca gtccccccag ctgctgatct acaaggtgtc caataggttt     180
tccggagtgc ccgacaggtt ctccggatcc ggatccggca ccgacttcac cctgaagatc     240
tccagggtgg aggccgagga cgtgggagtg tactactgct tccagggcag ccacgtgccc     300
cctacattcg gaggcggcac caagctggag atcaagagg                            339
```

<210> SEQ ID NO 387
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 387

```
caggtcaccc tgaaggagtc cggccccgtg ctggtgaaac ccaccgagac cctcaccctg      60
acctgcaccg tctccggctt ctccctgtcc acctccggca tgggagtgtc ctggatcagg     120 cagcccccctg gaaaggctct ggagtggctg gcccacatct tctgggacga cgacaagtgg     180
tacaacccct ccctgaagtc caggctgacc atctccaagg acacctccaa gtcccaggtg     240
gtgctgacca tgaccaacat ggaccccgtg gacaccgcca cctactactg cgctaccttc     300
```

```
tacggcctgt acttcgccta ctggggccag ggaaccctgg tgaccgtgtc ctcc        354
```

<210> SEQ ID NO 388
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 388

```
gacatcgtga tgacccagtc ccccgattcc ctggctgtga gcctgggaga gagggccacc   60
atcaactgcg agtcctccca gtccctgctg tacaactcca accagaagaa ctacctggcc  120
tggtaccagc agaagcccgg acagcccccc aagctgctga tctactgggc ttccacaagg  180
gagtccggag tgcccgatcg gttcagcgga tccggatccg gcaccgactt caccctcacc  240
atcagctccc tgcaagccga ggacgtggcc gtgtactact gccagcagta cttcaactac  300
cctctgacct tcggccaggg caccaagctg gagatcaaga gg                     342
```

<210> SEQ ID NO 389
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 389

```
caggtgcagc tggtccagtc cggagctgag gtgaagaagc ccggcgcctc cgtgaaggtg   60
tcctgcaagg ccagcggctt caccttctcc gatgcctgga tggactgggt gaggcaggct  120
cctggccaaa ggctggagtg gatgggcgag atcaggtcca agcccaacaa ccacgccacc  180
tactacgccg agagcgtgaa gggcagggtg accatcacaa gggatacatc cgcctccacc  240
gcctacatgg agctgtcctc cctgaggtcc gaggacaccg ccgtgtacta ctgtgccagg  300 accggaaacct cctactgggg ccagggcaca ctggtgaccg tgtcctcc              348
```

<210> SEQ ID NO 390
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 390

```
gaaattgtgt tgacacagtc tccagccacc ctgtctttgt ctccagggga aagagccacc   60
ctctcctgca gggccagtca gagtgttgac tataatggaa ttagctacat gcactggtac  120
caacagaaac ctggccaggc tcccaggctc ctcatctatg ctgcatccaa cgtgcagagt  180
ggcatcccag ccaggttcag tggcagtggg tctgggacag acttcactct caccatcagc  240
agcctagagc ctgaagattt tgcagtttat tactgtcagc agagtattga ggatcctccg  300
acgttcggtg gaggcaccaa ggtggaaatc aaac                              334
```

<210> SEQ ID NO 391
<211> LENGTH: 341
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 391

| | | | | | |
|---|---|---|---|---|---|
| gaggtgcagc | tggtgcagtc | tggagcagag | gtgaaaaagc | ccggggagtc | tctgaagatc | 60 |
| tcctgtaagg | gttctggata | cagctttacc | agctcctgga | tcaactgggt | gcgccagatg | 120 |
| cccgggaaag | gcctggagtg | gatggggaga | atctatcctg | gtgagggtga | taccaactac | 180 |
| agcgggaact | tcgaaggcca | ggtcaccatc | tcagccgaca | agtccatcag | caccgcctac | 240 |
| ctgcagtgga | gcagcctgaa | ggcctcggac | accgccatgt | attactgtac | aagaggacta | 300 |
| gtcatggact | actggggcca | aggcacccct | gtcacagtct | c | | 341 |

<210> SEQ ID NO 392
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 392

| | | | | | |
|---|---|---|---|---|---|
| gaaattgtgt | tgacacagtc | tccagccacc | ctgtctttgt | ctccagggga | aagagccacc | 60 |
| ctctcctgca | gggccagtca | gagtgttgac | tatgatggaa | ttagctacat | gcactggtac | 120 |
| caacagaaac | ctggccaggc | tcccaggctc | ctcatctatg | ctgcatccaa | cgtgcagagt | 180 |
| ggcatcccag | ccaggttcag | tggcagtggg | tctgggacag | acttcactct | caccatcagc | 240 |
| agcctagagc | ctgaagattt | tgcagtttat | tactgtcagc | agagtattga | ggatcctccg | 300 |
| acgttcggtg | gaggcaccaa | ggtggaaatc | aaac | | | 334 |

<210> SEQ ID NO 393
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 393

| | | | | | |
|---|---|---|---|---|---|
| caggtgcagc | tggtgcagtc | tggggctgag | gtgaagaagc | ctggggcctc | agtgaaggtt | 60 |
| tcctgcaagg | catctggata | caccttcgac | agctactgga | tgcactgggt | gcgacaggcc | 120 |
| cctggacaag | gcttgagtg | gatgggagaa | atccacccta | ataatggtag | cacaaactac | 180 |
| aacgagaagt | tcaagggcag | agtcaccatg | accagggaca | cgtccacgag | cacagtctac | 240 |
| atggagctga | gcagcctgag | atctgaggac | acggccgtgt | attactgtgc | gagatggact | 300 |
| ttgtttactt | actggggcca | agggactctg | gtcactgtct | c | | 341 |

<210> SEQ ID NO 394
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 394

```
caggtgcagc tggtgcagtc tggggctgag gtgaagaagc ctggggcctc agtgaaggtt      60
tcctgcaagg catctggata caccttcacc agctactgga tgcactgggt gcgacaggcc     120
cctggacaag ggcttgagtg gatgggagaa atccacccta ataatggtag cacaaactac     180
aacgagaagt tcaagggcag agtcaccatg accaggaca cgtccacgag cacagtctac      240
atggagctga gcagcctgag atctgaggac acggccgtgt attactgtgc gagatggact     300
ttgtttactt actggggcca agggactctg gtcactgtct c                         341
```

<210> SEQ ID NO 395
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 395

```
caggtgcagc tggtgcagtc tggggctgag gtgaagaagc ctggggcctc agtgaaggtt      60
tcctgcaagg catctggata caccttcaac tactactgga tgcactgggt gcgacaggcc     120
cctggacaag ggcttgagtg gatgggagaa atccacccta ataatggtag cacaaactac     180
aacgagaagt tcaagggcag agtcaccatg accaggaca cgtccacgag cacagtctac      240
atggagctga gcagcctgag atctgaggac acggccgtgt attactgtgc gagatggact     300
ttgtttactt actggggcca agggactctg gtcactgtct c                         341
```

<210> SEQ ID NO 396
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 396

```
caggtgcagc tggtgcagtc tggggctgag gtgaagaagc ctggggcctc agtgaaggtt      60
tcctgcaagg catctggata caccttcaac agctactgga tgcactgggt gcgacaggcc     120
cctggacaag ggcttgagtg gatgggagaa atccacccta atgatggtag cacaaactac     180
aacgagaagt tcaagggcag agtcaccatg accaggaca cgtccacgag cacagtctac      240
atggagctga gcagcctgag atctgaggac acggccgtgt attactgtgc gagatggact     300
ttgtttactt actggggcca agggactctg gtcactgtct c                         341
```

<210> SEQ ID NO 397
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 397

```
caggtgcagc tggtgcagtc tggggctgag gtgaagaagc ctggggcctc agtgaaggtt      60
tcctgcaagg catctggata caccttcaac agctactgga tgcactgggt gcgacaggcc     120
cctggacaag ggcttgagtg gatgggagaa atccacccta atggtggtag cacaaactac     180
```

```
aacgagaagt tcaagggcag agtcaccatg accagggaca cgtccacgag cacagtctac    240
atggagctga gcagcctgag atctgaggac acggccgtgt attactgtgc gagatggact    300
ttgtttactt actggggcca agggactctg gtcactgtct c                        341
```

<210> SEQ ID NO 398
<211> LENGTH: 341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 398

```
caggtgcagc tggtgcagtc tggggctgag gtgaagaagc ctggggcctc agtgaaggtt    60
tcctgcaagg catctggata caccttcaac agctactgga tgcactgggt gcgacaggcc    120
cctggacaag gcttgagtg gatgggagaa atccacccta atagtggtag cacaaactac    180
aacgagaagt tcaagggcag agtcaccatg accagggaca cgtccacgag cacagtctac    240
atggagctga gcagcctgag atctgaggac acggccgtgt attactgtgc gagatggact    300
ttgtttactt actggggcca agggactctg gtcactgtct c                        341
```

<210> SEQ ID NO 399
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 399

```
gaggtgcagc tggtggaatc cggaggcggc ctggtgcaac ctggaggatc cctcaggctg    60
tcctgtgccg cttccggatt caccttctcc gatgcctgga tggactgggt gaggcaggcc    120
cctggcaaag gactggaatg ggtgggcgag atcaggtcca aacccaacaa ccacgccacc    180
tactacgccg agtccgtgaa gggcaggttc accatctcca gggacgactc caagaactcc    240
ctgtacctgc agatgaactc cctgaagacc gaggacaccg ccgtgtacta ctgcgctagg    300
accggcacct cctattgggg acagggcacc ctggtgaccg tgtcctcc                 348
```

<210> SEQ ID NO 400
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 9xHis tag"

<400> SEQUENCE: 400

```
His His His His His His His His His
1               5
```

<210> SEQ ID NO 401
<211> LENGTH: 7
<212> TYPE: PRT
<213> ORGANISM: Unknown
<220> FEATURE:
<221> NAME/KEY: source
<223> OTHER INFORMATION: /note="Description of Unknown: Antibody epitope peptide"
<220> FEATURE:

```
<221> NAME/KEY: MOD_RES
<222> LOCATION: (2)..(2)
<223> OTHER INFORMATION: Xaa is any amino acid
<220> FEATURE:
<221> NAME/KEY: MOD_RES
<222> LOCATION: (4)..(4)
<223> OTHER INFORMATION: Xaa is any amino acid

<400> SEQUENCE: 401

Gln Xaa Pro Xaa Ile Glu Glu
1               5

<210> SEQ ID NO 402
<211> LENGTH: 7
<212> TYPE: PRT
<213> ORGANISM: Unknown
<220> FEATURE:
<221> NAME/KEY: source
<223> OTHER INFORMATION: /note="Description of Unknown: Antibody
      epitope peptide"

<400> SEQUENCE: 402

Leu Pro Phe Gln Pro Asp Pro
1               5

<210> SEQ ID NO 403
<211> LENGTH: 4
<212> TYPE: PRT
<213> ORGANISM: Unknown
<220> FEATURE:
<221> NAME/KEY: source
<223> OTHER INFORMATION: /note="Description of Unknown: SEZ6 C-terminal
      cytoplasmic domain motif peptide"

<400> SEQUENCE: 403

Asn Pro Thr Tyr
1
```

ANTI SEZ6 ANTIBODIES AND METHODS OF USE

CROSS REFERENCED APPLICATIONS

This application claims priority from U. S. Provisional Patent Application Ser. No. 61/603,203 filed on Feb. 24, 2012 which is incorporated herein by reference in its entirety.

SEQUENCE LISTING

The instant application contains a sequence listing which has been submitted in ASCII format via EFS-Web and is hereby incorporated by reference in its entirety. Said ASCII copy, created on Feb. 19, 2013, is named 11200.0014-00304 and is 450,013 bytes in size.

FIELD OF THE INVENTION

This application generally relates to novel compounds, compositions and methods of their use in diagnosing, preventing, treating or ameliorating proliferative disorders and an expansion, recurrence, relapse or metastasis thereof. In a broad aspect, the present invention relates to the use of seizure related 6 homolog (SEZ6), modulators, including anti-SEZ6 antibodies and fusion constructs, for the treatment, diagnosis or prophylaxis of neoplastic disorders. Selected embodiments of the present invention provide for the use of such SEZ6 modulators, including antibody drug conjugates, for the immunotherapeutic treatment of malignancies preferably comprising a reduction in tumor initiating cell frequency.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. In the normal course of events cellular differentiation and proliferation is controlled by numerous factors and signals that are generally balanced to maintain cell fate decisions and tissue architecture. Thus, to a large extent it is this controlled microenvironment that regulates cell division and tissue maturation where signals are properly generated based on the needs of the organism. In this regard cell proliferation and differentiation normally occur only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including proliferative disorders such as cancer.

Conventional treatments for cancer include chemotherapy, radiotherapy, surgery, immunotherapy (e.g., biological response modifiers, vaccines or targeted therapeutics) or combinations thereof. Unfortunately, certain cancers are non-responsive or minimally responsive to such treatments. For example, in some patients tumors exhibit gene mutations that render them non-responsive despite the general effectiveness of selected therapies. Moreover, depending on the type of cancer and what form it takes some available treatments, such as surgery, may not be viable alternatives. Limitations inherent in current standard of care therapeutics are particularly evident when attempting to treat patients who have undergone previous treatments and have subsequently relapsed. In such cases the failed therapeutic regimens and resulting patient deterioration may contribute to refractory tumors which often manifest themselves as a relatively aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies for proliferative disorders.

SUMMARY OF THE INVENTION

These and other objectives are provided for by the present invention which, in a broad sense, is directed to methods, compounds, compositions and articles of manufacture that may be used in the treatment of SEZ6 associated disorders (e.g., proliferative disorders or neoplastic disorders). To that end, the present invention provides novel seizure related 6 homolog (or SEZ6) modulators that effectively target tumor cells and/or cancer stem cells and may be used to treat patients suffering from a wide variety of malignancies. As will be discussed in more detail herein, there are at least two naturally occurring SEZ6 isoforms or variants and the disclosed modulators may comprise or associate selectively with one isoform or the other or with both. Moreover, in certain embodiments the disclosed SEZ6 modulators may further react with one or more SEZ family members (e.g., SEZ6L or SEZ6L2) or, in other embodiments, may be generated and selected for so as to exclusively associate or react with SEZ6 isoform(s). In any event the modulators may comprise any compound that recognizes, competes, agonizes, antagonizes, interacts, binds or associates with a SEZ6 polypeptide or gene (or fragment thereof) and modulates, adjusts, alters, changes or modifies the impact of the SEZ6 protein on one or more physiological pathways. Thus, in a broad sense the present invention is generally directed to isolated SEZ6 modulators and use thereof. In preferred embodiments the invention is more particularly directed to isolated SEZ6 modulators comprising antibodies (i.e., antibodies that immunopreferentially bind, react with or associate with at least one isoform of SEZ6) that, in particularly preferred embodiments, are associated or conjugated to one or more cytotoxic agents. Moreover, as discussed extensively below, such modulators may be used to provide pharmaceutical compositions useful for the prophylaxis, diagnosis or treatment of proliferative disorders.

In selected embodiments of the invention, SEZ6 modulators may comprise a SEZ6 polypeptide or fragments thereof, either in an isolated form or fused or associated with other moieties (e.g., Fc-SEZ6, PEG-SEZ6 or SEZ6 associated with a targeting moiety). In other selected embodiments SEZ6 modulators may comprise SEZ antagonists which, for the purposes of the instant application, shall be held to mean any construct or compound that recognizes, competes, interacts, binds or associates with SEZ6 and neutralizes, eliminates, reduces, sensitizes, reprograms, inhibits or controls the growth of neoplastic cells including tumor initiating cells. In preferred embodiments the SEZ6 modulators of the instant invention comprise anti-SEZ6 antibodies, or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells. In particularly preferred embodiments the antibodies or immunoreactive fragments may be associated with or conjugated to one or more anti-cancer agents (e.g., a cytotoxic agent).

With regard to such modulators it will be appreciated that compatible antibodies may take on any one of a number of forms including, for example, polyclonal and monoclonal antibodies, chimeric, CDR grafted, humanized and human antibodies and immunoreactive fragments and/or variants of each of the foregoing. Preferred embodiments will comprise antibodies that are relatively non-immunogenic such as humanized or fully human constructs. Of course, in view of the instant disclosure those skilled in the art could readily identify one or more complementarity determining regions (CDRs) associated with heavy and light chain variable regions of SEZ6 antibody modulators and use those CDRs to engineer or fabricate chimeric, humanized or CDR grafted antibodies without undue experimentation. Accordingly, in certain preferred embodiments the SEZ6 modulator comprises an antibody that incorporates one or more CDRs as defined in FIGS. 10A and 10B and derived from the light (FIG. 10A) or heavy (FIG. 10B) contiguous chain murine variable regions (SEQ ID NOS: 20-169) set forth therein. Such CDR grafted variable regions having a human framework and variants thereof are also shown in FIG. 10 comprising SEQ ID NOS: 170-199. In preferred embodiments such antibodies will comprise monoclonal antibodies and, in even more preferred embodiments, will comprise chimeric, CDR, grafted or humanized antibodies.

Exemplary nucleic acid sequences encoding each of the amino acid sequences set forth in FIGS. 10A and 10B are appended hereto in the sequence listing and comprise SEQ ID NOS: 220 to 399. In this respect it will be appreciated that the invention further comprises nucleic acid molecules (and associated constructs, vectors and host cells) encoding disclosed antibody variable region amino acid sequences including those set forth in the attached sequence listing.

More particularly, in selected embodiments compatible SEZ6 modulators may comprise an antibody having a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166 and SEQ ID NO: 168 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167 and SEQ ID NO: 169. In other preferred embodiments the selected modulators will comprise heavy and light chain variable regions that comprise 65, 70, 75 or 80% identity to the aforementioned murine sequences. In still other embodiments the modulators will comprise heavy and light chain variable regions that comprise 85, 90 or even 95% identity to the disclosed murine sequences.

Of course, in view of the instant disclosure those skilled in the art could readily identify CDRs associated with each of the aforementioned heavy and light chain variable regions and use those CDRs to engineer or fabricate chimeric, humanized or CDR grafted antibodies without undue experimentation. As such, in selected embodiments the present invention is directed to anti-SEZ6 antibodies comprising one or more CDRs from a variable region sequence set forth in FIG. 10A or FIG. 10B. In preferred embodiments such antibodies will comprise monoclonal antibodies and, in even more preferred embodiments will comprise chimeric, CDR grafted or humanized antibodies. As discussed in more detail below still other embodiments will comprise such antibodies conjugated or associated with one or more cytotoxic agents.

Another aspect of the invention comprises modulators obtained or derived from SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200.

In yet other compatible embodiments the instant invention will comprise the CDR grafted or humanized SEZ6 modulators hSC17.16, hSC17.17, hSC17.24, hSC17.28, SC17.34, hSC17.46, SC17.151, SC17.155, SC17.156, SC17.161 and SC17.200. Still other embodiments are directed to a SEZ6 modulator comprising a humanized antibody wherein said humanized antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184, SEQ ID NO: 186, SEQ ID NO: 188 and SEQ ID NO: 190 and wherein said heavy chain variable region comprises an amino acid sequence having at least 60% identity to an amino acid sequence selected from the group consisting of amino acid sequences as set forth in SEQ ID NO: 171, SEQ ID NO: 173, SEQ ID NO: 175, SEQ ID NO: 177, SEQ ID NO: 179 and SEQ ID NO: 181, SEQ ID NO: 183, SEQ ID NO: 185, SEQ ID NO: 187, SEQ ID NO: 189 and SEQ ID NO: 191. Additionally, certain humanized variants of light (SEQ ID NO: 192) and heavy (SEQ ID NO: 193, SEQ ID NO: 194, SEQ ID NO: 195, SEQ ID NO: 196, SEQ ID NO: 197, SEQ ID NO: 198 and SEQ ID NO: 199) chain variable regions are provided in accordance with the teachings herein. Moreover, as described immediately above nucleic acid sequences encoding the exemplified humanized heavy and light chain variable regions are set forth in the sequence listing appended hereto as SEQ ID NOS: 370-399.

Besides the aforementioned aspects, other preferred embodiments of the instant invention will comprise SEZ6 modulators associated or conjugated to one or more drugs to provide modulator conjugates that may be particularly effective in treating proliferative disorders (alone or in combination with other pharmaceutically active agents). More generally, once the modulators of the invention have been fabricated and selected they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. Such conjugates may be represented by the formula N-[L-D]n where M stands for a disclosed modulator or target binding moiety, L is an optional linker or linker unit, D is a compatible drug or prodrug and n is an integer from about 1 to about 20. It will be appreciated that, unless otherwise dictated by context, the terms "antibody-drug conjugate" or "ADC" or the formula M-[L-D]n shall be held to encompass conjugates comprising both therapeutic and diagnostic moieties. In such embodiments antibody-drug conjugate compounds will typically comprise anti-SEZ6 as the modulator unit (M), a therapeutic or diagnostic moiety (D), and optionally a linker (L) that joins the drug and the antigen binding agent. In a preferred embodiment, the antibody is a SEZ6 mAb comprising at least one CDR from the heavy and light chain variable regions as described above.

As previously indicated one aspect of the invention may comprise the unexpected association of SEZ6 polypeptides with cancer stem cells. Thus, in certain other embodiments the invention will comprise a SEZ6 modulator that reduces the frequency of tumor initiating cells upon administration to a subject. Preferably the reduction in frequency will be determined using in vitro or in vivo limiting dilution analysis. In particularly preferred embodiments such analysis may be conducted using in vivo limiting dilution analysis comprising transplant of live human tumor cells into immunocompromised mice. Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodology such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, in another preferred embodiment of the instant invention comprises a method of treating a SEZ6 associated disorder comprising administering a therapeutically effective amount of a SEZ6 modulator to a subject in need thereof whereby the frequency of tumor initiating cells is reduced. Preferably the SEZ6 associated disorder comprises a neoplastic disorder. Again, the reduction in the tumor initiating cell frequency will preferably be determined using in vitro or in vivo limiting dilution analysis.

In this regard it will be appreciated that the present invention is based, at least in part, upon the discovery that SEZ6 immunogens are associated with tumor perpetuating cells (i.e., cancer stem cells) that are involved in the etiology of various neoplasia. More specifically, the instant application unexpectedly demonstrates that the administration of various exemplary SEZ6 modulators can mediate, reduce, deplete, inhibit or eliminate tumorigenic signaling by tumor initiating cells (i.e., reduce the frequency of tumor initiating cells). This reduced signaling, whether by depletion, neutralization, reduction, elimination, reprogramming or silencing of the tumor initiating cells or by modifying tumor cell morphology (e.g., induced differentiation, niche disruption), in turn allows for the more effective treatment of SEZ6 associated disorders by inhibiting tumorigenesis, tumor maintenance, expansion and/or metastasis and recurrence.

Besides the aforementioned association with cancer stem cells, there is evidence that SEZ6 isoforms may be implicated in the growth, recurrence or metastatic potential of tumors comprising neuroendocrine features. For the purposes of the instant invention such tumors will comprise neuroendocrine tumors and pseudo neuroendocrine tumors. Intervention in the proliferation of such tumorigenic cells using the novel SEZ6 modulators described herein, may thereby ameliorate or treat a disorder by more than one mechanism (i.e., tumor initiating cell reduction and disruption of oncogenic pathway signaling) to provide additive or synergistic effects. Still other preferred embodiments may take advantage of the cellular internalization of cell surface SEZ6 to deliver a modulator mediated anti-cancer agent. In this regard it will be appreciated that the present invention is not limited by any particular mechanism of action but rather encompasses the broad use of the disclosed modulators to treat SEZ6 associated disorders (including various neoplasia).

Thus, in other embodiments the present invention will comprise the use of the disclosed modulators to treat tumors comprising neuroendocrine features in a subject in need thereof. Of course the same modulators may be used for the prophylaxis, prognosis, diagnosis, theragnosis, inhibition or maintenance therapy of these same tumors.

Other facets of the instant invention exploit the ability of the disclosed modulators to potentially disrupt oncogenic pathways while simultaneously silencing tumor initiating cells. Such multi-active SEZ6 modulators (e.g., SEZ6 antagonists) may prove to be particularly effective when used in combination with standard of care anti-cancer agents or debulking agents. Accordingly preferred embodiments of the instant invention comprise using the disclosed modulators as anti-metastatic agents for maintenance therapy following initial treatments. In addition, two or more SEZ6 antagonists (e.g. antibodies that specifically bind to two discrete epitopes on SEZ6) may be used in combination in accordance with the present teachings. Moreover, as discussed in some detail below, the SEZ6 modulators of the present invention may be used in a conjugated or unconjugated state and, optionally, as a sensitizing agent in combination with a variety of chemical or biological anti-cancer agents.

Accordingly another preferred embodiment of the instant invention comprises a method of sensitizing a tumor in a subject for treatment with an anti-cancer agent comprising the step of administering a SEZ6 modulator to said subject. Other embodiments comprise a method of reducing metastasis or tumor recurrence following treatment comprising administering a SEZ6 modulator to a subject in need thereof. In a particularly preferred aspect of the invention the SEZ6 modulator will specifically result in a reduction of tumor initiating cell frequency as determined using in vitro or in vivo limiting dilution analysis.

More generally preferred embodiments of the invention comprise a method of treating a SEZ6 associated disorder in a subject in need thereof comprising the step of administering a SEZ6 modulator to the subject. In particularly preferred embodiments the SEZ6 modulator will be associated (e.g., conjugated) with an anti-cancer agent. In yet other embodiments the SEZ6 modulator will internalize following association or binding with SEZ6 on or near the surface of the cell. Moreover the beneficial aspects of the instant invention, including any disruption of signaling pathways and collateral benefits, may be achieved whether the subject tumor tissue exhibits elevated levels of SEZ6 or reduced or depressed levels of SEZ6 as compared with normal adjacent tissue. Particularly preferred embodiments will comprise the treatment of disorders exhibiting elevated levels of SEZ6 on tumorigenic cells as compared to normal tissue or non-tumorigenic cells.

In yet another aspect the present invention will comprise a method of treating a subject suffering from a neoplastic disorder comprising the step of administering a therapeutically effective amount of at least one internalizing SEZ6 modulator. Preferred embodiments will comprise the administration of internalizing antibody modulators wherein, in other selected embodiments, the internalizing antibody modulators are conjugated or associated with a cytotoxic agent.

Other embodiments are directed to a method of treating a subject suffering from a SEZ6 associated disorder comprising the step of administering a therapeutically effective amount of at least one depleting SEZ6 modulator.

In yet another embodiment the present invention provides methods of maintenance therapy wherein the disclosed effectors or modulators are administered over a period of time following an initial procedure (e.g., chemotherapeutic, radiation or surgery) designed to remove at least a portion of the tumor mass. Such therapeutic regimens may be administered over a period of weeks, a period of months or even a period of years wherein the SEZ6 modulators may act prophylactically to inhibit metastasis and/or tumor recurrence. In yet other embodiments the disclosed modulators may be administered in concert with known debulking regimens to prevent or retard metastasis, tumor maintenance or recurrence.

It will further be appreciated that the SEZ6 modulators of the instant invention may be generated and selected to react with known isoform(s) of SEZ6 or a single isoform of the protein or, conversely, may comprise a pan-SEZ6 modulator that reacts or associates with at least one additional SEZ6 family member (e.g., SEZ6L or SEZ6L2 and isoforms thereof) in addition to SEZ6. More specifically, as disclosed herein preferred modulators such as antibodies may be generated and selected so that they react with domains (or epitopes therein) that are exhibited by SEZ6 only or with domains that are at least somewhat conserved across two or more of the SEZ6 family members.

In yet other preferred embodiments the modulators will associate or bind to a specific epitope, portion, motif or domain of SEZ6. As will be discussed in some detail below both SEZ6 isoforms incorporate an identical extracellular region (see FIG. 1E) comprising at least an N-terminal domain, two alternating Sushi and CUB domains, and three additional tandem Sushi domain repeats. In addition the SEZ6 protein comprises a transmembrane domain and a cytoplasmic domain. Accordingly, in certain embodiments the modulators will bind or associate with the N-terminal domain of SEZ6 (i.e. amino acids 1-335 in the mature protein) or to an epitope therein. Other aspects of the instant invention comprise modulators that associate or bind to a specific epitope located in a particular Sushi domain of SEZ6. In this regard the particular modulator may associate or bind to an epitope located in Sushi Domain 1 (amino acids 336-395), Sushi Domain 2 (amino acids 511-572), Sushi Domain 3 (amino acids 690-748), Sushi Domain 4 (amino acids 750-813) or Sushi Domain 5 (amino acids 817-878). Other aspects of the instant invention comprise modulators that associate or bind to a specific epitope located in a particular CUB-like domain of SEZ6. In this regard the particular modulator may associate or bind to an epitope located in CUB Domain 1 (amino acids 397-508) or CUB Domain 2 (amino acids 574-685). Of course it will be appreciated that each of the aforementioned domains may comprise more than one epitope and may be associated with more than one bin.

With regard to modulator or antibody "bins" it will be appreciated that the SEZ6 antigen may be analyzed or mapped through competitive antibody binding using art recognized techniques to define specific bins located along the protein. While discussed in more detail herein and shown in Examples 9 and 10 below, two antibodies (one of which may be termed a "reference antibody," "bin delineating antibody" or "delineating antibody") may be considered to be in the same bin if they substantially compete with each other for binding to the target antigen. In such cases the subject antibody epitopes may be identical, substantially identical or close enough (either in a linear sense where they are separated by a few amino acids or conformationally) so that both antibodies are sterically or electrostatically inhibited or precluded from binding to the antigen. Such defined bins may be generally associated with certain SEZ6 domains (e.g. the reference antibody will bind with an epitope contained in a specific domain) though the correlation is not always precise (e.g., there may be more than one bin in a domain or the bin may be defined conformationally and comprise more than one domain). It will be appreciated that those skilled in the art can readily determine the relationship between the SEZ6 domains and empirically determined bins.

With regard to the present invention competitive binding analysis using art-recognized techniques (e.g., ELISA, surface plasmon resonance or bio-layer interferometry) defined at least seven distinct bins, each of which was found to contain a number of antibody modulators. For the purposes of the instant disclosure the seven bins were termed bins A-F and bin U. Bins A-F are unique bins and the antibodies contained in each of these bins compete with each other for binding to the SEZ6 protein. Bin U contains antibodies that do not compete with antibodies in Bins A-F, but may compete for binding with each other. Thus, in selected embodiments the present invention will comprise a modulator residing in a bin selected from the group consisting of bin A, bin B, bin C, bin D, bin E, bin F, and bin. U. In other embodiments the present invention comprises a modulator residing in a bin defined by a reference antibody selected from the group consisting of SC17.1, SC17.2, SC17.3, SC17.4, SC17.8, SC17.9, SC17.10, SC17.11, SC17.14, SC17.15, SC17.16, SC17.17. SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76SC17.77, SC17.79, SC17.81, SC17.82, SC17.84, SC17.85, SC17.87, SC17.89, SC17.90SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200. In still other embodiments the invention will comprise modulators from bin A, modulators from bin B, modulators from bin C, modulators from bin D, modulators from bin E, modulators from bin F or modulators from bin U. Yet other preferred embodiments will comprise a reference antibody modulator and any antibody that competes with the reference antibody.

The term "compete" or "competing antibody" when used in the context of the disclosed modulators means binding competition between antibodies as determined by an assay in which a reference antibody or immunologically functional fragment substantially prevents or inhibits (e.g., greater than 40%, 45%, 50%, 55%, 60%, 65%, 70%, 75%, 80%, 85% or 90%.) specific binding of a test antibody to a common antigen. Compatible methods for determining such competition comprise art known techniques such as, for example, bio-layer interferometry, surface plasmon resonance, flow cytometry, competitive ELISA, etc.

In a selected embodiment the invention comprises a pan-SEZ6 modulator that associates with SEZ6 and at least one other SEZ6 family member (e.g., SEZ6L, or SEZ6L2). In other selected embodiments the invention comprises a SEZ6 modulator that immunospecifically associates with one or more isoform of SEZ6 but does not immunospecifically associate with any other SEZ6 family member. In yet other embodiments the present invention comprises a method of treating a subject in need thereof comprising administering a therapeutically effective amount of a pan-SEZ6 modulator. Still other embodiments comprise a method of treating a subject in need thereof comprising administering a therapeutically effective amount of a SEZ6 modulator that immunospecifically associates with one or more isoforms of SEZ6 but does not immunospecifically associate with any other SEZ6 family member.

Beyond the therapeutic uses discussed above it will also be appreciated that the modulators of the instant invention may be used to detect, diagnose or classify SEZ6 related disorders and, in particular, proliferative disorders. In some embodiments the modulator may be administered to the subject and detected or monitored in vivo. Those of skill in the art will appreciate that such modulators may be labeled or associated with markers or reporters as disclosed below and detected using any one of a number of standard techniques (e.g., MRI, CAT scan PET scan, etc.).

Thus, in some embodiments the invention will comprise a method of diagnosing, detecting or monitoring a SEZ6 associated disorder in vivo in a subject in need thereof comprising the step of administering a SEZ6 modulator.

In other instances the modulators may be used in an in vitro diagnostic setting using art-recognized procedures. As such, a preferred embodiment comprises a method of diagnosing a proliferative disorder in a subject in need thereof comprising the steps of:
  a. obtaining a tissue sample from said subject;
  b. contacting the tissue sample with at least one SEZ6 modulator; and
  c. detecting or quantifying the SEZ6 modulator associated with the sample.

Such methods may be easily discerned in conjunction with the instant application and may be readily performed using generally available commercial technology such as automatic plate readers, dedicated reporter systems, etc. In selected embodiments the SEZ6 modulator will be associated with tumor perpetuating cells present in the sample. In other preferred embodiments the detecting or quantifying step will comprise a reduction of tumor initiating cell frequency and detection thereof. Moreover, limiting dilution analysis may be conducted as previously alluded to above and will preferably employ the use of Poisson distribution statistics to provide an accurate accounting as to the reduction of frequency.

In a similar vein the present invention also provides kits or devices and associated methods that are useful in the diagnosis and monitoring of SEZ6 associated disorders such as cancer. To this end the present invention preferably provides an article of manufacture useful for diagnosing or treating SEZ6 associated disorders comprising a receptacle comprising a SEZ6 modulator and instructional materials for using said SEZ6 modulator to treat or diagnose the SEZ6 associated disorder. In selected embodiments the devices and associated methods will comprise the step of contacting at least one circulating tumor cell.

Other preferred embodiments of the invention also exploit the properties of the disclosed modulators as an instrument useful for identifying, characterizing, isolating, sectioning or enriching populations or subpopulations of tumor initiating cells through methods such as flow cytometric analysis including fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with a SEZ6 modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 1A-1E are various representations of SEZ6 including nucleic acid or amino acid sequences pertaining to the SEZ6 modulators described herein. FIGS. 1A and 1B (SEQ ID NOS: 1 and 2) depict the full length mRNA sequence containing the open reading frames (ORFS) (underlined) encoding the SEZ6 variants 1 and 2, respectively. FIGS. 1C and 1D (SEQ ID. NOS: 3 and 4) provide the corresponding amino acid sequences of the ORFs denoted in FIGS. 1A and 1B, respectively, with the single underlined amino acid residues indicating the predicted transmembrane spanning domain for each protein isoform and the double underlined amino acid residues indicating the signal peptide; FIG. 1E depicts the alignment of the two protein isoforms (SEQ NOS: 3 and 4) to illustrate the sequence differences in the cytoplasmic termini of each isoform, with the underlined residues indicating the differences between the two sequences.

FIGS. 2A-2C provide a tabular representation of the percent identity at the protein level between the closest human isoform of SEZ6 and rhesus, cynomolgus, mouse or rat SEZ6 proteins (FIG. 2A); a tabular listing of various cDNA or protein sequence accessions for each of the reported isoforms of the SEZ6 family of genes (FIG. 2B); and the percent identity at the protein level between the longest isoforms of human SEZ6, SEZ6L, and SEZ6L2 proteins (FIG. 2C).

FIGS. 3A-3C provide various representations of nucleic acid or amino acid sequences related to the production of the immunogens or cell lines used to generate or characterize the SEZ6 modulators described herein. For human SEZ6 a specific cDNA clone (FIG. 3A; SEQ ID NO: 5) encoding the complete mature human SEZ6 protein (FIG. 3B; SEQ ID NO: 6) was constructed from a commercial cDNA clone (BC146292; SEQ ID NO: 7) with known differences (FIG. 3C) from a database reference sequence, NP_849191 (SEQ ID NO: 3), for the SEZ6 protein.

FIGS. 4A and 4B provide a cDNA (FIG. 4A; SEQ ID NO: 8) used to express an Fe-SEZ6 construct in CHO-S cells and yield a protein immunogen (FIG. 4B; SEQ ID NO: 9), comprising the ECD of human SEZ6 fused to a human IgG-2 Fc domain, in which the underlined sequences correspond to the human IgG2 Fc domain, the double underlined sequences correspond to the IgK signal peptide, and the amino acids in bold font correspond to residues contributed by the restriction sites used to clone the hSCRx17 fragment.

FIGS. 5A-5J provide various representations of nucleic acid or amino acid sequences related to the production of the immunogens or cell lines used to generate or characterize the SEZ6 modulators described herein, wherein the underlined sequences denote the ECD of protein for the specific SEZ6 or SEZ6 family member being illustrated, and the figures comprise the cDNA sequences for the constructs encoding mature murine SEZ6 (FIG. 5A, SEQ ID NO: 10), mature rat SEZ6 (FIG. 5C, SEQ ID NO: 12), mature cynomolgus SEZ6 (FIG. 5E, SEQ ID NO: 14), mature ECD of the human SEZ6L protein (FIG. 5G, SEQ ID NO: 16), or the mature ECD of the human SEZ6L2 protein (FIG. 5I, SEQ ID NO: 18), or the corresponding proteins encoded by these cDNA constructs, namely mature murine SEZ6 (FIG. 5B, SEQ ID NO: 11), mature rat SEZ6 (FIG. 5D, SEQ ID NO: 13), mature cynomolgus SEZ6 (FIG. 5F, SEQ ID NO: 15), the mature ECD of the human SEZ6L protein (FIG. 5H, SEQ ID NO: 17), or the mature ECD of the human SEZ6L2 protein (FIG. 5J, SEQ ID NO: 19).

FIGS. 6A and 6B are depictions of mRNA expression levels of various genes as measured using whole transcriptome (SOLID) sequencing of mRNA derived from tumor cell subpopulations or normal tissues. FIG. 6A is a tabular representation of genes associated with tumors having neuroendocrine features; and FIG. 6B is a graphical representation of SEZ6 mRNA expression in normal tissues and several non-traditional xenograft (NTX) tumors derived from lung cancers.

FIG. 7A-7F depict mRNA expression levels analyzed using microarray. FIG. 7A is a graphical representation of unsupervised clustering of microarray profiles for 46 tumor lines and two normal tissues; FIGS. 7B and 7C are tabular representations of normalized intensity values corresponding to relative expression levels of selected genes related to neuroendocrine phenotypes (FIG. 7B) or the Notch signaling pathway (FIG. 7C) wherein relatively low numbers indicate little to no expression and relatively high numbers indicate higher expression levels; FIG. 7D is a graphical representation showing relative expression levels of HES6 mRNA in various tumors and control tissues as measured using qRT-PCR; FIG. 7E is a tabular representation of normalized intensity values corresponding to relative expression levels of selected genes indicative of neurogenesis, neural commitment, or differentiation towards neural fates; and FIG. 7F is a graphical representation of normalized intensity values corresponding to relative expression of SEZ6 in various NTX tumor lines.

FIGS. 10A and 10B provide, in a tabular form, the continuous amino acid sequences of heavy and light chain variable regions of a number of murine and humanized exemplary SEZ6 modulators isolated, cloned and engineered as described in the Examples herein.

FIG. 11 sets forth various characteristics of exemplary modulators of the invention. FIG. 11A shows the biochemical and immunological properties of exemplary SEZ6 modulators as represented in a tabular format.

FIG. 12A shows SEZ6 expression in HEK-293T cells engineered to over-express human SEZ6 protein (h293T-HuSEZ6) using the anti-SEZ6 antibody SC17.33; FIG. 12B shows the relative protein expression of human SEZ6 in various NTX tumor and normal tissue lysates as measured using an electrochemiluminescent assay.

FIGS. 13A and 13B show detection by flow cytometry of SEZ6 protein expression on NTX tumor cells using various anti-SEZ6 antibodies (FIG. 13A); whereas FIG. 13B shows enhanced expression of SEZ6 protein in CSCs compared to NTG subpopulations using various anti-SEZ6 antibodies (FIG. 13B).

FIGS. 14A and 14B show that CSCs expressing SEZ6 exhibit enhanced tumorigenicity compared to CSCs that do not express SEZ6. FIG. 14A is a contour plot showing cell sorting by FACS of the cells in a lung tumor (LU37) on the basis of expression of CD324 (a marker of CSCs) and SEZ6; FIG. 14B is a graphical representation of the growth of tumor cells that are either CD324$^+$SEZ6$^+$ (black circles) or CD324$^+$SEZ6$^-$ (white circles) after implantation into immunocompromised mice. Tumor cells expressing both CD324 and SEZ6 exhibit enhanced tumorigenicity.

FIGS. 15A and 15B provide, respectively, a tabular and graphical representation illustrating that the disclosed modulators may effectively be used as targeting moieties to direct cytotoxic payloads to cells engineered to express SEZ6 (FIG. 15A) and NTX lung tumors (LU80, LU37 and LU100) grown in vitro (FIG. 15B) where the decrease in normalized relative luminescence units (RLU) is indicative of cell killing through internalization of the saporin toxin.

FIG. 16 is a tabular representation of immunohistochemistry results showing expression of SEZ6 on various NTX tumors.

FIG. 17A shows the results of an in vitro killing assay using anti-SEZ6 ADCs on SEZ6-overexpressing HEK293 cells; whereas FIG. 17B shows the effect of anti-SEZ6 ADCs on in vivo growth of SCLC (LU86) and LCNEC (LU50) tumors.

DETAILED DESCRIPTION OF THE INVENTION

I. Introduction

Figure 1F:
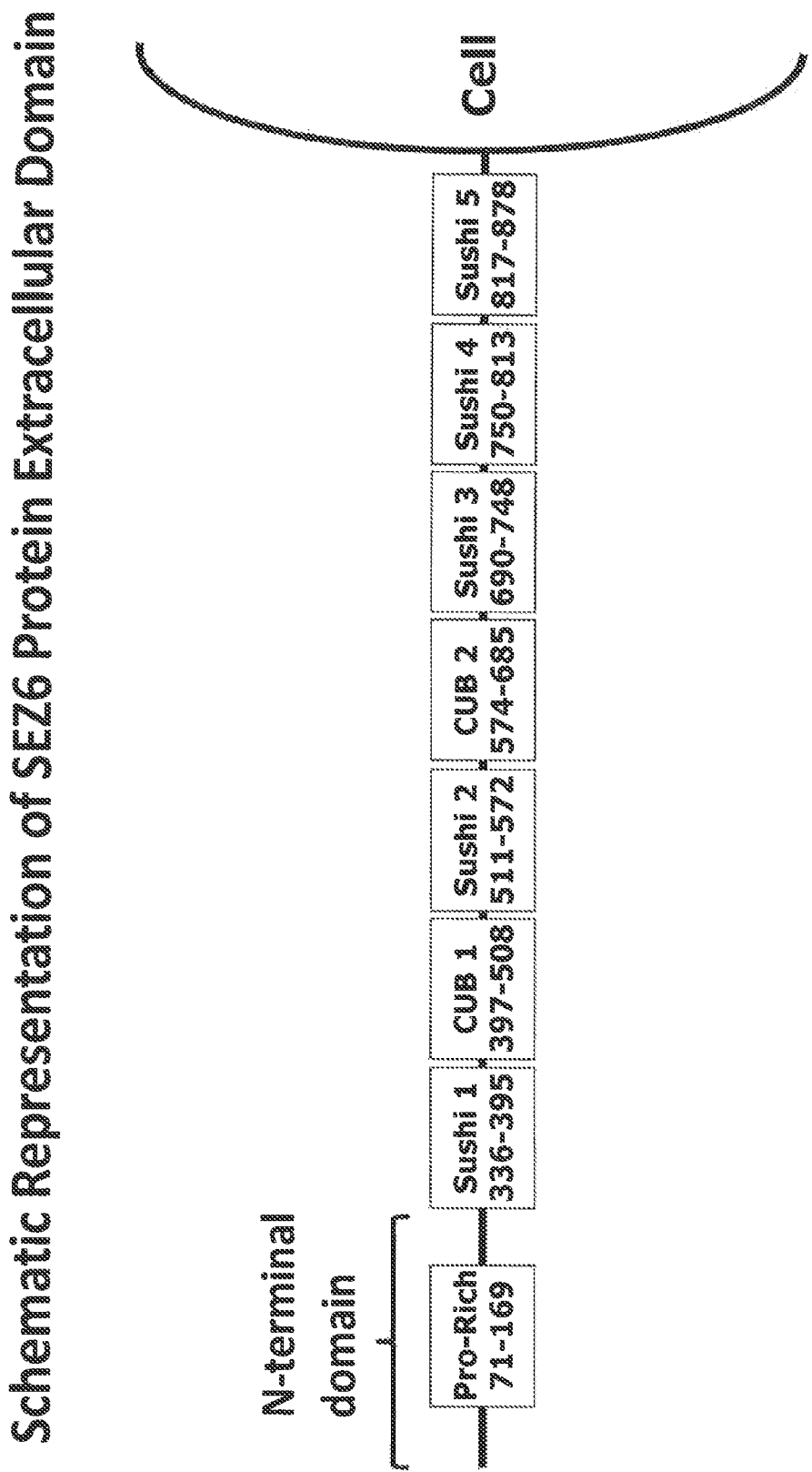
FIG. 1F provides a schematic representation of the extracellular region of the SEZ6 protein illustrating the positions of the various domains.

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described. Finally, for the purposes of the instant disclosure all identifying sequence Accession numbers may be found in the NCBI Reference Sequence (RefSeq) database and/or the NCBI GenBank® archival sequence database unless otherwise noted.

As previously alluded to, it has surprisingly been found that the expression of SEZ6 is associated with neoplastic growth and proliferative disorders, particularly in the instance of tumors with neuroendocrine features, and that SEZ6 and variants or isoforms thereof provide useful tumor markers which may be exploited in the treatment of related diseases. Moreover, as shown in the instant application it has unexpectedly been found that SEZ6 markers or determinants such as cell surface SEZ6 protein are associated with cancer stem cells (also known as tumor perpetuating cells) and may be effectively exploited to eliminate or silence the same. The ability to selectively reduce or eliminate cancer stem cells (e.g., through the use of conjugated SEZ6 modulators) is particularly surprising in that such cells are known to generally be resistant to many conventional treatments. That is, the effectiveness of traditional, as well as more recent targeted treatment methods, is often limited by the existence and/or emergence of resistant cancer stem cells that are capable of perpetuating the cancer even in the face of these diverse treatment methods. Further, determinants associated with cancer stem cells often make poor therapeutic targets due to low or inconsistent expression, failure to remain associated with the tumorigenic cell or failure to present at the cell surface. In sharp contrast to the teachings of the prior art, the instantly disclosed compounds and methods effectively overcome this inherent resistance to specifically eliminate, deplete, silence or promote the differentiation of such cancer stem cells thereby negating their ability to sustain or re-induce the underlying tumor growth.

More specifically, it has been discovered that SEZ6 modulators such as those disclosed herein may advantageously be used in the prognosis, diagnosis, theragnosis, treatment or prevention of proliferative disorders (e.g. neoplastic disorders) in subjects in need thereof. Accordingly, while preferred embodiments of the invention will be discussed extensively below, particularly in terms of particular domains, regions or epitopes or in the context of cancer stem cells or tumors comprising neuroendocrine features and their interactions with the disclosed modulators, those skilled in the art will appreciate that the scope of the instant invention is not limited by such exemplary embodiments. Rather, the most expansive embodiments of the present invention and the appended claims are broadly and expressly directed to SEZ6 modulators (including conjugated modulators) and their use in the prognosis, diagnosis, theragnosis, treatment or prevention of a variety of SEZ6 associated or mediated disorders, including neoplastic or proliferative disorders, regardless of any particular mechanism of action or specifically targeted tumor, cellular or molecular component.

To that end, and as demonstrated in the instant application, it has unexpectedly been found that the disclosed SEZ6 modulators can effectively be used to target and eliminate or otherwise incapacitate proliferative or tumorigenic cells and treat SEZ6 associated disorders (e.g., neoplasia). As used herein a. "SEZ6 associated disorder" shall be held to mean any disorder or disease (including proliferative disorders) that is marked, diagnosed, detected or identified by a phenotypic or genotypic aberration of SEZ6 genetic components or expression during the course or etiology of the disease or disorder. In this regard a SEZ6 phenotypic aberration or determinant may, for example, comprise elevated or depressed levels of SEZ6 protein expression, abnormal SEZ6 protein expression on certain definable cell populations or abnormal SEZ6 protein expression at an inappropriate phase or stage of a cell lifecycle. Of course, it will be appreciated that similar expression patterns of genotypic determinants (e.g., mRNA transcription levels) of SEZ6 may also be used to classify or detect SEZ6 associated disorders.

As used herein the term "determinant" or "SEZ6 determinant" shall mean any detectable trait, property, marker or factor that is identifiably associated with, or specifically found in or on a particular cell, cell population or tissue including those identified in or on a tissue, cell or cell population affected by a SEZ6 associated disease or disorder. In selected preferred embodiments the SEZ6 modulators may associate, bind or react directly with the SEZ6 determinant (e.g., cell surface SEZ6 protein or SEZ6 mRNA) and thereby ameliorate the disorder. More generally determinants may be morphological, functional or biochemical in nature and may be genotypic or phenotypic. In other preferred embodiments the determinant is a cell surface antigen or genetic component that is differentially or preferentially expressed (or is not) by specific cell types (e.g., cancer stem cells) or by cells under certain conditions (e.g., during specific points of the cell cycle or cells in a particular niche). In still other preferred embodiments the determinant may comprise a gene or genetic entity that is differently regulated (up or down) in a specific cell or discrete cell population, a gene that is differentially modified with regard to its physical structure and chemical composition or a protein or collection of proteins physically associated with a gene that show differential chemical modifications. Determinants contemplated herein are specifically held to be positive or negative and may denote a cell, cell subpopulation or tissue (e.g., tumors) by its presence (positive) or absence (negative).

In a similar vein "SEZ6 modulators" of the invention broadly comprise any compound that recognizes, reacts, competes, antagonizes, interacts, binds, agonizes, or associates with a SEZ6 variant or isoform (or specific domains, regions or epitopes thereof) or its genetic component. By these interactions, the SEZ6 modulators may advantageously eliminate, reduce or moderate the frequency, activity, recurrence, metastasis or mobility of tumorigenic cells (e.g., tumor perpetuating cells or cancer stem cells). Exemplary modulators disclosed herein comprise nucleotides, oligonucleotides, polynucleotides, peptides or polypeptides. In certain preferred embodiments the selected modulators will comprise antibodies to a SEZ6 protein isoform or immunoreactive fragments or derivatives thereof. Such antibodies may be antagonistic or agonistic in nature and may optionally be conjugated or associated with a therapeutic or diagnostic agent. Moreover, such antibodies or antibody fragments may comprise depleting, neutralizing or internalizing antibodies. In other embodiments, modulators within the instant invention will constitute a SEZ6 construct comprising a SEZ6 isoform or a reactive fragment thereof. It will be appreciated that such constructs may comprise fusion proteins and can include reactive domains from other polypeptides such as immunoglobulins or biological response modifiers. In still other aspects, the SEZ6 modulator will comprise a nucleic acid moiety (e.g. miRNA, siRNA, shRNA, antisense constructs, etc.) that exerts the desired effects at a genomic level. Still other modulators compatible with the instant teachings will be discussed in detail below.

More generally SEZ6 modulators of the present invention broadly comprise any compound that recognizes, reacts, competes, antagonizes, interacts, binds, agonizes, or associates with a SEZ6 determinant (genotypic or phenotypic) including cell surface SEZ6 protein. Whichever form of modulator is ultimately selected it will preferably be in an isolated and purified state prior to introduction into a subject. In this regard the term "isolated SEZ6 modulator" or "isolated SEZ6 antibody" shall be construed in a broad sense and in accordance with standard pharmaceutical practice to mean any preparation or composition comprising the modulator in a state substantially free of unwanted contaminants (biological or otherwise). Moreover these preparations may be purified and formulated as desired using various art recognized techniques. Of course, it will be appreciated that such "isolated" preparations may be intentionally formulated or combined with inert or active ingredients as desired to improve the commercial, manufacturing or therapeutic aspects of the finished product and provide pharmaceutical compositions. In a broader sense the same general considerations may be applied to an "isolated" SEZ6 isoform or variant or an "isolated" nucleic acid encoding the same.

Further, it has surprisingly been found that modulators interacting, associating or binding to particular SEZ6 domains, motifs or epitopes are especially effective in eliminating tumorigenic cells and/or silencing or attenuating cancer stem cell effects on tumor growth or propagation. That is, while modulators that react or associate with domains that are proximal to the cell surface (e.g. one of the Sushi or CUB-like domains) are effective in depleting or neutralizing tumorigenic cells it has unexpectedly been discovered that modulators associating or binding to domains, motifs or regions that are relatively more distal to the cell surface are also effective in eliminating, neutralizing, depleting or silencing tumorigenic cells. This is especially true of conjugated modulators such as, for example, anti-SEZ6 antibody drug conjugates comprising a cytotoxic agent.

While the present invention expressly contemplates the use of any SEZ6 modulator in the treatment of any SEZ6 disorder, including any type of neoplasia, in particularly preferred embodiments the disclosed modulators may be used to prevent, treat or diagnose tumors comprising neuroendocrine features (genotypic or phenotypic) including neuroendocrine tumors. True or "canonical neuroendocrine tumors" (NETs) arise from the dispersed endocrine system and are typically highly aggressive. Neuroendocrine tumors occur in the kidney, genitourinary tract (bladder, prostate, ovary, cervix, and endometrium), gastrointestinal tract (stomach, colon), thyroid (medullary thyroid cancer), and lung (small cell lung carcinoma and large cell neuroendocrine carcinoma). Moreover, the disclosed modulators may advantageously be used to treat, prevent or diagnose pseudo neuroendocrine tumors (pNETs) that genotypically or phenotypically mimic, comprise, resemble or exhibit common traits with canonical neuroendocrine tumors. "Pseudo neuroendocrine tumors" are tumors that arise from cells of the diffuse neuroendocrine system or from cells in which a neuroendocrine differentiation cascade has been aberrantly reactivated during the oncogenic process. Such pNETs commonly share certain genotypic, phenotypic or biochemical characteristics with traditionally defined neuroendocrine tumors, including the ability to produce subsets of biologically active amines, neurotransmitters, and peptide hormones. Accordingly, for the purposes of the instant invention the phrases "tumors comprising neuroendocrine features" or "tumors exhibiting neuroendocrine features" shall be held to comprise both neuroendocrine tumors and pseudo neuroendocrine tumors unless otherwise dictated by context.

Besides the association with tumors generally discussed above, there are also indications of phenotypic or genotypic association between selected tumor initiating cells (TIC) and SEZ6 determinants. In this regard selected TICs (e.g., cancer stem cells) may express elevated levels of SEZ6 proteins when compared to normal tissue and non-tumorigenic cells (NTG), which together typically comprise much of a solid tumor. Thus, SEZ6 determinants may comprise a tumor associated marker (or antigen or immunogen) and the disclosed modulators may provide effective agents for the detection and suppression of TIC and associated neoplasia due to altered levels of the proteins on cell surfaces or in the tumor microenvironment. Accordingly, SEZ6 modulators, including immunoreactive antagonists and antibodies that associate, bind or react with the proteins, may effectively reduce the frequency of tumor initiating cells and could be useful in eliminating, depleting, incapacitating, reducing, promoting the differentiation of, or otherwise precluding or limiting the ability of these tumor-initiating cells to lie dormant and/or continue to fuel tumor growth, metastasis or recurrence in a patient. In this regard those skilled in the art will appreciate that the present invention further provides SEZ6 modulators and their use in reducing the frequency of tumor initiating cells.

II. SEZ6 Physiology

SEZ6 (also known as seizure related 6 homolog) is a type I transmembrane protein originally cloned from mouse cerebrum cortex-derived cells treated with the convulsant pentylentetrazole (Shimizu-Nishikawa, 1995; PMID: 7723619). Representative SEZ6 protein orthologs include, but are not limited to, human (NP_849191; NP_001092105), chimpanzee (XP_511368, NP_001139913), mouse (NP_067261), and rat (NP_001099224). In humans, the SEZ6 gene consists of 17 exons spanning 51.1 kBp located on chromosome 17q11.2. Alternate splice acceptor sites only 16 base pairs apart within the last exon gives rise to two processed transcripts, one of approximately 4210 bases (NM_178860; FIG. 1A) and one of approximately 4194 bases (NM_001098635, FIG. 1B). The former transcript encodes a 994 amino acid protein (NP_849191; FIG. 1C), whereas the latter encodes a 993 amino acid protein (Np_001092105; FIG. 1D). These two protein isoforms of SEZ6 share overall 100% identity across their extracellular domains and their transmembrane domains, differing only in the final ten amino acid residues (FIG. 1E). A third splice variant has been reported to generate a secreted from of SEZ6 (Shimizu-Nishikawa, 1995; PMID: 7723619), however it has not been included in the RefSeqs associated within the NCBI database Gene page entry. The modulators of the invention may bind to any of the splice variants.

The biological relevance of the isoforms is unclear, although one study has suggested opposing actions for the membrane versus soluble proteins when their expression is restored in neurons from murine SEZ6 knockout mice (Gunnersen of al, 2007, PMID: 18031681). Cross species protein sequence identity for the SEZ6 proteins are listed in FIG. 2A. In the human genome, there are two closely related genes—seizure related 6 homolog-like (SEZ6L) and seizure related 6 homolog like-2 (SEZ6L2), each of which has multiple splice variants encoding numerous isoforms (FIG. 2B). Percent identities for the longest protein of each of the members of this family of SEZ6-like proteins in humans are shown in FIG. 2C. Taken together SEZ6, SEZ6L, and SEZ6L2, including their various isoforms, will be termed the SEZ6 family for the purposes of the instant application. SEZ6 modulators of the invention comprise modulators that are specific for each of SEZ6, SEZ6L or SEZ6L2. Alternatively, the modulators of the invention may cross react with SEZ6 and one or both of SEZ6L and/or SEZ6L2.

The mature SEZ6 protein is composed of a series of structural domains: a cytoplasmic domain, a transmembrane domain and an extracellular domain comprising a unique N-terminal domain, followed by two alternating Sushi and CUB-like domains, and three additional tandem Sushi domain repeats. Two isoforms of the SEZ6 antigen exist, and differ only on the extreme carboxy terminal, cytoplasmic domain.

FIG. 1F provides a schematic diagram of the extracellular region of the SEZ6 protein, illustrating the general juxtaposition of the Sushi and CUB domains, and the N-terminal domain. Generally, the domains are recognized as occurring at about amino acid residues 336-395 (Sushi Domain 1), 397-508 (CUB Domain 1), 511-572 (Sushi Domain 2), 574-685 (CUB Domain 2), 690-748 (Sushi Domain 3), 750-813 (Sushi Domain 4), 817-878 (Sushi Domain 5), with the N terminal domain at about amino acid residues 1-335, and a compositional bias of proline-rich residues at about amino acid residues 71-169.

The Sushi repeats are similar to the short consensus repeats found in the other human complement regulatory proteins (i.e., complement C3b/C4b binding sites). The CUB-like domains are similar to CUB domains found in other mammalian complement binding proteins which are associated with a wide range of proteins that participate in numerous biological processes other than complement activation, including but not limited to patterning, axon guidance, inflammation, and tumor suppression (Bork and Beckman, 1993, PMID: 8510165). Both the Sushi and CUB domains imply a function for SEZ6 involving binding of other proteins extracellularly. Proteins containing CUB domains also have been linked to cell signaling pathways, and consistent with this function, the SEZ6 C-terminal cytoplasmic domains contain the Asn-Pro-Thr-Tyr motif (SEQ ID NO: 403), which is a potential target for phosphorylation by Src tyrosine kinase family members. If true, this would link SEZ6 to a cellular signal transduction pathway leading to the activation of Ras, suggesting that SEZ6 may be a neurotrophic receptor.

Note that, the terms "mature protein" or "mature polypeptide" as used herein refers to the form(s) of the SEZ6 protein produced without the signal peptide of 19 amino acids that may be cleaved prior to cell surface expression. Unless otherwise indicated SEZ6 amino acid numbering (for domains, regions, epitopes, etc.) will be in the context of a mature protein without the leader.

SEZ6 is detectable by RT-PCR at low levels in kidney, liver, heart, lung and thymus of rodents, although strong protein expression was seen only in brain, with a significant level expressed in testis (Herbst and Nicklin, 1997, PMID: 9073173). Using polyclonal sera to SEZ6, protein expression was detected in day 13 of developing mouse forebrain. Strong staining was detected in the post-mitotic, maturing neurons of the developing cortical plate and sub-plate. This staining is diminished in the adult brain where the SEZ6 expression can be detected in other brain regions associated with ongoing morphological plasticity, such as the hippocampus, cerebellum, and olfactory bulb and in neurons of the retina and spinal cord (Gunnersen et al., 2007, PMID: 18031681). The densest signals are found in regions with greatest concentration of neuronal cell bodies. In spite of widespread retinal expression of SEZ6, retinal function in the absence of SEZ6 was not affected (Gunnersen et al, 2009, PMID: 19662096). The SEZ6 staining pattern is closely tied with the emergence of the neocortical layers and hippocampus, and implies a forebrain-specific role for this gene during development. In human and mice SEZ6 was found to be differentially expressed in highly specific regions of the neocortex (Gunnersen et al, 2007, supra).

Mutations in the human SEZ6 gene have been linked to febrile seizures (FS), a convulsion associated with a rise in body temperature and the most common type of seizure in childhood (Yu et al., 2007, PMID:17086543). FS may be classified as simple or complex, depending upon duration, recurrence, and extent of the body affected by the seizure. In a Chinese cohort, no mutations in SEZ6 were found in 15 healthy controls, but mutations were found in 21 of 60 patients with FS, with the most common type of mutation being a heterozygous, cytosine insertion (frame shift mutation) at position 1435 of the cDNA. The mutation incidence was significantly higher in patients with complex FS and in patients with a positive family history. As there is an 80% chance that children with complex FS will have seizures later in life, the authors suggest that screening for mutations in SEZ6 may be valuable in predicting FS recurrence or the development of epilepsy (Yu et al., 2007, supra). Later studies have questioned the incidence, relevance, and ability of this study to have adequate power to imply causality, but do support that SEZ6 may be one gene among many that may play a role in seizure disorders (Mulley et al., 2011, PMID: 21785725).

The specific molecular functions of SEZ6 remain unclear. As discussed above, analysis of the structural modules of the protein identified by homology and sequence analysis suggest a possible role in signaling, cell-cell communication, and neural development. The neuronal dendritic branching and connectivity that form the signaling networks that constitute the brain's circuitry arise and are specified both by intrinsic molecular programs in the neural cell as well as extrinsic signals. The process of dendritic growth in pyramidal neurons, the principal neuron in the mammalian forebrain, yields neurons with distinctive morphologies—a pyramidal cell body, and two distinct, complex dendritic trees: one emerging from the apex and the other from the base of the cell body. Gunnersen et al. (2007, supra) have shown that SEZ6 null mice exhibit an excess of short dendrites in the dendritic trees of these neurons, yet display no increase in the overall dendritic field, the range of neurons with which a given neuron connects. Restoring the expression of the membrane bound SEZ6 isoforms in the knockout neurons results in an anti-branching effect. In behavioral tests the SEZ6 null mice display specific exploratory, motor, and cognitive deficits. These data suggest that SEZ6 is important for the achievement of the necessary balance between dendrite elongation and branching during the elaboration of a complex dendritic arbor during development.

Together, the studies above strongly suggest that the SEZ6 protein is important in the context of neural development, and is likely to have some role in cell-cell communication and signaling. Inappropriate reactivation of developmental signaling pathways or disregulation of normal signaling pathways are commonly observed in tumors (Harris et al., 2012). One collection of tumors sharing features indicative of partial reactivation of developmental programs are tumors with neuroendocrine phenotypes (Yao 2008; PMID: 18565894), in which various hormone and endocrine markers are expressed and/or secreted, and various neural markers indicative of neurogenesis, neural commitment, or differentiation towards neural fates are expressed. Tumors with neuroendocrine features arise infrequently in a wide range of primary sites, and while their exhaustive classification remains problematic (Yao; PMID: 18565894; Klimstra 2010; PMID: 20664470; Klöppel, 2011; PMID: 22005112), they may be classified into four major types: low grade benign carcinoids, low-grade well-differentiated neuroendocrine tumors with malignant behavior, tumors with mixed neuroendocrine and epithelial features, and high-grade poorly differentiated neuroendocrine carcinomas. Of these classifications, the poorly differentiated neuroendocrine carcinomas, which include small cell lung cancer (SCLC) and subsets of non-small cell lung cancer (NSCLC), are cancer types with dismal prognoses. It has been postulated that SCLC is bronchogenic in origin, arising in part from pulmonary neuroendocrine cells (Galluzzo and Bocchetta, 2011; PMID: 21504320). Whatever the cellular source of origin for these tumors, it is clear that they show a poorly differentiated endocrine phenotype, often are highly proliferative and aggressive, and frequently over-express neural proteins. The resultant elevation of neural expression markers in these tumors that otherwise may be primarily restricted to the nervous system or show limited expression during development, of which SEZ6 may be an exemplar, may therefore offer a unique therapeutic target for tumors with the neuroendocrine phenotype.

III. Cancer Stem Cells

As alluded to above it has surprisingly been discovered that aberrant SEZ6 expression (genotypic and/or phenotypic) is associated with various tumorigenic cell subpopulations. In this respect the present invention provides SEZ6 modulators that may be particularly useful for targeting such cells, and especially tumor perpetuating cells, thereby facilitating the treatment, management or prevention of neoplastic disorders. Thus, in preferred embodiments modulators of SEZ6 determinants (phenotypic or genotypic) may be advantageously be used to reduce tumor initiating cell frequency in accordance with the present teachings and thereby facilitate the treatment or management of proliferative disorders.

For the purposes of the instant application the term "tumor initiating cell" (TIC) encompasses both "tumor perpetuating cells" (TPC; i.e., cancer stem cells or CSC) and highly proliferative "tumor progenitor cells" (termed TProg), which together generally comprise a unique subpopulation (i.e. 0.1-40%) of a bulk tumor or mass. For the purposes of the instant disclosure the terms "tumor perpetuating cells" and "cancer stem cells" or "neoplastic stem cells" are equivalent and may be used interchangeably herein. TPC differ from TProg in that TPC can completely recapitulate the composition of tumor cells existing within a tumor and have unlimited self-renewal capacity as demonstrated by serial transplantation (two or more passages through mice) of low numbers of isolated cells, whereas TProg will not display unlimited self-renewal capacity.

Those skilled in the art will appreciate that fluorescence-activated cell sorting (FACS) using appropriate cell surface markers is a reliable method to isolate highly enriched cancer stem cell subpopulations (e.g., >99.5% purity) due, at least in part, to its ability to discriminate between single cells and clumps of cells (i.e. doublets, etc.). Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a "non-tumorigenic cell" (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such SEZ6 positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non TPC derived cells (e.g., fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many prior art treatments, the novel compositions of the present invention preferably reduce the frequency of tumor initiating cells upon administration to a subject regardless of the form or specific target (e.g., genetic material, SEZ6antibody or ligand fusion construct) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to influence the tumor environment or other cells, in turn allows for the more effective treatment of SEZ6 associated disorders by inhibiting tumorigenesis, tumor maintenance and/or metastasis and recurrence.

Among art-recognized methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis comprise preferred methods of calculating reduction of tumor initiating cell frequency other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMID: 18560594 & Hoey et al. 2009, PMID: 19664991; each of which is incorporated herein by reference in its entirety and, in particular, for the disclosed methods.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated populations, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art-recognized cell surface proteins known to enrich for tumor initiating cells (e.g., potentially compatible markers as are set forth in PCT application 2012/031280 which is incorporated herein in its entirety) and thereby measure TIC levels from various samples. In still another compatible method one skilled in the art might enumerate TIC frequency in situ (e.g., in a tissue section) by immunohistochemistry using one or more antibodies or reagents that are able to bind cell surface proteins thought to demarcate these cells.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, ADAM9, oncostatin M, Lgr5, Lgr6, CD324, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, IL1R1, OPN3, DAF, MUC1, MCP, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010. PMID: 20185329, U.S. Pat. No. 7,632,678 and U.S.P.Ns. 2007/0292414, 2008/0175870, 2010/0275280, 2010/0162416 and 2011/0020221 each of which is incorporated herein by reference. It will further be appreciated that each of the aforementioned markers may also be used as a secondary target antigen in the context of the bispecific or multispecific antibodies of the instant invention.

Similarly, non-limiting examples of cell surface phenotypes associated with cancer stem cells of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other cancer stem cell surface phenotypes that are known in the art. See, for example, Schulenburg et al., 2010, supra, Visvader et at, 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), melanoma ("Mel"), ovarian ("OV"), and head and neck cancer ("HN") tumor cells, regardless of whether the tumor specimens being analyzed were primary patient tumor specimens or patient-derived NTX tumors.

Using any of the above-referenced methods and selected markers as known in the art it is then possible to quantify the reduction in frequency of TIC (or the TPC therein) provided by the disclosed SEZ6 modulators (including those conjugated to cytotoxic agents) in accordance with the teachings herein. In some instances, the compounds of the instant invention may reduce the frequency of TIC or TPC (by a variety of mechanisms noted above, including elimination, induced differentiation, niche disruption, silencing, etc.) by 10%, 15%, 20%, 25%, 30% or even by 35%. In other embodiments, the reduction in frequency of TIC or TPC may be on the order of 40%, 45%, 50%, 55%, 60% or 65%. In certain embodiments, the disclosed compounds my reduce the frequency of TIC or TPC by 70%, 75%, 80%, 85%, 90% or even 95%. Of course it will be appreciated that any reduction of the frequency of the TIC or TPC likely results in a corresponding reduction in the tumorigenicity, persistence, recurrence and aggressiveness of the neoplasia.

IV. SEZ6 Modulators

In any event, the present invention is directed to the use of SEZ6 modulators, including SEZ6 antagonists, for the diagnosis, theragnosis, treatment and/or prophylaxis of various disorders including any one of a number of SEZ6 associated malignancies. The disclosed modulators may be used alone or in conjunction with a wide variety of anticancer compounds such as chemotherapeutic or immunotherapeutic agents (e.g., therapeutic antibodies) or biological response modifiers. In other selected embodiments, two or more discrete SEZ6 modulators may be used in combination to provide enhanced anti-neoplastic effects or may be used to fabricate multispecific constructs.

In certain embodiments, the SEZ6 modulators of the present invention will comprise nucleotides, oligonucleotides, polynucleotides, peptides or polypeptides. More particularly, exemplary modulators of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. In certain embodiments the modulators will comprise soluble SEZ6 (sSEZ6) or a form, variant, derivative or fragment thereof including, for example, SEZ6 fusion constructs (e.g., SEZ6-Fc, SEZ6-targeting moiety, etc.) or SEZ6-conjugates (e.g., SEZ6-PEG, SEZ6-cytotoxic agent, SEZ6-brm, etc.). It will also be appreciated that, in other embodiments, the SEZ6 modulators comprise antibodies or immunoreactive fragments or derivatives thereof. In particularly preferred embodiments the modulators of the instant invention will comprise neutralizing antibodies or derivatives or fragments thereof. In other embodiments the SEZ6 modulators may comprise internalizing antibodies or fragments thereof. In still other embodiments the SEZ6 modulators may comprise depleting antibodies or fragments thereof. Moreover, as with the aforementioned fusion constructs, these antibody modulators may be conjugated, linked or otherwise associated with selected cytotoxic agents, polymers, biological response modifiers (BRMs) or the like to provide directed immunotherapies with various (and optionally multiple) mechanisms of action. As alluded to above such antibodies may be pan-SEZ6 antibodies and associate with two or more SEZ6 family members (e.g., SEZ6 and SEZ6L as shown in FIG. 11A) or immunospecific antibodies that selectively react with one or both isoforms of SEZ6. In yet other embodiments the modulators may operate on the genetic level and may comprise compounds as antisense constructs, siRNA, miRNA and the like that interact or associate with the genotypic component of a SEZ6 determinant.

It will farther be appreciated that the disclosed SEZ6 modulators may deplete, silence, neutralize, eliminate or inhibit growth, propagation or survival of tumor cells, including TPC, and/or associated neoplasia through a variety of mechanisms, including agonizing or antagonizing selected pathways or eliminating specific cells depending, for example, on the form of SEZ6 modulator, any associated payload or dosing and method of delivery. Thus, while preferred embodiments disclosed herein are directed to the depletion, inhibition or silencing of specific tumor cell subpopulations such as tumor perpetuating cells or to modulators that interact with a specific epitope or domain, it must be emphasized that such embodiments are merely illustrative and not limiting in any sense. Rather, as set forth in the appended claims, the present invention is broadly directed to SEZ6 modulators and their use in the treatment, management or prophylaxis of various SEZ6 associated disorders irrespective of any particular mechanism, binding region or target tumor cell population.

Regardless of the form of the modulator selected it will be appreciated that the chosen compound may be antagonistic in nature. As used herein an "antagonist" refers to a molecule capable of neutralizing, blocking, inhibiting, abrogating, reducing or interfering with the activities of a particular or specified target (e.g., SEZ6), including the binding of receptors to ligands or the interactions of enzymes with substrates. In this respect it will be appreciated that SEZ6 antagonists of the instant invention may comprise any ligand, polypeptide, peptide, fusion protein, antibody or immunologically active fragment or derivative thereof that recognizes, reacts, binds, combines, competes, associates or otherwise interacts with the SEZ6 protein or fragment thereof and eliminates, silences, reduces, inhibits, hinders, restrains or controls the growth of tumor initiating cells or other neoplastic cells including bulk tumor or NTG cell. Compatible antagonists may further include small molecule inhibitors, aptamers, antisense constructs, siRNA, miRNA and the like, receptor or ligand molecules and derivatives thereof which recognize or associate with a SEZ6 genotypic or phenotypic determinant thereby altering expression patterns or sequestering its binding or interaction with a substrate, receptor or ligand.

As used herein an antagonist refers to a molecule capable of neutralizing, blocking, inhibiting, abrogating, reducing or interfering with the activities of a particular or specified protein, including the binding of receptors to ligands or the interactions of enzymes with substrates. More generally antagonists of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. Antagonists may also include small molecule inhibitors, fusion proteins, receptor molecules and derivatives which bind specifically to the protein thereby sequestering its binding to its substrate target, antagonist variants of the protein, antisense molecules directed to the protein, RNA aptamers, and ribozymes against the protein.

As used herein and applied to two or more molecules or compounds, the terms "recognizes" or "associates" shall be held to mean the reaction, binding, specific binding, combination, interaction, connection, linkage, uniting, coalescence, merger or joining, covalently or non-covalently of the molecules whereby one molecule exerts an effect on the other molecule.

Moreover, as demonstrated in the examples herein (e.g., see FIG. 11), some modulators of human SEZ6 may, in certain cases, cross-react with SEZ6 from a species other than human (e.g., rat or cynomolgus monkey). In other cases exemplary modulators may be specific for one or more isoforms of human SEZ6 and will not exhibit cross-reactivity with SEZ6 orthologs from other species. Of course, in conjunction with the teachings herein such embodiments may comprise pan-SEZ6 antibodies that associate with two or more SEZ6 family members from a single species or antibodies that exclusively associate with SEZ6.

In any event, and as will be discussed in more detail below, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, anti-cancer agents, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated herein the selected conjugate may be covalently or non-covalently linked to the SEZ6 modulator in various molar ratios depending, at least in part, on the method used to effect the conjugation.

V. Modulator Fabrication and Supply

A. Antibody Modulators
1. Overview

As previously alluded to particularly preferred embodiments of the instant invention comprise SEZ6 modulators in the form of antibodies that preferentially associate with one or more isoforms of SEZ6 (and, optionally, may cross-react with other SEZ6 family members). Those of ordinary skill in the art will appreciate the well developed knowledge base on antibodies such as set forth, for example, in Abbas et al., Cellular and Molecular Immunology, 6$^{th}$ ed., W.B. Saunders Company (2010) or Murphey et al., Janeway's Immunobiology, 8$^{th}$ ed., Garland Science (2011), each of which is incorporated herein by reference in its entirety.

The term "antibody" is intended to cover polyclonal antibodies, multiclonal antibodies, monoclonal antibodies, chimeric antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; antibody fragments such as Fab fragments, F(ab') fragments, single-chain FvFcs, single-chain Fvs; and derivatives thereof including Fc fusions and other modifictaions, and any other immunologically active molecule so long as they exhibit the desired biological activity (i.e., antigen association or binding). Moreover, the term further comprises all classes of antibodies (i.e. IgA, IgD, IgE, IgG, and IgM) and all isotypes (i.e., IgG1, IgG2, IgG3, IgA1 and IgA2), as well as variations thereof unless otherwise dictated by context. Heavy-chain constant domains that correspond to the different classes of antibodies are denoted by the corresponding lower case Greek letter α, δ, ε, γ, and μ, respectively. Light chains of the antibodies from any vertebrate species can be assigned to one of two clearly distinct types, called kappa (κ) and lambda (λ), based on the amino acid sequences of their constant domains.

While all such antibodies are within the scope of the present invention, preferred embodiments comprising the IgG class of immunoglobulin will be discussed in some detail herein solely for the purposes of illustration. It will be understood that such disclosure is, however, merely demonstrative of exemplary compositions and methods of practicing the present invention and not in any way limiting of the scope of the invention or the claims appended hereto.

As is well known, the variable domains of both the light ($V_L$) and heavy ($V_H$) chain portions determine antigen recognition and specificity and the constant domains of the light chain ($C_L$) and the heavy chain ($C_H1$, $C_H2$ or $C_H3$) confer and regulate important biological properties such as secretion, transplacental mobility, circulation half-life, complement binding, and the like.

The "variable" region includes hypervariable sites that manifest themselves in three segments commonly termed complementarity determining regions (CDRs), in both the light-chain and the heavy-chain variable domains. The more highly conserved portions of variable domains flanking the CDRs are termed framework regions (FRs). For example, in naturally occurring monomeric immunoglobulin G (IgG) antibodies, the six CDRs present on each arm of the "Y" are short, non-contiguous sequences of amino acids that are specifically positioned to form the antigen binding site as the antibody assumes its three dimensional configuration in an aqueous environment. Thus, each naturally occurring IgG antibody comprises two identical binding sites proximal to the amino-terminus of each arm of the Y.

It will be appreciated that the position of CDRs can be readily identified by one of ordinary skill in the art using standard techniques. Also familiar to those in the art is the numbering system described in Kabat et al. (1991, Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain sequence, without reliance on any experimental data beyond the sequence itself. Unless otherwise specified, references to the numbering of specific amino acid residue positions in an antibody are according to the Kabat numbering system.

Thus, according to Kabat, in the $V_H$, residues 31-35 comprise CDR1, residues 50-65 make up CDR2 and 95-102 comprise CDR3, while in the $V_L$, residues 24-34 are CDR1, 50-56 comprise CDR2, and 89-97 make up CDR3. For context, in a $V_H$, FR1 corresponds to the domain of the variable region encompassing amino acids 1-30; FR2 corresponds to the domain of the variable region encompassing amino acids 36-49; FR3 corresponds to the domain of the variable region encompassing amino acids 66-94, and FR4 corresponds to the domain of the variable region from amino acids 103 to the end of the variable region. The FRs for the light chain are similarly separated by each of the light chain variable region CDRs.

Note that CDRs vary considerably from antibody to antibody (and by definition will not exhibit homology with the Kabat consensus sequences). In addition, the identity of certain individual residues at any given Kabat site number may vary from antibody chain to antibody chain due to interspecies or allelic divergence. Alternative numbering is set forth in Chothia et al., *J. Mol. Biol.* 196:901-917 (1987) and MacCallum et al. *Biol.* 262:732-745 (1996), although as in Kabat, the FR boundaries are separated by the respective CDR termini as described above. See also Chothia et al., Nature 342, pp. 877-883 (1989) and S. Dubel, ed., *Handbook of Therapeutic Antibodies*, 3$^{rd}$ ed., WILEY-VCH Verlag GmbH and Co. (2007), where the definitions include overlapping or subsets of amino acid residues when compared against each other. Each of the aforementioned references is incorporated herein by reference in its entirety and the amino acid residues which comprise binding regions or CDRs as defined by each of the above cited references and are set forth for comparison below.

| CDR Definitions | | | |
|---|---|---|---|
|  | Kabat[1] | Chothia[2] | MacCallum[3] |
| $V_H$ CDR1 | 31-35 | 26-32 | 30-35 |
| $V_H$ CDR2 | 50-65 | 50-58 | 47-58 |
| $V_H$ CDR3 | 95-102 | 95-102 | 93-101 |
| $V_L$ CDR1 | 24-34 | 23-34 | 30-36 |
| $V_L$ CDR2 | 50-56 | 50-56 | 46-55 |
| $V_L$ CDR3 | 89-97 | 89-97 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra In the context of the instant invention it will be appreciated that any of the disclosed light and heavy chain CDRs derived from the murine variable region amino acid sequences set forth in FIG. 10A or FIG. 10B may be combined or rearranged to provide optimized anti-SEZ6 (e.g. humanized, CDR grafted or chimeric anti-hSEZ6) antibodies in accordance with the instant teachings. That is, one or more of the CDRs derived from the light chain variable region amino acid sequences set forth in FIG. 10A (SEQ ID NOS: 20-168, even numbers) or the heavy chain variable region amino acid sequences set forth in FIG. 10B (SEQ ID NOS: 21-169, odd numbers) may be incorporated in a SEZ6 modulator and, in particularly preferred embodiments, in a CDR grafted or humanized antibody that immunospecifically associates with one or more SEZ6 isoforms. Examples of light (SEQ ID NOS: 170-192, even numbers) and heavy (SEQ ID NOS: 171-193, odd numbers and 194-199) chain variable region amino acid sequences of such humanized modulators are also set forth in FIGS. 10A and 10B.

Note that hSC17.200vL1 (SEQ ID NO: 192) is a variant of the humanized light chain construct hSC17.200 (SEQ ID NO: 190), hSC17.155vH1-vH6 (SEQ ID NOS: 193-198) are variants of the heavy chain construct hSC.155 (SEQ ID NO: 184) which is derived from SC17.90 (SEQ ID NO: 127) and that hSC161vH1 (SEQ ID NO: 199) is a variant of the heavy chain construct hSC17.161 (SEQ ID NO: 189). As will be discussed in more detail below these variants were constructed and tested to optimize one or more biochemical properties of the parent antibody.

Taken together these novel amino acid sequences depict seventy-five murine and eleven humanized exemplary modulators (along with reported variants) in accordance with the instant invention. Moreover, corresponding nucleic acid sequences of each of the seventy-five exemplary murine modulators and eleven humanized modulators and variants set forth in FIGS. 10A and 10B are included in sequence listing of the instant application (SEQ ID NOS: 220-399).

In FIGS. 10A and 10B the annotated CDRs are defined using Chothia numbering. However, as discussed herein and demonstrated in Example 8 below, one skilled in the art could readily define, identify, derive and/or enumerate the CDRs as defined by Kabat et al., Chothia et al. or MacCallum et al. for each respective heavy and light chain sequence set forth in FIG. 10A or FIG. 10B. Accordingly, each of the subject CDRs and antibodies comprising CDRs defined by all such nomenclature are expressly included within the scope of the instant invention. More broadly, the terms "variable region CDR amino acid residue" or more simply "CDR" includes amino acids in a CDR as identified using any sequence or structure based method as set forth above.

2. Antibody Modulator Generation a. Polyclonal Antibodies

The production of polyclonal antibodies in various host animals, including rabbits, mice, rats, etc. is well known in the art. In some embodiments, polyclonal anti-SEZ6 antibody-containing serum is obtained by bleeding or sacrificing the animal. The serum may be used for research purposes in the form obtained from the animal or, in the alternative, the anti-SEZ6 antibodies may be partially or fully purified to provide immunoglobulin fractions or homogeneous antibody preparations.

Briefly the selected animal is immunized with a SEZ6 immunogen (e.g., soluble SEZ6 or sSEZ6) which may, for example, comprise selected isoforms, domains and/or peptides, or live cells or cell preparations expressing SEZ6 or immunoreactive fragments thereof. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably the immunization schedule will involve two or more administrations of the selected immunogen spread out over a predetermined period of time.

The amino acid sequence of a SEZ6 protein as shown in FIG. 1C or 1D can be analyzed to select specific regions of the SEZ6 protein for generating antibodies. For example, hydrophobicity and hydrophilicity analyses of a SEZ6 amino acid sequence are used to identify hydrophilic regions in the SEZ6 structure. Regions of a SEZ6 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each SEZ6 region, domain or motif identified by any of these programs or methods is within the scope of the present invention and may be isolated or engineered to provide immunogens giving rise to modulators comprising desired properties. Preferred methods for the generation of SEZ6 antibodies are further illustrated by way of the Examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents are effective. Administration of a SEZ6 immunogen is often conducted by injection over a suitable time period and with use of a suitable adjuvant, as is understood in the art. During the immunization schedule, titers of antibodies can be taken as described in the Examples below to determine adequacy of antibody formation.

b. Monoclonal Antibodies

In addition, the invention contemplates use of monoclonal antibodies. As known in the art, the term "monoclonal antibody" (or mAb) refers to an antibody obtained from a population of substantially homogeneous antibodies, i.e., the individual antibodies comprising the population are identical except for possible mutations (e.g., naturally occurring mutations), that may be present in minor amounts. In certain embodiments, such a monoclonal antibody includes an antibody comprising a polypeptide sequence that binds or associates with an antigen wherein the antigen-binding polypeptide sequence was obtained by a process that includes the selection of a single target binding polypeptide sequence from a plurality of polypeptide sequences.

More generally, and as exemplified in Example 6 herein, monoclonal antibodies can be prepared using a wide variety of techniques known in the art including hybridoma, recombinant techniques, phage display technologies, transgenic animals (e.g., a XENOMOUSE®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, $1^{st}$ ed, 2009; Shire et. al. (eds.) *Current Trends in Monoclonal Antibody Development and Manufacturing*, Springer Science+Business Media LLC, $1^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this invention.

c. Chimeric Antibodies

In another embodiment, the antibody of the invention may comprise chimeric antibodies derived from covalently joined protein segments from at least two different species or types of antibodies. As known in the art, the term "chimeric" antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

In one embodiment, a chimeric antibody in accordance with the teachings herein may comprise murine $V_H$ and $V_L$ amino acid sequences and constant regions derived from human sources. In other compatible embodiments a chimeric antibody of the present invention may comprise a humanized antibody as described below. In another embodiment, the so-called "CDR-grafted" antibody, the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, selected rodent CDRs may be grafted into a human antibody, replacing one or more of the naturally occurring variable regions or CDRs of the human antibody. These constructs generally have the advantages of providing full strength modulator functions (e.g., CDC (complement dependent cytotoxicity), ADCC (antibody-dependent cell-mediated cytotoxicity), etc.) while reducing unwanted immune responses to the antibody by the subject.

d. Humanized Antibodies

Similar to the CDR-grafted antibody is a "humanized" antibody. As used herein, "humanized" forms of non-human (e.g., murine) antibodies are chimeric antibodies that contain a minimal sequence derived from one or more non-human immunoglobulins. In one embodiment, a humanized antibody is a human immunoglobulin (recipient or acceptor antibody) in which residues from a CDR of the recipient are replaced by residues from a CDR of a non-human species (donor antibody) such as mouse, rat, rabbit, or nonhuman primate having the desired specificity, affinity, and/or capacity. In certain preferred embodiments, residues in one or more FRs in the variable domain of the human immunoglobulin are replaced by corresponding non-human residues from the donor antibody to help maintain the appropriate three-dimensional configuration of the grafted CDR(s) and thereby improve affinity. Furthermore, humanized antibodies may comprise residues that are not found in the recipient antibody or in the donor antibody to, for example, further refine antibody performance.

CDR grafting and humanized antibodies are described, for example, in U.S. Pat. Nos. 6,180,370 and 5,693,762. The humanized antibody optionally may also comprise at least a portion of an immunoglobulin Fc, typically that of a human immunoglobulin. For further details, see, e.g., Jones et al., Nature 321:522-525 (1986); and U.S. Pat. Nos. 6,982,321 and 7,087,409. Still another method is termed "humaneering" which is described, for example, in U.S.P.N. 2005/0008625. Additionally, a non-human antibody may also be modified by specific deletion of human T-cell epitopes or "deimmunization" by the methods disclosed in WO 98/52976 and WO 00/34317. Each of the aforementioned references are incorporated herein in their entirety.

Humanized antibodies may also be bioengineered using common molecular biology techniques, such as isolating, manipulating, and expressing nucleic acid sequences that encode all or part of immunoglobulin variable regions from at least one of a heavy or light chain. In addition to the sources of such nucleic acid noted above, human germline sequences are available as disclosed, for example, in Tomlinson., I. A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 114:4628-4638. The V-BASE directory (VBASE2—Retter et al., Nucleic Acid Res. 33; 671-674, 2005) provides a comprehensive directory of human immunoglobulin variable region sequences (compiled by Tomlinson, I. A, et al. MRC Centre for Protein Engineering, Cambridge, UK). Consensus human FRs can also be used, e.g., as described in U.S. Pat. No. 6,300,064.

In selected embodiments, and as detailed in Example 8 below, at least 60%, 65%, 70%, 75%, or 80% of the humanized antibody heavy or light chain variable region amino acid residues will correspond to those of the recipient FR and CDR sequences. In other embodiments at least 85% or 90% of the humanized antibody variable region residues will correspond to those of the recipient FR and CDR sequences. In a further preferred embodiment, greater than 95% of the humanized antibody variable region residues will correspond to those of the recipient FR and CDR sequences.

e. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; and Barbas et al., *Proc. Natl. Acad. Sci. USA* 88:7978-7982 (1991)).

In one embodiment, recombinant human antibodies may be isolated by screening a recombinant combinatorial antibody library prepared as above. In one embodiment, the library is a scFv phage display library, generated using human $V_L$ and $V_H$ cDNAs prepared from mRNA isolated from B-cells.

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., *Technique*, 1: 11-15 (1989)). Additionally, affinity maturation can be performed by randomly mutating one or more CDRs, e.g. using PCR with primers carrying random sequence spanning the CDR of interest, in selected individual Fv clones and screening for higher-affinity clones. WO 9607754 described a method for inducing mutagenesis in a CDR of an immunoglobulin light chain to create a library of light chain genes. Another effective approach is to recombine the $V_H$ or $V_L$ domains selected by phage display with repertoires of naturally occurring V domain variants obtained from unimmunized donors and to screen for higher affinity in several rounds of chain reshuffling as described in Marks et al., *Biotechnol.,* 10: 779-783 (1992). This technique allows the production of antibodies and antibody fragments with a dissociation constant $K_D$ ($k_{off}/k_{on}$) of about $10^{-9}$ M or less.

In other embodiments, similar procedures may be employed using libraries comprising eukaryotic cells (e.g., yeast) that express binding pairs on their surface. See, for example, U.S. Pat. No. 7,700,302 and U.S. Ser. No. 12/404, 059. In one embodiment, the human antibody is selected from a phage library, where that phage library expresses human antibodies (Vaughan et al. *Nature Biotechnology* 14:309-314 (1996): Sheets et al. *Proc. Natl. Acad. Sci. USA* 95:6157-6162 (1998). In other embodiments, human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and U.S. Pat. Nos. 6,075,181 and 6,150,584 regarding XenoMouse technology; and Lonberg and Huszar, *Intern. Rev. Immunol.* 13:65-93 (1995), Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., *J. Immunol,* 147 (0:86-95 (1991); and U.S. Pat. No. 5,750,373.

3. Further Processing

No matter how obtained, modulator-producing cells (e.g., hybridomas, yeast colonies, etc.) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

B. Recombinant Modulator Production

1. Overview

Once the source is perfected DNA encoding the desired SEZ6 modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, isolated DNA (which may be modified) can be used to clone constant and variable region sequences for the manufacture antibodies.

Accordingly, in exemplary embodiments antibodies may be produced recombinantly, using conventional procedures (such as those set forth in Al-Rubeai; An, and Shire et al. all supra, and Sambrook S. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002)) in which the isolated and subcloned hybridoma cells (or phage or yeast derived colonies) serve as a preferred source of nucleic acid molecules.

The term "nucleic acid molecule", as used herein, is intended to include DNA molecules and RNA molecules and artificial variants thereof (e.g., peptide nucleic acids), whether single-stranded or double-stranded. The nucleic acids may encode one or both chains of an antibody of the invention, or a fragment or derivative thereof. The nucleic acid molecules of the invention also include polynucleotides sufficient for use as hybridization probes, PCR primers or sequencing primers for identifying, analyzing, mutating or amplifying a polynucleotide encoding a polypeptide; antisense nucleic acids for inhibiting expression of a polynucleotide, and as well as complementary sequences. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. It will be appreciated that such nucleic acid sequences can further be manipulated to create modulators including chimeric, humanized or fully human antibodies. More particularly, isolated nucleic acid molecules (which may be modified) can be used to clone constant and variable region sequences for the manufacture antibodies as described in U.S. Pat. No. 7,709,611.

The term "isolated nucleic acid" means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

Whether the source of the nucleic acid encoding the desired immunoreactive portion of the antibody is obtained or derived from phage display technology, yeast libraries, hybridoma-based technology or synthetically, it is to be understood that the present invention encompasses the nucleic acid molecules and sequences encoding the antibodies or antigen-binding fragments or derivatives thereof. Further, the instant invention is directed to vectors and host cells comprising such nucleic acid molecules.

2. Hybridization and Sequence Identity

As indicated, the invention further provides nucleic acids that hybridize to other nucleic acids under particular hybridization conditions. More specifically the invention encompasses nucleic acids molecules that hybridize under moderate or high stringency hybridization conditions (e.g., as defined below), to the nucleic acid molecules of the invention. Methods for hybridizing nucleic acids are well-known in the art. As is well known, a moderately stringent hybridization conditions comprise a prewashing solution containing 5× sodium chloride/sodium citrate (SSC), 0.5% SDS, 1.0 InM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. By way of comparison hybridization under highly stringent hybridization conditions comprise washing with 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The invention also includes nucleic acid molecules that are "substantially identical" to the described nucleic acid molecules. In one embodiment, the term substantially identical with regard to a nucleic acid sequence means may be construed as a sequence of nucleic acid molecules exhibiting at least about 65%, 70%, 75%, 80%, 85%, or 90% sequence identity. In other embodiments, the nucleic acid molecules exhibit 95% or 98% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, the sequence analysis tool GCG (Accelrys Software Inc.) contains programs such as "GAP" and "BEST-FIT" which can be used with default parameters to determine sequence homology or sequence identity between closely related polypeptides, such as homologous polypeptides from different species of organisms or between a wild type protein and a mutein thereof. (See, e.g., GCG Version 6.1 or Durbin et. Al., *Biological Sequence Analysis: Probabilistic models of proteins and nucleic acids.*, Cambridge Press (1998)).

Polypeptide sequences can also be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215: 403 410 and Altschul et al. (1997) Nucleic Acids Res. 25:3389 402, each of which is herein incorporated by reference.

In this regard the invention also includes nucleic acid molecules that encode polypeptides that are "substantially identical" with respect to an antibody variable region polypeptide sequence (e.g., either the donor light or heavy chain variable region, acceptor light or heavy chain variable region or resulting humanized construct). As applied to such polypeptides, the term "substantial identity" or "substantially identical" means that two peptide sequences, when optimally aligned, such as by the programs GAP or BEST-FIT using default gap weights, share at least 60% or 65% sequence identity, preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

3. Expression

The varied processes of recombinant expression, i.e., the production of RNA or of RNA and protein/peptide, are well known as set forth, for example, in Berger and Kimmel, Guide to Molecular Cloning Techniques, *Methods in Enzymology* volume 152 Academic Press, Inc., San Diego, Calif.; Sambrook et al., *Molecular Cloning-A Laboratory Manual* (3rd Ed.), Vol. 1-3, Cold Spring Harbor Laboratory, Cold Spring Harbor, N.Y., (2000); and *Current Protocols in Molecular Biology*, F. M. Ausubel et al., eds., Current Protocols, a joint venture between Greene Publishing Associates, Inc. and John Wiley & Sons, Inc., (supplemented through 2006).

Certain terms of interest include "expression control sequence" which comprises promoters, ribosome binding sites, enhancers and other control elements which regulate transcription of a gene or translation of mRNA. As is well known, a "promoter" or "promoter region" relates to a nucleic acid sequence which generally is located upstream (5') to the nucleic acid sequence being expressed and controls expression of the sequence by providing a recognition and binding site for RNA-polymerase.

Exemplary promoters which are compatible according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g., human GAPDH (glyceraldehyde-3-phosphate dehydrogenase), and including or not including (an) additional intron(s).

In certain embodiments, the nucleic acid molecule may be present in a vector, where appropriate with a promoter, which controls expression of the nucleic acid. The well known term "vector" comprises any intermediary vehicle for a nucleic acid which enables said nucleic acid, for example, to be introduced into prokaryotic and/or eukaryotic cells and, where appropriate, to be integrated into a genome. Methods of transforming mammalian cells are well known in the art. See, for example, U.S. Pat. Nos. 4,399,216, 4,912,040, 4,740,461, and 4,959,455. The vectors may include a nucleotide sequence encoding an antibody of the invention (e.g., a whole antibody, a heavy or light chain of an antibody, a $V_H$ or $V_L$ of an antibody, or a portion thereof, or a heavy- or tight-chain CDR, a single chain Fv, or fragments or variants thereof), operably linked to a promoter (see, e.g., PCT Publication WO 86/05807; PCT Publication WO 89/01036; and U.S. Pat. No. 5,122,464).

A variety of host-expression vector systems are commercially available, and many are compatible with the teachings herein and may be used to express the modulators of the invention. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant viral expression vectors (e.g., cauliflower mosaic virus; tobacco mosaic virus) or transfected with recombinant plasmid expression vectors (e.g., Ti plasmid) containing modulator coding sequences; or mammalian cell systems (e.g., COS, CHO, BHK, 293, 3T3 cells, etc.) harboring recombinant expression constructs containing promoters derived from the genome of mammalian cells (e.g., metallothionein promoter) or from mammalian viruses (e.g., the adenovirus late promoter; the vaccinia virus 7.5K promoter).

As used herein, the term "host cell" covers any kind of cellular system which can be engineered to generate the polypeptides and antigen-binding molecules of the present invention. In one embodiment, the host cell is engineered to allow the production of an antigen binding molecule with modified glycoforms. In a preferred embodiment, the antigen binding molecule, or variant antigen binding molecule, is an antibody, antibody fragment, or fusion protein. In certain embodiments, the host cells have been further manipulated to express increased levels of one or more polypeptides having N-acetylglucosaminyltransferase III (GnTI11) activity. Compatible host cells include cultured cells, e.g., mammalian cultured cells, such as CHO cells, BHK cells, NSO cells, SP2/0 cells, YO myeloma cells, P3X63 mouse myeloma cells, PER cells. PER.C6 cells or hybridoma cells, yeast cells, insect cells, and plant cells, to name only a few, but also cells comprised within a transgenic animal, transgenic plant or cultured plant or animal tissue.

For long-term, high-yield production of recombinant proteins stable expression is preferred. Accordingly, cell lines that stably express the selected modulator may be engineered using standard art-recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 and U.S. Pat. Nos. 5,591,639 and 5,879,936 each of which is incorporated herein by reference. Another preferred expression system, the FREEDOM™ CHO-S Kit is commercially provided by Life Technologies (Catalog Number A13696-01) also allows for the development of stable cell lines that may be used for modulator production.

Such host-expression systems represent vehicles by which the coding sequences of interest may be produced and subsequently purified, but also represent cells which may, when transformed or transfected with the appropriate nucleotide coding sequences, express a molecule of the invention in situ. The host cell may be co-transfected with two expression vectors of the invention, for example, the first vector encoding a heavy chain derived polypeptide and the second vector encoding a light chain derived polypeptide.

Thus, in certain embodiments, the present invention provides recombinant host cells allowing for the expression of antibodies or portions thereof. Antibodies produced by expression in such recombinant host cells are referred to herein as recombinant antibodies. The present invention also provides progeny cells of such host cells, and antibodies produced by the same.

C. Chemical Synthesis

In addition, the modulators may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). Furthermore, if desired, nonclassical amino acids or chemical amino acid analogs (such as D-isomers of the common amino acids, 2,4-diaminobutyric acid, a-amino isobutyric acid, 4-aminobutyric acid, and the like) can be introduced as a substitution or addition into a polypeptide sequence.

D. Transgenic Systems

In other embodiments modulators may be produced transgenically through the generation of a mammal or plant that is transgenic for recombinant molecules such as the immunoglobulin heavy and light chain sequences and that produces the desired compounds in a recoverable form. This includes, for example, the production of protein modulators (e.g., antibodies) in, and recovery from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized to produce antibodies.

Other transgenic techniques are set forth in Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999) and U.S. Pat. No. 6,417,429. In some embodiments, the non-human animals are mice, rats, sheep, pigs, goats, cattle or horses, and the desired product is produced in blood, milk, urine, saliva, tears, mucus and other bodily fluids from which it is readily obtainable using art-recognized purification techniques.

Other compatible production systems include methods for making antibodies in plants such as described, for example, in U.S. Pat. Nos. 6,046,037 and 5,959,177 which are incorporated herein with respect to such techniques.

E. Isolation/Purification

Once a modulator of the invention has been produced by recombinant expression or any other of the disclosed techniques, it may be purified by any method known in the art for purification of immunoglobulins or proteins. In this respect the modulator may be "isolated" which means that it has been identified and separated and/or recovered from a component of its natural environment. Contaminant components of its natural environment are materials that would interfere with diagnostic or therapeutic uses for the polypeptide and may include enzymes, hormones, and other proteinaceous or nonproteinaceous solutes. Isolated modulators include a modulator in situ within recombinant cells because at least one component of the polypeptide's natural environment will not be present.

If the desired molecule is produced intracellularly, as a first step, the particulate debris, either host cells or lysed fragments, may be removed, for example, by centrifugation or ultrafiltration. Where the modulator is secreted into the medium, supernatants from such expression systems are generally first concentrated using a commercially available protein concentration filter, for example, an Amicon or Pellicon ultrafiltration unit (Millipore Corp.). Once the insoluble contaminants are removed the modulator preparation may be further purified using standard techniques such as, for example, hydroxylapatite chromatography, gel electrophoresis, dialysis, and affinity chromatography, with affinity chromatography of particular interest. In this regard protein A can be used to purify antibodies that are based on human IgG1, IgG2 or IgG4 heavy chains (Lindmark, et al., J Immunol Meth 62:1 (1983)) while protein G is recommended for all mouse isotypes and for human IgG3 (Guss, et al., EMBO J 5:1567 (1986)). Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

VI. SEZ6 Modulator Fragments and Derivatives

Whatever generation and production methodology is selected, modulators of the instant invention will react, bind, combine, complex, connect, attach, join, interact or otherwise associate with a target determinant (e.g., antigen) and thereby provide the desired results. Where the modulator comprises an antibody or fragment, construct or derivative thereof such associations may be through one or more "binding sites" or "binding components" expressed on the antibody, where a binding site comprises a region of a polypeptide that is responsible for selectively binding to a target molecule or antigen of interest. Binding domains comprise at least one binding site (e.g., an intact IgG antibody will have two binding domains and two binding sites). Exemplary binding domains include an antibody variable domain, a receptor-binding domain of a ligand, a ligand-binding domain of a receptor or an enzymatic domain.

A. Antibodies

As noted above, the term "antibody" is intended to cover, at least, polyclonal antibodies, multiclonal antibodies, chimeric antibodies, CDR grafted antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, as well as synthetic antibodies.

B. Fragments

Regardless of which form of the modulator (e.g. chimeric, humanized, etc.) is selected to practice the invention it will be appreciated that immunoreactive fragments of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary fragments include: $V_L$, $V_H$, scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active fragment comprises a portion of the antibody that retains its ability to interact with the antigen/substrates or receptors and modify them in a manner similar to that of an intact antibody (though maybe with somewhat less efficiency).

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

As would be well recognized by those skilled in the art, fragments can be obtained via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments.

C. Derivatives

The invention further includes immunoreactive modulator derivatives and antigen binding molecules comprising one or more modifications.

1. Multivalent Antibodies

In one embodiment, the modulators of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105. In each case at least one of the binding sites will comprise an epitope, motif or domain associated with a SEZ6 isoform.

In one embodiment, the modulators are bispecific antibodies in which the two chains have different specificities, as described in Millstein et al., 1983, *Nature*, 305:537-539. Other embodiments include antibodies with additional specificities such as trispecific antibodies. Other more sophisticated compatible multispecific constructs and methods of their fabrication are set forth in U.S.P.N. 2009/0155255, as well as WO 94/04690; Suresh et al., 1986, *Methods in Enzymology,* 121:210; and WO96/27011.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-SEZ6 antibodies only bind two antigens (i.e. bispecific antibodies), antibodies with additional specificities such as trispecific antibodies are also encompassed by the instant invention. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

In yet other embodiments, antibody variable domains with the desired binding specificities (antibody-antigen combining sites) are fused to immunoglobulin constant domain sequences, such as an immunoglobulin heavy chain constant domain comprising at least part of the hinge, $C_H2$, and/or $C_H3$ regions, using methods well known to those of ordinary skill in the art.

2. Fc Region Modifications

In addition to the various modifications, substitutions, additions or deletions to the variable or binding region of the disclosed modulators (e.g., Fc-SEZ6 or anti-SEZ6 antibodies) set forth above, those skilled in the art will appreciate that selected embodiments of the present invention may also comprise substitutions or modifications of the constant region (i.e. the Fc region). More particularly, it is contemplated that the SEZ6 modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding to an Fc receptor (FcR), enhanced or reduced "ADCC" (antibody-dependent cell mediated cytotoxicity) or "CDC" (complement-dependent cytotoxicity) activity, altered glycosylation and/or disulfide bonds and modified binding specificity. In this regard it will be appreciated that these Fc variants may advantageously be used to enhance the effective anti-neoplastic properties of the disclosed modulators.

To this end certain embodiments of the invention may comprise substitutions or modifications of the Fc region, for example the addition of one or more amino acid residue, substitutions, mutations and/or modifications to produce a compound with enhanced or preferred Fc effector functions. For example, changes in amino acid residues involved in the interaction between the Fc domain and an Fc receptor (e.g., FcγRI, FcγRIIA and B, FcγRIII and FcRn) may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995) each of which is incorporated herein by reference).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

3. Altered Glycosylation

Still other embodiments comprise one or more engineered glycoforms, i.e., a SEZ6 modulator comprising an altered glycosylation pattern or altered carbohydrate composition that is covalently attached to the protein (e.g., in the Fc domain). See, for example, Shields, R. L. et al. (2002) *J. Biol. Chem.* 277:26733-26740. Engineered glycoforms may be useful for a variety of purposes, including but not limited to enhancing or reducing effector function, increasing the affinity of the modulator for a target or facilitating production of the modulator. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed (see, for example, WO 2012/117002).

4. Additional Processing

The modulators may be differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Various post-translational modifications also encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the modulators may also be modified with a detectable label, such as an enzymatic, fluorescent, radioisotopic or affinity label to allow for detection and isolation of the modulator.

VII. Modulator Characteristics

No matter how obtained or which of the aforementioned forms the modulator takes, various embodiments of the disclosed modulators may exhibit certain characteristics. In selected embodiments, antibody-producing cells (e.g., hybridomas or yeast colonies) may be selected, cloned and further screened for favorable properties including, for example, robust growth, high modulator production and, as discussed in more detail below, desirable modulator characteristics. In other cases characteristics of the modulator may be imparted or influenced by selecting a particular antigen (e.g., a specific SEZ6 isoform or fragment thereof) or immunoreactive fragment of the target antigen for inoculation of the animal. In still other embodiments the selected modulators may be engineered as described above to enhance or refine immunochemical characteristics such as affinity or pharmacokinetics.

A. Neutralizing Modulators

In certain embodiments, the modulators will comprise "neutralizing" antibodies or derivatives or fragments thereof. That is, the present invention may comprise antibody molecules that bind specific domains, motifs or epitopes and are capable of blocking, reducing or inhibiting the biological activity of SEZ6. More generally the term "neutralizing antibody" refers to an antibody that binds to or interacts with a target molecule or ligand and prevents binding or association of the target molecule to a binding partner such as a receptor or substrate, thereby interrupting a biological response that otherwise would result from the interaction of the molecules.

It will be appreciated that competitive binding assays known in the art may be used to assess the binding and specificity of an antibody or immunologically functional fragment or derivative thereof. With regard to the instant invention an antibody or fragment will be held to inhibit or reduce binding of SEZ6 to a binding partner or substrate (e.g., a neurotrophic ligand) when an excess of antibody reduces the quantity of binding partner bound to SEZ6 by at least about 20%, 30%, 40%, 50%, 60%, 70%, 80%, 85%, 90%, 95%, 97%, 99% or more as measured, for example, by impaired neurotrophic ligand activity or in an in vitro competitive binding assay. In the case of antibodies to SEZ6 for example, a neutralizing antibody or antagonist will preferably alter ligand activity by at least about 20%, 30%, 40%, 50%, 60%, 70%, 80%, 85%, 90%, 95%, 97%, 99% or more. It will be appreciated that this modified activity may be measured directly using art-recognized techniques or may be measured by the impact the altered activity has downstream (e.g., oncogenesis, cell survival or pathway activation).

B. Internalizing Modulators

While evidence indicates that SEZ6 or selected isoforms thereof may be present in a soluble form, at least some SEZ6 likely remains associated with the cell surface thereby allowing for internalization of the disclosed modulators. Accordingly, the anti-SEZ6 antibodies of the instant invention may be internalized, at least to some extent, by cells that express SEZ6. For example, an anti-SEZ6 antibody that binds to SEZ6 on the surface of a tumor-initiating cell may be internalized by the tumor-initiating cell. In particularly preferred embodiments such anti-SEZ6 antibodies may be associated with or conjugated to anti-cancer agents such as cytotoxic moieties that kill the cell upon internalization. In particularly preferred embodiments the modulator will comprise an internalizing antibody drug conjugate.

As used herein, a modulator that "internalizes" is one that is taken up (along with any payload) by the cell upon binding to an associated antigen or receptor. As will be appreciated, the internalizing modulator may, in preferred embodiments, comprise an antibody including antibody fragments and derivatives thereof, as well as antibody conjugates. Internalization may occur in vitro or in vivo. For therapeutic applications, internalization will preferably occur in vivo in a subject in need thereof. The number of antibody molecules internalized may be sufficient or adequate to kill an antigen-expressing cell, especially an antigen-expressing cancer stem cell. Depending on the potency of the antibody or antibody conjugate, in some instances, the uptake of a single antibody molecule into the cell is sufficient to kill the target cell to which the antibody binds. For example, certain toxins are so highly potent that the internalization of a few molecules of the toxin conjugated to the antibody is sufficient to kill the tumor cell. Whether an antibody internalizes upon binding to a mammalian cell can be determined by various assays including those described in the Examples below (e.g., Example 15, 17 and 18). Methods of detecting whether an antibody internalizes into a cell are also described in U.S. Pat. No. 7,619,068 which is incorporated herein by reference in its entirety.

C. Depleting Modulators

In other embodiments the antibodies will comprise depleting antibodies or derivatives or fragments thereof. The term "depleting" antibody refers to an antibody that preferably binds to or associates with an antigen on or near the cell surface and induces, promotes or causes the death or elimination of the cell (e.g., by CDC, ADCC or introduction of a cytotoxic agent). In some embodiments, the selected depleting antibodies will be associated or conjugated to a cytotoxic agent.

Preferably a depleting antibody will be able to remove, incapacitate, eliminate or kill at least 20%, 30%, 40%, 50%, 60%, 70%, 80%, 85%, 90%, 95%, 97%, or 99% of SEZ6 tumorigenic cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below (e.g., Examples 14 and 15) may be used to monitor and quantify the depletion of tumorigenic cells or tumor perpetuating cells in accordance with the teachings herein.

D. Binning and Epitope Binding

It will further be appreciated the disclosed anti-SEZ6 antibody modulators will associate with, or bind to, discrete epitopes or immunogenic determinants presented by the selected target or fragment thereof. In certain embodiments, epitope or immunogenic, determinants include chemically active surface groupings of molecules such as amino acids, sugar side chains, phosphoryl groups, or sulfonyl groups, and, in certain embodiments, may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In certain embodiments, an antibody is said to specifically bind (or immunospecifically bind or react) an antigen when it preferentially recognizes its target antigen in a complex mixture of proteins and/or macromolecules. In preferred embodiments, an antibody is said to specifically bind an antigen when the equilibrium dissociation constant ($K_D$) is less than or equal to $10^{-6}$M or less than or equal to $10^{-7}$M, more preferably when the equilibrium dissociation constant is less than or equal to $10^{-8}$M, and even more preferably when the dissociation constant is less than or equal to $10^{-9}$M.

More directly the term "epitope" is used in its common biochemical sense and refers to that portion of the target antigen capable of being recognized and specifically bound by a particular antibody modulator. When the antigen is a polypeptide such as SEZ6, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect it will be appreciated that, in certain embodiments, an epitope may be associated with, or reside in, one or more regions, domains or motifs of the SEZ6 protein (e.g., amino acids 1-906 of mature isoform 1). As discussed in more detail herein the extracellular region of the SEZ6 protein comprises a series of generally recognized domains including five Sushi domains and two CUB domains along with an N-terminal domain. For the purposes of the instant disclosure the term "domain" will be used in accordance with its generally accepted meaning and will be held to refer to an identifiable or definable conserved structural entity within a protein that exhibits a distinctive secondary structure content. In many cases, homologous domains with common functions will usually show sequence similarities and be found in a number of disparate proteins (e.g., Sushi domains are reportedly found in a large number of different proteins). Similarly, the art-recognized term "motif" will be used in accordance with its common meaning and shall generally refer to a short, conserved region of a protein that is typically ten to twenty contiguous amino acid residues. As discussed throughout, selected embodiments comprise modulators that associate with or bind to an epitope within specific regions, domains or motifs of SEZ6.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising modulator competition or antigen fragment expression on yeast is set forth in Examples 9 and 10 below.

As used herein, the term "binning" refers to methods used to group or classify antibodies based on their antigen binding characteristics and competition. While the techniques are useful for defining and categorizing modulators of the instant invention, the bins do not always directly correlate with epitopes and such initial determinations of epitope binding may be further refined and confirmed by other art-recognized methodology as described herein. However, as discussed and shown in the Examples below, empirical assignment of antibody modulators to individual bins provides information that may be indicative of the therapeutic potential of the disclosed modulators.

More specifically, one can determine whether a selected reference antibody (or fragment thereof) binds to the same epitope or cross competes for binding with a second test antibody (i.e., is in the same bin) by using methods known in the art and set forth in the Examples herein. In one embodiment, a reference antibody modulator is associated with SEZ6 antigen under saturating conditions and then the ability of a secondary or test antibody modulator to bind to SEZ6 is determined using standard immunochemical techniques. If the test antibody is able to substantially bind to SEZ6 at the same time as the reference anti-SEZ6 antibody, then the secondary or test antibody binds to a different epitope than the primary or reference antibody. However, if the test antibody is not able to substantially bind to SEZ6 at the same time, then the test antibody binds to the same epitope, an overlapping epitope, or an epitope that is in close proximity (at least sterically) to the epitope bound by the primary antibody. That is, the test antibody competes for antigen binding and is in the same bin as the reference antibody.

The term "compete" or "competing antibody" when used in the context of the disclosed modulators means competition between antibodies as determined by an assay in which a test antibody or immunologically functional fragment under test prevents or inhibits specific binding of a reference antibody to a common antigen. Typically, such an assay involves the use of purified antigen (e.g., SEZ6 or a domain or fragment thereof) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess and/or allowed to bind first. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 30%, 40%, 45%, 50%, 55%, 60%, 65%, 70% or 75%. In some instance, binding is inhibited by at least 80%, 85%, 90%, 95%, or 97% or more.

Conversely, when the reference antibody is bound it will preferably inhibit binding of a subsequently added test antibody (i.e., a SEZ6 modulator) by at least 30%, 40%, 45%, 50%, 55%, 60%, 65%, 70% or 75%. In some instances binding of the test antibody is inhibited by at least 80%, 85%, 90%, 95%, or 97% or more.

With regard to the instant invention, and as set forth in the Examples 9 and 10 below, it has been determined (via surface plasmon resonance or bio-layer interferometry) that the extracellular domain of SEZ6 defines at least seven bins by competitive binding termed "bin A" to "bin F" and bin U herein.

In this respect, and as known in the art and detailed in the Examples below, the desired binning or competitive binding data can be obtained using solid phase direct or indirect radioimmunoassay (RIA), solid phase direct or indirect enzyme immunoassay (EIA or ELISA), sandwich competition assay, a BIACORE™ 2000 system (i.e., surface plasmon resonance GE Healthcare), a FORTEBIO® Analyzer (i.e., bio-layer interferometry—FORTEBIO®, Inc.) or flow cytometric methodology. The term "surface plasmon resonance," as used herein, refers to an optical phenomenon that allows for the analysis of real-time specific interactions by detection of alterations in protein concentrations within a biosensor matrix. The term "bio-layer interferometry" refers to an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. In particularly preferred embodiments the analysis (whether surface plasmon resonance, bio-layer interferometry or flow cytometry) is performed using a BIACORE™ or FORTEBIO® instrument or a flow cytometer (e.g., FACSARIA II®) as demonstrated in the Examples below.

In order to further characterize the epitopes that the disclosed SEZ6 antibody modulators associate with or bind to, domain-level epitope mapping was performed using a modification of the protocol described by Cochran et al. (J Immunol Methods. 287 (1-2):147-158 (2004) Which is incorporated herein by reference). Briefly, individual domains of SEZ6 comprising specific amino acid sequences were expressed on the surface of yeast and binding by each SEZ6 antibody was determined through flow cytometry. The results are discussed below in Example 10 and shown in FIGS. 14A and 14B.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety). In other embodiments Modification-Assisted Profiling (MAP), also known as Antigen Structure-based Antibody Profiling (ASAP) provides a method that categorizes large numbers of monoclonal antibodies (mAbs) directed against the same antigen according to the similarities of the binding profile of each antibody to chemically or enzymatically modified antigen surfaces (U.S.P.N. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. It will be appreciated that MAP may be used to sort the hSEZ6 antibody modulators of the invention into groups of antibodies binding different epitopes.

Agents useful for altering the structure of the immobilized antigen include enzymes such as proteolytic enzymes (e.g., trypsin, endoproteinase Glu-C, endoproteinase Asp-N, chymotrypsin, etc.). Agents useful for altering the structure of the immobilized antigen may also be chemical agents, such as, succinimidyl esters and their derivatives, primary amine-containing compounds, hydrazines and carbohydrazines, free amino acids, etc.

The antigen protein may be immobilized on either biosensor chip surfaces or polystyrene beads. The latter can be processed with, for example, an assay such as multiplex LUMINEX® detection assay (LUMINEX® Corp.). Because of the capacity of LUMINEX® to handle multiplex analysis with up to 100 different types of beads, LUMINEX® provides almost unlimited antigen surfaces with various modifications, resulting in improved resolution in antibody epitope profiling over a biosensor assay.

E. Modulator Binding Characteristics

Besides epitope specificity the disclosed antibodies may be characterized using physical characteristics such as, for example, binding affinities. In this regard the present invention further encompasses the use of antibodies that have a high binding affinity for one or more SEZ6 isoforms or, in the case of pan-antibodies, more than one member of the SEZ6 family.

The term "$K_D$", as used herein, is intended to refer to the dissociation constant of a particular antibody-antigen interaction. An antibody of the invention is said to immunospecifically bind its target antigen when the dissociation constant $K_D$ ($k_{off}/k_{on}$) is $\leq 0^{-7}$M. The antibody specifically binds antigen with high affinity when the $K_D$ is $\leq 5 \times 10^{-9}$M, and with very high affinity when the $K_D$ is $\leq 5 \times 10^{-10}$M. In one embodiment of the invention, the antibody has a $K_D$ of $\leq 10^{-9}$M and an off-rate of about $1 \times 10^{-4}$/sec. In one embodiment of the invention, the off-rate is $<1 \times 10^{-5}$/sec. In other embodiments of the invention, the antibodies will bind to SEZ6 with a $K_D$ of between about $10^{-7}$M and $10^{-10}$M, and in yet another embodiment it will bind with a $K_D \leq 2 \times 10^{-10}$M. Still other selected embodiments of the present invention comprise antibodies that have a disassociation constant or $K_D$ ($k_{off}/k_{on}$) of less than $10^{-2}$M, less than $5 \times 10^{-2}$M, less than $10^{-3}$M, less than $5 \times 10^{-3}$M, less than $10^{-4}$M, less than $5 \times 10^{-4}$M, less than $10^{-5}$M, less than $5 \times 10^{-5}$M, less than $10^{-6}$M, less than $5 \times 10^{-6}$M, less than $10^{-7}$M, less than $5 \times 10^{-7}$M, less than $10^{-8}$M, less than $5 \times 10^{-8}$M, less than $10^{-9}$M, less than $5 \times 10^{-9}$M, less than $10^{-10}$M, less than $5 \times 10^{-10}$M, less than $10^{-11}$M, less than $5 \times 10^{-11}$M, less than $10^{-12}$M, less than $5 \times 10^{-12}$M, less than $10^{-13}$M, less than $5 \times 10^{-13}$M, less than $10^{-14}$M, less than $5 \times 10^{-14}$M, less than $10^{-15}$M or less than $5 \times 10^{-15}$M.

In specific embodiments, an antibody of the invention that immunospecifically binds to SEZ6 has an association rate constant or $k_{on}$, (or $k_a$) rate (SEZ6 (Ab)+antigen $(Ag)^k_{on} \leftarrow Ab-Ag$) of at least $10^5 M^{-1}s^{-1}$, at least $2 \times 10^5 M^{-1}s^{-1}$, at least $5 \times 10^5 M^{-1}s^{-1}$, at least $10^6 M^{-1}s^{-1}$, at least $5 \times 10^6 M^{-1}s^{-1}$, at least $10^7 M^{-1}s^{-1}$, at least $5 \times 10^7 M^{-1}s^{-1}$, or at least $10^8 M^{-1}s^{-1}$.

In another embodiment, an antibody of the invention that immunospecifically binds to SEZ6 has a disassociation rate constant or $k_{off}$ (or $k_d$) rate (SEZ6 (Ab)+antigen $(Ag)^k_{off} \leftarrow$ (Ab–Ag) of less than $10^{-1}s^{-1}$, less than $5 \times 10^{-1}s^{-1}$, less than $10^{-2}s^{-1}$, less than $5 \times 10^{-2}s^{-1}$, less than $10^{-3}s^{-1}$, less than $5 \times 10^{-3}s^{-1}$, less than $10^{-4}s^{-1}$, less than $5 \times 10^{-4}s^{-1}$, less than $10^{-5}s^{-1}$, less than $5 \times 10^{-5}s^{-1}$, less than $10^{-6}s^{-1}$, less than $5 \times 10^{-6}s^{-1}$ less than $10^{-7}s^{-1}$, less than $5 \times 10^{-7}s^{-1}$, less than $10^{-8}s^{-1}$, less than $5 \times 10^{-8}s^{-1}$, less than $10^{-9}s^{-1}$, less than $5 \times 10^{-9}s^{-1}$ or less than $10^{-10}s^{-1}$.

In other selected embodiments of the present invention anti-SEZ6 antibodies will have an affinity constant or ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12} M^{-1}$, at least $5 \times 10^{12} M^{-M}$, at least $10^{13} M^{-1}$, at least $5 \times 10^{13} M^{-1}$, at least $10^{14} M^{-1}$, at least $5 \times 10^{14} M^{-1}$, at least $10^{15} M^{-1}$ or at least $5 \times 10^{15} M^{-1}$.

Besides the aforementioned modulator characteristics antibodies of the instant invention may further be characterized using additional physical characteristics including, for example, thermal stability (i.e., melting temperature; Tm), and isoelectric points. (See, e.g., Bjellqvist et al., 1993, Electrophoresis 14:1023; Vermeer et al., 2000, Biophys. J. 78:394-404; Vermeer et al., 2000, Biophys. J. 79: 2150-2154 each of which is incorporated by reference).

VIII. Conjugated Modulators

A. Overview

Once the modulators of the invention have been generated and/or fabricated and selected according to the teachings herein they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. It will be appreciated that, unless otherwise dictated by context, the term "antibody-drug conjugate" or "ADC" or the formula M[L-D]n shall be held to encompass conjugates comprising both therapeutic and diagnostic moieties. In such embodiments antibody-drug conjugate compounds will comprise a SEZ6 modulator (typically an anti-SEZ6 antibody) as the modulator or cellular binding unit (abbreviated as CBA, M, or Ab herein), a therapeutic (e.g., anti-cancer agent) or diagnostic moiety (D), and optionally a linker (L) that joins the drug and the antigen binding agent. For the purposes of the instant disclosure "n" shall be held to mean an integer from 1 to 20. In a preferred embodiment, the modulator is a SEZ6 mAb comprising at least one CDR from the heavy and light chain variable regions as described above.

Those skilled in the art will appreciate that a number of different reactions are available for the attachment or association of therapeutic or diagnostic moieties and/or linkers to binding agents. In selected embodiments this may be accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates and azlactones can also be used as coupling agents for covalently attaching drugs to binding agents.

In other embodiments the disclosed modulators of the invention may be conjugated or associated with proteins, polypeptides or peptides that impart selected characteristics (e.g., biotoxins, biomarkers, purification tags, etc.). In certain preferred embodiments the present invention encompasses the use of modulators or fragments thereof recombinantly fused or chemically conjugated (including both covalent and non-covalent conjugations) to a heterologous protein or peptide wherein the protein or peptide comprises at least 10, at least 20, at least 30, at least 40, at least 50, at least 60, at least 70, at least 80, at least 90 or at least 100 amino acids. The construct does not necessarily need to be directly linked, but may occur through amino acid linker sequences. For example, antibodies may be used to target heterologous polypeptides to particular cell types expressing SEZ6, either in vitro or in vivo, by fusing or conjugating the modulators of the present invention to antibodies specific for particular cell surface receptors to provide bispecific constructs. Moreover, modulators fused or conjugated to heterologous polypeptides may also be used in in vitro immunoassays and may be particularly compatible with purification methodology (e.g., his-tags) as is known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428.4432; and Fell et al., 1991, J. Immunol. 146:2446-2452.

B. Linkers

Besides the aforementioned peptide linkers or spacers, it will be appreciated that several other varieties or types of linker may be used to associate the disclosed modulators with pharmaceutically active or diagnostic moieties or biocompatible modifiers. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

The linkers of the ADC are preferably stable extracellularly, prevent aggregation of ADC molecules and keep the ADC freely soluble in aqueous media and in a monomeric state. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

To this end certain embodiments of the invention comprise the use a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since Cathepsin-B has been found to be highly expressed in cancerous tissue. Other examples of such linkers are described, for example, in U.S. Pat. No. 6,214,345 and U.S.P.N. 2012/0078028 each of which incorporated herein by reference in its entirety. In a specific preferred embodiment, the peptidyl linker cleavable by an intracellular protease is a Val-Cit linker, an Ala-Val linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA. (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyldithio)toluene). In yet other specific embodiments, the linker is a malonate linker (Johnson et al., 1995, *Anticancer Res.* 15:1387-93), a maleimidobenzoyl linker (Lau et al., 1995, *Bioorg-Med-Chem,* 3(10):1299-1304), or a 3'-N-amide analog (Lau et al., 1995, *Bioorg-Med-Chem.* 3(10):1305-12). In yet other embodiments, the linker unit is not cleavable and the drug is released by antibody degradation. (See U.S. Publication No. 2005/0238649 incorporated by reference herein in its entirety and for all purposes).

More particularly, in preferred embodiments (set forth in U.S.P.N. 2011/0256157 which is incorporated herein by reference in its entirety) compatible linkers will comprise:

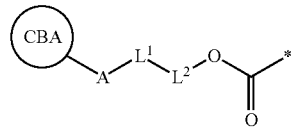

where the asterisk indicates the point of attachment to the cytotoxic agent, CBA is a cell binding agent/modulator, $L^1$ is a linker, A is a connecting group connecting $L^1$ to the cell binding agent, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g.

acid or base labile), temperature or upon irradiation (e.g. photolabile) may also be used. Linkers that are cleavable under reducing or oxidising conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of $R^{10}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:
—C(=O)NH—, —C(=O)O—, —NHC(=O)—, —OC(=O)—, —OC(=O)O—, —NHC(=O)O—, OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in; (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, $^3$H, $^{14}$C, $^{15}$N), protected forms, and racemic mixtures thereof.

In one embodiment, —C(=O)O— and $L^2$ together form the group:

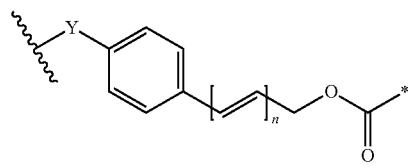

where the asterisk indicates the point of attachment to the drug or cytotoxic agent position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

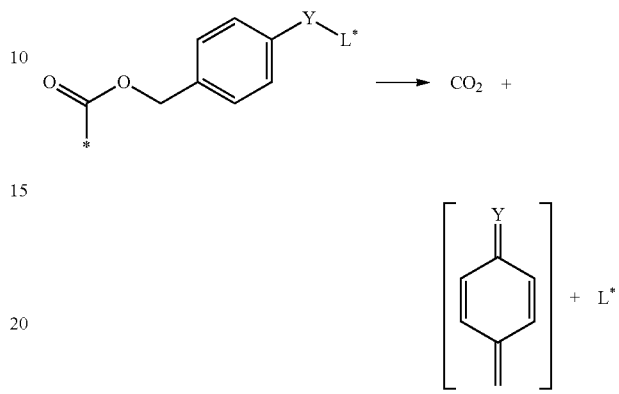

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

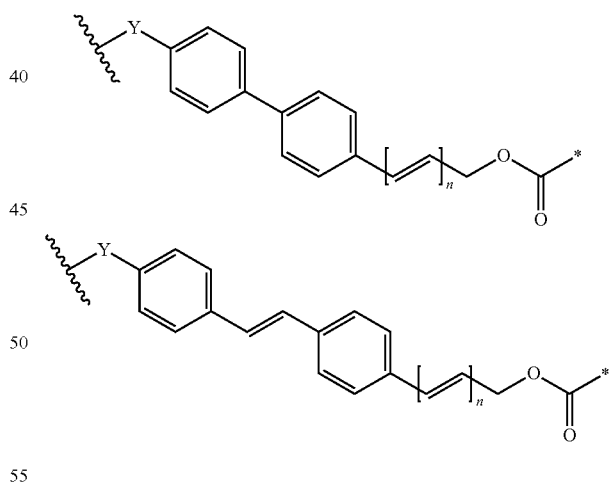

where the asterisk, the wavy line, Y, and ii are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

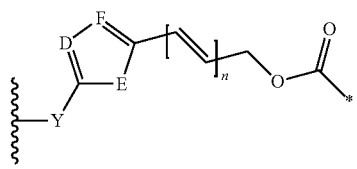

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the linker is a cathepsin labile linker.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
-Phe-Lys-, -Val-Ala-, -Val-Lys-, -Ala-Lys-, -Val-Cit-, -Phe-Cit-, -Leu-Cit-, -Ile-Cit-, -Phe-Arg- and -Trp-Cit- where Cit is citrulline.

Preferably, the group —$X_1$—$X_2$— in dipeptide, —NH—$X_1$—$X_2$—CO—, is selected from:
-Phe-Lys-, -Val-Ala-, -Val-Lys-, -Ala-Lys-, and -Val-Cit-.

Most preferably, the group —$X_1$—$X_2$— in dipeptide, —NH—$X_1$—$X_2$—CO—, is -Phe-Lys- or -Val-Ala-.

Other dipeptide combinations may be used, including those described by Dubowchik et al, *Bioconjugate Chemistry*, 2002, 13, 855-869, which is incorporated herein by reference.

In one embodiment, the amino acid side chain is derivatised, where appropriate. For example, an amino group or carboxy group of an amino acid side chain may be derivatised.

In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. Protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:
Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO—PABC—. The PABC group is connected directly to the cytotoxic agent. Preferably, the self-immolative linker and the dipeptide together form the group —NH-Phe-Lys-CO—NH—PABC—, which is illustrated below:

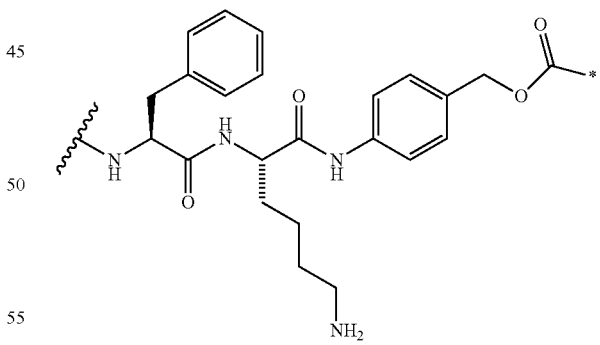

where the asterisk indicates the point of attachment to the selected cytotoxic moiety, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Aloe, as described above.

Alternatively, the self-immolative linker and the dipeptide together form the group —NH-Val-Ala-CO—NH—PABC— which is illustrated below:

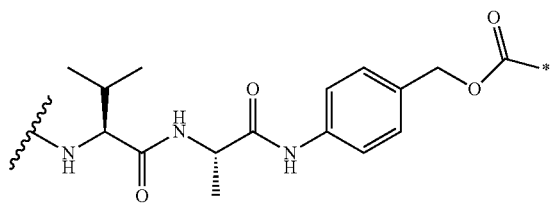 [SMILES: *N[C@H](C(=O)N[C@@H](C)C(=O)Nc1ccc(COC(*)=O)cc1)C(C)C]

where the asterisk and the wavy line are as defined above.

Alternatively, the self-immolative linker and the dipeptide together form the group —NH-Val-Cit-CO—NH—PABC—, which is illustrated below:

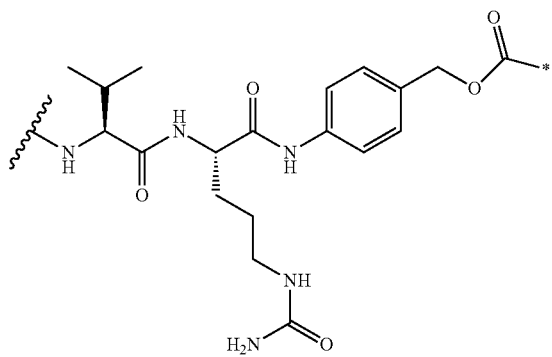 [SMILES: *N[C@H](C(=O)N[C@@H](CCCNC(N)=O)C(=O)Nc1ccc(COC(*)=O)cc1)C(C)C]

where the asterisk and the wavy line are as defined above.

In some embodiments of the present invention, it may be preferred that if the drug moiety contains an unprotected imine bond, e.g. if moiety B is present, then the linker does not contain a free amino ($H_2N$—) group. Thus if the linker has the structure -A-$L^1$-$L^2$- then this would preferably not contain a free amino group. This preference is particularly relevant when the linker contains a dipeptide, for example as $L^1$; in this embodiment, it would be preferred that one of the two amino acids is not selected from lysine.

Without wishing to be bound by theory, the combination of an unprotected imine bond in the drug moiety and a free amino group in the linker can cause dimerisation of the drug-linker moiety which may interfere with the conjugation of such a drug-linker moiety to an antibody. The cross-reaction of these groups may be accelerated in the case the free amino group is present as an ammonium ion ($H_3N^+$—), such as when a strong acid (e.g., TFA) has been used to deprotect the free amino group.

In one embodiment, A is a covalent bond. Thus, $L^1$ and the cell binding agent are directly connected. For example, where $L^1$ comprises a contiguous amino acid sequence, the N-terminus of the sequence may connect directly to the cell binding agent.

Thus, where A is a covalent bond, the connection between the cell binding agent and $L^1$ may be selected from:
—C(=O)NH—, —C(=O)O—, —NHC(=O)—, —OC(=O)—, —OC(=O)O—, —NHC(=O)O—, —OC(=O)NH—, —NHC(=O)NH—, —C(=O)NHC(=O)—, —S—, —S—S—, —$CH_2$C(=O)—, and =N—NH—.

An amino group of $L^1$ that connects to the SEZ6 modulator may be the N-terminus of an amino acid or may be derived from an amino group of an amino acid side chain, for example a lysine amino acid side chain.

A carboxyl group of $L^1$ that connects to the modulator may be the C-terminus of an amino acid or may be derived from a carboxyl group of an amino acid side chain, for example a glutamic acid amino acid side chain.

A hydroxyl group of $L^1$ that connects to the cell binding agent may be derived from a hydroxyl group of an amino acid side chain, for example a serine amino acid side chain.

A thiol group of $L^1$ that connects to a modulator agent may be derived from a thiol group of an amino acid side chain, for example a serine amino acid side chain.

The comments above in relation to the amino, carboxyl, hydroxyl and thiol groups of $L^1$ also apply to the cell binding agent.

In one embodiment, $L^2$ together with —OC(=O)— represents:

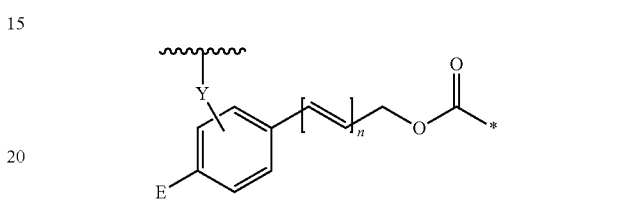

where the asterisk indicates the point of attachment to the N10 position, the wavy line indicates the point of attachment to $L^1$, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, $NO_2$, R air OR. Preferably n is 0 or 1, most preferably 0.

E is selected such that the group is susceptible to activation, e.g. by light or by the action of an enzyme. E may be —$NO_2$ or glucoronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

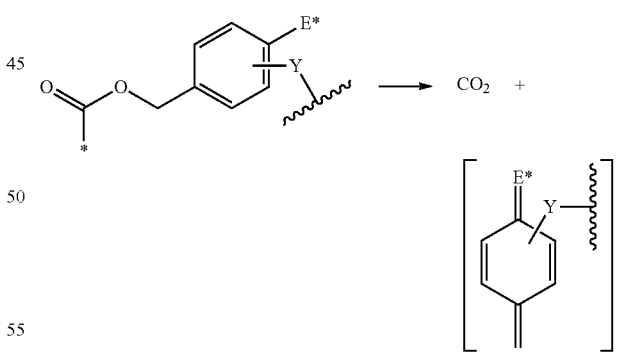

where the asterisk indicates the point of attachment to the N10 position, E* is the activated form of E, and Y is as described above. These groups have the advantage of separating the site of activation from the compound being protected. As described above, the phenylene group may be optionally further substituted.

The group Y may be a covalent bond to $L^1$.

The group Y may be a functional group selected from:
—C(=O)—, —NH—, —O—, —C(=O)NH—, —C(=O)O—, —NHC(=O)—, —OC(=O)—, —OC (=O)O—, —NHC(=O)O—, —OC(=O)NH—, —NHC(=O)NH—, —NHC(=O)NH, —C(=O)NHC(=O)—, and —S—.

Where L¹ is a dipeptide, his preferred that Y is —NH— or —C(=O)—, thereby to form an amide bond between L¹ and Y. In this embodiment, the dipeptide sequence need not be a substrate for an enzymatic activity.

In another embodiment, A is a spacer group. Thus, L¹ and the cell binding agent are indirectly connected.

L¹ and A may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

Preferably, the linker contains an electrophilic functional group for reaction with a nucleophilic functional group on the modulator. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

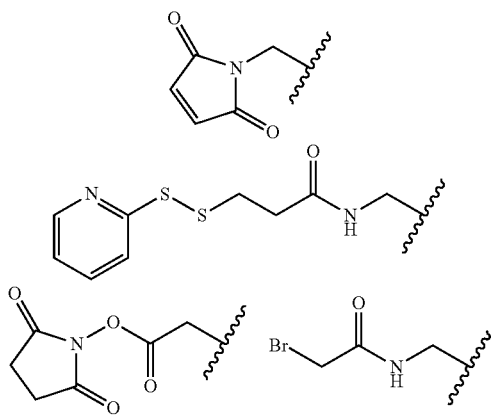

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Trout's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, a linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

In one embodiment, the group A is:

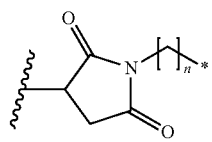

where the asterisk indicates the point of attachment to L¹, the wavy line indicates the point of attachment to the cell binding agent, and n is 0 to 6. In one embodiment, a is 5.

In one embodiment, the group A is:

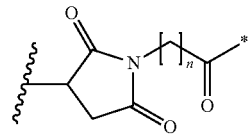

where the asterisk indicates the point of attachment to L¹, the wavy line indicates the point of attachment to the cell binding agent, and n is 0 to 6. In one embodiment, n is 5.

In one embodiment, the group A is:

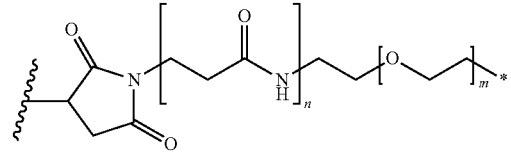

where the asterisk indicates the point of attachment to L¹, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

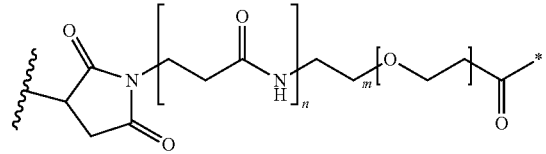

where the asterisk indicates the point of attachment to L¹, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the connection between the cell binding agent and A is through a thiol residue of the cell binding agent and a maleimide group of A.

In one embodiment, the connection between the cell binding agent and A is:

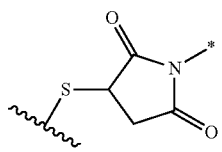 [SMILES: *SC1CC(=O)N(*)C1=O]

where the asterisk indicates the point of attachment to the remaining portion of A and the wavy line indicates the point of attachment to the remaining portion of the cell binding agent. In this embodiment, the S atom is typically derived from the modulator.

In each of the embodiments above, an alternative functionality may be used in place of the maleimide-derived group shown below:

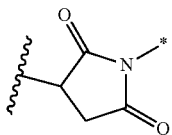 [SMILES: *C1CC(=O)N(*)C1=O]

where the wavy line indicates the point of attachment to the cell binding agent as before, and the asterisk indicates the bond to the remaining portion of the A group.

In one embodiment, the maleimide-derived group is replaced with the group:

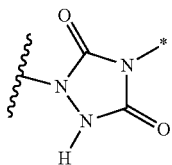 [SMILES: *n1[nH]c(=O)n(*)c1=O]

where the wavy line indicates point of attachment to the cell binding agent, and the asterisk indicates the bond to the remaining portion of the A group.

In one embodiment, the maleimide-derived group is replaced with a group, which optionally together with the cell binding agent, is selected from:
—C(=O)NH—, —C(=O)O—, —NHC(=O)—, —OC(=O)—, —OC(=O)O—, —NHC(=O)O—, —OC(=O)NH—, —NHC(=O)NH—, —NHC(=O)NH, —C(=O)NHC(=O)—, —S—, —S—S—, —CH₂C(=O)—, —C(=O)CH₂—, =N—NH— and —NH—N=.

In one embodiment, the maleimide-derived group is replaced with a group, which optionally together with the cell binding agent, is selected from:

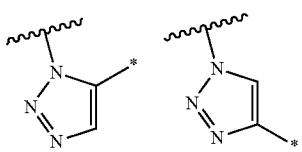 [SMILES: *c1cnnn1* ; *c1cn(*)nn1]

where the wavy line indicates either the point of attachment to the cell binding agent or the bond to the remaining portion of the A group, and the asterisk indicates the other of the point of attachment to the cell binding agent or the bond to the remaining portion of the A group.

Other groups suitable for connecting $L^1$ to the selected modulator are described in WO 2005/082023.

In another preferred embodiment the modulators of the instant invention may be associated with biocompatible polymers comprising drug linker units. In this respect one such type of compatible polymer comprises FLEXIMER® polymers (Mersana Therapeutics). Such polymers are reportedly biodegradable, well tolerated and have been clinically validated. Moreover, such polymers are compatible with a number of customizable linker technologies and chemistries allowing for control of pharmacokinetics, localization of drug release and improved biodistribution.

The selected modulators can also be directly conjugated radioisotopes or may comprise macrocyclic chelators useful for conjugating radiometal ions (as described herein). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

More generally, techniques for conjugating therapeutic moieties or cytotoxic agents to modulators are well known. As discussed above moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119.

In preferred embodiments a SEZ6 modulator that is conjugated to a therapeutic moiety or cytotoxic agent may be internalized by a cell upon binding to a SEZ6 molecule associated with the cell surface thereby delivering the therapeutic payload.

C. Biocompatible Modifiers

In selected embodiments the modulators of the invention may be conjugated or otherwise associated with biocompatible modifiers that may be used to adjust, alter, improve or moderate modulator characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored).

PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

D. Diagnostic or Detection Agents

In other preferred embodiments, modulators of the present invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled modulators can be useful for monitoring the development or progression of a hyperproliferative disorder or as part of a clinical testing procedure to determine the efficacy of a particular therapy including the disclosed modulators (i.e. theragnostics) or to determine a future course of treatment. Such markers or reporters may also be useful in purifying the selected modulator, modulator analytics (e.g., epitope binding or antibody binning), separating or isolating TIC or in preclinical procedures or toxicology studies.

Such diagnosis analysis and/or detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In preferred embodiments, the marker comprises a his-tag such as that provided by the pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

E. Therapeutic Moieties

As previously alluded to the modulators or fragments or derivatives thereof may also be conjugated, linked or fused to or otherwise associated with a "therapeutic moiety" or "drug" such as an anti-proliferative or anti-cancer agent including, but not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents.

Preferred exemplary anti-cancer agents include cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional compatible cytotoxins comprise dolastatins and auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (Spirogen, Ltd.), splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins. Furthermore, in certain embodiments the SEZ6 modulators of the instant invention may be associated with anti-CD3 binding molecules to recruit cytotoxic T-cells and have them target the tumor initiating cells (BiTE technology; see e.g., Fuhrmann, S. et. al, Annual Meeting of AACR Abstract No. 5625 (2010) which is incorporated herein by reference).

Still additional compatible anti-cancer agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa, chlorambucil, melphalan, carmustine (BCNU) and lomustine (CCNU), busulfan, dibromomannitol, streptozotocin, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

As indicated above selected embodiments of the instant invention are directed to conjugated SEZ6 modulators such as anti-SEZ6 antibody drug conjugates that comprise pyrrolobenzodiazepine (PBD) as a cytotoxic agent. It will be appreciated that PBDs are alkylating agents that exert antitumor activity by covalently binding to DNA in the minor groove and inhibiting nucleic acid synthesis. In this respect PBDs have been shown to have potent antitumor properties while exhibiting minimal bone marrow depression. PBDs compatible with the present invention may be linked to the SEZ6 modulator using any one of several types of linker (e.g., a peptidyl linker comprising a maleimido moiety with a free sulfhydryl) and, in certain embodiments are dimeric in form (i.e., PBD dimers). Compatible PBDs (and optional linkers) that may be conjugated to the disclosed modulators are described, for example, in U.S. Pat. Nos. 6,362,331, 7,049,311, 7,189,710, 7,429,658, 7,407,951, 7,741,319, 7,557,099, 8,034,808, 8,163,736 U.S.P.N. 2011/0256157 and PCT filings WO2011/130613, WO2011/128650 and WO2011/130616 each of which is incorporated herein by reference. Accordingly, in particularly preferred embodiments the modulator will comprise an anti SEZ6 antibody conjugated or associated with one or more PBD dimers (i.e., a SEZ6-PBD ADC).

In particularly preferred embodiments compatible PBDs that may be conjugated to the disclosed modulators are described in U.S.P.N, 2011/0256157. In this disclosure, PBD dimers, i.e. those comprising two PBD moieties may be preferred. Thus, preferred conjugates of the present invention are those having the formula (AB) or (AC):

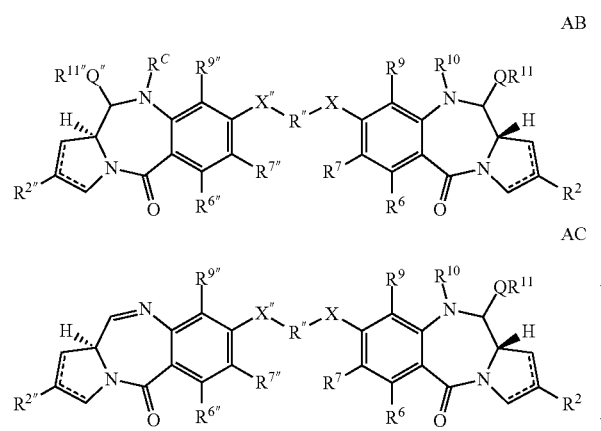

AB

AC wherein:
the dotted lines indicate the optional presence of a double bond between C1 and C2 or C2 and C3;
$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo;
where $R^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;
$R^7$ is independently selected from H, R, OH, OR, SH, SR, NH$_2$, NHR, NRR', NO$_2$, Me$_3$Sn and halo;
$R^{10}$ is a linker connected to a modulator or fragment or derivative thereof, as described above;
Q is independently selected from O, S and NH;
$R^{11}$ is either H, or R or, where Q is O, SO$_3$M, where M is a metal cation;
R and R' are each independently selected from optionally substituted. C$_{1-12}$ alkyl, C$_{3-20}$ heterocyclyl and C$_{5-20}$ aryl groups, and optionally in relation to the group NRR', R and R' together with the nitrogen atom to which they are attached form an optionally substituted 4-, 5-, 6 or 7-membered heterocyclic ring; and
wherein $R^{2''}$, $R^{6''}$, $R^{7''}$, $R^{9''}$, X", Q" and $R^{11''}$ and are as defined according to $R^2$, $R^6$, $R^7$, $R^9$, X, Q and $R^{11}$ respectively, and $R^C$ is a capping group.

Double Bond

In one embodiment, there is no double bond present between C1 and C2, and C2 and C3.

In one embodiment, the dotted lines indicate the optional presence of a double bond between C2 and C3, as shown below:

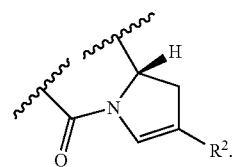

In one embodiment, a double bond is present between C2 and C3 when $R^2$ is C$_{5-20}$ aryl or C$_{1-12}$ alkyl, In one embodiment, the dotted lines indicate the optional presence of a double bond between C1 and C2, as shown below:

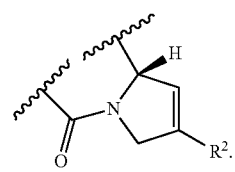

In one embodiment, a double bond is present between C1 and C2 when $R^2$ is C$_{5-20}$ aryl or C$_{1-12}$ alkyl.

$R^2$

In one embodiment, $R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo.

In one embodiment, $R^2$ is independently selected from H, OH, =O, =CH$_2$, CN, R, OR, =CH—R$^D$, =C(R$^D$)$_2$, O—SO$_2$—R, CO$_2$R and COR.

In one embodiment, $R^2$ is independently selected from H, =O, =CH$_2$, R, =CH—R$^D$, and =C(R$^D$)$_2$.

In one embodiment, $R^2$ is independently H.

In one embodiment, $R^2$ is independently =O.

In one embodiment, $R^2$ is independently =CH$_2$.

In one embodiment, $R^2$ is independently =CH—R$^5$. Within the PBD compound, the group =CH—R$^D$ may have either configuration shown below:

(I)

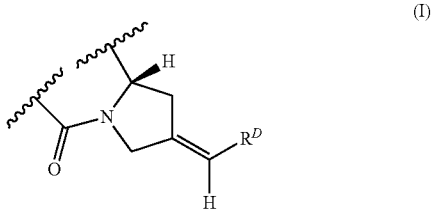

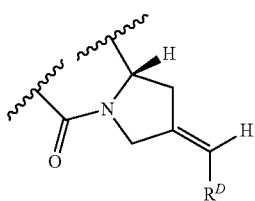
(II)

In one embodiment, the configuration is configuration (I).
In one embodiment, $R^2$ is independently $=C(R^D)_2$.
In one embodiment, $R^2$ is independently $=CF_2$.
In one embodiment, $R^2$ is independently R.
In one embodiment, $R^2$ is independently optionally substituted $C_{5-20}$ aryl.
In one embodiment, $R^2$ is independently optionally substituted $C_{1-12}$ alkyl.
In one embodiment, $R^2$ is independently optionally substituted $C_{5-20}$ aryl.
In one embodiment, $R^2$ is independently optionally substituted $C_{5-7}$ aryl.
In one embodiment, $R^2$ is independently optionally substituted $C_{8-10}$ aryl.
In one embodiment, $R^2$ is independently optionally substituted phenyl.
In one embodiment, $R^2$ is independently optionally substituted napthyl.
In one embodiment, $R^2$ is independently optionally substituted pyridyl.
In one embodiment, R2 is independently optionally substituted quinolinyl or isoquinolinyl.
In one embodiment, $R^2$ bears one to three substituent groups, with 1 and 2 being more preferred, and singly substituted groups being most preferred. The substituents may be any position.
Where $R^2$ is a $C_{5-7}$ aryl group, a single substituent is preferably on a ring atom that is not adjacent the bond to the remainder of the compound, i.e. it is preferably γ or γ to the bond to the remainder of the compound. Therefore, where the $C_{5-7}$ aryl group is phenyl, the substituent is preferably in the meta- or para-positions, and more preferably is in the para-position.
In one embodiment, $R^2$ is selected from:

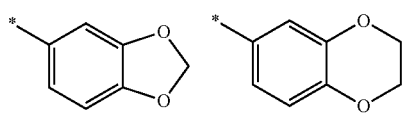

where the asterisk indicates the point of attachment.
Where R is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).
In one embodiment, where $R^2$ is optionally substituted, the substituents are selected from those substituents given in the substituent section below.
Where R is optionally substituted, the substituents are preferably selected from:
Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In one embodiment, where R or $R^2$ is optionally substituted, the substituents are selected from the group consisting of R, OR, SR, NRR', $NO_2$, halo, $CO_2R$, COR, $CONH_2$, CONHR, and CONRR'.

Where $R^2$ is $C_{1-12}$ alkyl, the optional substituent may additionally include $C_{3-20}$ heterocyclyl and $C_{5-20}$ aryl groups.

Where $R^2$ is $C_{3-20}$ heterocyclyl, the optional substituent may additionally include $C_{1-12}$ alkyl and $C_{5-20}$ aryl groups.

Where $R^2$ is $C_{5-20}$ aryl groups, the optional substituent may additionally include $C_{3-20}$ heterocyclyl and $C_{1-12}$ alkyl groups.

It is understood that the term "alkyl" encompasses the sub-classes alkenyl and alkynyl as well as cycloalkyl. Thus, where $R^2$ is optionally substituted $C_{1-12}$ alkyl, it is understood that the alkyl group optionally contains one or more carbon-carbon double or triple bonds, which may form part of a conjugated system. In one embodiment, the optionally substituted $C_{1-12}$ alkyl group contains at least one carbon-carbon double or triple bond, and this bond is conjugated with a double bond present between C1 and C2, or C2 and C3. In one embodiment, the $C_{1-12}$ alkyl group is a group selected from saturated $C_{1-12}$ alkyl, $C_{2-12}$ alkenyl, $C_{2-12}$ alkynyl and $C_{3-12}$ cycloalkyl.

If a substituent on $R^2$ is halo, it is preferably F or Cl, more preferably Cl.

If a substituent on $R^2$ is ether, it may in some embodiments be an alkoxy group, for example, a $C_{1-7}$ alkoxy group (e.g. methoxy, ethoxy) or it may in some embodiments be a $C_{5-7}$ aryloxy group (e.g. phenoxy, pyridyloxy, furanyloxy).

If a substituent on $R^2$ is $C_{1-7}$ alkyl, it may preferably be a $C_{1-4}$ alkyl group (e.g. methyl, ethyl, propyl, butyl), If a substituent on $R^2$ is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If a substituent on $R^2$ is bis-oxy-$C_{1-3}$ alkylene, this is preferably bis-oxy-methylene or bis-oxy-ethylene.

Particularly preferred substituents for $R^2$ include methoxy, ethoxy, fluoro, chloro, cyano, bis-oxy-methylene, methyl-piperazinyl, morpholino and methyl-thienyl.

Particularly preferred substituted $R^2$ groups include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl methoxynaphthyl, and naphthyl.

In one embodiment, $R^2$ is halo or dihalo. In one embodiment, $R^2$ is —F or —$F_2$, which substituents are illustrated below as (III) and (IV) respectively:

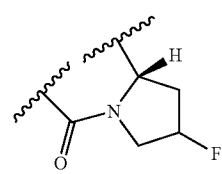
(III)

(IV)

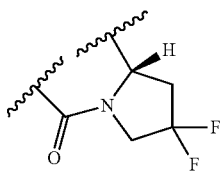

$R^D$

In one embodiment, $R^D$ is independently selected from R, $CO_2R$, COR, CHO, $CO_2H$, and halo.

In one embodiment, $R^D$ is independently R.

In one embodiment, $R^D$ is independently halo.

$R^6$

In one embodiment, $R^6$ is independently selected from H, R, OH, OR, SH, SR, $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

In one embodiment, the compound is a dimer where the $R^7$ groups of each monomer form together a dimer bridge having the formula X—R"—X linking the monomers.

$R^8$

In one embodiment, the compound is a dimer where the $R^8$ groups of each monomer form together a dimer bridge having the formula X—R"—X linking the monomers.

In one embodiment, $R^8$ is independently $OR^{8A}$, where $R^{8A}$ is independently optionally substituted $C_{1-4}$ alkyl.

In one embodiment, $R^{8A}$ is independently optionally substituted saturated $C_{1-6}$ alkyl or optionally substituted $C_{2-4}$ alkenyl.

In one embodiment, $R^{8A}$ is independently Me.

In one embodiment, $R^{8A}$ is independently $CH_2Ph$.

In one embodiment, $R^{8A}$ is independently allyl.

In one embodiment, $R^8$ and $R^7$ together form a group —O—$(CH_2)_p$—O—, where p is 1 or 2.

In one embodiment, $R^8$ and $R^9$ together form a group —O—$(CH_2)_p$—O—, where p is 1 or 2.

$R^9$

In one embodiment, $R^9$ is independently selected from H, R, OH, OR, SH, SR, $NH_2$, NHR, NRR', $NO_2$, $Me_3Sn$— and Halo.

In one embodiment, $R^9$ is independently H.

In one embodiment, $R^9$ is independently R or OR.

R and R'

In one embodiment, R is independently selected from optionally substituted $C_{1-12}$ alkyl, $C_{3-20}$ heterocyclyl and $C_{5-20}$ aryl groups. These groups are each defined in the substituents section below.

In one embodiment, R is independently optionally substituted $C_{1-12}$ alkyl.

In one embodiment, R is independently optionally substituted $C_{3-20}$ heterocyclyl.

In one embodiment, R is independently optionally substituted $C_{5-20}$ aryl.

In one embodiment, R is independently optionally substituted $C_{1-12}$ alkyl.

Described above in relation to $R^2$ are various embodiments relating to preferred alkyl and aryl groups and the identity and number of optional substituents. The preferences set out for $R^2$ as it applies to R are applicable, where appropriate, to all other groups R, for examples where $R^6$, $R^7$, $R^8$ or $R^9$ is R.

The preferences for R apply also to R'.

In some embodiments of the invention there is provided a compound having a substituent group —NRR'. In one embodiment, R and R' together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.

R"

R" is a $C_{3-12}$ alkylene group, which chain may be interrupted by one or more heteroatoms, e.g. O, S, N(H), NMe and/or aromatic rings, e.g. benzene or pyridine, which rings are optionally substituted.

In one embodiment, R" is a $C_{3-12}$ alkylene group, which chain may be interrupted by one or more heteroatoms and/or aromatic rings, e.g. benzene or pyridine.

In one embodiment, the alkylene group is optionally interrupted by one or more heteroatoms selected from O, S, and NMe and/or aromatic rings, which rings are optionally substituted.

In one embodiment, the aromatic ring is a $C_{5-20}$ arylene group, where arylene pertains to a divalent moiety obtained by removing two hydrogen atoms from two aromatic ring atoms of an aromatic compound, which moiety has from 5 to 20 ring atoms.

In one embodiment, R" is a $C_{3-12}$ alkylene group, which chain may be interrupted by one or more heteroatoms, e.g. O, S, N(H), NMe and/or aromatic rings, e.g. benzene or pyridine, which rings are optionally substituted by $NH_2$.

In one embodiment, R" is a $C_{3-12}$ alkylene group.

In one embodiment, R" is selected from a $C_3$, $C_5$, $C_7$, $C_9$ and a $C_{11}$ alkylene group.

In one embodiment, R" is selected from a $C_3$, $C_5$ and a $C_7$ alkylene group.

In one embodiment, R" is selected from a $C_3$ and a $C_5$ alkylene group.

In one embodiment, R" is a $C_3$ alkylene group.

In one embodiment, R" is a $C_5$ alkylene group.

The alkylene groups listed above may be optionally interrupted by one or more heteroatoms and/or aromatic rings, e.g. benzene or pyridine, which rings are optionally substituted.

The alkylene groups listed above may be optionally interrupted by one or more heteroatoms and/or aromatic rings, e.g. benzene or pyridine.

The alkylene groups listed above may be unsubstituted linear aliphatic alkylene groups.

X

In one embodiment, X is selected from O, S, or N(H). Preferably, X is O.

$R^{10}$

Preferably compatible linkers such as those described above attach a SEZ6 modulator (CBA/Ab/M), to a MID drug moiety D through covalent bond(s) at the $R^{10}$ position (i.e., N10). The linker is a bifunctional or multifunctional moiety which can be used to link one or more drug moiety (D) and a modulator (preferably an antibody) to form antibody-drug conjugates (ADC). The linker (L) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, PBD drug moiety (D) or drug-linker reagent (D-L).

Many functional groups on the linker attached to the N10 position of the PBD moiety may be useful to react with the cell binding agent. For example, ester, thioester, amide, thioamide, carbamate, thiocarbamate, urea, thiourea, ether, thioether, or disulfide linkages may be formed from reaction of the linker-PBD drug intermediates and the cell binding agent.

In another embodiment, the linker may be substituted with groups that modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In one preferred embodiment, $R^{10}$ is a group:

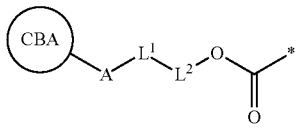

where the asterisk indicates the point of attachment to the N10 position, CBA is a cell binding agent/modulator, $L^1$ is a linker, A is a connecting group connecting $L^1$ to the cell binding agent, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

As discussed in the linker section above the nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidizing conditions may also find use in the present invention.

$L^1$ may comprise a contiguous sequence of amino acids. The amino acid sequence may be the target substrate for enzymatic cleavage, thereby allowing release of $R^{10}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of $R^{10}$ from the N10 position.

In one embodiment, where $L^1$ is cleavable by the action of an enzyme and $L^2$ is present, the enzyme cleaves the bond between $L^1$ and $L^2$.

With regard to attaching the chosen linker to a selected PBD the group $R^C$ is removable from the N10 position of certain PBD moieties to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine.

In one embodiment, $R^C$, may be a protecting group that is removable to leave an N10-C11 imine bond, a carbinolamine, a substituted cabinolamine, or, where $QR^{11}$ is $OSO_3M$, a bisulfite adduct. In one embodiment, $R^C$ is a protecting group that is removable to leave an N10-C11 imine bond.

The group $R^C$ is intended to be removable under the same conditions as those required for the removal of the group $R^{10}$, for example to yield an N10-C11 imine bond, a carbinolamine and so on. The capping group acts as a protecting group for the intended functionality at the N10 position. The capping group is intended not to be reactive towards a cell binding agent. For example, $R^C$ is not the same as $R^L$.

Compounds having a capping group may be used as intermediates in the synthesis of dimers having an imine monomer. Alternatively, compounds having a capping group may be used as conjugates, where the capping group is removed at the target location to yield an imine, a carbinolamine, a substituted cabinolamine and so on. Thus, in this embodiment, the capping group may be referred to as a therapeutically removable nitrogen protecting group, as defined in WO 00/12507.

In one embodiment, the group $R^C$ is removable under the conditions that cleave the linker $R^L$ of the group $R^{10}$. Thus, in one embodiment, the capping group is cleavable by the action of an enzyme.

In an alternative embodiment, the capping group is removable prior to the connection of the linker $R^L$ to the modulator. In this embodiment, the capping group is removable under conditions that do not cleave the linker $R^L$.

Where a compound includes a functional group $G^1$ to form a connection to the cell binding agent, the capping group is removable prior to the addition or unmasking of $G^1$.

The capping group may be used as part of a protecting group strategy to ensure that only one of the monomer units in a dimer is connected to a cell binding agent.

The capping group may be used as a mask for a N10-C11 imine bond. The capping group may be removed at such time as the imine functionality is required in the compound. The capping group is also a mask for a carbinolamine, a substituted cabinolamine, and a bisulfite adduct, as described above.

In one embodiment, $R^C$ is a carbamate protecting group.

In one embodiment, the carbamate protecting group is selected from:

Alloc, Fmoc, Boc, Troc, Teoc, Psec, Cbz and PNZ.

Optionally, the carbamate protecting group is further selected from Moc.

In one embodiment, $R^C$ is a linker group $R^L$ lacking the functional group for connection to the cell binding agent.

This application is particularly concerned with those $R^C$ groups which are carbamates.

In one embodiment, $R^C$ is a group:

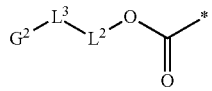

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{10}$.

$L^2$ is as defined above in relation to $R^{10}$.

Various terminating groups are described below, including those based on well known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from: Alloc, Fmoc, Boc, Troc, Teoc, Psec, Cbz and PNZ. Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

where the asterisk indicates the point of attachment to $L^3$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, and preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

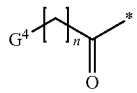

where the asterisk indicates the point of attachment to $L^3$, and n and $G^4$ are as defined above, In one embodiment, the group $G^2$ is:

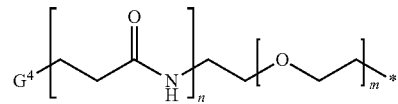

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

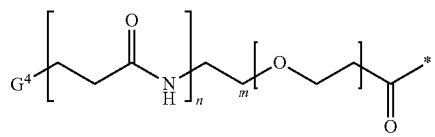

where the asterisk indicates the point of attachment to $L^3$, and n, m and $G^4$ are as defined above.

In one embodiment, the group $G^2$ is:

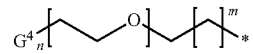

where n is 1-20, m is 0-6, and $G^4$ is selected from OH, OR, SH, SR, COOR, $CONH_2$, CONHR, CONRR', $NH_2$, NHR, NRR', $NO_2$, and halo. In one embodiment, n is 1-10. In another embodiment, n is 10 to 50, preferably 20 to 40. In one embodiment, n is 1. In one embodiment, m is 1. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

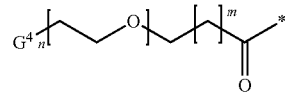

where the asterisk indicates the point of attachment to $L^3$, and n, m and $G^4$ are as defined above.

In each of the embodiments above $G^4$ may be OH, SH, $NH_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or NHR are protected with Boc, Moc, Z—Cl, Fmoc, Z, or Alloc.

In one embodiment, the group $G^2$ is present in combination with a group $L^3$, which group is a dipeptide.

The capping group is not intended for connection to the modulator. Thus, the other monomer present in the dimer serves as the point of connection to the modulator via a linker. Accordingly, it is preferred that the functionality present in the capping group is not available for reaction with a modulator. Thus, reactive functional groups such as OH, SH, $NH_2$, COOH are preferably avoided. However, such functionality may be present in the capping group if protected, as described above.

Thus, in accordance with the teachings herein one embodiment of the invention comprises a conjugate comprising a compound:

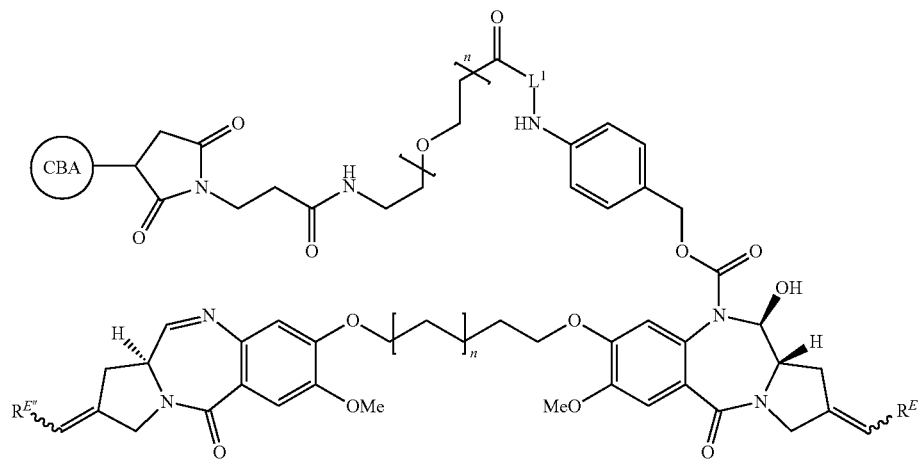

wherein CBA is a cell binding agent/modulator, and n is 0 or 1. $L^1$ is as previously defined, and $R^E$ and $R^{E''}$ are each independently selected from H or $R^D$.

In another embodiment, the conjugate comprises a compound:

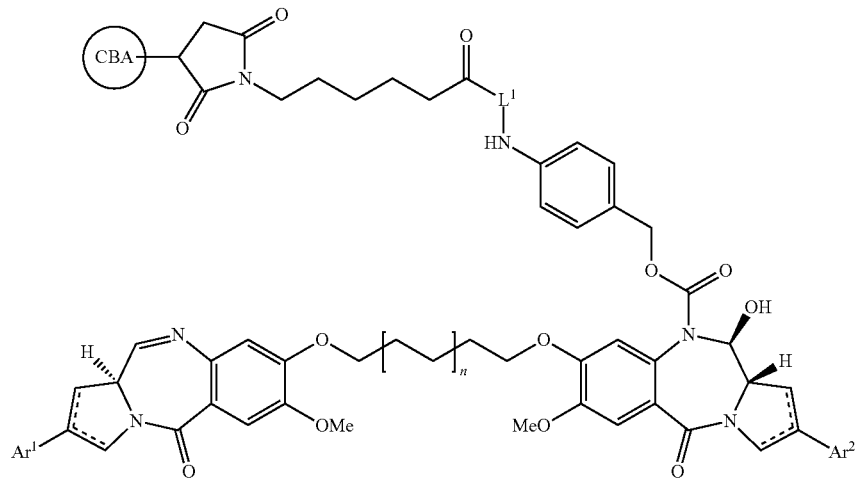

wherein CBA is a cell binding agent/modulator, $L^1$ is as previously defined, $Ar^1$ and $Ar^2$ are each independently optionally substituted $C_{5-20}$ aryl, and n is 0 or 1.

Those of skill in the art will appreciate that other symmetric and asymmetric PBD dimers and linkers are compatible with the instant invention and could be selected without undue experimentation based on the teachings herein and the prior art.

Another aspect of the invention includes ADCs comprising radioisotopes. Exemplary radioisotopes that may be compatible with such embodiments include, but are not limited to, iodine ($^{131}I$, $^{125}I$, $^{123}I$, $^{121}I$), carbon ($^{14}C$), copper ($^{62}Cu$, $^{64}Cu$, $^{67}Cu$), sulfur ($^{35}S$), tritium ($^{3}H$), indium ($^{115}In$, $^{113}In$, $^{112}In$, $^{111}In$), bismuth ($^{212}Bi$, $^{213}Bi$), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, $^{117}Sn$, $^{225}Ac$, $^{76}Br$, and $^{211}At$. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

SEZ6 modulators of the present invention may also be conjugated to a therapeutic moiety or drug that modifies a given biological response (e.g., biological response modifiers or BRMs). That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337 each of which is incorporated herein by reference. Moreover, as set forth above the association of a modulator with such moieties does not necessarily need to be direct, but may occur through linker sequences. As previously alluded to, such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

IX. Diagnostics and Screening

A. Diagnostics

In yet other embodiments, the invention provides in vitro or in vivo methods for detecting, diagnosing or monitoring proliferative disorders and methods of screening cells from a patient to identify tumorigenic cells including CSCs. Such methods include identifying an individual having cancer for treatment or monitoring progression of a cancer comprising contacting the patient or a sample obtained from a patient (i.e. either in vivo or in vitro) with a modulator as described herein and detecting presence or absence, or level of association, of the modulator to bound or free target molecules in the sample. In particularly preferred embodiments the modulator will comprise a detectable label or reporter molecule as described herein.

In some embodiments, the association of the modulator, such as an antibody, with particular cells in the sample likely denotes that the sample may contain CSCs, thereby indicating that the individual having cancer may be effectively treated with a modulator as described herein. The methods may further comprise a step of comparing the level of binding to a control. Conversely, when the modulator is a Fc-construct, the binding properties may be exploited and monitored (directly or indirectly, in vivo or in vitro) when in contact with the sample to provide the desired information.

Exemplary compatible assay methods include radioimmunoassays, enzyme immunoassays, competitive-binding assays, fluorescent immunoassay, immunoblot assays, Western Blot analysis, flow cytometry assays, and ELISA assays. Compatible in vivo theragnostics or diagnostics may comprise art-recognized imaging or monitoring techniques such as magnetic resonance imaging, computerized tomography (e.g. CAT scan), positron tomography (e.g., PET scan) radiography, ultrasound, etc., as would be known by those skilled in the art.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in-vivo. In another embodiment, the size and shape of secondary tumors are analyzed. In some embodiments, further ex viva analysis is performed.

In another embodiment, the invention provides a method of analyzing cancer progression and/or pathogenesis in vivo including determining cell metastasis or detecting and quantifying the level of circulating tumor cells. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

Accordingly, in a particularly preferred embodiment the modulators of the instant invention may be used to detect and quantify SEZ6 levels in a patient sample (e.g., plasma or blood) which may, in turn, be used to detect, diagnose or monitor SEZ6 associated disorders including proliferative disorders. In related embodiments the modulators of the instant invention may be used to detect, monitor and/or quantify circulating tumor cells either in vivo or in vitro (see, for example, WO 2012/0128801 which is incorporated herein by reference). In still other preferred embodiments the circulating tumor cells may comprise cancer stem cells.

In certain examples, the tumorigenic cells in a subject or a sample from a subject may be assessed or characterized using the disclosed modulators prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

Yet another aspect of the instant invention comprises the use of labeled SEZ6 for immunohistochemistry (IHC). In this respect SEZ6 IHC may be used as a diagnostic tool to aid in the diagnosis of various proliferative disorders and to monitor the potential response to treatments including SEZ6 modulator therapy. Compatible diagnostic assays may be performed on tissues that have been chemically fixed (including but not limited to: formaldehyde, gluteraldehyde, osmium tetroxide, potassium dichromate, acetic acid, alcohols, zinc salts, mercuric chloride, chromium tetroxide and picric acid) and embedded (including but not limited to: glycol methacrylate, paraffin and resins) or preserved via freezing. As discussed in more detail below such assays could be used to guide treatment decisions and determine dosing regimens and timing.

B. Screening

In certain embodiments, the modulators can also be used to screen for or identify compounds or agents (e.g., drugs) that alter a function or activity of tumorigenic cells or progeny thereof by interacting with an antigen (e.g., genotypic or phenotypic components thereof). Such compounds and agents can be drug candidates that are screened for the treatment of a proliferative disorder, for example. In one embodiment, a system or method includes tumorigenic cells comprising SEZ6 and a compound or agent (e.g., drug), wherein the cells and compound or agent are in contact with each other. In such embodiments the subject cells may have been identified, monitored and/or enriched using the disclosed modulators.

In yet another embodiment, a method includes contacting, directly or indirectly, tumorigenic cells or progeny thereof with a test agent or compound and determining if the test agent or compound modulates an activity or function of the antigen-associated tumorigenic cells. One example of a direct interaction is physical interaction, while an indirect interaction includes the action of a composition upon an intermediary molecule that, in turn, acts upon the referenced entity (e.g., cell or cell culture). Exemplary activities or functions that can be modulated include changes in cell morphology or viability, expression of a marker, differentiation or de-differentiation, cell respiration, mitochondrial activity, membrane integrity, maturation, proliferation, viability, apoptosis or cell death.

Methods of screening and identifying agents and compounds include those suitable for high throughput screening, which include arrays of cells (e.g., microarrays) positioned or placed, optionally at pre-determined locations or addresses. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish). High-throughput robotic or manual handling methods can probe chemical interactions and determine levels of expression of many genes in a short period of time. Techniques have been developed that utilize molecular signals (e.g., via fluorophores) and automated analyses that process information at a very rapid rate (see, e.g., Pinhasov et al., Comb. Chem. High Throughput Screen. 7:133 (2004)). For example, microarray technology has been extensively used to probe the interactions of thousands of genes at once, while providing information for specific genes (see, e.g., Mocellin and Rossi, Adv. Exp. Med. Biol. 593:19 (2007)).

Libraries that can be screened include, for example, small molecule libraries, phage display libraries, fully human antibody yeast display libraries (Adimab, LLC), siRNA libraries, and adenoviral transfection vectors.

X. Pharmaceutical Preparations and Therapeutic Uses

A. Formulations and Routes of Administration

Depending on the form of the modulator along with any optional conjugate, the mode of intended delivery, the disease being treated or monitored and numerous other variables, compositions of the invention may be formulated as desired using art-recognized techniques. In some embodiments, the therapeutic compositions of the invention may be administered neat or with a minimum of additional components while others may optionally be formulated to contain suitable pharmaceutically acceptable carriers comprising excipients and auxiliaries that are well known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, $7^{th}$ ed., Lippencott Williams and Wilkins (2004); Kibbe et al., *Handbook of Pharmaceutical Excipients*, $3^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the SEZ6 modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics or stability of the modulator. Suitable excipients or additives include, but are not limited to, stabilizing agents, wetting and emulsifying agents, salts for varying osmolarity, encapsulating agents, buffers, and skin penetration enhancers. In certain preferred embodiments the pharmaceutical compositions may be provided in a lyophilized form and reconstituted in, for example, buffered saline prior to administration.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, hexylsubstituted poly(lactide), sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising SEZ6 modulators may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by, implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

Similarly, the particular dosage regimen, i.e., dose, timing and repetition, will depend on the particular individual and that individual's medical history, as well as empirical considerations such as pharmacokinetics (e.g., half-life, clearance rate, etc.). Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In other embodiments the dosage administered may be adjusted or attenuated to manage potential side effects and/or toxicity. Alternatively, sustained continuous release formulations of a subject therapeutic composition may be appropriate.

In general, the modulators of the invention may be administered in various ranges. These include about 10 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

In selected embodiments the modulators will be administered at approximately 10, 20, 30, 40, 50, 60, 70, 80, 90 or 100 µg/kg body weight per dose. Other embodiments will comprise the administration of modulators at 200, 300, 400, 500, 600, 700, 800 or 900 µg/kg body weight per dose. In other preferred embodiments the disclosed modulators will be administered at 1, 2, 3, 4, 5, 6, 7, 8, 9 or 10 mg/kg. In still other embodiments the modulators may be administered at 12, 14, 16, 18 or 20 mg/kg body weight per dose. In yet other embodiments the modulators may be administered at 25, 30, 35, 40, 45, 50, 55, 60, 65, 70, 75, 80, 90 or 100 mg/kg body weight per dose. In accordance with the teachings herein it will be appreciated that the aforementioned dosages are applicable to both unconjugated modulators and modulators conjugated to a cytotoxic agent. One of skill in the art could readily determine appropriate dosages for various conjugated and unconjugated modulators based on preclinical animal studies, clinical observations and standard medical and biochemical techniques and measurements.

With regard to conjugated modulators particularly preferred embodiments will comprise dosages of between about 50 µg/kg to about 5 mg/kg body weight per dose. In this regard conjugated modulators may be administered at 50, 75 or 100 µg/kg or at 0.2, 0.3, 0.4, 0.5, 0.6, 0.7, 0.8, 0.9 or 1 mg/kg body weight per dose. In other preferred embodiments the conjugated modulators of the instant invention may be administered at 1.25, 1.5, 1.75, 2, 2.25, 2.5, 2.75, 3, 3.25, 3.5, 3.75, 4, 4.25, 4.5, 4.75 or 5 mg/kg body weight per dose. In particularly preferred embodiments such conjugated modulator dosages will be administered intravenously over a period of time. Moreover, such dosages may be administered multiple times over a defined course of treatment.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the modulators may be administered in dosages from 10 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$.

It will also be appreciated that art recognized and empirical techniques may be used to determine appropriate dosage for conjugated modulators (i.e., ADCs).

In any event, SEZ6 modulators (both conjugated and unconjugated) are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the SEZ6 modulator is administered to a subject one or more times. More particularly, an effective dose of the modulator is administered to the subject once a month, more than once a month, or less than once a month. In certain embodiments, the effective dose of the SEZ6 modulator may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed modulators.

In certain preferred embodiments the course of treatment involving conjugated modulators will comprise multiple doses of the selected drug product (i.e., an ADC) over a period of weeks or months. More specifically, conjugated modulators of the instant invention may administered once every day, every two days, every four days, every week, every ten days, every two weeks, every three weeks, every month, every six weeks, every two months, every ten weeks or every three months. In this regard it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

C. Combination Therapies

Combination therapies may be particularly useful in decreasing or inhibiting unwanted neoplastic cell proliferation, decreasing the occurrence of cancer, decreasing or preventing the recurrence of cancer, or decreasing or preventing the spread or metastasis of cancer. In such cases the modulators of the instant invention may function as sensitizing or chemosensitizing agents by removing the CSCs that would otherwise prop up and perpetuate the tumor mass and thereby allow for more effective use of current standard of care debulking or anti-cancer agents. That is, the disclosed modulators may, in certain embodiments provide an enhanced effect (e.g., additive or synergistic in nature) that potentiates the mode of action of another administered therapeutic agent. In the context of the instant invention "combination therapy" shall be interpreted broadly and merely refers to the administration of a modulator and one or more anti-cancer agents that include, but are not limited to, cytotoxic agents, cytostatic agents, anti-angiogenic agents, debulking agents, chemotherapeutic agents, radiotherapy and radiotherapeutic agents, targeted anti-cancer agents (including both monoclonal antibodies and small molecule entities), BRMs, therapeutic antibodies, cancer vaccines, cytokines, hormone therapies, radiation therapy and anti-metastatic agents and immunotherapeutic agents, including both specific and non-specific approaches.

There is no requirement for the combined results to be additive of the effects observed when each treatment (e.g., antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

In practicing combination therapy, the modulator and anti-cancer agent may be administered to the subject simultaneously, either in a single composition, or as two or more distinct compositions using the same or different administration routes. Alternatively, the modulator may precede, or follow, the anti-cancer agent treatment by, e.g., intervals ranging from minutes to weeks. The time period between each delivery is such that the anti-cancer agent and modulator are able to exert a combined effect on the tumor. In at least one embodiment, both the anti-cancer agent and the modulator are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent.

The combination therapy may be administered once, twice or at least for a period of time until the condition is treated, palliated or cured. In some embodiments, the combination therapy is administered multiple times, for example, from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. The combination therapy may be administered via any route, as noted previously. The combination therapy may be administered at a site distant from the site of the tumor.

In one embodiment a modulator is administered in combination with one or more anti-cancer agents for a short treatment cycle to a subject in need thereof. The invention also contemplates discontinuous administration or daily doses divided into several partial administrations. The modulator and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the SEZ6 modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed modulators one or more times even though there is little or no indication of disease using standard diagnostic procedures. In some embodiments, the modulators will be administered on a regular schedule over a period of time, such as weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the modulators of the present invention may be used to prophylactically or as an adjuvant therapy to prevent or reduce the possibility of tumor metastasis following a debulking procedure. As used in the instant disclosure a "debulking procedure" is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed modulators may be administered as suggested by clinical, diagnostic or theragnostic procedures to reduce tumor metastasis. The modulators may be administered one or more times at pharmaceutically effective dosages as determined using standard techniques. Preferably the dosing regimen will be accompanied by appropriate diagnostic or monitoring techniques that allow it to be modified.

Yet other embodiments of the invention comprise administering the disclosed modulators to subjects that are asymptomatic but at risk of developing a proliferative disorder. That is, the modulators of the instant invention may be used in a truly preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical Observation or through accepted clinical practices.

D. Anti-Cancer Agents

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with modulators prior to administration. In certain embodiments the disclosed anti-cancer agent will be linked to a SEZ6 modulator to provide an ADC as set forth herein.

As used herein the term "cytotoxic agent" means a substance that is toxic to the cells and decreases or inhibits the function of cells and/or causes destruction of cells. Typically, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI. Again, in selected embodiments such chemotherapeutic agents may be conjugated to the disclosed modulators.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

In other embodiments the modulators of the instant invention may be used in combination with any one of a number of antibodies (or immunotherapeutic agents) presently in clinical trials or commercially available. To this end the disclosed modulators may be used in combination with an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinaturnomab, brentuximab, cautuzumab, catomaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuxiniab, ganitumab, gemtuzumab, girentuximab, glembatumumab, ibritumomab, igovomab, imgatuzumab, indatuximab, inotuzumab, intetumtumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovonlab, panitumumab, parsatuzumab, patritumab, pemtumomab, pertuzumab, pintumomab, pritumumab, racotumomab, radretumab, rilotumumab, rituximab, robatumumab, satuniomab, sibrotuzumab, siltuximab, simtuzumab, solitomab, tacatuzumab, taplitumumab, tenatumomab, teproturnumab, tigatuzumab, tositumomab, trastuzumab, tucotuzumab, ublituximab, veltuzumab, vorsetuzumab, votuinumab, zalutumumab, CC49, 3F8 and combinations thereof.

Still other particularly preferred embodiments will comprise the use of antibodies approved for cancer therapy including, but not limited to, rituximab, trastuzumab, gemtuzumab ozogamcin, alemtuzumab, ibritumomab tiuxetan, tositumomab, bevacizumab, cetuximab, panitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of modulators with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

XI. Indications

It will be appreciated that the modulators of the instant invention may be used to diagnose, treat or inhibit the occurrence or recurrence of any SEZ6 associated disorder. Accordingly, whether administered alone or in combination with an anti-cancer agent or radiotherapy, the modulators of the invention are particularly useful for generally treating neoplastic conditions in patients or subjects which may include benign or malignant tumors (e.g., adrenal, liver, kidney, bladder, breast, gastric, ovarian, colorectal, prostate, pancreatic, lung, thyroid, hepatic, cervical, endometrial, esophageal and uterine carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly, key targets for treatment are neoplastic conditions comprising solid tumors, although hematologic malignancies are within the scope of the invention. Preferably the "subject" or "patient" to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posteriors unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In certain preferred embodiments the proliferative disorder will comprise a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other preferred embodiments, and as shown in the Examples below, the disclosed modulators are especially effective at treating small cell lung cancer (SCLC) and non-small cell lung cancer (NSCLC) (e.g., squamous cell non-small cell lung cancer or squamous cell small cell lung cancer). In one embodiment, the lung cancer is refractory, relapsed or resistant to a platinum based agent (e.g., carboplatin, cisplatin, oxaliplatin, topotecan) and/or a taxane (e.g., docetaxel, paclitaxel, larotaxel or cabazitaxel). Further, in particularly preferred embodiments the disclosed modulators may be used in a conjugated form to treat small cell lung cancer.

With regard to small cell lung cancer particularly preferred embodiments will comprise the administration of conjugated modulators (ADCs). In selected embodiments the conjugated modulators will be administered to patients exhibiting limited stage disease. In other embodiments the disclosed modulators will be administered to patients exhibiting extensive stage disease. In other preferred embodiments the disclosed conjugated modulators will be administered to refractory patients (i.e., those who recur during or shortly after completing a course of initial therapy). Still other embodiments comprise the administration of the disclosed modulators to sensitive patients (i.e., those whose relapse is longer than 2-3 months after primary therapy). In each case it will be appreciated that compatible modulators may be in a conjugated or unconjugated state depending the selected dosing regimen and the clinical diagnosis.

As discussed above the disclosed modulators may further be used to prevent, treat or diagnose tumors with neuroendocrine features or phenotypes including neuroendocrine tumors. True or canonical neuroendocrine tumors (NETs) arising from the dispersed endocrine system are relatively rare, with an incidence of 2-5 per 100,000 people, but highly aggressive. Neuroendocrine tumors occur in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). These tumors may secrete several hormones including serotonin and/or chromogranin A that can cause debilitating symptoms known as carcinoid syndrome. Such tumors can be denoted by positive immunohistochemical markers such as neuron-specific enolase (NSE, also known as gamma enolase, gene symbol=ENO2), CD56 (or NCAM1), chromogranin A (CHGA), and synaptophysin (SYP) or by genes known to exhibit elevated expression such as ASCL1. Unfortunately traditional chemotherapies have not been particularly effective in treating NETs and liver metastasis is a common outcome.

While the disclosed modulators may be advantageously used to treat neuroendocrine tumors they may also be used to treat, prevent or diagnose pseudo neuroendocrine tumors (pNETs) that genotypically or phenotypically mimic, resemble or exhibit common traits with canonical neuroendocrine tumors. Pseudo neuroendocrine tumors or tumors with neuroendocrine features are tumors that arise from cells of the diffuse neuroendocrine system or from cells in which a neuroendocrine differentiation cascade has been aberrantly reactivated during the oncogenic process. Such pNETs commonly share certain phenotypic or biochemical characteristics with traditionally defined neuroendocrine tumors, including the ability to produce subsets of biologically active amines, neurotransmitters, and peptide hormones. Histologically, such tumors (NETs and pNETs) share a common appearance often showing densely connected small cells with minimal cytoplasm of bland cytopathology and round to oval stippled nuclei. For the purposes of the instant invention commonly expressed histological markers or genetic markers that may be used to define neuroendocrine and pseudo neuroendocrine tumors include, but are not limited to, chromogranin A, CD56, synaptophysin, PGP9.5, ASCL1 and neuron-specific enolase (NSE).

Accordingly the modulators of the instant invention may beneficially be used to treat both pseudo neuroendocrine tumors and canonical neuroendocrine tumors. In this regard the modulators may be used as described herein to treat neuroendocrine tumors (both NET and pNET) arising in the kidney, genitourinary tract (bladder, prostate, ovary, cervix, and endometrium), gastrointestinal tract (colon, stomach), thyroid (medullary thyroid cancer), and lung (small cell lung carcinoma and large cell neuroendocrine carcinoma). Moreover, the modulators of the instant invention may be used to treat tumors expressing one or more markers selected from the group consisting of NSE, CD56, synaptophysin, chromogranin A, ASCL1 and PGP9.5 (UCHL1). That is, the present invention may be used to treat a subject suffering from a tumor that is $NSE^+$ or $CD56^+$ or $PGP9.5^+$ or $ASCL1^+$ or $SYP^+$ or $CHGA^+$ or some combination thereof.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al. "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

The present invention also provides for a preventative or prophylactic treatment of subjects who present with benign or precancerous tumors. Beyond being a SEZ6 associated disorder it is not believed that any particular type of tumor or proliferative disorder should be excluded from treatment using the present invention. However, the type of tumor cells may be relevant to the use of the invention in combination with secondary therapeutic agents, particularly chemotherapeutic agents and targeted anti-cancer agents.

XII. Articles of Manufacture

Pharmaceutical packs and kits comprising one or more containers, comprising one or more doses of a SEZ6 modulator are also provided. In certain embodiments, a unit dosage is provided wherein the unit dosage contains a predetermined amount of a composition comprising, for example, an anti-SEZ6 antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of a SEZ6 modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed modulators in a conjugated or unconjugated form. In other preferred embodiments the container(s) comprise a sterile access port (for example the container may be an intravenous solution bag or a vial having a stopper pierceable by a hypodermic injection needle). Such kits will generally contain in a suitable container a pharmaceutically acceptable formulation of the SEZ6 modulator and, optionally, one or more anti-cancer agents in the same or different containers. The kits may also contain other pharmaceutically acceptable formulations, either for diagnosis or combined therapy. For example, in addition to the SEZ6 modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the SEZ6 modulator with an anti-cancer agent or diagnostic agent (e.g., see U.S. Pat. No. 7,422,739 which is incorporated herein by reference in its entirety).

More specifically the kits may have a single container that contains the SEZ6 modulator, with or without additional components, or they may have distinct containers for each desired agent. Where combined therapeutics are provided for conjugation, a single solution may be pre-mixed, either in a molar equivalent combination, or with one component in excess of the other. Alternatively, the SEZ6 modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the SEZ6 modulator composition is used for treating cancer, for example small cell lung cancer.

In other preferred embodiments the modulators of the instant invention may be used in conjunction with, or comprise, diagnostic or therapeutic devices useful in the diagnosis or treatment of proliferative disorders. For example, in on preferred embodiment the compounds and compositions of the instant invention may be combined with certain diagnostic devices or instruments that may be used to detect, monitor, quantify or profile cells or marker compounds involved in the etiology or manifestation of proliferative disorders. For selected embodiments the marker compounds may comprise NSF, CD56, synaptophysin, chromogranin A, and PGP9.5.

In particularly preferred embodiments the devices may be used to detect, monitor and/or quantify circulating tumor cells either in vivo or in vitro (see, for example, WO 2012/0128801 which is incorporated herein by reference). In still other preferred embodiments, and as discussed above, the circulating tumor cells may comprise cancer stem cells.

XIII. Research Reagents

Other preferred embodiments of the invention also exploit the properties of the disclosed modulators as an instrument useful for identifying, monitoring, isolating, sectioning or enriching populations or subpopulations of tumor initiating cells through methods such as flow cytometry, fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Ser. Nos. 12/686,359, 12/669,136 and 12/757,649 each of which is incorporated herein by reference in its entirety).

XIV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins, reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, 6th ed., W.B, Saunders Company (2010); Sambrook J, & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology,* Wiley, John & Sons, Inc. (2002); Harlow and Lane *Using Antibodies: A Laboratory Manual,* Cold Spring Harbor Laboratory Press, Cold Spring Harbor, N.Y. (1998); and Coligan et al., *Short Protocols in Protein Science,* Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Moreover, any section headings used herein are for organizational purposes only and are not to be construed as limiting the subject matter described.

XV. SEZ6 References

All references or documents disclosed or cited within this specification are, without limitation, incorporated herein by reference in their entirety. Moreover, any section headings used herein are for organizational purposes only and are not to be construed as limiting the subject matter described.
1. Bork P, Beckmann G. (1993). The CUB domain. A widespread module in developmentally regulated proteins. J Mol Biol. 231:539-45. PMID: 8510165.
2. Galluzzo P, and Bocchetta M (2011). Notch signaling in lung cancer. Expert Rev Anticancer Ther. 11:533-40. PMID: 21504320.
3. Gunnersen J M et al. (2007). Sez-6 proteins affect dendritic arborization patterns and excitability of cortical pyramidal neurons. Neuron. 56:621-39. PMID: 18031681.
4. Gunnersen J M et al. (2009). Seizure-related gene 6 (Sez-6) in amacrine cells of the rodent retina and the consequence of gene deletion. PLoS One. 4:e6546. PMID:19662096.
5. Herbst R, Nicklin M J (1997). SEZ-6: promoter selectivity, genomic structure and localized expression in the brain. Brain Res Mol Brain Res. 44:309-22. PMID: 9073173.
6. Klimstra D S, et al. (2010). The pathologic classification of neuroendocrine tumors: a review of nomenclature, grading, and staging systems. Pancreas. 39:707-12. PMID: 20664470.
7. Klöppel G, (2011). Classification and pathology of gastroenteropancreatic neuroendocrine neoplasms. Endocr Relat Cancer, 18 Suppl 1:S146. PMID: 22005112.
8. Mulley J C et al. (2011). The Role of Seizure-Related SEZ6 as a Susceptibility Gene in Febrile Seizures. Neurol Res Int. 2011:917565, PMID: 21785725.
9. Shimizu-Nishikawa K et at, (1995). Cloning and expression of SEZ-6, a brain-specific and seizure-related cDNA, Brain Res Mol. Brain Res. 28:201-10. PMID: 7723619.
10. Yao J C et al. (2008). One hundred years after "carcinoid": epidemiology of and prognostic factors for neuroendocrine tumors in 35,825 cases in the United States. J Clin Oncol. 26:3063-72, PMID: 18565894.
11. Yu Z L et al., (2007). Febrile seizures are associated with mutation of seizure-related (SEZ) 6, a brain-specific gene. J Neurosci Res. 85:166-72. PMID: 17086543.

XVI. Selected Embodiments of the Invention

In addition to the disclosure and Examples herein, the present invention is directed to selected embodiments specifically set forth immediately below.

Putative Claims
1. An isolated SEZ6 modulator.
2. The isolated SEZ6 modulator of claim 1, wherein the SEZ6 modulator comprises a SEZ6 antagonist.
3. The isolated SEZ6 modulator of claim 1, wherein the SEZ6 modulator comprises an antibody or immunoreactive fragment thereof.
4. The isolated SEZ6 modulator of claim 3 wherein the antibody or immunoreactive fragment thereof comprises a monoclonal antibody.
5. The isolated SEZ6 modulator of claim 4 wherein the monoclonal antibody is selected from the group consisting of chimeric antibodies, humanized antibodies and human antibodies.
6. The isolated SEZ6 modulator of claim 4 wherein said monoclonal antibody comprises a neutralizing antibody.
7. The isolated SEZ6 modulator of claim 4 wherein said monoclonal antibody comprises a depleting antibody.
8. The isolated SEZ6 modulator of claim 4 wherein said monoclonal antibody comprises an internalizing antibody.
9. The isolated SEZ6 modulator of claim 8 wherein said monoclonal antibody further comprises a cytotoxic agent.
10. The isolated SEZ6 modulator of claim 4 wherein said monoclonal antibody comprises a light chain variable region having three complementarity determining regions and a heavy chain variable region having three complementarity determining regions wherein the heavy and light chain complementarity determining regions comprise at least one complementarity determining region set forth in FIG. 10A or FIG. 10B, respectively.
11. The isolated SEZ6 modulator of claim 4 wherein said monoclonal antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166 and SEQ ID NO: 168 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEE ID NO: 27, SEQ ID NO: 29, SEQ ID NO: 31, SEQ ID NO: 33 SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167 and SEQ ID NO: 169.

12. An isolated SEZ6 modulator comprising a CDR from any one of the heavy or light chain variable regions set forth in claim 11.

13. An isolated SEZ6 modulator comprising a competing antibody wherein said competing antibody inhibits the binding of an isolated SEZ6 modulator of claim 10 or 11 to SEZ6 by at least about 40%.

14. A nucleic acid encoding an amino acid heavy chain variable region or an amino acid light chain variable region of claim 11.

15. A vector comprising the nucleic acid of claim 14.

16. The isolated SEZ6 modulator of claim 1 comprising an amino acid sequence selected from the group consisting of SEQ ID NO: 3, SEQ ID NO: 4 and fragments thereof.

17. The isolated SEZ6 modulator of claim 16 wherein the SEZ6 modulator further comprises at least a portion of an immunoglobulin constant region.

18. The isolated SEZ6 modulator of claim 1 wherein said modulator reduces the frequency of tumor initiating cells upon administration to a subject in need thereof.

19. The isolated SEZ6 modulator of claim 18 wherein the reduction in frequency is determined using flow cytometric analysis of tumor cell surface markers known to enrich for tumor initiating cells.

20. The isolated SEZ6 modulator of claim 18 wherein the reduction in frequency is determined using immunohistochemical detection of tumor cell surface markers known to enrich for tumor initiating cells.

21. The isolated SEZ6 modulator of claim 18 wherein said tumor initiating cells comprise tumor perpetuating cells.

22. The isolated SEZ6 modulator of claim 1 further comprising a cytotoxic agent.

23. A pharmaceutical composition comprising the isolated SEZ6 modulator of claim 1.

24. The pharmaceutical composition of claim 23 wherein said isolated SEZ6 modulator comprises a monoclonal antibody.

25. The pharmaceutical composition of claim 24 wherein said monoclonal antibody comprises a humanized antibody.

26. The pharmaceutical composition of claim 25 wherein said humanized antibody comprises a cytotoxic agent.

27. The isolated SEZ6 modulator of claim 26 wherein said cytotoxic agent comprises a pyrrolobenzodiazepine.

28. The isolated SEZ6 modulator of claim 26 wherein said cytotoxic agent comprises an auristatin.

29. A method of treating a SEZ6 associated disorder comprising administering a therapeutically effective amount of a SEZ6 modulator to a subject in need thereof.

30. The method of claim 29 wherein said SEZ6 modulator comprises a SEZ6 antagonist.

31. The method of claim 29 wherein said SEZ6 modulator comprises an antibody or immunoreactive fragment thereof.

32. The method of claim 31 wherein the antibody or immunoreactive fragment thereof comprises a monoclonal antibody.

33. The method of claim 32 wherein the monoclonal antibody is selected from the group consisting of chimeric antibodies, humanized antibodies and human antibodies.

34. The method of claim 33 wherein said monoclonal antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20. SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78 SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 144, SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166 and SEQ ID NO: 168 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO:

65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, SEQ ID NO: 143, SEQ ID NO: 145, SEQ ID NO: 147, SEQ ID NO: 149, SEQ ID NO: 151, SEQ ID NO: 153, SEQ ID NO: 155, SEQ ID NO: 157, SEQ ID NO: 159, SEQ ID NO: 161, SEQ ID NO: 163, SEQ ID NO: 165, SEQ ID NO: 167 and SEQ ID NO: 169.

35. The method of claim 34 wherein said monoclonal antibody is a humanized antibody.

36. The method of claim 32 wherein said monoclonal antibody comprises a neutralizing antibody.

37. The method of claim 32 wherein said monoclonal antibody comprises an internalizing antibody.

38. The method of claim 37 wherein said internalizing antibody comprises a cytotoxic agent.

39. The method of claim 38 wherein said cytotoxic agent comprises a pyrrolobenzodiazepine.

40. The method of claim 38 wherein said cytotoxic agent comprises an auristatin.

41. The method of claim 39 wherein said SEZ6 associated disorder comprises a neoplastic disorder.

42. The method of claim 41 wherein said neoplastic disorder comprises a tumor exhibiting neuroendocrine features.

43. The method of claim 42 wherein said tumor exhibiting neuroendocrine features comprises a neuroendocrine tumor.

44. The method of claim 41 wherein the subject is suffering from a neoplastic disorder selected from the group consisting of adrenal cancer, bladder cancer, cervical cancer, endometrial cancer, gastric cancer, kidney cancer, liver cancer, lung cancer, ovarian cancer, colorectal cancer, pancreatic cancer, prostate cancer and breast cancer.

45. The method of claim 44 wherein the subject is suffering from lung cancer.

46. The method of claim 45 wherein the subject is suffering from small cell lung cancer.

47. The method of claim 41 wherein the subject suffering from said neoplastic disorder exhibits tumors comprising tumor initiating cells.

48. The method of claim 47 further comprising the step of reducing the frequency of tumor initiating cells in said subject.

49. The method of claim 48 wherein the reduction in frequency is determined using flow cytometric analysis of tumor cell surface markers known to enrich for tumor initiating cells or immunohistochemical detection of tumor cell surface markers known to enrich for tumor initiating cells.

50. The method of claim 48 wherein the reduction in frequency is determined using a method from the group consisting of in vitro and in vivo limiting dilution analysis.

51. The method of claim 50 wherein the reduction in frequency is determined using in vivo limiting dilution analysis comprising transplant of live human tumor cells into immunocompromised mice.

52. The method of claim 51 wherein the reduction of frequency is determined using in vivo limiting dilution analysis comprising quantification of tumor initiating cell frequency using Poisson distribution statistics.

53. The method of claim 50 wherein the reduction of frequency is determined using in vitro limiting dilution analysis comprising limiting dilution deposition of live human tumor cells into in vitro colony supporting conditions.

54. The method of claim 53 wherein the reduction of frequency determined using in vitro limiting dilution analysis comprises quantification of tumor initiating cell frequency using Poisson distribution statistics.

55. The method of claim 29 further comprising the step of administering an anti-cancer agent.

56. The method of claim 29 wherein said SEZ6 modulator comprises one or more CDRs from any one of SEQ ID NOS: 20 to 169.

57. The method of claim 29 wherein said SEZ6 modulator comprises a pan-SEZ6 modulator.

58. The method of claim 57 wherein said SEZ6 modulator comprises a cytotoxic agent.

59. A method of reducing the frequency of tumor initiating cells in a subject in need thereof comprising the step of administering a SEZ6 modulator to said subject.

60. The method of claim 59 wherein the tumor initiating cells comprise tumor perpetuating cells.

61. The method of claim 60 wherein said tumor perpetuating cells are selected from cells expressing markers selected from the group consisting of $CD44^+$, $CD324^+$ and $CD133^+$ cells.

62. The method of claim 59 wherein said SEZ6 modulator comprises an antibody.

63. The method of claim 62 wherein said antibody comprises a monoclonal antibody.

64. The method of claim 63 wherein said monoclonal antibody further comprises a cytotoxic agent.

65. The method of claim 59 wherein the subject is suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer and breast cancer.

66. The method of claim 65 wherein the subject is suffering from lung cancer.

67. The method of claim 66 wherein the subject is suffering from small cell lung cancer.

68. The method of claim 59 wherein the frequency of tumor initiating cells is reduced by at least 10%.

69. The method of claim 59 wherein the reduction in frequency is determined using flow cytometric analysis of tumor cell surface markers known to enrich for tumor initiating cells or immunohistochemical detection of tumor cell surface markers known to enrich for tumor initiating cells.

70. A method of sensitizing a tumor in a subject for treatment with an anti-cancer agent comprising the step of administering a SEZ6 modulator to said subject.

71. The method of claim 70 wherein said SEZ6 modulator comprises an antibody.

72. The method of claim 70 wherein said tumor is a solid tumor.

73. The method of claim 70 wherein said anti-cancer agent comprises a chemotherapeutic agent.

74. The method of claim 70 wherein said anti-cancer agent comprises an immunotherapeutic agent.

75. A method of diagnosing a proliferative disorder in a subject in need thereof comprising the steps of:
i. obtaining a tissue sample from said subject;
ii. contacting the tissue sample with at least one SEZ6 modulator; and
iii. detecting or quantifying the SEZ6 modulator associated with the sample.

76. The method of claim 75 wherein the SEZ6 modulator comprises a monoclonal antibody.

77. The method of claim 76 wherein the monoclonal antibody is operably associated with a reporter.

78. An article of manufacture useful for diagnosing or treating SEZ6 associated disorders comprising a receptacle comprising a SEZ6 modulator and instructional materials for using said SEZ6 modulator to treat or diagnose the SEZ6 associated disorder.

79. The article of manufacture of claim 78 wherein said SEZ6 modulator is a monoclonal antibody.

80. The article of manufacture of claim 78 wherein the receptacle comprises a readable plate.

81. A method of treating a subject suffering from a neoplastic disorder comprising the step of administering a therapeutically effective amount of at least one internalizing SEZ6 modulator.

82. The method of claim 81 wherein said SEZ6 modulator comprises an antibody.

83. The method of claim 82 wherein said antibody comprises a monoclonal antibody.

84. The method of claim 83 wherein said monoclonal antibody comprises a humanized antibody.

85. The method of claim 83 wherein the monoclonal antibody further comprises a cytotoxic agent.

86. The method of claim 81 further comprising the step of administering an anti-cancer agent.

87. The method of claim 81 wherein the neoplastic disorder comprises a tumor exhibiting neuroendocrine features.

88. The method of claim 81 wherein the neoplastic disorder comprises a tumor exhibiting neural features.

89. The method of claim 81 wherein the neoplastic disorder comprises lung cancer.

90. The method of claim 81 wherein the neoplastic disorder comprises small cell lung cancer.

91. A method of treating a subject suffering from a neoplastic disorder comprising the step of administering a therapeutically effective amount of at least one neutralizing SEZ6 modulator.

92. The method of claim 91 wherein said SEZ6 modulator comprises an antibody.

93. The method of claim 92 wherein said antibody comprises a monoclonal antibody.

94. The method of claim 93 wherein said monoclonal antibody comprises a humanized antibody.

95. The method of claim 94 wherein said humanized antibody further comprises a cytotoxic agent.

96. The method of claim 91 further comprising the step of administering an anti-cancer agent.

97. The method of claim 91 wherein the neoplastic disorder comprises a tumor exhibiting neural features.

98. The method of claim 91 wherein the neoplastic disorder comprises a tumor exhibiting neuroendocrine features.

99. The method of claim 91 wherein the neoplastic disorder comprises lung cancer.

100. The method of claim 99 wherein the neoplastic disorder comprises small cell lung cancer.

101. A method of identifying, isolating, sectioning or enriching a population of tumor initiating cells comprising the step of contacting said tumor initiating cells with a SEZ6 modulator.

102. The method of claim 101 wherein said SEZ6 modulator comprises an antibody.

103. A SEZ6 modulator comprising a humanized antibody wherein said humanized antibody comprises a light chain variable region and a heavy chain variable region wherein said light chain variable region comprises an amino acid sequence having at least 60% identity to the amino acid sequence selected from the group consisting of SEQ ID NO: 170, SEQ ID NO: 172, SEQ ID NO: 174, SEQ ID NO: 176, SEQ ID NO: 178, SEQ ID NO: 180, SEQ ID NO: 182, SEQ ID NO: 184. SEQ ID NO: 186, SEQ ID NO: 188, SEQ ID NO: 190 and SEQ ID NO: 192 and wherein said heavy chain variable region comprises an amino acid sequence having at least 60% identity to an amino acid sequence selected from the group consisting of amino acid sequences selected from the group consisting of SEQ ID NO: 171, SEQ ID NO: 173, SEQ ID NO: 175, SEQ ID NO: 177, SEQ ID NO: 179, SEQ ID NO: 181, SEQ ID NO: 183, SEQ ID NO: 185, SEQ ID NO: 187, SEQ ID NO: 189, SEQ ID NO: 191, SEQ ID NO: 193, SEQ ID NO: 194, SEQ ID NO: 195, SEQ ID NO: 196, SEQ ID NO: 197, SEQ ID NO: 198 and SEQ ID NO: 199.

104. A method of inhibiting or preventing metastasis in a subject in need thereof comprising the step of administering a pharmaceutically effective amount of a SEZ6 modulator.

105. The method of claim 104 wherein the subject undergoes a debulking procedure before or after the administration of the SEZ6 modulator.

106. The method of claim 105 wherein said debulking procedure comprises the administration of at least one anti-cancer agent.

107. A method of performing maintenance therapy on a subject in need thereof comprising the step of administering a pharmaceutically effective amount of a SEZ6 modulator.

108. The method of claim 107 wherein said subject was treated for a neoplastic disorder prior to the administration of the SEZ6 modulator.

109. A method of depleting tumor initiating cells in a subject suffering from a proliferative disorder comprising the step of administering a SEZ6 modulator.

110. A method of diagnosing, detecting or monitoring a SEZ6 associated disorder in vivo in a subject in need thereof comprising the step of administering a SEZ6 modulator.

111. A method of diagnosing, detecting or monitoring a SEZ6 associated disorder in a subject in need thereof comprising the step of contacting circulating tumor cells with a SEZ6 modulator.

112. The method of claim 111 wherein said contacting step occurs in vivo.

113. The method of claim 111 wherein said contacting step occurs in vitro.

114. A method of treating a tumor exhibiting neuroendocrine features in a patient in need thereof comprising the step of administering a therapeutically effective amount of a SEZ6 modulator.

115. The method of claim 114 wherein said tumor exhibiting neuroendocrine features is a neuroendocrine tumor.

116. A SEZ6 modulator derived from an antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC171.40, SC17.151, SC17.156, SC17.161, SC17.166, SC17.187, SC17.191, SC17.193, SC17.199 and SC17.200.

117. An isolated SEZ6 modulator that binds to an epitope associated with the Sushi Domain 1 of SEZ6.

118. The SEZ6 modulator of claim 117 wherein said SEZ6 modulator comprises an antibody or immunoreactive fragment thereof.

119. The SEZ6 modulator of claim 118 wherein said antibody or immunoreactive fragment thereof comprises a monoclonal antibody.

120. The SEZ6 modulator of claim 119 wherein said SEZ6 modulator comprises an ADC.

121. The SEZ6 modulator of claim 120 wherein said ADC comprises a pyrrolobenzodiazepine.

122. The SEZ6 modulator of claim 121 further comprising a linker.

123. An isolated SEZ6 modulator that binds to an epitope associated with the Sushi Domain 2 of SEZ6.

124. The SEZ6 modulator of claim 123 wherein said SEZ6 modulator comprises an antibody or immunoreactive fragment thereof.

125. The SEZ6 modulator of claim 124 wherein said antibody or immunoreactive fragment thereof comprises a monoclonal antibody.

126. The SEZ6 modulator of claim 125 wherein said SEZ6 modulator comprises an ADC.

127. The SEZ6 modulator of claim 126 wherein said ADC comprises a pyrrolobenzodiazepine.

128. The SEZ6 modulator of claim 127 further comprising a linker.

129. An isolated SEZ6 modulator that binds to an epitope associated with the Sushi Domain 3 of SEZ6.

130. The SEZ6 modulator of claim 129 wherein said SEZ6 modulator comprises an antibody or immunoreactive fragment thereof.

131. The SEZ6 modulator of claim 130 wherein said antibody or immunoreactive fragment thereof comprises a monoclonal antibody.

132. The SEZ6 modulator of claim 131 wherein said SEZ6 modulator comprises an ADC.

133. The SEZ6 modulator of claim 132 wherein said ADC comprises a pyrrolobenzodiazepine.

134. The SEZ6 modulator of claim 133 further comprising a linker.

135. An isolated SEZ6 modulator that binds to an epitope associated with the Sushi Domain 4 of SEZ6.

136. The SEZ6 modulator of claim 135 wherein said SEZ6 modulator comprises an antibody or immunoreactive fragment thereof.

137. The SEZ6 modulator of claim 136 wherein said antibody or immunoreactive fragment thereof comprises a monoclonal antibody.

138. The SEZ6 modulator of claim 137 wherein said SEZ6 modulator comprises an ADC.

139. The SEZ6 modulator of claim 138 wherein said ADC comprises a pyrrolobenzodiazepine.

140. The SEZ6 modulator of claim 139 further comprising a linker.

141. An isolated SEZ6 modulator that binds to an epitope associated with the Sushi Domain 5 of SEZ6.

142. The SEZ6 modulator of claim 141 wherein said SEZ6 modulator comprises an antibody or immunoreactive fragment thereof.

143. The SEZ6 modulator of claim 142 wherein said antibody or immunoreactive fragment thereof comprises a monoclonal antibody.

144. The SEZ6 modulator of claim 143 wherein said SEZ6 modulator comprises an ADC.

145. The SEZ6 modulator of claim 144 wherein said ADC comprises pyrrolobenzodiazepine.

146. The SEZ6 modulator of claim 145 further comprising a linker.

147. An isolated SEZ6 modulator that binds to an epitope associated with the CUB Domain 1 of SEZ6.

148. The SEZ6 modulator of claim 147 wherein said SEZ6 modulator comprises an antibody or immunoreactive fragment thereof.

149. The SEZ6 modulator of claim 148 wherein said antibody or immunoreactive fragment thereof comprises a monoclonal antibody.

150. The SEZ6 modulator of claim 149 wherein said SEZ6 modulator comprises an ADC.

151. The SEZ6 modulator of claim 150 wherein said ADC comprises a pyrrolobenzodiazepine.

152. The SEZ6 modulator of claim 151 further comprising a linker.

153. An isolated SEZ6 modulator that binds to an epitope associated with the CUB Domain 2 of SEZ6.

154. The SEZ6 modulator of claim 153 wherein said SEZ6 modulator comprises an antibody or immunoreactive fragment thereof.

155. The SEZ6 modulator of claim 154 wherein said antibody or immunoreactive fragment thereof comprises a monoclonal antibody.

156. The SEZ6 modulator of claim 155 wherein said SEZ6 modulator comprises an ADC.

157. The SEZ6 modulator of claim 156 wherein said ADC comprises a pyrrolobenzodiazepine.

158. The SEZ6 modulator of claim 157 further comprising a linker.

159. An isolated SEZ6 modulator that binds to an epitope associated with the N-terminal domain of SEZ6.

160. The SEZ6 modulator of claim 159 wherein said SEZ6 modulator comprises an antibody or immunoreactive fragment thereof.

161. The SEZ6 modulator of claim 160 wherein said antibody or immunoreactive fragment thereof comprises a monoclonal antibody.

162. The SEZ6 modulator of claim 161 wherein said SEZ6 modulator comprises an ADC.

163. The SEZ6 modulator of claim 162 wherein said ADC comprises a pyrrolobenzodiazepine.

164. The SEZ6 modulator of claim 163 further comprising a linker.

165. An isolated SEZ6 modulator residing in a bin selected from the group consisting of bin A, bin B, bin C, bin D, bin E, bin F and bin U.

166. An isolated SEZ6 modulator residing in a bin defined by a reference antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200.

167. An antibody drug conjugate of the formula M-[L-D]n or a pharmaceutically acceptable salt thereof wherein:
a. M comprises a SEZ6 modulator;
b. L comprises a linker;
c. D is an anti-proliferative agent; and
d. n is an integer from about 1 to about 20.

168. The antibody drug conjugate of claim 167 wherein said SEZ6 modulator comprises an antibody or immunoreactive fragment thereof.

169. The antibody drug conjugate of claim 168 wherein said antibody comprises a monoclonal antibody.

170. The antibody drug conjugate of claim 169 wherein said antibody is derived from an antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200.

171. The antibody drug conjugate of claim 169 wherein said antibody is humanized.

172. The antibody drug conjugate of claim 167 wherein the linker comprises a cleavable linker.

173. The antibody drug conjugate of claim 172 wherein said cleavable linker comprises a peptidyl linker.

174. The antibody drug conjugate of claim 167 wherein said anti-proliferative agent comprises a cytotoxic agent.

175. The antibody drug conjugate of claim 174 wherein said cytotoxic agent comprises a pyrrolobenzodiazepine.

176. The antibody drug conjugate of claim 175 wherein said pyrrolobenzodiazepine comprises a pyrrolobenzodiazepine dimer.

177. An isolated SEZ6 modulator residing in a bin selected from the group consisting of bin A, bin B, bin C, bin D, bin E, bin F and bin U.

178. An isolated SEZ6 modulator residing in a bin defined by a reference antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200.

179. An antibody drug conjugate of the formula:

M-[L-D]-n or a pharmaceutically acceptable salt thereof wherein
a) M comprises a SEZ6 modulator;
b) L comprises an optional linker;
c) D is a cytotoxic agent selected from the group consisting of auristatins, maytansinoids, amanitins and pyrrolobenzodiazepine dimers.
d) n is an integer from about 1 to about 20.

180. The antibody drug conjugate of claim 179 wherein said SEZ6 modulator comprises an antibody or immunoreactive fragment thereof.

181. The antibody drug conjugate of claim 180 wherein said antibody comprises a monoclonal antibody.

182. The antibody drug conjugate of claim 181 wherein said antibody is derived from an antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191, SC17.193, SC17.199 and SC17.200.

183. The antibody drug conjugate of claim 182 wherein said antibody is humanized.

184. The antibody drug conjugate of claim 183 wherein the linker comprises a cleavable linker.

185. The antibody drug conjugate of claim 184 wherein said cleavable linker comprises a peptidyl linker.

186. The antibody drug conjugate of claim 185 wherein said anti-proliferative agent comprises a cytotoxic agent.

187. The antibody drug conjugate of claim 186 wherein said cytotoxic agent comprises a pyrrolobenzodiazepine.

188. The antibody drug conjugate of claim 187 wherein said pyrrolobenzodiazepine comprises a pyrrolobenzodiazepine dimer.

189. A SEZ6 modulator comprising a CDR from any one of SEQ ID NOS: 20-203.

190. The SEZ6 modulator of claim 189 wherein said modulator comprises a plurality of CDRs from any one of SEQ ID NOS: 20-203.

191. A SEZ6 antibody modulator that competes for binding to a SEZ6 protein with a reference antibody selected from the group consisting of SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28, SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17.121, SC17.122, SC17.140, SC17.151, SC17.156, SC17.161, SC17.166, SC17.187, SC17.191, SC17.193, SC17.199 and SC17.200 wherein binding of the SEZ6 antibody modulator to the SEZ6 protein is inhibited by at least 30%.
192. A SEZ6 modulator that binds to a SEZ6 protein epitope comprising amino acids Q12, P14, I16, E17 and E18 (SEQ ID NO: 401).
193. A SEZ6 modulator that binds to a SEZ6 protein epitope comprising amino acids L73, P74, F75, Q76, P77, D78 and P79 (SEQ ID NO: 402).
194. A method of treating a subject suffering from a proliferative disorder comprising the step of administering a SEZ6 modulator that binds to an epitope contained in a SEZ6 domain selected from the group consisting of the N-terminal domain, the Sushi 1 domain, the Cub 1 domain, the Sushi 2 domain, the Cub 2 domain, the Sushi 3 domain, the Sushi 4 domain and the Sushi S domain.
195. A humanized SEZ6 antibody modulator selected from the group consisting of hSC17.16, hSC17.17, hSC17.24, hSC17.28, SC17.34, hSC17.46, SC17.151, SC17.155, SC17.156, SC17.161 and SC17.200.

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Identification of Tumors Having Neuroendocrine Features and Analysis of Marker Expression using Whole Transcriptome Sequencing Neuroendocrine tumors (NETs) arising from the dispersed endocrine system are rare, with an incidence of 2-5 per 100,000 people, but highly aggressive. Neuroendocrine tumors occur in the adrenal gland, kidney, genitourinary tract (bladder, prostate, ovary, cervix, and endometrium), pancreas, gastrointestinal tract (stomach and colon), thyroid (medullary thyroid cancer), and lung (small cell lung carcinoma, large cell neuroendocrine carcinoma, and carcinoid). These tumors may secrete several hormones including serotonin and/or chromogranin A that can cause debilitating symptoms known as carcinoid syndrome. These tumors can be denoted by positive immunohistochemical markers such as neuron-specific enolase (NSE, also known as gamma enolase, gene symbol=ENO2), CD56/NCAM1, and synaptophysin. Traditional chemotherapies have not been successful in treating NETs, and mortality due to metastatic spread is a common outcome. Unfortunately, in most cases surgery is the only potential curative treatment, provided it takes place following early detection and prior to tumor metastasis. In this context work was undertaken to identify novel therapeutic targets associated with tumors comprising neuroendocrine features.

To identify and characterize such tumors as they exist in cancer patients a large non-traditional xenograft (NTX) tumor bank was developed and maintained using art-recognized techniques. The NTX tumor bank, comprising a substantial number of discrete tumor cell lines, was propagated in immunocompromised mice through multiple passages of heterogeneous tumor cells originally obtained from numerous cancer patients afflicted by a variety of solid tumor malignancies. (Note that in some of the Examples and FIGS. herein the passage number of the tested sample is indicated by p0-p# appended to the sample designation where p0 is indicative of an unpassaged sample obtained directly from a patient tumor and p# is indicative of the number of times the tumor has been passaged through a mouse prior to testing.) The continued availability of a large number of discrete early passage NTX tumor cell lines having well defined lineages greatly facilitate the identification and characterization of cells purified from the cell lines. In such work the use of minimally passaged NTX cell lines simplifies in vivo experimentation and provides readily verifiable results. Moreover, early passage NTX tumors respond to therapeutic agents such as irinotecan (i.e. CAMPTOSAR®) and Cisplatin/Etoposide regimens, which provides clinically relevant insights into underlying mechanisms driving tumor growth, resistance to current therapies and tumor recurrence.

As the NTX tumor cell lines were established, their phenotype was characterized in various ways to examine global gene expression. To identify which NTX lines in the bank might be NETs, gene expression profiles were generated by whole transcriptome sequencing and/or microarray analysis. Specifically, the data was examined to identify tumors expressing high levels of specific genes known to be elevated in NETs or used as histochemical markers of neuroendocrine differentiation (e.g., ASCL1, NCAM1, CHGA) as well as tumors with changes in NOTCH pathway genes indicative of suppression of NOTCH signaling (e.g., reduced levels of NOTCH receptors, and changes to ligands and effector molecules).

More particularly, upon establishing various NTX tumor cell lines as is commonly done for human tumors in severely immune compromised mice, the tumors were resected after reaching 800-2,000 mm$^3$ and the cells were dissociated and dispersed into suspension using art-recognized enzymatic digestion techniques (see, for example, U.S.P.N. 2007/0292414 which is incorporated herein). The dissociated cell preparations from these NTX lines were then depleted of murine cells, and human tumor cell subpopulations were then further isolated by fluorescence activated cell sorting and lysed in RLTPLUS™ RNA lysis buffer (Qiagen). These lysates were then stored at −80° C. until used. Upon thawing, total RNA was extracted using a RNEASY® isolation kit (Qiagen) following the vendor's instructions and quantified on a THERMO SCIENTIFIC™ NANODROP™ spectrophotometer and a BIOANALYZER® 2100 (Agilent Technologies) again using the manufacturer's protocols and recommended instrument settings. The resulting total RNA preparations were suitable for genetic sequencing and gene expression analysis.

Whole transcriptome sequencing using an Applied Biosystems (ABI) SOLID™ (Sequencing by Oligo Ligation/Detection) 4.5 or SOLID™ 5500x1 next generation sequencing system (Life Technologies) was performed on RNA samples from NTX lines. cDNA was generated from total RNA samples using either a modified whole transcriptome (WT) protocol from ABI designed for low input total RNA or OVATION® RNA-SEQ SYSTEM V2™ (NuGEN Technologies Inc.). The modified low input WT protocol uses 1.0 ng of total RNA to amplify mRNA at the 3' end which leads to a heavy 3' bias of mapped gene expression, while NuGen's system allows for a more consistent amplification throughout the transcript, and includes amplification of both mRNA and non-polyadenylated transcript cDNA using random hexamers. The cDNA library was fragmented, and barcodes adapters were added to allow pooling of fragment libraries from different samples.

ABI's SOLID™ 4.5 and SOLID™ 5500x1 next generation sequencing platforms enables parallel sequencing of transcriptomes from multiple NTX lines and sorted populations. A cDNA library is constructed from each RNA sample, which is fragmented and barcoded. Barcodes on each fragment library allow multiple samples to be pooled at equal concentrations and run together while ensuring sample specificity. The samples are taken through emulsion PCR using ABI's SOLID™ EZ BEAD™ robotics system, which ensures sample consistency. Paired-end sequencing generates a 50 base read in the 5' to 3' direction and a 25 base read in the 3' to 5' direction for each clonally amplified fragment on a single bead that exists in the pool. In the case of the 5500x1 platform, for every set of 8 samples pooled in the method mentioned above, beads are evenly deposited into 6 single channel lanes on a single chip. This will, on average, generate more than 50 million 50 base reads and 50 million 25 base reads for each of the 8 samples and generates a very accurate representation of mRNA transcript level in the tumor cells. Data generated by the SOLID™ platform mapped to 34,609 genes as annotated by RefSeq version 47 using NCBI version hg19.2 of the published human genome and provided verifiable measurements of RNA levels in most samples.

The SOLID™ platform is able to capture not only expression, but SNPs, known and unknown alternative splicing events, small non-coding RNAs, and potentially new exon discoveries based solely on read coverage (reads mapped uniquely to previously un-annotated genomic locations). Thus, use of this next generation sequencing platform paired with proprietary data analysis and visualization software thus allowed for discovery of differential transcript expression as well as differences and/or preferences for specific splice variants of expressed mRNA transcripts. Sequencing data from the SOLID™ platform is nominally represented as a transcript expression value using the metrics RPM (reads per million) and RPKM (read per kilobase per million), enabling basic differential expression analysis as is standard practice.

Whole transcriptome sequencing of four small cell lung cancer (SCLC) tumors (LU73, LU64, LU86 and LU95), one ovarian tumor (OV26) and a large cell neuroendocrine carcinoma (LCNEC; LU37) resulted in the determination of gene expression patterns commonly found in NETs (FIG. 6A). More specifically, these tumors had high expression of several NET markers (ASCL1, NCAM1, CHGA) as well as reduced levels of Notch receptors and effector molecules (e.g., HES1, HEY1) and elevated markers of Notch suppression (e.g., DLL3 and HES6). In contrast, 4 normal lung samples, 3 lung adenocarcinoma tumors (LU137, LU146 and LU153), and 3 squamous cell lung carcinomas (LU49, LU70 and LU76) all have expression of various Notch receptors and effector molecules, and do not show elevated expression of Notch suppressors such as HES6 and DLL3.

Figure 6B:
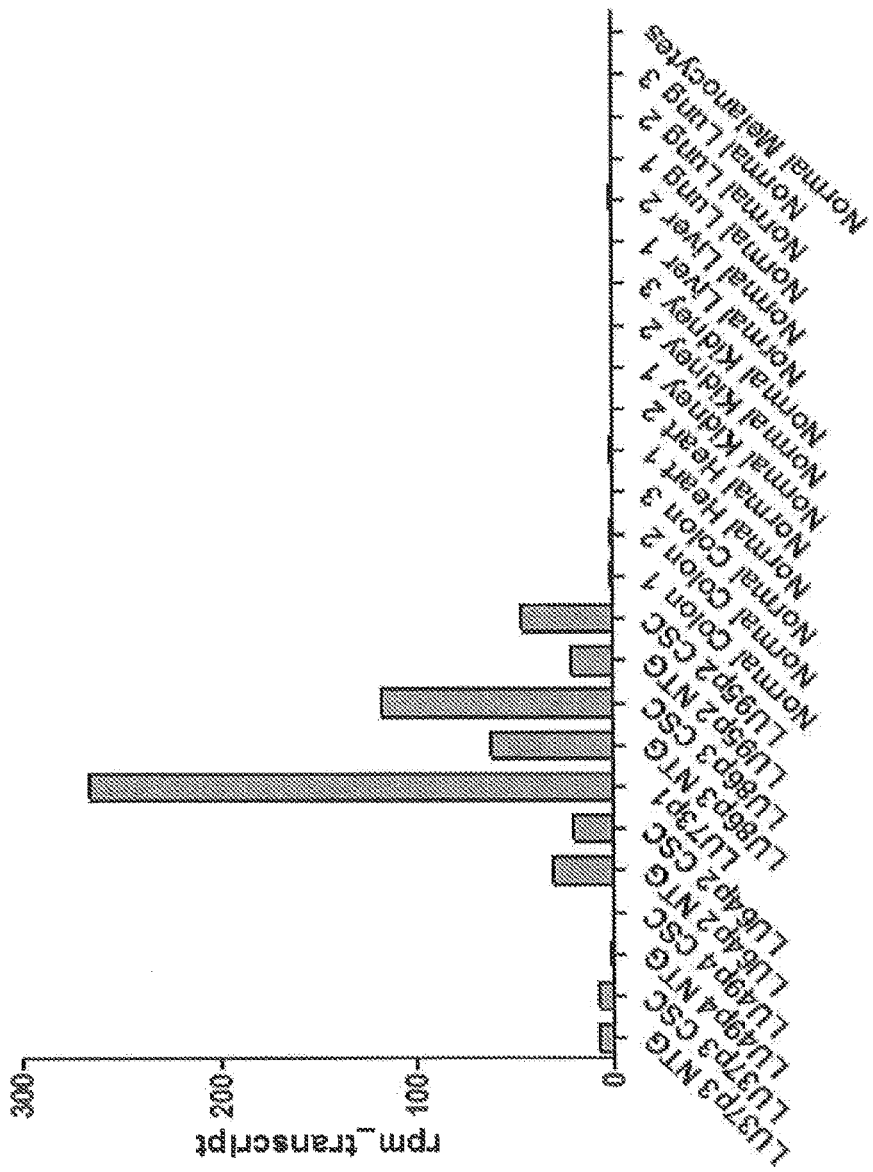

Moreover, as seen in FIG. 6B, an analysis of the whole transcriptome data comparing normal tissue samples to various lung NTX populations having neuroendocrine features, showed that SEZ6 was up-regulated at the mRNA transcript level in four lung cancer populations having neuroendocrine features (LU73, LU64, LU86 and LU95) compared to extremely low or no transcript expression in the normal tissues tested. These results suggest that SEZ6 may play an important role in the tumorigenesis and maintenance of particular cancers (including lung cancers with neuroendocrine features). On this basis, SEZ6 was selected for further analysis as a potential immunotherapeutic target Example 2

Microarray and RT-PCR Analysts of Gene Expression in Selected NTX Tumors with Neuroendocrine Features In an effort to identify additional NETs in the aforementioned NTX bank beyond those for which SOLID™ whole transcriptome data existed, a larger set of NTX lines was examined using microarray analysis. Specifically, 2-6 µg of total RNA samples derived from whole tumors in 46 NTX lines or from 2 normal tissues were analyzed using a ONEARRAY® microarray platform (Phalanx Biotech Group), which contains 29,187 probes designed against 19,380 genes in the human genome. More specifically, RNA samples were obtained (as described in Example 1) from forty-six patient derived whole NTX tumors comprising colorectal (CR), melanoma (SK), kidney (KD), lung (LU), ovarian (OV), endometrial (EM), breast (BR), liver (LIV), or pancreatic (PA) cancers. Normal colorectal (NormCR) and normal pancreas (NormPA) tissues were used as controls. Still more specifically, lung tumors were further subclassified as small cell lung cancers (SCLC), squamous cell cancers (SCC), or large cell neuroendocrine carcinoma (LCNEC). RNA samples were run in triplicate using the manufacturer's protocols and the resulting data was analyzed using standard industry practices for normalizing and transforming the measured intensity values obtained for the subject gene in each sample. An unbiased Pearson Spearman hierarchical clustering algorithm in the IR/BioConductor suite of packages called hclust.2 was used to create a standard microarray dendrogram for these 48 samples. As known in the art R/BioConductor is an open-source, statistical programming language widely used in academia, finance and the pharmaceutical industry for data analysis. Generally the tumors were arranged and clustered based on gene expression patterns, expression intensity, etc.

Figure 7A:
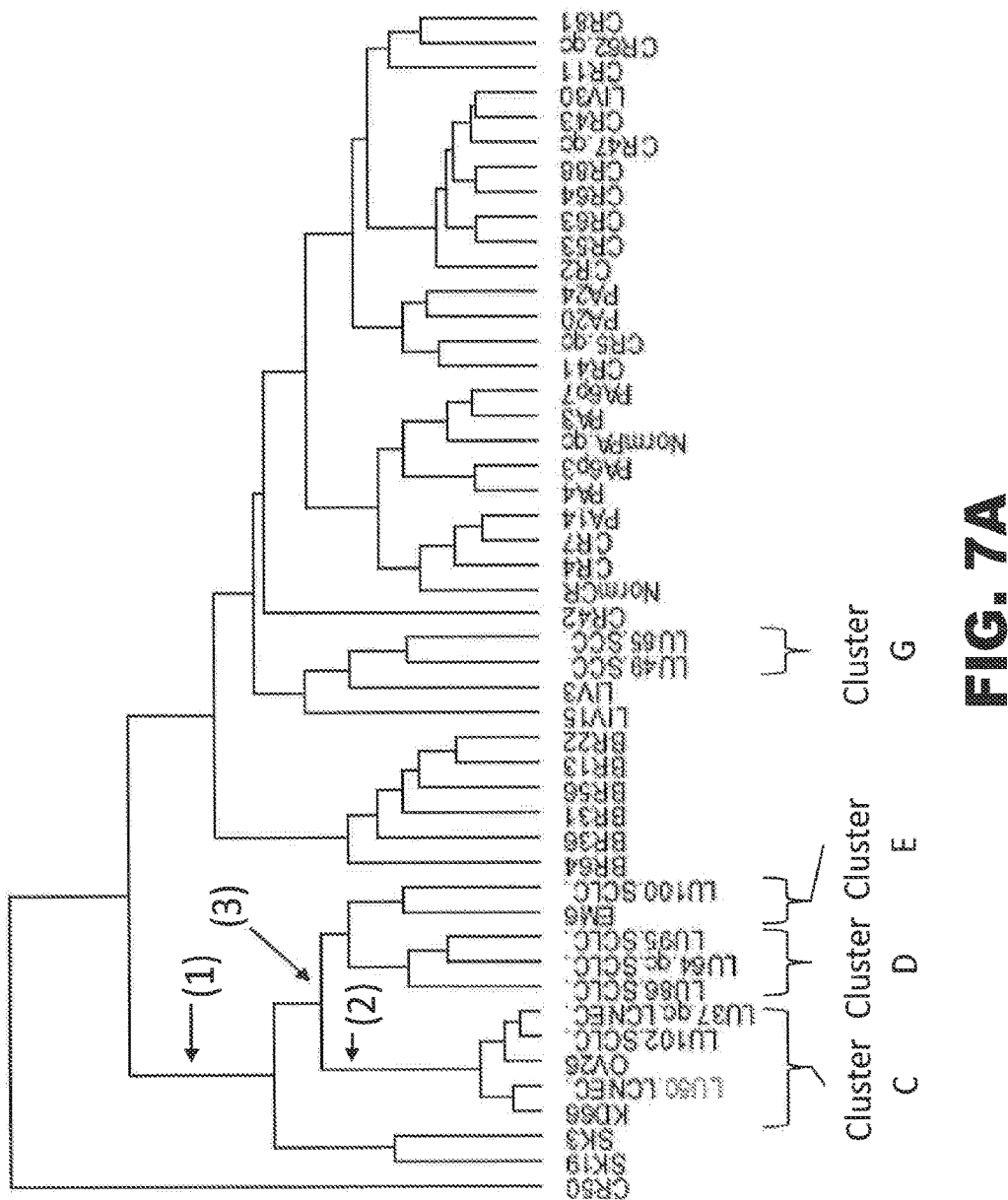

As shown in FIG. 7A, the dendrogram derived from the 48 samples and across all 19380 genes, clustered NTX lines together based upon their tumor type or tissue of origin. Several tumors typically associated with neuroendocrine phenotypes clustered together on the branch denoted by (1); these included skin cancers, numerous lung cancers and other NETs. Interestingly, a sub-branch, denoted by (2), showed that two large cell lung cancers with neuroendocrine features (LU50.LCNEC and LU37.LCNEC) and a small cell lung cancer (LU102.SCLC) clustered with an ovarian (OV26) and a kidney (KD66) tumor (cluster C) suggesting these later tumors also possessed neuroendocrine phenotypes. Moreover, FIG. 7A shows cluster D which consists of 3 additional SCLC tumors, and to its right is a small cluster (cluster E) containing an additional SCLC tumor (LU100) and a neuroendocrine endometrial tumor (EM6). All of the tumors in clusters D and E are generally understood to possess some neuroendocrine features based on the academic literature and pathology experience in the clinic. The fact that cluster G, comprising SCC, can be found on a completely different branch of the dendrogram of FIG. 7A, indicates that the clustering is not driven exclusively by the organ of origin of the tumor.

Closer inspection of a collection of gene markers associated with NETs (FIG. 7B) shows that they are strongly expressed in tumors comprising clusters C and D, while they are minimally expressed in tumors in Cluster G (squamous cell carcinoma of the lung), suggesting clusters C and D represent NETs or tumors with a neuroendocrine phenotype. More specifically, cluster C NETs highly express ASCL1, CALCA, GHGA, SST and NKX2-1, while cluster D NETs highly express CHGA, ENO2, and NCAM1, and it is the expression of these neuroendocrine phenotype genes that is in part responsible for the clustering of these tumors. An interesting feature is the strong expression of KIT in cluster D, a gene occasionally reported to be associated with neuroendocrine tumors, but clearly linked to oncogenesis in other contexts. This is in contrast to the SCC tumors in cluster G which lack strong expression any of these genes (FIG. 7B).

Tumors in cluster C show a phenotype consistent with a reduction in Notch signaling: a lack of expression of any Notch receptor, a relative lack of JAG1 and HES1 expression, and strong levels of ASCL1 expression (FIG. 7C). Interestingly, cluster D shows high expression of HES6, a transcription factor that can support ASCL1 activity by antagonizing HES1 activity through heterodimer formation.

In view of the aforementioned results, mRNA expression of HES6 was examined from various NTX lines and normal tissues using an Applied Biosystems 7900HT Machine (Life Technologies) to perform Taqman real-time quantitative RT-PCR (qRT-PCR) in accordance with the manufacturer's protocols. RNA was isolated as described above and checked to ensure quality was suitable for gene expression analysis. RNA from normal tissues was purchased (Agilent Technologies and Life Technologies). 200 ng of RNA was used for cDNA synthesis using the cDNA archive kit (Life Technologies). cDNA was used for qRT-PCR analysis on Taqman Low Density Arrays (TLDA; Life Technologies) which contained the HES6 Taqman assay to measure mRNA levels of HES6.

Figure 7D:
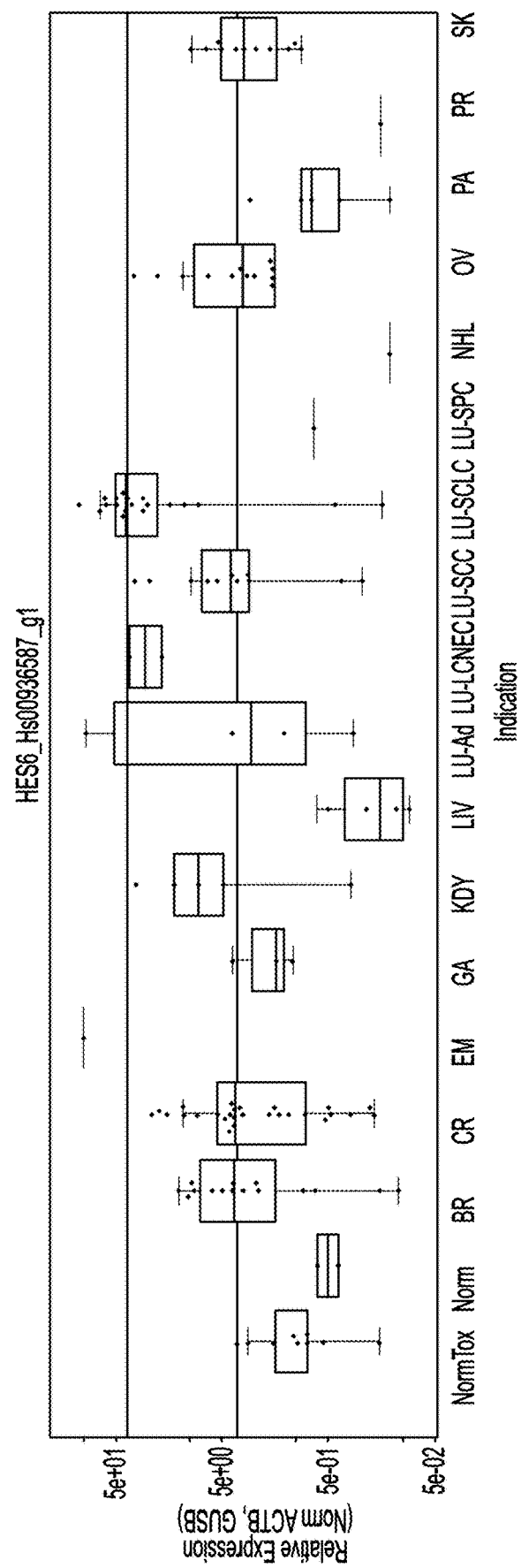

HES6 mRNA levels are shown for each NTX line or normal tissue sample (single dot on graph) after normalization to endogenous controls. Normalized values are plotted relative to the average expression in the normal tissues of toxicity concern (NormTox). This technique allowed for the rapid identification and characterization of a variety of tumors having neuroendocrine features from the NTX tumor hank through measurement of HES6 and other relevant markers. FIG. 7D illustrates general overexpression of HES6 in the sampled tumors with neuroendocrine features (e.g., LU-SCLC, LU-LCNEC) compared to normal tissues, breast, colon, liver and other selected tumors. Significantly these microarray and qPCR data show that at least some endometrial, kidney and ovarian tumors may exhibit neuroendocrine tumor features (FIGS. 7A and 7D).

The microarray data generated as described above not only showed that the tumors in clusters C, D and E exhibited various neuroendocrine markers, but also showed that the tumors in those clusters expressed markers indicative of neurogenesis, neural commitment, or differentiation towards neural fates (FIG. 7E). Of particular interest, the tumors in Cluster D frequently show a stronger and more consistent upregulation of many of these markers (e.g., BEX1 and BEX4, CD56, NRCAM, SEMA receptors, SOX and ZIC factors) and frequently reduced hormone upregulation versus other clusters, suggesting a more neural phenotype.

Example 3

Expression of SEZ6 mRNA in Tumors Having Neuroendocrine and Neural Features

Various techniques were used to identify tumors exhibiting neuroendocrine features including whole transcriptome sequencing (Example 1) and microarray and qRT-PCR (Example 2). The data thus generated was further analyzed in order to find potential therapeutic targets that are highly expressed in neuroendocrine tumors when compared to non-neuroendocrine tumors and normal tissues. As discussed in Example 1 it was found that SEZ6, a single pass transmembrane protein that is mainly expressed in the normal brain, has high expression in many neuroendocrine tumors (FIG. 6B).

Figure 7F:
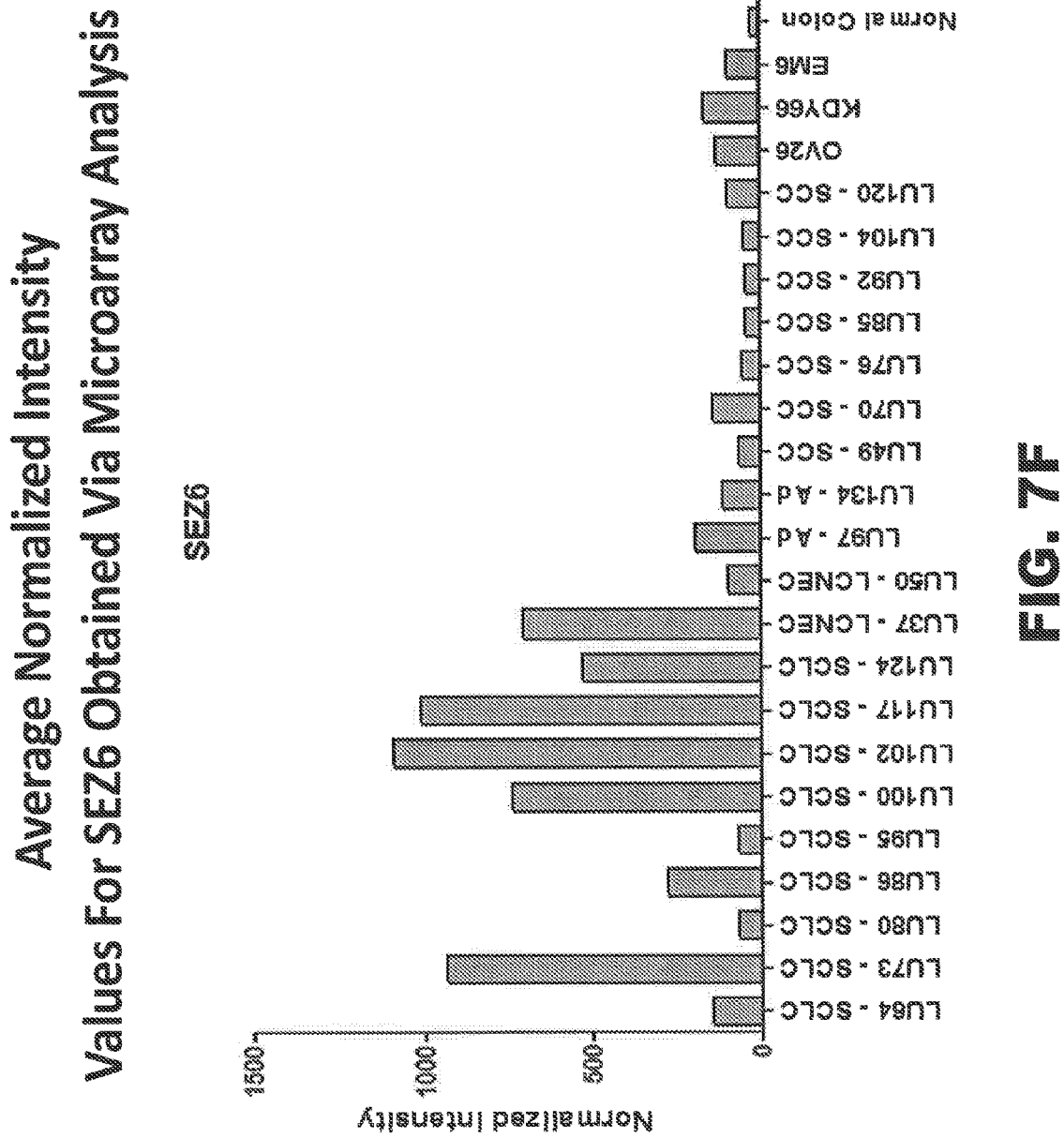

The microarray data generated in Example 2 showed that tumors located in clusters C, D and E expressed neuroendocrine markers (FIG. 7B) and neural markers (FIG. 7E). Remarkably, the tumors in those same clusters also showed high levels of SEZ6 transcript, suggesting that SEZ6 is associated with tumors having neuroendocrine and neural features (FIG. 7F). This is in line with the known role of SEZ6 in postnatal forebrain development and continued expression in the specific regions of the hippocampus in the adult. SEZ6 is thought to play important roles in cell-cell recognition and signaling. Often developmental pathways are inappropriately expressed in tumors.

Figure 8A:
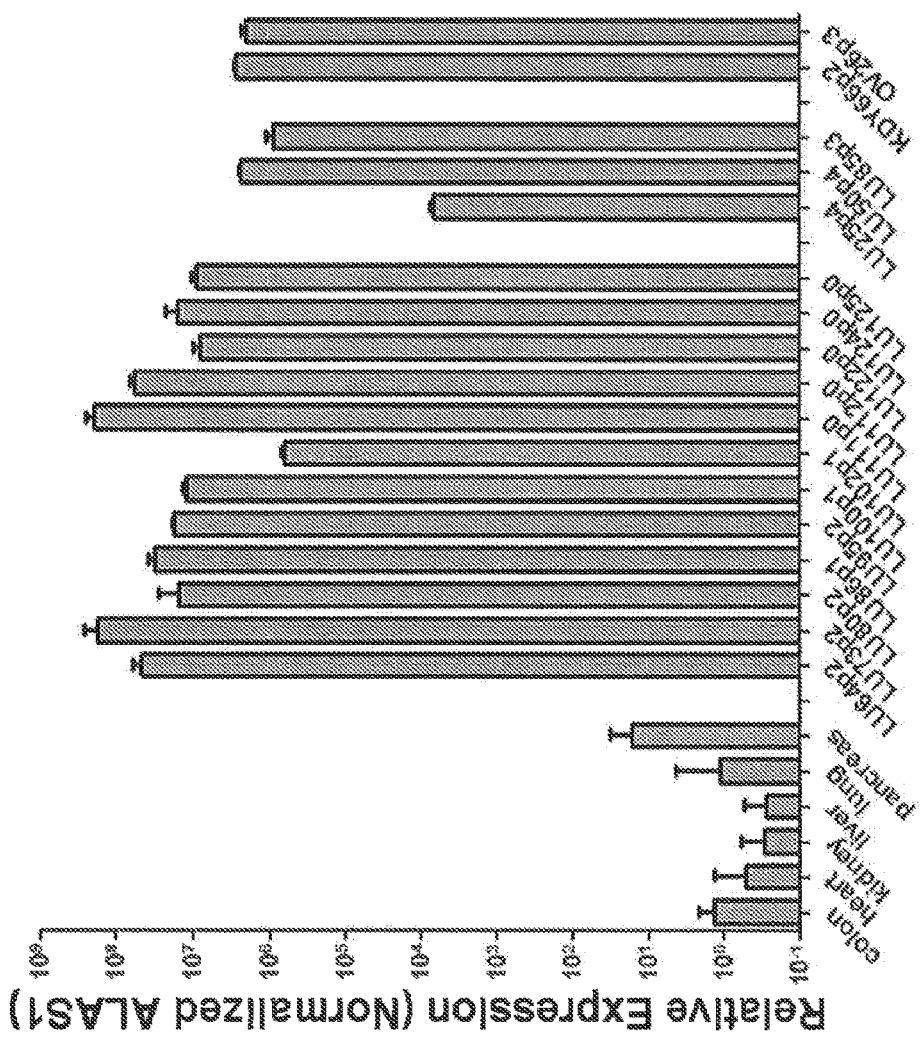
FIGS. 8A and 8B are graphical representations showing relative expression levels of SEZ6 mRNA transcripts as measured by RT-PCR in a variety of RNA samples isolated from normal tissues or bulk neuroendocrine NTX tumors (FIG. 8A) and a variety of other NTX tumors (FIG. 8B).

In order to determine SEZ6 mRNA expression levels in various sample NTX tumor lines, qRT-PCR was performed using the SEZ6 Taqman assay essentially as described in Example 2 above. FIG. 8A shows SEZ6 expression relative to the average expression in normal tissues and normalized to expression of the endogenous control gene ALAS1. SEZ6 gene expression is elevated more than 10,000,000-fold in neuroendoerine NTX populations versus normal tissues. Five of the SCLC NTX lines shown in FIG. 8A are mRNA samples extracted directly from primary biopsies (p0). The expression of SEZ6 in these unpassaged tumors demonstrates that SEZ6 expression is not an artifact that results from growing human tumors in mice. Three subtypes of NSCLC are also represented in FIG. 8A: LU25 is spindle cell carcinoma, LU50 is a large cell neuroendoerine carcinoma (LCNEC), and LU85 is a squamous cell carcinoma (SCC). KDY66 and OV26, a kidney and ovarian tumor, respectively, clustered on the microarray with SCLC and LCNEC tumors (FIG. 7A), suggesting they also have neuroendocrine features.

Figure 8B:
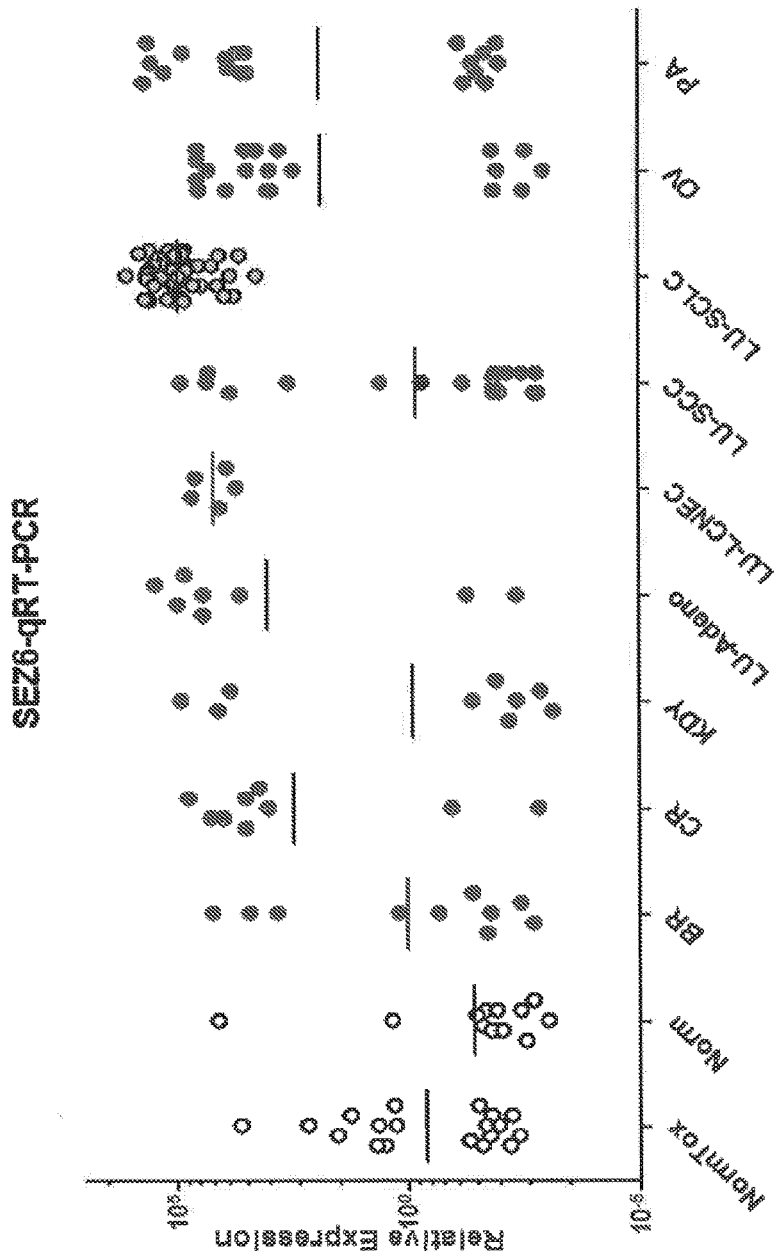

To extend the analysis of SEZ6 expression to a wider array of tumor specimens, qRT-PCR was performed using the FLUIDIGM BIOMARK™ HD System. Briefly, 1 ng of RNA, prepared as described in Example 1, was converted to cDNA using the cDNA archive kit (Life Technologies). The cDNA was pre-amplified using a SEZ6 specific Taqman assay and was then used to perform qRT-PCR. Expression in normal tissues (NormTox or Norm) was compared to expression in the following NTX lines, where the number in brackets indicates the number of unique NTX lines tested: BR (5), CR (6), KDY (9), OV (16), PA (9), lung adenocarcinoma (LU-Adeno) (7), LCNEC (2), SCC (11) and SCLC (15) (FIG. 8B). SCLC and LCNEC NTX show the highest expression of SEZ6, although some expression of SEZ6 was also seen in OV, PA, CR and LU-Adeno NTX lines compared to normal tissue samples.

"NormTox" represents the following samples of normal tissue: two colon, two kidney, two liver, two lung, two pancreas, two heart, one esophagus, one skeletal muscle, one skin, one small intestine, one spleen, one stomach, and one trachea sample. Another set of normal tissues designated "Norm" represents the following samples of normal tissue: brain, breast, cervix, ovary, peripheral blood mononuclear cells, placenta, prostate, testes, thymus, and thyroid. Most normal tissues have no expression of SEZ6, while low expression is seen in pancreas, colon, liver and lung and high expression in brain. A different SEZ6 specific Taqman assay, using essentially the same method as above, was conducted on various NTX tumor lines. The number of tumor lines that were tested for each type of tumor is denoted as the denominator, whereas the number of tumors that expressed SEZ6 is denoted as the numerator: 1/5 CR, 2/2 GA, 1/1 GB (glioblastoma), 1/1 KDY, 2/6 SK, 2/4 LU-Adeno, 2/2 LCNEC, 3/10 LU-SCC, 10/10 SCLC and 1/2 OV (data not shown).

Taken together, these data suggest that SEZ6 is upregulated in tumors exhibiting neuroendocrine and neural features suggesting it may serve as a therapeutic target for treatment of these types of tumors.

Example 4

Expression of SEZ6 mRNA in Various Tumor and Normal Tissue Specimens Using qRT-PCR To extend the analysis of SEZ6 expression to a wider array of tumor specimens, Taqman qRT-PCR was performed substantially as described in the previous Examples on a TissueScan™ qPCR (Origene Technologies) 384-well array. This array enables comparison of gene expression across 18 different solid tumor types, with multiple patient derived samples for each tumor type and from normal adjacent tissue.

Figure 9B:
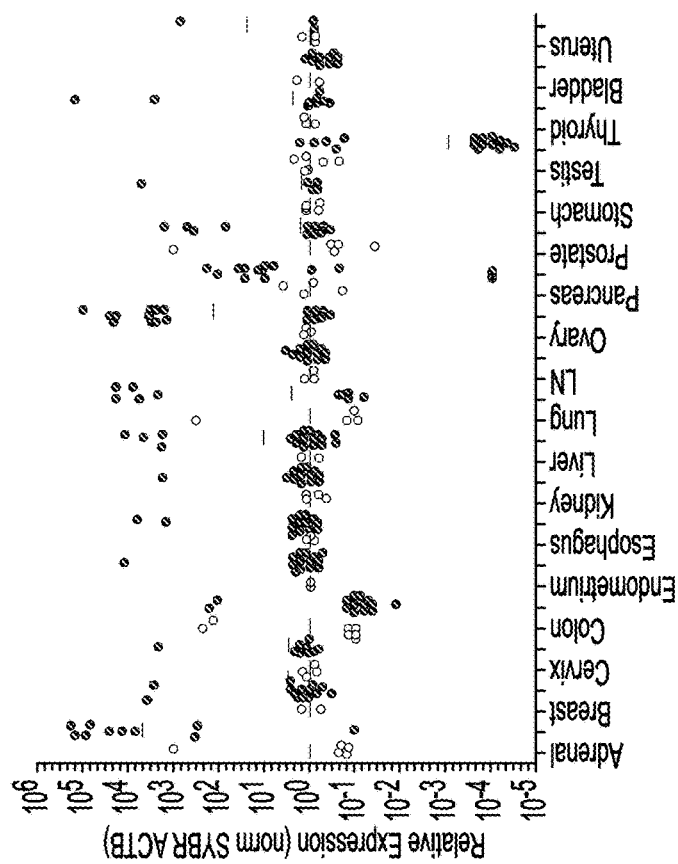
FIGS. 9A and 9B are graphical representations showing the absolute (FIG. 9A) or normalized (FIG. 9B) mRNA expression levels of human SEZ6 as measured by RT-PCR in whole tumor specimens (black dot) or matched normal adjacent tissue (NAT; white dot) from patients with one of eighteen different solid tumor types.
Figure 9A:
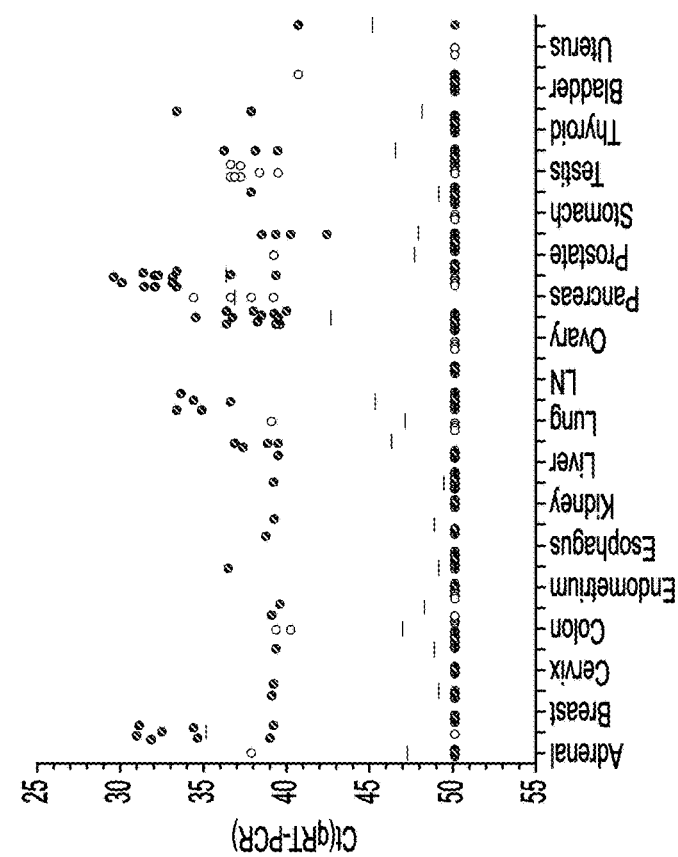

In this regard, FIGS. 9A and 9B show the absolute and relative gene expression levels, respectively, of SEZ6 in whole tumor specimens (black dots) or normal adjacent tissue (NAT; white dots) from patients with one of eighteen different solid tumor types. More specifically, FIG. 9A shows the absolute mRNA expression level of SEZ6 in various whole tumor specimens or matched normal adjacent tissue. FIG. 9B shows the expression level of SEZ6 as normalized against β-actin and plotted relative to expression in normal adjacent tissue for each tumor type analyzed. Specimens in which SEZ6 was not detected were assigned a Ct value of 50, which represents the last cycle of amplification in the experimental protocol. Each dot represents a single tissue specimen, with the geometric mean value represented as a black line.

Using this Origene Array, overexpression of SEZ6 was seen in a subset of adrenal, liver, lung, ovarian, and pancreatic cancer, many of which may represent neuroendocrine tumors or tumors with poorly differentiated neuroendocrine phenotypes. As shown by the absolute gene expression in FIG. 9A, normal testis and pancreas are the only normal tissues with high expression of SEZ6. This suggests that SEZ6 may play a role in tumorigenesis and/or tumor progression in a wide variety of tumors including but not limited to those with neuroendocrine and neural features.

Example 5

Cloning and Expression of Recombinant SEZ6 Proteins

Human SEZ6

In order to generate and develop all molecular and cellular materials required in the present invention pertaining to human SEZ6, cDNA (FIG. 3A; SEQ ID NO: 5) encoding the complete mature human SEZ6 protein (FIG. 3B, SEQ ID NO: 6) was created as follows. A commercial human SEZ6 cDNA was purchased from Open Biosystems where this cDNA sequence corresponded to NCBI accession BC146292. Sequence alignments showed the protein encoded by BC146292 differed by several residues from that of RefSeq NP_849191 (see residues 414, 415 and 417, FIG. 3C), encoding the endogenous human SEZ6 protein. PCR was used to amplify two separate cDNA fragments from the BC146292 clone, in which the primers used introduced the desired changes into the cDNA at residues 414-417 during the process of overlap PCR to create a cDNA encoding a mature SEZ6 protein with identical sequence to that encoded by NM_178860, the mRNA sequence encoding endogenous human SEZ6 protein. The repaired cDNA clone, termed hSCRx17 (FIG. 3A), was used for all subsequent engineering of constructs expressing the mature human SEZ6 protein or fragments thereof.

In order to generate immunoreactive or immunospecific modulators to the SEZ6 molecule, a chimeric fusion gene was generated in which the ECD portion of the human SEZ6 protein was fused to the human IgG2 Fc domain (FIG. 4A, SEQ ID NO: 8). This was done as follows: cDNA encoding the ECD of SEZ6 was PCR amplified from the hSCRx17 cDNA clone (FIG. 3A), and this PCR product was subsequently subcloned into a CMV driven expression vector in frame and downstream of an IgK signal peptide sequence and upstream of a human IgG2 Fc cDNA, using standard molecular techniques. The cDNA sequence encoding the hSEZ6-Fc fusion protein, termed hSCRx17-Fc ORF, is shown in FIG. 4A; the corresponding protein sequence encoded by hSCRx17-Fc ORF is shown in FIG. 4B (SEQ ID NO: 9). The underlined regions of the sequences correspond to the human IgG2 Fc. The bolded underlined regions correspond to the signal peptide, and the sequences in bold font correspond to the portions of the fusion protein encoded by the cloning restriction sites flanking the SEZ6 ECD.

To generate recombinant hSEZ6 ECD protein a similar PCR-based strategy was used. The cDNA fragment encoding the ECD of SEZ6 was amplified from the hSCRx17 cDNA clone and subcloned into a CMV driven expression vector in frame and downstream of an IgK signal peptide sequence and in frame upstream of a sequence encoding an 9-Histidine epitope tag (SEQ ID NO: 400).

The CMV driven expression vector permits high level transient expression in HEK-293T and/or CIO-S cells. Suspension or adherent cultures of HEK-293T cells, or suspension CHO-S cells were transfected with expression constructs encoding either the hSEZ6 ECD-FC or hSEZ6-ECD-His proteins, using polyethylenimine polymer as the transfecting reagent. Three to five days after transfection, the hSEZ6 ECD-Fc or hSEZ6-ECD-His proteins were purified from clarified cell-supernatants using an AKTA explorer and either MABSELECT SURE™ Protein A (GE Healthcare Life Sciences) or Nickel-EDTA (Qiagen) columns, respectively.

A stable cell line overexpressing recombinant human SEZ6 was constructed using lentiviral vectors to transduce HEK-293T cells as follows: PCR amplification was performed using the hSCRx17 clone as a template in order to produce a cDNA fragment encoding the mature human SEZ6 protein. The fragment that was generated was subcloned in frame downstream of a sequence encoding an IgK signal peptide and DDK epitope tag previously engineered upstream of the multiple cloning site of pCDH-EF1-MCS-T2A-GFP (System Biosciences) using standard molecular cloning techniques. The resulting bicistronic lentiviral vector was used to engineer cell lines overexpressing a human SEZ6-T2A peptide-GFP polypeptide. The T2A sequence promotes ribosomal skipping of a peptide bond condensation, resulting in two independent proteins, in this case SEZ6 and GFP.

Murine SEZ6

Figure 5C:
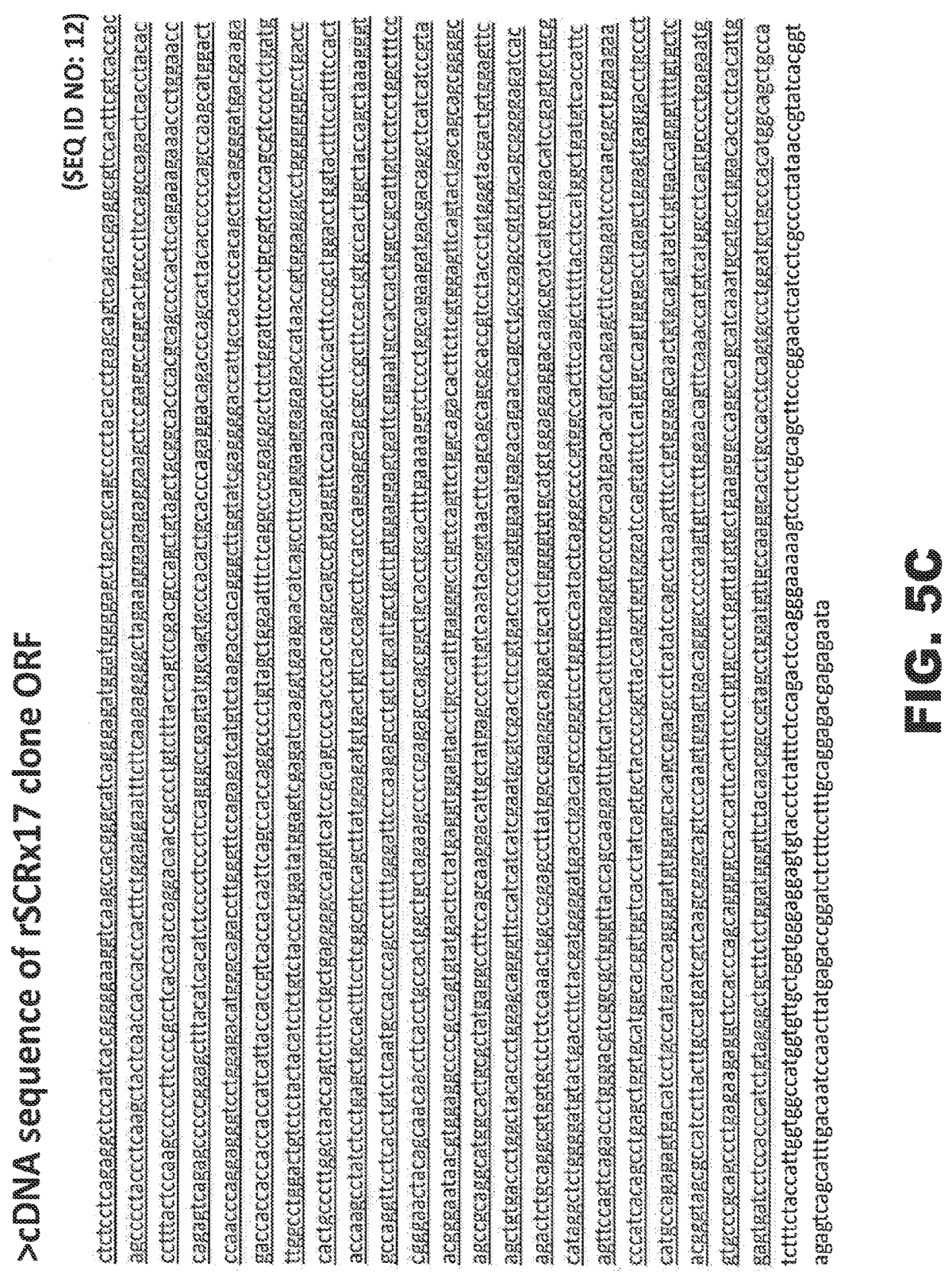

A stable cell line overexpressing recombinant murine SEZ6 was engineered essentially as described above for recombinant human SEZ6. HEK-293T cells were transduced with a lentiviral vector expressing murine SEZ6. The vector was engineered essentially as follows. A cDNA fragment (FIG. 5A; SEQ ID NO: 10) encoding the mature murine SEZ6 protein listed as RefSeq NM_021286 in the NCBI database (FIG. 5B; SEQ ID NO: 11) was obtained by PCR amplification from a commercial murine SEZ6 cDNA (Origene; #MC203634) and subcloned downstream of an IgK signal peptide sequence and DDK epitope tag sequence previously engineered upstream of the multiple cloning site of pCDH-EF1-MCS-IRES-RFP (System Biosciences) using standard molecular cloning techniques. This yielded a bicistronic lentiviral vector that was used to produce a HEK-293T cell line overexpressing murine SEZ6 and RFP.

Rat SEZ6

To generate and develop all molecular and cellular materials required in the present invention pertaining to rat SEZ6 proteins, cDNA (FIG. 5C, SEQ ID NO: 12) encoding the complete mature rat SEZ6 protein (FIG. 5D, SEQ ID NO: 13) was obtained as follows. A cDNA encoding the full length mature rat protein (i.e., the full length protein minus the wild-type signal peptide) was amplified from rat brain marathon-ready cDNA (Clontech #639412). Sequence alignments showed the ECD of the encoded protein to be homologous to the endogenous rat SEZ6 protein listed as RefSeq NP_001099224 in the NCBI database. This cDNA clone, termed rSCRx17 (FIG. 5D), was used for subsequent engineering of constructs expressing the rat SEZ6 protein fragments.

Cynomolgus SEZ6

Figure 5E:
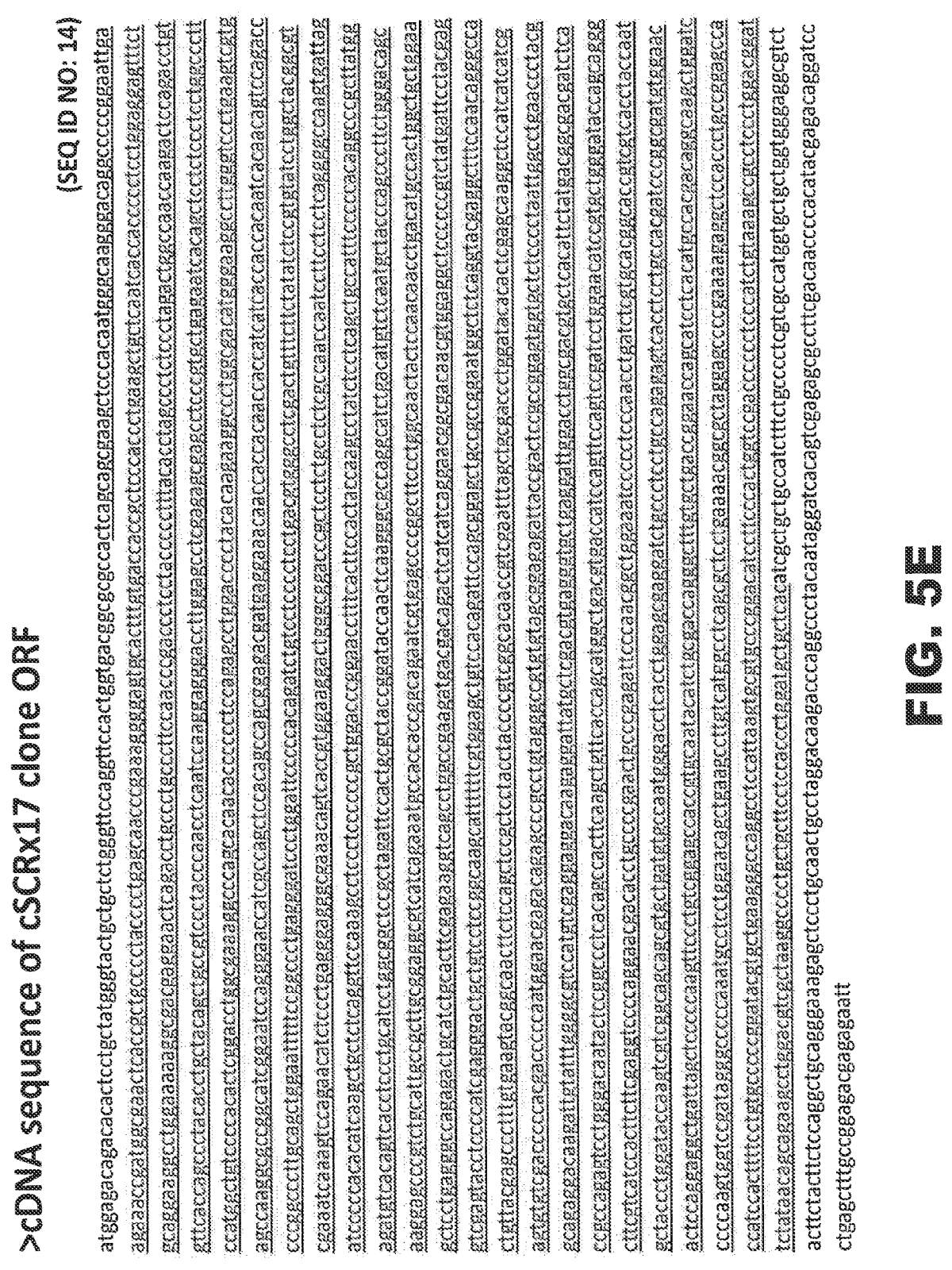

To generate and develop all molecular and cellular materials required in the present invention pertaining to cynomolgus SEZ6 proteins, cDNA (FIG. 5E, SEQ ID NO: 14) encoding the cynomolgus SEZ6 protein (FIG. 5F, SEQ ID NO: 15) was obtained as follows: A predicted cynomolgus SEZ6 ORF sequence was assembled by bioinformatics analysis in the following way: the ORF of the human SEZ6 gene was obtained from NCBI accession NM_178860 and compared, using the BLAST algorithm, to the whole genome shotgun sequencing contigs in the NCBI database. The BLAST results were then used to assemble a putative cynomolgus SEZ6 ORF. The sequence encoding the predicted wild-type signal peptide of cynomolgus SEZ6 was removed from this BLAST derived sequence, and replaced with a sequence encoding an IgK signal peptide sequence. After codon optimization for production in mammalian cells, this complete hybrid ORF sequence was ordered as a synthetic gene (GeneWiz). This optimized cDNA clone, termed cSCRx17 (FIG. 3E), was used for subsequent engineering of constructs expressing the cynomolgus SEZ6 protein fragments.

Human SEZ6L and SEZ6L2

Figure 5G:
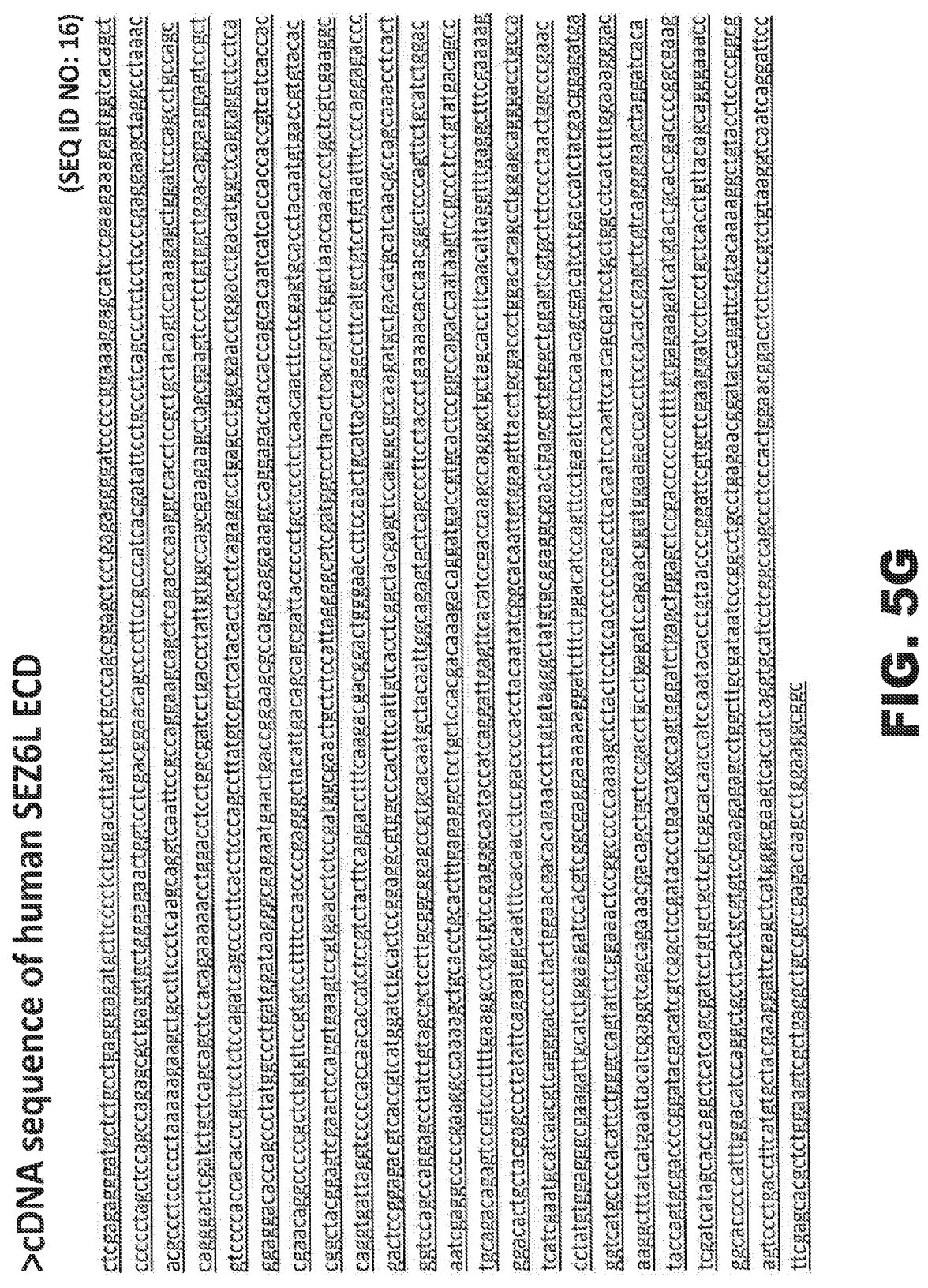

In the human genome, there are two genes closely related to SEZ6-seizure related 6 homolog-like (SEZ6L) and seizure related 6 homolog like-2 (SEZ6L2). Although the overall percent identity is relatively low between the three proteins (~42%), there are smaller stretches of perfect identity between pairs or all three of the proteins. In order to investigate any possible cross reactivity of the anti-SEZ6 modulators with human SEZ6L and SEZ6L2 proteins, the open reading frames encoding the ECDs of human SEZ6L protein (NP_0066938) and human SEZ6L2 protein (NP_001230261) were codon optimized and synthesized (GeneWiz). These optimized cDNA sequences encoding the ECDs of human SEZ6L or SEZ6L2 proteins are shown in FIGS. 5G and 5I.

Material for Cross-Reactivity Studies

Material was generated in order to study whether the SEZ6 modulators of the invention cross-reacted with rat and/or cynomolgus SEZ6 homologues, or with the closely related human SEZ6L and SEZ6L2 proteins. Chimeric fusion genes were designed in which the ECD portion of either the rat or the cynomolgus SEZ6 protein (underlined in FIGS. 5D and 5F, respectively) was fused to a 9-Histidine epitope tag (SEQ ID NO: 400), Using PCR, the cDNA fragment encoding the ECD of either rat or cynomolgus SEZ6 was amplified from either rSCRx17 or cSCRx17, respectively, and subcloned into a CMV driven expression vector in frame and downstream of an IgK signal peptide sequence and in frame and upstream of a sequence encoding an 9-Histidine epitope tag (SEQ ID NO: 400). Similarly, chimeric fusion genes were designed in which the open reading frame encoding the ECD portion of the human SEZ6L or SEZ6L2 proteins was subcloned into a CMV driven expression vector in frame and downstream of an IgK signal peptide sequence and in frame and upstream of a sequence encoding an 9-Histidine epitope tag (SEQ ID NO: 400). The resultant encoded protein sequences for these fusion proteins are shown in FIGS. 5H and 5J, respectively, with the underlined sequence representing the ECD of the particular protein under consideration.

The rat and cynomolgus SEZ6 ECD-His vectors generated above, were used to produce and purify recombinant rSEZ6-ECD-His protein and cSEZ6-ECD-His protein, respectively, as follows: using art-recognized techniques, suspension or adherent cultures of HEK-293T cells, or suspension CHO-S cells were transfected with the expression vectors encoding rSEZ6-ECD-His or cSEZ6-ECD-His protein. Polyethylenimine polymer was used as the transfecting reagent. Three to five days after transfection, the rSEZ6-ECD-His or cSEZ6-ECD-His protein was purified from clarified cell-supernatants using AKTA explorer and Nickel-EDTA (Qiagen) columns. Similarly, the human SEZ6L and SEZ6L2 ECD-His vectors were used to produce and purify recombinant human SEZ6L and human SEZ6L2 ECD-His proteins, as described for the rat and cynomolgus homologs.

Example 6

Generation of Anti-SEZ6 Murine Modulators

SEZ6 modulators in the form of murine antibodies were produced in accordance with the teachings herein through inoculation with human SEZ6-Fc. In this regard three strains of mice were used to generate high affinity, murine, monoclonal antibody modulators that can be used to associate with and/or inhibit the action of SEZ6 for the prevention and/or treatment of various proliferative disorders. Specifically, Balb/c, CD-1 and FVB mouse strains were immunized with human recombinant SEZ6-Fc and used to produce Hybridomas.

The SEZ6-Fc antigen was purified from supernatant from CHO-S cells over expressing the construct SEZ6-Fc as set forth in Example 5 (FIGS. 4A and 4B). 10 μg of SEZ6-Fc immunogen was used for the first immunization, followed by 5 μg and 2.5 μg of SEZ6-Fc immunogen for the subsequent three immunizations and five immunizations, respectively. All immunizations were performed with the immunogen emulsified with an equal volume of TITERMAX® Gold (CytRx Corporation) or alum adjuvant. Murine antibodies were generated by immunizing six female mice (two each of: Balb/c, CD-1, FVB) via footpad route for all injections.

Solid-phase ELISA assays were used to screen mouse sera for mouse IgG antibodies specific for human SEZ6. A positive signal above background was indicative of antibodies specific for SEZ6. Briefly, 96 well plates (VWR International, Cat. #610744) were coated with recombinant SEZ6-His at 0.5 μg/ml in ELISA coating buffer overnight. After washing with PBS containing 0.02% (v/v) Tween 20, the wells were blocked with 3% (w/v) BSA in PBS, 200 μL/well for 1 hour at room temperature (RT). Mouse serum was titrated (1:100, 1:200, 1:400, and 1:800) and added to the SEZ6 coated plates at 50 μL/well and incubated at RT for 1 hour. The plates are washed and then incubated with 50 μL/well HRP-labeled goat anti-mouse IgG diluted 1:10,000 in 3% BSA-PBS or 2% FCS in PBS for 1 hour at RT. Again the plates were washed and 40 μl /well of a TMB substrate solution (THERMO SCIENTIFIC™ 34028) was added for 15 minutes at RT. After developing, an equal volume of 2N $H_2SO_4$ was added to stop substrate development and the plates were analyzed by spectrophotometer at OD 450.

Sera-positive immunized mice were sacrificed and draining lymph nodes (popliteal and inguinal, and medial iliac if enlarged) were dissected out and used as a source for antibody producing cells. A single cell suspension of B cells ($228.9 \times 10^6$ cells) was fused with non-secreting P3x63Ag8.653 myeloma cells (ATCC #CRT-1580) at a ratio of 1:1 by electrofusion. Electrofusion was performed using the BTX HYBRIMMUNE™ System, (BTX Harvard Apparatus) as per the manufacturer's directions. After the fusion procedure the cells were resuspended in hybridoma selection medium supplemented with Azaserine (Sigma #A9666), high glucose DMEM medium with sodium pyruvate (Cellgro cat#15-017-CM) containing 15% Fetal Clone I serum (Hyclone), 10% BM Condimed (Roche Applied Sciences), 4 mM L-glutamine, 100 IU Penicillin-Streptomycin and 50 μM 2-mercaptoethanol and then plated in three T225 flasks in 90 mL selection medium per flask. The flasks were then placed in a humidified 37° C. incubator containing 5% $CO_2$ and 95% air for 6-7 days.

After six to seven days of growth the library consisting of the cells grown in bulk in the T225s was plated at 1 cell per well in Falcon 96 well U-bottom plates using the Aria I cell sorter. The selected hybridomas were then grown in 200 μL of culture medium containing 15% Fetal Clone 1 serum (Hyclone), 10% BM-Condimed (Roche Applied Sciences), 1 mM sodium pyruvate, 4 mM L-glutamine, 100 IU Penicillin-Streptaraycin, 50 μM 2-mercaptoethanol, and 100 μM hypoxanthine. Any remaining unused hybridoma library cells were frozen for future library testing. After ten to eleven days of growth supernatants from each well of the plated cells were assayed for antibodies reactive for SEZ6 by ELISA and FACS assays.

For screening by ELISA 96 well plates were coated with SEZ6-Fc at 0.3 μg/mL in PBS overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates were washed and probed with HRP labeled goat anti-mouse IgG diluted 1:10,000 in 3% BSA-PBS for one hour at RT. The plates were then incubated with substrate solution as described above and read at OD 450. Wells containing immunoglobulin that preferentially bound human SEZ6, as determined by a signal above background, were transferred and expanded.

Selected growth positive hybridoma wells secreting murine immunoglobulin were also screened for human SEZ6 specificity and cynomolgus, rat and marine SEZ6 cross reactivity using a flow cytometry based assay with 293 cells engineered to over-express the selected antigen or constructs fabricated in the previous Example.

For the flow cytometry assays, $50 \times 10^4$ h293 cells transduced respectively with human, cynomolgus, rat or murine SEZ6 were incubated for 30 minutes with 25-100 μL hybridoma supernatant. Cells were washed with PBS, 2% FCS, twice and then incubated with 50 μL of a goat-anti-mouse IgG Fc fragment specific secondary conjugated to DyLight 649 diluted 1:200 in PBS/2% FCS. After 15 minutes of incubation, cells were washed twice with PBS, 2% FCS, and re-suspended in the same buffer with DAPI and analyzed by flow cytometry using a FACSCanto II as per the manufacturer's instructions. Wells containing immunoglobulin that preferentially bound the SEZ6$^+$ GET$^+$ cells were transferred and expanded. The resulting hSEZ6 specific clonal hybridomas were cryopreserved in CS-10 freezing medium (Biolife Solutions) and stored in liquid nitrogen. Antibodies that bound with human, cynomolgus, rat or murine SEZ6 cells were noted as cross-reactive (see FIG. 11A).

ELISA and flow cytometry analysis confirmed that purified antibody from most or all of these hybridomas bound SEZ6 in a concentration-dependent manner. Wells containing immunoglobulin that bound SEZ6 GFP cells were transferred and expanded. The resulting clonal hybridomas were cryopreserved in CS-10 freezing medium (Biolife Solutions) and stored in liquid nitrogen.

One fusion was performed and seeded in 48 plates (4608 wells at approximately 40% cloning efficiency). The initial screen yielded sixty-three marine antibodies that associated with human SEZ6. A second screen was subsequently performed and yielded 134 antibodies that associated with human. SEZ6.

Example 7

Sequencing of SEZ6 Murine Modulators

Based on the foregoing, a number of exemplary distinct monoclonal antibodies that bind immobilized human SEZ6 or h293-hSEZ6 cells with apparently high affinity were selected for sequencing and further analysis. As shown in a tabular fashion in FIGS. 10A and 10B, sequence analysis of the light chain variable regions (FIG. 10A) and heavy chain variable regions (FIG. 10B) from selected monoclonal antibodies generated in Example 6 confirmed that many had novel complementarity determining regions and often displayed novel VDJ arrangements. Note that the complementarity determining regions set forth in FIGS. 10A and 10B are defined as per Chothia et al., supra.

As a first step in sequencing exemplary modulators, the selected hybridoma cells were lysed in TRIZOL® reagent (TRIZOL® Plus RNA Purification System, Life Technologies) to prepare the RNA. In this regard between $10^4$ and $10^5$ cells were resuspended in 1 mL TRIZOL® and shaken vigorously after addition of 200 µL of chloroform. Samples were then centrifuged at 4° C., for 10 minutes and the aqueous phase was transferred to a fresh microfuge tube where an equal volume of isopropanol was added. The tubes were again shaken vigorously and allowed to incubate at RT for 10 minutes before being centrifuged at 4° C. for 10 minutes. The resulting RNA pellets were washed once with 1 mL of 70% ethanol and dried briefly at RT before being resuspended in 40 µL of DEPC-treated water. The quality of the RNA preparations was determined by fractionating 3 µL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse $V_H$ repertoire, in combination with a 3' mouse Cγ primer specific for all mouse Ig isotypes. A 400 bp PCR fragment of the $V_H$ was sequenced from both ends using the same PCR primers. Similarly a mix of thirty-two 5' $V_\kappa$ leader sequence primers designed to amplify each of the $V_\kappa$ mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the $V_\kappa$ light chain and four for the V gamma heavy chain (γ1). The One Step RT-PCR kit was used for amplification (Qiagen). This kit provides a blend of Sensiscript and Omniscript Reverse Transcriptases, HotStar-Taq DNA Polymerase, dNTP mix, buffer and Q-Solution, a novel additive that enables efficient amplification of "difficult" (e.g., GC-rich) templates. Reaction mixtures were prepared that included 3 µL of RNA, 0.5 of 100 µM of either heavy chain or kappa light chain primers (custom synthesized by IDT), 5 µL of 5× RT-PCR buffer, 1 µL dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was set for an RT step 50° C. for 30 minutes, 95° C. for 15 minutes, followed by 30 cycles of PCR (95° C. for 30 seconds, 48° C. for 30 seconds, 72° C. for one minute). There was then a final incubation at 72° C. for 10 minutes.

To prepare the PCR products for direct DNA sequencing, they were purified using the QIAQUICK™ PCR Purification Kit (Qiagen) according to the manufacturer's protocol. The DNA was eluted from the spin column using 50 µL of sterile water and then sequenced directly from both strands. The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions using V-BASE2 (Retter et al., supra) and by alignment of $V_H$ and $V_L$ genes to the mouse germline database to provide the annotated sequences set forth in FIGS. 10A and 10B.

More specifically, FIG. 10A depicts the contiguous amino acid sequences of seventy-five novel murine light chain variable regions from anti-SEZ6 antibodies (SEQ ID NOS: 20-168, even numbers) and eleven humanized light chain variable regions (SEQ ID NOS: 170-192, even numbers) derived from representative murine light chains. Similarly, FIG. 10B depicts the contiguous amino acid sequences of seventy-five novel murine heavy chain variable regions (SEQ ID NOS: 21-169, odd numbers) from the same anti-SEZ6 antibodies and eleven humanized heavy chain variable regions ((SEQ ID NOS: 171-193, odd numbers) from the same murine antibodies providing the humanized light chains. Thus, taken together FIGS. 10A and 10B provide the annotated sequences of sevety-five operable murine anti-SEZ6 antibodies (termed SC17.1, SC17.2, SC17.3, SC17.4, SC17.8, SC17.9, SC17.10, SC17.11, SC17.14, SC17.15, SC17.16, SC17.17, SC17.18, SC17.19, SC17.22, SC17.24, SC17.27, SC17.28SC17.29, SC17.30, SC17.32, SC17.34, SC17.35, SC17.36, SC17.38, SC17.39, SC17.40, SC17.41, SC17.42, SC17.45, SC17.46, SC17.47, SC17.49, SC17.50, SC17.53, SC17.54, SC17.56, SC17.57, SC17.59, SC17.61, SC17.63, SC17.71, SC17.72, SC17.74, SC17.76, SC17.77, SC17.79, SC17.81, SC17.82, SC17.84, SC17.85, SC17.87, SC17.89, SC17.90, SC17.91, SC17.93, SC17.95, SC17.97, SC17.99, SC17.102, SC17.114, SC17.115, SC17.120, SC17121, SC17.122, SC17.140, SC17.151, SC17.156, SC17.161, SC17.166, SC17.187, SC17.191SC17.193, SC17.199 and SC17.200) and eleven humanized antibodies (termed hSC17.16, hSC17.17, hSC17.24, hSC17.28, hSC17.34, hSC17.46, hSC17.151, hSC17.155, hSC17.156, hSC17.161 and hSC17.200). Note that these same designations may refer to the clone that produces the subject antibody and, as such, the use of any particular designation should be interpreted in the context of the surrounding disclosure.

Additionally, hSC17.200vL1 (SEQ ID NO: 192) is a variant of the humanized light chain construct hSC17.200 (SEQ ID NO: 190), hSC17.155vH1-vH6 (SEQ ID NOS: 193-198) are variants of the heavy chain construct hSC.155 (SEQ ID NO: 184) which is derived from SC17.90 (SEQ ID NO: 127) and that hSC161vH1 (SEQ ID NO: 199) is a variant of the heavy chain construct hSC17.161 (SEQ ID NO: 189). As will be discussed in more detail below these variants were constructed and tested to optimize one or more biochemical properties of the parent antibody.

Further, corresponding nucleic acid sequences of each of the seventy-five exemplary murine modulators and eleven humanized modulators and variants set forth in FIGS. 10A and 10B are included in sequence listing of the instant application (SEQ ID NOS: 220-399).

For the purposes of the instant application the SEQ ID NOS of each particular antibody are sequential. Thus mAb SC17.1 comprises SEQ ID NOS: 20 and 21 for the light and heavy chain variable regions respectively. In this regard SC17.2 comprises SEQ ID NOS: 22 and 23, SC17.9 comprises SEQ ID NOS: 24 and 25, and so on. Moreover, corresponding nucleic acid sequences for each antibody amino acid sequence in FIGS. 10A and 10B are appended to the instant application in the sequence listing filed herewith. In the subject sequence listing the included nucleic acid sequences comprise SEQ ID NOS that arc two hundred greater than the corresponding amino acid sequence (light or heavy chain). Thus, nucleic acid sequences encoding the light and heavy chain variable region amino acid sequences of mAb SC17.1 (i.e., SEQ ID NOS: 20 and 21) comprise SEQ ID NOS: 220 and 221 in the sequence listing. In this regard nucleic acid sequences encoding all of the disclosed light and heavy chain variable region amino acid sequences, including those encoding the humanized constructs and variants thereof, are numbered similarly and comprise SEQ ID NOS: 220-399.

Example 8

Generation of Chimeric and Humanized SEZ6 Modulators

As alluded to above, eleven of the murine antibodies from Example 7 were humanized using complementarity determining region (CDR) grafting. Human frameworks for heavy and light chains were selected based on sequence and structure similarity with respect to functional human germline genes. In this regard structural similarity was evaluated by comparing the mouse canonical CDR structure to human candidates with the same canonical structures as described in Chothia et al. (supra).

More particularly eleven murine antibodies SC17.16, SC17.17, SC17.24, SC17.28, SC17.34, SC17.46, SC17.151, SC17.155, SC17.156, SC17.161 and SC17.200 were humanized using a computer-aided CDR-grafting method (Abysis Database, UCL Business Plc.) and standard molecular engineering techniques to provide hSC17.16, hSC17.17, hSC17.24, hSC17.28, hSC17.34, hSC17.46, hSC17.151, hSC17.155, hSC17.156, hSC17.161 and hSC17.200 modulators. The human framework regions of the variable regions were selected based on their highest sequence homology to the subject mouse framework sequence and its canonical structure. For the purposes of the humanization analysis, the assignment of amino acids to each of the CDR domains is in accordance with Kabat et al, numbering (supra).

Molecular engineering procedures were conducted using art-recognized techniques. To that end total mRNA was extracted from the hybridomas and amplified as set forth in Example 7 immediately above.

From the nucleotide sequence information, data regarding V, D and J gene segments of the heavy and light chains of subject murine antibodies were obtained. Based on the sequence data new primer sets specific to the leader sequence of the Ig $V_H$ and $V_K$ light chain of the antibodies were designed for cloning of the recombinant monoclonal antibody. Subsequently the V-(D)-J sequences were aligned with mouse Ig germ line sequences. The resulting genetic arrangements for each of the eleven humanized constructs are shown in Table 1 immediately below.

TABLE 1

| mAb | human VH | human DH | human JH | FW changes | human VK | human JK | FW changes |
|---|---|---|---|---|---|---|---|
| hSC17.16 | IGHV1-2 | IGHD3-16 | JH5 | none | IGKV-O2 | JK1 | none |
| hSC17.17 | IGHV1-2 | IGHD4-11 | JH4 | none | IGKV-L6 | JK2 | none |
| hSC17.24 | VH1-f | IGHD5-12 | JH4 | 48I, 73K | VKB3 | JK1 | none |
| hSC17.28 | IGHV1-2 | IGHD3-16 | JH4 | none | IGKV-A10 | JK4 | none |
| hSC17.34 | IGHV1-3 | IGHD3-10 | JH4 | 71V | IGKV-L1 | JK1 | 71Y |
| hSC17.46 | IGHV1-2 | IGHD4-23 | JH4 | 48I, 69L | IGKV-L11 | JK1 | 87F |
| hSC17.151 | IGHV1-46 | IGHD1-14 | JH4 | none | VKL6 | JK2 | none |
| hSC17.155 | IGHV1-46 | IGHD2-2 | JH4 | none | VKB3 | JK1 | none |
| hSC17.156 | IGHV2-26 | IGHD4-17 | JH4 | none | VKO1 | JK4 | none |
| hSC17.161 | IGHV1-2 | IGHD1-14 | JH4 | none | VKB3 | JK2 | none |
| hSC17.200 | IGHV5-51 | IGHD4-17 | JH4 | none | IGKV-L6 | JK4 | none |

The humanized antibodies listed in Table 1 correspond to the annotated light and heavy chain sequences set forth in FIGS. 10A and 10B (SEQ ID NOS: 170-191). The corresponding nucleic acid sequences of the light and heavy chain variable regions are set forth in the sequence listing. TABLE 1 further demonstrates that very few framework changes were necessary to maintain the favorable properties of the binding modulators. In this respect framework changes or back mutations were only made in three of the heavy chain variable regions and only two framework modifications were undertaken in the light chain variable regions.

Note that, for some humanized light and heavy chain variable regions (e.g. hSC17.200, hSC17.155 and hSC17.161), conservative amino acid mutations were introduced in the CDRs to address stability concerns while maintaining antigen binding. In each case, the binding affinity of the antibodies with modified CDR's was found to be equivalent to either the corresponding chimeric or murine antibody. The sequences of nine exemplary humanized variant chains (light and heavy) are listed at the end of FIGS. 10A and 10B (SEQ ID NOS: 192-199) where they retain the designation of the humanized parent chain with notation to indicate they have been altered (e.g. hSC17.200vL1, hSC17.155vH1-6 and hSC17.161vH1).

Following humanization of all selected antibodies by CDR grafting, the resulting light and heavy chain variable region amino acid sequences were analyzed to determine their homology with regard to the murine donor and human acceptor light and heavy chain variable regions. The results, shown in Table 2 below, reveal that the humanized constructs consistently exhibited a higher homology with respect to the human acceptor sequences than with the marine donor sequences. More specifically, the humanized heavy and light chain variable regions generally show a higher percentage homology to a closest match of human germline genes (84%-95%) as compared to the homology of the humanized variable region sequences and the donor hybridoma protein sequences (74%-89%).

TABLE 2

| mAb | Homology to Human (CDR acceptor) | Homology to Murine Parent (CDR donor) |
|---|---|---|
| hSC17.16 HC | 91% | 80% |
| hSC17.16 LC | 86% | 85% |
| hSC17.17 HC | 93% | 80% |
| hSC17.17 LC | 87% | 77% |
| hSC17.24 HC | 86% | 79% |
| hSC17.24 LC | 93% | 89% |

TABLE 2-continued

| mAb | Homology to Human (CDR acceptor) | Homology to Murine Parent (CDR donor) |
|---|---|---|
| hSC17.28 HC | 89% | 77% |
| hSC17.28 LC | 92% | 78% |
| hSC17.34 HC | 85% | 83% |
| hSC17.34 LC | 84% | 86% |
| hSC17.46 HC | 85% | 83% |
| hSC17.46 LC | 84% | 80% |
| hSC17.151 HC | 90% | 79% |
| hSC17.151 LC | 87% | 80% |
| hSC17.155 HC | 90% | 80% |
| hSC17.155 LC | 95% | 87% |
| hSC17.156 HC | 89% | 79% |
| hSC17.156 LC | 86% | 93% |
| hSC17.161 HC | 89% | 86% |

TABLE 2-continued

| mAb | Homology to Human (CDR acceptor) | Homology to Murine Parent (CDR donor) |
|---|---|---|
| hSC17.161 LC | 93% | 87% |
| hSC17.200 HC | 90% | 74% |
| hSC17.200 LC | 88% | 82% |

Upon testing, and as will be discussed in Example 9, each of the humanized constructs exhibited favorable binding characteristics roughly comparable to those shown by the murine parent antibodies (Data not shown).

Whether humanized or murine, once the nucleic acid sequences of the variable regions are determined the antibodies of the instant invention may be expressed and isolated using art-recognized techniques. To that end synthetic DNA fragments of the chosen heavy chain (humanized or murine) variable region were cloned into a human IgG1 expression vector. Similarly the variable region light chain DNA fragment (again humanized or marine) was cloned into a human light chain expression vector. The selected antibody was then expressed by co-transfection of the derived heavy and the light chain nucleic acid constructs into CHO cells.

More particularly, one compatible method of antibody production comprised directional cloning of murine or humanized variable region genes (amplified using PCR) into selected human immunoglobulin expression vectors. All primers used in Ig gene-specific PCRs included restriction sites which allowed direct cloning into expression vectors containing human IgG1 heavy chain and light chain constant regions. In brief, PCR products were purified with QIAQUICK™ PCR purification kit (Qiagen) followed by digestion with AgeI and XhoI (for the heavy chain) and XmaI and DraIII (for the light chain), respectively. Digested PCR products were purified prior to ligation into expression vectors. Ligation reactions were performed in a total volume of 10 μL with 200 U T4-DNA Ligase (New England Biolabs), 7.5 μL of digested and purified gene-specific PCR product and 25 ng linearized vector DNA. Competent E. coli DH10B bacteria (Life Technologies) were transformed via heat shock at 42° C. with 3 μL ligation product and plated onto ampicillin plates (100 μg/mL). The AgeI-EcoRI fragment of the $V_H$ region was than inserted into the same sites of pEE6.4HuIgG1 expression vector while the synthetic XmaI-DraIII VK insert was cloned into the XmaI-DraIII sites of the respective pEE12.4Hu-Kappa expression vector.

Cells producing the selected antibody were generated by transfection of HEK 293 cells with the appropriate plasmids using 293fectin. In this respect plasmid DNA was purified with QIAPREP™ Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 μg/mL streptomycin, 100 U/mL penicillin G (all from Life Technologies).

For transient transfections cells were grown to 80% confluency. Equal amounts of IgH and corresponding IgL chain vector DNA (12.5 μg of each) was added to 1.5 mL Opti-MEM mixed with 50 μL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared of cell debris by centrifugation at 800×g for 10 min and stored at 4° C. Recombinant chimeric and humanized antibodies were purified with Protein G beads (GE Healthcare) and stored under appropriate conditions.

Example 9

Characteristics of SEZ6 Modulators

Various methods were used to analyze the binding and immunochemical characteristics of selected SEZ6 modulators generated as set forth above. Specifically, a number of the antibody modulators were characterized as to affinity, binning, and cross reactivity with regard to human, cynomolgus, rat and mouse SEZ6 antigen along with SEZ6L and SEZ6L2 proteins by art-recognized methods including flow cytometry. Affinities and kinetic constants $k_{on}$ and $k_{off}$ of the selected modulators were measured using bio-layer interferometry analysis on a FORTEBIO® RED (FORTEBIO®, Inc.) or surface plasmon resonance using a BIACORE™ 2000 each according to the manufacturer's instructions.

The characterization results are set forth in tabular form in FIG. 11A where it may be seen that the selected modulators generally exhibited relatively high affinities in the nanomolar range and, in many cases, were cross-reactive with one or more SEZ6 orthologs. FIG. 12 further lists the empirically determined bin occupied by the subject modulator. Taken together, these data demonstrate the varied binding properties of the disclosed modulators as well as their potential suitability for pharmaceutical development based on their reactivity in animal models.

In this regard flow cytometry was performed using a FACSCanto II as per the manufacturer's instructions in order to confirm that selected SC17 antibody modulators can immunospecifically associate with human SEZ6 and to determine whether the same modulators cross-react with cynomolgus, rat and/or murine SEZ6 in addition to SEZ6L and SEZ6L2. More particularly modulators were tested for cross reactivity to murine SEZ6 and rat SEZ6 by flow cytometry against Neuro2a (ATCC Cat #CCL131), and RIN-m5F (ATCC cat #CRL-11605) cell lines which express mouse SEZ6 and rat SEZ6, respectively. For examining cross reactivity to cynomolgus SEZ6, yeast displaying the extracellular domain of cynomolgus SEZ6 (Boder et al, 1997) were used for flow cytometry analysis.

Briefly 1×10⁵ cells per well of Neuro2a, RIN-5mF, or yeast displaying cynomolgus SEZ6 cells were incubated for 30 minutes with 50 μL PBS (2% FCS) buffer with 5 μg/mL antibody. Cells were washed twice with the same buffer and then incubated with 50 μL per sample DyLight 649 labeled goat-anti-mouse IgG, Fc fragment specific secondary diluted 1:200 in PBS buffer. After incubating for 15 minutes cells were washed twice with the PBS buffer and re-suspended in the same with DAPI for flow cytometry analysis of Neuro2a and Rin-m5F or buffer without DAPI for flow cytometric analysis of yeast cells with cSEZ6. Antibodies that bound to the Neuro2a or RIN-m5F cell lines, or yeast displaying cynomolgus SEZ6 were considered to be cross reactive to murine SEZ6, rat SEZ6, or cynomolgus SEZ6, respectively. FIG. 11A shows the cross reactivity results. Six antibodies were cross reactive for human and mouse SEZ6 (SC17.6, SC17.7, SC17.19, SC17.24, SC17.26 and SC17.42); six for human and rat SEZ6 (SC17.6, SC17.17, SC17.19, SC17.26, SC17.28, SC17.34 and SC17.42); and six for human and cynomolgus SEZ6 (SC17.17, SC17.24, SC17.26, SC17.34, SC17.36 and SC17.45). Note that SC17.6 is duplicative of SC17.16 and exhibits the same binding characteristics.

To verify the cross reactivity data above for rat SEZ6 and to determine the affinity and kinetic constants $k_{on}$ and $k_{off}$ of the selected effectors, either bio-layer interferometry analysis on a FORTEBIO® RED (FORTEBIO®, Inc.) or surface plasmon resonance on a BIACORE™ 2000 (GE Healthcare) were conducted. Affinities were determined to both human recombinant SEZ6-His and rat recombinant SEZ6-His generated in Example 5. As seen in FIG. 11A, a number of the antibodies tested, cross reacted with rat SEZ6. The selected modulators exhibited relatively high affinities for both rat and human SEZ6 in the nanomolar range.

To determine cross reactivity to family member proteins, SEZ6L and SEZ6L2, an ELISA-based assay was used. Plates were coated with SEZ6, SEZ6L, or SEZ6L2 proteins at 0.2 µg/mL in PBS overnight. After washing with PBS containing 0.05% (v/v) Tween 20 (PBST), the wells were blocked with 2% (w/v) BSA in PBS (PBSA), 100 µL/well for 1 hour at room temperature. Antibody was then added at 1 µg/mL in 100 µL PBSA for 1 hour at room temperature. After washing with PBST, 100 µL/well HRP-labeled goat anti-mouse IgG diluted 1:2,000 in PBSA for 1 hour at room temperature. The plates were washed and 100 µL/well of the TMB substrate solution (Thermo Scientific 34028) was added for 15 minutes at room temperature. After developing, an equal volume of 2M $H_2SO_4$ was added to stop substrate development and analyzed by spectrophotometer at OD 450. FIG. 11A shows that one antibody was cross reactive with SEZ6L (SC17.7) and five were cross-reactive with SEZ6L2 (SC17.6, SC17.7, SC17.19, SC17.26 and SC17.28). As discussed above, such pan-SEZ6 antibodies are compatible with the teachings herein and may be used in conjunction with the disclosed methods.

Binding characteristics of the following humanized constructs from Example 8, hSC17.16, hSC17.17, hSC17.24, hSC17.28, hSC17.34 and hSC17.46, were analyzed in order to determine whether the CDR grafting process had appreciably altered their binding characteristics. The humanized constructs (CDR grafted) were compared with "traditional" chimeric antibodies comprising the murine parent (or donor) heavy and light chain variable domains and a human constant region substantially equivalent to that used in the humanized constructs. With these constructs surface plasmon resonance was conducted using a BIACORE™ 2000 (GE Healthcare) to identify any subtle changes in rate constants brought about by the humanization process. In all cases, the humanized antibodies had binding affinity equivalent or better than the corresponding murine antibodies (Data not shown).

Antibody binning was determined for various SEZ6 modulators as shown in FIG. 11A. A FORTEBIO® RED was used per manufacturer's instructions to identify competing antibodies that bound to the same or different bins. Briefly, a reference antibody (Ab1) was captured onto an anti-mouse capture chip, a high concentration of non-binding antibody was then used to block the chip and a baseline was collected. Monomeric, recombinant human SEZ6 (described in Example 5) was then captured by the specific antibody (Ab1) and the tip was dipped into a well with either the same antibody (Ab1) as a control or into a well with a different test antibody (Ab2). If additional binding was observed with a new antibody, then Ab1 and Ab2 were determined to be in a different bin. If no further binding occurred, as determined by comparing binding levels with the control Ab1, then Ab2 was determined to be in the same bin. As known in the art this process can be expanded to screen large libraries of unique antibodies using a full row of antibodies representing unique bins in a 96-well plate. In the instant case this binning process showed the screened antibodies bound to at least seven different bins on the SEZ6 protein. Bins A-F are unique bins and the antibodies contained in each of these bins compete with each other (but not with antibodies from other defined bins) for binding to the SEZ6 protein. Bin U contains antibodies that do not compete with antibodies in bins A-F, but may compete for binding with each other.

Example 10

Epitope Mapping of SEZ6 Modulators

In order to characterize the epitopes that the disclosed SEZ6 antibody modulators associate with or bind to, domain-level epitope mapping was performed using a modification of the protocol described by Cochran et al. (J Immunol Methods. 287 (1-2):147-158 (2004)) which is incorporated herein by reference). Individual domains of SEZ6 were expressed on the surface of yeast and binding by each SEZ6 antibody was determined through flow cytometry.

Yeast display plasmid constructs were created for the expression of the following constructs: SEZ6 extracellular domain (amino acids 1-904); Sushi Domain 1 (amino acids 336-395), CUB Domain 1 (amino acids 297-508), Sushi Domain 2 (amino acids 511-572), CUB Domain 2 (amino acids 574-685), Sushi Domain 3 (amino acids 690-748), Sushi Domain 4 (amino acids 750-813), Sushi Domain 5 (amino acids 817-878), and Sushi Domain 5+C-terminus (amino acids 817-904). Additionally, the N terminal domain (amino acids 1-335) was divided into 3 fragments termed N1 (amino acids 1-70), N2 (amino acids 71-169) and N3 (amino acids 169-335), each of which was cloned into the yeast display plasmid. Amino acid numbering does not include the leader peptide. For domain information see generally UniProtKB/Swiss-Prot database entry Q53EL9. These plasmids were transformed into yeast, which were then grown and induced as described in Cochran et al. Note that all amino acid numbering is based on mature SEZ6 protein without the 19aa leader sequence.

To test for binding to a particular construct, 200,000 induced yeast cells expressing the desired construct were washed twice in PBS+1 mg/mL BSA (PBSA), and incubated in 50 µL of PBSA with chicken anti c-myc (Life Technologies) at 0.1 µg/mL and either 50 nM purified antibody or 1:2 dilution of unpurified supernatant from hybridomas cultured for 7 days. Cells were incubated for 90 minutes on ice and then washed twice in PBSA. Cells were then incubated in 50 µL PBSA with the appropriate secondary antibodies: for murine antibodies, Alexa 488 conjugated anti-chicken, and Alexa 647 conjugated goat anti-mouse (both Life Technologies) were added at 1 µg/mL each, and for humanized or chimeric antibodies, Alexa 647 conjugated anti-chicken (Life Technologies) and R-phycoerythrin conjugated goat anti-human (Jackson Immunoresearch) were added at 1 µg/mL each. After twenty minutes' incubation on ice, cells were washed twice with PBSA and analyzed on a FACS Canto II.

All modulators bound uniquely to a single domain expressed on yeast cells. In some cases, antibody clones bound specifically to yeast expressing Sushi Domain 5+C-terminus but not to yeast expressing Sushi Domain 5. These antibody clones were concluded to bind to the C-terminal region only (amino acids 879-904).

Epitopes were classified either as conformational (i.e. discontinuous) or linear. Yeast displaying the SEZ6 ECD construct was heat treated for 30 minutes at 80° C. in order to denature the antigen, washed twice in ice-cold PBSA and then subjected to the same staining protocol and flow cytometry analysis as described above. Antibodies that bound to both the denatured and native yeast were classified as binding to a linear epitope, whereas antibodies that bound native yeast but not denatured yeast were classified as conformationally specific.

A summary of the domain-level epitope mapping data of the antibodies tested is presented in TABLE 3 below. Antibodies that bind a linear epitope are underlined and antibodies that bind SEZ6 family members SEZ6L and SEZ6L2 are designated with an asterisk and/or a dagger, respectively.

TABLE 3

| Domain | Antibody Clones |
|---|---|
| N1 (aa 1-70) | SC17.4, SC17.7†*, SC17.9, SC17.56, SC17.81, SC17.101, SC17.114, SC17.120, SC17.134, SC17.151, SC17.162, SC17.SC177, SC17.182, SC17.185, SC17.196, SC17.197, SC17.199 |
| N2 (aa 71-169) | SC17.24, SC17.49, SC17.104, SC17.144, SC17.149, SC17.168, SC17.SC176, SC17.198 |
| N3 (aa 170-335) | SC17.26†, SC17.42, SC17.83, SC17.85, SC17.88, SC17.91, SC17.92, SC17.99, SC17.125, SC17.128, SC17.130, SC17.137, SC17.145, SC17.161, SC17.192, SC17.195 |
| Sushi Domain 1 (aa 336-395) | SC17.34, SC17.36, SC17.46, SC17.75, SC17.82, SC17.87, SC17.97, SC17.116, SC17.129, SC17.SC178, SC17.187, SC17.200 |
| CUB Domain 1 (aa 397-508) | SC17.73, SC17.76, SC17.86, SC17.100, SC17.105, SC17.107, SC17.1SC17, SC17.122, SC17.124, SC17.136, SC17.138, SC17.146, SC17.154, SC17.SC170, SC17.SC174, SC17.189, SC17.201, SC17.202 |
| Sushi Domain 2 (aa 511-572) | SC17.90, SC17.108, SC17.112, SC17.135, SC17.167, SC17.SC173, SC17.SC179, SC17.184, SC17.203, SC17.204 |
| CUB Domain 2 (aa 574-685) | SC17.6†, SC17.28†, SC17.103, SC17.109, SC17.119, SC17.181, SC17.186, SC17.194 |
| Sushi Domain 3 (aa 690-748) | SC17.72, SC17.84, SC17.95, SC17.141, SC17.143, SC17.163 |
| Sushi Domain 4 (aa 750-813) | SC17.SC17, SC17.19†, SC17.93, SC17.102, SC17.121, SC17.140, SC17.156, SC17.159, SC17.166, SC17.SC175, SC17.180, SC17.191, SC17.193 |
| Sushi Domain 5 (aa 817-878) | SC17.74, SC17.106, SC17.142, SC17.190 |
| C terminus (aa 879-904) | SC17.96, SC17.132 |

Figure 11B:
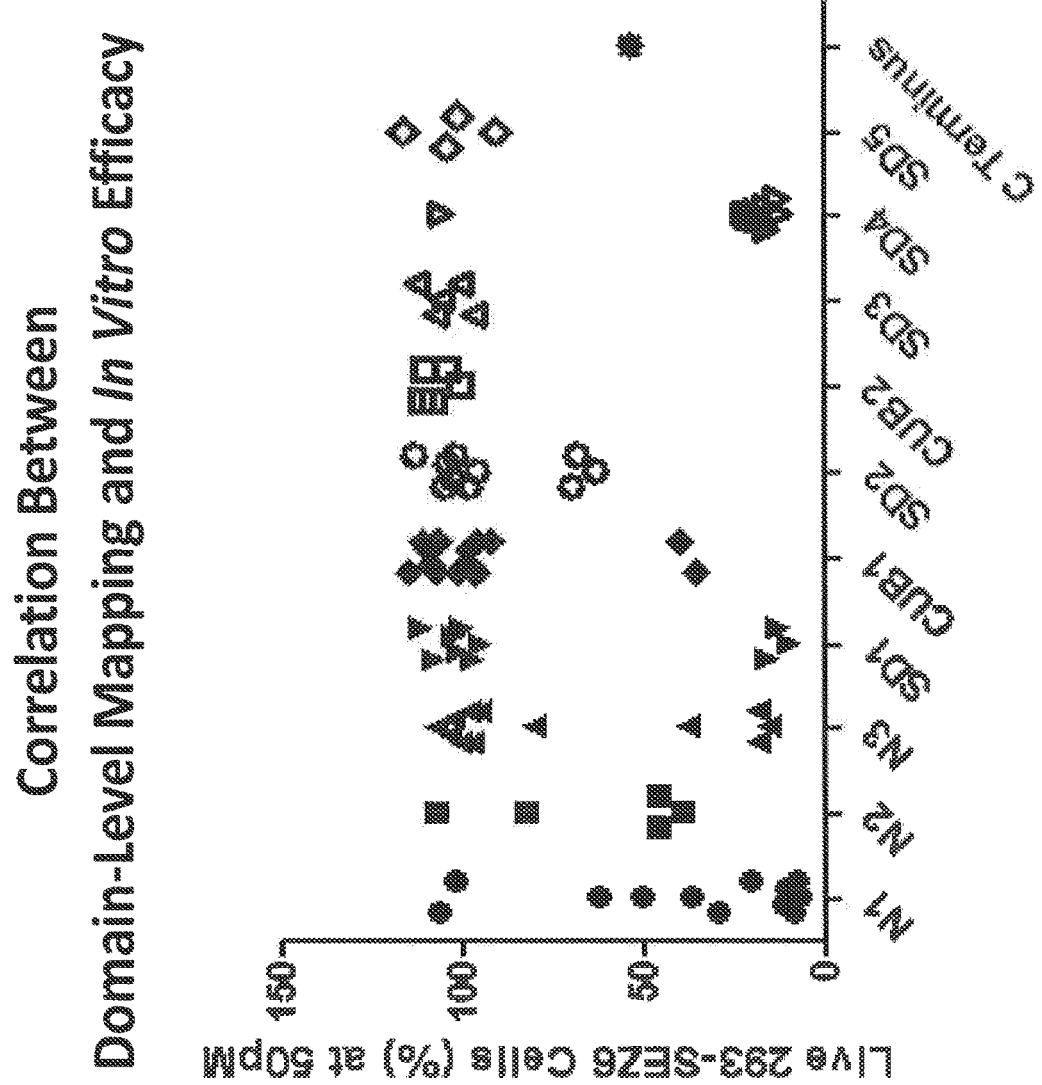
FIG. 11B provides a correlation between the domain to which an antibody binds and the antibody's efficacy in an in vitro killing assay.

An interesting and surprising trend was observed when an in vitro cell killing assay was performed using the domain-mapped SEZ6 antibody modulators described in this Example 10. The in vitro killing assay, performed essentially as described below in Example 14, determined the ability of a particular antibody to internalize and kill HEK-293 cells. FIG. 11B is a plot of efficacy of the tested antibodies versus the domains to which they bind. Antibodies that bind to certain domains including: N1, N3, Sushi Domain 1, and Sushi Domain 4, exhibited enhanced in vitro killing. The antibodies that associate with Sushi Domain 4, which are very effective at internalizing and killing cells, exhibit a strong correlation with the IGHV1-34 and IKV4-59 murine germline framework regions.

Fine epitope mapping was further performed on selected antibodies to determine the specific amino acids to which they bound. Antibodies that bound to a linear epitope were mapped using the Ph.D.-12 phage display peptide library kit (New England Biolabs E8110S). The antibody selected for epitope mapping was coated onto a Nunc MaxiSorp tube (Nunc) at 50 μg/mL in 3 mL, 0.1 M sodium bicarbonate solution, pH 8 and incubated overnight. The tube was blocked with 3% BSA solution in bicarbonate solution. Then, $10^{11}$ input phage in PBS+0.1% Tween-20 was allowed to bind, followed by ten consecutive washes with 0.1% Tween-20 to wash away non-binding phage. Remaining phage were eluted with 1 mL 0.2 M glycine for 10 minutes at room temperature with gentle agitation, followed by neutralization with 150 μL 1 M Tris-HCl pH 9. Eluted phage were amplified and panned again with $10^{11}$ input phage, using 0.5% Tween-20 during the wash steps to increase selection stringency. DNA from 24 plaques of the eluted phage from the second round was isolated using the Qiaprep M13 Spin kit (Qiagen) and sequenced. Binding of clonal phage was confirmed using an ELISA assay, where the mapped antibody or a control antibody was coated onto an ELISA plate, blocked, and exposed to each clone phage. Phage binding was detected using horseradish peroxidase conjugated anti-M13 antibody (GE Healthcare), and the 1-Step Turbo TMB ELISA solution (Pierce). Phage peptide sequences from specifically binding phage were aligned using Vector NTI (Life Technologies) against the antigen ECD peptide sequence to determine the epitope of binding.

Antibodies that bound to a discontinuous epitope were mapped using the technique described by Chao et al. (2007). Libraries of SEZ6 ECD mutants were generated with error prone PCR using nucleotide analogues 8-oxo-2'deoxyguanosine-5'-triphosphate and 2'-deoxy-p-nucleoside-5'triphosphate (both from TriLink Bio) for a target mutagenesis rate of one amino acid mutation per clone. These were transformed into a yeast display format. Using the technique described above for domain-level mapping, the library was stained for c-myc and antibody binding at 50 nM. Using a FACS Aria (BD), clones that exhibited a loss of binding compared to wild type SEZ6 ECD were sorted. These clones were re-grown, and subjected to another round of FACS sorting for loss of binding to the target antibody. Using the Zymoprep Yeast Plasmid Miniprep kit (Zymo Research), individual ECD clones were isolated and sequenced. Where necessary, mutations were reformatted as single-mutant ECD clones using the Quikchange site directed mutagenesis kit (Agilent).

Individual ECD clones were next screened to determine whether loss of binding was due to a mutation in the epitope, or a mutation that caused misfolding. Mutations that involved cysteine, proline, and stop codons were automatically discarded due to the high likelihood of a misfolding mutation. Remaining ECD clones were then screened for binding to a non-competing, conformationally specific antibody. ECD clones that lost binding to non-competing, conformationally specific antibodies were concluded to contain misfolding mutations, whereas ECD clones that retained equivalent binding as wild type SEZ6 ECD were concluded to be properly folded. Mutations in the ECD clones in the latter group were concluded to be in the epitope. Homology models of isolated domains were also constructed using MODELLER to confirm that residues identified to be in the epitope: 1) were localized in close proximity to each other in the folded homology model, and 2) had side chains that were solvent exposed, and not buried, since buried residues would have a higher chance of causing misfolding, and would unlikely be part of the epitope of binding. A summary of antibodies with their epitopes are listed in Table 4.

TABLE 4

| Antibody Clone | Epitope | Discontinuous | SEQ ID NO: |
|---|---|---|---|
| SC17.4 | Q12, P14, I16, E17, E18 | No | 401 |
| SC17.17 | R762, D781, Q782 | Yes | NR |
| SC17.24 | L73, P74, F755 Q76, P77, D78, P79 | No | 402 |
| SC17.34 | T352, S353, H375 | Yes | NR |
| SC17.36 | T352, S353, H375, S359 | Yes | NR |
| SC17.46 | R343, K389 | Yes | NR |

NR indicates that no SEQ ID NO was assigned as the epitopes were discontinuous.

In the case of SC17.34, SC17.36 and SC17.46, point mutations were constructed on the isolated domain, Sushi Domain 1, which was determined to be the domain of binding by domain-level epitope mapping. In the case of SC17.46, candidate mutations for screening were not identified in a library-based screen; rather they were identified on the basis of domain mapping, lack of cross reactivity to cynomolgus SEZ6 ECD and rat SEZ6 ECD, and sequence alignments of the different species to identify differences in the species' primary sequence. These candidate mutations were subjected to the same analysis as other antibodies to confirm the epitope of SC17.46.

Example 11

Detection of SEZ6 Surface Expression by Flow Cytometry

Flow cytometry was used to assess the specificity of the anti-SEZ6 antibodies that were generated for detecting the presence of human SEZ6 protein on the surface of engineered HEK-293T cell lines, constructed as described in Example 5. Isotype-stained and fluorescence minus one (FMO) controls were employed to confirm staining specificity. Briefly, HEK-293T transduced with human SEZ6 and GFP (see Example 5) or harvested NTX tumor samples were dissociated and dispersed into suspension using art-recognized enzymatic digestion techniques (see, for example, U.S.P.N. 2007/0292414 which is incorporated herein), were incubated for 30 minutes with an anti-SEZ6 antibody. Cells were washed in PBS (2% FCS) twice and then incubated with 50 µl per sample DyLight 649 labeled goat-anti-mouse IgG, Fc fragment specific secondary diluted 1:200 in PBS buffer. After a 15 minute incubation cells were washed twice with PBS and re-suspended in PBS with DAPI and analyzed by flow cytometry as previously discussed.

Figure 12A:
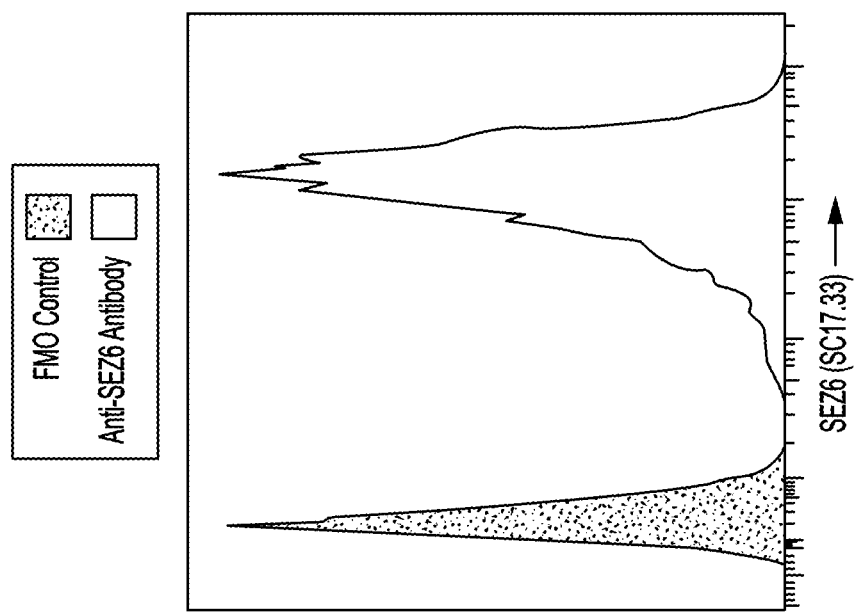
FIGS. 12A and 12B show detection of expression of SEZ6.

As demonstrated by the representative data shown in FIG. 12A for SC17.33, the SEZ6 modulator strongly recognized HEK-293T-HuSEZ6 cells. These data demonstrate that modulators were produced that specifically recognized human SEZ6 expressed on the cell surface.

Figure 13A:
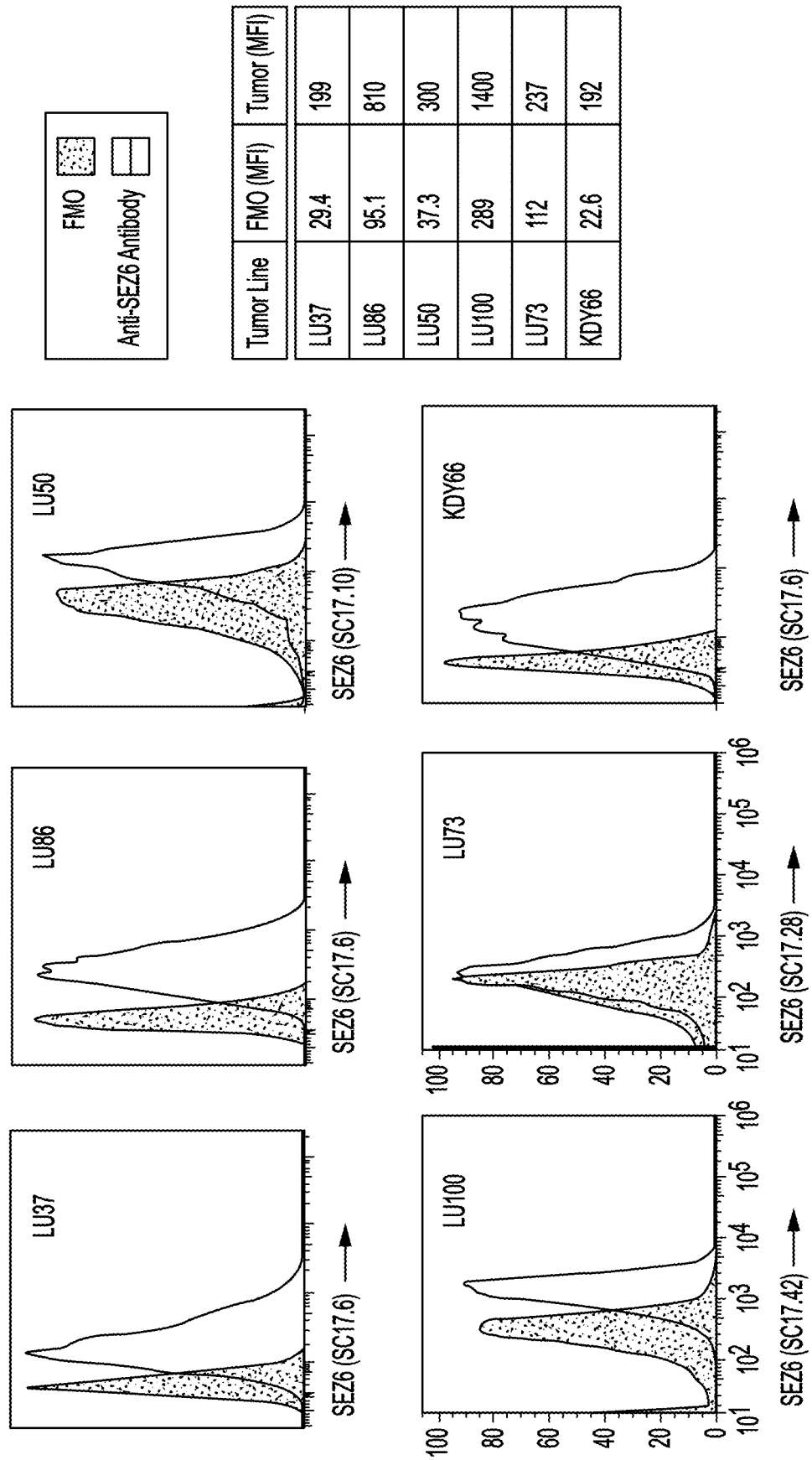

Human SEZ6 protein expression on the surface of selected NTX tumors was assessed by flow cytometry using several exemplary SC17 antibodies. The expression of SEZ6 in LU37, LU86 and KDY66 was tested using the SC17.6 antibody while expression of SEZ6 in LU50, LU100 and LU73 was tested using the SC17.10, SC17.42 and SC17.28 antibodies respectively. The results are set forth in FIG. 13A. NTX tumors were harvested, dissociated, and co-stained with commercially available anti-mouse CD45, anti-mouse H-2Kd, anti-human EpCAM and one the above-described mouse anti-human SEZ6 antibodies. Data shown in FIG. 13A was generated using cells that did not stain positively for the above mentioned anti-mouse antibodies but did stain positively for anti-human EpCAM. Similar to the HEK-293T-staining experiments described above, isotype-stained and fluorescence minus one (FMO) controls were employed to confirm staining specificity. As seen in FIG. 13A, anti-SEZ6 staining was higher than FMO in all of the human NTX tumor cells, as indicated by the fluorescent profile shift to the right, and by changes in the mean fluorescence intensity (MFI) values, for the lung NTX tumors LU37, LU50 and LU86 and kidney NTX tumor, KDY66. These data suggest that the SEZ6 protein is expressed on the surface of various NTX tumors and therefore amenable to modulation using an anti-SEZ6 antibody.

Example 12

Expression of SEZ6 Protein in Various Tumors

Given the elevated SEZ6 mRNA transcript levels associated with various tumors, work was undertaken to demonstrate a corresponding increase in the expression of SEZ6 protein in NTX tumors. SEZ6 protein expression was detected with (i) an electrochemiluminscence SEZ6 sandwich ELISA assay using the MSD Discovery Platform (Meso Scale Discovery, LLC); and (ii) immunohistochemistry staining.

NTX tumors were excised from mice and flash frozen on dry ice/ethanol. Protein Extraction Buffer (Biochain Institute, Inc.) was added to the thawed tumor pieces and tumors were pulverized using a TissueLyser system (Qiagen). Lysates were cleared by centrifugation (20,000 g, 20 minutes, 4° C.) and the total protein concentration in each lysate was quantified using bicinchoninic acid. Protein lysates were stored at −80° C. until assayed. Normal tissue lysates were purchased from Novas Biologicals.

SEZ6 protein concentrations from the lysate samples were determined by interpolating the values from a standard protein concentration curve that was generated using purified recombinant SEZ6 protein (Example 5). The SEZ6 protein standard curve and protein quantification assay were conducted as follows:

MSD standard plates were coated overnight at 4° C. with 30 µL of SC17.17 antibody at 2 µg/mL in PBS. Plates were washed in PBST and blocked in 150 µL MSD 3% Blocker A solution for one hour. Plates were again washed in PBST. The SC17.36 antibody was then conjugated to the MSD sulfo-tag and 25 µL of the tagged SC17.36 was added to the washed plates at 0.5 µg/ml, in MSD 1% Blocker A. 25 µL of 10× diluted lysate in MSD 1% Blocker A or serially diluted recombinant SEZ6 standard in MSD 1% Blocker A containing 10% Protein Extraction Buffer was also added to the wells and incubated for two hours. Plates were washed in PBST. MSD Read Buffer T with surfactant was diluted to 1× in water and 150 µL was added to each well. Plates were read on a MSD Sector Imager 2400 using an integrated software analysis program to derive SEZ6 concentrations in NTX samples via interpolation from the standard curve. Values were then divided by total protein concentration to yield nanograms of SEZ6 per milligram of total lysate protein. The resulting concentrations are set forth in FIG. 12B wherein each spot represents SEZ6 protein concentrations derived from a single NTX tumor line. While each spot is derived from a single NTX line, in most cases multiple biological samples were tested from the same mix line and values were averaged to provide the data point.

Figure 12B:
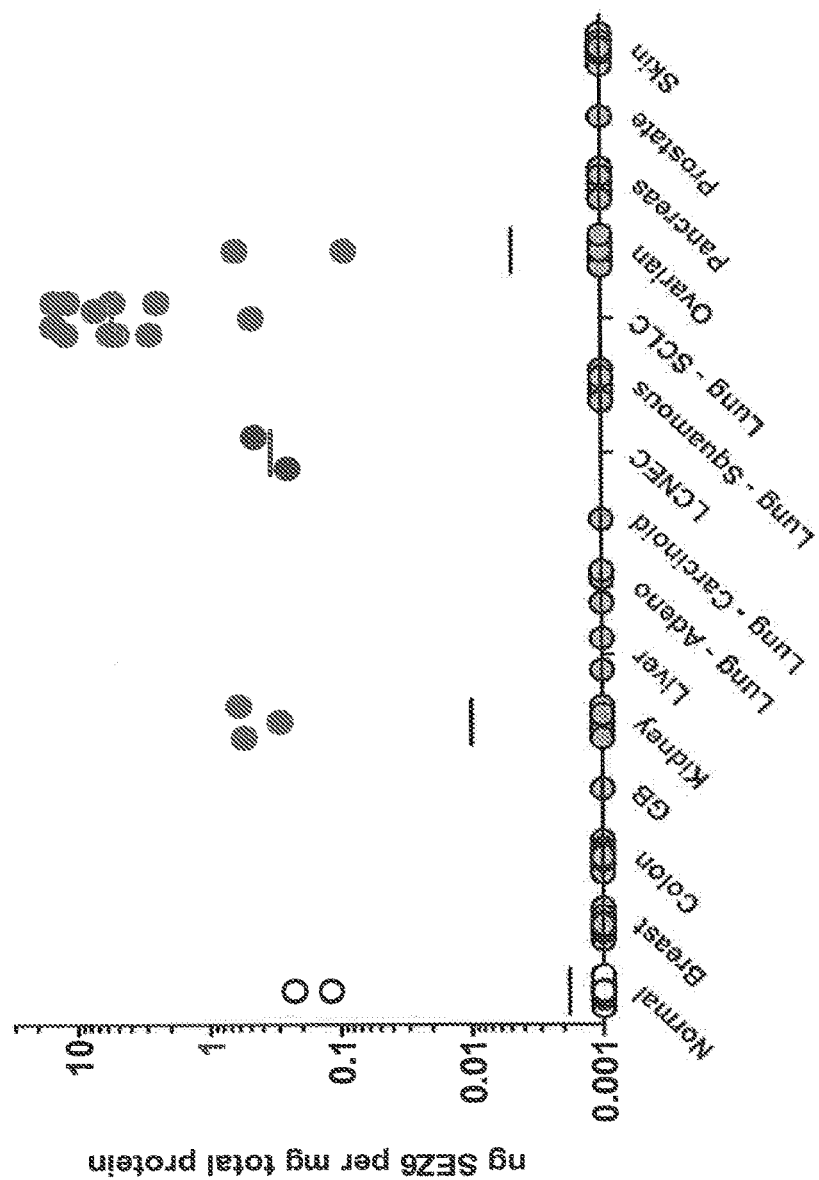

FIG. 12B shows that compared to normal tissue lysates, selected kidney, ovarian and LCNEC tumor samples exhibited moderate SEZ6 protein expression whereas the highest SEZ6 protein expression was seen in SCLC tumors. All normal tissue lysates were negative for SEZ6 protein expression with the exception of normal human brain and eye lysate.

Immunohistochemistry (IHC) was performed on PDX tumors to confirm that SEZ6 is expressed on the surface of certain PDX tumors; and in order to determine the location of the SEZ6 protein in the tumor architecture.

IHC was performed on formalin fixed paraffin embedded tissue sections using an indirect detection method which included murine monoclonal primary antibody against SEZ6 (clone 17.140), mouse specific biotin conjugated secondary antibodies, avidin/biotin complex coupled with horse radish peroxidase, and DAB detection (Nakene PK 1968; 16:557.-60). When staining xenograft PDX tumors, a mouse IgG blocking agent (Vector Laboratories; catalog no. PK-2200) was used. SC17.140 was validated and confirmed to be appropriate for IHC by showing specific staining on sections of HEK-293T cell pellets overexpressing SEZ6 compared to naïve HEK-293T cell pellets, prepared as known in the art. Specificity was further confirmed by competing signal with a 5 molar excess of purified recombinant SEZ6 on HEK-293T cells overexpressing human SEZ6 and xenograft tumors that were shown by IHC to express SEZ6 (data not shown). FIG. 16 shows SEZ6 expression as measured by IHC in SCLC NTX tumors. Staining intensity was scored to take into account intensity of staining from 0 (negative) to 3 (strong staining). The results show that 64% of the SCLC NTX tumors tested, expressed SEZ6.

These data, combined with the mRNA transcription data for SEZ6 expression set forth above (Example 4), and cell surface protein expression of SEZ6 (Example 11), strongly reinforces the proposition that SEZ6 determinants provide attractive targets for therapeutic intervention.

Example 13

Enrichment of Tumor Initiating Cell Populations

Tumor cells can be divided broadly into two types of cell subpopulations: non-tumorigenic cells (NTG) and tumor initiating cells (TICs). TICs have the ability to form tumors when implanted into immunocompromised mice. Cancer stem cells (CSCs) are a subset of TICs and are able to self-replicate indefinitely while maintaining the capacity for multilineage differentiation. To determine whether SEZ6 expression could be correlated with enhanced tumorigenicity whole transcriptome sequencing, flow cytometry and a tumorigenicity assay were performed, all of which are described below.

Whole transcriptome analysis of SEZ6 expression in various tumor samples was performed as described in Example 1. CSCs were identified on the basis of expression of CD324 which has been shown to be a marker of stem cells in various tumors (see PCT application 2012/031280). The results in FIG. 6A show that SEZ6 mRNA expression was elevated in CSCs compared to NTG cells isolated from two SCLC NTX tumor lines (LU86 and LU95).

Figure 13B:
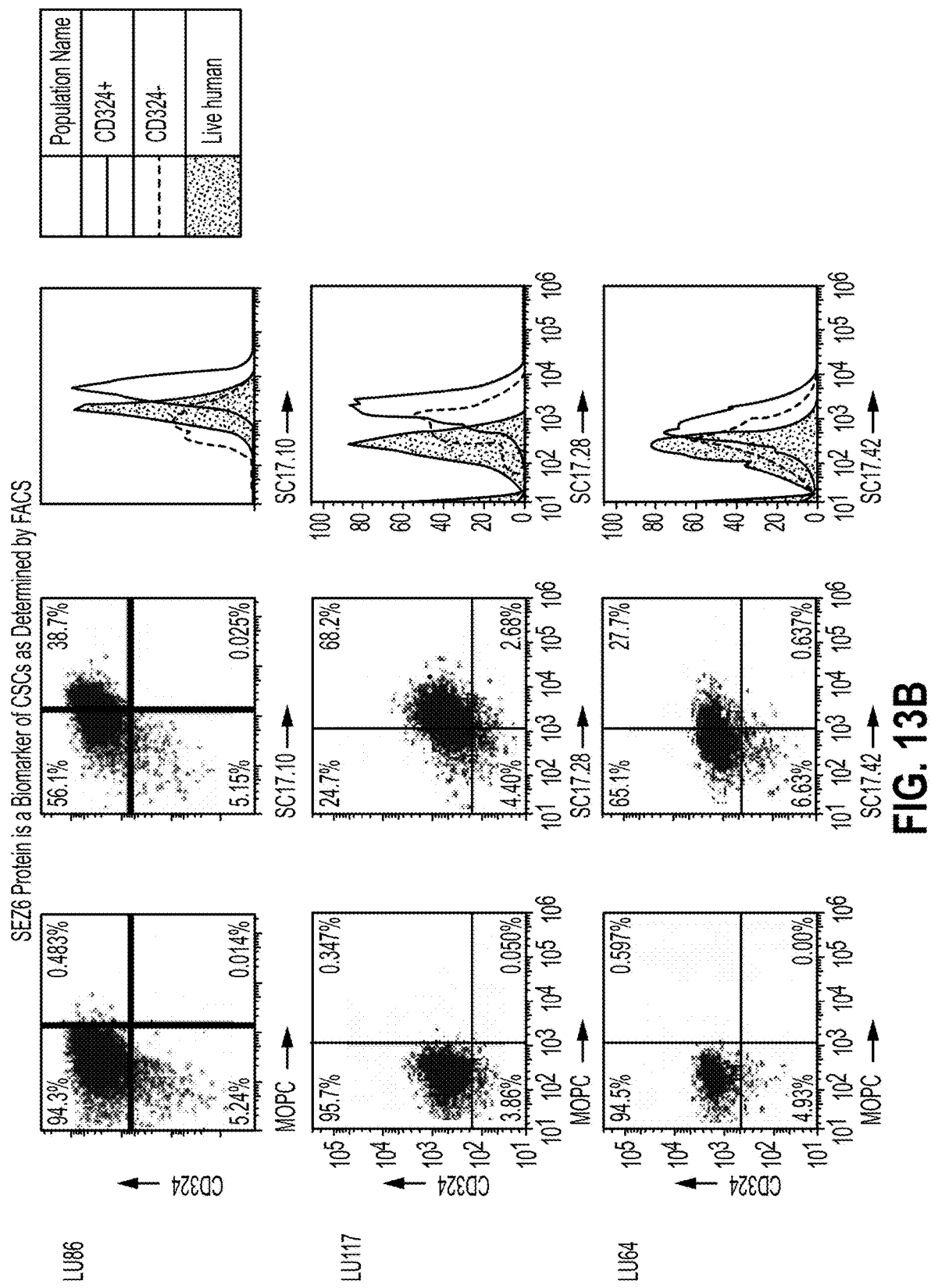

Flow cytometry was performed on cells from NTX lung tumors essentially as described in Example 11. LU86, LU117 and LU64 cells were co-stained with CD324, a marker of CSC populations (see PCT application 2012/031280), and the anti-SEZ6 antibody, SC17.10, SC17.28 or SC17.42, respectively to determine if SEZ6 is differentially expressed on these populations. As indicated in FIG. 13B, LU86, LU117 and LU64 cells staining positive for both CD324 and SEZ6 (solid black line) shift further to the right compared to cells staining positive for SEZ6 alone (dotted black line), indicating that SEZ6 is more highly expressed on CSCs compared to the NTG cell population. The bulk population isotype control is shown as a gray filled histogram (MOPC=IgG1).

To determine whether cell surface SEZ6 expression could be correlated with enhanced ability to generate tumors, a tumorigenicity study was conducted. NTX tumor samples were dissociated and dispersed into suspension using art-recognized enzymatic digestion techniques (see, for example, U.S.P.N. 2007/0292414 which is incorporated herein). The dissociated cell preparations from these NTX lines were stained with fluorescently conjugated antibodies specifically recognizing murine CD45, H2kD, human CD324, and human SEZ6, clone SC17.42. Two subsets of human cells, both identified based on the absence of staining with murine CD45 or H2kD (to deplete the cell preparations of murine cells) were isolated using a FACSARIA™ Flow Cytometer (BD Biosciences). One subset was isolated on the basis of a CD324 and SEZ6 co-expression, while the other subset was isolated on the basis of a $CD324^+SEZ6^-$ phenotype. The distinct marker-enriched subpopulations were subsequently transplanted into female NOD/SCID immuno-compromised mice by subcutaneous injection into the mammary fat pad at a dose of approximately 50 cells per mouse.

FIGS. 14A and 14B illustrate the results of such experiments conducted using representative NTX cell lines derived from NSCLC tumors obtained from patients. FIG. 14A is a scatter plot (gated using CD324 and SEZ6) showing the distribution of $mCD45^-H2kD^-$ subset of the parent tumor and sorted putative tumorigenic cells. FIG. 14B graphically shows the measured tumor volume arising from the implantation of sorted cell subpopulations into immu-nocompromised mice. Values in parenthesis indicate the number of tumors generated per mice implanted.

Significantly, the data from FIG. 14 show that tumorigenicity was consistently associated with the subpopulation of cells expressing SEZ6 in combination with high levels of CD324. Conversely, these same data demonstrate that tumor cells expressing either no, or low levels of SEZ6 were much less tumorigenic than their high or positive counterparts. Based on the generated data it was surprisingly found that subpopulations of tumor cells expressing the $CD324^+SEZ6^+$ phenotype generally contain the vast majority of tumori-genic capability and suggest that SEZ6 may provide an effective therapeutic target for tumorigenic cell modulation.

Example 14

SEZ6 Modulators Facilitate Delivery of Cytotoxic Agents to SEZ6-Expressing HEK-293T Cells To demonstrate that. SEZ6 modulators of the instant invention are able to mediate the delivery of a cytotoxic agent to live cells, an in vitro cell killing assay was performed using selected SEZ6 antibody modulators bound to a saporin toxin. Saporin kills cells by deactivating ribosomes in the cytoplasm. Thus cell death using the following assay is an indication that the SEZ6 antibodies are able to internalize and deliver cytotoxic agents to the cytoplasm of a target cell.

An anti-Mouse IgG Fab fragment covalently linked to saporin ("Fab-Saporin") (Advanced Targeting Systems, #IT-48) was combined with unlabeled SEZ6 antibodies and incubated with HEK-293T cells expressing human SEZ6 (see Example 5). The ability of the resulting saporin complexes to internalize and kill cells was measured 72 hours later by measuring cell viability.

Specifically, 500 cells per well in DMEM supplemented with 10% fetal bovine serum, were plated into 96 well tissue culture treated plates one day before the addition of antibodies and toxin. HEK-293T cells expressing human SEZ6 were treated with a control (IgG1, IgG2a or IgG2b) or purified murine SEZ6 modulators at a concentration of 100, 50 or 10 pM, together with 2 nM Fab-Saporin. The cells were cultured for three days, after which, viable cell numbers were enumerated using Cell Titer Glo® (Promega) as per manufacturer's instructions. Raw Luminescence Units (RLU) using cultures containing cells with the Saporin Fab fragment were set as 100% reference values and all other counts calculated accordingly (referred to as Normalized RLU or "% live cells"). FIG. 15A shows that many of the SEZ6 modulators tested mediated the killing of HEK-293T cells in a concentration dependent manner. Isotype controls (IgG2a, IgG2b, and IgG1) did not affect cell counts as shown by the results in the first three rows of FIG. 15A (ND=Not Determined).

This assay demonstrates that internalization may occur upon binding of the SEZ6-specific antibody to the cell surface, without the need for additional crosslinking or dimerization.

Example 15

SEZ6 Modulators Mediate Cytotoxicity in Lung Tumor Cells In Vitro

To corroborate the results of Example 14 and determine whether SEZ6 modulators can mediate toxin internalization and cell killing of human tumor cells (as opposed to engineered cells), mouse lineage-depleted NTX cells were plated and subsequently exposed to anti-SEZ6 antibodies and Fab-saporin.

NTX tumors were dissociated into a single cell suspension and plated on PRIMARIA™ plates (ED Biosciences) in growth factor supplemented serum free media as is known in the art. After culturing the cells for one day at 37° C./5% $CO_2$/5% $O_2$, they were treated with a control (IgG1, IgG2a or IgG2b) or a murine SEZ6 modulator and Fab-saporin as described in Example 14. After seven days, the modulator-mediated saporin cytotoxicity was assessed by quantifying the remaining number of live cells using Cell Titer Glo.

Figure 15B:
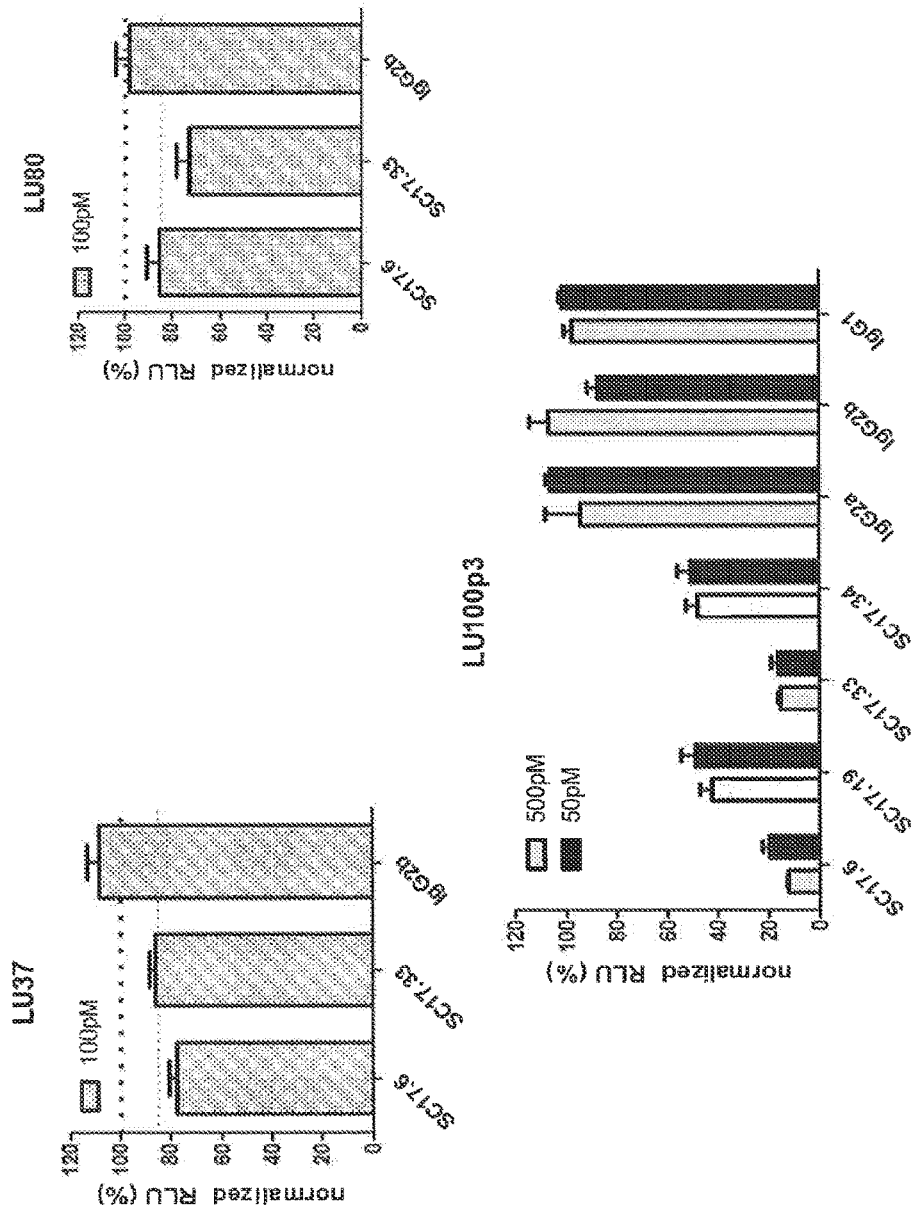

As seen in FIG. 15B a reduction in the number of tumor cells was evident when LU37, a NSCLC tumor and LU80, a SCLC tumor were exposed to SC17.6 (duplicative of SC17.16) and SC17.33 SEZ6 modulators. Similarly when LU100, a SCLC tumor was exposed to four SEZ6 modulators, SC17.6, SC17.19, SC17.33 and SC17.34, at 50 and 500 pM a reduction of tumor cells was effected. In contrast, isotype control antibodies did not impact the number of live cells after treatment.

Not only does this data demonstrate that exemplary antibodies described herein are able to bind SEZ6 antigen on the cell surface and facilitate the delivery of a cytotoxic payload resulting in cell death, but the above data also demonstrated that multiple anti-SEZ6 antibodies can mediate killing of various NTX tumor cells.

Example 16

Preparation of SEZ6 Antibody-Drug Conjugates

Based on the in vitro killing assays with saporin in Examples 14 and 15 and to further demonstrate the versatility of the instant invention, anti-SEZ6 antibody drug conjugates were prepared having the M-[L-D] structure as described above. That is, anti-SEZ6 antibody drug conjugates (SEZ6-ADCs) were prepared using covalently linked cytotoxic agents. More specifically, SEZ6-ADCs were prepared comprising a linker as described herein, or in the references immediately below, and selected pyrrolobenzodiazepine (PBD) dimers that were covalently attached to the disclosed modulators (see, e.g., U.S.P.Ns. 2011/0256157 and 2012/0078028 and U.S. Pat. No. 6,214,345 each of which is incorporated herein by reference in its entirety).

PBD drug-linker combinations were synthesized and purified using art-recognized techniques in view of the cited references. While various PBD dimers and linkers were employed to fabricate the selected drug-linker combinations, each linker unit comprised a terminal maleimido moiety with a free sulfhydryl. Using these linkers, conjugations were prepared via partial reduction of the mAb with tris (2-carboxyethyl)-phosphine (TCEP) followed by reaction of reduced Cys residues with the maleimido-linker payload.

More particularly, the selected SEZ6 antibody modulator was reduced with 1.3 mol TCEP per mol mAb for 2 hr at 37° C. in 25 mM Tris HCl pH 7.5 and 5 mM EDTA buffer. The reaction was allowed to cool to 15° C. and the linker payload in DMSO was added at a ratio of 2.7 mol/mol mAb followed by an additional amount of DMSO to a final concentration of 6% (v/v). The reaction was allowed to proceed for 1 hour. The unreacted drug-linker was capped by addition of an excess of N-acetyl cysteine. The SEZ6-ADC (or SC17-ADC) was then purified by ion exchange column using an AKTA Explorer FPLC system (G.E. Healthcare) to remove aggregated high molecular weight antibody, co-solvent and small molecules. The eluted ADC was then buffer-exchanged by tangential flow filtration (TFF) into formulation buffer followed by concentration adjustment and addition of a detergent. The final ADC was analyzed for protein concentration (by measuring UV), aggregation (SEC), drug to antibody ratio (DAR) by reverse phase (RP) HPLC, presence of unconjugated antibody by hydrophobic interaction chromatography (HIC) HPLC, non-proteinaceous materials by RP HPLC and in vitro cytotoxicity using a SEZ6 expressing cell line.

Using the aforementioned procedure, or substantially similar methodology, a number of ADCs (i.e., M-[L-D]n) comprising various SEZ6 modulators and PBD dimers were generated and tested in a variety of in vivo and in vitro models. For the purposes of these Examples and the instant disclosures, such ADCs may generally be termed SEZ6-ADCs or SC17-ADCs. Discrete ADCs will be named according to the antibody (e.g., SC17.17) and the specific linker-cytotoxic agent designation ADC1, ADC2, etc. Thus, exemplary modulators compatible with the instant invention may comprise SC17.17-ADC1 or SC17.24-ADC2 where ADC1 and ADC2 represent individual PBD dimer cytotoxic agents (and optionally a linker).

As an initial benchmark, the in vitro cytotoxicity of hSC17.17-ADC1 was measured at an IC50 of 11 nM when exposed to HEK293 cells overexpressing SEZ6 (data not shown).

Example 17

Conjugated SEZ6 Modulators Mediate Cytotoxicity in Lung Tumor Cells In Vitro

The ADCs generated in Example 16 above were tested to determine whether they were able to mediate toxin internalization and cell killing of primary human tumor cells in vitro.

Figure 17A:
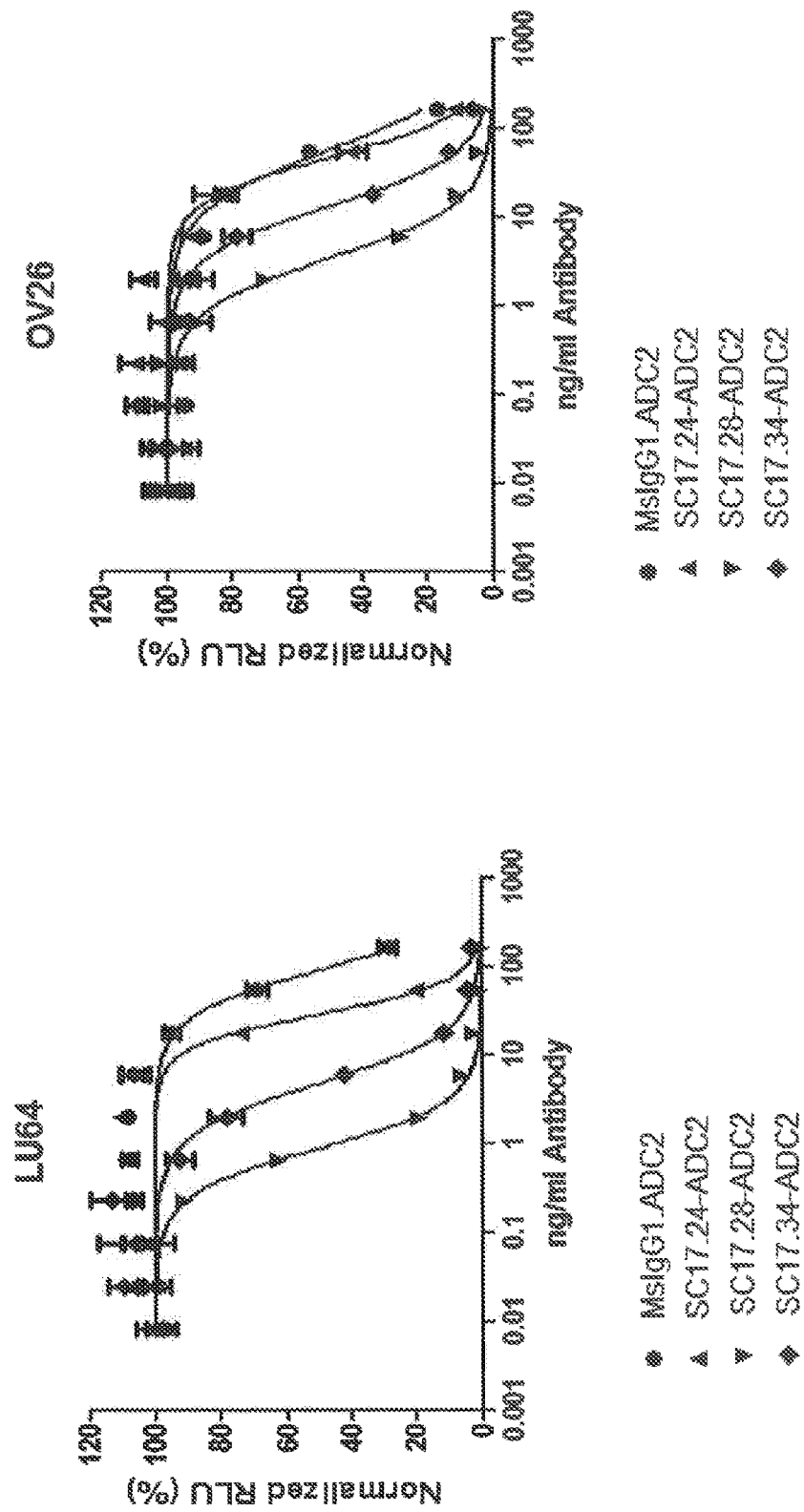
FIGS. 17A and 17B depict the ability of conjugated anti-SEZ6 mouse antibodies to retard in vitro and in vivo growth of NTX tumor cells.

Mouse lineage-depleted NTX tumor cells were exposed to anti-SEZ6 ADCs or a mouse isotype control (mIgG1) using the same method as described in Example 15, except that Fab-saporin was not added. When LU64, a SCLC tumor and OV26, a NET ovarian tumor, were treated with anti-SEZ6 ADCs (SC17.24-ADC2, SC17.28-ADC2 and SC17.34-ADC2), an increased reduction in percent viable cells was observed compared to the control mIgG1 (FIG. 17A). While mIgG1 can be cytotoxic to cells at high concentrations, all three anti-SEZ6 ADCs tested were more potent, indicating an imunospecific response to SEZ6 rather than a general response to the PBD cytotoxin.

Example 18

Conjugated SEZ6 Modulators Suppress In Vivo Tumor Growth

The ADCs generated in Example 16 above were tested to demonstrate their ability to shrink and suppress human NTX tumor growth in immunodeficient mice.

Patient-derived NTX tumors were grown subcutaneously in the flanks of female NOD/SCID recipient mice using art-recognized techniques. Tumor volumes and mouse weights were monitored twice per week. When tumor volumes reached 150-250 mm$^3$, mice were randomly assigned to treatment groups and injected intraperitoneally with SC17-ADC1 or an anti-hapten control MsIgG1-ADC1. Mice were given three injections of 1 mg/kg (indicated by the vertical lines in FIG. 17B and FIGS. 18A and 18B) over a period of seven days. Following treatment, tumor volumes and mouse weights were monitored until tumors exceeded 800 mm$^3$ or mice became sick.

Figure 17B:
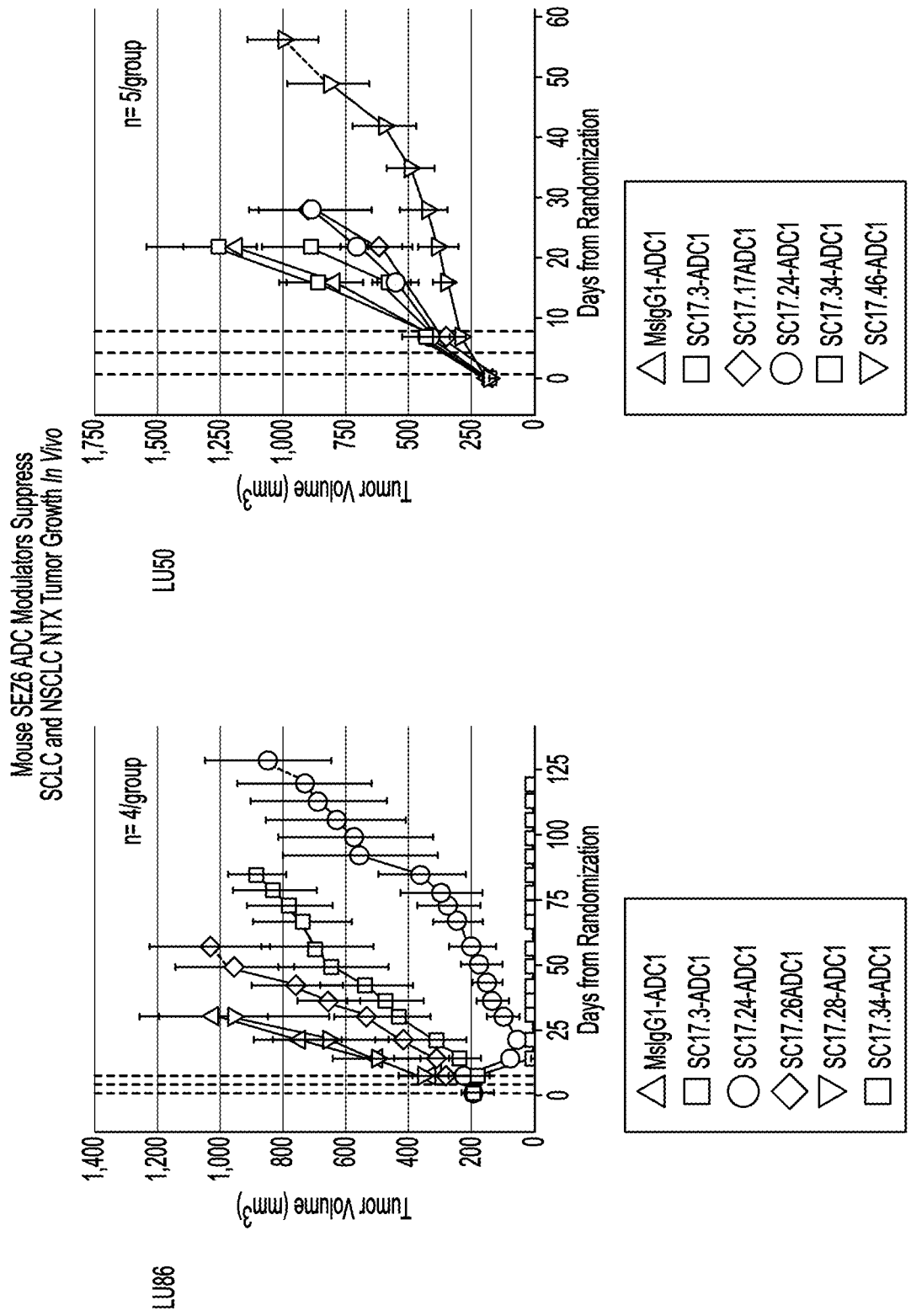

FIG. 17B shows that anti-SEZ6 ADCs are able to inhibit in vivo growth of a SCLC tumor (LU86) and a LCNEC (LU50) mice. In the case of LU86 the five ADCs tested (SC17.3-ADC1, SC17.24-ADC1, SC17.26-ADC1, SC17.28-ADC1 and SC17.34-ADC1) produced durable remissions lasting, in some cases, beyond 120 days post-treatment. In particular, SC17.34-ADC1 treatment inhibited tumor growth for the duration of the study at this dose, while SC17.24-ADC1 led to significant tumor growth inhibition with time to progression of greater than 50 days. Similarly, treatment of LU50 with five exemplary ADCs (SC17.3-ADC1, SC17.17-ADC1, SC17.24-ADC1, SC17.34-ADC1 and SC17.46-ADC1) resulted in tumor growth suppression lasting as long as 35 days with SC17.46. Moreover, mice treated with SC17-ADC1 did not exhibit adverse health effects beyond those typically seen in immunodeficient, tumor-bearing NOD/SCID mice. These results suggest that the disclosed ADCs may be used to effectively suppress tumor growth and that the particulars of SC17 modulator binding can have an impact on in vivo efficacy.

More directly the ability of a variety of conjugated modulators to dramatically retard or suppress tumor growth in vivo for extended periods further validates the use of SEZ6 as a therapeutic target for the treatment of proliferative disorders.

Example 19

Humanized Conjugated SEZ6 Modulators Suppress Tumor Growth In Vivo

Given the impressive results obtained with murine anti-SEZ6 ADC modulators, additional experiments were performed to demonstrate the efficacy of exemplary humanized anti-SEZ6 ADC modulators in treating SCLC tumors in vivo. Selected humanized anti-SEZ6 ADCs (using modulators hSC17.17, hSC17.24, hSC17.34 and hSC17.46), produced as set forth in Example 16, and the human IgG1 isotype control ADC (huIgG1) were administered to immunodeficient mice bearing various NTX tumors. The dosing regimen was the same as that set out in Example 18.

Figure 18A:
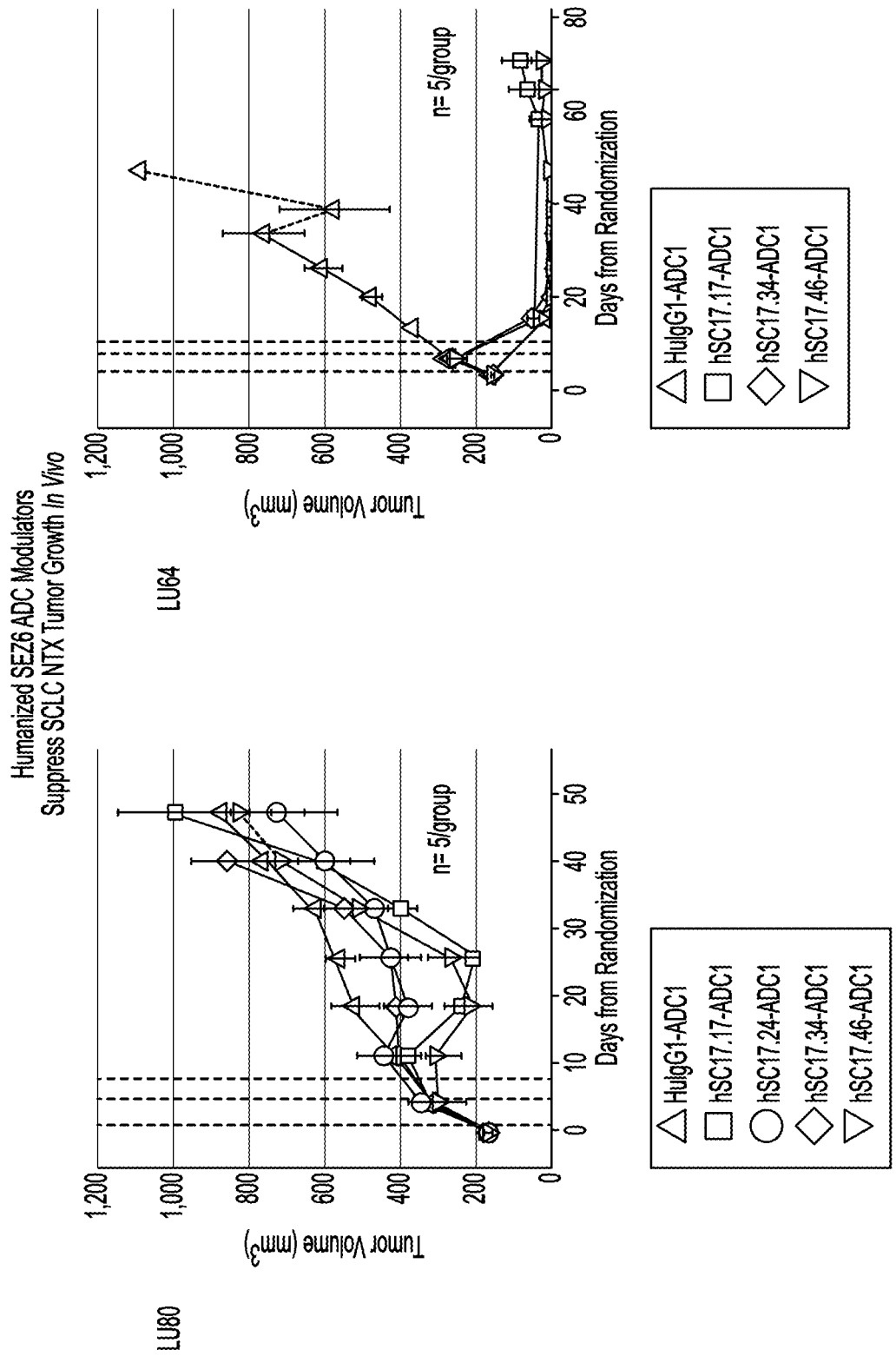
FIGS. 18A and 18B depict the ability of conjugated humanized anti-SEZ6 antibodies to retard in vivo growth of four SCLC tumors (LU80, LU64, LU111 and LU117) and achieve durable remission in immunodeficient mice.
Figure 18B:
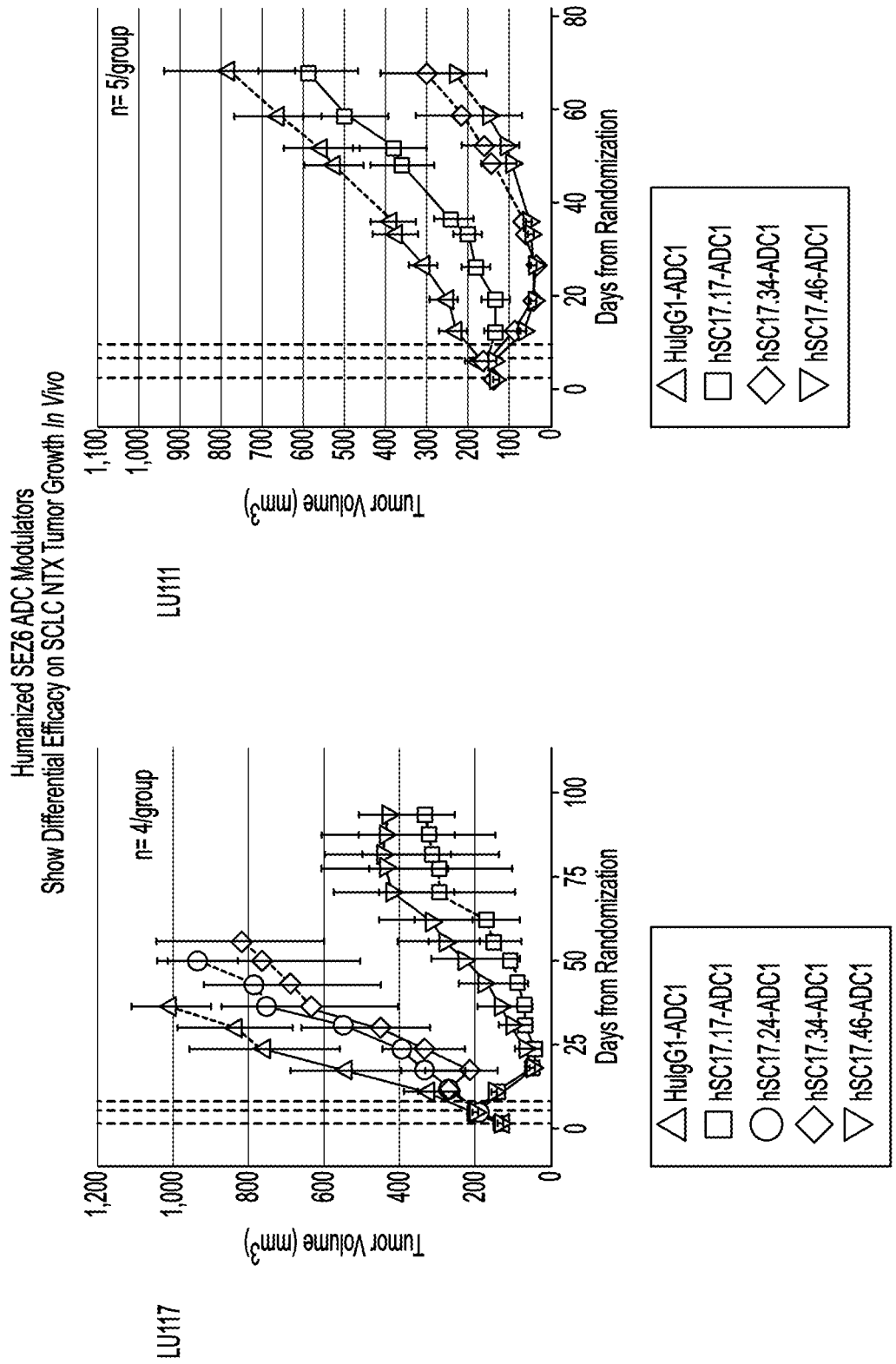

The results of these experiments are presented in FIGS. 18A and 18B. Complete and durable elimination of tumor mass was achieved by the administration of humanized anti-SEZ6 ADCs in four SCLC tumors. FIG. 18A shows reduction of the LU80 tumor by hSC17.17-ADC1 and hSC17.46-ADC1; and elimination of the LU64 tumor by hSC17.17-ADC1, hSC17.34-ADC1 and hSC17.46-ADC1. FIG. 18B shows reduction of the LU 117 tumor by hSC17.17-ADC1 and hSC17.46-ADC1; and reduction of the LU111 tumor by hSC17.34-ADC1 and hSC17.46-ADC1. Absence of tumor recurrence was observed for more than 50 days in 3 out of 4 of these studies. In each study tumor volumes and mouse weights of the control animals were monitored until tumors exceeded 800 mm$^3$ or mice became sick.

These results demonstrate the surprising applicability of a variety of humanized SEZ6 modulators to effectively retard the growth of different tumors.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A monoclonal antibody that specifically binds a human seizure related 6 homolog (SEZ6) protein, comprising three complementarity determining regions of a light chain variable region (CDR-L1, CDR-L2, and CDR-L3) comprising an amino acid sequence set forth as SEQ ID NO: 190 and three complementarity determining regions of a heavy chain variable region (CDR-H1, CDR-H2, and CDR-H3) comprising an amino acid sequence set forth as SEQ ID NO: 191.

2. The monoclonal antibody of claim 1, wherein the monoclonal antibody is selected from the group consisting of a chimeric antibody, a CDR-grafted antibody, and a humanized antibody.

3. The monoclonal antibody of claim 2, comprising:
   (a) residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2 and residues 95-102 of SEQ ID NO: 191 for CDR-H3, wherein the residues are numbered according to Kabat;
   (b) residues 23-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 50-58 of SEQ ID NO: 191 for CDR-H2 and residues 95-102 of SEQ ID NO: 191 for CDR-H3, wherein the residues are numbered according to Chothia; or
   (c) residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2 and residues 93-101 of SEQ ID NO: 191 for CDR-H3, wherein the residues are numbered according to Mac-Callum.

4. The monoclonal antibody of claim 1, wherein the monoclonal antibody is conjugated to a cytotoxic agent.

5. The monoclonal antibody of claim 4, wherein the cytotoxic agent is a pyrrolobenzodiazepine, a duocarmycin, an amanitin, an auristatin, a maytansinoid, a calicheamicin, or a radioisotope.

6. The monoclonal antibody of claim 1, wherein the antibody comprises
   a light chain variable region comprising an amino acid sequence set forth as SEQ ID NO: 190 and a heavy chain variable region comprising an amino acid sequence set forth as SEQ ID NO: 191.

7. An antibody drug conjugate comprising a monoclonal antibody conjugated, linked or otherwise associated with a cytotoxic agent, wherein the monoclonal antibody specifically binds a human seizure related 6 homolog (SEZ6) protein and comprises
   three complementarity determining regions of a light chain variable region (CDR-L1, CDR-L2, and CDR-L3) comprising an amino acid sequence set forth as SEQ ID NO: 190 and three complementarity determining regions of a heavy chain variable region (CDR-H1, CDR-H2, and CDR-H3) comprising an amino acid sequence set forth as SEQ ID NO: 191.

8. The antibody drug conjugate of claim 7, wherein the antibody drug conjugate has the formula: Ab-[L-D]n wherein:
   (a) Ab comprises the monoclonal antibody;
   (b) L comprises an optional linker;
   (c) D comprises a drug, which is the cytotoxic agent; and
   (d) n is an integer from 1 to 20.

9. The antibody drug conjugate of claim 7, wherein the cytotoxic agent is a pyrrolobenzodiazepine, a duocarmycin, an amanitin, an auristatin, a maytansinoid, a calicheamicin, or a radioisotope.

10. The antibody drug conjugate of claim 7, wherein the antibody drug conjugate comprises a linker.

11. The antibody drug conjugate of claim 10, wherein the linker comprises a non-cleavable linker.

12. An antibody drug conjugate comprising a monoclonal antibody conjugated to a cytotoxic agent,
   wherein the monoclonal antibody specifically binds a human seizure related 6 homolog (SEZ6) protein and comprises three complementarity determining regions of a light chain variable region (CDR-L1, CDR-L2, and CDR-L3) comprising an amino acid sequence set forth as SEQ ID NO: 190 and three complementarity determining regions of a heavy chain variable region (CDR-H1, CDR-H2, and CDR-H3) comprising an amino acid sequence set forth as SEQ ID NO: 191; and
   wherein the cytotoxic agent is a calicheamicin.

13. The antibody drug conjugate of claim 12,
   wherein the monoclonal antibody comprises residues 24-34 of SEQ ID NO: 190 for CDR-L1, residues 50-56 of SEQ ID NO: 190 for CDR-L2, residues 89-97 of SEQ ID NO: 190 for CDR-L3, residues 31-35 of SEQ ID NO: 191 for CDR-H1, residues 50-65 of SEQ ID NO: 191 for CDR-H2 and residues 95-102 of SEQ ID NO: 191 for CDR-H3, wherein the residues are numbered according to Kabat.

14. The antibody drug conjugate of claim 12,
   wherein the monoclonal antibody comprises residues 23-34 of SEQ ID NO: 190 for CDR-L1, residues 50-56 of SEQ ID NO: 190 for CDR-L2, residues 89-97 of SEQ ID NO: 190 for CDR-L3, residues 26-32 of SEQ ID NO: 191 for CDR-H1, residues 50-58 of SEQ ID NO: 191 for CDR-H2 and residues 95-102 of SEQ ID NO: 191 for CDR-H3, wherein the residues are numbered according to Chothia.

15. The antibody drug conjugate of claim 12,
   wherein the monoclonal antibody comprises residues 30-36 of SEQ ID NO: 190 for CDR-L1, residues 46-55 of SEQ ID NO: 190 for CDR-L2, residues 89-96 of SEQ ID NO: 190 for CDR-L3, residues 30-35 of SEQ ID NO: 191 for CDR-H1, residues 47-58 of SEQ ID NO: 191 for CDR-H2 and residues 93-101 of SEQ ID NO: 191 for CDR-H3, wherein the residues are numbered according to MacCallum.

16. The antibody drug conjugate of claim 12, wherein the antibody drug conjugate comprises a linker.

17. The antibody drug conjugate of claim 16, wherein the linker comprises a non-cleavable linker.

* * * * *